United States Patent
Zhang et al.

(10) Patent No.: US 12,091,418 B2
(45) Date of Patent: *Sep. 17, 2024

(54) ANTI-TUMOR COMPOUND AND PREPARATION METHOD AND USE THEREOF

(71) Applicant: DUALITY BIOLOGICS (SUZHOU) CO., LTD., Shanghai (CN)

(72) Inventors: Yu Zhang, Shanghai (CN); Zhongyuan Zhu, Shanghai (CN); Haiqing Hua, Shanghai (CN); Bing Li, Shanghai (CN); Jian Li, Shanghai (CN); Shengchao Lin, Shanghai (CN); Xi Li, Shanghai (CN); Hongxia Shen, Shanghai (CN)

(73) Assignee: DUALITY BIOLOGICS (SUZHOU) CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/495,455

(22) Filed: Oct. 26, 2023

(65) Prior Publication Data

US 2024/0132516 A1   Apr. 25, 2024

Related U.S. Application Data

(63) Continuation of application No. 18/187,935, filed on Mar. 22, 2023, which is a continuation of application No. 17/825,090, filed on May 26, 2022, now Pat. No. 11,685,742, which is a continuation of application No. PCT/CN2021/121721, filed on Sep. 29, 2021.

(30) Foreign Application Priority Data

Sep. 30, 2020 (CN) .......................... 202011061580.7

(51) Int. Cl.
  *C07D 491/22* (2006.01)
  *A61K 47/65* (2017.01)
  *A61K 47/68* (2017.01)
  *A61P 35/00* (2006.01)

(52) U.S. Cl.
  CPC ............ *C07D 491/22* (2013.01); *A61K 47/65* (2017.08); *A61K 47/6803* (2017.08); *A61K 47/6855* (2017.08); *A61P 35/00* (2018.01)

(58) Field of Classification Search
  CPC ............ A61K 31/4745; A61K 47/6803; A61K 47/6849
  See application file for complete search history.

(56) References Cited

U.S. PATENT DOCUMENTS

| | | | |
|---|---|---|---|
| 4,687,777 A | 8/1987 | Meguro et al. | |
| 11,607,459 B1 * | 3/2023 | Zhang | A61K 47/6803 |
| 11,685,742 B2 * | 6/2023 | Zhang | A61K 47/6803 |
| | | | 514/279 |
| 2015/0352224 A1 | 12/2015 | Naito | |
| 2017/0035906 A1 * | 2/2017 | Naito | C07K 16/3061 |
| 2021/0347894 A1 * | 11/2021 | Ying | C07K 16/2827 |
| 2021/0353764 A1 * | 11/2021 | Xu | A61K 47/6855 |
| 2021/0393792 A1 | 12/2021 | Wijdeven et al. | |
| 2023/0212182 A1 | 7/2023 | Zhang | |
| 2023/0331738 A1 | 10/2023 | Zhang | |

FOREIGN PATENT DOCUMENTS

| | | | |
|---|---|---|---|
| CN | 105829346 A | 8/2016 | |
| CN | 109106951 A | 1/2019 | |
| CN | 109789211 A | 5/2019 | |
| CN | 110016026 A | 7/2019 | |
| CN | 111689980 A | 9/2020 | |
| CN | 113816969 A | 12/2021 | |
| CN | 114569739 A | 6/2022 | |
| WO | 2014057687 A1 | 4/2014 | |
| WO | 2020063673 A1 | 4/2020 | |
| WO | 2020063676 A1 | 4/2020 | |
| WO | WO-2020063673 A1 * | 4/2020 | ......... A61K 31/4745 |
| WO | WO-2020063676 A1 * | 4/2020 | ......... A61K 31/4738 |
| WO | 2021007435 A1 | 1/2021 | |
| WO | 2021052402 A1 | 3/2021 | |
| WO | 2022078260 A1 | 4/2022 | |
| WO | 2022078279 A1 | 4/2022 | |
| WO | 2022166762 A1 | 8/2022 | |
| WO | 2022236136 A1 | 11/2022 | |

OTHER PUBLICATIONS

PCT/CN2021/121721 International Search Report dated Dec. 30, 2021.
Ogitani, Y., et al., DS-8301a, A Novel HER2-Targeting ADC with a Novel DNA Topoisomerase I Inhibitor, Demonstrates a Promising Antitumor Efficacy with Differentiation from T-DM1 published in Clinical Cancer Research, 22(20), pp. 5097-5108, first published online on Mar. 29, 2016, Am Assoc for Cancer Research, Oct. 15, 2016.
Takeda Chemical Industries, Ltd., U.S. Court of Appeals for the Federal Circuit Decision 06-1329, titled, *Takeda Chemical Industries, Ltd. and Takeda Pharmaceuticals North America, Inc. v. Alphapharm Pty., Ltd. and Genpharm Inc.* Jun. 28, 2007.
Cardillo, Thomas M et al. "Sacituzumab Govitecan (IMMU-132), an Anti-Trop-2/SN-38 Antibody-Drug Conjugate: Characterization and Efficacy in Pancreatic, Gastric, and Other Cancers." Bioconjugate chemistry 26 5 (2015): 919-931.
Notice of Allowance mailed on Apr. 28, 2024 in CN Application No. 202211407530.9.

\* cited by examiner

*Primary Examiner* — Clinton A Brooks
*Assistant Examiner* — George W Kosturko
(74) *Attorney, Agent, or Firm* — Honigman LLP

(57) ABSTRACT

The present application relates to an anti-tumor compound and a preparation method and use thereof, and in particular to a compound or a tautomer, a mesomer, a racemate, an enantiomer or a diastereoisomer thereof, or a mixture thereof, or a pharmaceutically acceptable salt thereof, and a preparation method and use thereof.

10 Claims, 8 Drawing Sheets

Specification includes a Sequence Listing.

SEQUENCE LISTING

```
Sequence total quantity: 40
SEQ ID NO: 1               moltype = AA  length = 11
FEATURE                    Location/Qualifiers
REGION                     1..11
                           note = Trastuzumab LCDR1
source                     1..11
                           mol_type = protein
                           organism = synthetic construct
SEQUENCE: 1
RASQDVNTAV A                                                              11

SEQ ID NO: 2               moltype = AA  length = 11
FEATURE                    Location/Qualifiers
REGION                     1..11
                           note = Pertuzumab LCDR1
source                     1..11
                           mol_type = protein
                           organism = synthetic construct
SEQUENCE: 2
KASQDVSIGV A                                                              11

SEQ ID NO: 3               moltype = AA  length = 11
FEATURE                    Location/Qualifiers
REGION                     1..11
                           note = Sacituzumab LCDR1
source                     1..11
                           mol_type = protein
                           organism = synthetic construct
SEQUENCE: 3
KASQDVSIAV A                                                              11

SEQ ID NO: 4               moltype = AA  length = 17
FEATURE                    Location/Qualifiers
REGION                     1..17
                           note = Zolbetuximab LCDR1
source                     1..17
                           mol_type = protein
                           organism = synthetic construct
SEQUENCE: 4
KSSQSLLNSG NQKNYLT                                                        17

SEQ ID NO: 5               moltype = AA  length = 7
FEATURE                    Location/Qualifiers
REGION                     1..7
                           note = Trastuzumab LCDR2
source                     1..7
                           mol_type = protein
                           organism = synthetic construct
SEQUENCE: 5
SASFLYS                                                                   7

SEQ ID NO: 6               moltype = AA  length = 7
FEATURE                    Location/Qualifiers
REGION                     1..7
                           note = Pertuzumab LCDR2
source                     1..7
                           mol_type = protein
                           organism = synthetic construct
SEQUENCE: 6
SASYRYT                                                                   7

SEQ ID NO: 7               moltype = AA  length = 7
FEATURE                    Location/Qualifiers
REGION                     1..7
                           note = Sacituzumab LCDR2
source                     1..7
                           mol_type = protein
                           organism = synthetic construct
SEQUENCE: 7
SASYRYT                                                                   7

SEQ ID NO: 8               moltype = AA  length = 7
FEATURE                    Location/Qualifiers
REGION                     1..7
                           note = Zolbetuximab LCDR2
source                     1..7
                           mol_type = protein
                           organism = synthetic construct
```

```
                                        -continued

SEQUENCE: 8
WASTRES                                                                      7

SEQ ID NO: 9          moltype = AA  length = 9
FEATURE               Location/Qualifiers
REGION                1..9
                      note = Trastuzumab LCDR3
source                1..9
                      mol_type = protein
                      organism = synthetic construct
SEQUENCE: 9
QQHYTTPPT                                                                    9

SEQ ID NO: 10         moltype = AA  length = 9
FEATURE               Location/Qualifiers
REGION                1..9
                      note = Pertuzumab LCDR3
source                1..9
                      mol_type = protein
                      organism = synthetic construct
SEQUENCE: 10
QQYYIYPYT                                                                    9

SEQ ID NO: 11         moltype = AA  length = 9
FEATURE               Location/Qualifiers
REGION                1..9
                      note = Sacituzumab LCDR3
source                1..9
                      mol_type = protein
                      organism = synthetic construct
SEQUENCE: 11
QQHYITPLT                                                                    9

SEQ ID NO: 12         moltype = AA  length = 9
FEATURE               Location/Qualifiers
REGION                1..9
                      note = Zolbetuximab LCDR3
source                1..9
                      mol_type = protein
                      organism = synthetic construct
SEQUENCE: 12
QNDYSYPFT                                                                    9

SEQ ID NO: 13         moltype = AA  length = 5
FEATURE               Location/Qualifiers
REGION                1..5
                      note = Trastuzumab HCDR1
source                1..5
                      mol_type = protein
                      organism = synthetic construct
SEQUENCE: 13
DTYIH                                                                        5

SEQ ID NO: 14         moltype = AA  length = 5
FEATURE               Location/Qualifiers
REGION                1..5
                      note = Pertuzumab HCDR1
source                1..5
                      mol_type = protein
                      organism = synthetic construct
SEQUENCE: 14
DYTMD                                                                        5

SEQ ID NO: 15         moltype = AA  length = 5
FEATURE               Location/Qualifiers
REGION                1..5
                      note = Sacituzumab HCDR1
source                1..5
                      mol_type = protein
                      organism = synthetic construct
SEQUENCE: 15
NYGMN                                                                        5

SEQ ID NO: 16         moltype = AA  length = 5
FEATURE               Location/Qualifiers
REGION                1..5
                      note = Zolbetuximab HCDR1
```

```
source                          1..5
                                mol_type = protein
                                organism = synthetic construct
SEQUENCE: 16
SYWIN                                                                    5

SEQ ID NO: 17                   moltype = AA  length = 17
FEATURE                         Location/Qualifiers
REGION                          1..17
                                note = Trastuzumab HCDR2
source                          1..17
                                mol_type = protein
                                organism = synthetic construct
SEQUENCE: 17
RIYPTNGYTR YADSVKG                                                      17

SEQ ID NO: 18                   moltype = AA  length = 17
FEATURE                         Location/Qualifiers
REGION                          1..17
                                note = Pertuzumab HCDR2
source                          1..17
                                mol_type = protein
                                organism = synthetic construct
SEQUENCE: 18
DVNPNSGGSI YNQRFKG                                                      17

SEQ ID NO: 19                   moltype = AA  length = 17
FEATURE                         Location/Qualifiers
REGION                          1..17
                                note = Sacituzumab HCDR2
source                          1..17
                                mol_type = protein
                                organism = synthetic construct
SEQUENCE: 19
WINTYTGEPT YTDDFKG                                                      17

SEQ ID NO: 20                   moltype = AA  length = 17
FEATURE                         Location/Qualifiers
REGION                          1..17
                                note = Zolbetuximab HCDR2
source                          1..17
                                mol_type = protein
                                organism = synthetic construct
SEQUENCE: 20
NIYPSDSYTN YNQKFKD                                                      17

SEQ ID NO: 21                   moltype = AA  length = 13
FEATURE                         Location/Qualifiers
REGION                          1..13
                                note = Trastuzumab HCDR3
source                          1..13
                                mol_type = protein
                                organism = synthetic construct
SEQUENCE: 21
SRWGGDGFYA MDY                                                          13

SEQ ID NO: 22                   moltype = AA  length = 12
FEATURE                         Location/Qualifiers
REGION                          1..12
                                note = Pertuzumab HCDR3
source                          1..12
                                mol_type = protein
                                organism = synthetic construct
SEQUENCE: 22
ARNLGPSFYF DY                                                           12

SEQ ID NO: 23                   moltype = AA  length = 14
FEATURE                         Location/Qualifiers
REGION                          1..14
                                note = Sacituzumab HCDR3
source                          1..14
                                mol_type = protein
                                organism = synthetic construct
SEQUENCE: 23
ARGGFGSSYW YFDV                                                         14
```

```
SEQ ID NO: 24           moltype = AA  length = 11
FEATURE                 Location/Qualifiers
REGION                  1..11
                        note = Zolbetuximab HCDR3
source                  1..11
                        mol_type = protein
                        organism = synthetic construct
SEQUENCE: 24
TRSWRGNSFD Y                                                           11

SEQ ID NO: 25           moltype = AA  length = 107
FEATURE                 Location/Qualifiers
REGION                  1..107
                        note = Trastuzumab VL
source                  1..107
                        mol_type = protein
                        organism = synthetic construct
SEQUENCE: 25
DIQMTQSPSS LSASVGDRVT ITCRASQDVN TAVAWYQQKP GKAPKLLIYS ASFLYSGVPS       60
RFSGSRSGTD FTLTISSLQP EDFATYYCQQ HYTTPPTFGQ GTKVEIK                    107

SEQ ID NO: 26           moltype = AA  length = 107
FEATURE                 Location/Qualifiers
REGION                  1..107
                        note = Pertuzumab VL
source                  1..107
                        mol_type = protein
                        organism = synthetic construct
SEQUENCE: 26
DIQMTQSPSS LSASVGDRVT ITCKASQDVS IGVAWYQQKP GKAPKLLIYS ASYRYTGVPS       60
RFSGSGSGTD FTLTISSLQP EDFATYYCQQ YYIYPYTFGQ GTKVEIK                    107

SEQ ID NO: 27           moltype = AA  length = 76
FEATURE                 Location/Qualifiers
REGION                  1..76
                        note = Sacituzumab VL
source                  1..76
                        mol_type = protein
                        organism = synthetic construct
SEQUENCE: 27
AVAWYQQKPG KAPKLLIYSA SYRYTGVPDR FSGSGSGTDF TLTISSLQPE DFAVYYCQQH       60
YITPLTFGAG TKVEIK                                                      76

SEQ ID NO: 28           moltype = AA  length = 113
FEATURE                 Location/Qualifiers
REGION                  1..113
                        note = Zolbetuximab VL
source                  1..113
                        mol_type = protein
                        organism = synthetic construct
SEQUENCE: 28
DIVMTQSPSS LTVTAGEKVT MSCKSSQSLL NSGNQKNYLT WYQQKPGQPP KLLIYWASTR       60
ESGVPDRFTG SGSGTDFTLT ISSVQAEDLA VYYCQNDYSY PFTFGSGTKL EIK             113

SEQ ID NO: 29           moltype = AA  length = 120
FEATURE                 Location/Qualifiers
REGION                  1..120
                        note = Trastuzumab VH
source                  1..120
                        mol_type = protein
                        organism = synthetic construct
SEQUENCE: 29
EVQLVESGGG LVQPGGSLRL SCAASGFNIK DTYIHWVRQA PGKGLEWVAR IYPTNGYTRY       60
ADSVKGRFTI SADTSKNTAY LQMNSLRAED TAVYYCSRWG GDGFYAMDYW GQGTLVTVSS     120

SEQ ID NO: 30           moltype = AA  length = 119
FEATURE                 Location/Qualifiers
REGION                  1..119
                        note = Pertuzumab VH
source                  1..119
                        mol_type = protein
                        organism = synthetic construct
SEQUENCE: 30
EVQLVESGGG LVQPGGSLRL SCAASGFTFT DYTMDWVRQA PGKGLEWVAD VNPNSGGSIY       60
NQRFKGRFTL SVDRSKNTLY LQMNSLRAED TAVYYCARNL GPSFYFDYWG QGTLVTVSS      119

SEQ ID NO: 31           moltype = AA  length = 89
FEATURE                 Location/Qualifiers
```

```
REGION                  1..89
                        note = Sacituzumab VH
source                  1..89
                        mol_type = protein
                        organism = synthetic construct
SEQUENCE: 31
GMNWVKQAPG QGLKWMGWIN TYTGEPTYTD DFKGRFAFSL DTSVSTAYLQ ISSLKADDTA    60
VYFCARGGFG SSYWYFDVWG QGSLVTVSS                                      89

SEQ ID NO: 32           moltype = AA  length = 118
FEATURE                 Location/Qualifiers
REGION                  1..118
                        note = Zolbetuximab VH
source                  1..118
                        mol_type = protein
                        organism = synthetic construct
SEQUENCE: 32
QVQLQQPGAE LVRPGASVKL SCKASGYTFT SYWINWVKQR PGQGLEWIGN IYPSDSYTNY    60
NQKFKDKATL TVDKSSSTAY MQLSSPTSED SAVYYCTRSW RGNSFDYWGQ GTTLTVSS     118

SEQ ID NO: 33           moltype = AA  length = 214
FEATURE                 Location/Qualifiers
REGION                  1..214
                        note = Trastuzumab light chain
source                  1..214
                        mol_type = protein
                        organism = synthetic construct
SEQUENCE: 33
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 34           moltype = AA  length = 214
FEATURE                 Location/Qualifiers
REGION                  1..214
                        note = Pertuzumab light chain
source                  1..214
                        mol_type = protein
                        organism = synthetic construct
SEQUENCE: 34
DIQMTQSPSS LSASVGDRVT ITCKASQDVS IGVAWYQQKP GKAPKLLIYS ASYRYTGVPS    60
RFSGSGSGTD FTLTISSLQP EDFATYYCQQ YYIYPYTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 35           moltype = AA  length = 214
FEATURE                 Location/Qualifiers
REGION                  1..214
                        note = Sacituzumab light chain
source                  1..214
                        mol_type = protein
                        organism = synthetic construct
SEQUENCE: 35
DIQLTQSPSS LSASVGDRVS ITCKASQDVS IAVAWYQQKP GKAPKLLIYS ASYRYTGVPD    60
RFSGSGSGTD FTLTISSLQP EDFAVYYCQQ HYITPLTFGA GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 36           moltype = AA  length = 220
FEATURE                 Location/Qualifiers
REGION                  1..220
                        note = Zolbetuximab light chain
source                  1..220
                        mol_type = protein
                        organism = synthetic construct
SEQUENCE: 36
DIVMTQSPSS LTVTAGEKVT MSCKSSQSLL NSGNQKNYLT WYQQKPGQPP KLLIYWASTR    60
ESGVPDRFTG SGSGTDFTLT ISSVQAEDLA VYYCQNDYSY PFTFGSGTKL EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                         220

SEQ ID NO: 37           moltype = AA  length = 449
FEATURE                 Location/Qualifiers
REGION                  1..449
                        note = Trastuzumab heavy chain
source                  1..449
                        mol_type = protein
                        organism = synthetic construct
```

```
SEQUENCE: 37
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPG                                    449

SEQ ID NO: 38           moltype = AA  length = 448
FEATURE                 Location/Qualifiers
REGION                  1..448
                        note = Pertuzumab heavy chain
source                  1..448
                        mol_type = protein
                        organism = synthetic construct
SEQUENCE: 38
EVQLVESGGG LVQPGGSLRL SCAASGFTFT DYTMDWVRQA PGKGLEWVAD VNPNSGGSIY    60
NQRFKGRFTL SVDRSKNTLY LQMNSLRAED TAVYYCARNL GPSFYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 39           moltype = AA  length = 451
FEATURE                 Location/Qualifiers
REGION                  1..451
                        note = Sacituzumab heavy chain
source                  1..451
                        mol_type = protein
                        organism = synthetic construct
SEQUENCE: 39
QVQLQQSGSE LKKPGASVKV SCKASGYTFT NYGMNWVKQA PGQGLKWMGW INTYTGEPTY    60
TDDFKGRFAF SLDTSVSTAY LQISSLKADD TAVYFCARGG FGSSYWYFDV WGQGSLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                 451

SEQ ID NO: 40           moltype = AA  length = 448
FEATURE                 Location/Qualifiers
REGION                  1..448
                        note = Zolbetuximab heavy chain
source                  1..448
                        mol_type = protein
                        organism = synthetic construct
SEQUENCE: 40
QVQLQQPGAE LVRPGASVKL SCKASGYTFT SYWINWVKQR PGQGLEWIGN IYPSDSYTNY    60
NQKFKDKATL TVDKSSSTAY MQLSSPTSED SAVYYCTRSW RGNSFDYWGQ GTTLTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSREEMT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                     448
```

ANTI-TUMOR COMPOUND AND PREPARATION METHOD AND USE THEREOF

CROSS-REFERENCE TO RELATED APPLICATIONS

This application is a Continuation of U.S. patent application Ser. No. 18/187,935, which is a Continuation of U.S. patent application Ser. No. 17/825,090, now issued as U.S. patent Ser. No. 11/685,742, which is a Continuation of and claims priority under 35 U.S.C. § 111 to Patent Cooperation Treaty application PCT/CN2021/121721, filed Sep. 29, 2021, which claims the benefit of Chinese Patent Application No. 202011061580.7, filed Sep. 30, 2020, priority is claimed to all of these applications and the disclosures of these prior applications are considered part of the disclosure of this application and to the extent allowed the entire contents of the aforementioned applications are incorporated herein.

SEQUENCE LISTING

This application incorporates by reference in its entirety the Sequence Listing entitled "262790-525522 Sequence-Listing.xml." is 54,027 bytes in size and was created on Mar. 14, 2023, and filed electronically herewith.

TECHNICAL FIELD

The present application relates to the field of biomedicine, and in particular to an anti-tumor compound and a preparation method and use thereof.

BACKGROUND OF THE INVENTION

Currently, small molecules with cytotoxicity for antibody-drug conjugates (ADCs) can be camptothecin derivatives, which produce an anti-tumor effect by inhibiting topoisomerase I. Camptothecin derivatives can be used in ADCs. There is still a need to develop camptothecin derivatives and ADC drugs with better therapeutic effect and/or safety.

SUMMARY OF THE INVENTION

The present application provides a compound or a tautomer, a mesomer, a racemate, an enantiomer or a diastereoisomer thereof, or a mixture thereof, or a pharmaceutically acceptable salt thereof, which may have one or more effects selected from the group consisting of: (1) having inhibitory activity against in vitro proliferation of tumor cells; (2) having targeting inhibition; (3) having plasma stability; (4) having in vivo tumor inhibiting effect; (5) having bystander effect; (6) having capacity in inhibiting transport via a transporter; (7) having in vivo tumor targeting capability; and (8) having good in vivo safety.

In one aspect, the present application provides a compound or a tautomer, a mesomer, a racemate, an enantiomer or a diastereoisomer thereof, or a mixture thereof, or a pharmaceutically acceptable salt thereof, wherein the compound comprises a structure shown as formula (II-A):

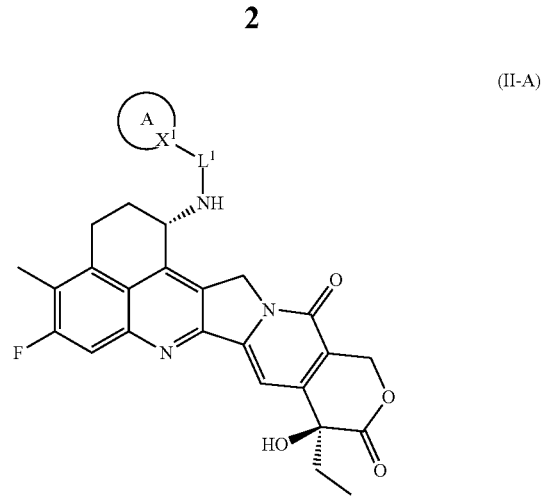

(II-A)

wherein, $X^1$ is saturated C, and $X^1$ is substituted with $R''$;
ring A is selected from the group consisting of: 3-10 membered saturated or partially unsaturated heterocyclyl and 3-10 membered saturated or partially unsaturated carbocyclyl, wherein ring A is substituted with 0 or at least 1 substituent $R^{1a}$;
when ring A is 3-10 membered saturated or partially unsaturated carbocyclyl, ring A is substituted with p $L^2$, and $L^2$ is not $R''$;
or, when ring A is 3-10 membered saturated or partially unsaturated heterocyclyl, ring A is substituted with p $L^2$;
$L^2$ is $-R^2-L^3-$, and $R^2$ is used for direct or indirect linking of a ligand;
$L^3$ is $-(C(R^{3a})(R^{3b}))_m-$, wherein when $L^3$ comprises a methylene unit, 0 or at least 1 methylene unit of $L^3$ is independently replaced by $-N(R^4)C(O)-$, $-C(O)N(R^4)-$, $-C(O)-$, $-OC(O)-$, $-C(O)O-$, $-NR^4-$, $-O-$, $-S-$, $-SO-$, $-SO_2-$, $-P(R^4)-$, $-P(=O)(R^4)-$, $-N(R^4)SO_2-$, $-SO_2N(R^4)-$, $-C(=S)-$, $-C(=NR^4)-$, $-N=N-$, $-C=N-$, $-N=C-$ or $-C(=N_2)-$;
$R^2$ is selected from the group consisting of: $-O-$, $-(R^{2a})N-$, $-S-$ and $-P(=O)(R^{2a})-$;
$L^1$ is $-(C(R^{5a})(R^{5b}))_n-$, wherein when $L^1$ comprises a methylene unit, 0 or at least 1 methylene unit of $L^1$ is independently replaced by $-N(R^6)C(O)-$, $-C(O)N(R^6)-$, $-C(O)-$, $-OC(O)-$, $-C(O)O-$, $-NR^6-$, $-O-$, $-S-$, $-SO-$, $-SO_2-$, $-P(R^6)-$, $-P(=O)(R^6)-$, $-N(R^6)SO_2-$, $-SO_2N(R^6)-$, $-C(=S)-$, $-C(=NR^6)-$, $-N=N-$, $-C=N-$, $-N=C-$ or $-C(=N_2)-$;
wherein each $R^{1a}$, each $R^{2a}$, each $R^{3a}$, each $R^{3b}$, each $R^4$, each $R^{5a}$, each $R^{5b}$, each $R^6$ and each $R''$ are each independently hydrogen, protium, deuterium, tritium, halogen, $-NO_2$, $-CN$, $-OR$, $-SR$, $-N(R^a)(R^b)$, $-C(O)R$, $-CO_2R$, $-C(O)C(O)R$, $-C(O)CH_2C(O)R$, $-S(O)R$, $-S(O)_2R$, $-C(O)N(R^a)(R^b)$, $-SO_2N(R^a)(R^b)$, $-OC(O)R$, $-N(R)SO_2R$, or a $C_{1-6}$ aliphatic group optionally substituted with R;
wherein each R, each $R^a$ and each $R^b$ are each independently hydrogen, protium, deuterium, tritium, halogen, $-NO_2$, $-CN$, $-OH$, $-SH$, $-NH_2$, $-C(O)H$, $-CO_2H$, $-C(O)C(O)H$, $-C(O)CH_2C(O)H$, $-S(O)H$, $-S(O)_2H$, $-C(O)NH_2$, $-SO_2NH_2$, $-OC(O)H$, $-N(H)SO_2H$ or a $C_{1-6}$ aliphatic group;
m and n are each independently selected from the group consisting of integers ≥0, and p is an integer ≥1.

In one aspect, the present application provides a compound of general formula (II-Ex) or a tautomer, a mesomer, a racemate, an enantiomer or a diastereoisomer thereof, or a mixture thereof, or a pharmaceutically acceptable salt thereof,

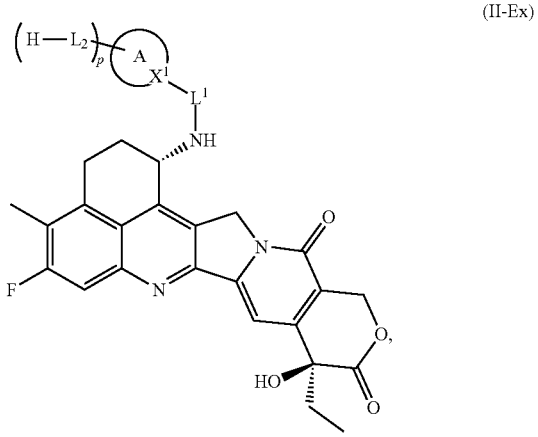

(II-Ex)

wherein, $X^1$ is saturated C, and $X^1$ is substituted with $R''$;
ring A is selected from the group consisting of: 3-10 membered saturated or partially unsaturated heterocyclyl and 3-10 membered saturated or partially unsaturated carbocyclyl, wherein ring A is substituted with 0 or at least 1 substituent $R^{1a}$;
when ring A is 3-10 membered saturated or partially unsaturated carbocyclyl, ring A is substituted with p $L^2$, and $L^2$ is not $R''$;
or, when ring A is 3-10 membered saturated or partially unsaturated heterocyclyl, ring A is substituted with p $L^2$;
$L^2$ is $-R^2-L^3-$, and $R^2$ is used for direct or indirect linking of a ligand;
$L^3$ is $-(C(R^{3a})(R^{3b}))_m-$, wherein when $L^3$ comprises a methylene unit, 0 or at least 1 methylene unit of $L^3$ is independently replaced by $-N(R^4)C(O)-$, $-C(O)N(R^4)-$, $-C(O)-$, $-OC(O)-$, $-C(O)O-$, $-NR^4-$, $-O-$, $-S-$, $-SO-$, $-SO_2-$, $-P(R^4)-$, $-P(=O)(R^4)-$, $-N(R^4)SO_2-$, $-SO_2N(R^4)-$, $-C(=S)-$, $-C(=NR^4)-$, $-N=N-$, $-C=N-$, $-N=C-$ or $-C(=N_2)-$;
$R^2$ is selected from the group consisting of: $-O-$, $-(R^{2a})N-$, $-S-$ and $-P(=O)(R^{2a})-$;
$L^1$ is $-(C(R^{5a})(R^{5b}))_n-$, wherein when $L^1$ comprises a methylene unit, 0 or at least 1 methylene unit of $L^1$ is independently replaced by $-N(R^6)C(O)-$, $-C(O)N(R^6)-$, $-C(O)-$, $-OC(O)-$, $-C(O)O-$, $-NR^6-$, $-O-$, $-S-$, $-SO-$, $-SO_2-$, $-P(R^6)-$, $-P(=O)(R^6)-$, $-N(R^6)SO_2-$, $-SO_2N(R^6)-$, $-C(=S)-$, $-C(=NR^6)-$, $-N=N-$, $-C=N-$, $-N=C-$ or $-C(=N_2)-$;
wherein each $R^{1a}$, each $R^{2a}$, each $R^{3a}$, each $R^{3b}$, each $R^4$, each $R^{5a}$, each $R^{5b}$, each $R^6$ and each $R''$ are each independently hydrogen, protium, deuterium, tritium, halogen, $-NO_2$, $-CN$, $-OR$, $-SR$, $-N(R^a)(R^b)$, $-C(O)R$, $-CO_2R$, $-C(O)C(O)R$, $-C(O)CH_2C(O)R$, $-S(O)R$, $-S(O)_2R$, $-C(O)N(R^a)(R^b)$, $-SO_2N(R^a)(R^b)$, $-OC(O)R$, $-N(R)SO_2R$, or a $C_{1-6}$ aliphatic group optionally substituted with R;
wherein each R, each $R^a$ and each $R^b$ are each independently hydrogen, protium, deuterium, tritium, halogen, $-NO_2$, $-CN$, $-OH$, $-SH$, $-NH_2$, $-C(O)H$, $-CO_2H$, $-C(O)C(O)H$, $-C(O)CH_2C(O)H$, $-S(O)H$, $-S(O)_2H$, $-C(O)NH_2$, $-SO_2NH_2$, $-OC(O)H$, $-N(H)SO_2H$ or a $C_{1-6}$ aliphatic group;
m and n are each independently selected from the group consisting of integers ≥0, and p is an integer ≥1.

In one aspect, the present application provides a compound or a tautomer, a mesomer, a racemate, an enantiomer or a diastereoisomer thereof, or a mixture thereof, or a pharmaceutically acceptable salt thereof, wherein the compound comprises a structure shown as formula (II-$C_x$):

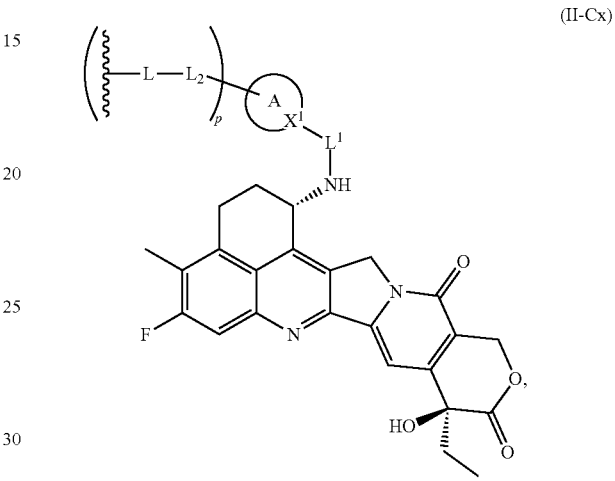

(II-Cx)

wherein, L is $-L_a-L_b-L_c-$;
$L_a-$ is selected from the group consisting of:

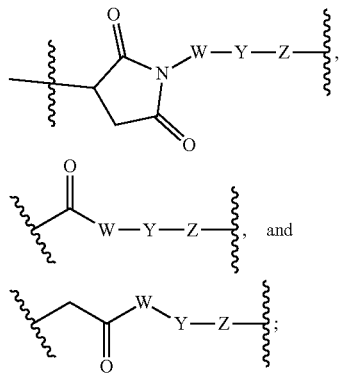

wherein W is $-(C(R^{wa})(R^{wb}))_{wn}-$, Y is $-(OCH_2-CH_2)_{yn}-O_{yp}-$, and Z is $-(C(R^{za})(R^{zb}))_{zn}-$;
wherein wn is selected from the group consisting of integers ≥0, and
0 or at least 1 methylene unit of W is independently replaced by -Cyr-, $-N(R^{wx})C(O)-$, $-C(O)N(R^{wx})-$, $-C(O)-$, $-OC(O)-$, $-C(O)O-$, $-NR^{wx}-$, $-O-$, $-S-$, $-SO-$, $-SO_2-$, $-P(R^{wx})-$, $-P(=O)(R^{wx})-$, $-N(R^{wx})SO_2-$, $-SO_2N(R^{wx})-$, $-C(=S)-$, $-C(=NR^{wx})-$, $-N=N-$, $-C=N-$, $-N=C-$ or $-C(=N_2)-$;
wherein yn is selected from the group consisting of integers ≥0, and yp is 0 or 1;
wherein zn is selected from the group consisting of integers ≥0, and 0 or at least 1 methylene unit of Z is independently replaced by -Cyr-, —N(R$^{zx}$)C(O)—, —C(O)N(R$^{zx}$)—, —C(O)—, —OC(O)—, —C(O)O—, —NR$^{zx}$—, —O—, —S—, —SO—, —SO$_2$—, —P(R$^{zx}$)—, —P(=O)(R$^{zx}$)—, —N(R$^{zx}$)SO$_2$—, —SO$_2$N(R$^{zx}$)—, —C(=S)—, —C(=NR$^{zx}$)—, —N=N—, —C=N—, —N=C— or —C(=N$_2$)—;

Cyr- is selected from the group consisting of: 6-10 membered arylene, 5-8 membered heteroarylene, 3-10 membered heterocyclylene and 3-10 membered saturated or partially unsaturated carbocyclylene, wherein -Cyr- is unsubstituted or independently substituted with at least 1 substituent R$^{cx}$;

wherein each R$^{wa}$, each R$^{wb}$, each R$^{za}$, each R$^{zb}$, each R$^{wx}$, each R$^{zx}$ and each R$^{cx}$ are each independently hydrogen, protium, deuterium, tritium, halogen, —NO$_2$, —CN, —OR$^r$, —SR$^r$, —N(R$^{ra}$)(R$^{rb}$), —C(O)R$^r$, —CO$_2$R, —C(O)C(O)R$^r$, —C(O)CH$_2$C(O)R$^r$, —S(O)R$^r$, —S(O)$_2$R$^r$, —C(O)N(R$^{ra}$)(R$^{rb}$), —SO$_2$N(R$^{ra}$)(R$^{rb}$), —OC(O)R$^r$, —N(R)SO$_2$R, or a C$_{1-6}$ aliphatic group optionally substituted with R$^r$;

wherein each R$^r$, each R$^{ra}$ and each R$^{rb}$ are each independently hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group;

L$_b$- represents a peptide residue consisting of 2 to 7 amino acids;

L$_c$- is selected from the group consisting of:

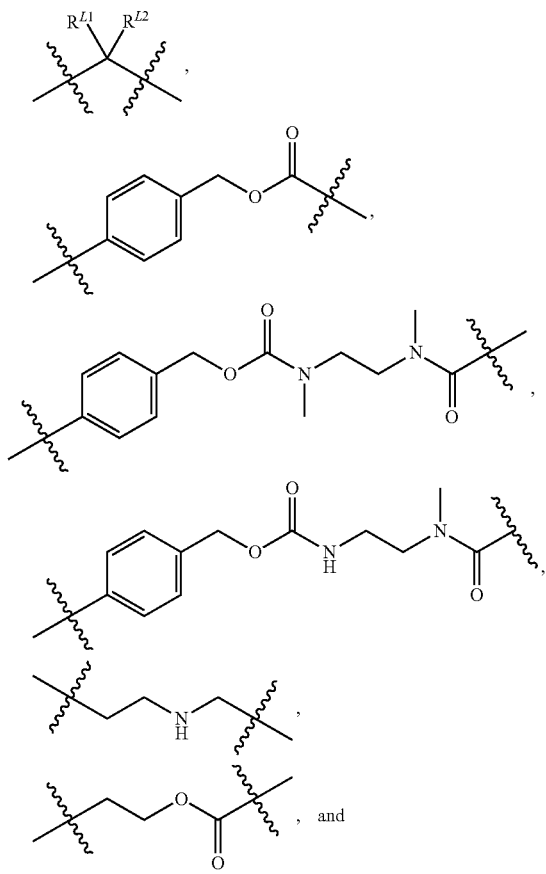

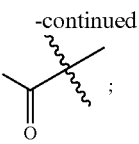

wherein R$^{L1}$ and R$^{L2}$ are each independently selected from the group consisting of: hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H and a C$_{1-6}$ aliphatic group;

wherein, X$^1$ is saturated C, and X$^1$ is substituted with R″;

ring A is selected from the group consisting of: 3-10 membered saturated or partially unsaturated heterocyclyl and 3-10 membered saturated or partially unsaturated carbocyclyl, wherein ring A is substituted with 0 or at least 1 substituent R$^{1a}$;

when ring A is 3-10 membered saturated or partially unsaturated carbocyclyl, ring A is substituted with p L$^2$, and L$^2$ is not R″;

or, when ring A is 3-10 membered saturated or partially unsaturated heterocyclyl, ring A is substituted with p L$^2$;

L$^2$ is —R$^2$-L$^3$-, and R$^2$ is used for direct or indirect linking of a ligand;

L$^3$ is —(C(R$^{3a}$)(R$^{3b}$))$_m$—, wherein when L$^3$ comprises a methylene unit, 0 or at least 1 methylene unit of L$^3$ is independently replaced by —N(R$^4$)C(O)—, —C(O)N(R$^4$)—, —C(O)—, —OC(O)—, —C(O)O—, —NR$^4$—, —O—, —S—, —SO—, —SO$_2$—, —P(R$^4$)—, —P(=O)(R$^4$)—, —N(R$^4$)SO$_2$—, —SO$_2$N(R$^4$)—, —C(=S)—, —C(=NR$^4$)—, —N=N—, —C=N—, —N=C— or —C(=N$_2$)—;

R$^2$ is selected from the group consisting of: —O—, —(R$^{2a}$)N—, —S— and —P(=O)(R$^{2a}$)—;

L$^1$ is —(C(R$^{5a}$)(R$^{5b}$))$_n$—, wherein when L$^1$ comprises a methylene unit, 0 or at least 1 methylene unit of L$^1$ is independently replaced by —N(R$^6$)C(O)—, —C(O)N(R$^6$)—, —C(O)—, —OC(O)—, —C(O)O—, —NR$^6$—, —O—, —S—, —SO—, —SO$_2$—, —P(R$^6$)—, —P(=O)(R$^6$)—, —N(R$^6$)SO$_2$—, —SO$_2$N(R$^6$)—, —C(=S)—, —C(=NR$^6$)—, —N=N—, —C=N—, —N=C— or —C(=N$_2$)—;

wherein each R$^{1a}$, each R$^{2a}$, each R$^{3a}$, each R$^{3b}$, each R$^4$, each R$^{5a}$, each R$^{5b}$, each R$^6$ and each R″ are each independently hydrogen, protium, deuterium, tritium, halogen, —NO$_2$, —CN, —OR, —SR, —N(R$^a$)(R$^b$), —C(O)R, —CO$_2$R, —C(O)C(O)R, —C(O)CH$_2$C(O)R, —S(O)R, —S(O)$_2$R, —C(O)N(R$^a$)(R$^b$), —SO$_2$N(R$^a$)(R$^b$), —OC(O)R, —N(R)SO$_2$R, or a C$_{1-6}$ aliphatic group optionally substituted with R;

wherein each R, each R$^a$ and each R$^b$ are each independently hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group;

m and n are each independently selected from the group consisting of integers ≥0, and p is an integer ≥1.

In one aspect, the present application provides a compound or a tautomer, a mesomer, a racemate, an enantiomer or a diastereoisomer thereof, or a mixture thereof, or a pharmaceutically acceptable salt thereof, wherein the compound comprises a structure shown as formula (II-Dx):

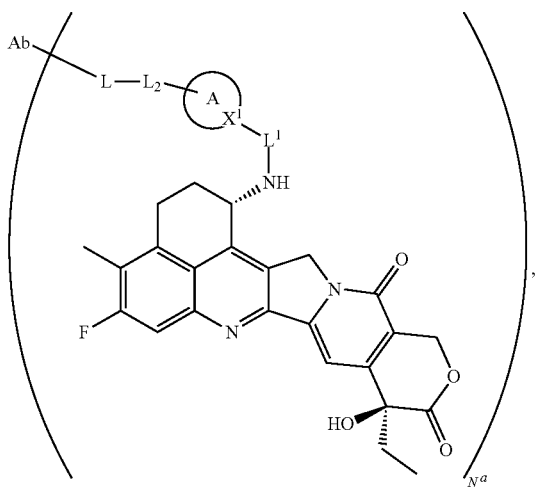

(II-Dx)

wherein, Ab is a ligand, and an average connection number Na is an integer or a decimal from 1 to 10;
L is -$L_a$-$L_b$-$L_c$-;
$L_a$- is selected from the group consisting of:

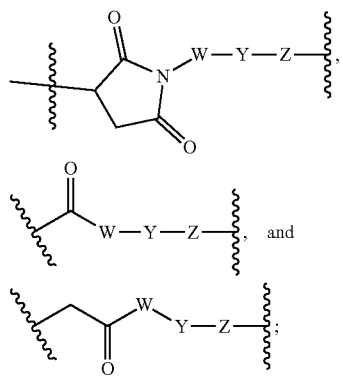

wherein W is —(C($R^{wa}$)($R^{wb}$))$_{wn}$—, Y is —(OCH$_2$—CH$_2$)$_{yn}$—O$_{yp}$—, and Z is —(C($R^{za}$)($R^{zb}$))$_{zn}$—;
wherein wn is selected from the group consisting of integers ≥0, and
0 or at least 1 methylene unit of W is independently replaced by -Cyr-, —N($R^{wx}$)C(O)—, —C(O)N($R^{wx}$)—, —C(O)—, —OC(O)—, —C(O)O—, —N$R^{wx}$—, —O—, —S—, —SO—, —SO$_2$—, —P($R^{wx}$)—, —P(=O)($R^{wx}$)—, —N($R^{wx}$)SO$_2$—, —SO$_2$N($R^{wx}$)—, —C(=S)—, —C(=N$R^{wx}$)—, —N=N—, —C=N—, —N=C— or —C(=N$_2$)—;
wherein yn is selected from the group consisting of integers ≥0, and yp is 0 or 1;
wherein zn is selected from the group consisting of integers ≥0, and
0 or at least 1 methylene unit of Z is independently replaced by -Cyr-, —N($R^{zx}$)C(O)—, —C(O)N($R^{zx}$)—, —C(O)—, —OC(O)—, —C(O)O—, —N$R^{zx}$—, —O—, —S—, —SO—, —SO$_2$—, —P($R^{zx}$)—, —P(=O)($R^{zx}$)—, —N($R^{zx}$)SO$_2$—, —SO$_2$N($R^{zx}$)—, —C(=S)—, —C(=N$R^{zx}$)—, —N=N—, —C=N—, —N=C— or —C(=N$_2$)—;

-Cyr- is selected from the group consisting of: 6-10 membered arylene, 5-8 membered heteroarylene, 3-10 membered heterocyclylene and 3-10 membered saturated or partially unsaturated carbocyclylene, wherein -Cyr- is unsubstituted or independently substituted with at least 1 substituent $R^{cx}$;

wherein each $R^{wa}$, each $R^{wb}$, each $R^{za}$, each $R^{zb}$, each $R^{wx}$, each $R^{zx}$ and each $R^{cx}$ are each independently hydrogen, protium, deuterium, tritium, halogen, —NO$_2$, —CN, —O$R^r$, —S$R^r$, —N($R^{ra}$)($R^{rb}$), —C(O)$R^r$, —CO$_2$R, —C(O)C(O)$R^r$, —C(O)CH$_2$C(O)$R^r$, —S(O)$R^r$, —S(O)$_2R^r$, —C(O)N($R^{ra}$)($R^{rb}$), —SO$_2$N($R^{ra}$)($R^{rb}$), —OC(O)$R^r$, —N(R)SO$_2$R, or a C$_{1-6}$ aliphatic group optionally substituted with $R^r$;

wherein each $R^r$, each $R^{ra}$ and each $R^{rb}$ are each independently hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group;

$L_b$- represents a peptide residue consisting of 2 to 7 amino acids;

$L_c$- is selected from the group consisting of:

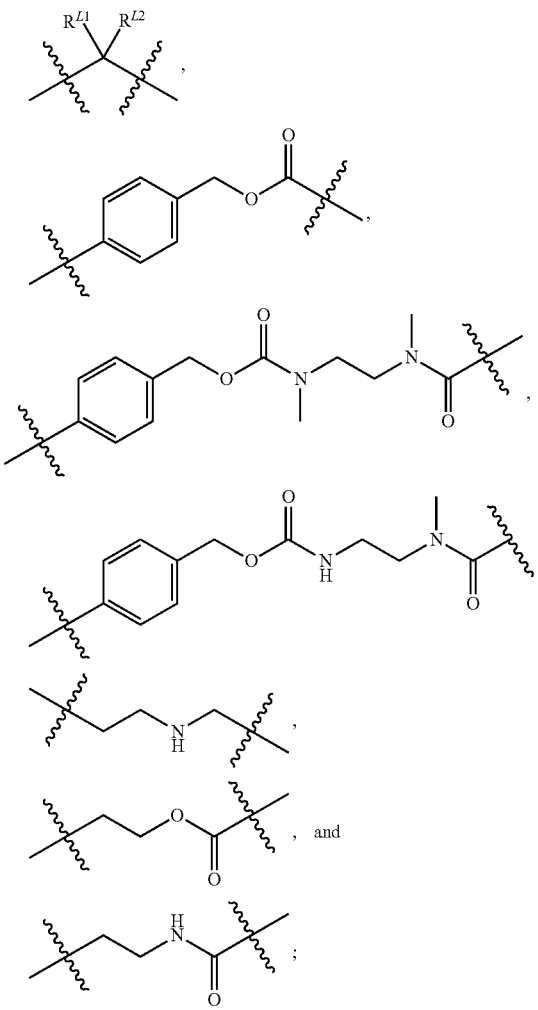

wherein $R^{L1}$ and $R^{L2}$ are each independently selected from the group consisting of: hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H and a C$_{1-6}$ aliphatic group;

wherein, $X^1$ is saturated C, and $X^1$ is substituted with $R^n$;

ring A is selected from the group consisting of: 3-10 membered saturated or partially unsaturated heterocyclyl and 3-10 membered saturated or partially unsaturated carbocyclyl, wherein ring A is substituted with 0 or at least 1 substituent $R^{1a}$;

when ring A is 3-10 membered saturated or partially unsaturated carbocyclyl, ring A is substituted with p $L^2$, and $L^2$ is not $R^n$;

or, when ring A is 3-10 membered saturated or partially unsaturated heterocyclyl, ring A is substituted with p $L^2$;

$L^2$ is —$R^2$-$L^3$-, and $R^2$ is used for direct or indirect linking of a ligand;

$L^3$ is —(C($R^{3a}$)($R^{3b}$))$_m$—, wherein when $L^3$ comprises a methylene unit, 0 or at least 1 methylene unit of $L^3$ is independently replaced by —N(R$^4$)C(O)—, —C(O)N(R$^4$)—, —C(O)—, —OC(O)—, —C(O)O—, —NR$^4$—, —O—, —S—, —SO—, —SO$_2$—, —P(R$^4$)—, —P(=O)(R$^4$)—, —N(R$^4$)SO$_2$—, —SO$_2$N(R$^4$)—, —C(=S)—, —C(=NR$^4$)—, —N=N—, —C=N—, —N=C— or —C(=N$_2$)—;

$R^2$ is selected from the group consisting of: —O—, —(R$^{2a}$)N—, —S— and —P(=O)(R$^{2a}$)—;

$L^1$ is —(C($R^{5a}$)($R^{5b}$))$_n$—, wherein when $L^1$ comprises a methylene unit, 0 or at least 1 methylene unit of $L^1$ is independently replaced by —N(R$^6$)C(O)—, —C(O)N(R$^6$)—, —C(O)—, —OC(O)—, —C(O)O—, —NR$^6$—, —O—, —S—, —SO—, —SO$_2$—, —P(R$^6$)—, —P(=O)(R$^6$)—, —N(R$^6$)SO$_2$—, —SO$_2$N(R$^6$)—, —C(=S)—, —C(=NR$^6$)—, —N=N—, —C=N—, —N=C— or —C(=N$_2$)—;

wherein each $R^{1a}$, each $R^{2a}$, each $R^{3a}$, each $R^{3b}$, each $R^4$, each $R^{5a}$, each $R^{5b}$, each $R^6$ and each $R^n$ are each independently hydrogen, protium, deuterium, tritium, halogen, —NO$_2$, —CN, —OR, —SR, —N(R$^a$)(R$^b$), —C(O)R, —CO$_2$R, —C(O)C(O)R, —C(O)CH$_2$C(O)R, —S(O)R, —S(O)$_2$R, —C(O)N(R$^a$)(R$^b$), —SO$_2$N(R$^a$)(R$^b$), —OC(O)R, —N(R)SO$_2$R, or a C$_{1-6}$ aliphatic group optionally substituted with R;

wherein each R, each R$^a$ and each R$^b$ are each independently hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group;

m and n are each independently selected from the group consisting of integers ≥0, and p is an integer ≥1.

In one aspect, the present application provides a compound of general formula (II-F$_x$) or a tautomer, a mesomer, a racemate, an enantiomer or a diastereoisomer thereof, or a mixture thereof, or a pharmaceutically acceptable salt thereof,

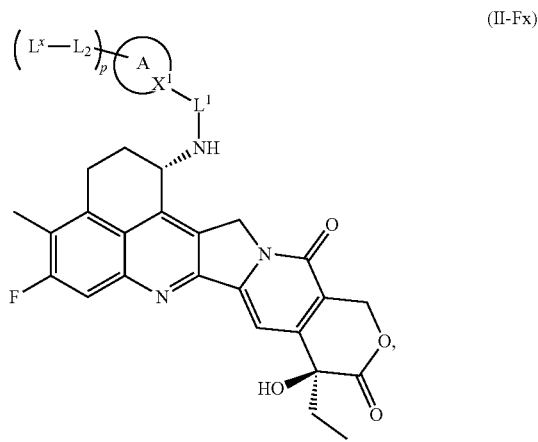

(II-Fx)

wherein, $L^x$ is $L_{ax}$-$L_b$-$L_c$-;

$L_{ax}$- is selected from the group consisting of:

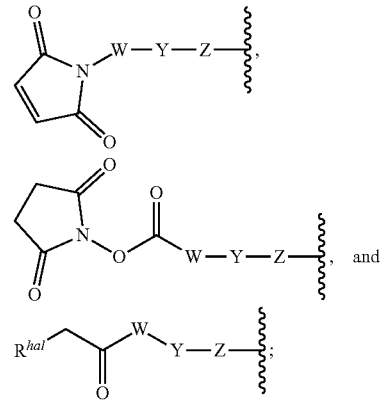

wherein $R^{hal}$ is iodine or bromine;

wherein W is —(C(R$^{wa}$)(R$^{wb}$))$_{wn}$—, Y is —(OCH$_2$CH$_2$)$_{yn}$—O$_{yp}$—, and Z is —(C(R$^{za}$)(R$^{zb}$))$_{zn}$—;

wherein wn is selected from the group consisting of integers ≥0, and 0 or at least 1 methylene unit of W is independently replaced by -Cyr-, —N(R$^{wx}$)C(O)—, —C(O)N(R$^{wx}$)—, —C(O)—, —OC(O)—, —C(O)O—, —NR$^{wx}$—, —O—, —S—, —SO—, —SO$_2$—, —P(R$^{wx}$)—, —P(=O)(R$^{wx}$)—, —N(R$^{wx}$)SO$_2$—, —SO$_2$N(R$^{wx}$)—, —C(=S)—, —C(=NR$^{wx}$)—, —N=N—, —C=N—, —N=C— or —C(=N$_2$)—;

wherein yn is selected from the group consisting of integers ≥0, and yp is 0 or 1;

wherein zn is selected from the group consisting of integers ≥0, and or at least 1 methylene unit of Z is independently replaced by -Cyr-, —N(R$^{zx}$)C(O)—, —C(O)N(R$^{zx}$)—, —C(O)—, —OC(O)—, —C(O)O—, —NR$^{zx}$—, —O—, —S—, —SO—, —SO$_2$—, —P(R$^{zx}$)—, —P(=O)(R$^{zx}$)—, —N(R$^{zx}$)SO$_2$—, —SO$_2$N(R$^{zx}$)—, —C(=S)—, —C(=NR$^{zx}$)—, —N=N—, —C=N—, —N=C— or —C(=N$_2$)—;

Cyr- is selected from the group consisting of: 6-10 membered arylene, 5-8 membered heteroarylene, 3-10 membered heterocyclylene and 3-10 membered saturated or partially unsaturated carbocyclylene, wherein -Cyr- is unsubstituted or independently substituted with at least 1 substituent $R^{cx}$;

wherein each $R^{wa}$, each $R^{wb}$, each $R^{za}$, each $R^{zb}$, each $R^{wx}$, each $R^{zx}$ and each $R^{cx}$ are each independently hydrogen, protium, deuterium, tritium, halogen, —NO$_2$, —CN, —OR$^r$, —SR$^r$, —N(R$^{ra}$)(R$^{rb}$), —C(O)R$^r$, —CO$_2$R, —C(O)C(O)R$^r$, —C(O)CH$_2$C(O)R$^r$, —S(O)R$^r$, —S(O)$_2$R$^r$, —C(O)N(R$^{ra}$)(R$^{rb}$), —SO$_2$N(R$^{ra}$)(R$^{rb}$), —OC(O)R$^r$, —N(R)SO$_2$R, or a C$_{1-6}$ aliphatic group optionally substituted with R$^r$;

wherein each R$^r$, each R$^{ra}$ and each R$^{rb}$ are each independently hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group;

$L_b$- represents a peptide residue consisting of 2 to 7 amino acids;

$L_c$- is selected from the group consisting of:

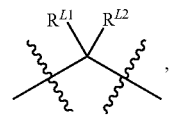

,

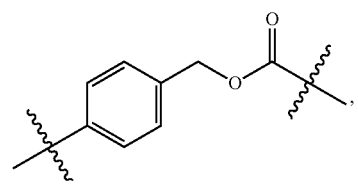

,

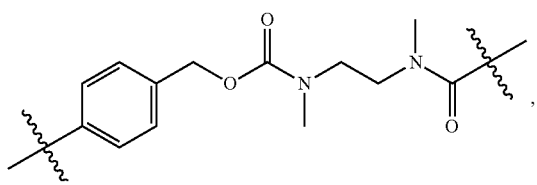

,

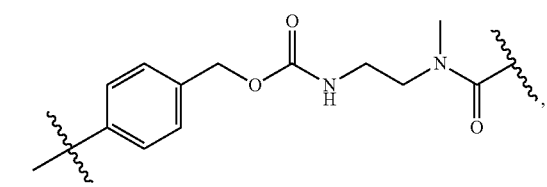

,

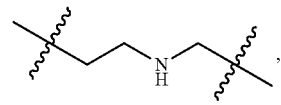

,

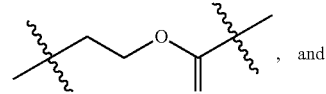

, and

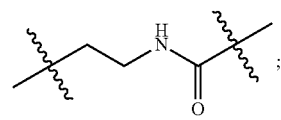

;

wherein $R^{L1}$ and $R^{L2}$ are each independently selected from the group consisting of: hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H and a C$_{1-6}$ aliphatic group;

wherein, X$^1$ is saturated C, and X$^1$ is substituted with R″;

ring A is selected from the group consisting of: 3-10 membered saturated or partially unsaturated heterocyclyl and 3-10 membered saturated or partially unsaturated carbocyclyl, wherein ring A is substituted with 0 or at least 1 substituent R$^{1a}$;

when ring A is 3-10 membered saturated or partially unsaturated carbocyclyl, ring A is substituted with p L$^2$, and L$^2$ is not R″;

or, when ring A is 3-10 membered saturated or partially unsaturated heterocyclyl, ring A is substituted with p L$^2$;

L$^2$ is —R$^2$-L$^3$-, and R$^2$ is used for direct or indirect linking of a ligand;

L$^3$ is —(C(R$^{3a}$)(R$^{3b}$))$_m$—, wherein when L$^3$ comprises a methylene unit, 0 or at least 1 methylene unit of L$^3$ is independently replaced by —N(R$^4$)C(O)—, —C(O)N(R$^4$)—, —C(O)—, —OC(O)—, —C(O)O—, —NR$^4$—, —O—, —S—, —SO—, —SO$_2$—, —P(R$^4$)—, —P(=O)(R$^4$)—, —N(R$^4$)SO$_2$—, —SO$_2$N(R$^4$)—, —C(=S)—, —C(=NR$^4$)—, —N=N—, —C=N—, —N=C— or —C(=N$_2$)—;

R$^2$ is selected from the group consisting of: —O—, —(R$^{2a}$)N—, —S— and —P(=O)(R$^{2a}$)—;

L$^1$ is —(C(R$^{5a}$)(R$^{5b}$))$_n$—, wherein when L$^1$ comprises a methylene unit, 0 or at least 1 methylene unit of L$^1$ is independently replaced by —N(R$^6$)C(O)—, —C(O)N(R$^6$)—, —C(O)—, —OC(O)—, —C(O)O—, —NR$^6$—, —O—, —S—, —SO—, —SO$_2$—, —P(R$^6$)—, —P(=O)(R$^6$)—, —N(R$^6$)SO$_2$—, —SO$_2$N(R$^6$)—, —C(=S)—, —C(=NR$^6$)—, —N=N—, —C=N—, —N=C— or —C(=N$_2$)—;

wherein each R$^{1a}$, each R$^{2a}$, each R$^{3a}$, each R$^{3b}$, each R$^4$, each R$^{5a}$, each R$^{5b}$, each R$^6$ and each R″ are each independently hydrogen, protium, deuterium, tritium, halogen, —NO$_2$, —CN, —OR, —SR, —N(R$^a$)(R$^b$), —C(O)R, —CO$_2$R, —C(O)C(O)R, —C(O)CH$_2$C(O)R, —S(O)R, —S(O)$_2$R, —C(O)N(R$^a$)(R$^b$), —SO$_2$N(R$^a$)(R$^b$), —OC(O)R, —N(R)SO$_2$R, or a C$_{1-6}$ aliphatic group optionally substituted with R;

wherein each R, each R$^a$ and each R$^b$ are each independently hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group;

m and n are each independently selected from the group consisting of integers ≥0, and p is an integer ≥1.

In one aspect, the present application provides a compound or a tautomer, a mesomer, a racemate, an enantiomer or a diastereoisomer thereof, or a mixture thereof, or a pharmaceutically acceptable salt thereof, wherein the compound comprises the following group of structures:

II-A-1
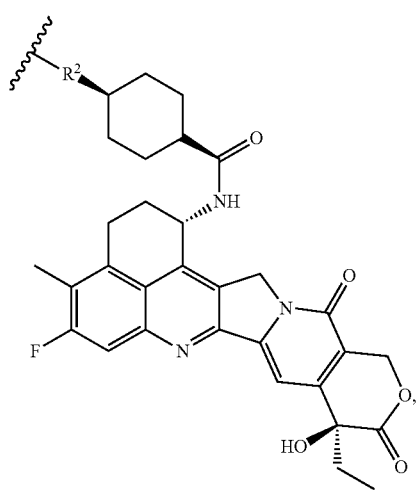
II-A-2
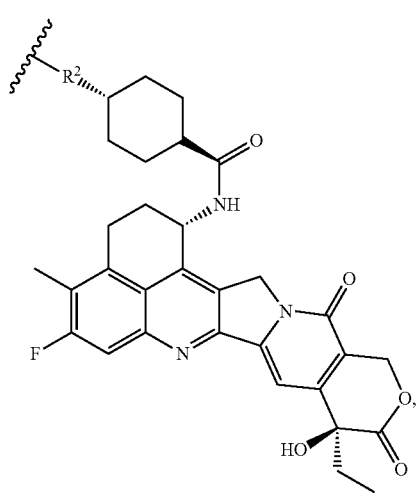
II-A-3
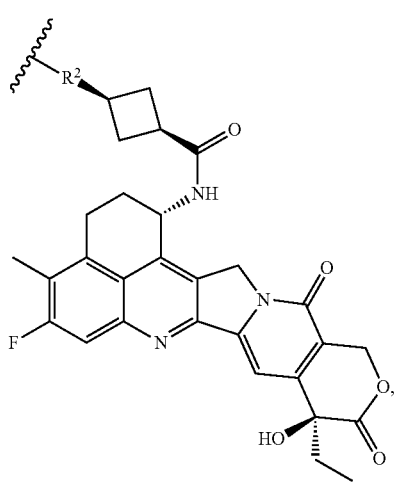
II-A-4
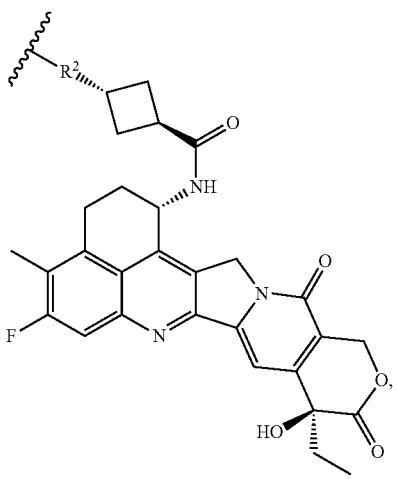
II-A-5
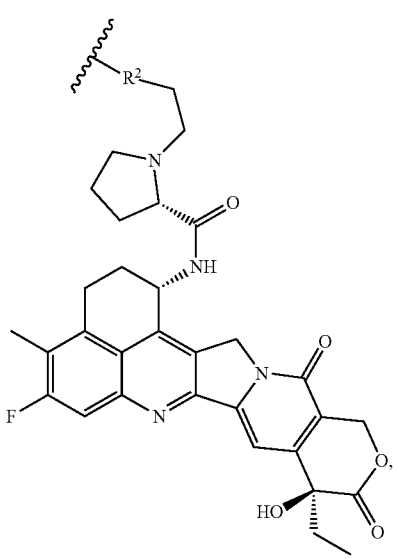
II-A-6
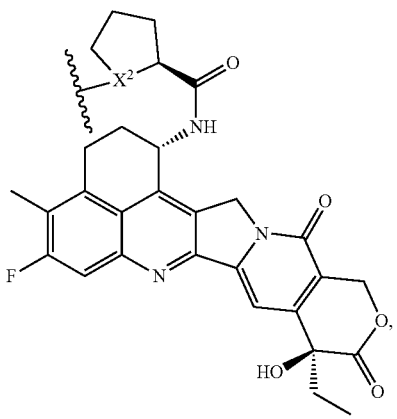

-continued
II-A-7
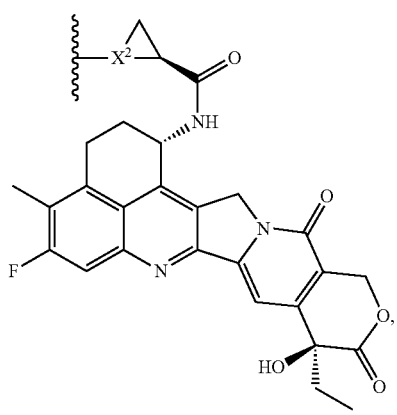
II-A-8
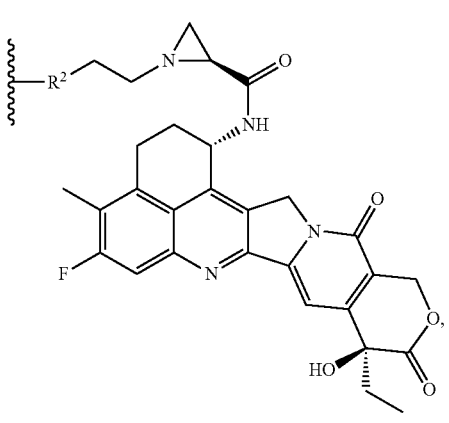
II-A-9
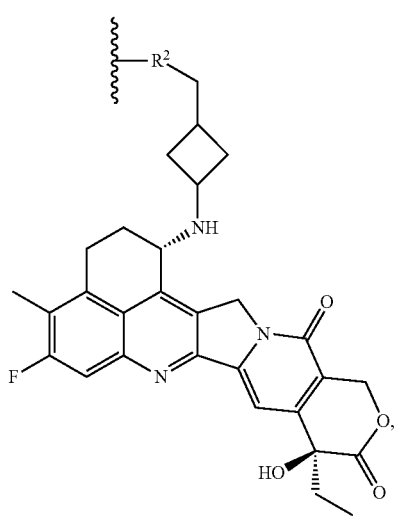
II-A-10
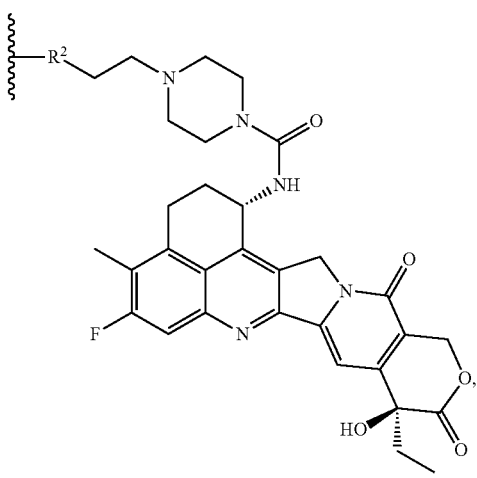
II-A-11
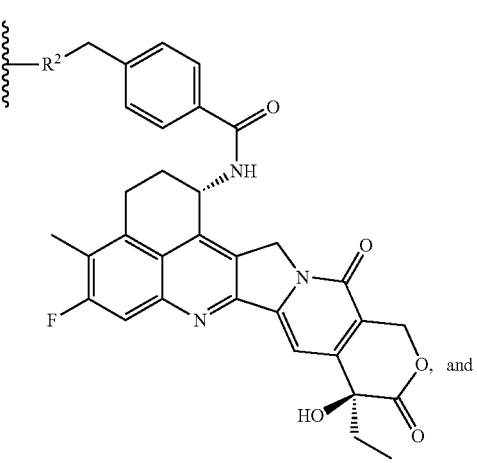
II-A-12
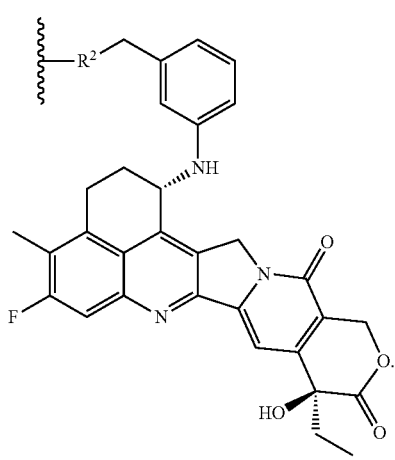
In one aspect, the present application provides a compound or a tautomer, a mesomer, a racemate, an enantiomer or a diastereoisomer thereof, or a mixture thereof, or a pharmaceutically acceptable salt thereof, wherein the compound comprises a structure shown as formula (III-A):

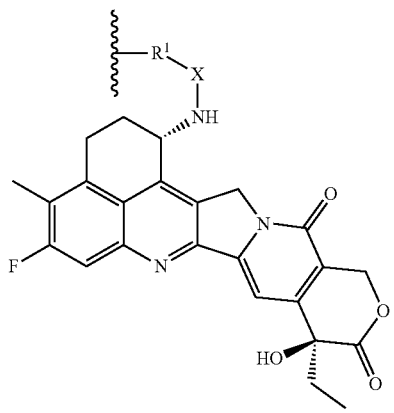

(III-A)

wherein, R¹ is selected from the group consisting of: —O—, —(R²)N—, —P(=O)(R²)— and —S—;

X is -L¹-CH₂—C(O)—;

L¹ is —(C(R³ᵃ)(R³ᵇ))ₘ—, wherein 0 or at least 1 methylene unit of L¹ is independently replaced by —C(O)—, —C(=S)—, —C(=NR⁴ᵇ)— or —C(=N₂)—;

wherein each R², each R³ᵃ, each R³ᵇ and each R⁴ᵇ are each independently hydrogen, protium, deuterium, tritium, halogen, —NO₂, —CN, —OR, —SR, —N(Rᵃ)(Rᵇ), —C(O)R, —CO₂R, —C(O)C(O)R, —C(O)CH₂C(O)R, —S(O)R, —S(O)₂R, —C(O)N(Rᵃ)(Rᵇ), —SO₂N(Rᵃ)(Rᵇ), —OC(O)R, —N(R)SO₂R, or a C₁₋₆ aliphatic group optionally substituted with R;

wherein each R, each Rᵃ and each Rᵇ are each independently hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a C₁₋₆ aliphatic group;

m is selected from the group consisting of integers ≥0, and n is selected from the group consisting of integers ≥1;

when R¹ is —O— or —HN—, at least 1 methylene unit of L¹ is independently replaced by —C(O)—, —C(=S)—, —C(=NR⁴ᵇ)— or —C(=N₂)—, or each R³ᵃ and each R³ᵇ are not both hydrogen.

In one aspect, the present application provides a compound of general formula (III-E) or a tautomer, a mesomer, a racemate, an enantiomer or a diastereoisomer thereof, or a mixture thereof, or a pharmaceutically acceptable salt thereof,

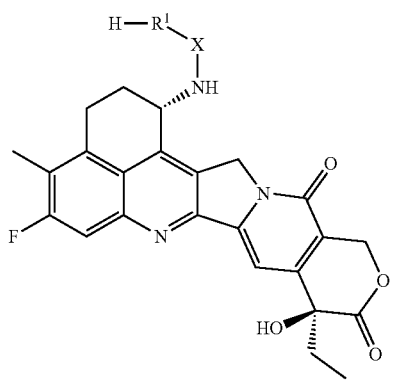

(III-E)

wherein R¹ is selected from the group consisting of: —O—, —(R²)N—, —P(=O)(R²)— and —S—;

X is -L¹-CH₂—C(O)—;

L¹ is —(C(R³ᵃ)(R³ᵇ))ₘ—, wherein 0 or at least 1 methylene unit of L¹ is independently replaced by —C(O)—, —C(=S)—, —C(=NR⁴ᵇ)— or —C(=N₂)—;

wherein each R², each R³ᵃ, each R³ᵇ and each R⁴ᵇ are each independently hydrogen, protium, deuterium, tritium, halogen, —NO₂, —CN, —OR, —SR, —N(Rᵃ)(Rᵇ), —C(O)R, —CO₂R, —C(O)C(O)R, —C(O)CH₂C(O)R, —S(O)R, —S(O)₂R, —C(O)N(Rᵃ)(Rᵇ), —SO₂N(Rᵃ)(Rᵇ), —OC(O)R, —N(R)SO₂R, or a C₁₋₆ aliphatic group optionally substituted with R;

wherein each R, each Rᵃ and each Rᵇ are each independently hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a C₁₋₆ aliphatic group;

m is selected from the group consisting of integers ≥0, and n is selected from the group consisting of integers ≥1;

when R¹ is —O— or —HN—, at least 1 methylene unit of L¹ is independently replaced by —C(O)—, —C(=S)—, —C(=NR⁴ᵇ)— or —C(=N₂)—, or each R³ᵃ and each R³ᵇ are not both hydrogen.

In one aspect, the present application provides a compound or a tautomer, a mesomer, a racemate, an enantiomer or a diastereoisomer thereof, or a mixture thereof, or a pharmaceutically acceptable salt thereof, wherein the compound comprises a structure shown as formula (III-C):

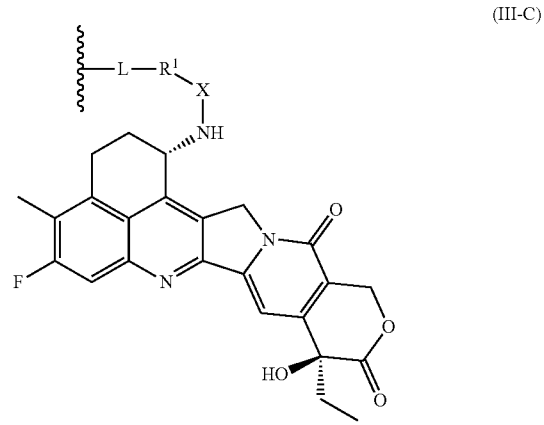

(III-C)

wherein, L is -Lₐ-Lᵦ-Lᵧ-;

Lₐ- is selected from the group consisting of:

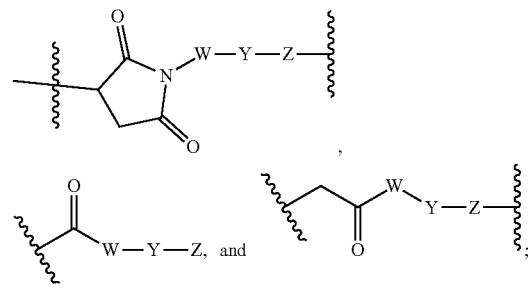

wherein W is —(C(R$^{wa}$)(R$^{wb}$))$_{wn}$—, Y is —(OCH$_2$-CH$_2$)$_{yn}$—O$_{yp}$, and Z is —(C(R$^{za}$)(R$^{zb}$))$_{zn}$;

wherein wn is selected from the group consisting of integers ≥0, and 0 or at least 1 methylene unit of W is independently replaced by -Cyr-, —N(R$^{wx}$)C(O)—, —C(O)N(R$^{wx}$)—, —C(O)—, —OC(O)—, —C(O)O—, —NR$^{wx}$—, —O—, —S—, —SO—, —SO$_2$—, —P(R$^{wx}$)—, —P(=O)(R$^{wx}$)—, —N(R$^{wx}$)SO$_2$—, —SO$_2$N(R$^{wx}$)—, —C(=S)—, —C(=NR$^{wx}$)—, —N=N—, —C=N—, —N=C— or —C(=N$_2$)—;

wherein yn is selected from the group consisting of integers ≥0, and yp is 0 or 1;

wherein zn is selected from the group consisting of integers ≥0, and 0 or at least 1 methylene unit of Z is independently replaced by -Cyr-, —N(R$^{zx}$)C(O)—, —C(O)N(R$^{zx}$)—, —C(O)—, —OC(O)—, —C(O)O—, —NR$^{zx}$—, —O—, —S—, —SO—, —SO$_2$—, —P(R$^{zx}$)—, —P(=O)(R$^{zx}$)—, —N(R$^{zx}$)SO$_2$—, —SO$_2$N(R$^{zx}$)—, —C(=S)—, —C(=NR$^{zx}$)—, —N=N—, —C=N—, —N=C— or —C(=N$_2$)—;

Cyr- is selected from the group consisting of: 6-10 membered arylene, 5-8 membered heteroarylene, 3-10 membered heterocyclylene and 3-10 membered saturated or partially unsaturated carbocyclylene, wherein -Cyr- is unsubstituted or independently substituted with at least 1 substituent R$^{cx}$;

wherein each R$^{wa}$, each R$^{wb}$, each R$^{za}$, each R$^{zb}$, each R$^{wx}$, each R$^{zx}$ and each R$^{cx}$ are each independently hydrogen, protium, deuterium, tritium, halogen, —NO$_2$, —CN, —OR$^r$, —SR$^r$, —N(R$^{ra}$)(R$^{rb}$), —C(O)R$^r$, —CO$_2$R, —C(O)C(O)R$^r$, —C(O)CH$_2$C(O)R$^r$, —S(O)R$^r$, —S(O)$_2$R$^r$, —C(O)N(R$^{ra}$)(R$^{rb}$), —SO$_2$N(R$^{ra}$)(R$^{rb}$), —OC(O)R$^r$, —N(R)SO$_2$R, or a C$_{1-6}$ aliphatic group optionally substituted with R$^r$;

wherein each R$^r$, each R$^{ra}$ and each R$^{rb}$ are each independently hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group;

L$_b$- represents a peptide residue consisting of 2 to 7 amino acids;

L$_c$- is selected from the group consisting of:

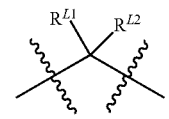

,

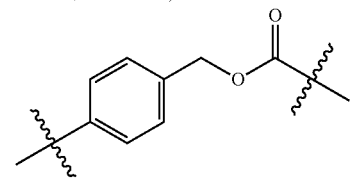

,

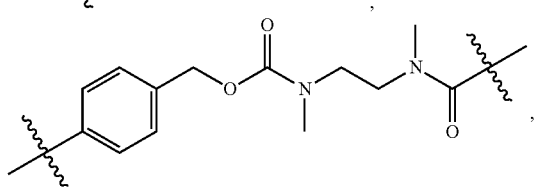

,

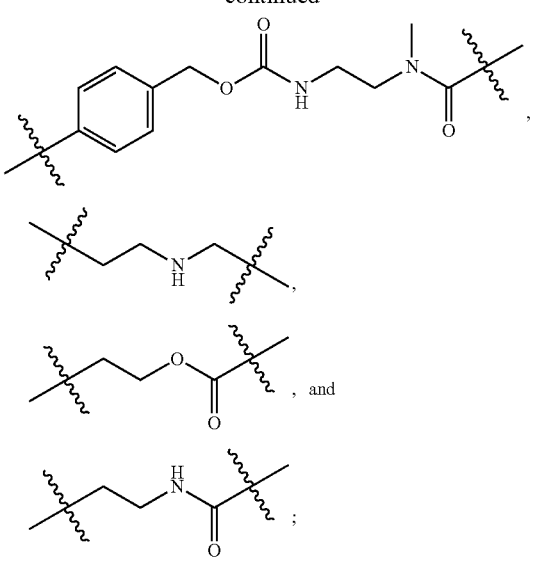

, and wherein R$^{L1}$ and R$^{L2}$ are each independently selected from the group consisting of: hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H and a C$_{1-6}$ aliphatic group;

wherein R$^1$ is selected from the group consisting of: —O—, —(R$^2$)N—, —P(=O)(R$^2$)— and —S—;

X is -L$^1$-CH$_2$—C(O)—;

L$^1$ is —(C(R$^{3a}$)(R$^{3b}$))$_m$—, wherein 0 or at least 1 methylene unit of L$^1$ is independently replaced by —C(O)—, —C(=S)—, —C(=NR$^{4b}$)— or —C(=N$_2$)—;

wherein each R$^2$, each R$^{3a}$, each R$^{3b}$ and each R$^{4b}$ are each independently hydrogen, protium, deuterium, tritium, halogen, —NO$_2$, —CN, —OR, —SR, —N(R$^a$)(R$^b$), —C(O)R, —CO$_2$R, —C(O)C(O)R, —C(O)CH$_2$C(O)R, —S(O)R, —S(O)$_2$R, —C(O)N(R$^a$)(R$^b$), —SO$_2$N(R$^a$)(R$^b$), —OC(O)R, —N(R)SO$_2$R, or a C$_{1-6}$ aliphatic group optionally substituted with R;

wherein each R, each R$^a$ and each R$^b$ are each independently hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group;

m is selected from the group consisting of integers ≥0, and n is selected from the group consisting of integers ≥1;

when R$^1$ is —O— or —HN—, at least 1 methylene unit of L$^1$ is independently replaced by —C(O)—, —C(=S)—, —C(=NR$^{4b}$)— or —C(=N$_2$)—, or each R$^{3a}$ and each R$^{3b}$ are not both hydrogen.

In one aspect, the present application provides a compound or a tautomer, a mesomer, a racemate, an enantiomer or a diastereoisomer thereof, or a mixture thereof, or a pharmaceutically acceptable salt thereof, wherein the compound comprises a structure shown as formula (III-D):

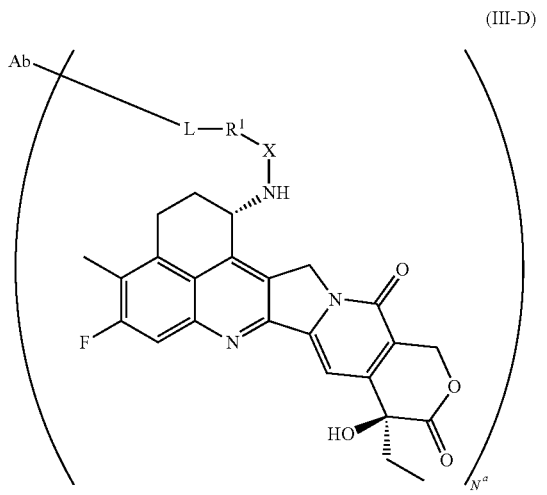

(III-D)

wherein, Ab is a ligand, and an average connection number Na is an integer or a decimal from 1 to 10;

$L$ is $-L_a-L_b-L_c-$;

$L_a-$ is selected from the group consisting of:

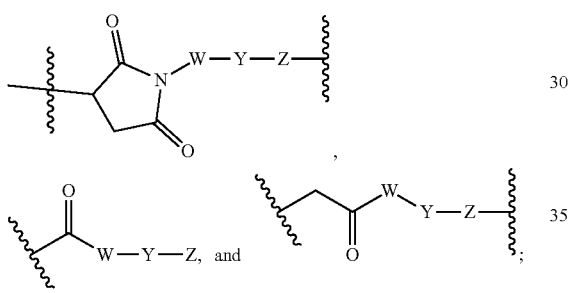

wherein W is $-(C(R^{wa})(R^{wb}))_{wn}-$, Y is $-(OCH_2-CH_2)_{yn}-O_{yp}$, and Z is $-(C(R^{za})(R^{zb}))_{zn}-$;

wherein wn is selected from the group consisting of integers $\geq 0$, and 0 or at least 1 methylene unit of W is independently replaced by -Cyr-, $-N(R^{wx})C(O)-$, $-C(O)N(R^{wx})-$, $-C(O)-$, $-OC(O)-$, $-C(O)O-$, $-NR^{wx}-$, $-O-$, $-S-$, $-SO-$, $-SO_2-$, $-P(R^{wx})-$, $-P(=O)(R^{wx})-$, $-N(R^{wx})SO_2-$, $-SO_2N(R^{wx})-$, $-C(=S)-$, $-C(=NR^{wx})-$, $-N=N-$, $-C=N-$, $-N=C-$ or $-C(=N_2)-$;

wherein yn is selected from the group consisting of integers $\geq 0$, and yp is 0 or 1;

wherein zn is selected from the group consisting of integers $\geq 0$, and 0 or at least 1 methylene unit of Z is independently replaced by -Cyr-, $-N(R^{zx})C(O)-$, $-C(O)N(R^{zx})-$, $-C(O)-$, $-OC(O)-$, $-C(O)O-$, $-NR^{zx}-$, $-O-$, $-S-$, $-SO-$, $-SO_2-$, $-P(R^{zx})-$, $-P(=O)(R^{zx})-$, $-N(R^{zx})SO_2-$, $-SO_2N(R^{zx})-$, $-C(=S)-$, $-C(=NR^{zx})-$, $-N=N-$, $-C=N-$, $-N=C-$ or $-C(=N_2)-$;

Cyr- is selected from the group consisting of: 6-10 membered arylene, 5-8 membered heteroarylene, 3-10 membered heterocyclylene and 3-10 membered saturated or partially unsaturated carbocyclylene, wherein -Cyr- is unsubstituted or independently substituted with at least 1 substituent $R^{cx}$;

wherein each $R^{wa}$, each $R^{wb}$, each $R^{za}$, each $R^{zb}$, each $R^{wx}$, each $R^{zx}$ and each $R^{cx}$ are each independently hydrogen, protium, deuterium, tritium, halogen, $-NO_2$, $-CN$, $-OR^r$, $-SR^r$, $-N(R^{ra})(R^{rb})$, $-C(O)R^r$, $-CO_2R$, $-C(O)C(O)R^r$, $-C(O)CH_2C(O)R^r$, $-S(O)R^r$, $-S(O)_2R^r$, $-C(O)N(R^{ra})(R^{rb})$, $-SO_2N(R^{ra})(R^{rb})$, $-OC(O)R^r$, $-N(R)SO_2R$, or a $C_{1-6}$ aliphatic group optionally substituted with $R^r$;

wherein each $R^r$, each $R^{ra}$ and each $R^{rb}$ are each independently hydrogen, protium, deuterium, tritium, halogen, $-NO_2$, $-CN$, $-OH$, $-SH$, $-NH_2$, $-C(O)H$, $-CO_2H$, $-C(O)C(O)H$, $-C(O)CH_2C(O)H$, $-S(O)H$, $-S(O)_2H$, $-C(O)NH_2$, $-SO_2NH_2$, $-OC(O)H$, $-N(H)SO_2H$ or a $C_{1-6}$ aliphatic group;

$L_b-$ represents a peptide residue consisting of 2 to 7 amino acids;

$L_c-$ is selected from the group consisting of:

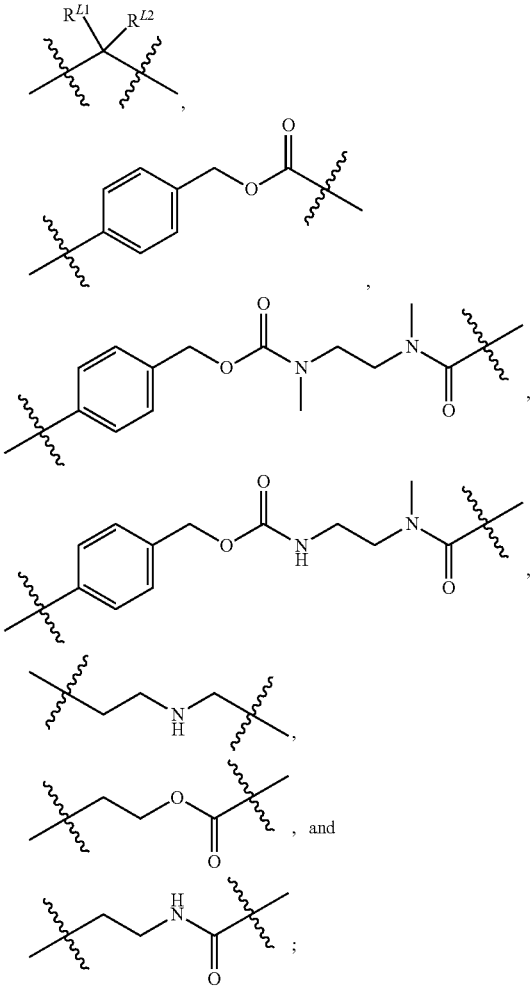

wherein $R^{L1}$ and $R^{L2}$ are each independently selected from the group consisting of: hydrogen, protium, deuterium, tritium, halogen, $-NO_2$, $-CN$, $-OH$, $-SH$, $-NH_2$, $-C(O)H$, $-CO_2H$, $-C(O)C(O)H$, $-C(O)CH_2C(O)H$, $-S(O)H$, $-S(O)_2H$, $-C(O)NH_2$, $-SO_2NH_2$, $-OC(O)H$, $-N(H)SO_2H$ and a $C_{1-6}$ aliphatic group;

wherein $R^1$ is selected from the group consisting of: $-O-$, $-(R^2)N-$, $-P(=O)(R^2)-$ and $-S-$;

X is -L¹-CH₂—C(O)—;

L¹ is —(C(R³ᵃ)(R³ᵇ))ₘ—, wherein 0 or at least 1 methylene unit of L¹ is independently replaced by —C(O)—, —C(=S)—, —C(=NR⁴ᵇ)— or —C(=N₂)—;

wherein each R², each R³ᵃ, each R³ᵇ and each R⁴ᵇ are each independently hydrogen, protium, deuterium, tritium, halogen, —NO₂, —CN, —OR, —SR, —N(Rᵃ)(Rᵇ), —C(O)R, —CO₂R, —C(O)C(O)R, —C(O)CH₂C(O)R, —S(O)R, —S(O)₂R, —C(O)N(Rᵃ)(Rᵇ), —SO₂N(Rᵃ)(Rᵇ), —OC(O)R, —N(R)SO₂R, or a C₁₋₆ aliphatic group optionally substituted with R;

wherein each R, each Rᵃ and each Rᵇ are each independently hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a C₁₋₆ aliphatic group;

m is selected from the group consisting of integers ≥0, and n is selected from the group consisting of integers ≥1;

when R¹ is —O— or —HN—, at least 1 methylene unit of L¹ is independently replaced by —C(O)—, —C(=S)—, —C(=NR⁴ᵇ)— or —C(=N₂)—, or each R³ᵃ and each R³ᵇ are not both hydrogen.

In one aspect, the present application provides a compound of general formula (III-F) or a tautomer, a mesomer, a racemate, an enantiomer or a diastereoisomer thereof, or a mixture thereof, or a pharmaceutically acceptable salt thereof,

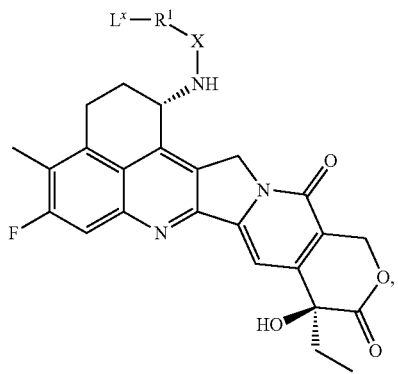

(III-F)

wherein, Lˣ is Lₐₓ-Lᵦ-L𝒸-;

Lₐₓ- is selected from the group consisting of:

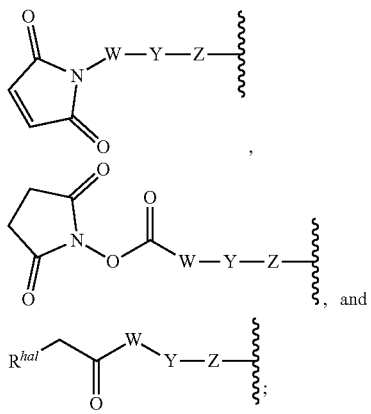

, and

;

wherein Rʰᵃˡ is iodine or bromine;

wherein W is —(C(Rʷᵃ)(Rʷᵇ))ʷⁿ—, Y is —(OCH₂CH₂)ʸⁿ—Oʸᵖ—, and Z is —(C(Rᶻᵃ)(Rᶻᵇ))ᶻⁿ—;

wherein wn is selected from the group consisting of integers ≥0, and 0 or at least 1 methylene unit of W is independently replaced by -Cyr-, —N(Rʷˣ)C(O)—, —C(O)N(Rʷˣ)—, —C(O)—, —OC(O)—, —C(O)O—, —NRʷˣ—, —O—, —S—, —SO—, —SO₂—, —P(Rʷˣ)—, —P(=O)(Rʷˣ)—, —N(Rʷˣ)SO₂—, —SO₂N(Rʷˣ)—, —C(=S)—, —C(=NRʷˣ)—, —N=N—, —C=N—, —N=C— or —C(=N₂)—;

wherein yn is selected from the group consisting of integers ≥0, and yp is 0 or 1;

wherein zn is selected from the group consisting of integers ≥0, and 0 or at least 1 methylene unit of Z is independently replaced by -Cyr-, —N(Rᶻˣ)C(O)—, —C(O)N(Rᶻˣ)—, —C(O)—, —OC(O)—, —C(O)O—, —NRᶻˣ—, —O—, —S—, —SO—, —SO₂—, —P(Rᶻˣ)—, —P(=O)(Rᶻˣ)—, —N(Rᶻˣ)SO₂—, —SO₂N(Rᶻˣ)—, —C(=S)—, —C(=NRᶻˣ)—, —N=N—, —C=N—, —N=C— or —C(=N₂)—;

Cyr- is selected from the group consisting of: 6-10 membered arylene, 5-8 membered heteroarylene, 3-10 membered heterocyclylene and 3-10 membered saturated or partially unsaturated carbocyclylene, wherein -Cyr- is unsubstituted or independently substituted with at least 1 substituent Rᶜˣ;

wherein each Rʷᵃ, each Rʷᵇ, each Rᶻᵃ, each Rᶻᵇ, each Rʷˣ, each Rᶻˣ and each Rᶜˣ are each independently hydrogen, protium, deuterium, tritium, halogen, —NO₂, —CN, —ORʳ, —SRʳ, —N(Rʳᵃ)(Rʳᵇ), —C(O)Rʳ, —CO₂R, —C(O)C(O)Rʳ, —C(O)CH₂C(O)Rʳ, —S(O)Rʳ, —S(O)₂Rʳ, —C(O)N(Rʳᵃ)(Rʳᵇ), —SO₂N(Rʳᵃ)(Rʳᵇ), —OC(O)Rʳ, —N(R)SO₂R, or a C₁₋₆ aliphatic group optionally substituted with Rʳ;

wherein each Rʳ, each Rʳᵃ and each Rʳᵇ are each independently hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a C₁₋₆ aliphatic group;

Lᵦ- represents a peptide residue consisting of 2 to 7 amino acids;

L𝒸- is selected from the group consisting of:

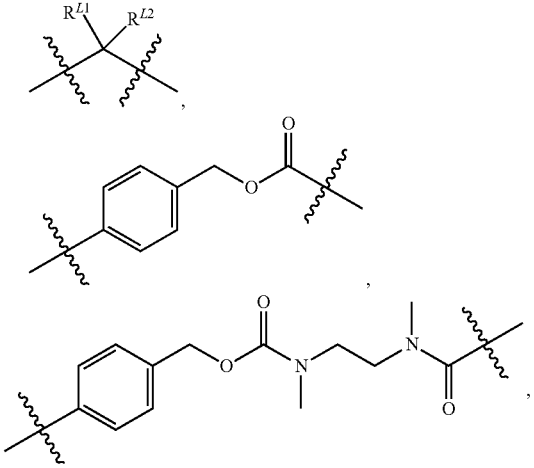

,

,

-continued

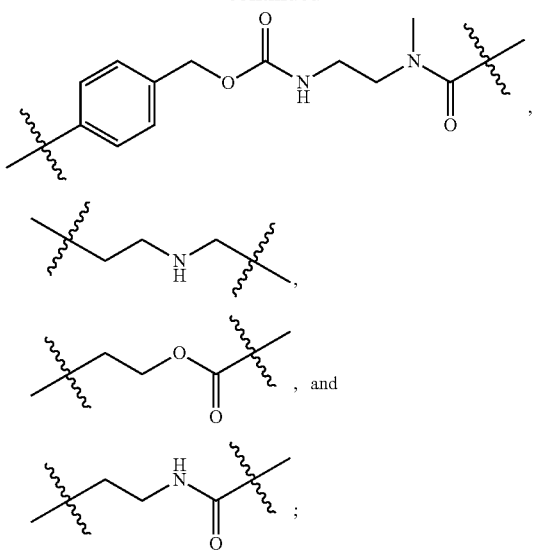

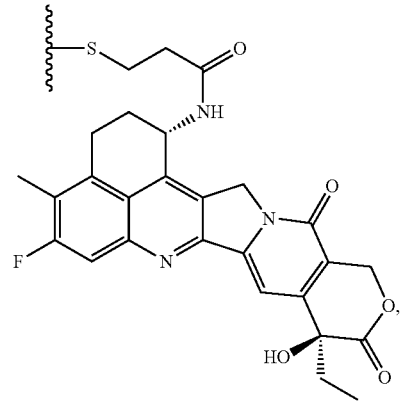

III-A-1

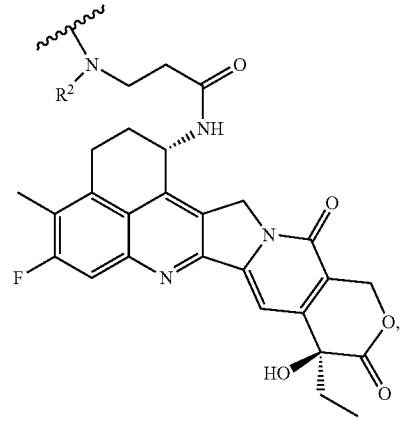

III-A-2

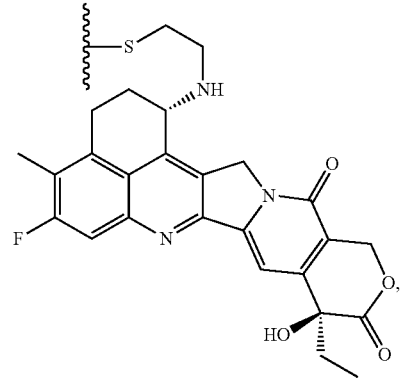

III-A-3

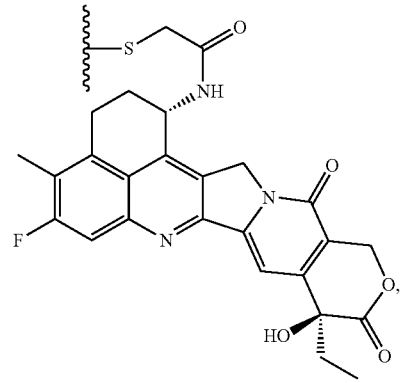

III-A-4 wherein $R^{L1}$ and $R^{L2}$ are each independently selected from the group consisting of: hydrogen, protium, deuterium, tritium, halogen, —$NO_2$, —CN, —OH, —SH, —$NH_2$, —C(O)H, —$CO_2$H, —C(O)C(O)H, —C(O)$CH_2$C(O)H, —S(O)H, —S(O)$_2$H, —C(O)$NH_2$, —$SO_2NH_2$, —OC(O)H, —N(H)$SO_2$H and a $C_{1-6}$ aliphatic group;

wherein $R^1$ is selected from the group consisting of: —O—, —($R^2$)N—, —P(=O)($R^2$)— and —S—;

X is -$L^1$-$CH_2$—C(O)—;

$L^1$ is —(C($R^{3a}$)($R^{3b}$))$_m$—, wherein 0 or at least 1 methylene unit of $L^1$ is independently replaced by —C(O)—, —C(=S)—, —C(=$NR^{4b}$)— or —C(=$N_2$)—;

wherein each $R^2$, each $R^{3a}$, each $R^{3b}$ and each $R^{4b}$ are each independently hydrogen, protium, deuterium, tritium, halogen, —$NO_2$, —CN, —OR, —SR, —N($R^a$)($R^b$), —C(O)R, —$CO_2$R, —C(O)C(O)R, —C(O)$CH_2$C(O)R, —S(O)R, —S(O)$_2$R, —C(O)N($R^a$)($R^b$), —$SO_2$N($R^a$)($R^b$), —OC(O)R, —N(R)$SO_2$R, or a $C_{1-6}$ aliphatic group optionally substituted with R;

wherein each R, each $R^a$ and each $R^b$ are each independently hydrogen, protium, deuterium, tritium, halogen, —$NO_2$, —CN, —OH, —SH, —$NH_2$, —C(O)H, —$CO_2$H, —C(O)C(O)H, —C(O)$CH_2$C(O)H, —S(O)H, —S(O)$_2$H, —C(O)$NH_2$, —$SO_2NH_2$, —OC(O)H, —N(H)$SO_2$H or a $C_{1-6}$ aliphatic group;

m is selected from the group consisting of integers ≥0, and n is selected from the group consisting of integers ≥1;

when $R^1$ is —O— or —HN—, at least 1 methylene unit of $L^1$ is independently replaced by —C(O)—, —C(=S)—, —C(=$NR^{4b}$)— or —C(=$N_2$)—, or each $R^{3a}$ and each $R^{3b}$ are not both hydrogen.

In one aspect, the present application provides a compound or a tautomer, a mesomer, a racemate, an enantiomer or a diastereoisomer thereof, or a mixture thereof, or a pharmaceutically acceptable salt thereof, wherein the ligand-drug conjugate comprises the following group of structures:

-continued
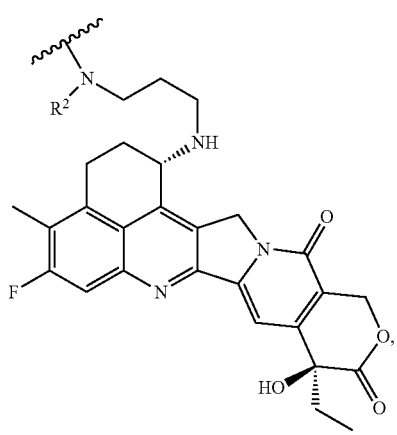
III-A-5
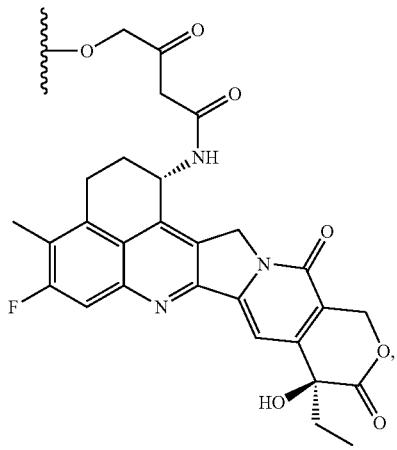
III-A-8
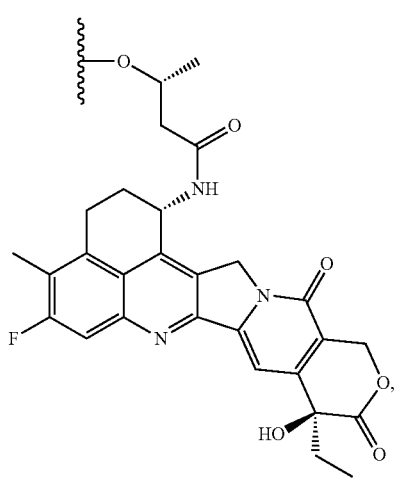
III-A-6
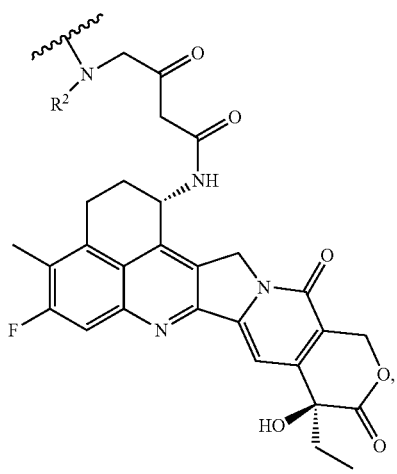
III-A-9
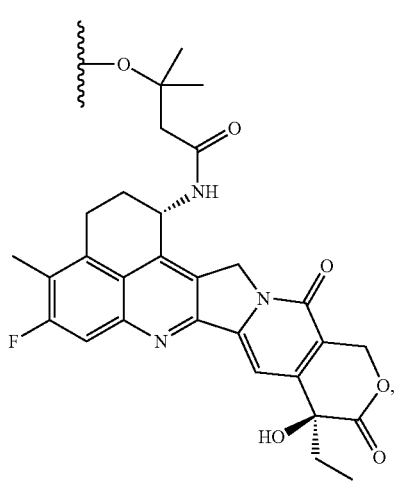
III-A-7
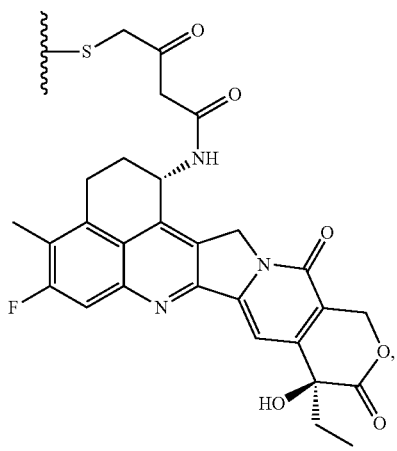
III-A-10

III-A-11
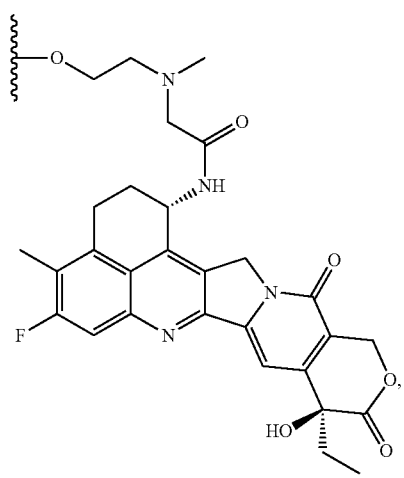
III-A-12
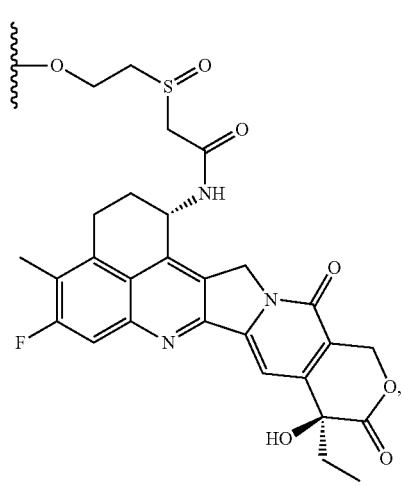
III-A-13
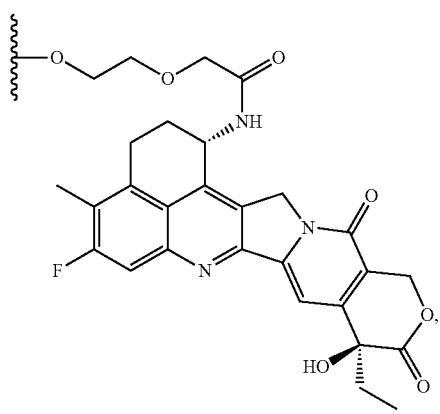
III-A-14
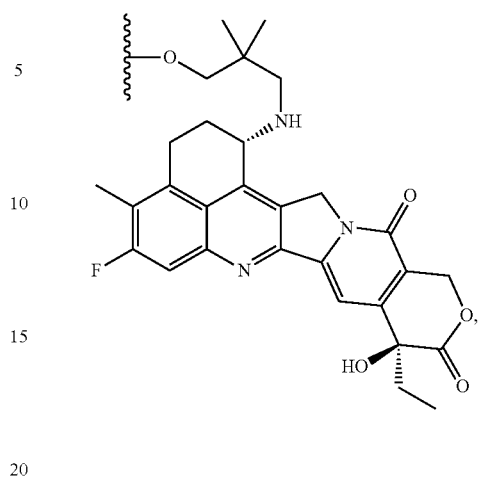
III-A-15
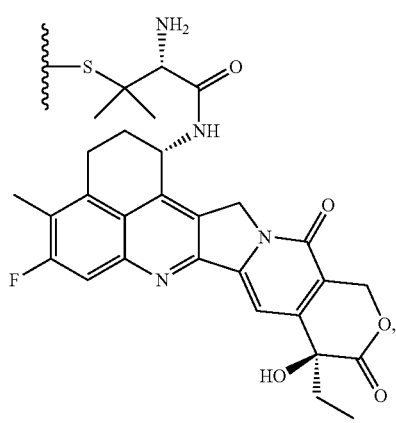
III-A-16
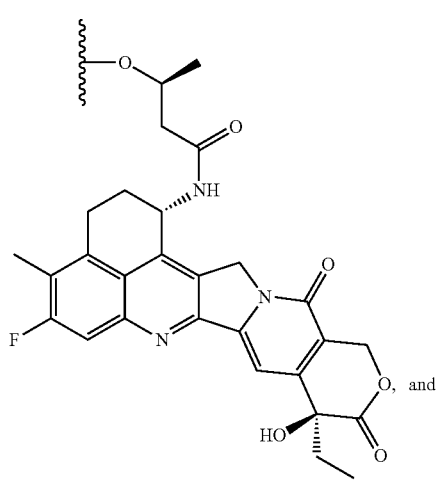

III-A-17

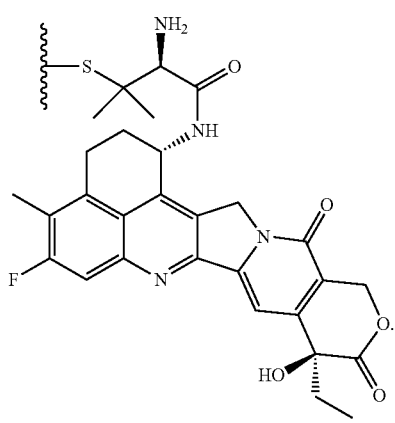

In one aspect, the present application provides a method for preparing the compound or the tautomer, the mesomer, the racemate, the enantiomer or the diastereoisomer thereof, or the mixture thereof, or the pharmaceutically acceptable salt thereof disclosed herein, which comprises contacting a ligand Ab with the structure shown as formula (II-F$_x$) disclosed herein.

In one aspect, the present application provides a method for preparing the compound or the tautomer, the mesomer, the racemate, the enantiomer or the diastereoisomer thereof, or the mixture thereof, or the pharmaceutically acceptable salt thereof disclosed herein, which comprises contacting a ligand Ab with the structure shown as formula (III-F) disclosed herein.

In one aspect, the present application provides a pharmaceutical composition, which comprises the compound or the tautomer, the mesomer, the racemate, the enantiomer or the diastereoisomer thereof, or the mixture thereof, or the pharmaceutically acceptable salt thereof disclosed herein, and a pharmaceutically acceptable carrier.

In one aspect, the present application provides use of the compound or the tautomer, the mesomer, the racemate, the enantiomer or the diastereoisomer thereof, or the mixture thereof, or the pharmaceutically acceptable salt thereof disclosed herein, and/or the pharmaceutical composition disclosed herein, in preparing a medicament for treating and/or preventing a tumor.

Other aspects and advantages of the present application will be readily apparent to those skilled in the art from the following detailed description. Only exemplary embodiments of the present application have been shown and described in the following detailed description. As those skilled in the art will recognize, the content of the present application enables those skilled in the art to make changes to the specific embodiments disclosed without departing from the spirit and scope of the invention to which the present application pertains. Accordingly, descriptions in the drawings and specification are only illustrative rather than restrictive.

BRIEF DESCRIPTION OF THE DRAWING

Specific features of the invention to which the present application pertains are set forth in appended claims. Features and advantages of the invention to which the present application pertains will be better understood by reference to the exemplary embodiments and drawings described in detail below. The drawings are briefly described as follows:

DETAILED DESCRIPTION

Figure 1:
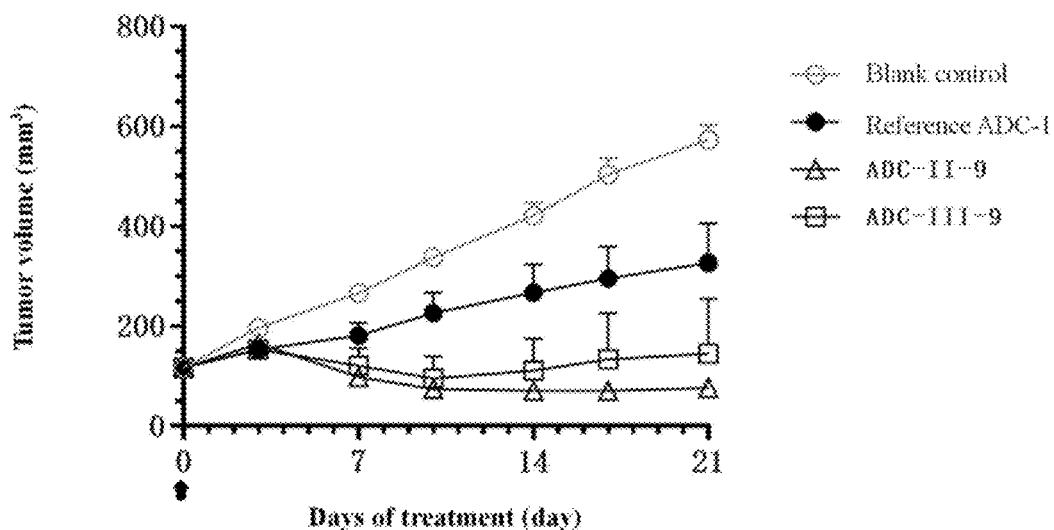
FIGS. 1-16 are graphs showing in vivo tumor inhibition results of the compounds disclosed herein.

The embodiments of the present invention are described below with reference to specific examples, and other advantages and effects of the present invention will be readily apparent to those skilled in the art from the disclosure of the present specification.

Definitions of Terms

In the present application, the term "ligand" generally refers to a macromolecular compound capable of recognizing and binding to an antigen or receptor associated with a target cell. The role of ligands may be to present the drug to a target cell population to which the ligand binds, and the ligands include, but are not limited to, protein hormones, lectin, growth factors, antibodies, or other molecules capable of binding to a cell, a receptor and/or an antigen. In the present application, the ligand may be represented as Ab, the ligand antigen forms a linking bond with the linking unit through a heteroatom on the ligand, and the ligand may be an antibody or an antigen-binding fragment thereof, wherein the antibody may be selected from the group consisting of a chimeric antibody, a humanized antibody, a fully human antibody or a murine antibody, and the antibody may be a monoclonal antibody. For example, the antibody may be an antibody that targets the following target points: HER2, HER3, B7H3, TROP2, Claudin 18.2, CD30, CD33, CD70 or EGFR. For example, the antibody may be an antibody that targets the following target points: 5T4, AGS-16, ANGPTL4, ApoE, CD19, CTGF, CXCR5, FGF2, MCPT8, MFI2, MS4A7, NCA, Sema5b, SLITRK6, STC2, TGF, 0772P, 5T4, ACTA2, ADGRE1, AG-7, AIF1, AKR1C1, AKR1C2, ASLG659, Axl, B7H3, BAFF-R, BCMA, BMPR1B, BNIP3, C1QA, C1QB, CA6, CADM1, CCD79b, CCL5, CCR5, CCR7, CD11c, CD123, CD138, CD142, CD147, CD166, CD19, CD19, CD22, CD21, CD20, CD205, CD22, CD223, CD228, CD25, CD30, CD33, CD37, CD38, CD40, CD45, CD45 (PTPRC), CD46, CD47, CD49D (ITGA4), CD56, CD66e, CD70, CD71, CD72, CD74, CD79a, CD79b, CD80, CDCP1, CDH11, CD11b, CEA, CEACAM5, c-Met, COL6A3, COL7A1, CRIPTO, CSF1R, CTSD, CTSS, CXCL11, CXCL10, DDIT4, DLL3, DLL4, DR5, E16, EFNA4, EGFR, EGFRvIII, EGLN, EGLN3, EMR2, ENPP3, EpCAM, EphA2, EphB2R, ETBR, FcRH2, FcRH1, FGFR2, FGFR3, FLT3, FOLR-α, GD2, GEDA, GPC-1, GPNMB, GPR20, GZMB, HER2, HER3, HLA-DOB, HMOX1, IFI6, IFNG, IGF-1R, IGFBP3, IL10RA1, IL-13R, IL-2, IL20Ra, IL-3, IL-4, IL-6, IRTA2, KISS1R, KRT33A, LIV-1, LOX, LRP-1, LRRC15, LUM, LY64, LY6E, Ly86, LYPD3, MDP, MMP10, MMP14, MMP16, MPF, MSG783, MSLN, MUC-1, NaPi2b, Napi3b, Nectin-4, Nectin-4, NOG, P2X5, pCAD, P-Cadherin, PDGFRA, PDK1, PD-L1, PFKFB3, PGF, PGK1, PIK3AP1, PIK3CD, PLOD2, PSCA, PSCAhlg, PSMA, PSMA, PTK7, P-Cadherin, RNF43, NaPi2b, ROR1, ROR2, SERPINE1, SLC39A6, SLTRK6, STAT1, STEAP1, STEAP2, TCF4, TENB2, TGFB1, TGFB2, TGFBR1, TNFRSF21, TNFSF9, Trop-2, TrpM4, Tyro7, UPK1B, VEGFA, WNT5A, epidermal growth factors, brevican, mesothelin, sodium phosphate cotransporter 2B, Claudin 18.2, endothelin receptors, mucins (such as mucin 1 and mucin 16), guanylate cyclase C, integrin a4p7, integrin a5p6, trophoblast glycoprotein, or tissue factors.

In the present application, the term "cytotoxic drug" generally refers to a toxic drug, and the cytotoxic drug may have a chemical molecule within the tumor cell that is strong enough to disrupt its normal growth. Cytotoxic drugs can kill tumor cells at a sufficiently high concentration. The "cytotoxic drug" may include toxins, such as small molecule toxins or enzymatically active toxins of bacterial, fungal, plant or animal origin, radioisotopes (e.g., $At^{211}$, $I^{131}$, $I^{125}$, $Y^{90}$, $Re^{186}$, $Re^{188}$, $Sm^{153}$, $Bi^{212}$, $P^{32}$ or radioactive isotopes of Lu), toxic drugs, chemotherapeutic drugs, antibiotics and nucleolytic enzymes; for example, the cytotoxic drug may be toxic drugs, including but not limited to camptothecin derivatives, which, for example, may be the camptothecin derivative exatecan (chemical name: (1S,9S)-1-amino-9-ethyl-5-fluoro-2,3-dihydro-9-hydroxy-4-methyl-1H,12H-benzo[de]pyrano[3',4':6,7]imidazo[1,2-b]quinoline-10,13 (9H,15H)-dione).

In the present application, the term "linker structure" generally refers to a chemical structural fragment or bond, which is linked to a ligand at one end and linked to a cytotoxic drug at the other end, or linked to other linkers and then linked to the cytotoxic drug. The direct or indirect linking of a ligand may mean that the group is directly linked to the ligand via a covalent bond, and may also be linked to the ligand via a linker structure. For example, the linker structure may be a structure shown as $-L_{ax}-L_b-L_c-$ and/or $-L_a-L_b-L_c-$ described herein. For example, a chemical structure fragment or bond comprising an acid-labile linker structure (e.g., hydrazone), a protease-sensitive (e.g., peptidase-sensitive) linker structure, a photolabile linker structure, a dimethyl linker structure or a disulfide-containing linker structure may be used as a linker structure.

In the present application, the term a structure being "optionally linked to other molecular moieties" generally means that the structure is not linked to any other chemical structure, or that the structure is linked (e.g., via a chemical bond or a linker structure) to one or more other chemical structures (e.g., ligands described herein) different from the structure.

In the present application, the term "ligand-drug conjugate" generally means that a ligand is linked to a biologically active cytotoxic drug via a stable linking unit. In the present application, the "ligand-drug conjugate" may be an antibody-drug conjugate (ADC), which may mean that a monoclonal antibody or an antibody fragment is linked to a biologically active cytotoxic drug via a stable linking unit.

In the present application, the term "antibody or antigen-binding fragment thereof" generally refers to that immunological binding reagents extend to all antibodies from all species, including dimeric, trimeric and multimeric antibodies; bispecific antibodies; chimeric antibodies; fully humanized antibodies; humanized antibodies; recombinant and engineered antibodies and fragments thereof. The term "antibody or fragment thereof" may refer to any antibody-like molecule having an antigen-binding region, and includes small molecule fragments, such as Fab', Fab, F(ab')$_2$, single domain antibodies (DABs), Fv, scFv (single chain Fv), linear antibodies, and diabodies. The term "antigen-binding fragment" may refer to one or more fragments of an antibody that retain the ability to specifically bind to an antigen. For example, a fragment of a full-length antibody can be used to perform the antigen-binding function of the antibody. Techniques for preparing and using various antibody-based constructs and fragments are well known in the art. The antibody may include one or more of an anti-HER2(ErbB2) antibody, an anti-EGFR antibody, an anti-B7-H3 antibody, an anti-c-Met antibody, an anti-HER3 (ErbB3) antibody, an anti-HER4(ErbB4) antibody, an anti-CD20 antibody, an anti-CD22 antibody, an anti-CD30 antibody, an anti-CD33 antibody, an anti-CD44 antibody, an anti-CD56 antibody, an anti-CD70 antibody, an anti-CD73 antibody, an anti-CD105 antibody, an anti-CEA antibody, an anti-A33 antibody, an anti-Cripto antibody, an anti-EphA2 antibody, an anti-G250 antibody, an anti-MUC1 antibody, an anti-Lewis Y antibody, an anti-TROP2 antibody, an anti-Claudin 18.2 antibody, an anti-VEGFR antibody, an anti-GPNMB antibody, an anti-Integrin antibody, an anti-PSMA antibody, an anti-Tenascin-C antibody, an anti-SLC44A4 antibody and an anti-Mesothelin antibody; for example, it may be trastuzumab or pertuzumab.

In the present application, the term "chimeric antibody" generally refers to an antibody obtained by fusing a variable region of a murine antibody and a constant region of a human antibody, which can reduce an immune response induced by the murine antibody. For establishment of a chimeric antibody, a hybridoma secreting murine specific monoclonal antibody can be established, and a variable region gene is cloned from the mouse hybridoma cells; then a constant region gene of human antibody can be cloned as required, and the mouse variable region gene and the human constant region gene are connected to form a chimeric gene; then the chimeric gene is inserted into an expression vector, wherein chimeric antibody molecules can be expressed in a eukaryotic system or a prokaryotic system.

In the present application, the term "humanized antibody", also referred to as CDR-grafted antibody, generally refers to an antibody produced by grafting mouse CDR sequences into a human antibody variable region framework, i.e., an antibody produced in a different type of human germline antibody framework sequence. Therefore, the heterogeneous reaction induced by the presence of a large number of mouse protein components in the chimeric antibody can be overcome. Such framework sequences can be obtained from public DNA databases or disclosed references that include germline antibody gene sequences. For example, germline DNA sequences of human heavy and light chain variable region genes can be obtained from the "VBase" human germline sequence database.

In the present application, the term "fully humanized antibody", "fully human antibody" or "completely human antibody", also known as "fully humanized monoclonal antibody", may have both humanized variable region and constant region so as to eliminate immunogenicity and toxic side effects. The development of monoclonal antibodies has four stages, namely murine monoclonal antibodies, chimeric monoclonal antibodies, humanized monoclonal antibodies and fully humanized monoclonal antibodies. The antibodies or ligands described herein can be fully humanized monoclonal antibodies. Relevant technologies for the preparation of fully human antibodies may be: human hybridoma technology, EBV-transformed B-lymphocyte technology, phage display technology, transgenic mouse antibody preparation technology, single B-cell antibody preparation technology, and the like.

In the present application, the term "CDR" generally refers to one of the 6 hypervariable regions within the variable domain of an antibody which contribute primarily to antigen binding. One of the most common definitions of the 6 CDRs is provided by Kabat E. A. et al., (1991) Sequences of proteins of immunological interest. NIH Publication 91-3242; Chothia et al., "Canonical Structures For the Hypervariable Regions of Immunoglobulins", *J. Mol. Biol.* 196:901 (1987); and MacCallum et al., "Antibody-Antigen Interactions: Contact Analysis and Binding Site Topography", *J. Mol. Biol.* 262:732 (1996). As used herein, the Kabat definition of CDRs can be applied to CDR1, CDR2 and CDR3 of the light chain variable domain (CDR L1, CDR L2, CDR L3 or L1, L2, L3), and CDR 1, CDR2 and CDR3 of the heavy chain variable domain (CDR H1, CDR H2, CDR H3 or H1, H2, H3).

In the present application, the term "methylene" generally refers to a residue derived by removal of two hydrogen atoms from a group having 1 carbon atom. Methylene may be substituted or unsubstituted, or replaced or unreplaced. The term "alkylene" generally refers to a saturated linear or branched aliphatic hydrocarbon group having 2 residues derived from the parent alkane by removal of two hydrogen atoms from the same carbon atom or two different carbon atoms, and it may be a linear or branched group containing 1 to 20 carbon atoms, such as alkylene containing 1 to 12 carbon atoms (e.g., 1 to 6 carbon atoms). Non-limiting examples of alkylene groups include, but are not limited to, methylene(—$CH_2$—), 1,1-ethylidene(—$CH(CH_3)$—), 1,2-ethylidene(—$CH_2CH_2$)—, 1,1-propylidene(—CH($CH_2CH_3$)—), 1,2-propylidene(—$CH_2CH(CH_3)$—), 1,3-propylidene(—$CH_2CH_2CH_2$—), 1,4-butylidene(—$CH_2CH_2CH_2CH_2$—), 1,5-butylidene(—$CH_2CH_2CH_2CH_2CH_2$—), and the like. Alkylene groups may be substituted or unsubstituted, replaced or unreplaced. For example, when it is substituted, substitution with a substituent may be performed at any available linking point, and the substituent is preferably independently optionally selected from one or more of alkyl, alkenyl, alkynyl, alkoxy, alkylthio, alkylamino, halogen, mercapto, hydroxy, nitro, cyano, cycloalkyl, heterocyclyl, aryl, heteroaryl, cycloalkoxy, heterocycloalkoxy, cycloalkylthio, heterocycloalkylthio, and oxo, and it may, e.g., be hydrogen, protium, deuterium, tritium, halogen, —$NO_2$, —CN, —OH, —SH, —$NH_2$, —C(O)H, —$CO_2$H, —C(O)C(O)H, —C(O)$CH_2$C(O)H, —S(O)H, —S(O)$_2$H, —C(O)$NH_2$, —$SO_2NH_2$, —OC(O)H, —N(H)$SO_2$H or a $C_{1-6}$ aliphatic group.

In the present application, the term "arylene" generally refers to a group having two residues derived by removal of two hydrogen atoms from the same carbon atom or two different carbon atoms of the aromatic ring. The term "aromatic ring" may refer to a 6-14 membered all-carbon monocyclic ring or fused polycyclic ring (i.e., rings which share adjacent pairs of carbon atoms) having a conjugated π-electron system, and it may be 6-10 membered, such as benzene and naphthalene. The aromatic ring can be fused to a heteroaryl, heterocyclyl or cycloalkyl ring, wherein the ring connected to the parent moiety is the aryl ring. Aryl may be substituted or unsubstituted, and when it is substituted, the substituent is preferably one or more of the following groups independently selected from the group consisting of: alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio and heterocycloalkylthio.

In the present application, the term "heteroarylene" generally refers to a group having two residues derived by removal of two hydrogen atoms from the same carbon atom or two different carbon atoms of the heteroaromatic ring. The term "heteroaromatic ring" refers to a heteroaromatic system comprising 1 to 4 heteroatoms and 5 to 14 ring atoms, wherein the heteroatoms may be selected from the group consisting of: oxygen, sulfur and nitrogen. Heteroaryl may be 5-10 membered and may be 5- or 6-membered, such as furanyl, thienyl, pyridinyl, pyrrolyl, N-alkylpyrrolyl, pyrimidinyl, pyrazinyl, imidazolyl and tetrazolyl. The heteroaromatic ring can be fused to an aryl, heterocyclyl or cycloalkyl ring, wherein the ring connected to the parent moiety is the heteroaromatic ring. Heteroarylene may be optionally substituted or unsubstituted, and when it is substituted, the substituent is preferably one or more of the following groups independently selected from the group consisting of: alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio and heterocycloalkylthio.

In the present application, the term "heterocyclylene" generally refers to a 3-7 membered monocyclic structure, a fused 7-10 membered bicyclic heterocyclic structure or a bridged 6-10 membered bicyclic heterocyclic structure that is stable and non-aromatic. These cyclic structures may be saturated or partially saturated, and contain one or more heteroatoms in addition to carbon atoms, wherein the heteroatoms may be selected from the group consisting of: oxygen, sulfur and nitrogen. For example, they contain 1 to 4 heteroatoms as defined above. When used to refer to atoms on a heterocyclic cyclic structure, the term "nitrogen" may include nitrogen that undergoes a substitution reaction. Heterocyclylene may be substituted or unsubstituted.

In the present application, the term "carbocyclylene" generally refers to a group having two residues derived by removal of two hydrogen atoms from the same carbon atom or two different carbon atoms of the carbon ring. The term "carbon ring" generally refers to a saturated or partially unsaturated monocyclic or polycyclic cyclic hydrocarbon, and it contains 3 to 20 carbon atoms, may contain 3 to 12 carbon atoms, may contain 3 to 10 carbon atoms, and may contain 3 to 8 carbon atoms. Non-limiting examples of monocyclic carbon ring include cyclopropane, cyclobutane, cyclopentane, cyclopentene, cyclohexane, cyclohexene, cyclohexadiene, cycloheptane, cycloheptatriene, cyclooctane, and the like; polycyclic carbon ring may include spiro, fused and bridged carbon rings. Carbocyclylene may be substituted or unsubstituted.

In the present application, the term "partially unsaturated" generally means that the cyclic structure contains at least one double or triple bond between the ring molecules. The term "partially unsaturated" encompasses cyclic structures having multiple sites of unsaturation, but is not intended to include aromatic or heteroaromatic rings defined herein. The term "unsaturated" means that the moiety has one or more degrees of unsaturation.

In the present application, the term "halogen" generally refers to fluorine, chlorine, bromine or iodine, and it may be, for example, fluorine or chlorine.

In the present application, the term "aliphatic group" generally refers to a linear hydrocarbon, branched hydrocarbon or cyclic hydrocarbon having 1 to 12 carbon atoms, and the hydrocarbon may be either a fully saturated hydrocarbon or a hydrocarbon with one or more unsaturated units, but the unsaturated units are not aromatic groups. For example, suitable aliphatic groups may include substituted or unsubstituted linear, branched or cyclic alkyl, alkenyl, alkynyl and mixtures thereof, such as (cycloalkyl)alkyl, (cycloalkenyl)alkyl or (cycloalkyl)alkenyl. For example, aliphatic groups have 1 to 12, 1 to 8, 1 to 6, 1 to 4 or 1 to 3 carbon atoms.

In the present application, the term "optional" or "optionally" generally means that the event or circumstance subsequently described may, but not necessarily, occur, and that the description includes instances where the event or circumstance occurs or does not occur. For example, "heterocyclyl group optionally substituted with alkyl" means that alkyl may be, but not necessarily, present, and that the description may include instances where the heterocyclyl group is or is not substituted with alkyl.

In the present application, the term "substituted" generally means that one or more hydrogen atoms in the group, for example, up to 5 (e.g., 1 to 3) hydrogen atoms, are each independently substituted with a corresponding number of substituents. A substituent is only in its possible chemical position, and those skilled in the art will be able to determine (by experiments or theories) possible or impossible substitution without undue efforts. For example, it may be unstable when amino or hydroxy having a free hydrogen is bound to a carbon atom having an unsaturated (such as olefin) bond.

In the present application, the term "0 or more (e.g., 0 or at least 1, 0 or 1, or 0) methylene units are replaced" generally means that when the structure comprises one or more methylene units, the one or more methylene units may be unsubstituted or replaced by one or more groups that are not methylene (e.g., —NHC(O)—, —C(O)NH—, —C(O)—, —OC(O)—, —C(O)O—, —NH—, —O—, —S—, —SO—, —SO$_2$—, —PH—, —P(=O)H—, —NHSO$_2$—, —SO$_2$NH—, —C(=S)—, —C(=NH)—, —N=N—, —C=N—, —N=C— or —C(=N$_2$)—).

One or more hydrogen atoms in the group, for example, up to 5 (e.g., 1 to 3) hydrogen atoms, are each independently substituted with a corresponding number of substituents. A substituent is only in its possible chemical position, and those skilled in the art will be able to determine (by experiments or theories) possible or impossible substitution without undue efforts. For example, it may be unstable when amino or hydroxy having a free hydrogen is bound to a carbon atom having an unsaturated (such as olefin) bond.

In the present application, the term "compound" generally refers to a substance having two or more different elements. For example, the compound disclosed herein may be an organic compound. For example, the compound disclosed herein may be a compound having a molecular weight of no more than 500, a compound having a molecular weight of no more than 1000, a compound having a molecular weight of no less than 1000, or a compound having a molecular weight of no less than 10,000 or no less than 100,000. In the present application, the compound may also refer to a compound that involves linking by a chemical bond, for example, a compound where one or more molecules having a molecular weight of no more than 1000 are linked, by a chemical bond, to a biological macromolecule, wherein the biological macromolecule may be polysaccharide, protein, nucleic acid, polypeptide, and the like. For example, the compound disclosed herein may include a compound where a protein is linked to one or more molecules having a molecular weight of no more than 1000, may include a compound where a protein is linked to one or more molecules having a molecular weight of no more than 10,000, and may include a compound where a protein is linked to one or more molecules having a molecular weight of no more than 100,000.

In some embodiments, the cytotoxic drug of the compound disclosed herein is directly or indirectly linked to a ligand. In some embodiments, the cytotoxic drug of the compound disclosed herein is directly linked to a ligand via a covalent bond. In some embodiments, the cytotoxic drug of the compound disclosed herein is linked to a ligand via a linker structure. In some embodiments, the compound disclosed herein is a ligand-drug conjugate having a ligand linked to a cytotoxic drug via a linker structure, wherein the cytotoxic drug comprises the structural formula II-A, II-A-1, II-A-2, II-A-3, II-A-4, II-A-5, II-A-6, II-A-7, II-A-8, II-A-9, II-A-10, II-A-11 or II-A-12 disclosed herein, wherein ring A, $X^1$, $L^1$, and $R^2$ are each defined as in embodiments of the first aspect.

In some embodiments, the compound disclosed herein is a ligand-drug conjugate or ADC. In some embodiments, a "mixture" of a compound refers to a composition comprising one or more of the compound and the tautomer, the mesomer, the racemate, the enantiomer and the diastereoisomer thereof. In some embodiments, a "mixture" of a compound refers to a composition comprising its heterogeneous DAR distribution. In one embodiment, a mixture of a compound comprises an ADC having a DAR distribution of 1 to 10, e.g., 1, 2, 3, 4, 5, 6, 7, 8, 9 or 10 (a drug loading of 1, 2, 3, 4, 5, 6, 7, 8, 9 or 10). In one embodiment, the ADC mixture comprises the following two: an ADC with DAR of 6 or less (a drug loading of 6 or less) and an ADC with DAR of 8 or more (a drug loading of 8 or more).

Unless otherwise indicated, the structures described herein may also include compounds that differ only in the presence or absence of one or more isotopically enriched atoms. For example, compounds having a structure identical to the structure disclosed herein except for the substitution of the hydrogen atom with deuterium or tritium or the substitution of the carbon atom with carbon 13 or carbon 14 are within the scope of the present application.

In the present application, the term "pharmaceutical composition" generally refers to a mixture containing one or more of the compounds described herein or a physiologically/pharmaceutically acceptable salt or pro-drug thereof, and other chemical components, for example physiologically/pharmaceutically acceptable carriers and excipients. The pharmaceutical composition may promote the administration to an organism, which facilitates the absorption of the active ingredient, thereby exerting biological activities. For preparation of conventional pharmaceutical compositions, reference can be made to Chinese Pharmacopoeia.

In the present application, the term "pharmaceutically acceptable salt" generally refers to a salt of a compound or ligand-drug conjugate disclosed herein, or a salt of a compound described herein. Such salts may be safe and/or effective when used in a mammals and may possess the required biological activity, and the antibody-antibody drug conjugate compound disclosed herein may form a salt with an acid, and non-limiting examples of pharmaceutically acceptable salts include: hydrochloride, hydrobromide, hydriodate, sulphate, bisulfate, citrate, acetate, succinate, ascorbate, oxalate, nitrate, sorbate, hydrophosphate, dihydrophosphate, salicylate, hydrocitrate, tartrate, maleate, fumarate, formate, benzoate, mesylate, ethanesulfonate, benzenesulphonate and p-toluenesulfonate.

In the present application, the term "solvate" or "solvent compound" generally refers to a pharmaceutical acceptable solvate formed by a ligand-drug conjugate compound disclosed herein and one or more solvent molecules, and non-limiting examples of solvent molecules include water, ethanol, acetonitrile, isopropanol, DMSO and ethyl acetate.

The term "drug loading" generally refers to the average amount of cytotoxic drug loaded per ligand and may also be expressed as the ratio of cytotoxic drug to antibody, and the cytotoxic drug loading may range from 0 to 12 (e.g., 1 to 10) cytotoxic drugs per ligand (Ab). In the embodiments of the present application, the drug loading is expressed as $N^a$, and exemplary values may be an average of 1, 2, 3, 4, 5, 6, 7, 8, 9 and 10. The drug loading per ADC molecule after the coupling reaction can be characterized by conventional methods such as UV/visible spectroscopy, mass spectrometry, ELISA assays and HPLC.

The pharmaceutical composition may be in the form of a sterile injectable aqueous or oily suspension for intramuscular and subcutaneous administration. The suspension can be prepared according to a known technique using those suitable dispersing agents or wetting agents and suspending agents described above. The sterile injectable formulation may also be a sterile injection or suspension prepared in a parenterally acceptable non-toxic diluent or solvent, such as a solution prepared in 1,3-butanediol. In addition, a sterile fixed oil may be conveniently used as a solvent or a suspending medium. For example, any blend fixed oil including synthetic mono- or di-glycerides can be used. In addition, fatty acids such as oleic acid may also be used in the preparation of injections.

In the present application, the term "comprise" "comprising", "contain" or "containing" is generally intended to include the explicitly specified features without excluding other elements. The terms "no less than" and "no more than" generally refer to the situations where the number itself is included.

In the present application, the term "about" generally means varying by 0.5%-10% above or below the stated value, for example, varying by 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% above or below the stated value.

DETAILED DESCRIPTION OF THE INVENTION

In a first aspect, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (I-A):

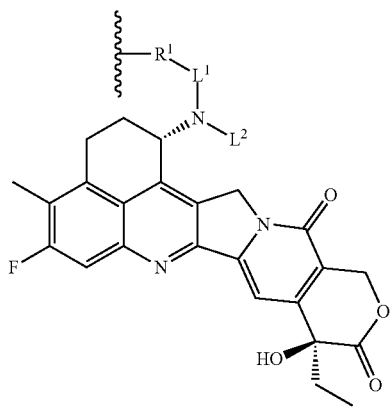

(I-A)

wherein, $R^1$ may be selected from the group consisting of: —O—, —(R²)N—, —P(=O)(R²)— and —S—;

$L^2$ may be —(C(R^{3a})(R^{3b}))_m—R, and m may be selected from the group consisting of integers ≥1;

wherein 0 or no less than 1 methylene unit of $L^2$ may be independently replaced by -Cy-, —N(R⁴)C(O)—, —C(O)N(R⁴)—, —C(O)—, —OC(O)—, —C(O)O—, —NR⁴—, —O—, —S—, —SO—, —SO₂—, —P(R⁴)—, —P(=O)(R⁴)—, —N(R⁴)SO₂—, —SO₂N(R⁴)—, —C(=S)—, —C(=NR⁴)—, —N=N—, —C=N—, —N=C— or —C(=N₂)—;

$L^1$ may be —(C(R^{5a})(R^{5b}))_n—, and n may be selected from the group consisting of integers ≥1;

wherein 0 or no less than 1 methylene unit of $L^1$ may be independently replaced by -Cy-, —N(R⁶)C(O)—, —C(O)N(R⁶)—, —C(O)—, —OC(O)—, —C(O)O—, —NR⁶—, —O—, —S—, —SO—, —SO₂—, —P(R⁶)—, —P(=O)(R⁶)—, —N(R⁶)SO₂—, —SO₂N(R⁶)—, —C(=S)—, —C(=NR⁶)—, —N=N—, —C=N—, —N=C— or —C(=N₂)—;

-Cy- may be selected from the group consisting of: 6-10 membered arylene, 5-8 membered heteroarylene, 3-10 membered heterocyclylene, and 3-10 membered saturated or partially unsaturated carbocyclylene, wherein -Cy- is unsubstituted or may be independently substituted with no less than 1 substituent R⁷;

wherein each $R^{3a}$, each $R^{3b}$, each $R^4$, each $R^{5a}$, each $R^{5b}$ and each $R^6$ may each independently be hydrogen, protium, deuterium, tritium, halogen, —NO₂, —CN, —OR, —SR, —N(R^a)(R^b), —C(O)R, —CO₂R, —C(O)C(O)R, —C(O)CH₂C(O)R, —S(O)R, —S(O)₂R, —C(O)N(R^a)(R^b), —SO₂N(R^a)(R^b), —OC(O)R, —N(R)SO₂R, or a $C_{1-6}$ aliphatic group which may be optionally substituted with R; or, $R^{3a}$ and $R^{5a}$, $R^4$ and $R^{5a}$, $R^{3a}$ and $R^6$ or $R^4$ and $R^6$ may each independently optionally form a ring B together with an atom therebetween, wherein the ring B may be selected from the group consisting of: 5-8 membered heteroarylene and 3-10 membered saturated or partially unsaturated heterocyclylene, and the ring B is unsubstituted or may be substituted with no less than 1 substituent R⁸;

wherein each $R^2$, each $R^7$ and each $R^8$ may each independently be hydrogen, protium, deuterium, tritium, halogen, —NO₂, —CN, —OR, —SR, —N(R^a)(R^b), —C(O)R, —CO₂R, —C(O)C(O)R, —C(O)CH₂C(O)R, —S(O)R, —S(O)₂R, —C(O)N(R^a)(R^b), —SO₂N(R^a)(R^b), —OC(O)R, —N(R)SO₂R, or a $C_{1-6}$ aliphatic group which may be optionally substituted with R;

wherein each R, each $R^a$ and each $R^b$ may each independently be hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a $C_{1-6}$ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (I-A):

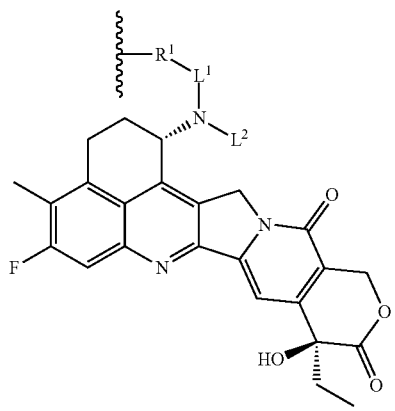

(I-A)

wherein, $R^1$ may be selected from the group consisting of: —O—, —($R^2$)N—, —P(=O)($R^2$)— and —S—;

$L^2$ may be —(C($R^{3a}$)($R^{3b}$))$_m$—R, and m may be selected from the group consisting of integers ≥1;

wherein 0 or no less than 1 methylene unit of $L^2$ may be independently replaced by -Cy-, —N($R^4$)C(O)—, —C(O)N($R^4$)—, —C(O)—, —OC(O)—, —C(O)O—, —N$R^4$—, —O—, —S—, —SO—, —SO$_2$—, —P($R^4$)—, —P(=O)($R^4$)—, —N($R^4$)SO$_2$—, —SO$_2$N($R^4$)—, —C(=S)—, —C(=N$R^4$)—, —N=N—, —C=N—, —N=C— or —C(=N$_2$)—;

$L^1$ may be —(C($R^{5a}$)($R^{5b}$))$_n$—, and n may be selected from the group consisting of integers ≥1;

wherein 0 or no less than 1 methylene unit of $L^1$ may be independently replaced by -Cy-, —N($R^6$)C(O)—, —C(O)N($R^6$)—, —C(O)—, —OC(O)—, —C(O)O—, —N$R^6$—, —O—, —S—, —SO—, —SO$_2$—, —P($R^6$)—, —P(=O)($R^6$)—, —N($R^6$)SO$_2$—, —SO$_2$N($R^6$)—, —C(=S)—, —C(=N$R^6$)—, —N=N—, —C=N—, —N=C— or —C(=N$_2$)—;

-Cy- may be selected from the group consisting of: 6-10 membered arylene, 5-8 membered heteroarylene, 3-10 membered heterocyclylene, and 3-10 membered saturated or partially unsaturated carbocyclylene, wherein -Cy- is unsubstituted or may be independently substituted with no less than 1 substituent $R^7$;

wherein each $R^{3a}$, each $R^{3b}$, each $R^4$, each $R^{5a}$, each $R^{5b}$ and each $R^6$ may each independently be hydrogen, protium, deuterium, tritium, halogen, —NO$_2$, —CN, —OR, —SR, —N($R^a$)($R^b$), —C(O)R, —CO$_2$R, —C(O)C(O)R, —C(O)CH$_2$C(O)R, —S(O)R, —S(O)$_2$R, —C(O)N($R^a$)($R^b$), —SO$_2$N($R^a$)($R^b$), —OC(O)R, —N(R)SO$_2$R, or a $C_{1-6}$ aliphatic group which may be optionally substituted with R;

wherein each $R^2$, each $R^7$ and each $R^8$ may each independently be hydrogen, protium, deuterium, tritium, halogen, —NO$_2$, —CN, —OR, —SR, —N($R^a$)($R^b$), —C(O)R, —CO$_2$R, —C(O)C(O)R, —C(O)CH$_2$C(O)R, —S(O)R, —S(O)$_2$R, —C(O)N($R^a$)($R^b$), —SO$_2$N($R^a$)($R^b$), —OC(O)R, —N(R)SO$_2$R, or a $C_{1-6}$ aliphatic group which may be optionally substituted with R;

wherein each R, each $R^a$ and each $R^b$ may each independently be hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a $C_{1-6}$ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (I-A):

for example, wherein $R^{3a}$ and $R^{5a}$, $R^4$ and $R^{5a}$, $R^{3a}$ and $R^6$ or $R^4$ and $R^6$ may each independently optionally form a ring B together with an atom therebetween, wherein the ring B may be selected from the group consisting of: 5-8 membered heteroarylene and 3-10 membered saturated or partially unsaturated heterocyclylene, and the ring B is unsubstituted or may be substituted with no less than 1 substituent $R^8$; each $R^{3a}$, each $R^{3b}$, each $R^4$, each $R^{5a}$, each $R^{5b}$ and each $R^6$ may each independently be hydrogen, protium, deuterium, tritium, halogen, —NO$_2$, —CN, —OR, —SR, —N($R^a$)($R^b$), —C(O)R, —CO$_2$R, —C(O)C(O)R, —C(O)CH$_2$C(O)R, —S(O)R, —S(O)$_2$R, —C(O)N($R^a$)($R^b$), —SO$_2$N($R^a$)($R^b$), —OC(O)R, —N(R)SO$_2$R, or a $C_{1-6}$ aliphatic group which may be optionally substituted with R; or $R^{3a}$ and $R^{5a}$, $R^4$ and $R^{5a}$, $R^{3a}$ and $R^6$ or $R^4$ and $R^6$ may each independently optionally form a ring B together with an atom therebetween, wherein the ring B may be selected from the group consisting of: 5-8 membered heteroarylene and 3-10 membered saturated or partially unsaturated heterocyclylene, and the ring B is unsubstituted or may be substituted with no less than 1 substituent $R^8$;

for example, wherein $R^{3a}$ and $R^{5a}$ may form a ring B together with an atom therebetween, wherein the ring B may be selected from the group consisting of: 5-8 membered heteroarylene and 3-10 membered saturated or partially unsaturated heterocyclylene, and the ring B is unsubstituted or may be substituted with no less than 1 substituent $R^8$; each $R^{3b}$, each $R^4$, each $R^{5b}$ and each $R^6$ may each independently be hydrogen, protium, deuterium, tritium, halogen, —NO$_2$, —CN, —OR, —SR, —N($R^a$)($R^b$), —C(O)R, —CO$_2$R, —C(O)C(O)R, —C(O)CH$_2$C(O)R, —S(O)R, —S(O)$_2$R, —C(O)N($R^a$)($R^b$), —SO$_2$N($R^a$)($R^b$), —OC(O)R, —N(R)SO$_2$R, or a $C_{1-6}$ aliphatic group which may be optionally substituted with R; or $R^{3a}$ and $R^{5a}$, $R^4$ and $R^{5a}$, $R^{3a}$ and $R^6$ or $R^4$ and $R^6$ may each independently optionally form a ring B together with an atom therebetween, wherein the ring B may be selected from the group consisting of: 5-8 membered heteroarylene and 3-10 membered saturated or partially unsaturated heterocyclylene, and the ring B is unsubstituted or may be substituted with no less than 1 substituent $R^8$;

for example, wherein $R^4$ and $R^{5a}$ may form a ring B together with an atom therebetween, wherein the ring B may be selected from the group consisting of: 5-8 membered heteroarylene and 3-10 membered saturated or partially unsaturated heterocyclylene, and the ring B is unsubstituted or may be substituted with no less than 1 substituent $R^8$; each $R^{3a}$, each $R^{3b}$, each $R^{5b}$ and each $R^6$ may each independently be hydrogen, protium, deuterium, tritium, halogen, —NO$_2$, —CN, —OR, —SR, —N($R^a$)($R^b$), —C(O)R, —CO$_2$R, —C(O)C(O)R, —C(O)CH$_2$C(O)R, —S(O)R, —S(O)$_2$R, —C(O)N($R^a$)($R^b$), —SO$_2$N($R^a$)($R^b$), —OC(O)R, —N(R)SO$_2$R, or a $C_{1-6}$ aliphatic group which may be optionally substituted with R; or $R^{3a}$ and $R^{5a}$, $R^4$ and $R^{5a}$, $R^{3a}$ and $R^6$ or $R^4$ and $R^6$ may each independently optionally form a ring B together with an atom therebetween, wherein the ring B may be selected from the group consisting of: 5-8 membered heteroarylene and 3-10 membered saturated or partially unsaturated heterocyclylene, and the ring B is unsubstituted or may be substituted with no less than 1 substituent $R^8$;

for example, wherein $R^{3a}$ and $R^6$ may form a ring B together with an atom therebetween, wherein the ring B may be selected from the group consisting of: 5-8 membered heteroarylene and 3-10 membered saturated or partially unsaturated heterocyclylene, and the ring B is unsubstituted or may be substituted with no less than 1 substituent $R^8$; each $R^{3b}$, each $R^4$, each $R^{5a}$ and each $R^{5b}$ may each independently be hydrogen, protium, deuterium, tritium, halogen, —NO$_2$, —CN, —OR, —SR, —N($R^a$)($R^b$), —C(O)R, —CO$_2$R, —C(O)C(O)R, —C(O)CH$_2$C(O)R, —S(O)R, —S(O)$_2$R, —C(O)N($R^a$)($R^b$), —SO$_2$N($R^a$)($R^b$), —OC(O)R, —N(R)SO$_2$R, or a $C_{1-6}$ aliphatic group which may be optionally substituted with R; or $R^{3a}$ and $R^{5a}$, $R^4$ and $R^{5a}$, $R^{3a}$ and $R^6$ or $R^4$ and $R^6$ may each independently optionally form a ring B together with an atom therebetween, wherein the ring B may be selected from the group consisting of: 5-8 membered heteroarylene and 3-10 membered saturated or partially unsaturated heterocyclylene, and the ring B is unsubstituted or may be substituted with no less than 1 substituent $R^8$;

for example, wherein $R^4$ and $R^6$ may independently optionally form a ring B together with an atom therebetween, wherein the ring B may be selected from the group consisting of: 5-8 membered heteroarylene and 3-10 membered saturated or partially unsaturated heterocyclylene, and the ring B is unsubstituted or may be substituted with no less than 1 substituent $R^8$; each $R^{3a}$, each $R^{3b}$, each $R^{5a}$ and each $R^{5b}$ may each independently be hydrogen, protium, deuterium, tritium, halogen, —$NO_2$, —CN, —OR, —SR, —N($R^a$)($R^b$), —C(O)R, —$CO_2$R, —C(O)C(O)R, —C(O)$CH_2$C(O)R, —S(O)R, —S(O)$_2$R, —C(O)N($R^a$)($R^b$), —$SO_2$N($R^a$)($R^b$), —OC(O)R, —N(R)$SO_2$R, or a $C_{1-6}$ aliphatic group which may be optionally substituted with R; or $R^{3a}$ and $R^{5a}$, $R^4$ and $R^{5a}$, $R^{3a}$ and $R^6$ or $R^4$ and $R^6$ may each independently optionally form a ring B together with an atom therebetween, wherein the ring B may be selected from the group consisting of: 5-8 membered heteroarylene and 3-10 membered saturated or partially unsaturated heterocyclylene, and the ring B is unsubstituted or may be substituted with no less than 1 substituent $R^8$;

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (I-A):

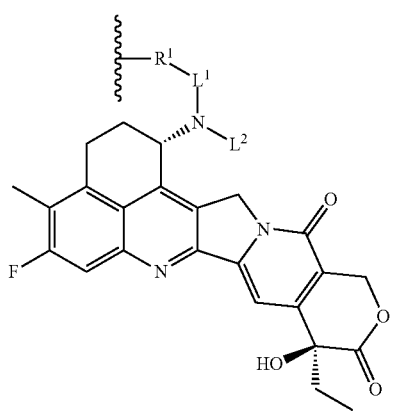

(I-A)

wherein, $R^1$ may be —O—;

$L^2$ may be —(C($R^{3a}$)($R^{3b}$))$_m$—R, and m may be selected from the group consisting of integers from 1 to 3;

wherein 0 methylene units of $L^2$ may be replaced;

$L^1$ may be —(C($R^{5a}$)($R^{1b}$))$_n$—, and n may be selected from the group consisting of integers from 2 to 4;

wherein 0, 1 or 2 methylene units of $L^1$ may be replaced by —N($R^6$)C(O)—, —C(O)—, —OC(O)—, —$NR^6$—, —O— or —C(=S)—;

wherein each $R^{3a}$, each $R^{3b}$, each $R^{5a}$, each $R^{5b}$ and each $R^6$ may each independently be hydrogen, halogen, or a $C_{1-6}$ aliphatic group which may be optionally substituted with R; or $R^{3a}$ and $R^{5a}$ may form a ring B together with an atom therebetween, wherein the ring B may be selected from 5 membered saturated heterocyclylene, and the ring B is unsubstituted;

R may be hydrogen or halogen.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (I-A):

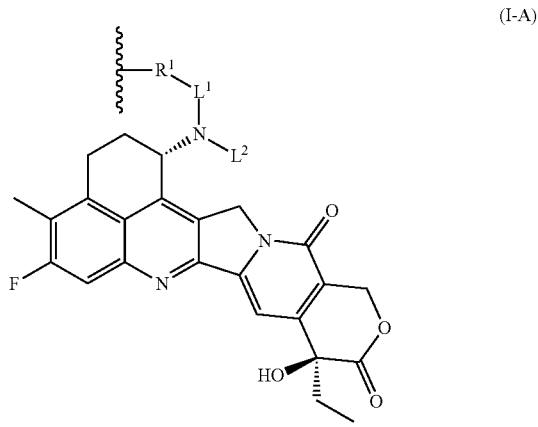

(I-A)

wherein, $R^1$ may be —O—;

$L^2$ may be —(C($R^{3a}$)($R^{3b}$))$_m$—R, and m may be selected from the group consisting of integers 1 and 2;

wherein 0 methylene units of $L^2$ may be replaced;

$L^1$ may be —(C($R^{5a}$)($R^{5b}$))$_n$—, and n may be selected from the group consisting of integers 2 and 3;

wherein 0 or 1 methylene unit of $L^1$ may be replaced by —C(O)—;

wherein each $R^{3a}$, each $R^{3b}$, each $R^{5a}$ and each $R^{5b}$ may each independently be hydrogen; or $R^{3a}$ and $R^{5a}$ may form a ring B together with an atom therebetween, wherein the ring B may be selected from 5 membered saturated heterocyclylene having 1 nitrogen heteroatom, and the ring B is unsubstituted;

R may be hydrogen.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (I-A):

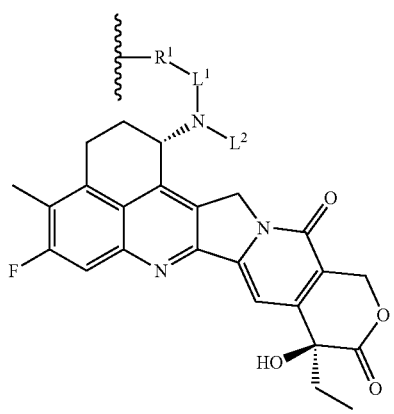

(I-A)

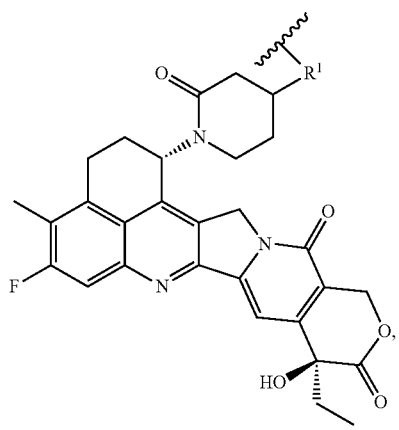

I-A-2 wherein, R¹ may be —O—;

L² may be —(C(R$^{3a}$)(R$^{3b}$))$_m$—R, and m may be selected from the group consisting of integers 1 and 2;

wherein 0 methylene units of L² may be replaced;

L¹ may be —(C(R$^{5a}$)(R$^{5b}$))$_2$—;

wherein 1 methylene unit of L¹ may be replaced by —C(O)—;

wherein each R$^{3a}$, each R$^{3b}$, each R$^{5a}$ and each R$^{5b}$ may each independently be hydrogen; or R$^{3a}$ and R$^{5a}$ may form a ring B together with an atom therebetween, wherein the ring B may be selected from 5 membered saturated heterocyclylene having 1 nitrogen heteroatom, and the ring B is unsubstituted;

R may be hydrogen.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise the following group of structures:

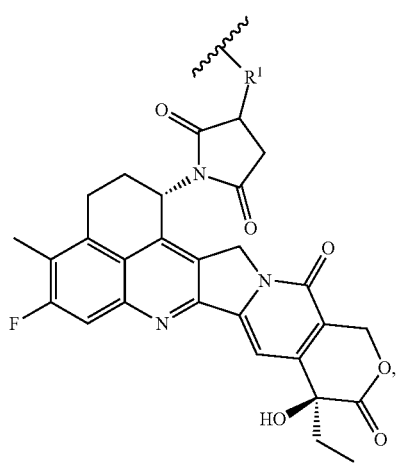

I-A-3

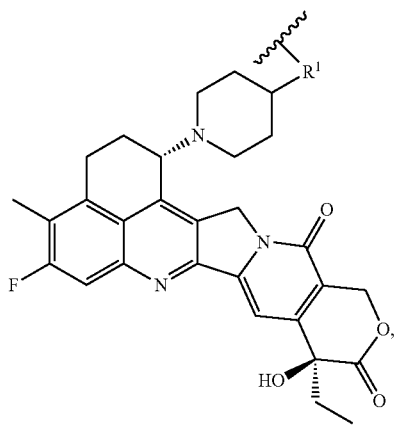

I-A-1

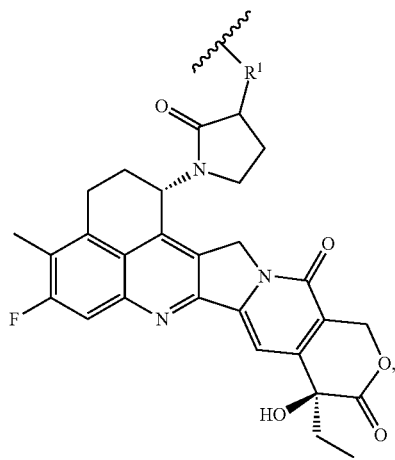

I-A-4

I-A-5
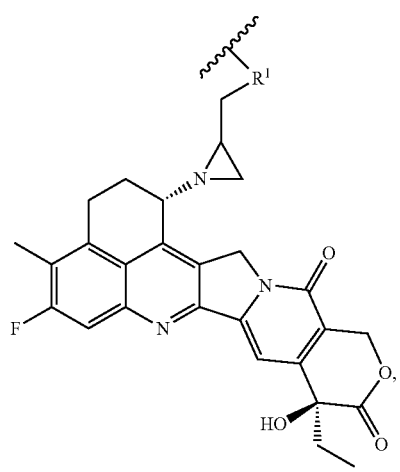
I-A-6
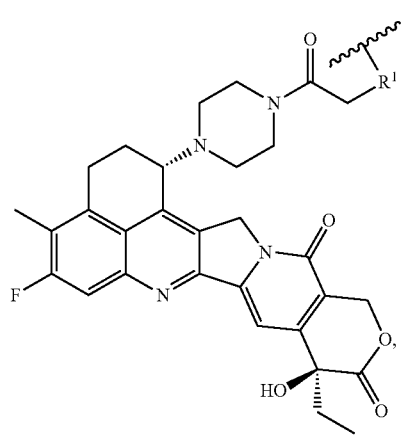
I-A-7
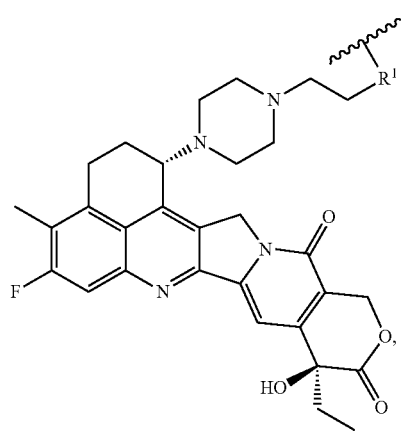
I-A-8
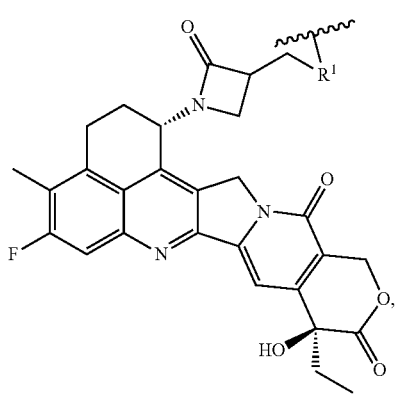
I-A-9
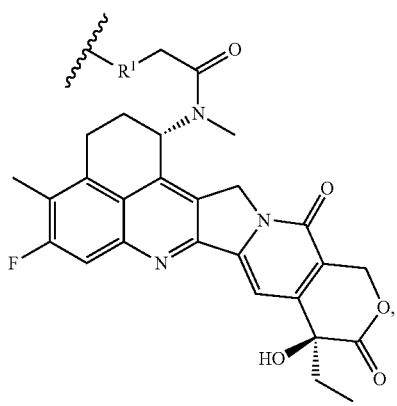
I-A-10
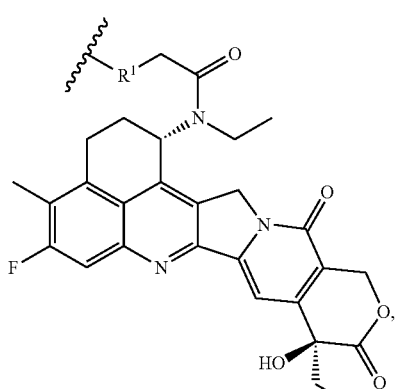
I-A-11
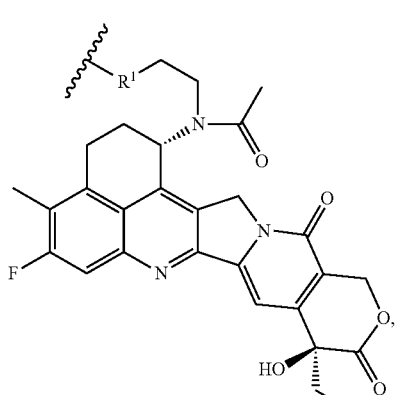

-continued

I-A-12
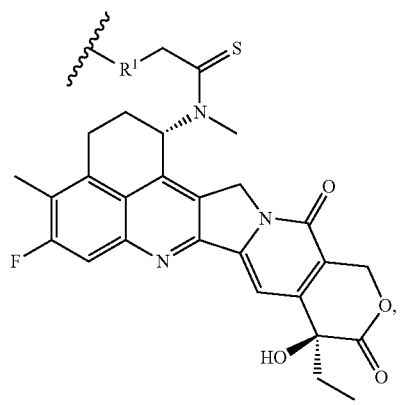

I-A-13
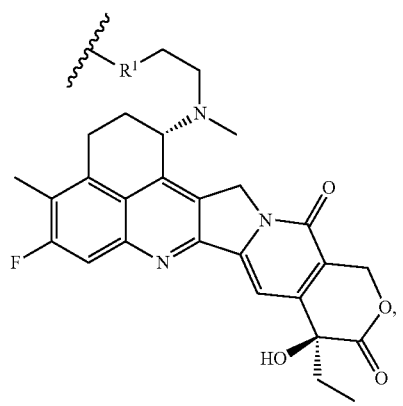

I-A-14
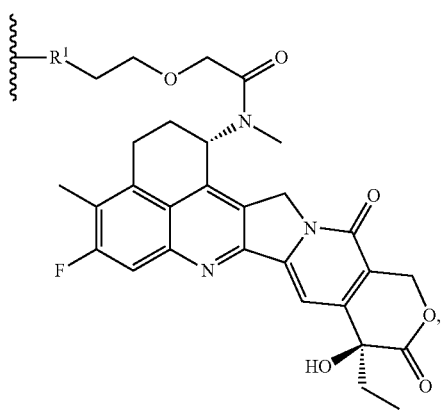

I-A-15
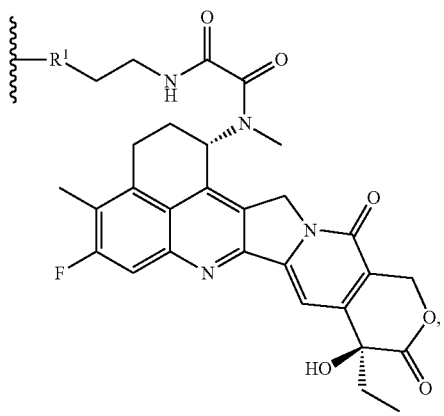

-continued

I-A-16
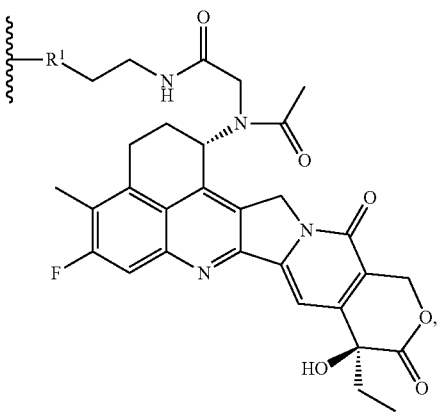

I-A-17
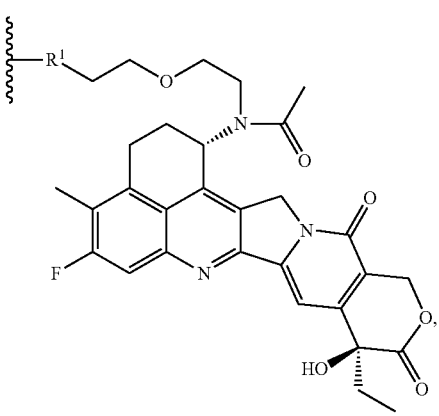

wherein, $R^1$ may be selected from the group consisting of: —O—, —HN—, —P(=O)H— and —S—.

In another embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-A):

(II-A)
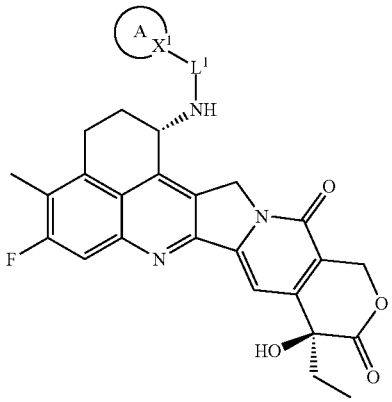

wherein, $X^1$ may be selected from the group consisting of: n, P, and saturated or unsaturated C; when $X^1$ may be saturated C, $X^1$ may be substituted with $R''$; ring A optionally links the structure shown as formula (II-A) to other molecular moieties;

when X¹ may be saturated C, ring A may be selected from the group consisting of: 3-10 membered saturated or partially unsaturated heterocyclyl, and 3-10 membered saturated or partially unsaturated carbocyclyl, wherein ring A may be substituted with 0 or no less than 1 substituent $R^{1a}$;

or, when X¹ may be unsaturated C, ring A may be selected from the group consisting of: 6-10 membered aryl, 5-8 membered heteroaryl, 3-10 membered partially unsaturated heterocyclyl, and 3-10 membered partially unsaturated carbocyclyl, wherein ring A may be substituted with 0 or no less than 1 substituent $R^{1b}$;

or, when X¹ may be N or P, ring A may be selected from the group consisting of: 5-8 membered heteroaryl and 3-10 membered saturated or partially unsaturated heterocyclyl, wherein ring A may be substituted with 0 or no less than 1 substituent $R^{1c}$;

when ring A may be selected from the group consisting of: 6-10 membered aryl, 5-8 membered heteroaryl, and 3-10 membered saturated or partially unsaturated carbocyclyl, ring A may be substituted with p L², wherein L² cannot be $R^n$;

or, when ring A may be 3-10 membered saturated or partially unsaturated heterocyclyl, ring A may be substituted with p L², or ring A may comprise q ring-forming heteroatom X², and X² is used to link the structure shown as formula (II-A) to other molecular moieties;

X² may be selected from the group consisting of: N and P;

L² may be —R²-L³-, and R² is used to link the structure shown as formula (II-A) to other molecular moieties;

L³ may be —(C($R^{3a}$)($R^{3b}$))$_m$—, wherein when L³ may comprise a methylene unit, 0 or no less than 1 methylene unit of L³ may be independently replaced by —N(R⁴)C(O)—, —C(O)N(R⁴)—, —C(O)—, —OC(O)—, —C(O)O—, —NR⁴—, —O—, —S—, —SO—, —SO₂—, —P(R⁴)—, —P(=O)(R⁴)—, —N(R⁴)SO₂—, —SO₂N(R⁴)—, —C(=S)—, —C(=NR⁴)—, —N=N—, —C=N—, —N=C— or —C(=N₂)—;

R² may be selected from the group consisting of: —O—, —($R^{2a}$)N—, —S— and —P(=O)($R^{2a}$)—;

L¹ may be —(C($R^{5a}$)($R^{5b}$))$_n$—, wherein when L¹ may comprise a methylene unit, 0 or no less than 1 methylene unit of L¹ may be independently replaced by —N(R⁶)C(O)—, —C(O)N(R⁶)—, —C(O)—, —OC(O)—, —C(O)O—, —NR⁶—, —O—, —S—, —SO—, —SO₂—, —P(R⁶)—, —P(=O)(R⁶)—, —N(R⁶)SO₂—, —SO₂N(R⁶)—, —C(=S)—, —C(=NR⁶)—, —N=N—, —C=N—, —N=C— or —C(=N₂)—;

wherein each $R^{1a}$, each $R^{1b}$, each $R^{1c}$, each $R^{2a}$, each $R^{3a}$, each $R^{3b}$, each R⁴, each $R^{5a}$, each $R^{5b}$ and each R⁶ may each independently be hydrogen, protium, deuterium, tritium, halogen, —NO₂, —CN, —OR, —SR, —N($R^a$)($R^b$), —C(O)R, —CO₂R, —C(O)C(O)R, —C(O)CH₂C(O)R, —S(O)R, —S(O)₂R, —C(O)N($R^a$)($R^b$), —SO₂N($R^a$)($R^b$), —OC(O)R, —N(R)SO₂R, or a $C_{1-6}$ aliphatic group which may be optionally substituted with R;

wherein each R, each $R^a$ and each $R^b$ may each independently be hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a $C_{1-6}$ aliphatic group;

m and n may each independently be selected from the group consisting of integers ≥0, and p and q may each independently be selected from the group consisting of integers ≥1.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-Ax):

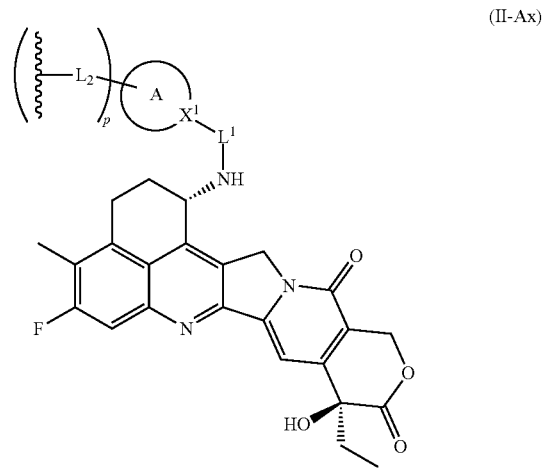

(II-Ax)

wherein, X¹ may be saturated C, and X¹ may be substituted with $R^n$;

ring A may be selected from the group consisting of: 3-10 membered saturated or partially unsaturated heterocyclyl and 3-10 membered saturated or partially unsaturated carbocyclyl, wherein ring A may be substituted with 0 or no less than 1 substituent $R^{1a}$;

ring A may be substituted with p L², wherein p may be selected from the group consisting of integers ≥1, and L² can not be $R^n$;

L² may be —R²-L³-;

L³ may be —(C($R^{3a}$)($R^{3b}$))$_m$—, and m may be selected from the group consisting of integers ≥0;

wherein when L³ may comprise a methylene unit, 0 or no less than 1 methylene unit of L³ may be independently replaced by —N(R⁴)C(O)—, —C(O)N(R⁴)—, —C(O)—, —OC(O)—, —C(O)O—, —NR⁴—, —O—, —S—, —SO—, —SO₂—, —P(R⁴)—, —P(=O)(R⁴)—, —N(R⁴)SO₂—, —SO₂N(R⁴)—, —C(=S)—, —C(=NR⁴)—, —N=N—, —C=N—, —N=C— or —C(=N₂)—;

R² may be selected from the group consisting of: —O—, —($R^{2a}$)N—, —S— and —P(=O)($R^{2a}$)—;

L¹ may be —(C($R^{5a}$)($R^{5b}$))$_n$—, and n may be selected from the group consisting of integers ≥0;

wherein when L¹ may comprise a methylene unit, 0 or no less than 1 methylene unit of L¹ may be independently replaced by —N(R⁶)C(O)—, —C(O)N(R⁶)—, —C(O)—, —OC(O)—, —C(O)O—, —NR⁶—, —O—, —S—, —SO—, —SO₂—, —P(R⁶)—, —P(=O)(R⁶)—, —N(R⁶)SO₂—, —SO₂N(R⁶)—, —C(=S)—, —C(=NR⁶)—, —N=N—, —C=N—, —N=C— or —C(=N₂)—;

wherein each $R^{1a}$, each $R^{2a}$, each $R^{3a}$, each $R^{3b}$, each R⁴, each $R^{5a}$, each $R^{5b}$, each R⁶ and each $R^n$ may each independently be hydrogen, protium, deuterium, tritium, halogen, —NO₂, —CN, —OR, —SR, —N(Rᵃ)
(Rᵇ), —C(O)R, —CO₂R, —C(O)C(O)R, —C(O)CH₂C
(O)R, —S(O)R, —S(O)₂R, —C(O)N(Rᵃ)(Rᵇ),
—SO₂N(Rᵃ)(Rᵇ), —OC(O)R, —N(R)SO₂R, or a C₁₋₆
aliphatic group which may be optionally substituted
with R;

wherein each R, each Rᵃ and each Rᵇ may each independently be hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a C₁₋₆ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-Ay):

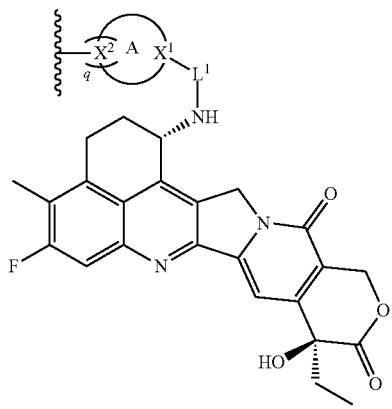

(II-Ay)

wherein, X¹ may be saturated C, and X¹ may be substituted with Rⁿ;
ring A may be 3-10 membered saturated or partially unsaturated heterocyclyl, and ring A can not be substituted or may be substituted with no less than 1 substituent R¹ᵃ;
ring A may comprise q ring-forming heteroatom X², and X² is used for direct or indirect linking of a ligand; q may be selected from the group consisting of integers ≥1, and X² may be selected from the group consisting of: N and P;
L¹ may be —(C(R⁵ᵃ)(R⁵ᵇ))ₙ—, and n may be selected from the group consisting of integers ≥0;
wherein 0 or no less than 1 methylene unit of L¹ may be independently replaced by —N(R⁶)C(O)—, —C(O)N(R⁶)—, —C(O)—, —OC(O)—, —C(O)O—, —NR⁶—, —O—, —S—, —SO—, —SO₂—, —P(R⁶)—, —P(=O)(R⁶)—, —N(R⁶)SO₂—, —SO₂N(R⁶)—, —C(=S)—, —C(=NR⁶)—, —N=N—, —C=N—, —N=C— or —C(=N₂)—;
wherein each R¹ᵃ, each R⁵ᵃ, each R⁵ᵇ, each R⁶ and each Rⁿ may each independently be hydrogen, protium, deuterium, tritium, halogen, —NO₂, —CN, —OR, —SR, —N(Rᵃ)(Rᵇ), —C(O)R, —CO₂R, —C(O)C(O)R, —C(O)CH₂C(O)R, —S(O)R, —S(O)₂R, —C(O)N(Rᵃ)(Rᵇ), —SO₂N(Rᵃ)(Rᵇ), —OC(O)R, —N(R)SO₂R, or a C₁₋₆ aliphatic group which may be optionally substituted with R;

wherein each R, each Rᵃ and each Rᵇ may each independently be hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a C₁₋₆ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-Ax):

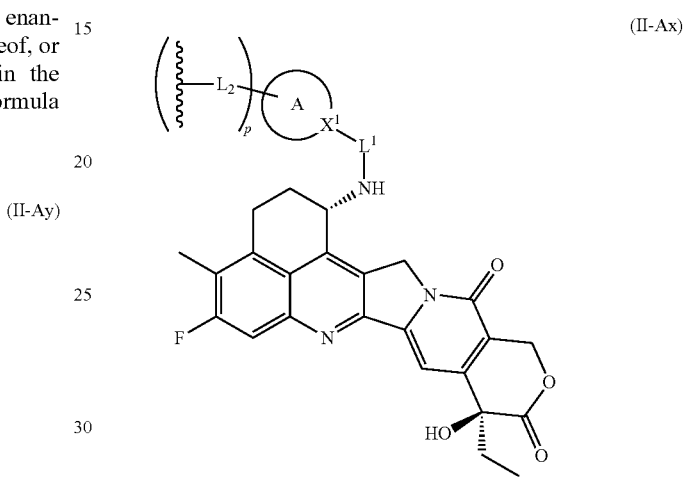

(II-Ax)

wherein, X¹ may be unsaturated C;
ring A may be selected from the group consisting of: 6-10 membered aryl, 5-8 membered heteroaryl, 3-10 membered partially unsaturated heterocyclyl, and 3-10 membered partially unsaturated carbocyclyl, and ring A can not be substituted or may be substituted with no less than 1 substituent R¹ᵇ;
ring A may be substituted with p L², wherein p may be selected from the group consisting of integers ≥1;
L² may be —R²-L³-, and R² is used for direct or indirect linking of a ligand;
L³ may be —(C(R³ᵃ)(R³ᵇ))ₘ—, and m may be selected from the group consisting of integers ≥0;
wherein 0 or no less than 1 methylene unit of L³ may be independently replaced by —N(R⁴)C(O)—, —C(O)N(R⁴)—, —C(O)—, —OC(O)—, —C(O)O—, —NR⁴—, —O—, —S—, —SO—, —SO₂—, —P(R⁴)—, —P(=O)(R⁴)—, —N(R⁴)SO₂—, —SO₂N(R⁴)—, —C(=S)—, —C(=NR⁴)—, —N=N—, —C=N—, —N=C— or —C(=N₂)—;
R² may be selected from the group consisting of: —O—, —(R²ᵃ)N—, —S— and —P(=O)(R²ᵃ)—;
L¹ may be —(C(R⁵ᵃ)(R⁵ᵇ))ₙ—, and n may be selected from the group consisting of integers ≥0;
wherein 0 or no less than 1 methylene unit of L¹ may be independently replaced by —N(R⁶)C(O)—, —C(O)N(R⁶)—, —C(O)—, —OC(O)—, —C(O)O—, —NR⁶—, —O—, —S—, —SO—, —SO₂—, —P(R⁶)—, —P(=O)(R⁶)—, —N(R⁶)SO₂—, —SO₂N(R⁶)—, —C(=S)—, —C(=NR⁶)—, —N=N—, —C=N—, —N=C— or —C(=N₂)—;
wherein each R¹ᵇ, each R²ᵃ, each R³ᵃ, each R³ᵇ, each R⁴, each R⁵ᵃ, each R⁵ᵇ and each R⁶ may each independently be hydrogen, protium, deuterium, tritium, halogen, —NO₂, —CN, —OR, —SR, —N(Rᵃ)(Rᵇ), —C(O)R, —CO₂R, —C(O)C(O)R, —C(O)CH₂C(O)R, —S(O)R, —S(O)₂R, —C(O)N(Rᵃ)(Rᵇ), —SO₂N(Rᵃ)(Rᵇ), —OC(O)R, —N(R)SO₂R, or a C₁₋₆ aliphatic group which may be optionally substituted with R;

wherein each R, each Rᵃ and each Rᵇ may each independently be hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a C₁₋₆ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-Ay):

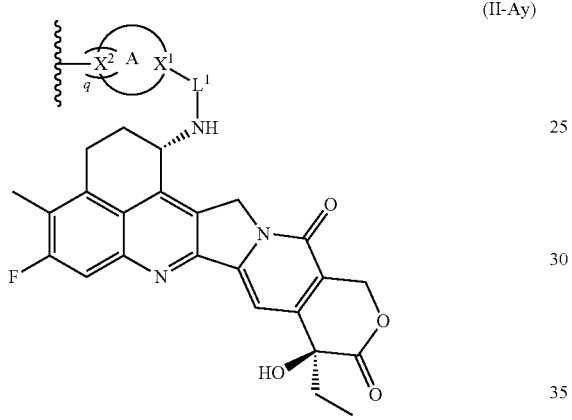

(II-Ay)

wherein, X¹ may be unsaturated C;

ring A may be 3-10 membered partially unsaturated heterocyclyl, and ring A can not be substituted or may be substituted with no less than 1 substituent R¹ᵇ;

ring A may comprise q ring-forming heteroatom X², and X² is used for direct or indirect linking of a ligand; q may be selected from the group consisting of integers ≥1, and X² may be selected from the group consisting of: N and P;

L¹ may be —(C(R⁵ᵃ)(R⁵ᵇ))ₙ—, and n may be selected from the group consisting of integers ≥0;

wherein 0 or no less than 1 methylene unit of L¹ may be independently replaced by —N(R⁶)C(O)—, —C(O)N(R⁶)—, —C(O)—, —OC(O)—, —C(O)O—, —NR⁶—, —O—, —S—, —SO—, —SO₂—, —P(R⁶)—, —P(=O)(R⁶)—, —N(R⁶)SO₂—, —SO₂N(R⁶)—, —C(=S)—, —C(=NR⁶)—, —N=N—, —C=N—, —N=C— or —C(=N₂)—;

wherein each R¹ᵇ, each R⁵ᵃ, each R⁵ᵇ and each R⁶ may each independently be hydrogen, protium, deuterium, tritium, halogen, —NO₂, —CN, —OR, —SR, —N(Rᵃ)(Rᵇ), —C(O)R, —CO₂R, —C(O)C(O)R, —C(O)CH₂C(O)R, —S(O)R, —S(O)₂R, —C(O)N(Rᵃ)(Rᵇ), —SO₂N(Rᵃ)(Rᵇ), —OC(O)R, —N(R)SO₂R, or a C₁₋₆ aliphatic group which may be optionally substituted with R;

wherein each R, each Rᵃ and each Rᵇ may each independently be hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a C₁₋₆ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-Ax):

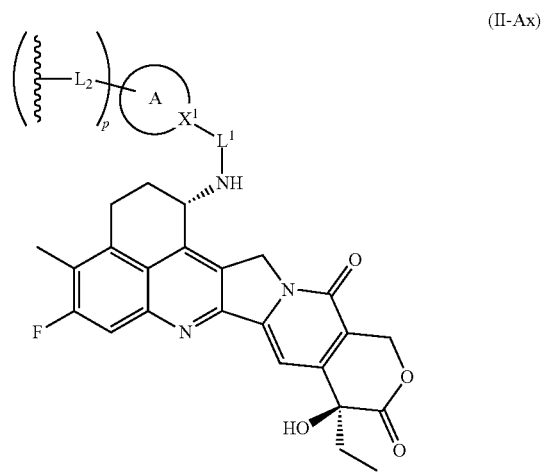

(II-Ax)

wherein, X¹ may be N or P;

ring A may be selected from the group consisting of: 5-8 membered heteroaryl and 3-10 membered saturated or partially unsaturated heterocyclyl, and ring A can not be substituted or may be substituted with no less than 1 substituent R¹ᶜ;

ring A may be substituted with p L², wherein p may be selected from the group consisting of integers ≥1;

L² may be —R²-L³-, and R² is used for direct or indirect linking of a ligand;

L³ may be —(C(R³ᵃ)(R³ᵇ))ₘ, and m may be selected from the group consisting of integers ≥0;

wherein 0 or no less than 1 methylene unit of L³ may be independently replaced by —N(R⁴)C(O)—, —C(O)N(R⁴)—, —C(O)—, —OC(O)—, —C(O)O—, —NR⁴—, —O—, —S—, —SO—, —SO₂—, —P(R⁴)—, —P(=O)(R⁴)—, —N(R⁴)SO₂—, —SO₂N(R⁴)—, —C(=S)—, —C(=NR⁴)—, —N=N—, —C=N—, —N=C— or —C(=N₂)—;

R² may be selected from the group consisting of: —O—, —(R²ᵃ)N—, —S— and —P(=O)(R²ᵃ)—;

L¹ may be —(C(R⁵ᵃ)(R⁵ᵇ))ₙ—, and n may be selected from the group consisting of integers ≥0;

wherein 0 or no less than 1 methylene unit of L¹ may be independently replaced by —N(R⁶)C(O)—, —C(O)N(R⁶)—, —C(O)—, —OC(O)—, —C(O)O—, —NR⁶—, —O—, —S—, —SO—, —SO₂—, —P(R⁶)—, —P(=O)(R⁶)—, —N(R⁶)SO₂—, —SO₂N(R⁶)—, —C(=S)—, —C(=NR⁶)—, —N=N—, —C=N—, —N=C— or —C(=N₂)—;

wherein each R¹ᶜ, each R²ᵃ, each R³ᵃ, each R³ᵇ, each R⁴, each R⁵ᵃ, each R⁵ᵇ and each R⁶ may each independently be hydrogen, protium, deuterium, tritium, halogen, —NO₂, —CN, —OR, —SR, —N(Rᵃ)(Rᵇ), —C(O)R, —CO₂R, —C(O)C(O)R, —C(O)CH₂C(O)R, —S(O)R, —S(O)₂R, —C(O)N(Rᵃ)(Rᵇ), —SO₂N(Rᵃ)(Rᵇ), —OC(O)R, —N(R)SO₂R, or a C₁₋₆ aliphatic group which may be optionally substituted with R;

wherein each R, each $R^a$ and each $R^b$ may each independently be hydrogen, protium, deuterium, tritium, halogen, —$NO_2$, —CN, —OH, —SH, —$NH_2$, —C(O)H, —$CO_2H$, —C(O)C(O)H, —C(O)$CH_2$C(O)H, —S(O) H, —S(O)$_2$H, —C(O)$NH_2$, —$SO_2NH_2$, —OC(O)H, —N(H)$SO_2$H or a $C_{1-6}$ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-Ay):

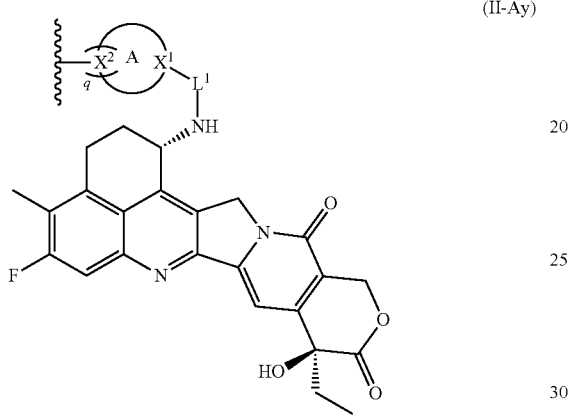

(II-Ay)

wherein, $X^1$ may be N or P;

ring A may be 3-10 membered saturated or partially unsaturated heterocyclyl, and ring A can not be substituted or may be substituted with no less than 1 substituent $R^{1c}$;

ring A may comprise q ring-forming heteroatom $X^2$, and $X^2$ is used for direct or indirect linking of a ligand; q may be selected from the group consisting of integers ≥1, and $X^2$ may be selected from the group consisting of: N and P;

$L^1$ may be —(C($R^{5a}$)($R^{5b}$))$_n$—, and n may be selected from the group consisting of integers ≥0;

wherein 0 or no less than 1 methylene unit of $L^1$ may be independently replaced by —N($R^6$)C(O)—, —C(O)N ($R^6$)—, —C(O)—, —OC(O)—, —C(O)O—, —N$R^6$—, —O—, —S—, —SO—, —SO$_2$—, —P($R^6$)—, —P(=O)($R^6$)—, —N($R^6$)SO$_2$—, —SO$_2$N ($R^6$)—, —C(=S)—, —C(=N$R^6$)—, —N=N—, —C=N—, —N=C— or —C(=N$_2$)—;

wherein each $R^{1c}$, each $R^{5a}$, each $R^{5b}$ and each $R^6$ may each independently be hydrogen, protium, deuterium, tritium, halogen, —$NO_2$, —CN, —OR, —SR, —N($R^a$) ($R^b$), —C(O)R, —$CO_2$R, —C(O)C(O)R, —C(O)$CH_2$C (O)R, —S(O)R, —S(O)$_2$R, —C(O)N($R^a$)($R^b$), —SO$_2$N($R^a$)($R^b$), —OC(O)R, —N(R)SO$_2$R, or a $C_{1-6}$ aliphatic group which may be optionally substituted with R;

wherein each R, each $R^a$ and each $R^b$ may each independently be hydrogen, protium, deuterium, tritium, halogen, —$NO_2$, —CN, —OH, —SH, —$NH_2$, —C(O)H, —$CO_2$H, —C(O)C(O)H, —C(O)$CH_2$C(O)H, —S(O) H, —S(O)$_2$H, —C(O)$NH_2$, —$SO_2NH_2$, —OC(O)H, —N(H)$SO_2$H or a $C_{1-6}$ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-Ax):

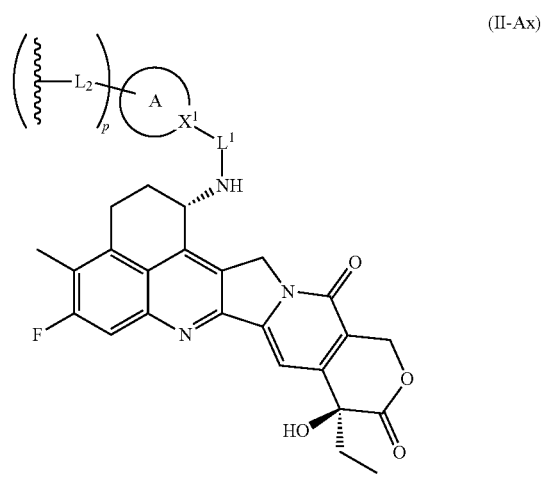

(II-Ax)

wherein, $X^1$ may be saturated C, and $X^1$ may be substituted with $R^n$;

ring A may be selected from the group consisting of: 3-6 membered saturated heterocyclyl and 3-6 membered saturated or partially unsaturated carbocyclyl;

p may be 1, and $L^2$ can not be $R^n$;

$L^2$ may be —$R^2$-$L^3$-;

$L^3$ may be —(C($R^{3a}$)($R^{3b}$))$_m$—, and m may be selected from the group consisting of integers from 0 to 2, wherein when $L^3$ may comprise a methylene unit, 0 or 1 methylene unit of $L^3$ may be replaced by —C(O)— or —C(=S)—;

$R^2$ may be selected from —O—;

$L^1$ may be —(C($R^{5a}$)($R^{5b}$))$_n$—, and n may be selected from the group consisting of 0 and 1;

wherein when $L^1$ may comprise a methylene unit, 0 or 1 methylene unit of $L^1$ may be replaced by —C(O)— or —C(=S)—;

wherein each $R^{3a}$, each $R^{3b}$, each $R^{5a}$, each $R^{5b}$ and each $R^n$ may each independently be hydrogen, halogen, or a $C_{1-6}$ aliphatic group which may be optionally substituted with R;

wherein each R may independently be hydrogen or halogen.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-Ax):

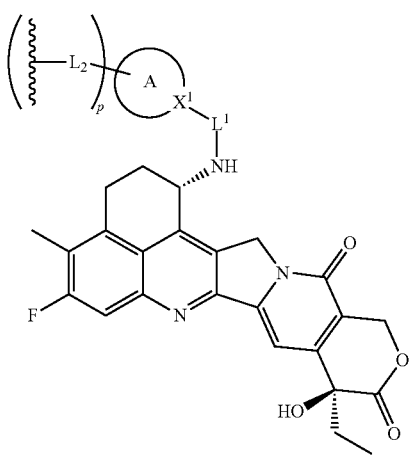

(II-Ax)

wherein, $X^1$ may be saturated C, and $X^1$ is linked to $R^n$, wherein $R^n$ may be H;
ring A may be selected from the group consisting of: 5 membered saturated heterocyclyl having 1 nitrogen heteroatom, and 4-6 membered saturated carbocyclyl;
P may be 1;
$L^2$ may be —$R^2$-$L^3$-, and $L^3$ is directly linked to ring A;
$L^3$ may be —$(C(R^{3a})(R^{3b}))_m$—, and m may be 0 or 2;
$R^2$ may be —O—;
$L^1$ may be —C(O)—;
wherein each $R^{3a}$ and each $R^{3b}$ may each independently be hydrogen.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-Ay):

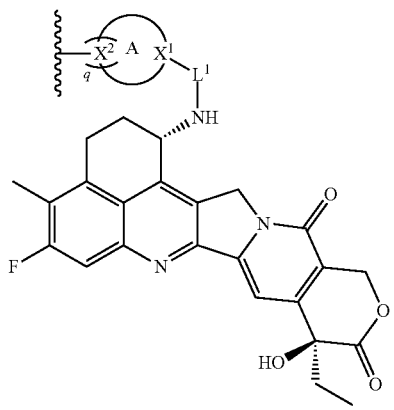

(II-Ay)

wherein, $X^1$ may be saturated C, and $X^1$ may be substituted with $R^n$;
ring A may be 3-6 membered saturated heterocyclyl;
ring A may comprise 1 ring-forming heteroatom N, and N is used for direct or indirect linking of a ligand;
$L^1$ may be —$(C(R^{5a})(R^{5b}))_n$—, and n may be selected from the group consisting of 0 and 1;
wherein 0 or 1 methylene unit of $L^1$ may be replaced by —C(O)— or —C(=S)—;

wherein each $R^{5a}$, each $R^{5b}$ and each $R^n$ may each independently be hydrogen, halogen, or a $C_{1-6}$ aliphatic group which may be optionally substituted with R;
wherein each R may independently be hydrogen or halogen.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-Ay):

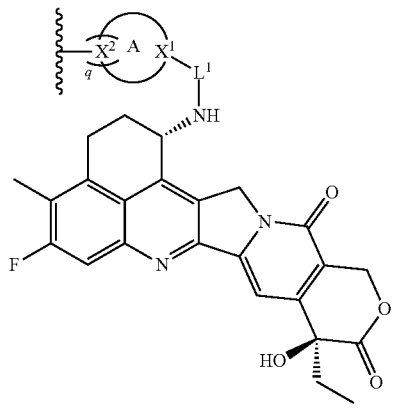

(II-Ay)

wherein, $X^1$ may be saturated C, and $X^1$ may be substituted with H;
ring A may be 5 membered saturated heterocyclyl having 1 heteroatom N;
ring A may comprise 1 ring-forming heteroatom N, and N is used for direct or indirect linking of a ligand;
$L^1$ may be —C(O)—.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-Ax):

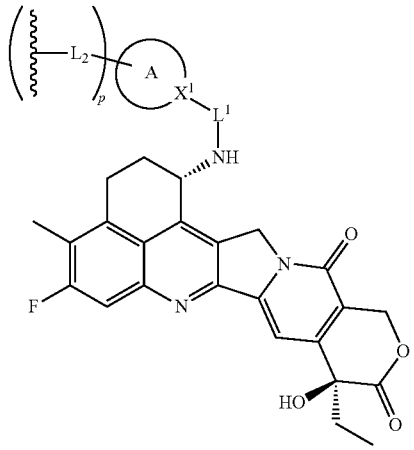

(II-Ax)

wherein, $X^1$ may be unsaturated C;
ring A may be selected from the group consisting of: 6 membered aryl, 5-8 membered heteroaryl, 3-10 membered partially unsaturated heterocyclyl, and 3-10 membered partially unsaturated carbocyclyl, and ring A can not be substituted or may be independently substituted with 1 substituent $R^{1b}$;

P may be 1;

$L^2$ may be —$R^2$-$L^3$-, and $R^2$ is used for direct or indirect linking of a ligand;

$L^3$ may be —$C(R^{3a})(R^{3b})$—;

$R^2$ may be selected from the group consisting of: —O—, —($R^{2a}$)N— and —S—;

$L^1$ may be —$C(R^{5a})(R^{5b})$—;

wherein 0 or 1 methylene unit of $L^1$ may be replaced by —C(O)— or —C(=S)—;

wherein each $R^{1b}$, each $R^{2a}$, each $R^{3a}$, each $R^{3b}$, each $R^{5a}$ and each $R^{5b}$ may each independently be hydrogen, halogen, or a $C_{1-6}$ aliphatic group which may be optionally substituted with R;

wherein each R may independently be hydrogen or halogen.

For example, the compound may comprise a structure shown as formula (II-Ax):

wherein, $X^1$ may be unsaturated C;

ring A may be selected from the group consisting of: 6 membered aryl and 5-8 membered heteroaryl;

P may be 1;

$L^2$ may be —$R^2$-$L^3$-, and $R^2$ is used for direct or indirect linking of a ligand;

$L^3$ may be —$C(R^{3a})(R^{3b})$—;

$R^2$ may be selected from the group consisting of: —O—, —($R^{2a}$)N— and —S—;

$L^1$ may be —$C(R^{5a})(R^{5b})$—;

wherein 0 or 1 methylene unit of $L^1$ may be replaced by —C(O)— or —C(=S)—;

wherein each $R^{2a}$, each $R^{3a}$, each $R^{3b}$, each $R^{5a}$ and each $R^{5b}$ may each independently be hydrogen, halogen, or a $C_{1-6}$ aliphatic group which may be optionally substituted with R;

wherein each R may independently be hydrogen or halogen.

For example, the compound may comprise a structure shown as formula (II-Ax):

wherein, $X^1$ may be unsaturated C;

ring A may be 6 membered aryl;

P may be 1;

$L^2$ may be —$R^2$-$L^3$-, and $R^2$ is used for direct or indirect linking of a ligand;

$L^3$ may be —$C(R^{3a})(R^{3b})$—;

$R^2$ may be —O—;

$L^1$ may be —C(O)—;

wherein each $R^{3a}$, each $R^{3b}$, each $R^{5a}$ and each $R^{5b}$ may each independently be hydrogen or a $C_{1-6}$ aliphatic group;

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-Ay):

wherein, $X^1$ may be unsaturated C;

ring A may be 5 membered partially unsaturated heterocyclyl;

ring A may comprise 1 ring-forming heteroatom N, and N is used for direct or indirect linking of a ligand;

$L^1$ may be —$C(R^{5a})(R^{5b})$—, wherein 0 or 1 methylene unit of $L^1$ may be replaced by —C(O)— or —C(=S)—;

wherein each $R^{5a}$ and each $R^{5b}$ may each independently be hydrogen, halogen, or a $C_{1-6}$ aliphatic group which may be optionally substituted with R;

wherein each R may independently be hydrogen or halogen.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-Ax):

wherein, $X^1$ may be N;

ring A may be 6 membered saturated heterocyclyl;

P may be 1;

$L^2$ may be —$R^2$-$L^3$-, and $R^2$ is used for direct or indirect linking of a ligand;

$L^3$ may be —$(C(R^{3a})(R^{3b}))_m$—, and m may be 1 or 2, wherein 0 or 1 methylene unit of $L^3$ may be replaced by —C(O)— or —C(=S)—;

$R^2$ may be selected from the group consisting of —O—, —($R^{2'}$)N— and —S—;

$L^1$ may be —$C(R^{5a})(R^{5b})$—, wherein 1 methylene unit of $L^1$ may be replaced by —C(O)— or —C(=S)—;

wherein each $R^{2a}$, each $R^{3a}$, each $R^{3b}$, each $R^{5a}$ and each $R^{5b}$ may each independently be hydrogen, halogen, or a $C_{1-6}$ aliphatic group which may be optionally substituted with R;

wherein each R may independently be hydrogen or halogen.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-Ay):

wherein, $X^1$ may be N;

ring A may be 5 membered partially unsaturated heterocyclyl;

ring A may comprise 1 ring-forming heteroatom N, and N is used for direct or indirect linking of a ligand;

$L^1$ may be —$C(R^{5a})(R^{5b})$, wherein no less than 1 methylene unit of $L^1$ may be replaced by —C(O)— or —C(=S)—;

wherein each $R^{5a}$ and each $R^{5b}$ may each independently be hydrogen, halogen, or a $C_{1-6}$ aliphatic group which may be optionally substituted with R;

wherein each R may independently be hydrogen or halogen.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise the following group of structures:

II-A-1
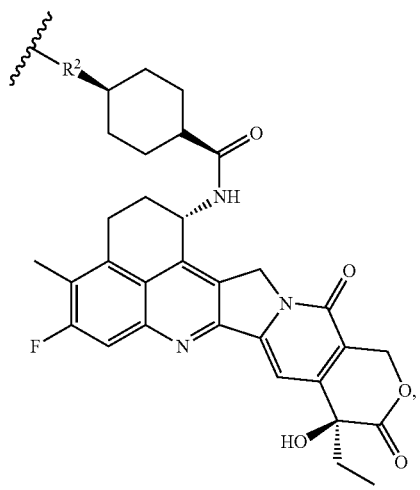
II-A-2
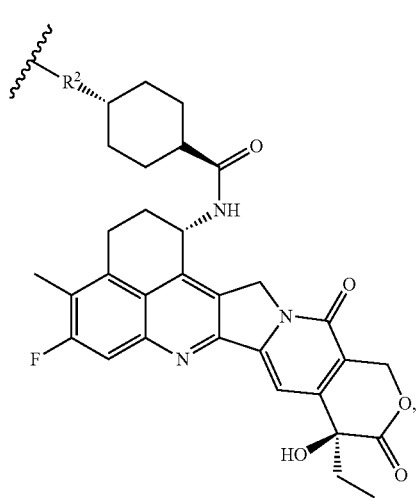
II-A-3
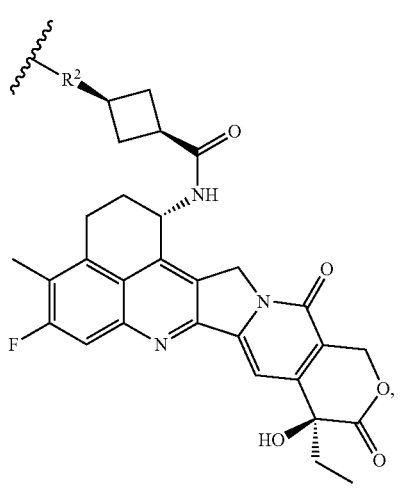
II-A-4
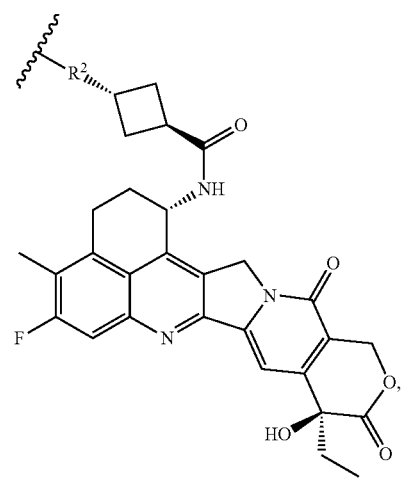
II-A-5
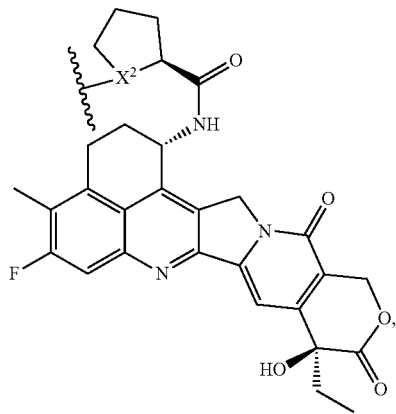
II-A-6

II-A-7

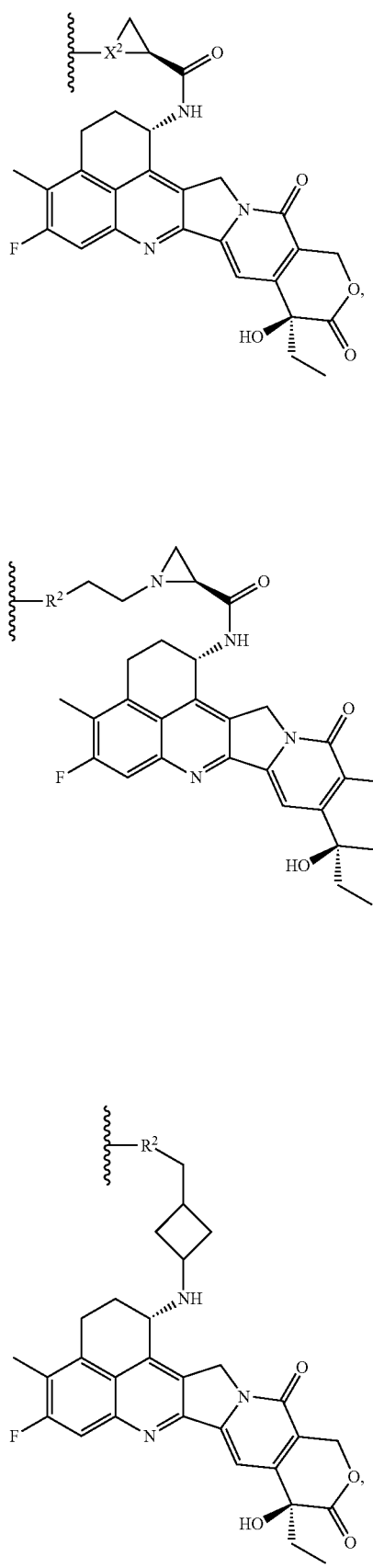

II-A-8

II-A-9

II-A-10

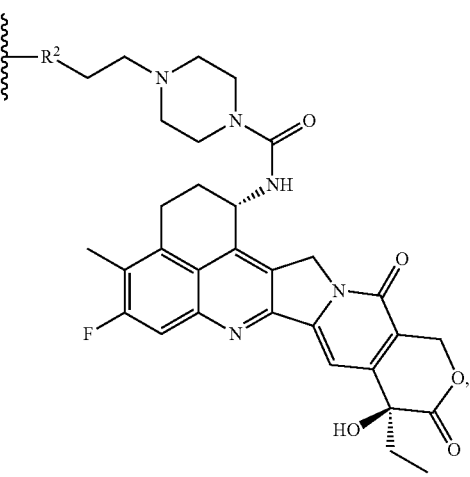

II-A-11

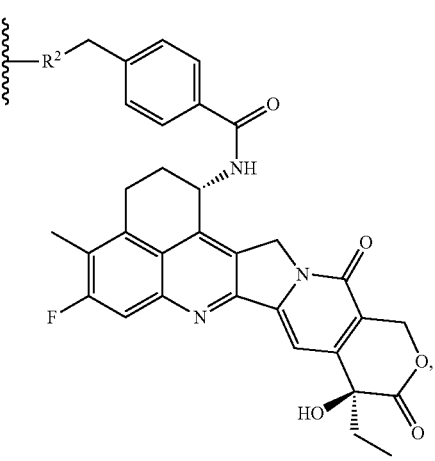

II-A-12

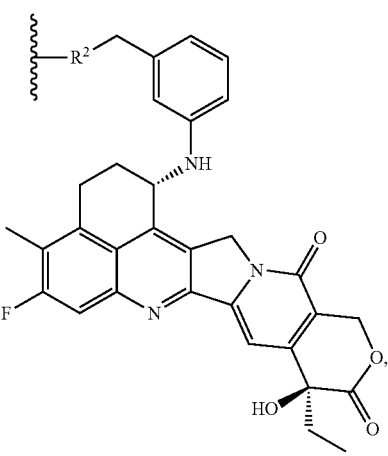

wherein, $R^2$ may be selected from the group consisting of: —O—, —HN—, —P(=O)H— and —S—.

In another embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

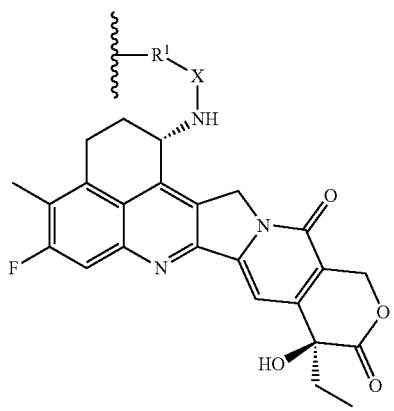

(III-A)

wherein, $R^1$ may be selected from the group consisting of: —O—, —($R^2$)N—, —P(=O)($R^2$)— and —S—;

X may be selected from the group consisting of: -$L^1$-C($R^{1a}$)($R^{1b}$)—C(O)—, -$L^1$-C($R^{1a}$)($R^{1b}$)—C(S)—, -$L^1$-$L^0$- and -$L^3$-$L^2$-;

$L^1$ may be —(C($R^{3a}$)($R^{3b}$))$_m$—, wherein when $L^1$ may comprise a methylene unit, 0 or no less than 1 methylene unit of $L^1$ may be independently replaced by —C(O)—, —C(=S)—, —C(=N$R^{4b}$)— or —C(=N$_2$)—;

$L^0$ may be —C($R^{2a}$)($R^{2b}$)—, or $L^0$ may be —C(=S)—, —C(=N$R^{4a}$)— or —C(=N$_2$)—;

$L^2$ may be —C($R^{5a}$)($R^{1b}$)—, wherein 0 or 1 methylene unit of $L^2$ may be replaced by —N($R^6$)C(O)—, —C(O)N($R^6$)—, —C(O)—, —OC(O)—, —C(O)O—, —N$R^6$—, —O—, —S—, —SO—, —SO$_2$—, —P($R^6$)—, —P(=O)($R^6$)—, —N($R^6$)SO$_2$—, —SO$_2$N($R^6$)—, —C(=S)—, —C(=N$R^6$)—, —N=N—, —C=N—, —N=C— or —C(=N$_2$)—;

$L^3$ may be —(C($R^{7a}$)($R^{7b}$))$_n$—, wherein no less than 1 methylene unit of $L^3$ may be independently replaced by —N($R^8$)C(O)—, —C(O)N($R^8$)—, —OC(O)—, —C(O)O—, —N$R^8$—, —O—, —S—, —SO—, —SO$_2$—, —P(R')—, —P(=O)(R')—, —N(R')SO$_2$—, —SO$_2$N($R^8$)—, —N=N—, —C=N— or —N=C—, and 0 or no less than 1 methylene unit of $L^3$ may also independently be replaced by —C(O)—, —C(=S)—, —C(=N$R^8$)— or —C(=N$_2$)—;

wherein each $R^{1a}$, each $R^{1b}$, each $R^2$, each $R^{2a}$, each $R^{2b}$, each $R^{3a}$, each $R^{3b}$, each $R^{4a}$, each $R^{4b}$, each $R^{5a}$, each $R^{5b}$, each $R^6$, each $R^{7a}$, each $R^{7b}$ and each $R^8$ may each independently be hydrogen, protium, deuterium, tritium, halogen, —NO$_2$, —CN, —OR, —SR, —N($R^a$)($R^b$), —C(O)R, —CO$_2$R, —C(O)C(O)R, —C(O)CH$_2$C(O)R, —S(O)R, —S(O)$_2$R, —C(O)N($R^a$)($R^b$), —SO$_2$N($R^a$)($R^b$), —OC(O)R, —N(R)SO$_2$R, or a C$_{1-6}$ aliphatic group which may be optionally substituted with R;

wherein each R, each $R^a$ and each $R^b$ may each independently be hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group;

m may be selected from the group consisting of integers ≥0, and n may be selected from the group consisting of integers ≥1;

when $R^1$ may be —O— or —HN—, and X may be -$L^1$-CH$_2$—C(O)—, and when $L^1$ may comprise a methylene unit, no less than 1 methylene unit of $L^1$ may be independently replaced by —C(O)—, —C(=S)—, —C(=N$R^{4b}$)— or —C(=N$_2$)—, or $R^{3a}$ and $R^{3b}$ can not be both hydrogen in each —C($R^{3a}$)($R^{3b}$)- of $L^1$;

when $R^1$ may be —HN—, X may be -$L^1$-$L^0$-, and $L^0$ may be —CH$_2$—, no less than 1 methylene unit of $L^1$ may be independently replaced by —C(O)—, —C(=S)—, —C(=N$R^{4b}$)— or —C(=N$_2$)—, or each $R^{3a}$ and each $R^{3b}$ can not be both hydrogen;

when $R^1$ may be —O—, X may be -$L^3$-C(O)—, and 1 methylene unit of $L^3$ may be replaced by —N$R^1$, $R^8$ can not be —CH$_2$—CH$_2$—NH$_2$;

when $R^1$ may be —NH—, and X may be -$L^3$-C(O)—, no less than 1 methylene unit of $L^3$ may be replaced by —N($R^8$)C(O)—, —OC(O)—, —C(O)O—, —S—, —SO—, —SO$_2$—, —P($R^8$)—, —P(=O)($R^8$)—, —N(R')SO$_2$—, —SO$_2$N($R^8$)—, —N=N—, —C=N— or —N=C—.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

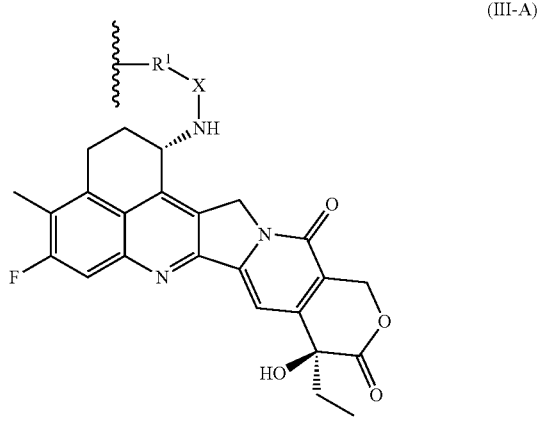

(III-A)

wherein, $R^1$ may be selected from the group consisting of: —O—, —($R^2$)N— and —S—;

X may be -$L^1$-C($R^{1a}$)($R^{1b}$)—C(S)—;

$L^1$ may be —(C($R^{3a}$)($R^{3b}$))$_m$, and m may be selected from the group consisting of integers ≥0;

wherein 0 or no less than 1 methylene unit of $L^1$ may be independently replaced by —C(O)—, —C(=S)—, —C(=N$R^{4b}$)— or —C(=N$_2$)—;

$R^2$ may be halogen, —NO$_2$, —CN, —OR, —SR, —N($R^a$)($R^b$), —C(O)R, —CO$_2$R, —C(O)C(O)R, —C(O)CH$_2$C(O)R, —S(O)R, —S(O)$_2$R, —C(O)N($R^a$)($R^b$), —SO$_2$N($R^a$)($R^b$), —OC(O)R, —N(R)SO$_2$R, or a C$_{1-6}$ aliphatic group which may be optionally substituted with R;

wherein each $R^{1a}$, each $R^{1b}$, each $R^{3a}$, each $R^{3b}$ and each $R^{4b}$ may each independently be hydrogen, protium, deuterium, tritium, halogen, —NO$_2$, —CN, —OR, —SR, —N($R^a$)($R^b$), —C(O)R, —CO$_2$R, —C(O)C(O)R, —C(O)CH$_2$C(O)R, —S(O)R, —S(O)$_2$R, —C(O)N($R^a$)($R^b$), —SO$_2$N($R^a$)($R^b$), —OC(O)R, —N(R)SO$_2$R, or a C$_{1-6}$ aliphatic group which may be optionally substituted with R;

wherein each R, each $R^a$ and each $R^b$ may each independently be hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

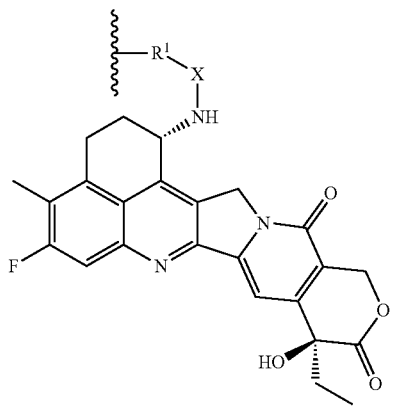
(III-A)

wherein, $R^1$ may be —S— or —($R^2$)N—;

X may be -L$^1$-C(R$^{1a}$)(R$^{1b}$)—C(O)—;

L$^1$ may be —(C(R$^{3a}$)(R$^{3b}$))$_m$—, and m may be selected from the group consisting of integers ≥0;

wherein 0 or no less than 1 methylene unit of L$^1$ may be independently replaced by —C(O)—, —C(=S)—, —C(=NR$^{4b}$)— or —C(=N$_2$)—;

$R^2$ may be halogen, —NO$_2$, —CN, —OR, —SR, —N(R$^a$)(R$^b$), —C(O)R, —CO$_2$R, —C(O)C(O)R, —C(O)CH$_2$C(O)R, —S(O)R, —S(O)$_2$R, —C(O)N(R$^a$)(R$^b$), —SO$_2$N(R$^a$)(R$^b$), —OC(O)R, —N(R)SO$_2$R, or a C$_{1-6}$ aliphatic group which may be optionally substituted with R;

wherein each $R^{1a}$, each $R^{1b}$, each $R^{3a}$, each $R^{3b}$ and each $R^{4b}$ may each independently be hydrogen, protium, deuterium, tritium, halogen, —NO$_2$, —CN, —OR, —SR, —N(R$^a$)(R$^b$), —C(O)R, —CO$_2$R, —C(O)C(O)R, —C(O)CH$_2$C(O)R, —S(O)R, —S(O)$_2$R, —C(O)N(R$^a$)(R$^b$), —SO$_2$N(R$^a$)(R$^b$), —OC(O)R, —N(R)SO$_2$R, or a C$_{1-6}$ aliphatic group which may be optionally substituted with R;

wherein each R, each $R^a$ and each $R^b$ may each independently be hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

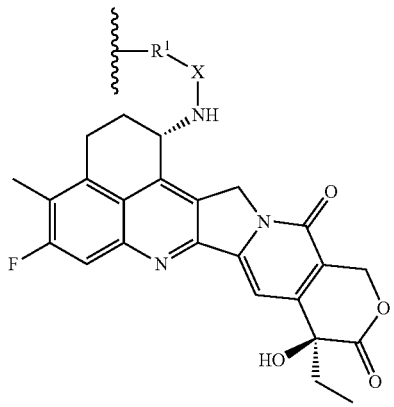
(III-A)

wherein, $R^1$ may be —O— or —HN—;

X may be -L$^1$-CH$_2$—C(O)—;

L$^1$ may be —(C(R$^{3a}$)(R$^{3b}$))$_m$—, and m may be selected from the group consisting of integers ≥1;

wherein no less than 1 methylene unit of L$^1$ may be independently replaced by —C(O)—, —C(=S)—, —C(=NR$^{4b}$)— or —C(=N$_2$)—;

wherein each $R^{3a}$, each $R^{3b}$ and each $R^{4b}$ may each independently be hydrogen, protium, deuterium, tritium, halogen, —NO$_2$, —CN, —OR, —SR, —N(R$^a$)(R$^b$), —C(O)R, —CO$_2$R, —C(O)C(O)R, —C(O)CH$_2$C(O)R, —S(O)R, —S(O)$_2$R, —C(O)N(R$^a$)(R$^b$), —SO$_2$N(R$^a$)(R$^b$), —OC(O)R, —N(R)SO$_2$R or a C$_{1-6}$ aliphatic group which may be optionally substituted with R;

wherein each R, each $R^a$ and each $R^b$ may each independently be hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

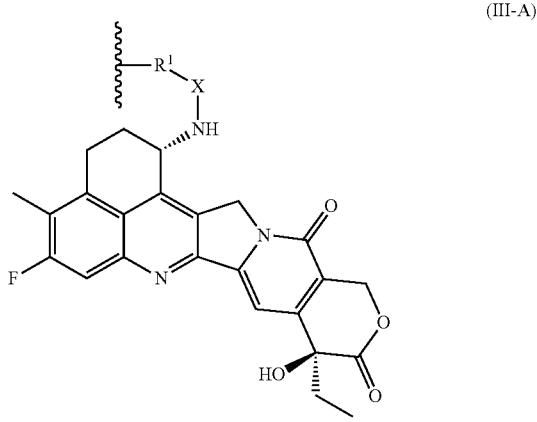
(III-A)

wherein, $R^1$ may be —O— or —HN—;

X may be -L$^1$-CH$_2$—C(O)—;

L¹ may be —(C(R³ᵃ)(R³ᵇ))ₘ—, and m may be selected from the group consisting of integers ≥0;

R³ᵃ and R³ᵇ can not be both hydrogen in each —C(R³ᵃ)(R³ᵇ)—, or no less than 1 methylene unit of L¹ may be independently replaced by —C(O)—, —C(=S)—, —C(=NR⁴ᵇ)— or —C(=N₂)—;

wherein each R³ᵃ, each R³ᵇ and each R⁴ᵇ may each independently be hydrogen, protium, deuterium, tritium, halogen, —NO₂, —CN, —OR, —SR, —N(Rᵃ)(Rᵇ), —C(O)R, —CO₂R, —C(O)C(O)R, —C(O)CH₂C(O)R, —S(O)R, —S(O)₂R, —C(O)N(Rᵃ)(Rᵇ), —SO₂N(Rᵃ)(Rᵇ), —OC(O)R, —N(R)SO₂R or a C₁₋₆ aliphatic group which may be optionally substituted with R;

wherein each R, each Rᵃ and each Rᵇ may each independently be hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a C₁₋₆ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

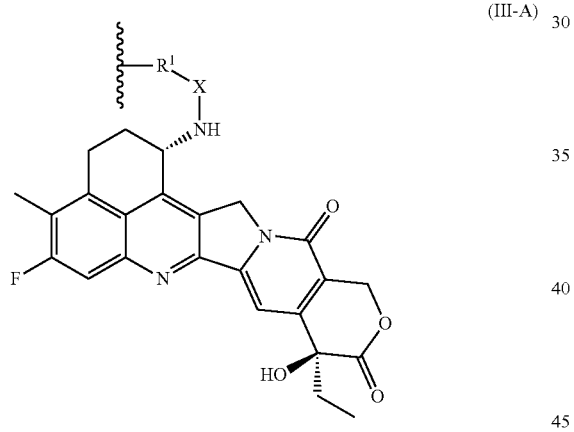

(III-A)

wherein, R¹ may be —O—, —S— or —(R²)N—;

X may be -L¹-L⁰-;

L⁰ may be —C(R²ᵃ)(R²ᵇ)—, or L⁰ may be —C(=S)—, —C(=NR⁴ᵃ)— or —C(=N₂)—;

L¹ may be —(C(R³ᵃ)(R³ᵇ))ₘ—, and m may be selected from the group consisting of integers ≥0;

wherein 0 or no less than 1 methylene unit of L¹ may be independently replaced by —C(O)—, —C(=S)—, —C(=NR⁴ᵇ)— or —C(=N₂)—;

R² may be halogen, —NO₂, —CN, —OR, —SR, —N(Rᵃ)(Rᵇ), —C(O)R, —CO₂R, —C(O)C(O)R, —C(O)CH₂C(O)R, —S(O)R, —S(O)₂R, —C(O)N(Rᵃ)(Rᵇ), —SO₂N(Rᵃ)(Rᵇ), —OC(O)R, —N(R)SO₂R, or a C₁₋₆ aliphatic group which may be optionally substituted with R;

wherein each R²ᵃ, each R²ᵇ, R³ᵃ, each R³ᵇ, each R⁴ᵃ and each R⁴ᵇ may each independently be hydrogen, protium, deuterium, tritium, halogen, —NO₂, —CN, —OR, —SR, —N(Rᵃ)(Rᵇ), —C(O)R, —CO₂R, —C(O)C(O)R, —C(O)CH₂C(O)R, —S(O)R, —S(O)₂R, —C(O)N(Rᵃ)(Rᵇ), —SO₂N(Rᵃ)(Rᵇ), —OC(O)R, —N(R)SO₂R, or a C₁₋₆ aliphatic group which may be optionally substituted with R;

wherein each R, each Rᵃ and each Rᵇ may each independently be hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a C₁₋₆ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

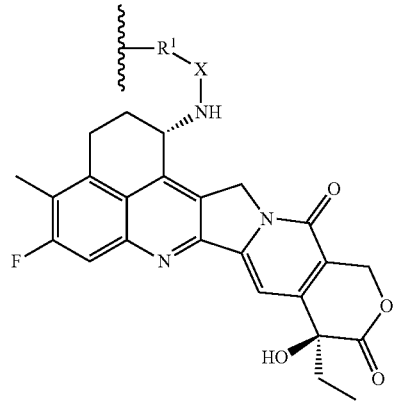

(III-A)

wherein, R¹ may be —HN—;

X may be -L¹-L⁰-;

L⁰ may be —C(R²ᵃ)(R²ᵇ)—, or L⁰ may be —C(=S)—, —C(=NR⁴ᵃ)— or —C(=N₂)—;

L¹ may be —(C(R³ᵃ)(R³ᵇ))ₘ—, m may be selected from the group consisting of integers ≥0, and each R³ᵃ and each R³ᵇ can not be both hydrogen;

wherein 0 or no less than 1 methylene unit of L¹ may be independently replaced by —C(O)—, —C(=S)—, —C(=NR⁴ᵇ)— or —C(=N₂)—;

wherein each R²ᵃ, each R¹ᵇ, R³ᵃ, each R³ᵇ, each R⁴ᵃ and each R⁴ᵇ may each independently be hydrogen, protium, deuterium, tritium, halogen, —NO₂, —CN, —OR, —SR, —N(Rᵃ)(Rᵇ), —C(O)R, —CO₂R, —C(O)C(O)R, —C(O)CH₂C(O)R, —S(O)R, —S(O)₂R, —C(O)N(Rᵃ)(Rᵇ), —SO₂N(Rᵃ)(Rᵇ), —OC(O)R, —N(R)SO₂R, or a C₁₋₆ aliphatic group which may be optionally substituted with R;

wherein each R, each Rᵃ and each Rᵇ may each independently be hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a C₁₋₆ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

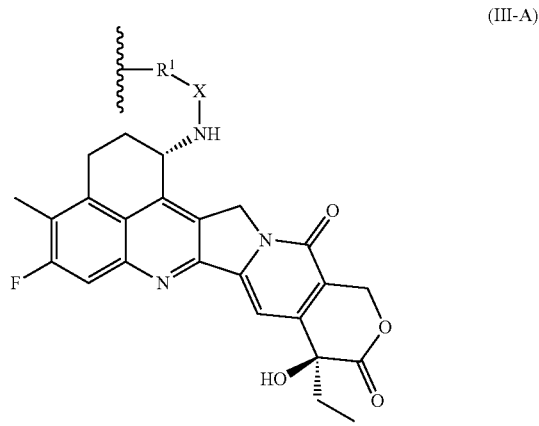

(III-A)

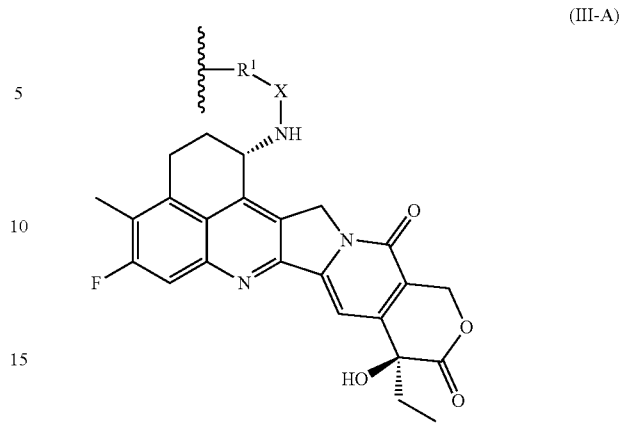

(III-A)

wherein, X may be -L³-L²-;
L² may be —C(R⁵ᵃ)(R⁵ᵇ)—, wherein 0 or 1 methylene unit of L² may be replaced by —N(R⁶)C(O)—, —C(O)N(R⁶)—, —C(O)—, —OC(O)—, —C(O)O—, —NR⁶—, —O—, —S—, —SO—, —SO₂—, —P(R⁶)—, —P(=O)(R⁶)—, —N(R⁶)SO₂—, —SO₂N(R⁶)—, —C(=S)—, —C(=NR⁶)—, —N=N—, —C=N—, —N=C— or —C(=N₂)—;
R¹ may be —S— or —(R²)N—; or R¹ may be —O— and L² can not be —C(O)—; or R¹ may be —NH— and L² can not be —C(O)—;
L³ may be —(C(R⁷ᵃ)(R⁷ᵇ))ₙ—, and n may be selected from the group consisting of integers ≥1;
wherein no less than 1 methylene unit of L³ may be independently replaced by —N(R⁸)C(O)—, —C(O)N(R⁸)—, —OC(O)—, —C(O)O—, —NR⁸—, —O—, —S—, —SO—, —SO₂—, —P(R')—, —P(=O)(R⁸)—, —N(R⁸)SO₂—, —SO₂N(R')—, —N=N—, —C=N— or —N=C—, and 0 or no less than 1 methylene unit of L³ may also be independently replaced by —C(O)—, —C(=S)—, —C(=NR⁸)— or —C(=N₂)—;
R² may be halogen, —NO₂, —CN, —OR, —SR, —N(Rᵃ)(Rᵇ), —C(O)R, —CO₂R, —C(O)C(O)R, —C(O)CH₂C(O)R, —S(O)R, —S(O)₂R, —C(O)N(Rᵃ)(Rᵇ), —SO₂N(Rᵃ)(Rᵇ), —OC(O)R, —N(R)SO₂R, or a C₁₋₆ aliphatic group which may be optionally substituted with R;
wherein each R⁵ᵃ, each R⁵ᵇ, each R⁶, each R⁷ᵃ, each R⁷ᵇ and each R⁸ may each independently be hydrogen, protium, deuterium, tritium, halogen, —NO₂, —CN, —OR, —SR, —N(Rᵃ)(Rᵇ), —C(O)R, —CO₂R, —C(O)C(O)R, —C(O)CH₂C(O)R, —S(O)R, —S(O)₂R, —C(O)N(Rᵃ)(Rᵇ), —SO₂N(Rᵃ)(Rᵇ), —OC(O)R, —N(R)SO₂R, or a C₁₋₆ aliphatic group which may be optionally substituted with R;
wherein each R, each Rᵃ and each Rᵇ may each independently be hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a C₁₋₆ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

wherein, R¹ may be —O—;
X may be -L³-L²-;
wherein L² may be —C(O)—;
L³ may be —(C(R⁷ᵃ)(R⁷ᵇ))ₙ—, and n may be selected from the group consisting of integers ≥0;
wherein no less than 1 methylene unit of L³ may be independently replaced by —N(R⁸)C(O)—, —C(O)N(R⁸)—, —OC(O)—, —C(O)O—, —NR⁸—, —O—, —S—, —SO—, —SO₂—, —P(R')—, —P(=O)(R⁸)—, —N(R')SO₂—, —SO₂N(R⁸)—, —N=N—, —C=N— or —N=C—, and 0 or no less than 1 methylene unit of L³ may also be independently replaced by —C(O)—, —C(=S)—, —C(=NR⁸)— or —C(=N₂)—;
wherein each R⁷ᵃ, each R⁷ᵇ and each R⁸ may each independently be hydrogen, protium, deuterium, tritium, halogen, —NO₂, —CN, —OR, —SR, —N(Rᵃ)(Rᵇ), —C(O)R, —CO₂R, —C(O)C(O)R, —C(O)CH₂C(O)R, —S(O)R, —S(O)₂R, —C(O)N(Rᵃ)(Rᵇ), —SO₂N(Rᵃ)(Rᵇ), —OC(O)R, —N(R)SO₂R or a C₁₋₆ aliphatic group which may be optionally substituted with R;
wherein R, Rᵃ and Rᵇ may each independently be hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a C₁₋₆ aliphatic group;
when 1 methylene unit of L³ may be replaced by —NR⁸, R⁸ can not be a C₁₋₆ aliphatic group which may be substituted with —NH₂.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

(III-A)

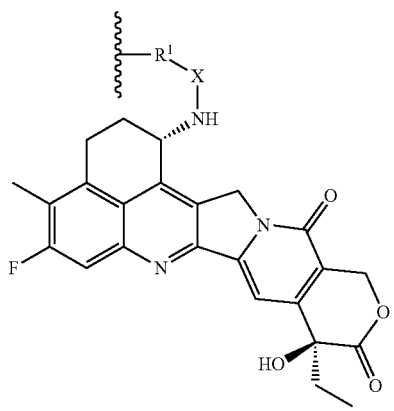

wherein, R¹ may be —HN—;
X may be -L³-L²-;
wherein L² may be —C(O)—;
L³ may be —(C(R$^{7a}$)(R$^{7b}$))$_n$—, and n may be selected from the group consisting of integers ≥1;
no less than 1 methylene unit of L³ may be replaced by —N(R⁸)C(O)—, —OC(O)—, —C(O)O—, —S—, —SO—, —SO$_2$—, —P(R⁸)—, —P(=O)(R⁸)—, —N(R')SO$_2$—, —SO$_2$N(R⁸)—, —N=N—, —C=N— or —N=C—, and 0 or no less than 1 methylene unit of L³ may also be independently replaced by —C(O)N(R')—, —NR⁸— or —O—, and 0 or no less than 1 methylene unit of L³ may also be independently replaced by —C(O)—, —C(=S)—, —C(=NR⁸)— or —C(=N$_2$)—;
wherein each R$^{7a}$, each R$^{7b}$ and each R⁸ may each independently be hydrogen, protium, deuterium, tritium, halogen, —NO$_2$, —CN, —OR, —SR, —N(R$^a$)(R$^b$), —C(O)R, —CO$_2$R, —C(O)C(O)R, —C(O)CH$_2$C(O)R, —S(O)R, —S(O)$_2$R, —C(O)N(R$^a$)(R$^b$), —SO$_2$N(R$^a$)(R$^b$), —OC(O)R, —N(R)SO$_2$R or a C$_{1-6}$ aliphatic group which may be optionally substituted with R;
wherein each R, each R$^a$ and each R$^b$ may each independently be hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

(III-A)

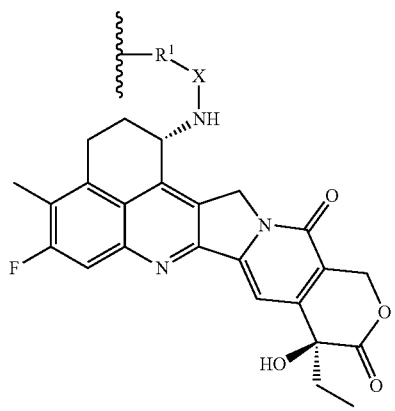

wherein, R¹ may be —O—, —S— or —(R²)N—;
X may be -L¹-C(R$^{1a}$)(R$^{1b}$)—C(S)—;
L¹ may be —(C(R$^{3a}$)(R$^{3b}$))$_m$—, and m may be 0, 1 or 2;
wherein 0 or 1 methylene unit of L¹ may be replaced by —C(O)—;
wherein each R$^{1a}$, each R$^{1b}$, each R², each R$^{3a}$ and each R$^{3b}$ may each independently be hydrogen, or a C$_{1-6}$ aliphatic group which may be optionally substituted with R;
wherein each R may be hydrogen.

For example, the compound may comprise a structure shown as formula (III-A):
wherein, R¹ may be —O—;
X may be -L¹-C(R$^{1a}$)(R$^{1b}$)—C(S)—;
L¹ may be —(CH$_2$)$_m$—, and m may be 1 or 2;
wherein 0 or 1 methylene unit of L¹ may be replaced by —C(O)—;
wherein each R$^{1a}$ and each R$^{1b}$ may each independently be hydrogen, or a C$_{1-6}$ aliphatic group which may be optionally substituted with R;
wherein each R may be hydrogen.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

(III-A)

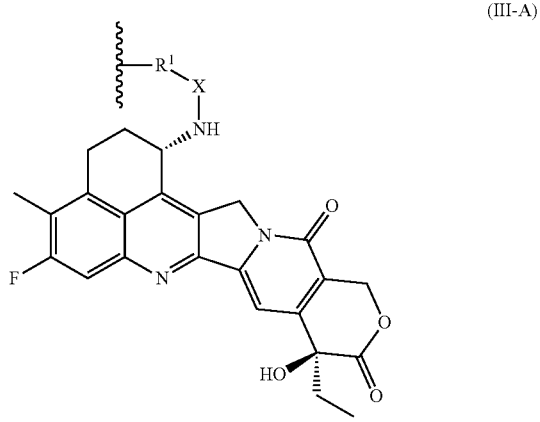

wherein, R¹ may be —S— or —(R²)N—;
X may be -L¹-C(R$^{1a}$)(R$^{1b}$)—C(O)—;

$L^1$ may be —$(C(R^{3a})(R^{3b}))_m$—, and m may be 0, 1 or 2;
wherein 0 or 1 methylene unit of $L^1$ may be replaced by —C(O)—;

$R^2$ may be a $C_{1-6}$ aliphatic group;

wherein each $R^{1a}$, each $R^{1b}$, each $R^{3a}$ and each $R^{3b}$ may each independently be hydrogen or a $C_{1-6}$ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

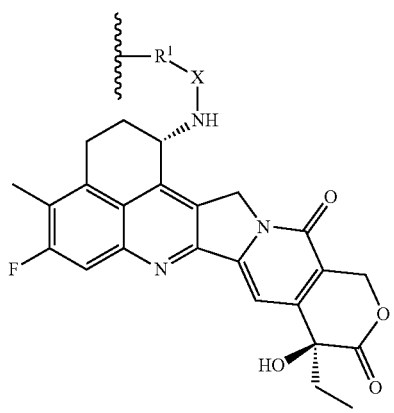

(III-A)

wherein, $R^1$ may be —S— or —$(R^2)$N—;
X may be -$L^1$-C($R^{1a}$)($R^{1b}$)—C(O)—;
$L^1$ may be —$(C(R^{3a})(R^{3b}))_m$—, and m may be 1 or 2;
wherein 0 or 1 methylene unit of $L^1$ may be replaced by —C(O)—;

$R^2$ may be a $C_{1-6}$ aliphatic group;

wherein each $R^{1a}$, each $R^{1b}$, each $R^{3a}$ and each $R^{3b}$ may each independently be hydrogen or a $C_{1-6}$ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

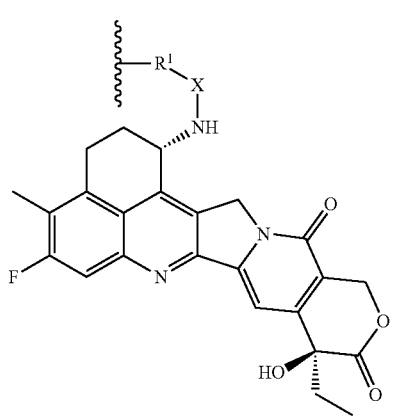

(III-A)

wherein, when $R^1$ may be —S— or —$(R^2)$N—,
X may be -$L^1$-C($R^{1a}$)($R^{1b}$)—C(O)—,
$L^1$ may be —$(C(R^{3a})(R^{3b}))_m$—, and m may be 0, 1 or 2,
0 or 1 methylene unit of $L^1$ may be replaced by —C(O)—;

$R^2$ may be a $C_{1-6}$ aliphatic group;

wherein each $R^{1a}$, each $R^{1b}$, each $R^{3a}$ and each $R^{3b}$ may each independently be hydrogen or a $C_{1-6}$ aliphatic group;

or, when $R^1$ may be —O—,
X may be -$L^1$-CH$_2$—C(O)—, and
$L^1$ may be —$(C(R^{3a})(R^{3b}))_2$—,
0 or 1 methylene unit of $L^1$ may be replaced by —C(O)—;

wherein each $R^{3a}$ and each $R^{3b}$ may each independently be hydrogen or a $C_{1-6}$ aliphatic group;

each $R^{3a}$ and each $R^{3b}$ can not be both hydrogen, or 1 methylene unit of $L^1$ may be replaced by —C(O)—;

wherein each $R^{3a}$ and each $R^{3b}$ may each independently be hydrogen or a $C_{1-6}$ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

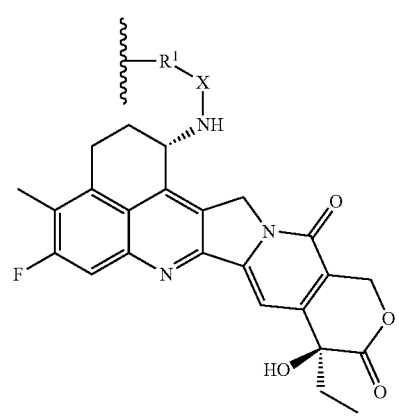

(III-A)

wherein, $R^1$ may be —O—;
X may be -$L^1$-CH$_2$—C(O)—;
$L^1$ may be —$(C(R^{3a})(R^{3b}))_2$—;
wherein 0 or 1 methylene unit of $L^1$ may be replaced by —C(O)—;

wherein each $R^{3a}$ and each $R^{3b}$ may each independently be hydrogen or a $C_{1-6}$ aliphatic group;

each $R^{3a}$ and each $R^{3b}$ can not be both hydrogen, or 1 methylene unit of $L^1$ may be replaced by —C(O)—;

wherein each $R^{3a}$ and each $R^{3b}$ may each independently be hydrogen or a $C_{1-6}$ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

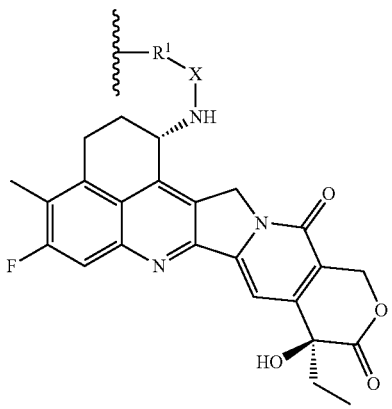

(III-A)

wherein, when R¹ may be —S— or —(R²)N—,
X may be -L¹-C(R$^{1a}$)(R$^{1b}$)—C(O)—,
L¹ may be —(C(R$^{3a}$)(R$^{3b}$))$_m$—, and m may be 0, 1 or 2,
0 or 1 methylene unit of L¹ may be replaced by —C(O)—;
R² may be a C$_{1-6}$ aliphatic group;
wherein each R$^{1a}$, each R$^{1b}$, each R$^{3a}$ and each R$^{3b}$ may each independently be hydrogen or a C$_{1-6}$ aliphatic group;
or, when R¹ may be —O—, and
X may be -L¹-CH$_2$—C(O)—,
L¹ may be —C(R$^{3a}$)(R$^{3b}$)—, and R$^{3a}$ and R$^{3b}$ can not be both hydrogen in each —C(R$^{3a}$)(R$^{3b}$)—;
wherein each R$^{3a}$ and each R$^{3b}$ may each independently be hydrogen or a C$_{1-6}$ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

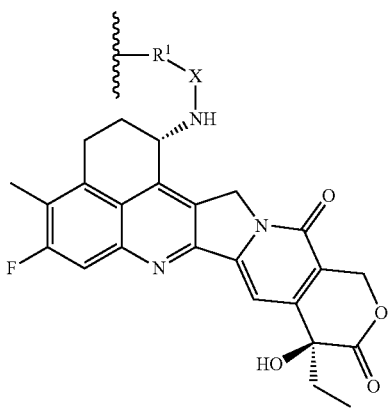

(III-A)

wherein, R¹ may be —O—;
X may be -L¹-CH$_2$—C(O)—;
L¹ may be —(C(R$^{3a}$)(R$^{3b}$))$_2$—;
wherein 0 or 1 methylene unit of L¹ may be replaced by —C(O)—;
wherein each R$^{3a}$ and each R$^{3b}$ may each independently be hydrogen or a C$_{1-6}$ aliphatic group;
R$^{3a}$ and R$^{3b}$ can not be both hydrogen in each —C(R$^{3a}$)(R$^{3b}$)—, or 1 methylene unit of L¹ may be replaced by —C(O)—;

wherein each R$^{3a}$ and each R$^{3b}$ may each independently be hydrogen or a C$_{1-6}$ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

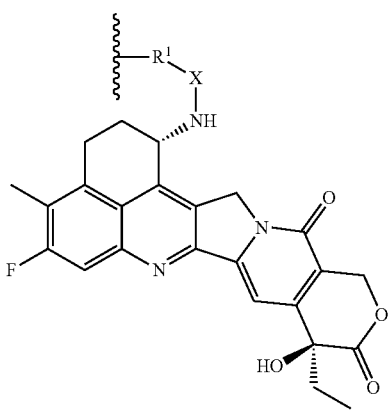

(III-A)

wherein, R¹ may be —O—;
X may be -L¹-CH$_2$—C(O)—;
L¹ may be —(CH$_2$)$_2$—;
wherein 1 methylene unit of L¹ may be replaced by —C(O)—.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

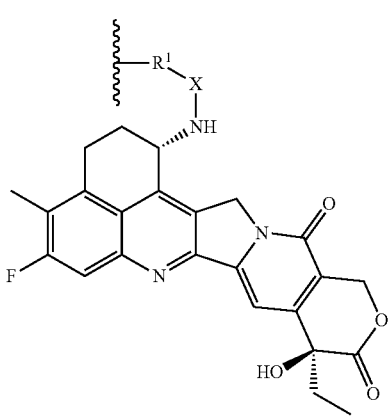

(III-A)

wherein, R¹ may be —O—;
X may be -L¹-CH$_2$—C(O)—;
L¹ may be —C(R$^{3a}$)(R$^{3b}$)—$_m$—, m may be selected from the group consisting of integers from 1 to 5, and R$^{3a}$ and R$^{3b}$ can not be both hydrogen in each —C(R$^{3a}$)(R$^{3b}$)—;
wherein each R$^{3a}$ and each R$^{3b}$ may each independently be hydrogen, halogen, or a C$_{1-6}$ aliphatic group which may be optionally substituted with R;

wherein each R may be hydrogen or halogen.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

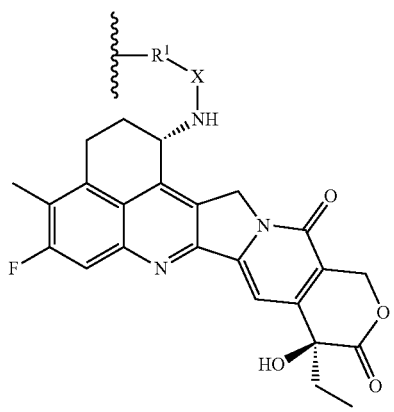

(III-A)

wherein, $R^1$ may be —O—;
X may be -$L^1$-$CH_2$—C(O)—;
$L^1$ may be —C($R^{3a}$)($R^{3b}$)—, and $R^{3a}$ and $R^{3b}$ can not be both hydrogen;
wherein each $R^{3a}$ and each $R^{3b}$ may each independently be hydrogen or a $C_{1-6}$ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

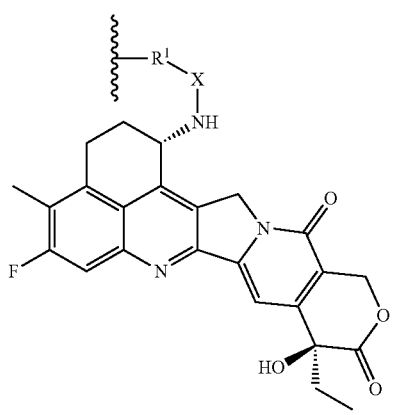

(III-A)

wherein, $R^1$ may be —O— or —($R^2$)N—;
X may be -$L^1$-$L^0$-;
$L^0$ may be —$CH_2$—, or $L^0$ may be —C(=S)—;
$L^1$ may be —($CH_2$)$_m$—, and m may be selected from the group consisting of integers from 0 to 2;
wherein 0 or 1 methylene unit of $L^1$ may be replaced by —C(O)— or —C(=S)—;
$R^2$ may be a $C_{1-6}$ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

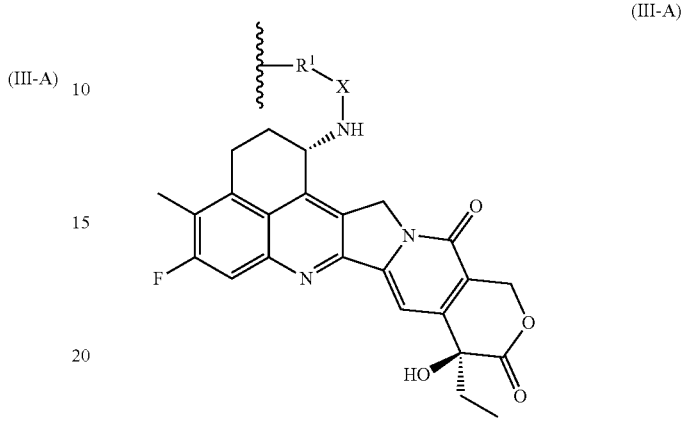

(III-A)

wherein, $R^1$ may be —NH—;
X may be -$L^1$-$L^0$-;
$L^0$ may be —$CH_2$—, or $L^0$ may be —C(=S)—;
$L^1$ may be —($CH_2$)$_m$—, and m may be selected from the group consisting of integers from 0 to 2;
wherein 0 or 1 methylene unit of $L^1$ may be replaced by —C(O)— or —C(=S)—.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

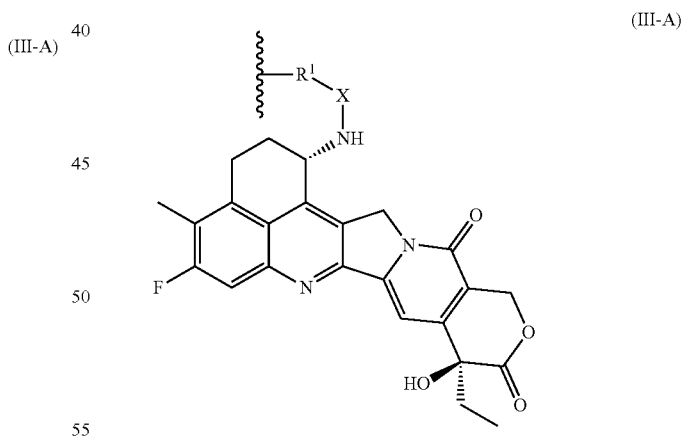

(III-A)

wherein, $R^1$ may be —S— or —($R^2$)N—;
X may be -$L^3$-$L^2$-;
wherein $L^2$ may be —C(O)—;
$L^3$ may be —($CH_2$)$_n$—, and n may be 4 or 5;
wherein 1 methylene unit of $L^3$ may be replaced by —$NR^8$—, —O—, —S— or —SO—;
$R^2$ may be a $C_{1-6}$ aliphatic group.

For example, the compound may comprise a structure shown as formula (III-A):
wherein, $R^1$ may be —S— or —(R')N—;
X may be -$L^3$-$L^2$-;

wherein L² may be —C(O)—;

L³ may be —(CH₂)ₙ—, and n may be 4 or 5;

wherein 1 methylene unit of L³ may be replaced by —O—;

R² may be a C₁₋₆ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

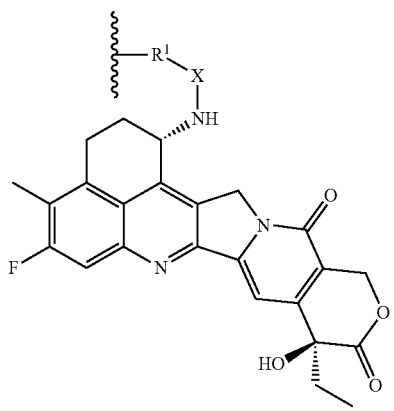

(III-A)

wherein, R¹ may be —O—;

X may be -L³-L²-;

wherein L² may be —C(O)—;

L³ may be —(C(R⁷ᵃ)(R⁷ᵇ))ₙ—, and n may be 4 or 5;

wherein 1 methylene unit of L³ may be replaced by —NR⁸— or —O—, and 0 or 1 methylene unit of L³ may also be independently replaced by —C(O)— or —C(=S)—;

wherein each R⁷ᵃ, each R⁷ᵇ and each R⁸ may each independently be hydrogen or a C₁₋₆ aliphatic group.

For example, the compound may comprise a structure shown as formula (III-A):

wherein, R¹ may be —O—;

X may be -L³-L²-;

wherein L² may be —C(O)—;

L³ may be —(C(R⁷ᵃ)(R⁷ᵇ))₄—;

wherein 1 methylene unit of L³ may be replaced by —NR⁸— or —O—;

wherein each R⁷ᵃ, each R⁷ᵇ and each R⁸ may each independently be hydrogen or a C₁₋₆ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

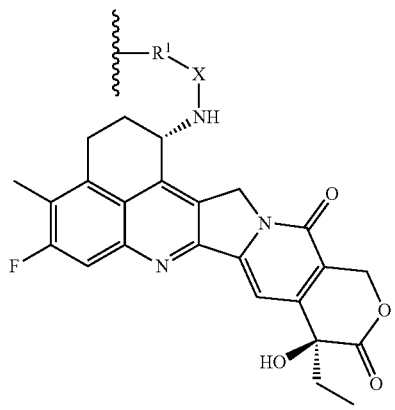

(III-A)

wherein, R¹ may be —O—;

X may be -L³-L²-;

wherein L² may be —C(O)—;

L³ may be —(C(R⁷ᵃ)(R⁷ᵇ))₄—;

wherein 1 methylene unit of L³ may be replaced by —NR⁸—;

wherein each R⁷ᵃ, each R⁷ᵇ and each R⁸ may each independently be hydrogen or a C₁₋₆ aliphatic group.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-A):

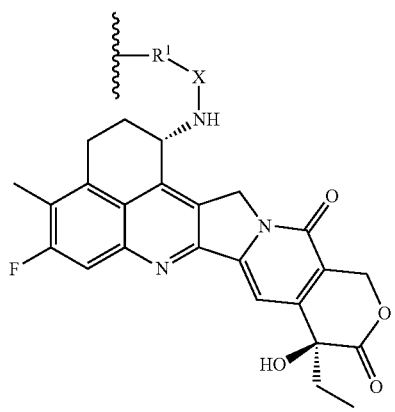

(III-A)

wherein, R¹ may be —NH—;

X may be -L³-L²-;

wherein L² may be —C(O)—;

L³ may be —(CH₂)ₙ—, and n may be 4 or 5;

wherein 1 methylene unit of L³ may be replaced by —S—.

In one embodiment, the present application provides a compound or a tautomer, a mesomer, a racemate, an enantiomer or a diastereoisomer thereof, or a mixture thereof, or a pharmaceutically acceptable salt thereof, wherein the compound may comprise the following group of structures:

III-A-1
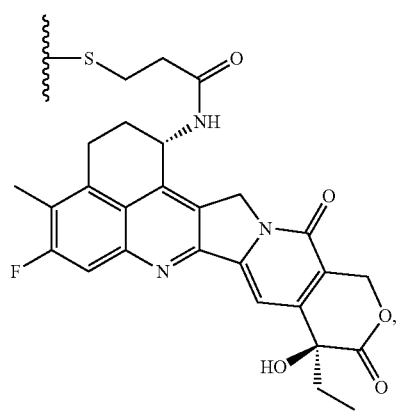
III-A-2
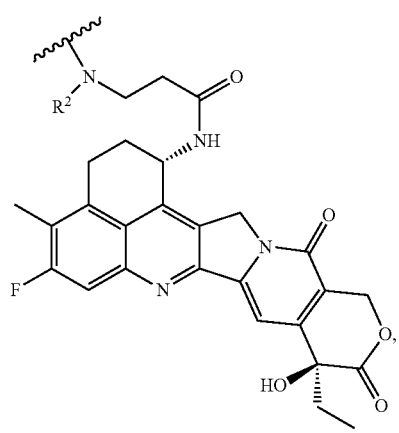
III-A-3
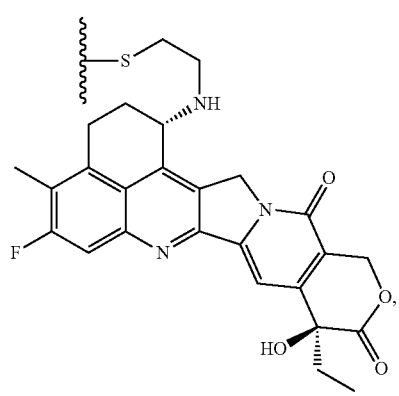
III-A-4
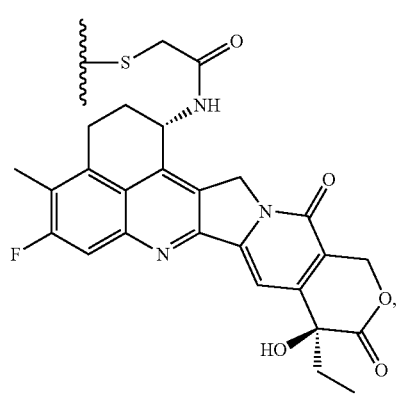
-continued
III-A-5
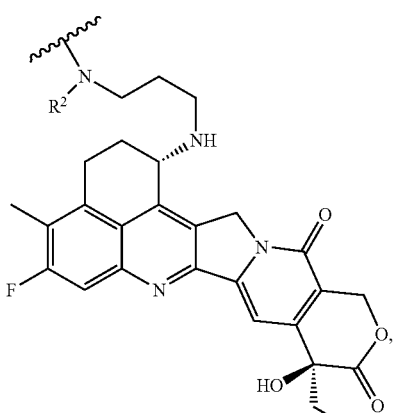
III-A-6
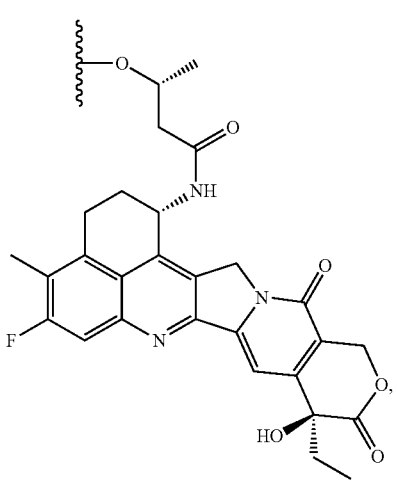
III-A-7
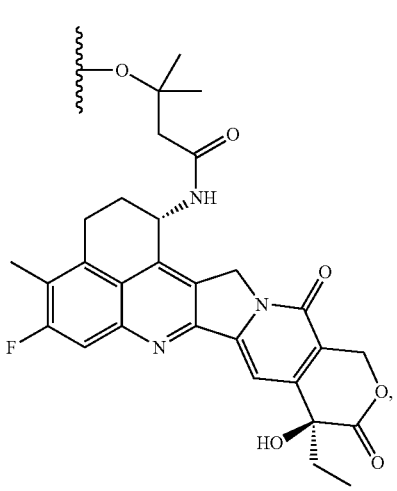

-continued
III-A-8
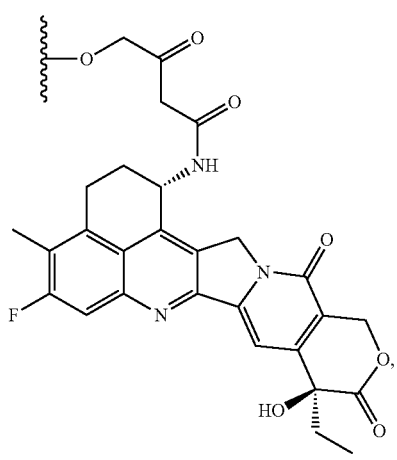
III-A-11
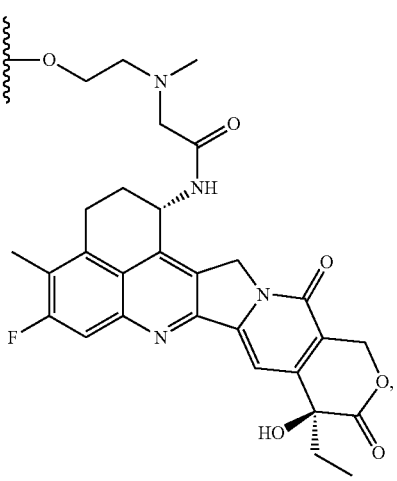
III-A-9
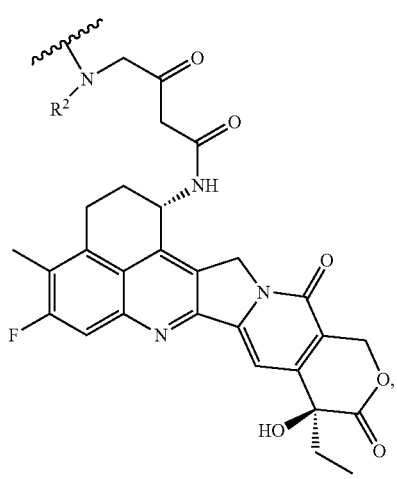
III-A-12
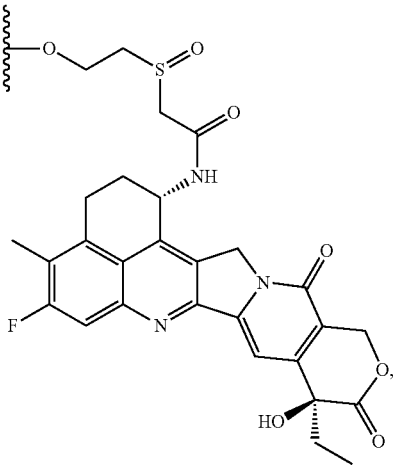
III-A-10
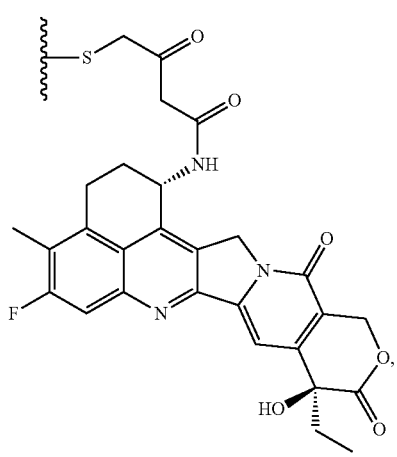
III-A-13
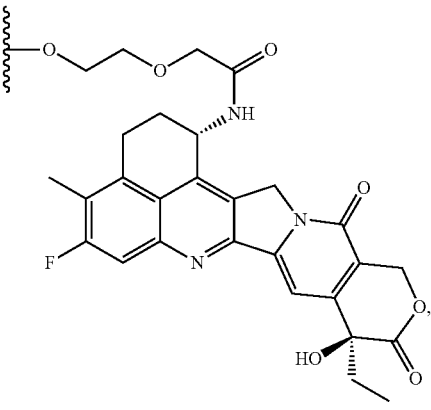

III-A-14

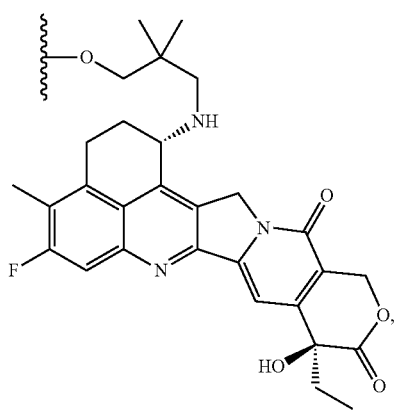

III-A-15

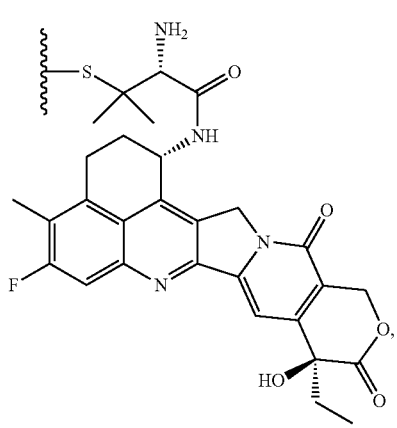

III-A-16

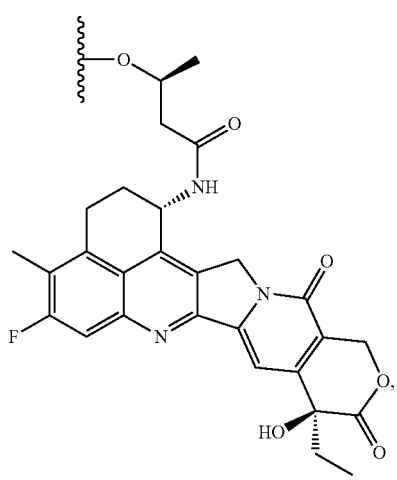

III-A-17

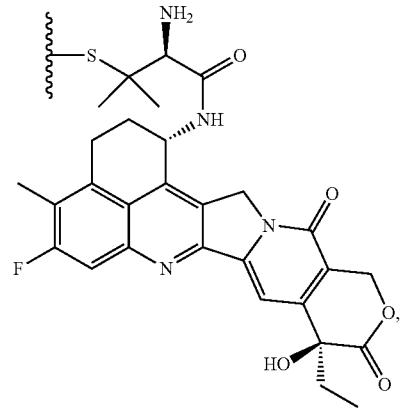

wherein R² may be a $C_{1-6}$ aliphatic group which may be optionally replaced by R, wherein R may be hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H, or a $C_{1-6}$ aliphatic group, or wherein, R² may be halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a $C_{1-6}$ aliphatic group.

For example, R² may be methyl which may be optionally substituted with one or more hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or $C_{1-6}$ aliphatic groups. For example, R² may be ethyl which may be optionally substituted with hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a $C_{1-6}$ aliphatic group. For example, R² may be propyl which may be optionally substituted with hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a $C_{1-6}$ aliphatic group.

In a second aspect, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (I-B):

(I-B)

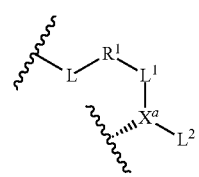

wherein, $X^a$ may be nitrogen generated by removal of two hydrogen atoms from an amino group of the cytotoxic drug;

L may be -$L_a$-$L_b$-$L_c$-;
$L_a$- may be selected from the group consisting of:

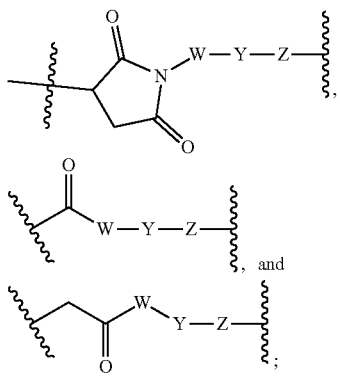

wherein W may be —$(C(R^{wa})(R^{wb}))_{wn}$—, Y may be —$(OCH_2CH_2)_{yn}$—$O_{yp}$—, and Z may be —$(C(R^{za})(R^{zb}))_{zn}$;

wherein wn may be selected from the group consisting of integers ≥0, and 0 or no less than 1 methylene unit of W may be independently replaced by -Cyr-, —$N(R^{wx})C(O)$—, —$C(O)N(R^{wx})$—, —$C(O)$—, —$OC(O)$—, —$C(O)O$—, —$NR^{wx}$—, —$O$—, —$S$—, —$SO$—, —$SO_2$—, —$P(R^{wx})$—, —$P(=O)(R^{wx})$—, —$N(R^{wx})SO_2$—, —$SO_2N(R^{wx})$—, —$C(=S)$—, —$C(=NR^{wx})$—, —$N=N$—, —$C=N$—, —$N=C$— or —$C(=N_2)$—;

wherein yn may be selected from the group consisting of integers ≥0, and yp may be 0 or 1;

wherein zn may be selected from the group consisting of integers ≥0, and 0 or no less than 1 methylene unit of Z may be independently replaced by -Cyr-, —$N(R^{zx})C(O)$—, —$C(O)N(R^{zx})$—, —$C(O)$—, —$OC(O)$—, —$C(O)O$—, —$NR^{zx}$—, —$O$—, —$S$—, —$SO$—, —$SO_2$—, —$P(R^{zx})$—, —$P(=O)(R^{zx})$—, —$N(R^{zx})SO_2$—, —$SO_2N(R^{zx})$—, —$C(=S)$—, —$C(=NR^{zx})$—, —$N=N$—, —$C=N$—, —$N=C$— or —$C(=N_2)$—;

Cyr- may be selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or may be independently substituted with no less than 1 substituent $R^{cx}$;

wherein each $R^{wa}$, each $R^{wb}$, each $R^{za}$, each $R^{zb}$, each $R^{wx}$, each $R^{zx}$ and each $R^{cx}$ may each independently be hydrogen, protium, deuterium, tritium, halogen, —$NO_2$, —CN, —$OR^r$, —$SR^r$, —$N(R^{ra})(R^{rb})$, —$C(O)R^r$, —$CO_2R^r$, —$C(O)C(O)R^r$, —$C(O)CH_2C(O)R^r$, —$S(O)R^r$, —$S(O)_2R^r$, —$C(O)N(R^{ra})(R^{rb})$, —$SO_2N(R^{ra})(R^{rb})$, —$OC(O)R^r$, —$N(R)SO_2R$ or a $C_{1-6}$ aliphatic group which may be optionally substituted with $R^r$;

wherein each $R^r$, each $R^{ra}$ and each $R^{rb}$ may each independently be hydrogen, protium, deuterium, tritium, halogen, —$NO_2$, —CN, —OH, —SH, —$NH_2$, —C(O)H, —$CO_2H$, —C(O)C(O)H, —$C(O)CH_2C(O)H$, —S(O)H, —$S(O)_2H$, —$C(O)NH_2$, —$SO_2NH_2$, —OC(O)H, —$N(H)SO_2H$ or a $C_{1-6}$ aliphatic group;

$L_b$- represents a peptide residue consisting of 2 to 7 amino acids;

$L_c$- may be selected from the group consisting of:

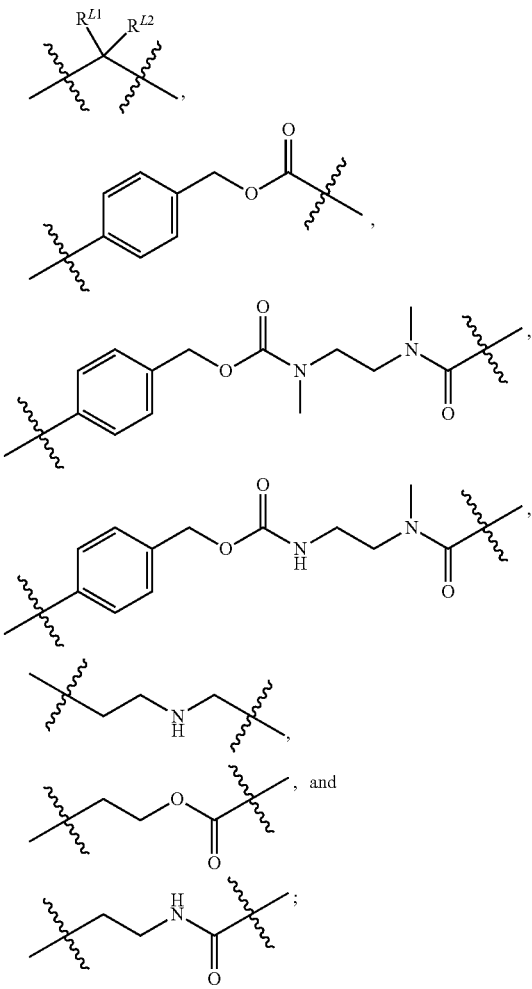

wherein $R^{L1}$ and $R^{L2}$ may each independently be selected from the group consisting of: hydrogen, protium, deuterium, tritium, halogen, —$NO_2$, —CN, —OH, —SH, —$NH_2$, —C(O)H, —$CO_2H$, —C(O)C(O)H, —$C(O)CH_2C(O)H$, —S(O)H, —$S(O)_2H$, —$C(O)NH_2$, —$SO_2NH_2$, —OC(O)H, —$N(H)SO_2H$ and a $C_{1-6}$ aliphatic group;

$R^1$, $L^1$ and $L^2$ are defined as in any formula (I-A) in embodiments of the first aspect.

In another embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-Bx) or formula (II-By):

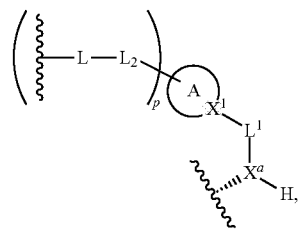

(II-Bx)

-continued

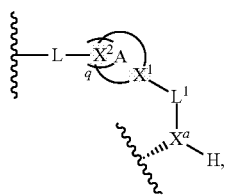
(II-By)

wherein, $X^a$ may be nitrogen generated by removal of two hydrogen atoms from an amino group of the cytotoxic drug;

L may be -$L_a$-$L_b$-$L_c$-;

$L_a$- may be selected from the group consisting of:

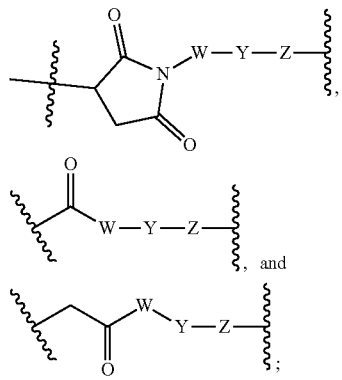

wherein W may be —$(C(R^{wa})(R^{wb}))_{wn}$—, Y may be —$(OCH_2CH_2)_{yn}$—$O_{yp}$—, and Z may be —$(C(R^{za})(R^{zb}))_{zn}$—;

wherein wn may be selected from the group consisting of integers ≥0, and 0 or no less than 1 methylene unit of W may be independently replaced by -Cyr-, —$N(R^{wx})C(O)$—, —$C(O)N(R^{wx})$—, —$C(O)$—, —$OC(O)$—, —$C(O)O$—, —$NR^{wx}$—, —O—, —S—, —SO—, —$SO_2$—, —$P(R^{wx})$—, —$P(=O)(R^{wx})$—, —$N(R^{wx})SO_2$—, —$SO_2N(R^{wx})$—, —$C(=S)$—, —$C(=NR^{wx})$—, —N=N—, —C=N—, —N=C— or —$C(=N_2)$—;

wherein yn may be selected from the group consisting of integers ≥0, and yp may be 0 or 1;

wherein zn may be selected from the group consisting of integers ≥0, and 0 or no less than 1 methylene unit of Z may be independently replaced by -Cyr-, —$N(R^{zx})C(O)$—, —$C(O)N(R^{zx})$—, —$C(O)$—, —$OC(O)$—, —$C(O)O$—, —$NR^{zx}$—, —O—, —S—, —SO—, —$SO_2$—, —$P(R^{zx})$—, —$P(=O)(R^{zx})$—, —$N(R^{zx})SO_2$—, —$SO_2N(R^{zx})$—, —$C(=S)$—, —$C(=NR^{zx})$—, —N=N—, —C=N—, —N=C— or —$C(=N_2)$—;

Cyr- may be selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or may be independently substituted with no less than 1 substituent $R^{cx}$;

wherein each $R^{wa}$, each $R^{wb}$, each $R^{za}$, each $R^{zb}$, each $R^{wx}$, each $R^{zx}$ and each $R^{cx}$ may each independently be hydrogen, protium, deuterium, tritium, halogen, —$NO_2$, —CN, —$OR^r$, —$SR^r$, —$N(R^a)(R^{rb})$, —C(O)R$^r$, —$CO_2R$, —$C(O)C(O)R^r$, —$C(O)CH_2C(O)R^r$, —$S(O)R^r$, —$S(O)_2R^r$, —$C(O)N(R^{ra})(R^{rb})$, —$SO_2N(R^{ra})(R^{rb})$, —$OC(O)R^r$, —$N(R)SO_2R$ or a $C_{1-6}$ aliphatic group which may be optionally substituted with $R^r$;

wherein each $R^r$, each $R^{ra}$ and each $R^{rb}$ may each independently be hydrogen, protium, deuterium, tritium, halogen, —$NO_2$, —CN, —OH, —SH, —$NH_2$, —C(O)H, —$CO_2H$, —C(O)C(O)H, —$C(O)CH_2C(O)H$, —S(O)H, —$S(O)_2H$, —$C(O)NH_2$, —$SO_2NH_2$, —OC(O)H, —$N(H)SO_2H$ or a $C_{1-6}$ aliphatic group;

$L_b$- represents a peptide residue consisting of 2 to 7 amino acids;

$L_c$- may be selected from the group consisting of:

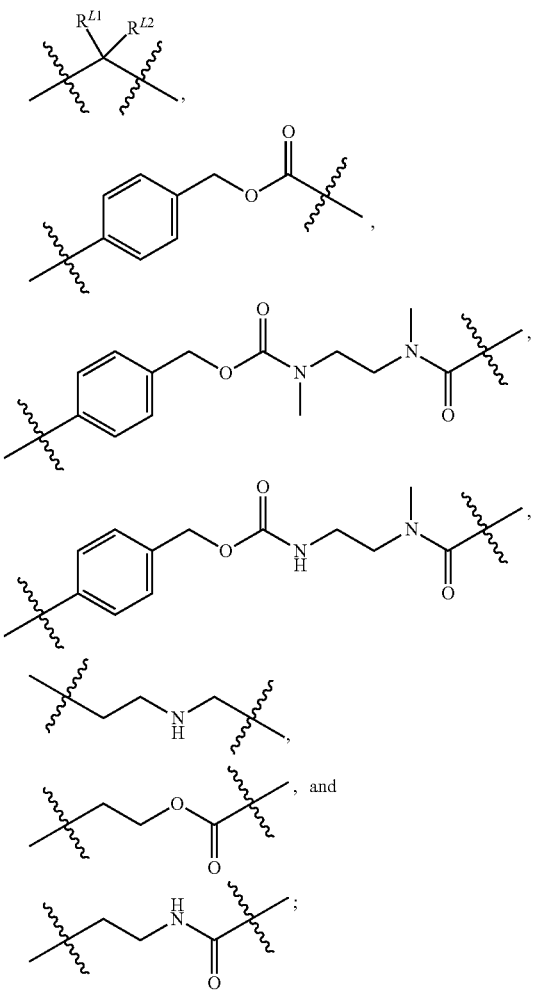

wherein $R^{L1}$ and $R^{L2}$ may each independently be selected from the group consisting of: hydrogen, protium, deuterium, tritium, halogen, —$NO_2$, —CN, —OH, —SH, —$NH_2$, —C(O)H, —$CO_2H$, —C(O)C(O)H, —$C(O)CH_2C(O)H$, —S(O)H, —$S(O)_2H$, —$C(O)NH_2$, —$SO_2NH_2$, —OC(O)H, —$N(H)SO_2H$ and a $C_{1-6}$ aliphatic group;

$L^2$, p, ring A, $X^1$ and $L^1$ are defined as in any formula (II-Ax) in embodiments of the first aspect;

or $X^2$, q, ring A, $X^1$ and $L^1$ are defined as in any formula (II-Ay) in embodiments of the first aspect.

In another embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-B):

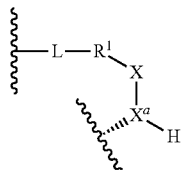
(III-B)

wherein, $X^a$ may be nitrogen generated by removal of two hydrogen atoms from an amino group of the cytotoxic drug;

L may be -$L_a$-$L_b$-$L_c$-;

$L_a$- may be selected from the group consisting of:

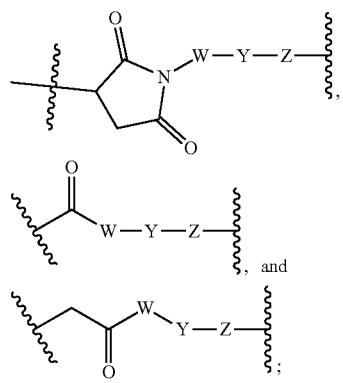

wherein W may be —$(C(R^{wa})(R^{wb}))_{wn}$—, Y may be —$(OCH_2CH_2)_{yn}$—$O_{yp}$, and Z may be —$(C(R^{za})(R^{zb}))_{zn}$—;

wherein wn may be selected from the group consisting of integers ≥0, and 0 or no less than 1 methylene unit of W may be independently replaced by -Cyr-, —$N(R^{wx})C(O)$—, —$C(O)N(R^{wx})$—, —C(O)—, —OC(O)—, —C(O)O—, —$NR^{wx}$—, —O—, —S—, —SO—, —$SO_2$—, —$P(R^{wx})$—, —$P(=O)(R^{wx})$—, —$N(R^{wx})SO_2$—, —$SO_2N(R^{wx})$—, —C(=S)—, —$C(=NR^{wx})$—, —N=N—, —C=N—, —N=C— or —$C(=N_2)$—;

wherein yn may be selected from the group consisting of integers ≥0, and yp may be 0 or 1;

wherein zn may be selected from the group consisting of integers ≥0, and 0 or no less than 1 methylene unit of Z may be independently replaced by -Cyr-, —$N(R^{zx})C(O)$—, —$C(O)N(R^{zx})$—, —C(O)—, —OC(O)—, —C(O)O—, —$NR^{zx}$—, —O—, —S—, —SO—, —$SO_2$—, —$P(R^{zx})$—, —$P(=O)(R^{zx})$—, —$N(R^{zx})SO_2$—, —$SO_2N(R^{zx})$—, —C(=S)—, —$C(=NR^{zx})$—, —N=N—, —C=N—, —N=C— or —$C(=N_2)$—;

Cyr- may be selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or may be independently substituted with no less than 1 substituent $R^{cx}$;

wherein each $R^{wa}$, each $R^{wb}$, each $R^{za}$, each $R^{zb}$, each $R^{wx}$, each $R^{zx}$ and each $R^{cx}$ may each independently be hydrogen, protium, deuterium, tritium, halogen, —$NO_2$, —CN, —$OR^r$, —$SR^r$, —$N(R^{ra})(R^{rb})$, —C(O)$R^r$, —$CO_2R^r$, —$C(O)C(O)R^r$, —$C(O)CH_2C(O)R^r$, —$S(O)R^r$, —$S(O)_2R^r$, —$C(O)N(R^{ra})(R^{rb})$, —$SO_2N(R^{ra})(R^{rb})$, —$OC(O)R^r$, —$N(R)SO_2R$ or a $C_{1-6}$ aliphatic group which may be optionally substituted with $R^r$;

wherein each $R^r$, each $R^{ra}$ and each $R^{rb}$ may each independently be hydrogen, protium, deuterium, tritium, halogen, —$NO_2$, —CN, —OH, —SH, —$NH_2$, —C(O)H, —$CO_2H$, —C(O)C(O)H, —$C(O)CH_2C(O)H$, —S(O)H, —$S(O)_2H$, —$C(O)NH_2$, —$SO_2NH_2$, —OC(O)H, —$N(H)SO_2H$ or a $C_{1-6}$ aliphatic group;

$L_b$- represents a peptide residue consisting of 2 to 7 amino acids;

$L_c$- may be selected from the group consisting of:

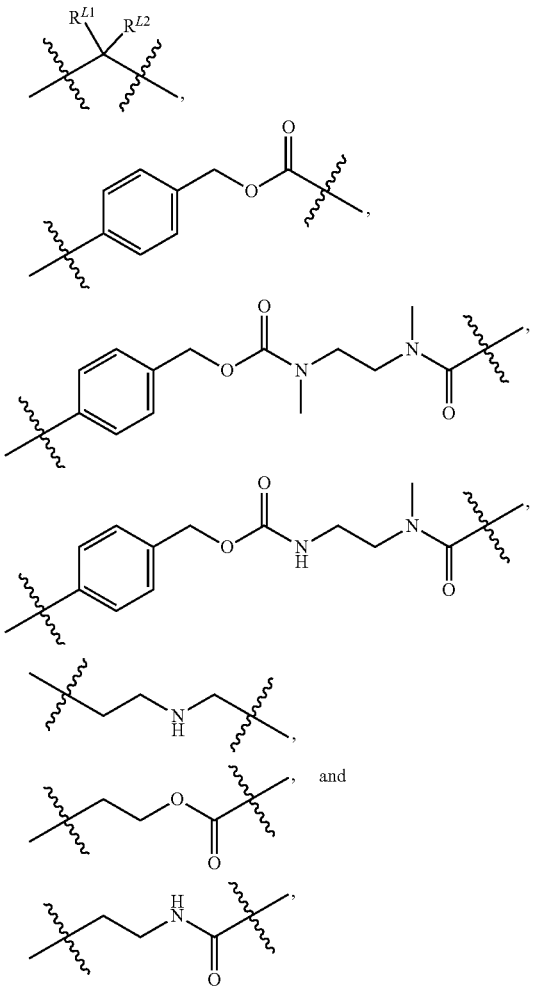

and wherein $R^{L1}$ and $R^{L2}$ may each independently be selected from the group consisting of: hydrogen, protium, deuterium, tritium, halogen, —$NO_2$, —CN, —OH, —SH, —$NH_2$, —C(O)H, —$CO_2H$, —C(O)C(O)H, —C(O)$CH_2C(O)H$, —S(O)H, —$S(O)_2H$, —$C(O)NH_2$, —$SO_2NH_2$, —OC(O)H, —$N(H)SO_2H$ and a $C_{1-6}$ aliphatic group;

wherein $R^1$ and X are defined as in any formula (III-A) in embodiments of the first aspect.

In another embodiment, wn may be selected from the group consisting of integers from 2 to 6, and 0 or 1 methylene unit of W may be independently replaced by -Cyr-, —N(R$^x$)C(O)—, —C(O)N(R$^{wx}$)—, —C(O)—, —NR$^{wx}$— or —O—.

For example, wn may be 1, 2, 3 or 6, and 1 methylene unit of W may be independently replaced by -Cyr-, —N(R$^{wx}$)C(O)—, —C(O)N(R$^{wx}$)— or —C(O)—.

In another embodiment, yn may be selected from the group consisting of integers from 0 to 12, and yp may be 0 or 1.

For example, yn may be 0, 4 or 8, and yp may be 0 or 1.

In another embodiment, zn may be selected from the group consisting of integers from 0 to 10, and 0 or 1 methylene unit of Z may be independently replaced by -Cyr-, —N(R$^{zx}$)C(O)—, —C(O)N(R$^{zx}$)— or —C(O)—.

For example, zn may be 1, 2 or 3, and 1 methylene unit of Z may be independently replaced by -Cyr-, —N(R$^{zx}$)C(O)—, —C(O)N(R$^{zx}$)— or —C(O)—.

In another embodiment, -Cyr- may be selected from the group consisting of: 6-10 membered arylene and 3-10 membered saturated or partially unsaturated carbocyclylene, wherein -Cyr- is unsubstituted or may be independently substituted with 1 to 3 substituent R$^{cx}$.

For example, -Cyr- may be 3-10 membered saturated carbocyclylene, wherein -Cyr- is unsubstituted or may be independently substituted with 1 to 3 substituent R$^{cx}$.

In another embodiment, each R$^{wa}$, each R$^{wb}$, each R$^{za}$, each R$^{zb}$, each R$^{wx}$, each R$^{zx}$ and each R$^{cx}$ may each independently be hydrogen, protium, deuterium, tritium, halogen, —NO$_2$, —CN, —OR$^r$, —SR$^r$, —N(R$^{ra}$)(R$^{rb}$), —C(O)R$^r$, —CO$_2$R$^r$, —C(O)C(O)R$^r$, —C(O)CH$_2$C(O)R$^r$, —S(O)R$^r$, —S(O)$_2$R$^r$, —C(O)N(R$^{ra}$)(R$^{rb}$), —SO$_2$N(R$^{ra}$)(R$^{rb}$), —OC(O)R$^r$, —N(R)SO$_2$R$^r$, or a C$_{1-6}$ aliphatic group which may be optionally substituted with R$^r$; each R$^r$, each R$^{ra}$ and each R$^{rb}$ may each independently be hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group.

For example, each R$^{wa}$, each R$^{wb}$, each R$^{za}$, each R$^{zb}$, each R$^{wx}$, each R$^{zx}$ and each R$^{cx}$ may each independently be hydrogen, halogen, —OR$^r$, or a C$_{1-6}$ aliphatic group which may be optionally substituted with R$^r$; each R$^r$ may independently be hydrogen, halogen or a C$_{1-6}$ aliphatic group.

In another embodiment, -L$_b$- represents a peptide residue consisting of 2 to 7 amino acids, and the peptide residue of -L$_b$- may be a peptide residue which may be formed of amino acids which may be selected from the group consisting of: phenylalanine, glycine, alanine, valine, citrulline, lysine, serine, glutamic acid and aspartic acid.

For example, -L$_b$- represents a peptide residue consisting of 2 to 4 amino acids, and the peptide residue of -L$_b$- may be a peptide residue which may be formed of amino acids which may be selected from the group consisting of: phenylalanine, glycine, alanine, valine, citrulline and lysine.

For example, -L$_b$- may be selected from the group consisting of:

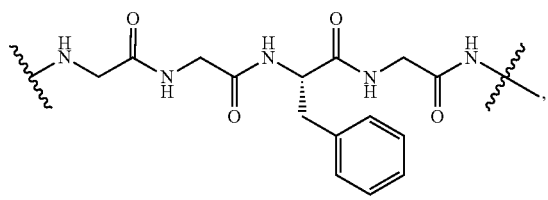 [SMILES: *NCC(=O)NCC(=O)N[C@@H](Cc1ccccc1)C(=O)NCC(=O)N*]

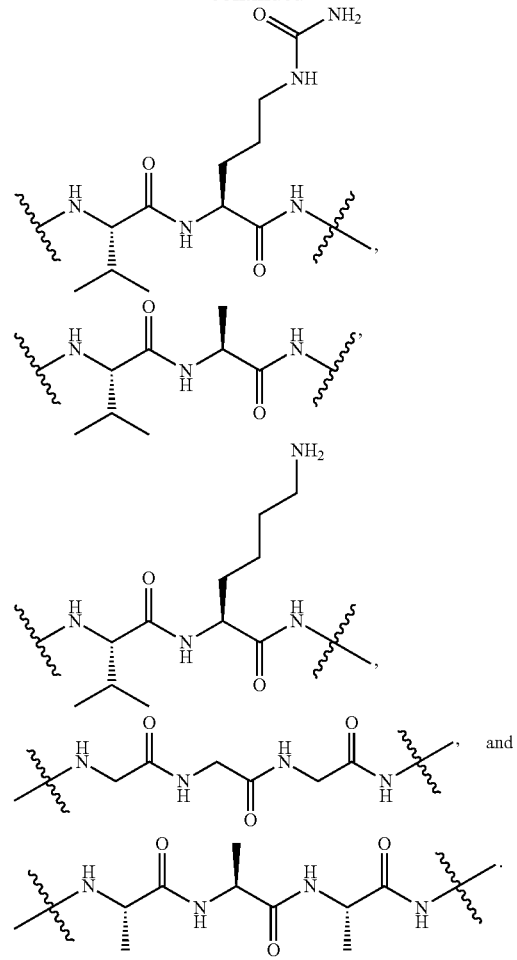

For example, -L$_b$- may be

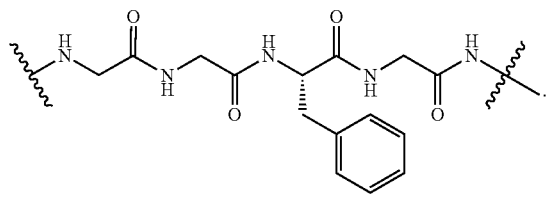

In another embodiment, -L$_c$- may be selected from the group consisting of:

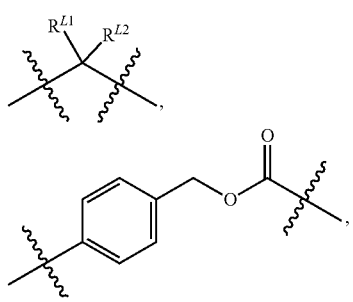

-continued

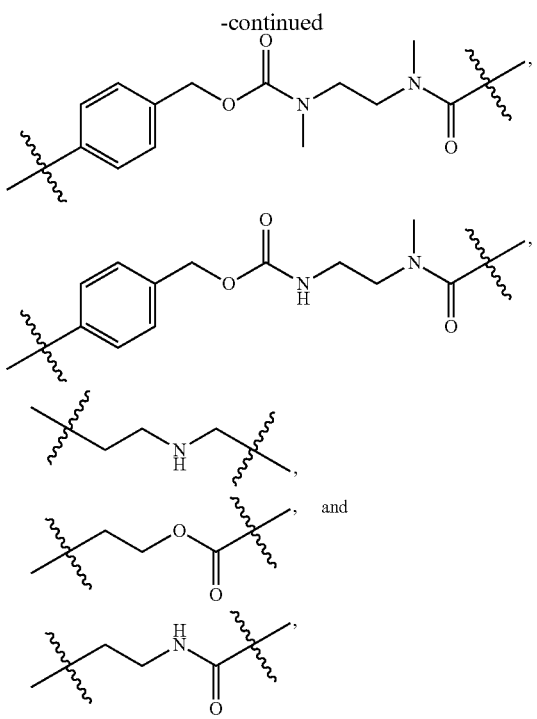

For example, -$L_c$- may be selected from the group consisting of:

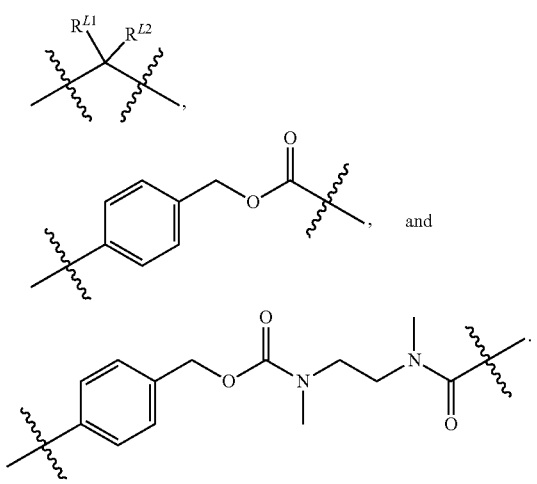

$L_c$- may be

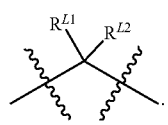

In another embodiment, $R^{L1}$ and $R^{L2}$ may each independently be selected from the group consisting of: hydrogen, protium, deuterium, tritium, halogen, —$NO_2$, —CN, —OH, —SH, —$NH_2$, —C(O)H, —$CO_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H and a $C_{1-6}$ aliphatic group.

For example, $R^{L1}$ and $R^{L2}$ may each independently be selected from the group consisting of: hydrogen, halogen, —OH and a $C_{1-6}$ aliphatic group.

In another embodiment, -$L_a$- may be

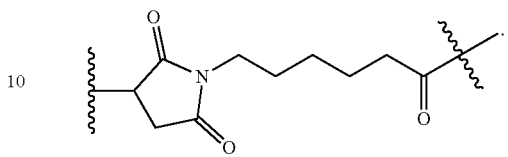

In another embodiment, -$L_b$- may be selected from the group consisting of:

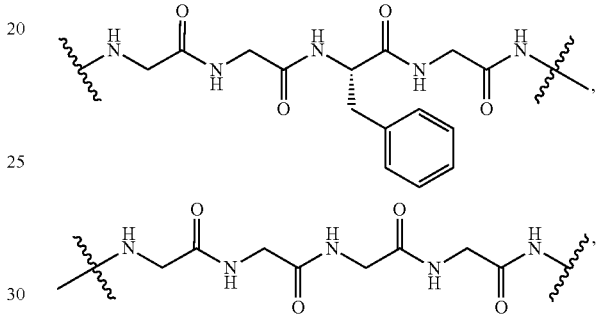

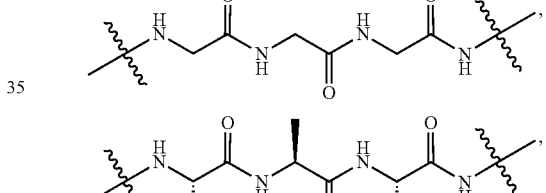

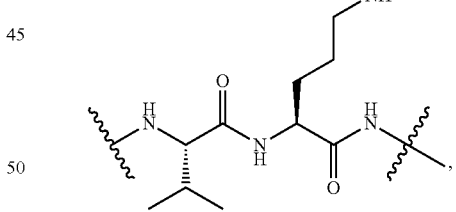

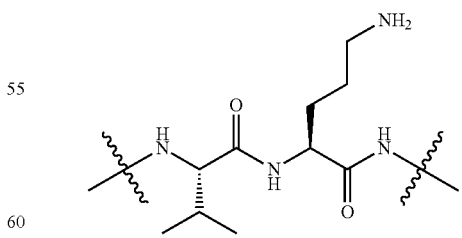

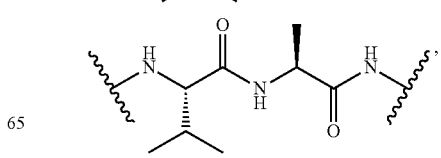

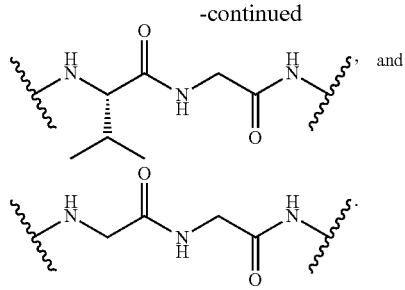
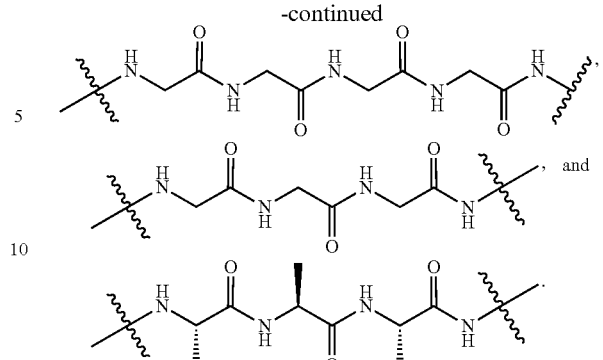
For example, -L$_b$- may be selected from the group consisting of:
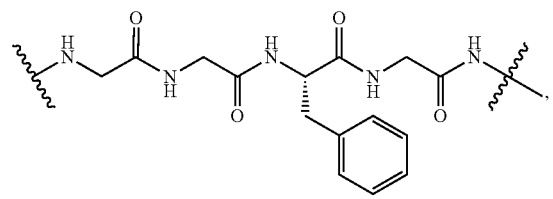
In one embodiment, -L$_c$- may be
In one embodiment, -L$_a$-L$_b$-L$_c$- may be selected from the group consisting of:
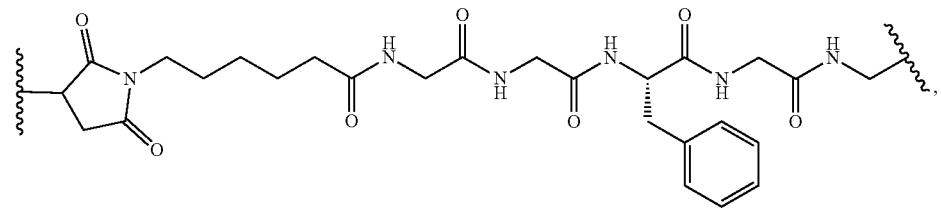
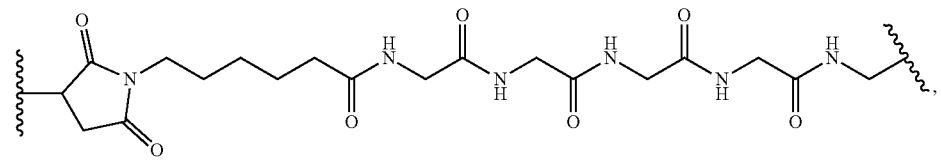
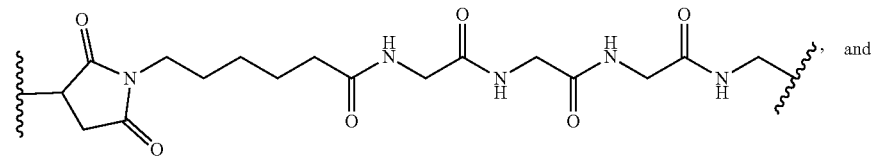
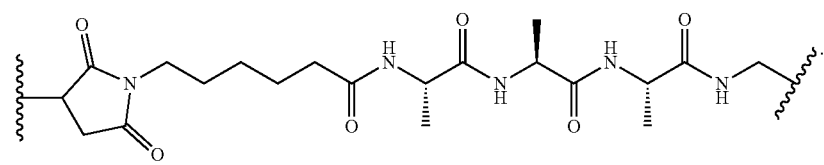

The cytotoxic drug is shown as formula (EXA):

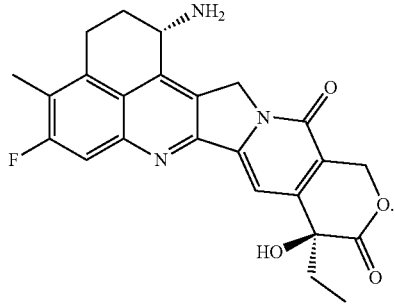

(EXA)

In a third aspect, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (I-C):

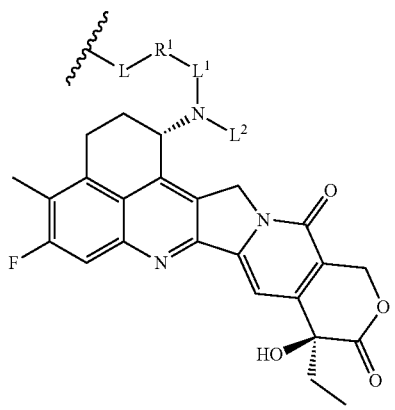

(I-C)

wherein, L may be -$L_a$-$L_b$-$L_c$-, and $L_a$, $L_b$ and $L_c$ are defined as in any formula (I-B) in embodiments of the second aspect;

$R^1$, $L^1$ and $L^2$ are defined as in any formula (I-A) in embodiments of the first aspect.

In another embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-$C_x$) or formula (II-Cy):

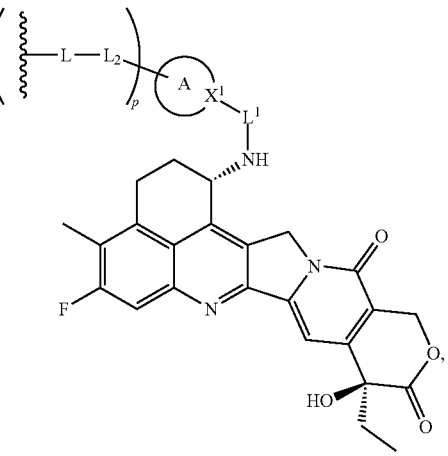

(II-Cx)

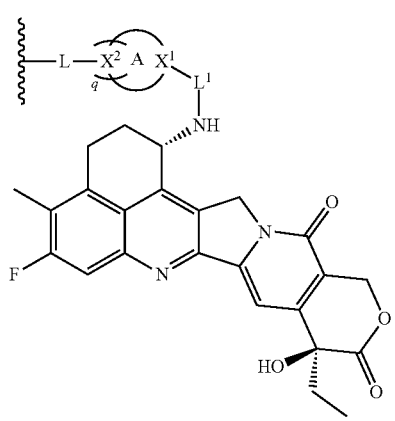

(II-Cy)

wherein, L may be -$L_a$-$L_b$-$L_c$-, and $L_a$, $L_b$ and $L_c$ are defined as in any formula (II-Bx) in embodiments of the second aspect;

L2, p, ring A, $X^1$ and $L^1$ are defined as in any formula (II-Ax) in embodiments of the first aspect;

or $X^2$, q, ring A, $X^1$ and $L^1$ are defined as in any formula (II-Ay) in embodiments of the first aspect.

In another embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-C):

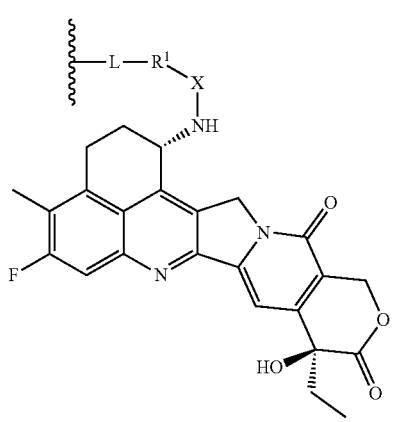

(III-C)

wherein, L may be -$L_a$-$L_b$-$L_c$-, and $L_a$, $L_b$ and $L_c$ are defined as in any formula (III-B) in embodiments of the second aspect;

wherein $R^1$ and X are defined as in any formula (III-A) in embodiments of the first aspect.

In a fourth aspect, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (I-D):

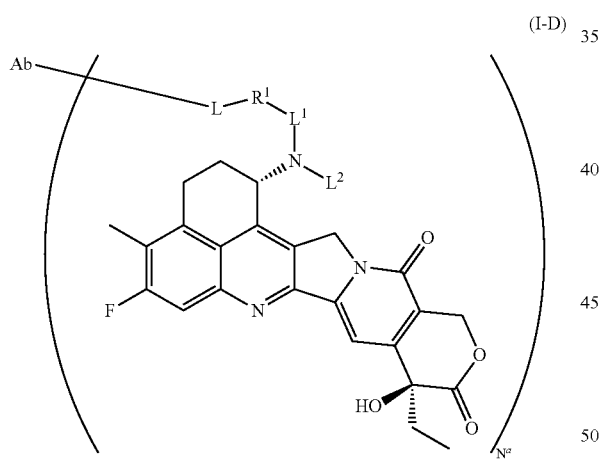

(I-D)

wherein, Ab may be a ligand, and an average connection number Na may be an integer or a decimal from 1 to 10;

L may be -$L_a$-$L_b$-$L_c$-, and $L_a$, $L_b$ and $L_c$ are defined as in any formula (I-B) in embodiments of the second aspect;

$R^1$, $L^1$ and $L^2$ are defined as in any formula (I-A) in embodiments of the first aspect.

In another embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (II-Dx) or formula (II-Dy):

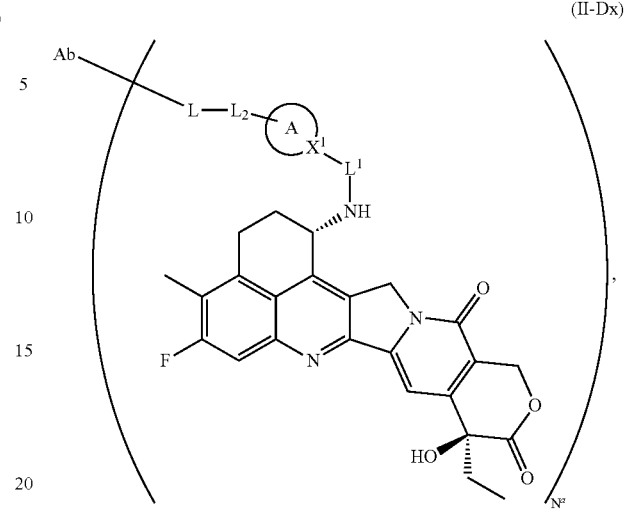

(II-Dx)

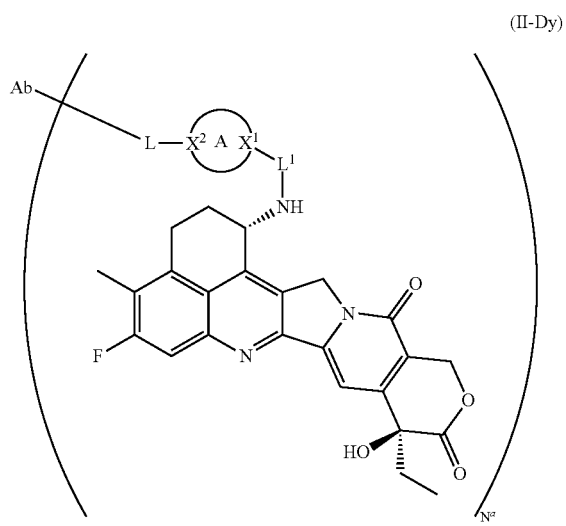

(II-Dy)

wherein, Ab may be a ligand, and an average connection number Na may be an integer or a decimal from 1 to 10;

L may be -$L_a$-$L_b$-$L_c$-, and $L_a$, $L_b$ and $L_c$ are defined as in any formula (II-Bx) in embodiments of the second aspect;

$L^2$, ring A, $X^1$ and $L^1$ are defined as in any formula (II-Ax) in embodiments of the first aspect;

or $X^2$, ring A, $X^1$ and $L^1$ are defined as in any formula (II-Ay) in embodiments of the first aspect.

In another embodiment, the present application provides a compound or a tautomer, a mesomer, a racemate, an enantiomer or a diastereoisomer thereof, or a mixture thereof, or a pharmaceutically acceptable salt thereof, wherein the compound may comprise a structure shown as formula (III-D):

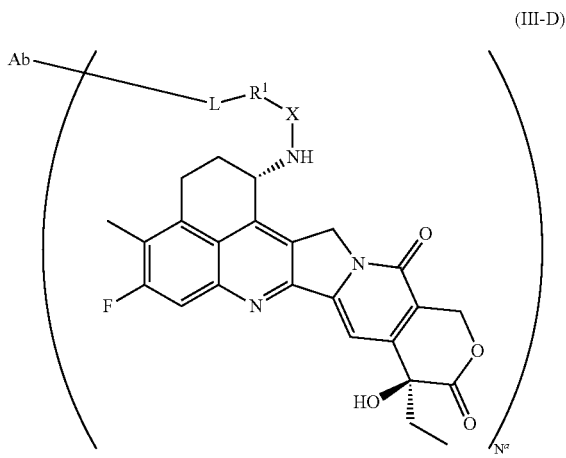

(III-D)

wherein, Ab may be a ligand, and an average connection number Na may be an integer or a decimal from 1 to 10;

L may be -$L_a$-$L_b$-$L_c$-, and $L_a$, $L_b$ and $L_c$ are defined as in any formula (III-B) in embodiments of the second aspect;

wherein $R^1$ and X are defined as in any formula (III-A) in embodiments of the first aspect.

In another embodiment, the ligand Ab may be an antibody or an antigen-binding fragment thereof.

For example, the ligand Ab may be selected from the group consisting of: a chimeric antibody, a humanized antibody and a fully humanized antibody.

For example, the ligand Ab targets the following: HER2, HER3, B7H3, TROP2, Claudin 18.2, CD30, CD33, CD70 and EGFR.

For example, the ligand Ab targets the following; for example, the antibody may be an antibody that targets the following target points: 5T4, AGS-16, ANGPTL4, ApoE, CD19, CTGF, CXCR5, FGF2, MCPT8, MFI2, MS4A7, NCA, Sema5b, SLITRK6, STC2, TGF, 0772P, 5T4, ACTA2, ADGRE1, AG-7, AIF1, AKR1C1, AKR1C2, ASLG659, Axl, B7H3, BAFF-R, BCMA, BMPR1B, BNIP3, C1QA, C1QB, CA6, CADM1, CCD79b, CCL5, CCR5, CCR7, CD11c, CD123, CD138, CD142, CD147, CD166, CD19, CD19, CD22, CD21, CD20, CD205, CD22, CD223, CD228, CD25, CD30, CD33, CD37, CD38, CD40, CD45, CD45 (PTPRC), CD46, CD47, CD49D (ITGA4), CD56, CD66e, CD70, CD71, CD72, CD74, CD79a, CD79b, CD80, CDCP1, CDH11, CD11b, CEA, CEACAM5, c-Met, COL6A3, COL7A1, CRIPTO, CSF1R, CTSD, CTSS, CXCL11, CXCL10, DDIT4, DLL3, DLL4, DR5, E16, EFNA4, EGFR, EGFRvIII, EGLN, EGLN3, EMR2, ENPP3, EpCAM, EphA2, EphB2R, ETBR, FcRH2, FcRH1, FGFR2, FGFR3, FLT3, FOLR-α, GD2, GEDA, GPC-1, GPNMB, GPR20, GZMB, HER2, HER3, HLA-DOB, HMOX1, IFI6, IFNG, IGF-1R, IGFBP3, IL10RA1, IL-13R, IL-2, IL20Ra, IL-3, IL-4, IL-6, IRTA2, KISS1R, KRT33A, LIV-1, LOX, LRP-1, LRRC15, LUM, LY64, LY6E, Ly86, LYPD3, MDP, MMP10, MMP14, MMP16, MPF, MSG783, MSLN, MUC-1, NaPi2b, Napi3b, Nectin-4, Nectin-4, NOG, P2X5, pCAD, P-Cadherin, PDGFRA, PDK1, PD-L1, PFKFB3, PGF, PGK1, PIK3AP1, PIK3CD, PLOD2, PSCA, PSCAhlg, PSMA, PSMA, PTK7, P-Cadherin, RNF43, NaPi2b, ROR1, ROR2, SERPINE1, SLC39A6, SLTRK6, STAT1, STEAP1, STEAP2, TCF4, TENB2, TGFB1, TGFB2, TGFBR1, TNFRSF21, TNFSF9, Trop-2, TrpM4, Tyro7, UPK1B, VEGFA, WNT5A, epidermal growth factors, brevican, mesothelin, sodium phosphate cotransporter 2B, Claudin 18.2, endothelin receptors, mucins (such as mucin 1 and mucin 16), guanylate cyclase C, integrin a4p7, integrin a5p6, trophoblast glycoprotein, and tissue factors.

In another embodiment, the average connection number Na may be an integer or a decimal from 2 to 8. For example, the average connection number Na may be an integer or a decimal from 3 to 8. For example, the average connection number Na may be an integer or a decimal from 1 to 2, 2 to 3, 3 to 4, 4 to 5, 5 to 6, 6 to 7, 7 to 8, 8 to 9, or 9 to 10.

In a fifth aspect, the present application provides a compound of general formula (I-E) or a tautomer, a mesomer, a racemate, an enantiomer or a diastereoisomer thereof, or a mixture thereof, or a pharmaceutically acceptable salt thereof,

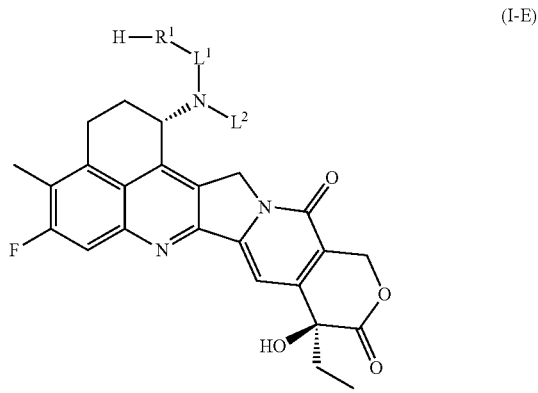

(I-E)

wherein $R^1$, $L^1$ and $L^2$ are defined as in any formula (I-A) in embodiments of the first aspect.

In another embodiment, the present application provides a compound of general formula (II-Ex) or (II-$E_y$), or a tautomer, a mesomer, a racemate, an enantiomer or a diastereoisomer thereof, or a mixture thereof, or a pharmaceutically acceptable salt thereof,

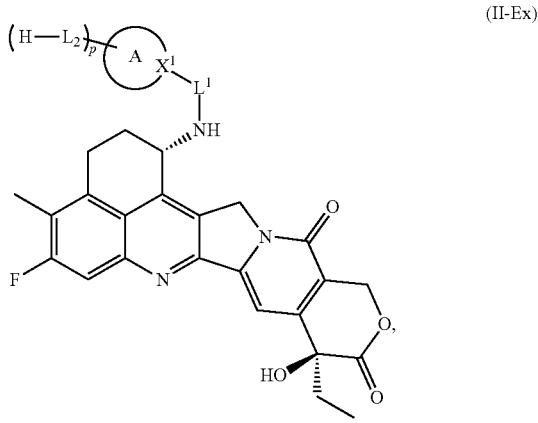

(II-Ex)

109
-continued

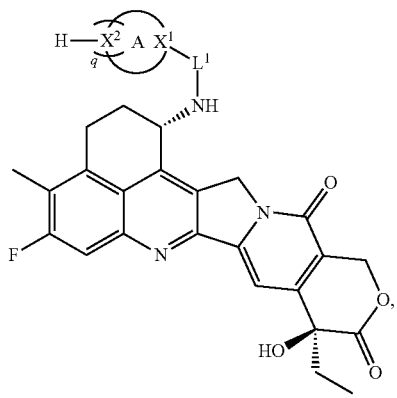

(II-Ey)

wherein L², p, ring A, X¹ and L¹ are defined as in any formula (II-Ax) in embodiments of the first aspect;
or X², q, ring A, X¹ and L¹ are defined as in any formula (II-Ay) in embodiments of the first aspect.

In another embodiment, the present application provides a compound of general formula (III-E) or a tautomer, a mesomer, a racemate, an enantiomer or a diastereoisomer thereof, or a mixture thereof, or a pharmaceutically acceptable salt thereof,

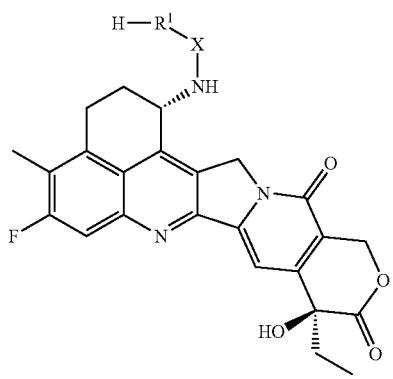

(III-E)

wherein R¹ and X are defined as in any formula (III-A) in embodiments of the first aspect.

In a sixth aspect, the present application provides a compound of general formula (I-F) or a tautomer, a mesomer, a racemate, an enantiomer or a diastereoisomer thereof, or a mixture thereof, or a pharmaceutically acceptable salt thereof,

110

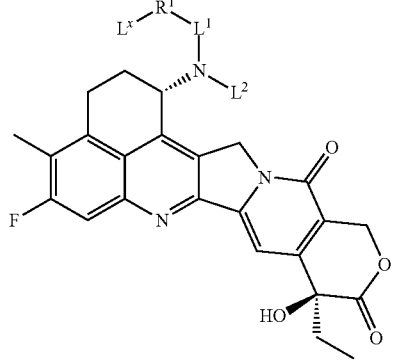

(I-F)

wherein, L may be $-L_{ax}-L_b-L_c-$;
$L_{ax}$- may be selected from the group consisting of:

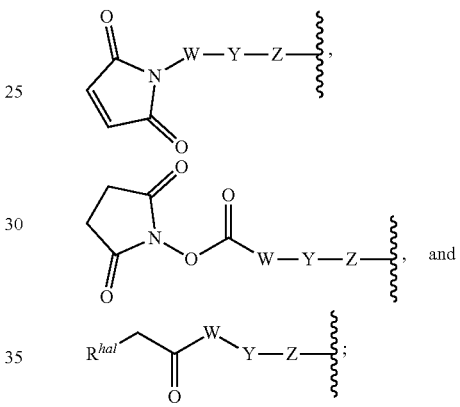

wherein $R^{hal}$ may be iodine or bromine;
wherein W may be $-(C(R^{wa})(R^{wb}))_{wn}-$, Y may be $-(OCH_2CH_2)_{yn}-O_{yp}-$, and Z may be $-(C(R^{za})(R^{zb}))_{zn}$;
wherein wn may be selected from the group consisting of integers ≥0, and
0 or no less than 1 methylene unit of W may be independently replaced by -Cyr-, $-N(R^{wx})C(O)-$, $-C(O)N(R^{wx})-$, $-C(O)-$, $-OC(O)-$, $-C(O)O-$, $-NR^{wx}-$, $-O-$, $-S-$, $-SO-$, $-SO_2-$, $-P(R^{wx})-$, $-P(=O)(R^{wx})-$, $-N(R^{wx})SO_2-$, $-SO_2N(R^{wx})-$, $-C(=S)-$, $-C(=NR^{wx})-$, $-N=N-$, $-C=N-$, $-N=C-$ or $-C(=N_2)-$;
wherein yn may be selected from the group consisting of integers ≥0, and yp may be 0 or 1;
wherein zn may be selected from the group consisting of integers ≥0, and
0 or no less than 1 methylene unit of Z may be independently replaced by -Cyr-, $-N(R^{zx})C(O)-$, $-C(O)N(R^{zx})-$, $-C(O)-$, $-OC(O)-$, $-C(O)O-$, $-NR^{zx}-$, $-O-$, $-S-$, $-SO-$, $-SO_2-$, $-P(R^{zx})-$, $-P(=O)(R^{zx})-$, $-N(R^{zx})SO_2-$, $-SO_2N(R^{zx})-$, $-C(=S)-$, $-C(=NR^{zx})-$, $-N=N-$, $-C=N-$, $-N=C-$ or $-C(=N_2)-$;
Cyr- may be selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or may be independently substituted with no less than 1 substituent $R^{cx}$;

wherein each $R^{wa}$, each $R^{wb}$, each $R^{za}$, each $R^{zb}$, each $R^{wx}$, each $R^{zx}$ and each $R^{cx}$ may each independently be hydrogen, protium, deuterium, tritium, halogen, —$NO_2$, —CN, —$OR^r$, —$SR^r$, —$N(R^{ra})(R^{rb})$, —C(O)$R^r$, —$CO_2R$, —C(O)C(O)$R^r$, —C(O)$CH_2$C(O)$R^r$, —S(O)$R^r$, —S(O)$_2R^r$, —C(O)N($R^{ra}$)($R^{rb}$), —$SO_2$N($R^{ra}$)($R^{rb}$), —OC(O)$R^r$, —N(R)$SO_2$R or a $C_{1-6}$ aliphatic group which may be optionally substituted with $R^r$;

wherein each $R^r$, each $R^{ra}$ and each $R^{rb}$ may each independently be hydrogen, protium, deuterium, tritium, halogen, —$NO_2$, —CN, —OH, —SH, —$NH_2$, —C(O)H, —$CO_2$H, —C(O)C(O)H, —C(O)$CH_2$C(O)H, —S(O)H, —S(O)$_2$H, —C(O)$NH_2$, —$SO_2NH_2$, —OC(O)H, —N(H)$SO_2$H or a $C_{1-6}$ aliphatic group;

$L^b$ and $L^c$ are defined as in any formula (I-B) in embodiments of the second aspect;

$R^1$, $L^1$ and $L^2$ are defined as in any formula (I-A) in embodiments of the first aspect.

In another embodiment, the present application provides a compound of general formula (II-$F_x$) or (II-Fy), or a tautomer, a mesomer, a racemate, an enantiomer or a diastereoisomer thereof, or a mixture thereof, or a pharmaceutically acceptable salt thereof,

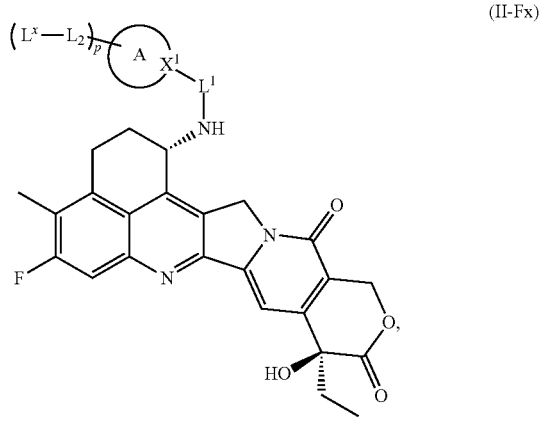

(II-Fx)

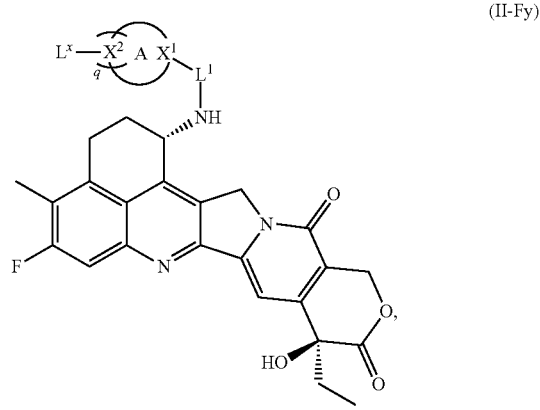

(II-Fy)

wherein, $L^x$ may be -$L_{ax}$-$L_b$-$L_c$-;
$L_{ax}$- may be selected from the group consisting of:

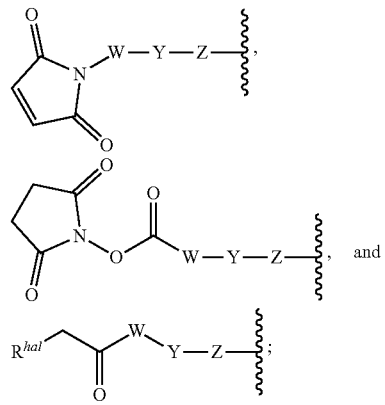

wherein $R^{hal}$ may be iodine or bromine;
wherein W may be —(C($R^{wa}$)($R^{wb}$))$_{wn}$—, Y may be —(OCH$_2$CH$_2$)$_{yn}$—O$_{yp}$—, and Z may be —(C($R^{za}$)($R^{zb}$))$_{zn}$;
wherein wn may be selected from the group consisting of integers ≥0, and
0 or no less than 1 methylene unit of W may be independently replaced by -Cyr-, —N($R^{wx}$)C(O)—, —C(O)N($R^{wx}$)—, —C(O)—, —OC(O)—, —C(O)O—, —NR$^{wx}$—, —O—, —S—, —SO—, —SO$_2$—, —P($R^{wx}$)—, —P(=O)($R^{wx}$)—, —N($R^{wx}$)SO$_2$—, —SO$_2$N($R^{wx}$)—, —C(=S)—, —C(=NR$^{wx}$)—, —N=N—, —C=N—, —N=C— or —C(=N$_2$)—;
wherein yn may be selected from the group consisting of integers ≥0, and yp may be 0 or 1;
wherein zn may be selected from the group consisting of integers ≥0, and
0 or no less than 1 methylene unit of Z may be independently replaced by -Cyr-, —N($R^{zx}$)C(O)—, —C(O)N($R^{zx}$)—, —C(O)—, —OC(O)—, —C(O)O—, —NR$^{zx}$—, —O—, —S—, —SO—, —SO$_2$—, —P($R^{zx}$)—, —P(=O)($R^{zx}$)—, —N($R^{zx}$)SO$_2$—, —SO$_2$N($R^{zx}$)—, —C(=S)—, —C(=NR$^{zx}$)—, —N=N—, —C=N—, —N=C— or —C(=N$_2$)—;
Cyr- may be selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or may be independently substituted with no less than 1 substituent $R^{cx}$;

wherein each $R^{wa}$, each $R^{wb}$, each $R^{za}$, each $R^{zb}$, each $R^{wx}$, each $R^{zx}$ and each $R^{cx}$ may each independently be hydrogen, protium, deuterium, tritium, halogen, —$NO_2$, —CN, —$OR^r$, —$SR^r$, —$N(R^a)(R^{rb})$, —C(O)$R^r$, —$CO_2R$, —C(O)C(O)$R^r$, —C(O)$CH_2$C(O)$R^r$, —S(O)$R^r$, —S(O)$_2R^r$, —C(O)N($R^{ra}$)($R^{rb}$), —$SO_2$N($R^{ra}$)($R^{rb}$), —OC(O)$R^r$, —N(R)$SO_2$R or a $C_{1-6}$ aliphatic group which may be optionally substituted with $R^r$;

wherein each $R^r$, each $R^{ra}$ and each $R^{rb}$ may each independently be hydrogen, protium, deuterium, tritium, halogen, —$NO_2$, —CN, —OH, —SH, —$NH_2$, —C(O)H, —$CO_2$H, —C(O)C(O)H, —C(O)$CH_2$C(O)H, —S(O)H, —S(O)$_2$H, —C(O)$NH_2$, —$SO_2NH_2$, —OC(O)H, —N(H)$SO_2$H or a $C_{1-6}$ aliphatic group;

$L^b$ and $L^c$ are defined as in any formula (II-Bx) in embodiments of the second aspect;
wherein $L^2$, p, ring A, $X^1$ and $L^1$ are defined as in any formula (II-Ax) in embodiments of the first aspect;

or $X^2$, q, ring A, $X^1$ and $L^1$ are defined as in any formula (II-Ay) in embodiments of the first aspect.

In another embodiment, the present application provides a compound of general formula (III-F) or a tautomer, a mesomer, a racemate, an enantiomer or a diastereoisomer thereof, or a mixture thereof, or a pharmaceutically acceptable salt thereof,

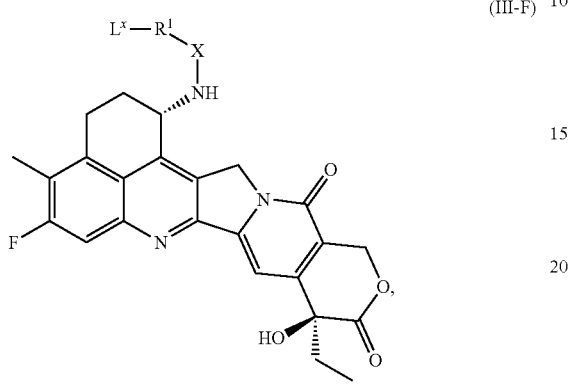
(III-F)

wherein, LX may be -$L_{ax}$-$L_b$-$L_c$-;
$L_{ax}$- may be selected from the group consisting of:

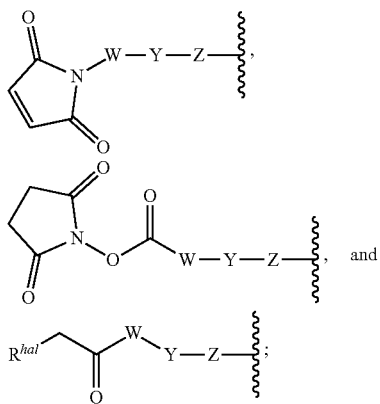

wherein $R^{hal}$ may be iodine or bromine;
wherein W may be —$(C(R^{wa})(R^{wb}))_{wn}$—, Y may be —$(OCH_2CH_2)_{yn}$—$O_{yp}$—, and Z may be —$(C(R^{za})(R^{zb}))_{zn}$;
wherein wn may be selected from the group consisting of integers ≥0, and
0 or no less than 1 methylene unit of W may be independently replaced by -Cyr-, —$N(R^{wx})C(O)$—, —$C(O)N(R^{wx})$—, —$C(O)$—, —$OC(O)$—, —$C(O)O$—, —$NR^{wx}$—, —$O$—, —$S$—, —$SO$—, —$SO_2$—, —$P(R^{wx})$—, —$P(=O)(R^{wx})$—, —$N(R^{wx})SO_2$—, —$SO_2N(R^{wx})$—, —$C(=S)$—, —$C(=NR^{wx})$—, —$N=N$—, —$C=N$—, —$N=C$— or —$C(=N_2)$—;
wherein yn may be selected from the group consisting of integers ≥0, and yp may be 0 or 1;
wherein zn may be selected from the group consisting of integers ≥0, and
0 or no less than 1 methylene unit of Z may be independently replaced by -Cyr-, —$N(R^{zx})C(O)$—, —$C(O)N(R^{zx})$—, —$C(O)$—, —$OC(O)$—, —$C(O)O$—, —$NR^{zx}$—, —$O$—, —$S$—, —$SO$—, —$SO_2$—, —$P(R^{zx})$—, —$P(=O)(R^{zx})$—, —$N(R^{zx})SO_2$—, —$SO_2N(R^{zx})$—, —$C(=S)$—, —$C(=NR^{zx})$—, —$N=N$—, —$C=N$—, —$N=C$— or —$C(=N_2)$—;

Cyr- may be selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or may be independently substituted with no less than 1 substituent $R^{cx}$;

wherein each $R^{wa}$, each $R^{wb}$, each $R^{za}$, each $R^{zb}$, each $R^{wx}$, each $R^{zx}$ and each $R^{cx}$ may each independently be hydrogen, protium, deuterium, tritium, halogen, —$NO_2$, —CN, —$OR^r$, —$SR^r$, —$N(R^{ra})(R^{rb})$, —$C(O)R^r$, —$CO_2R$, —$C(O)C(O)R^r$, —$C(O)CH_2C(O)R^r$, —$S(O)R^r$, —$S(O)_2R^r$, —$C(O)N(R^{ra})(R^{rb})$, —$SO_2N(R^{ra})(R^{rb})$, —$OC(O)R^r$, —$N(R)SO_2R$ or a $C_{1-6}$ aliphatic group which may be optionally substituted with $R^r$;

wherein each $R^r$, each $R^{ra}$ and each $R^{rb}$ may each independently be hydrogen, protium, deuterium, tritium, halogen, —$NO_2$, —CN, —OH, —SH, —$NH_2$, —$C(O)H$, —$CO_2H$, —$C(O)C(O)H$, —$C(O)CH_2C(O)H$, —$S(O)H$, —$S(O)_2H$, —$C(O)NH_2$, —$SO_2NH_2$, —$OC(O)H$, —$N(H)SO_2H$ or a $C_{1-6}$ aliphatic group;

$L^b$ and $L^c$ are defined as in any formula (III-B) in embodiments of the second aspect;
wherein $R^1$ and X are defined as in any formula (III-A) in embodiments of the first aspect.

In another embodiment, $L_{ax}$- may be selected from the group consisting of:

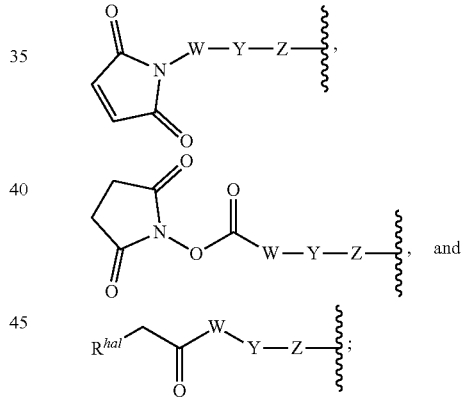

wherein $R^{hal}$ may be iodine or bromine;
wherein W may be —$(C(R^{wa})(R^{wb}))_{wn}$—, Y may be —$(OCH_2CH_2)_{yn}$—$O_{yp}$—, and Z may be —$(C(R^{za})(R^{zb}))_{zn}$.

In another embodiment, wn may be selected from the group consisting of integers from 2 to 6, and 0 or 1 methylene unit of W may be independently replaced by -Cyr-, —$N(R^{wx})C(O)$—, —$C(O)N(R^{wx})$—, —$C(O)$—, —$NR^{wx}$— or —O—.

For example, wn may be 1, 2, 3 or 6, and 1 methylene unit of W may be independently replaced by -Cyr-, —$N(R^{wx})C(O)$—, —$C(O)N(R^{wx})$— or —$C(O)$—.

In another embodiment, yn may be selected from the group consisting of integers from 0 to 12, and yp may be 0 or 1.

For example, yn may be 0, 4 or 8, and yp may be 0 or 1.

In another embodiment, zn may be selected from the group consisting of integers from 0 to 10, and 0 or 1 methylene unit of Z may be independently replaced by -Cyr-, —N(R$^{zx}$)C(O)—, —C(O)N(R$^{zx}$)— or —C(O)—.

For example, zn may be 1, 2 or 3, and 1 methylene unit of Z may be independently replaced by -Cyr-, —N(R$^{zx}$)C(O)—, —C(O)N(R$^{zx}$)— or —C(O)—.

In another embodiment, -Cyr- may be selected from the group consisting of: 6-10 membered arylene and 3-10 membered saturated or partially unsaturated carbocyclylene, wherein -Cyr- is unsubstituted or may be independently substituted with 1 to 3 substituent R$^{cx}$.

For example, -Cyr- may be 3-10 membered saturated carbocyclylene, wherein -Cyr- is unsubstituted or may be independently substituted with 1 to 3 substituent R$^{cx}$.

In another embodiment, each R$^{wa}$, each R$^{wb}$, each R$^{za}$, each R$^{zb}$, each R$^{wx}$, each R$^{zx}$ and each R$^{cx}$ may each independently be hydrogen, protium, deuterium, tritium, halogen, —NO$_2$, —CN, —OR$^r$, —SR$^r$, —N(R$^{ra}$)(R$^{rb}$), —C(O)R$^r$, —CO$_2$R$^r$, —C(O)C(O)R$^r$, —C(O)CH$_2$C(O)R$^r$, —S(O)R$^r$, —S(O)$_2$R$^r$, —C(O)N(R$^{ra}$)(R$^{rb}$), —SO$_2$N(R$^{ra}$)(R$^{rb}$), —OC(O)R$^r$, —N(R)SO$_2$R$^r$, or a C$_{1-6}$ aliphatic group which may be optionally substituted with R$^r$; each R$^r$, each R$^{ra}$ and each R$^{rb}$ may each independently be hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group.

For example, each R$^{wa}$, each R$^{wb}$, each R$^{za}$, each R$^{zb}$, each R$^{wx}$, each R$^{zx}$ and each R$^{cx}$ may each independently be hydrogen, halogen, —OR$^r$, or a C$_{1-6}$ aliphatic group which may be optionally substituted with R$^r$; each R$^r$ may independently be hydrogen, halogen or a C$_{1-6}$ aliphatic group.

In another embodiment, -L$_{ax}$- may be

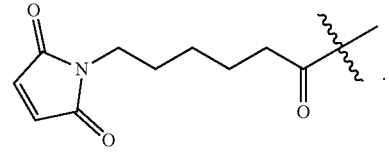 [SMILES: *C(=O)CCCCCN1C(=O)C=CC1=O]

In another embodiment, L$_{ax}$-L$_b$-L$_c$- may be selected from the group consisting of:

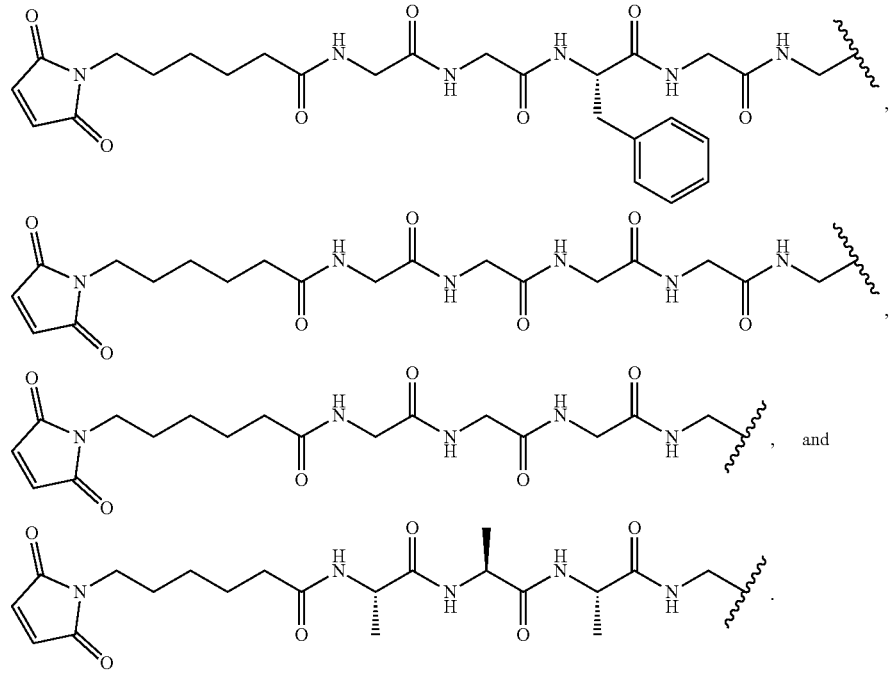

, and

.

Compounds Disclosed Herein

In one embodiment, the compounds disclosed herein include, but are not limited to:

| No. | Structure |
|---|---|
| P-I-1 | 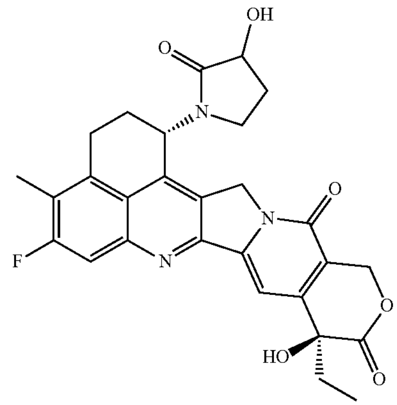 [SMILES: CC[C@@]1(O)C(=O)OCc2c1cc1n(c2=O)Cc2c-1nc1cc(F)c(C)c3c1c2[C@@H](N1CCC(O)C1=O)CC3] |
| P-I-2 | 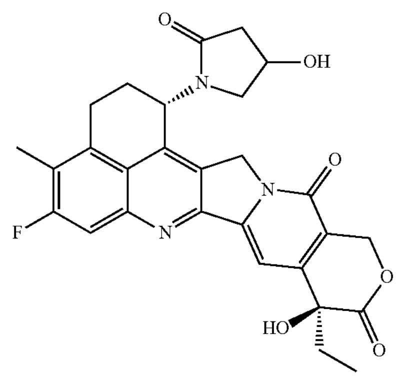 [SMILES: CC[C@@]1(O)C(=O)OCc2c1cc1n(c2=O)Cc2c-1nc1cc(F)c(C)c3c1c2[C@@H](N1CC(O)CC1=O)CC3] |

| No. | Structure |
|---|---|
| P-I-3 | 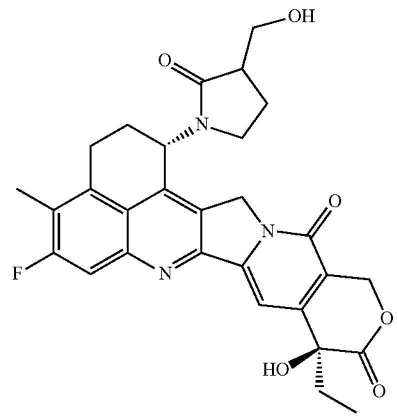 [SMILES: CC[C@@]1(O)C(=O)OCc2c1cc1n(c2=O)Cc2c-1nc1cc(F)c(C)c3c1c2[C@@H](N1CCC(CO)C1=O)CC3] |
| P-I-4 | 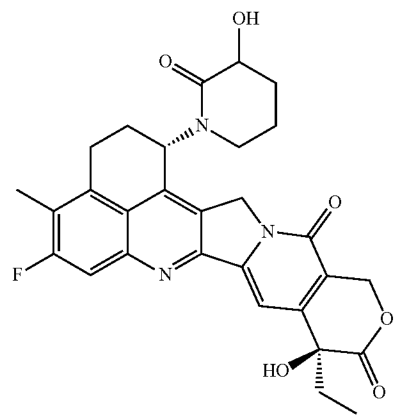 [SMILES: CC[C@@]1(O)C(=O)OCc2c1cc1n(c2=O)Cc2c-1nc1cc(F)c(C)c3c1c2[C@@H](N1CCCC(O)C1=O)CC3] |

| No. | Structure |
|---|---|
| P-I-5 | 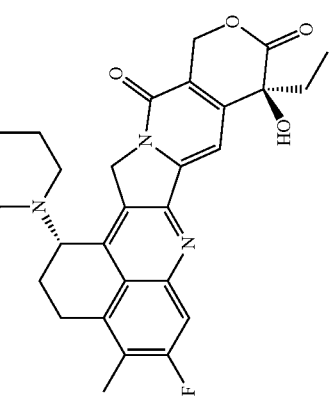 |
| P-I-6 | 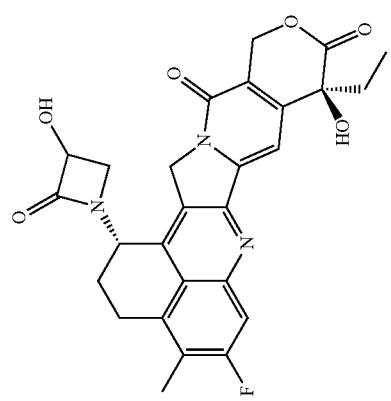 |

| No. | Structure |
|---|---|
| P-I-7 | 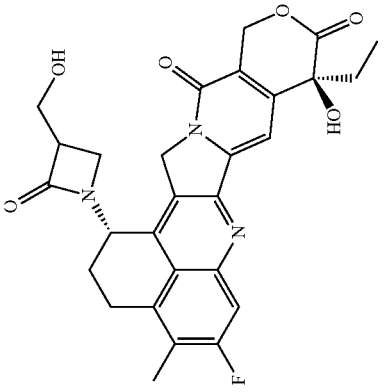 |
| P-I-8 | 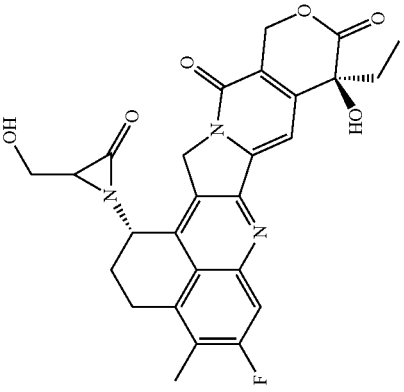 |

| No. | Structure |
|---|---|
| P-I-9 | *(chemical structure)* |
| P-I-10 | *(chemical structure)* |

-continued
| No. | Structure |
|---|---|
| P-I-11 | 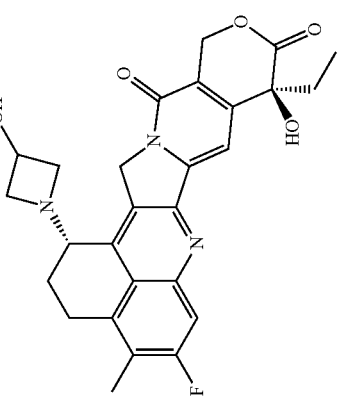 |
| P-I-12 | 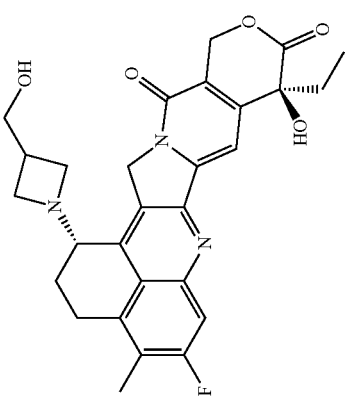 |

-continued
| No. | Structure |
|---|---|
| P-I-13 | 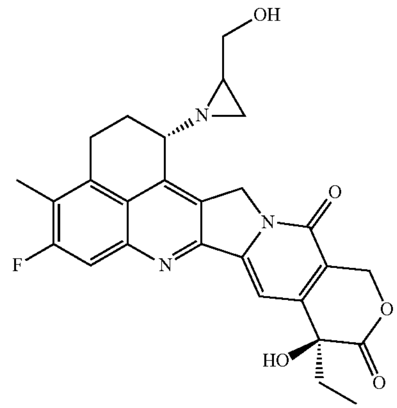 [SMILES: CC[C@@]1(O)C(=O)OCc2c1cc1n(c2=O)Cc2c-1nc1cc(F)c(C)c3c1c2[C@@H](N1CC1CO)CC3] |
| P-I-14 | 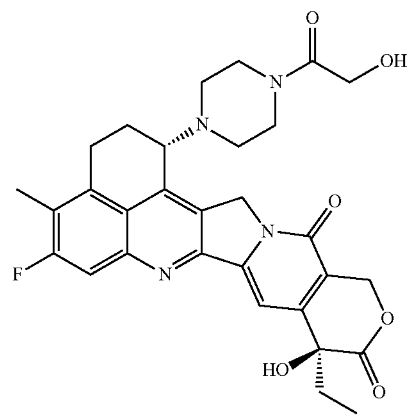 [SMILES: CC[C@@]1(O)C(=O)OCc2c1cc1n(c2=O)Cc2c-1nc1cc(F)c(C)c3c1c2[C@@H](N1CCN(C(=O)CO)CC1)CC3] |
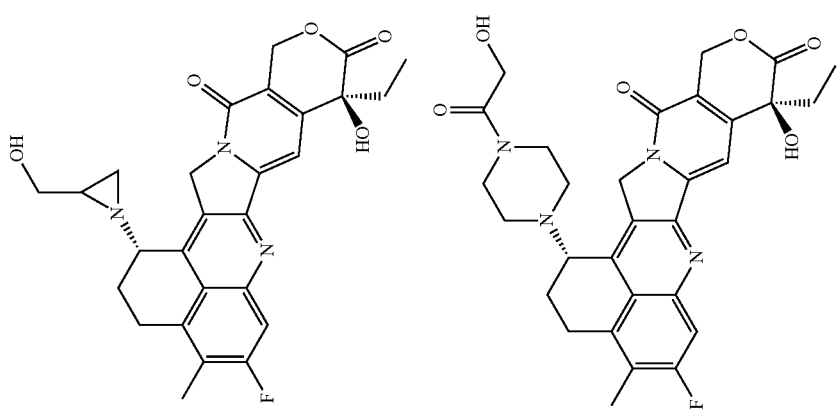

| No. | Structure |
|---|---|
| P-I-15 | 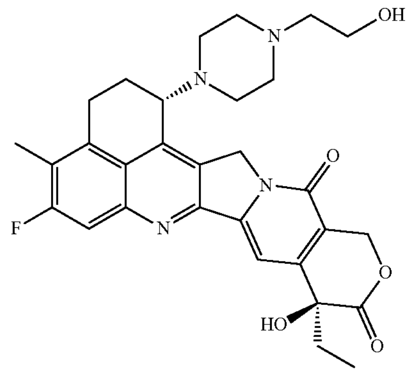 [SMILES: CC[C@@]1(O)C(=O)OCc2c1cc1n(c2=O)Cc2c-1nc1cc(F)c(C)c3c1c2[C@@H](N1CCN(CCO)CC1)CC3] |
| P-I-16 | 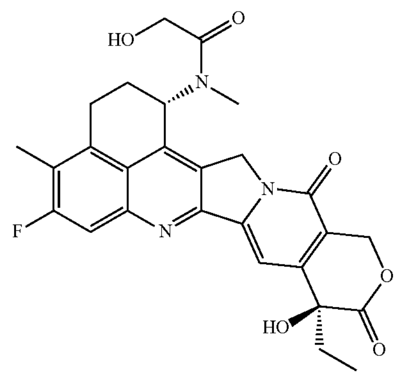 [SMILES: CC[C@@]1(O)C(=O)OCc2c1cc1n(c2=O)Cc2c-1nc1cc(F)c(C)c3c1c2[C@@H](N(C)C(=O)CO)CC3] |

| No. | Structure |
|---|---|
| P-I-17 | 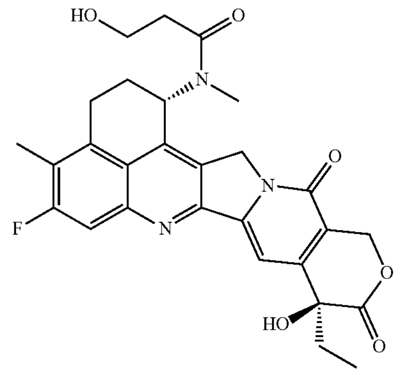 [SMILES: CC[C@@]1(O)C(=O)OCc2c1cc1n(c2=O)Cc2c-1nc1cc(F)c(C)c3c1c2[C@@H](N(C)C(=O)CCO)CC3] |
| P-I-18 | 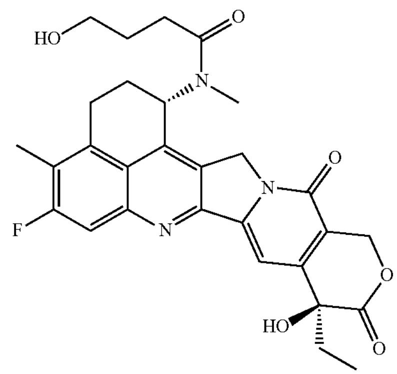 [SMILES: CC[C@@]1(O)C(=O)OCc2c1cc1n(c2=O)Cc2c-1nc1cc(F)c(C)c3c1c2[C@@H](N(C)C(=O)CCCO)CC3] |

-continued
| No. | Structure |
|---|---|
| P-I-19 | 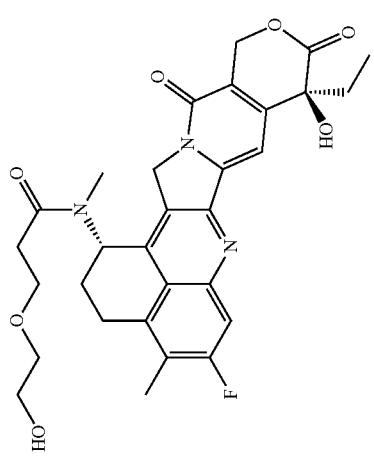 |
| P-I-20 | 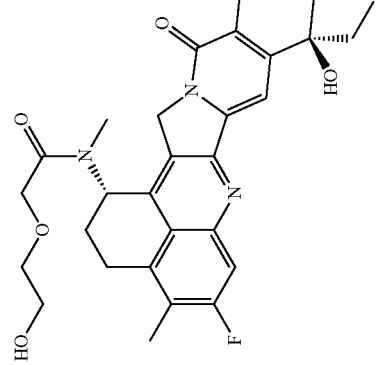 |

| No. | Structure |
|---|---|
| P-I-21 | 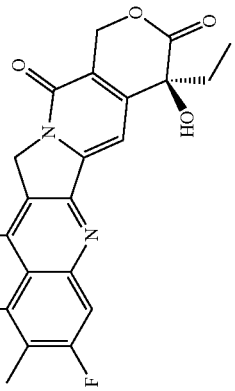 |
| P-I-22 | 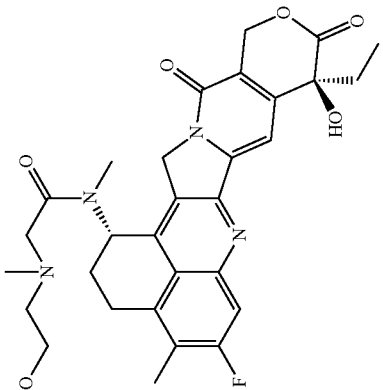 |

-continued

| No. | Structure |
|---|---|
| P-I-23 | 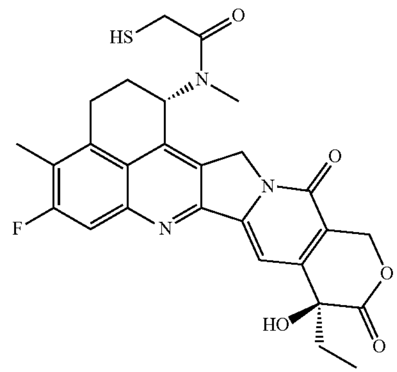 |
| P-I-24 | 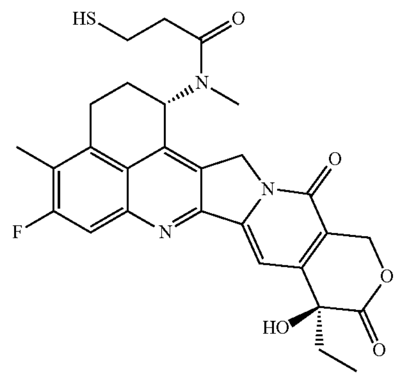 |

-continued

| No. | Structure |
|---|---|
| P-I-25 | 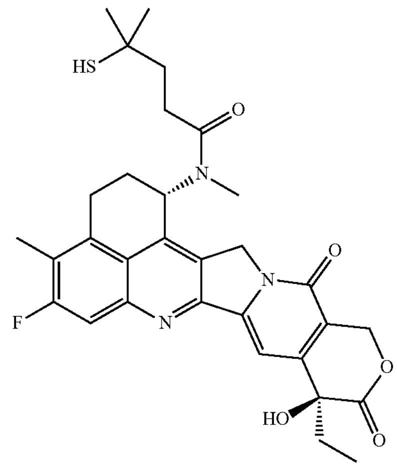 [SMILES: CC[C@@]1(O)C(=O)OCc2c1cc1n(c2=O)Cc2c-1nc1cc(F)c(C)c3c1c2[C@@H](N(C)C(=O)CCC(C)(C)S)CC3] |
| P-I-26 | 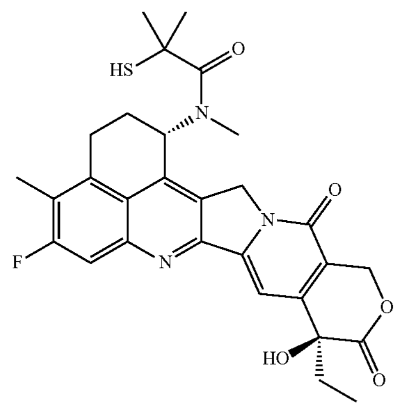 [SMILES: CC[C@@]1(O)C(=O)OCc2c1cc1n(c2=O)Cc2c-1nc1cc(F)c(C)c3c1c2[C@@H](N(C)C(=O)C(C)(C)S)CC3] |

| No. | Structure |
|---|---|
| P-I-27 | 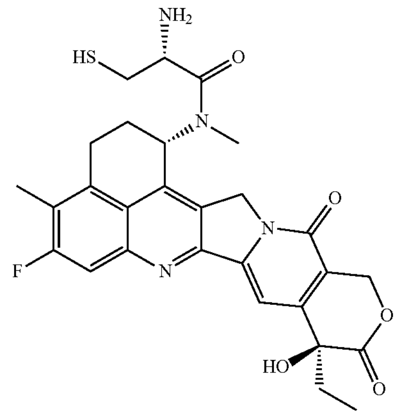 [SMILES: CC[C@@]1(O)C(=O)OCc2c1cc1n(c2=O)Cc2c-1nc1cc(F)c(C)c3c1c2[C@@H](N(C)C(=O)[C@@H](N)CS)CC3] |
| P-I-28 | 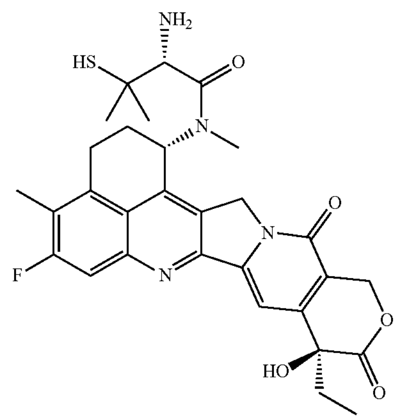 [SMILES: CC[C@@]1(O)C(=O)OCc2c1cc1n(c2=O)Cc2c-1nc1cc(F)c(C)c3c1c2[C@@H](N(C)C(=O)[C@@H](N)C(C)(C)S)CC3] |

| No. | Structure |
|---|---|
| P-I-29 | 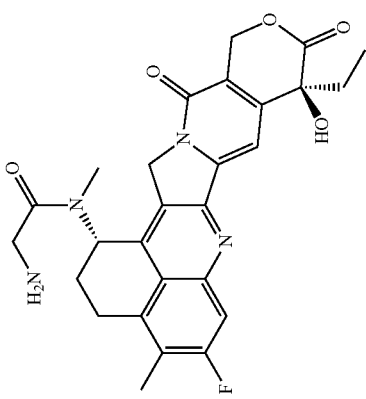 |
| P-I-30 | 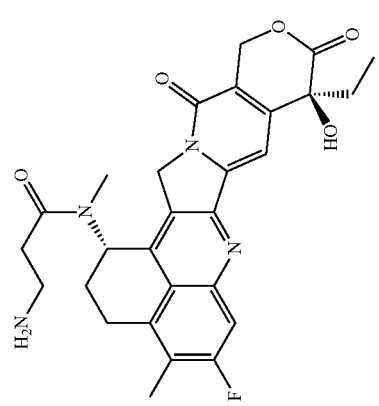 |

| No. | Structure |
|---|---|
| P-I-31 | 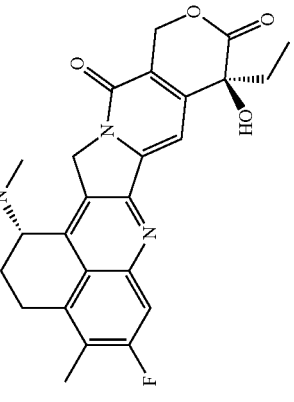 |
| P-I-32 | 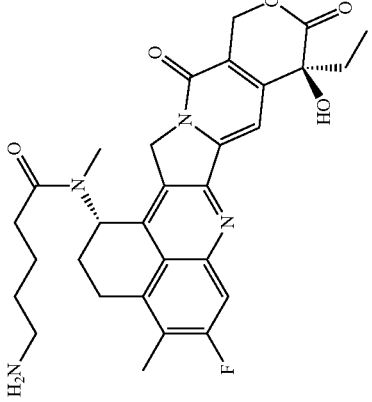 |

-continued
| No. | Structure |
|---|---|
| P-I-33 | 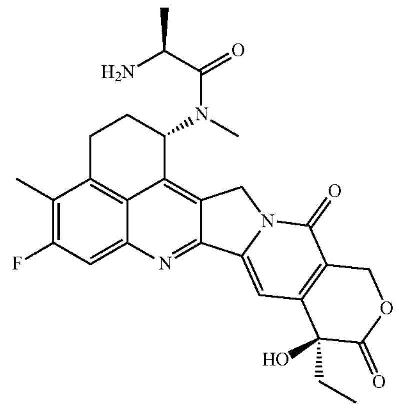 [SMILES: CC[C@@]1(O)C(=O)OCc2c1cc1n(c2=O)Cc2c-1nc1cc(F)c(C)c3c1c2[C@@H](N(C)C(=O)[C@H](C)N)CC3] |
| P-I-34 | 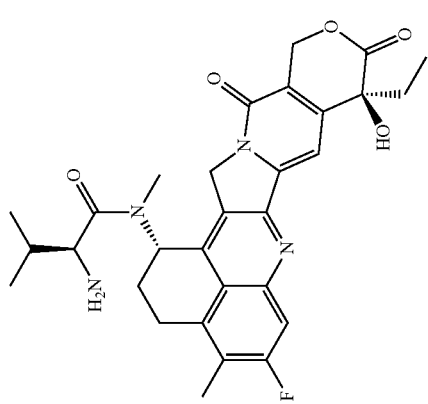 |

| No. | Structure |
|---|---|
| P-I-35 | 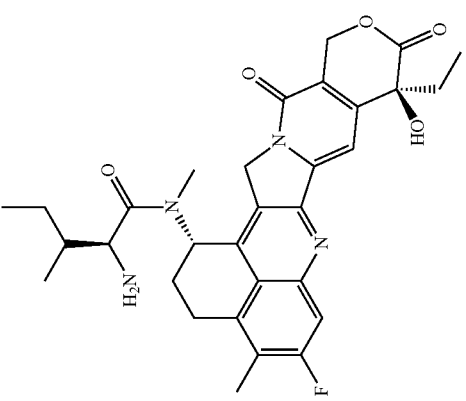 |
| P-I-36 | 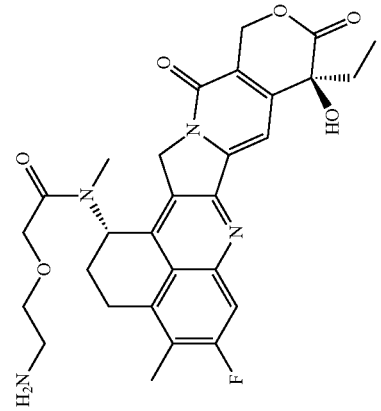 |

| No. | Structure |
|---|---|
| P-I-37 | 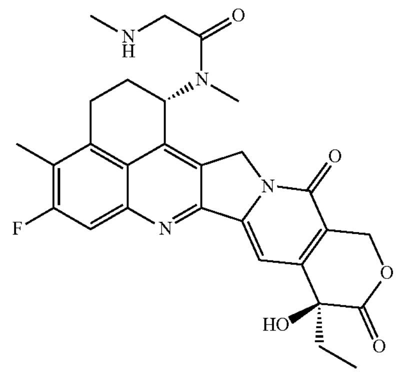 [SMILES: CC[C@@]1(O)C(=O)OCc2c1cc1n(c2=O)Cc2c-1nc1cc(F)c(C)c3c1c2[C@@H](N(C)C(=O)CNC)CC3] |
| P-I-38 | 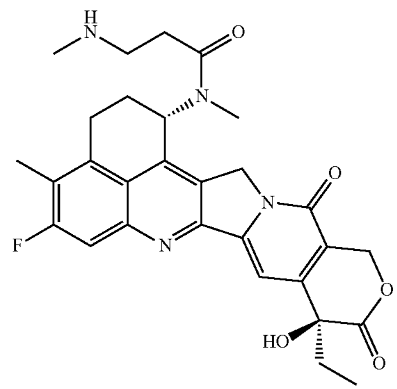 [SMILES: CC[C@@]1(O)C(=O)OCc2c1cc1n(c2=O)Cc2c-1nc1cc(F)c(C)c3c1c2[C@@H](N(C)C(=O)CCNC)CC3] |

| No. | Structure |
|---|---|
| P-I-39 | 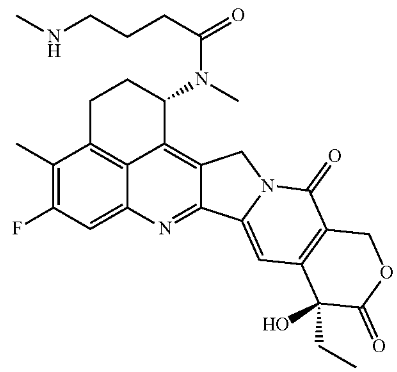 [SMILES: CC[C@@]1(O)C(=O)OCc2c1cc1n(c2=O)Cc2c-1nc1cc(F)c(C)c3c1c2[C@@H](N(C)C(=O)CCCNC)CC3] |
| P-I-40 | 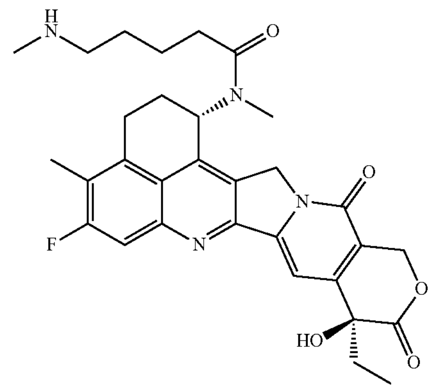 [SMILES: CC[C@@]1(O)C(=O)OCc2c1cc1n(c2=O)Cc2c-1nc1cc(F)c(C)c3c1c2[C@@H](N(C)C(=O)CCCCNC)CC3] |

| No. | Structure |
|---|---|
| P-I-41 | 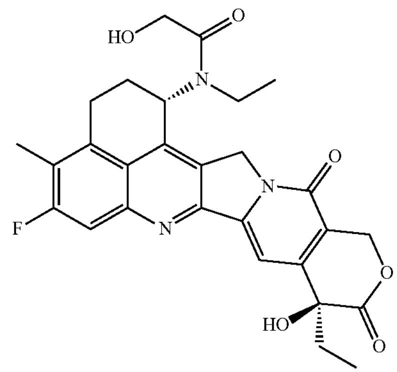 [SMILES: CCN(C(=O)CO)[C@H]1CCc2c(C)c(F)cc3nc4c(c1c23)Cn1c-4cc2c(c1=O)COC(=O)[C@]2(O)CC] |
| P-I-42 | 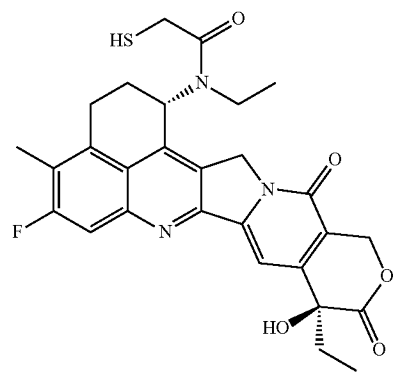 [SMILES: CCN(C(=O)CS)[C@H]1CCc2c(C)c(F)cc3nc4c(c1c23)Cn1c-4cc2c(c1=O)COC(=O)[C@]2(O)CC] |

-continued

| No. | Structure |
|---|---|
| P-I-43 | 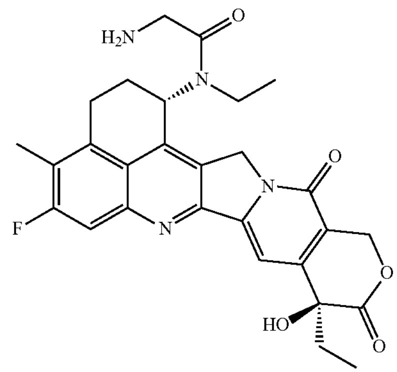 [SMILES: CCN(C(=O)CN)[C@H]1CCc2c(C)c(F)cc3nc4c(c1c23)Cn1c-4cc2c(c1=O)COC(=O)[C@]2(O)CC] |
| P-I-44 | 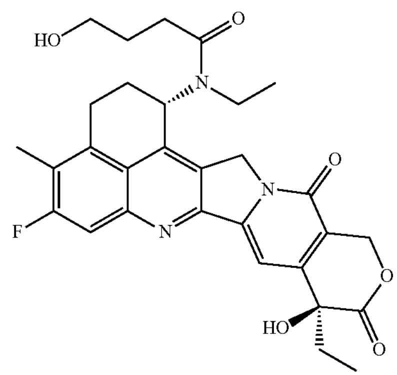 [SMILES: CCN(C(=O)CCCO)[C@H]1CCc2c(C)c(F)cc3nc4c(c1c23)Cn1c-4cc2c(c1=O)COC(=O)[C@]2(O)CC] |

| No. | Structure |
|---|---|
| P-I-45 | 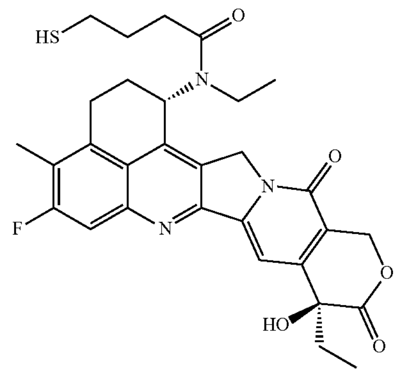 [SMILES: CCN(C(=O)CCCS)[C@H]1CCc2c(C)c(F)cc3nc4c(c1c23)Cn1c-4cc2c(c1=O)COC(=O)[C@]2(O)CC] |
| P-I-46 | 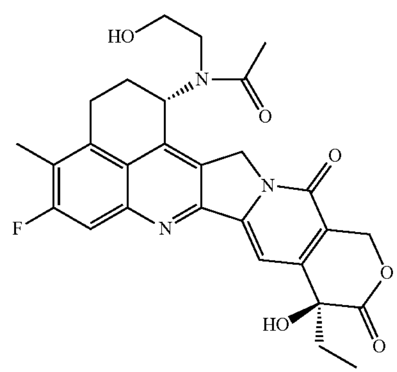 [SMILES: CC[C@@]1(O)C(=O)OCc2c1cc1n(c2=O)Cc2c-1nc1cc(F)c(C)c3c1c2[C@@H](N(CCO)C(C)=O)CC3] |

| No. | Structure |
|---|---|
| P-I-47 | 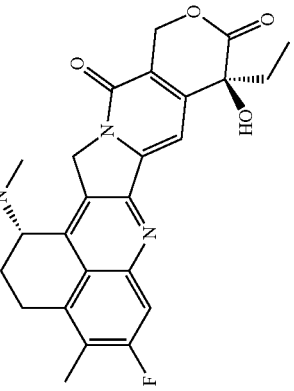 |
| L-I-1 | 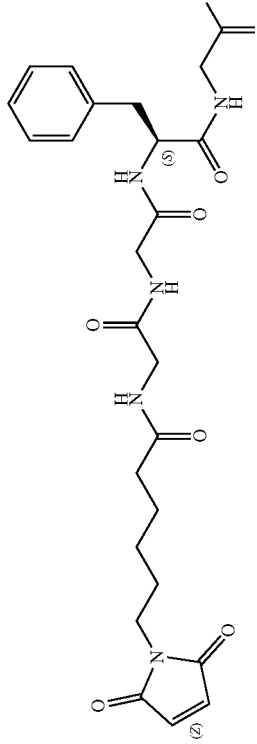 |

-continued
| No. | Structure |
|---|---|
| L-I-2 | 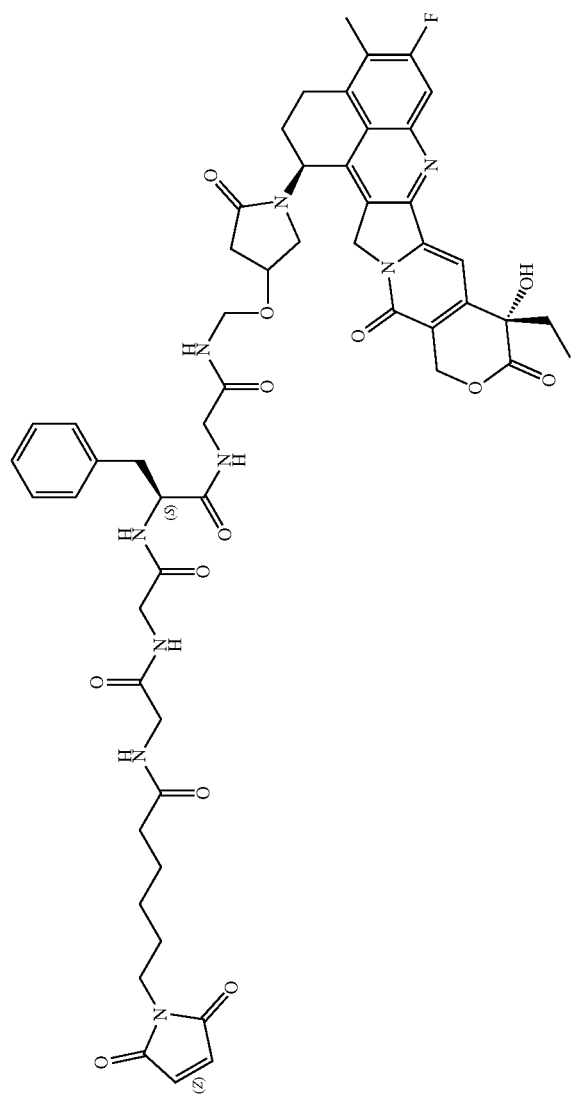 |

| No. | Structure |
|---|---|
| L-I-3 | 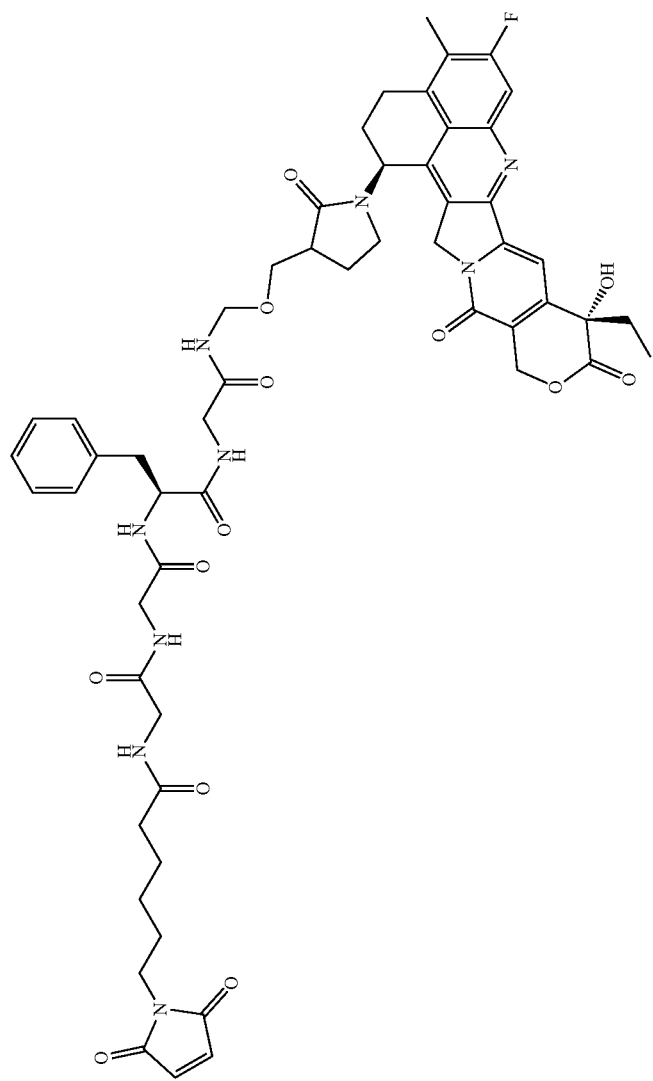 |

| No. | Structure |
|---|---|
| L-I-4 | 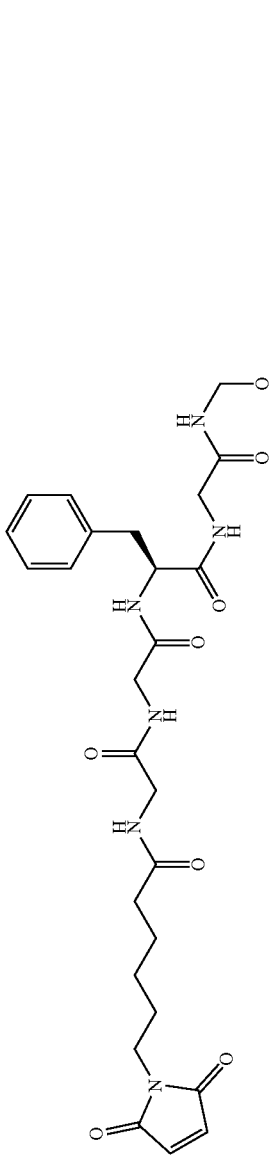 |

| No. | Structure |
|---|---|
| L-I-5 | 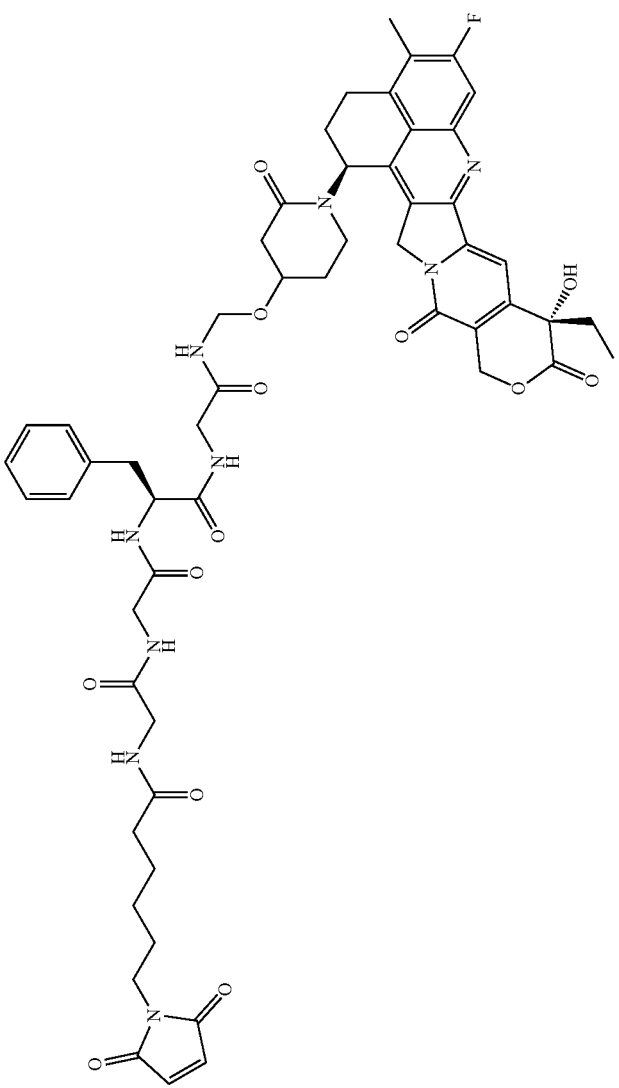 |

| No. | Structure |
|---|---|
| L-I-6 | *-continued* (chemical structure) |

| No. | Structure |
|---|---|
| L-I-7 | 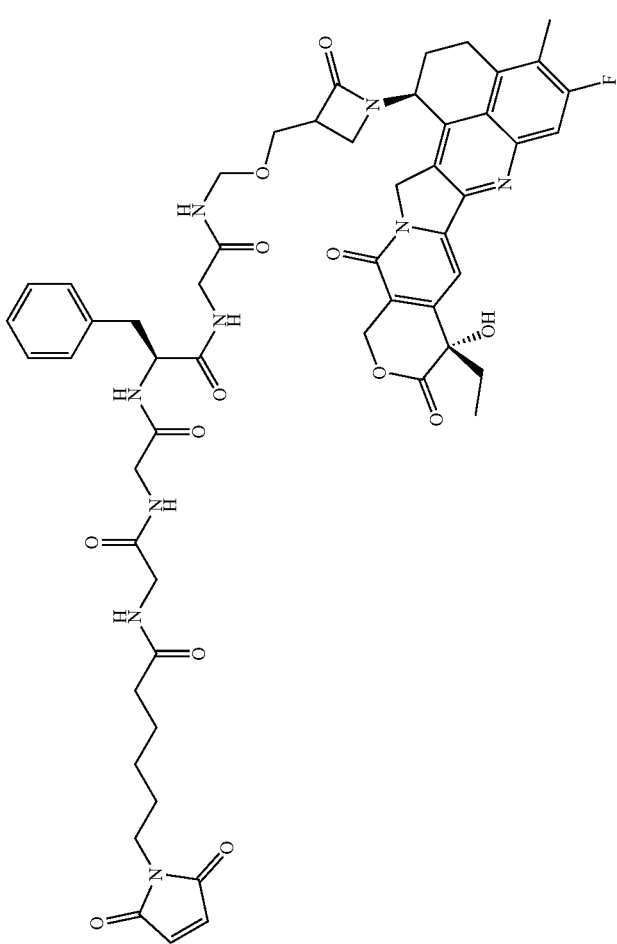 |

| No. | Structure |
|---|---|
| L-I-8 | 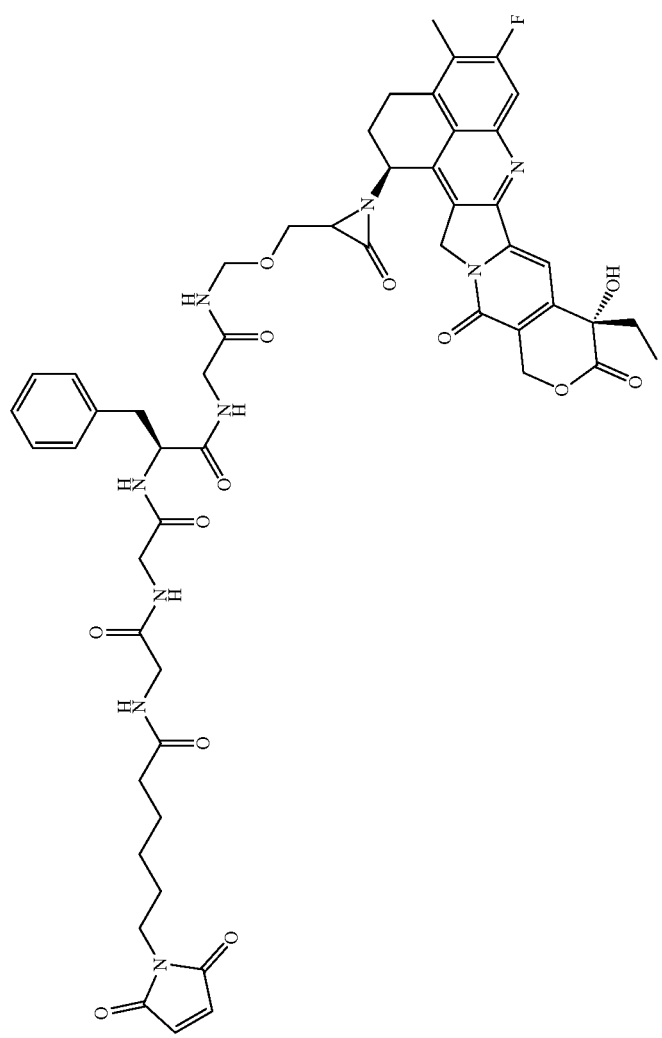 |

| No. | Structure |
|---|---|
| L-I-9 | 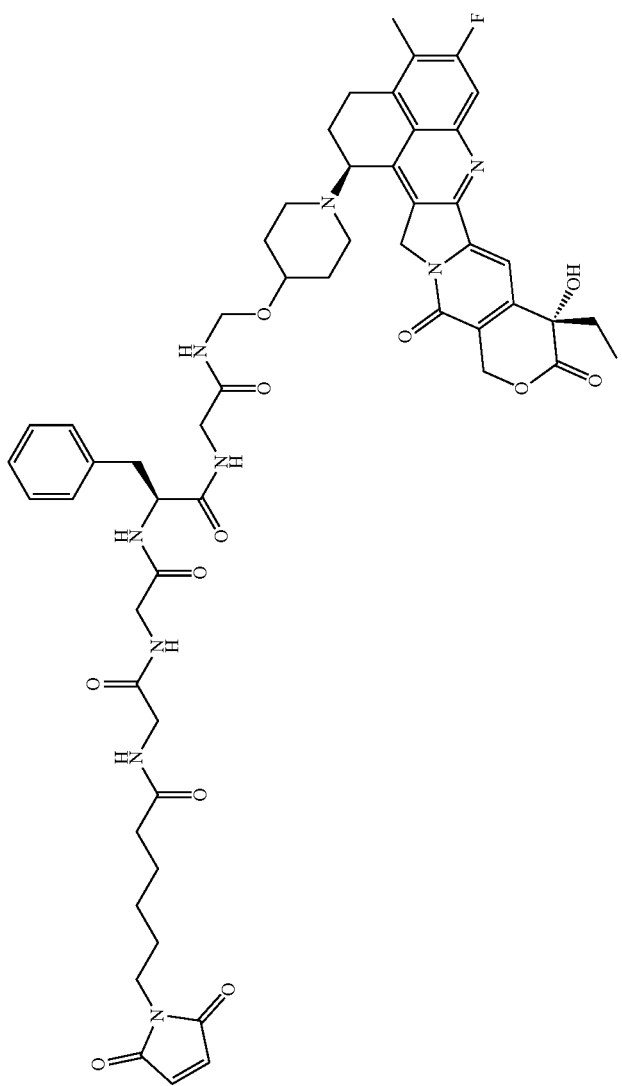 |

| No. | Structure |
|---|---|
| L-I-10 | 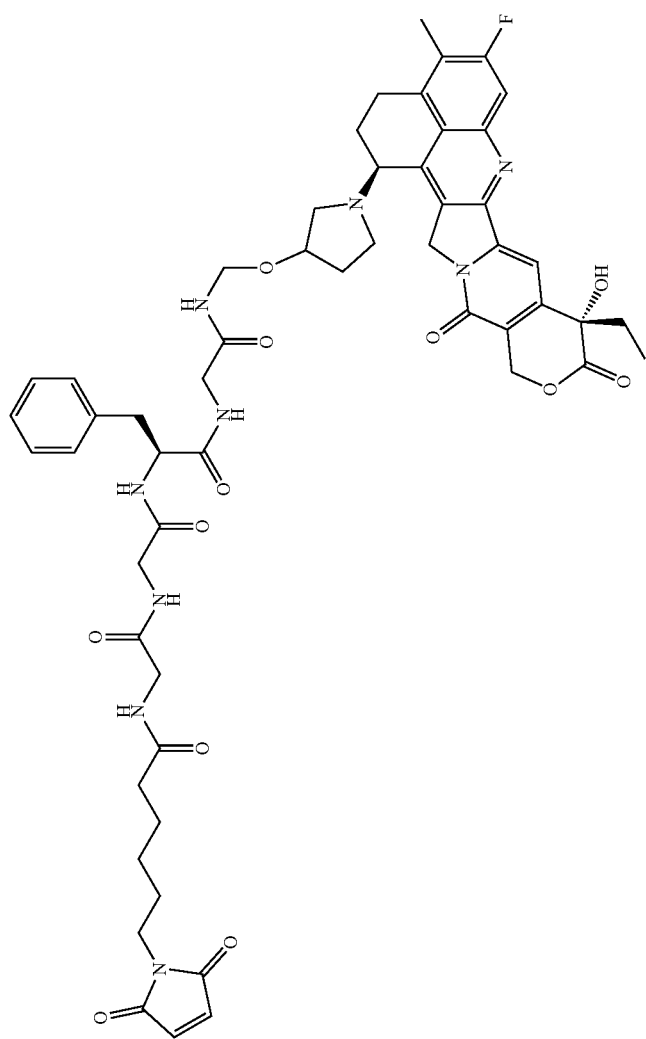 |

-continued
| No. | Structure |
|---|---|
| L-I-11 | 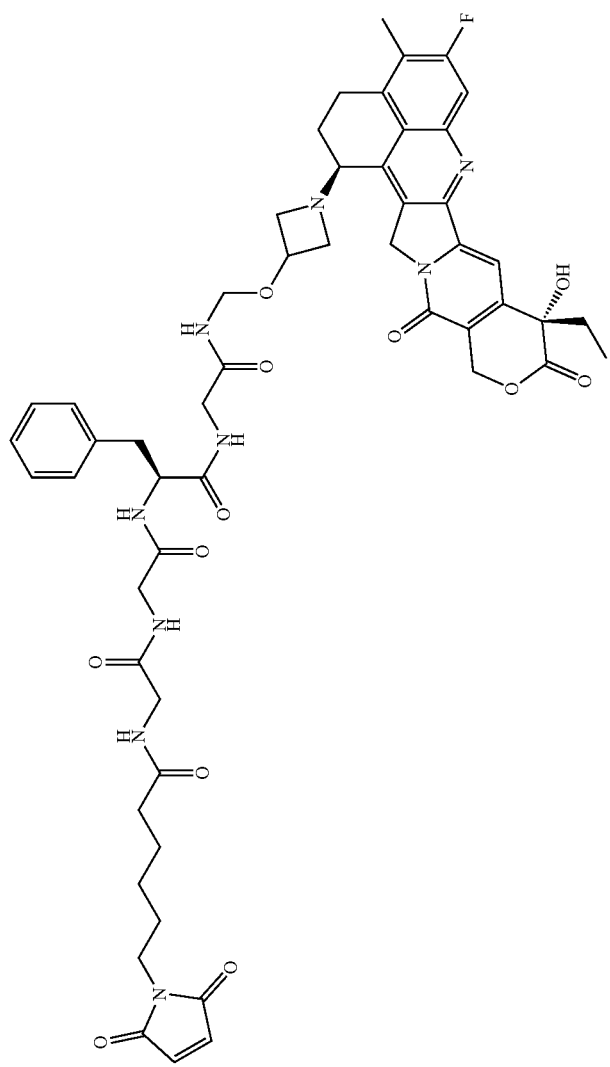 |

| No. | Structure |
|---|---|
| L-I-12 | 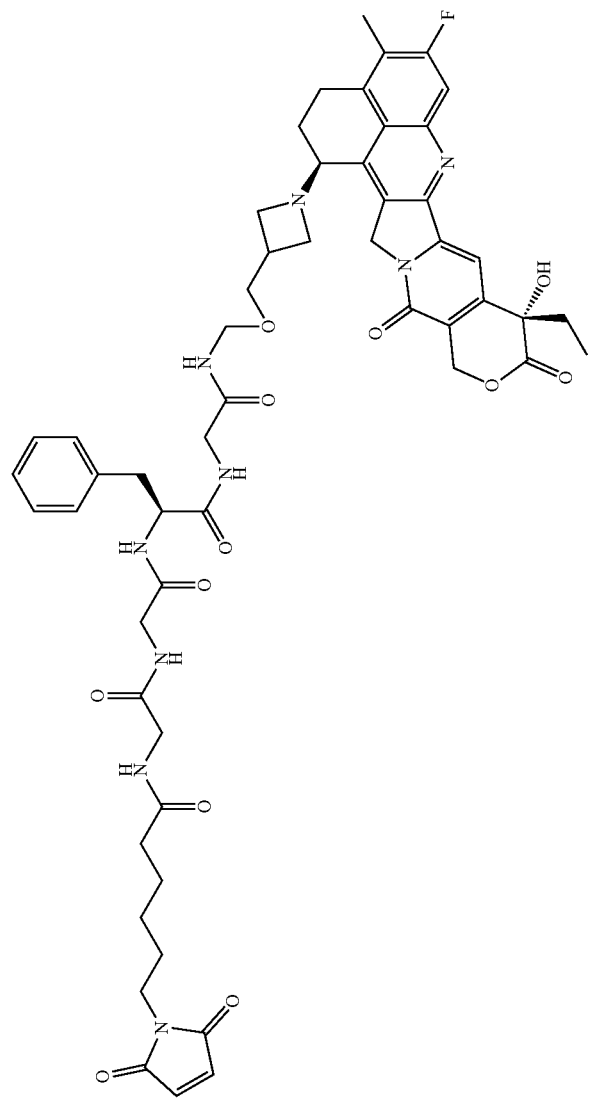 |
-continued

| No. | Structure |
|---|---|
| L-I-13 | 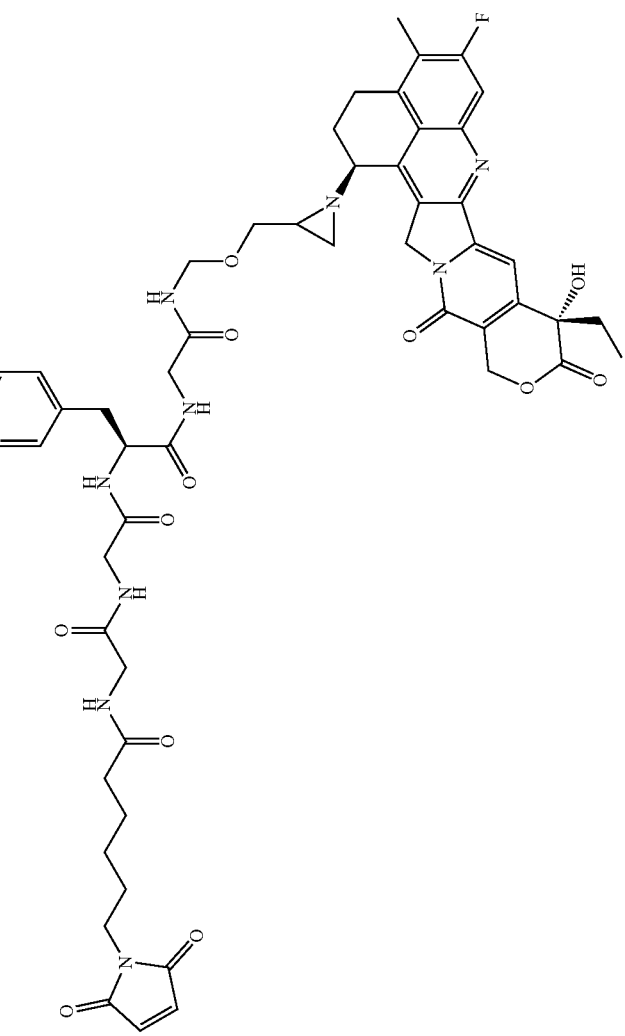 |

| No. | Structure |
|---|---|
| L-I-14 | 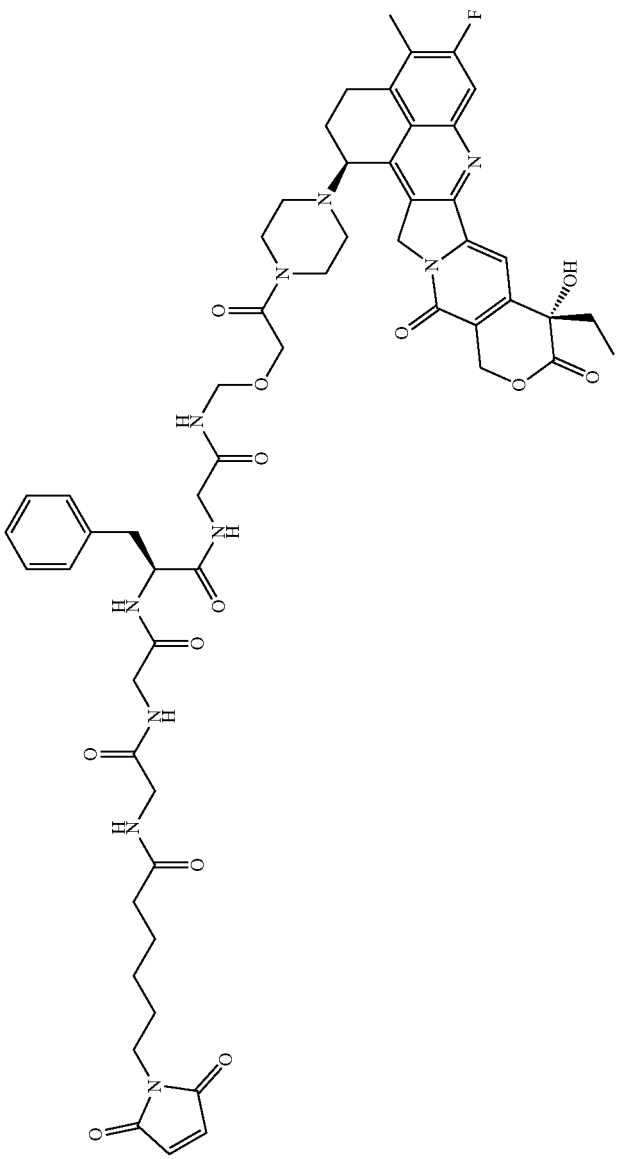 |

-continued
| No. | Structure |
|---|---|
| L-I-15 | 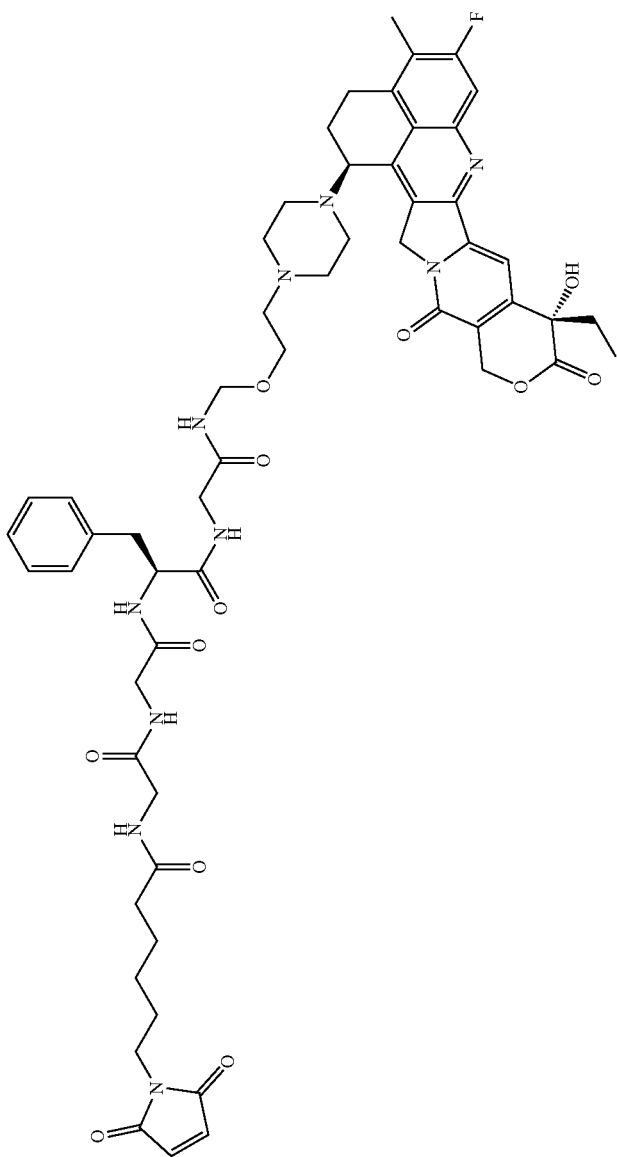 |
| L-I-16 | 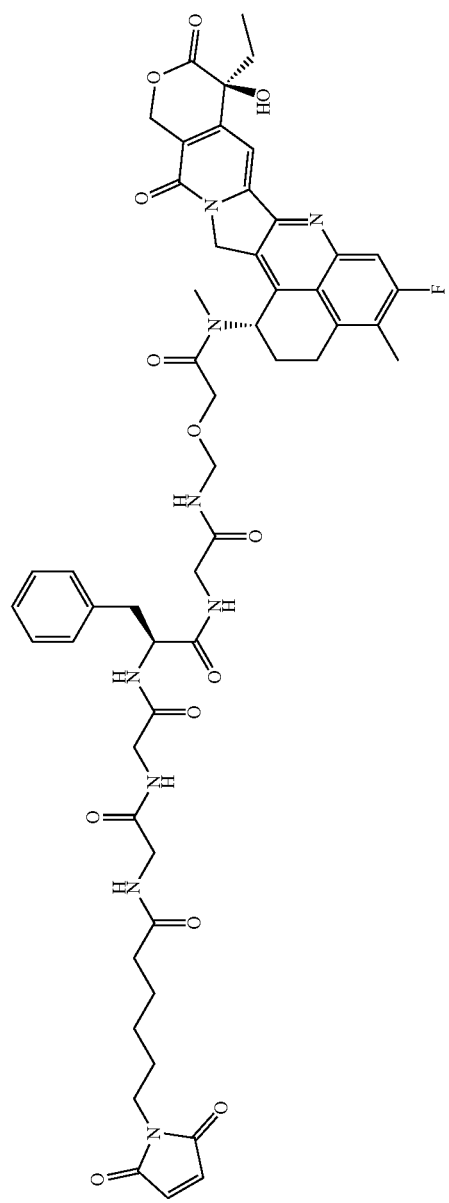 |

| No. | Structure |
|---|---|
| L-I-17 | 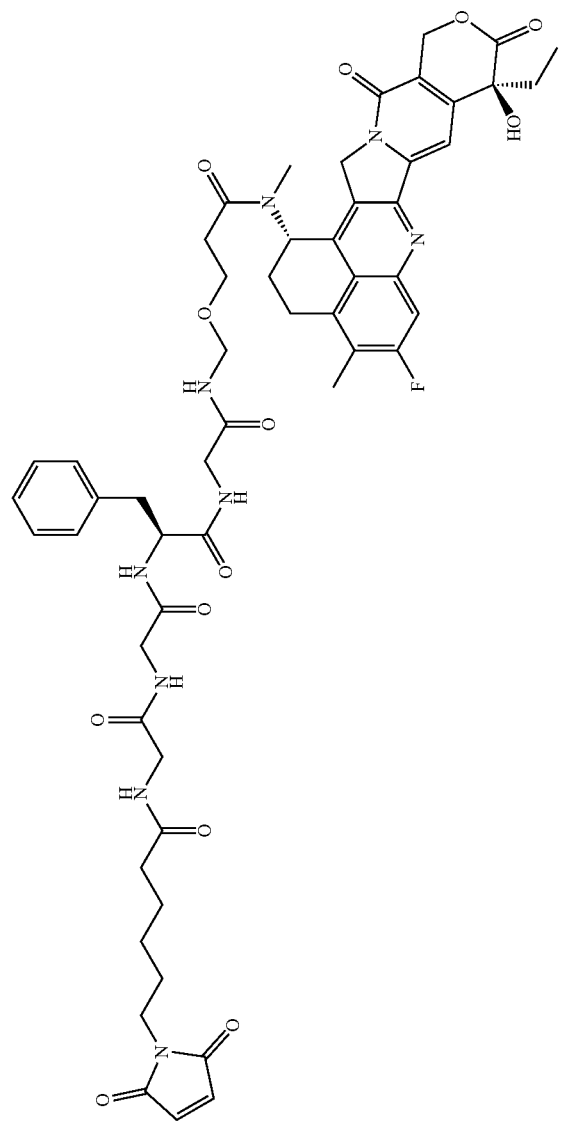 |

| No. | Structure |
|---|---|
| L-I-18 | 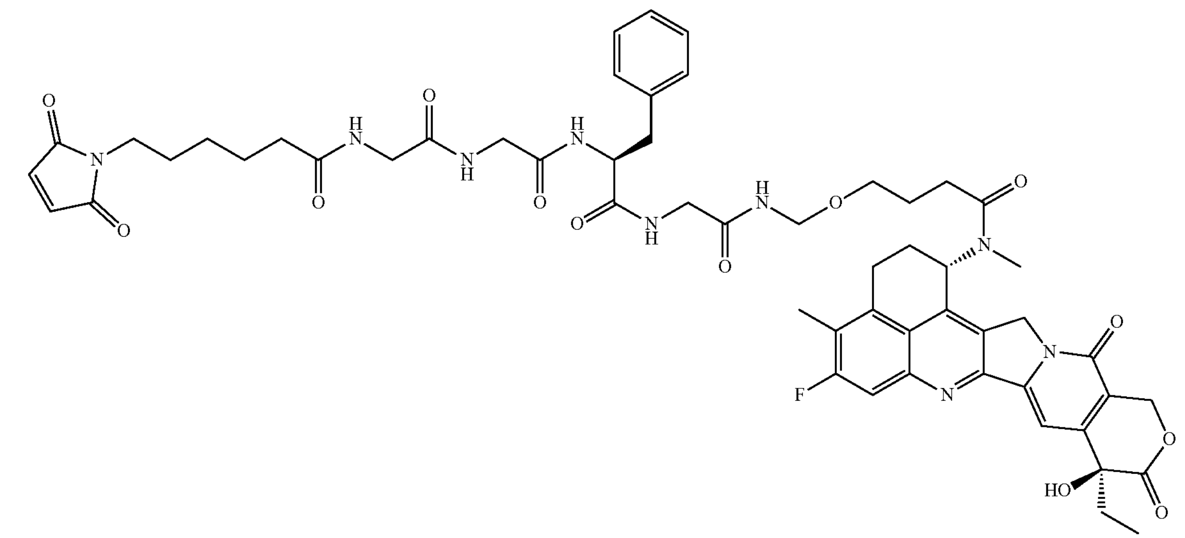 [SMILES: CC[C@@]1(O)C(=O)OCc2c1cc1n(c2=O)Cc2c-1nc1cc(F)c(C)c3c1c2[C@@H](N(C)C(=O)CCCOCNC(=O)CNC(=O)[C@H](Cc1ccccc1)NC(=O)CNC(=O)CNC(=O)CCCCCN1C(=O)C=CC1=O)CC3] |
| L-I-19 | 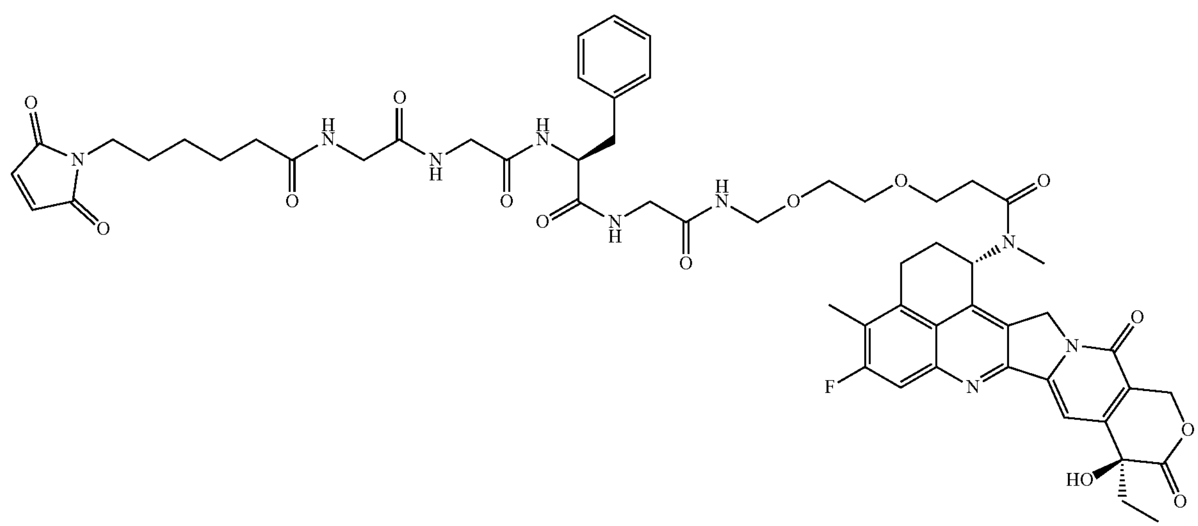 [SMILES: CC[C@@]1(O)C(=O)OCc2c1cc1n(c2=O)Cc2c-1nc1cc(F)c(C)c3c1c2[C@@H](N(C)C(=O)CCOCCOCNC(=O)CNC(=O)[C@H](Cc1ccccc1)NC(=O)CNC(=O)CNC(=O)CCCCCN1C(=O)C=CC1=O)CC3] |

| No. | Structure |
|---|---|
| L-I-20 | 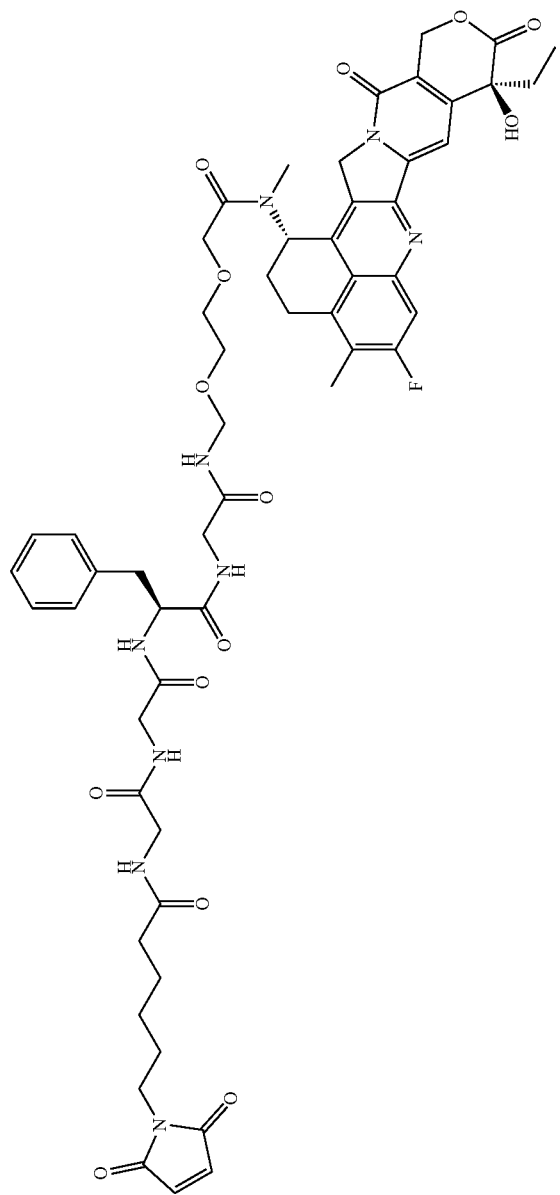 |

| No. | Structure |
|---|---|
| L-I-21 | 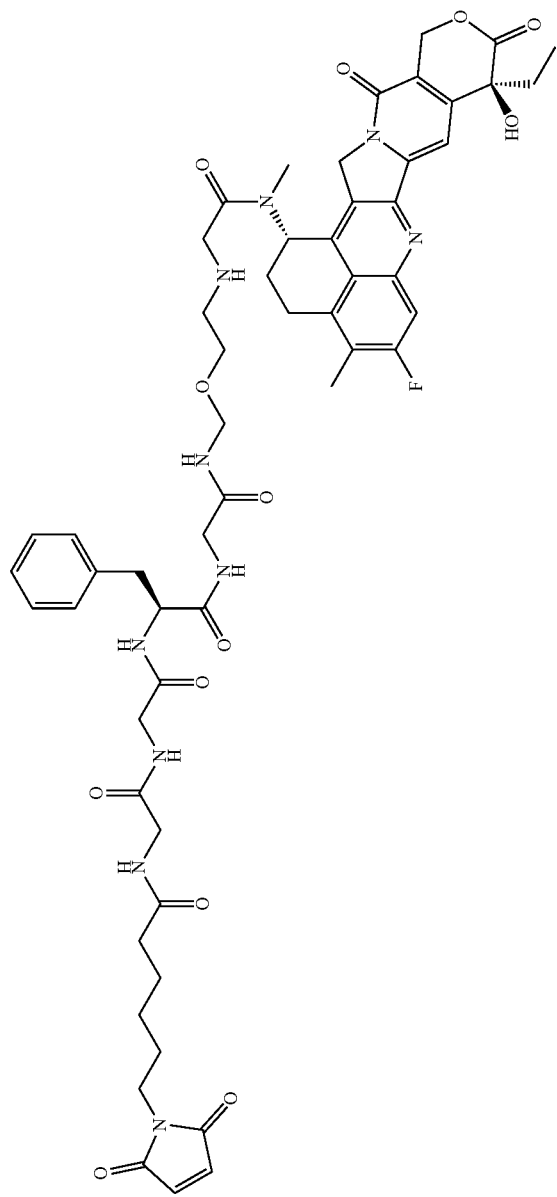 |

| No. | Structure |
|---|---|
| L-I-22 | *(chemical structure)* |

| No. | Structure |
|---|---|
| L-I-23 | 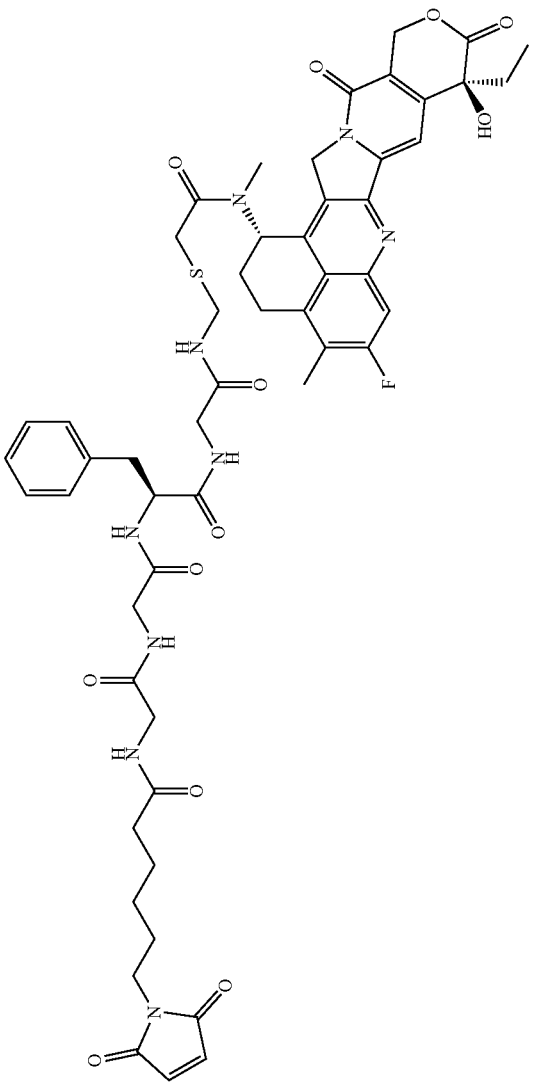 |

| No. | Structure |
|---|---|
| L-I-24 | 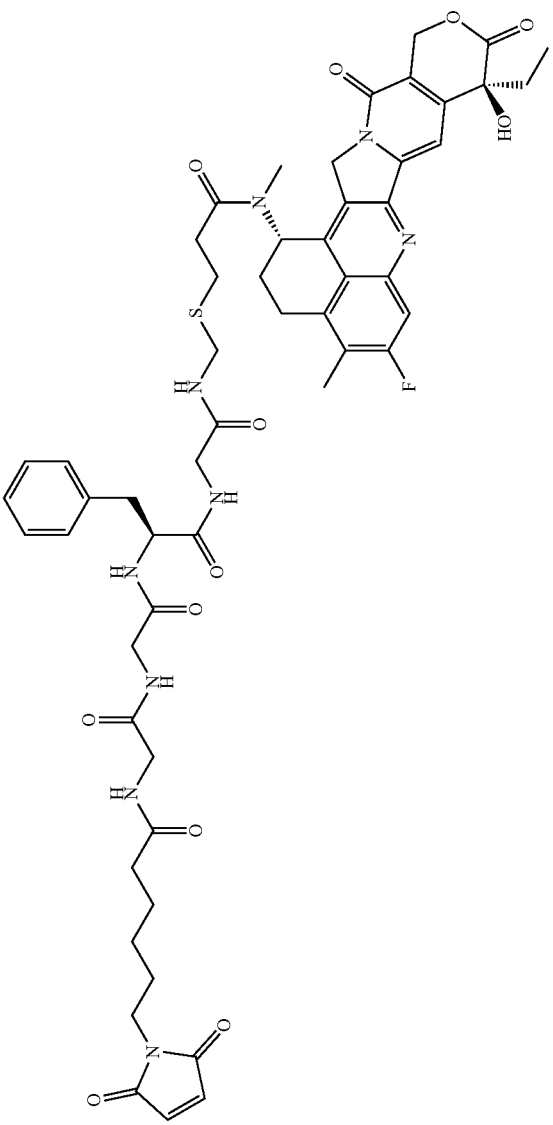 |

| No. | Structure |
|---|---|
| L-I-25 | 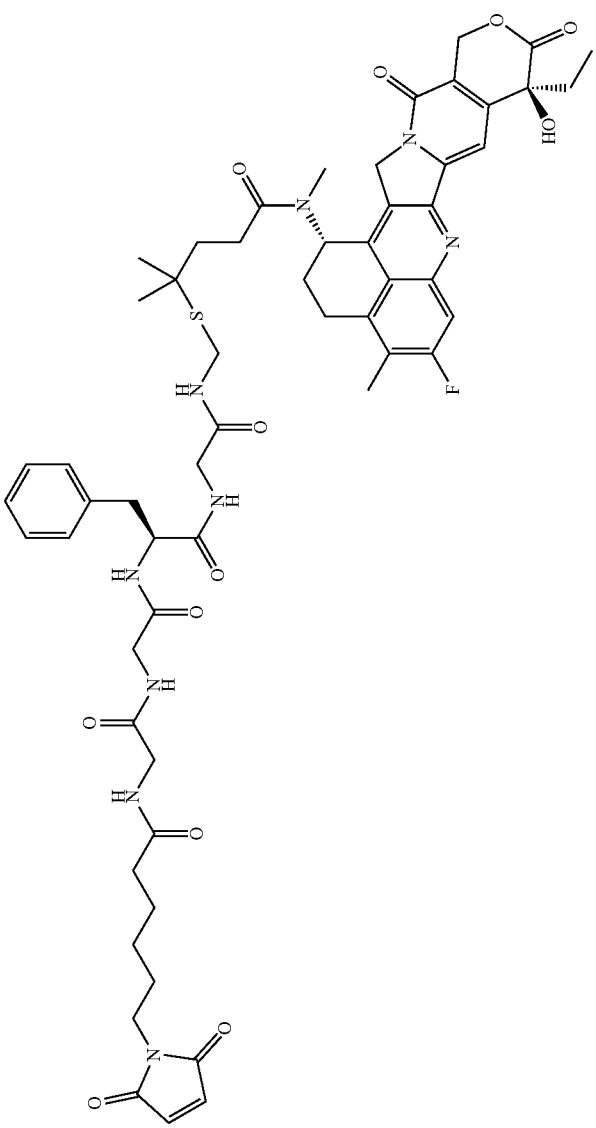 |

| No. | Structure |
|---|---|
| L-I-26 | 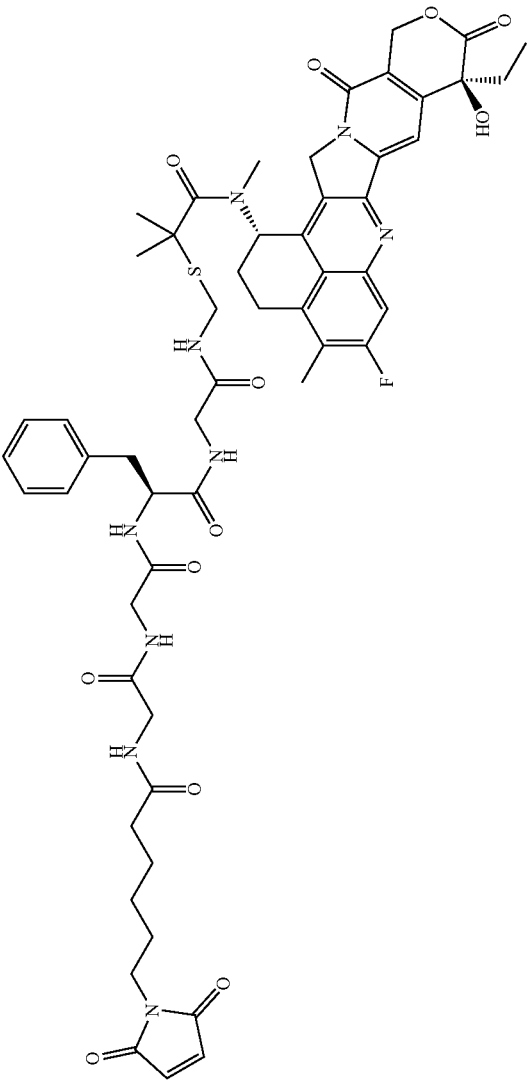 |

-continued
| No. | Structure |
|---|---|
| L-I-27 | 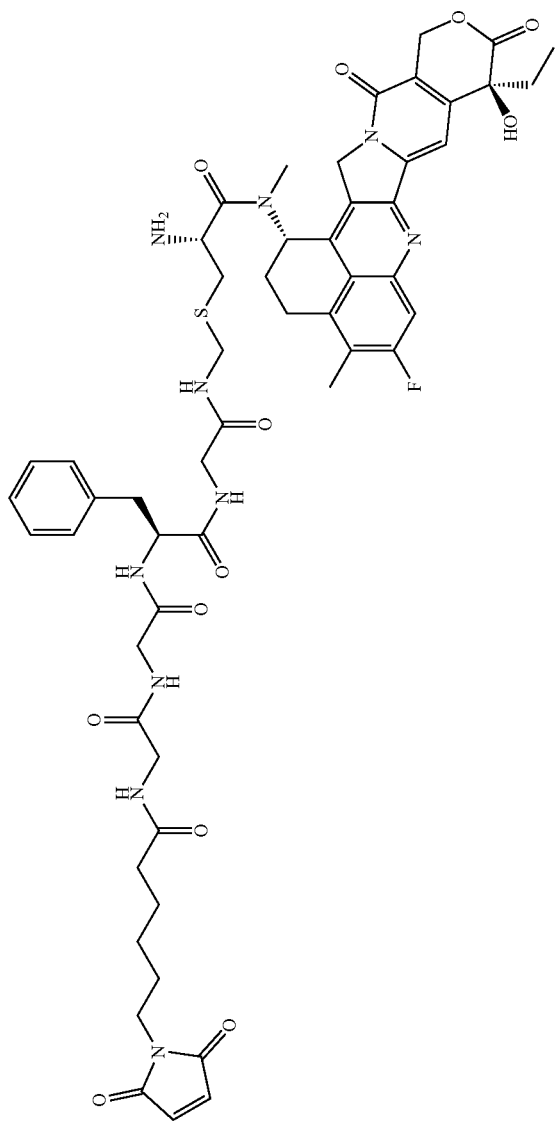 |

-continued
| No. | Structure |
|---|---|
| L-I-28 | 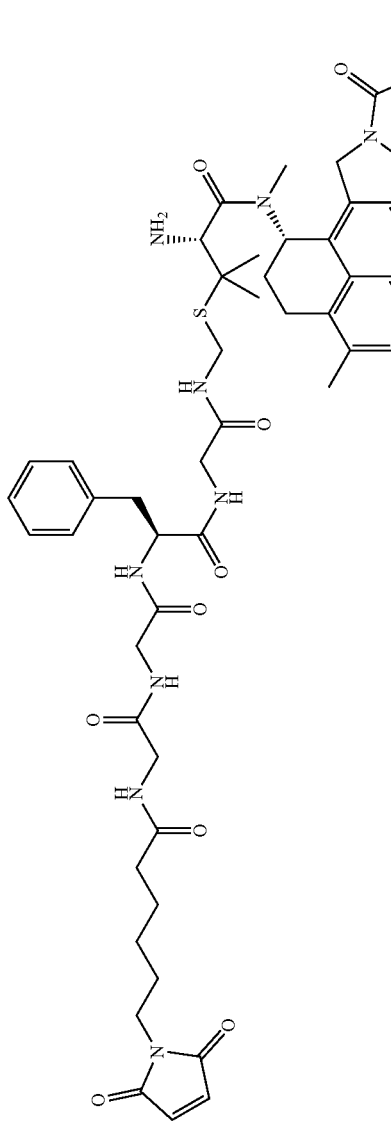 |
| L-I-29 | 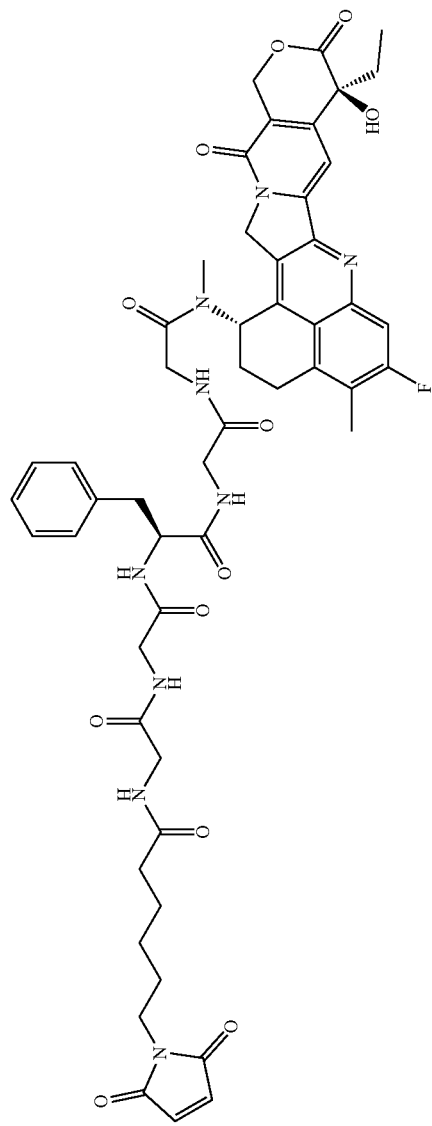 |

| No. | Structure |
|---|---|
| L-I-30 | 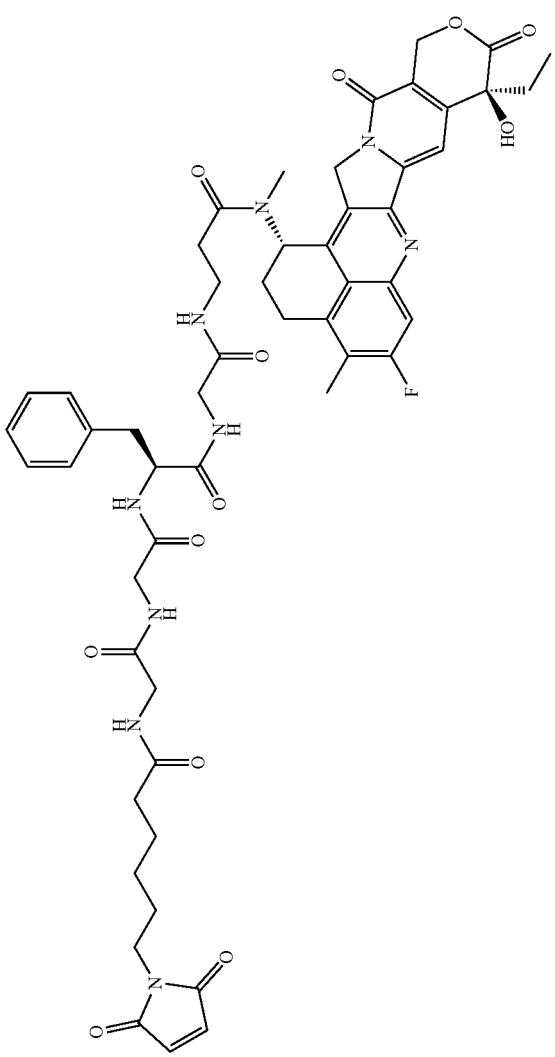 |

| No. | Structure |
|---|---|
| L-I-31 | 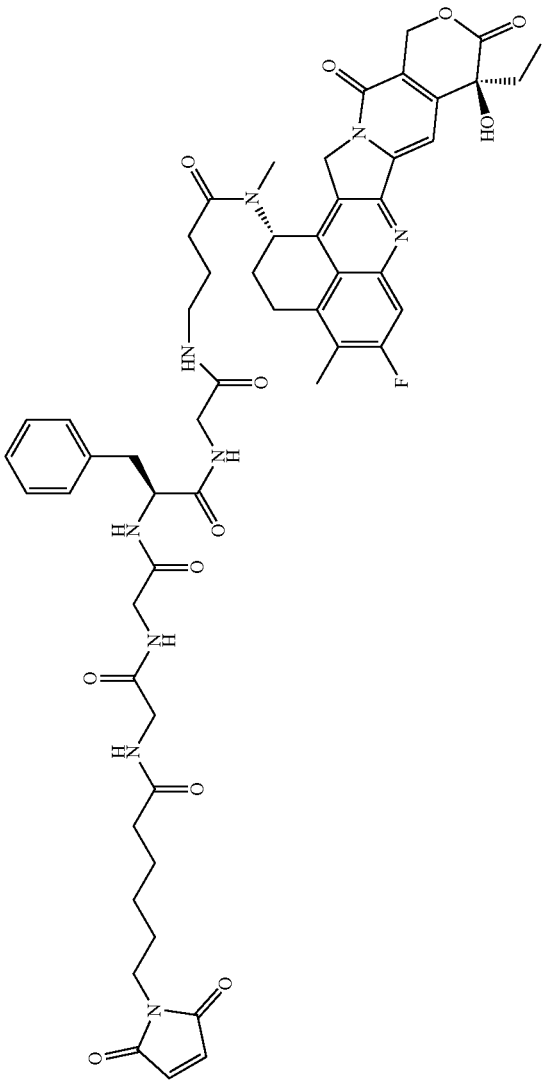 |

| No. | Structure |
|---|---|
| L-I-32 | 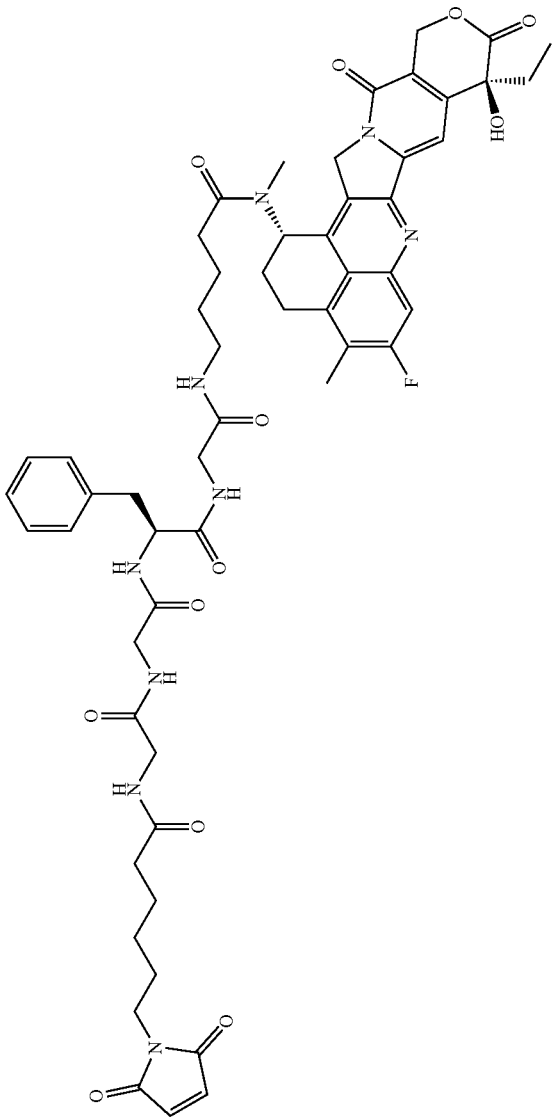 |
| L-I-33 | 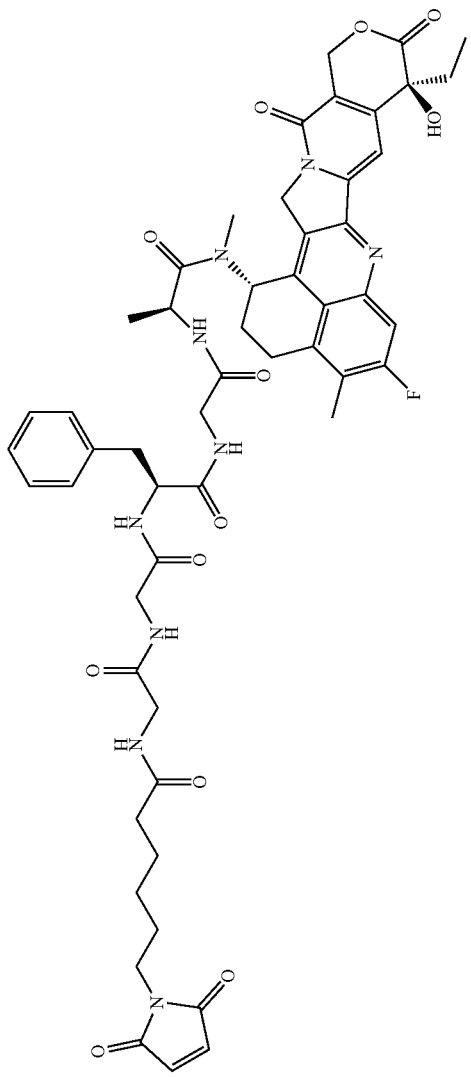 |

-continued
| No. | Structure |
|---|---|
| L-I-34 | 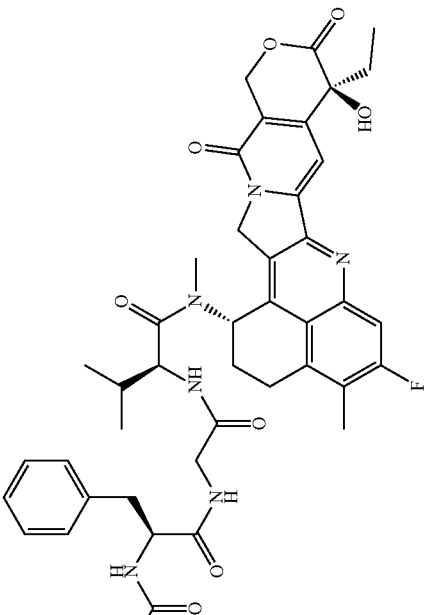 |
| L-I-35 | 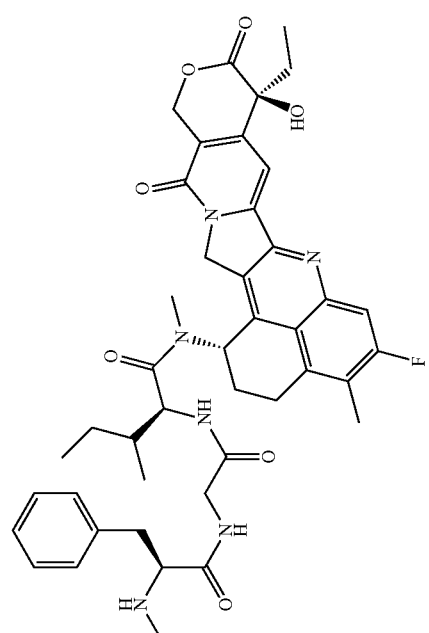 |

-continued
| No. | Structure |
|---|---|
| L-I-36 | 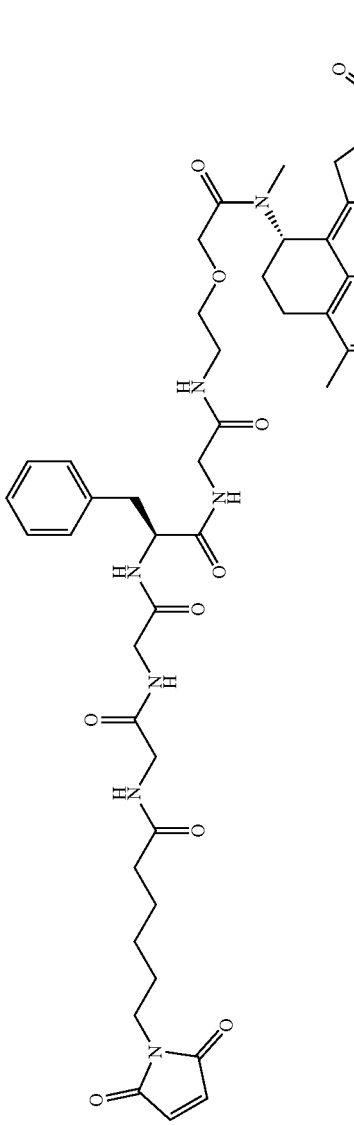 |
| L-I-37 | 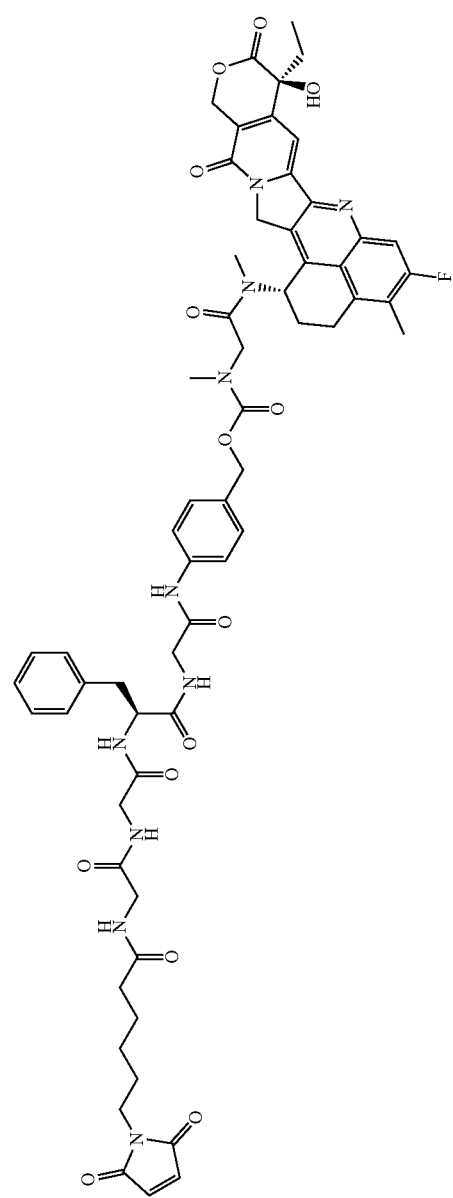 |

| No. | Structure |
|---|---|
| L-I-38 | 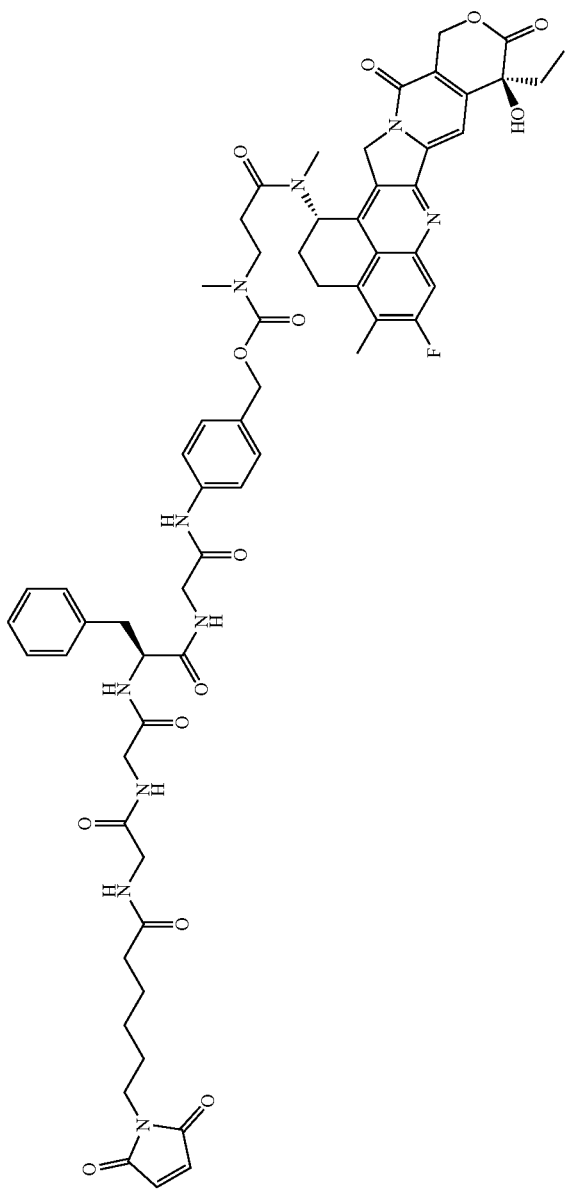 |

| No. | Structure |
|---|---|
| L-I-39 | 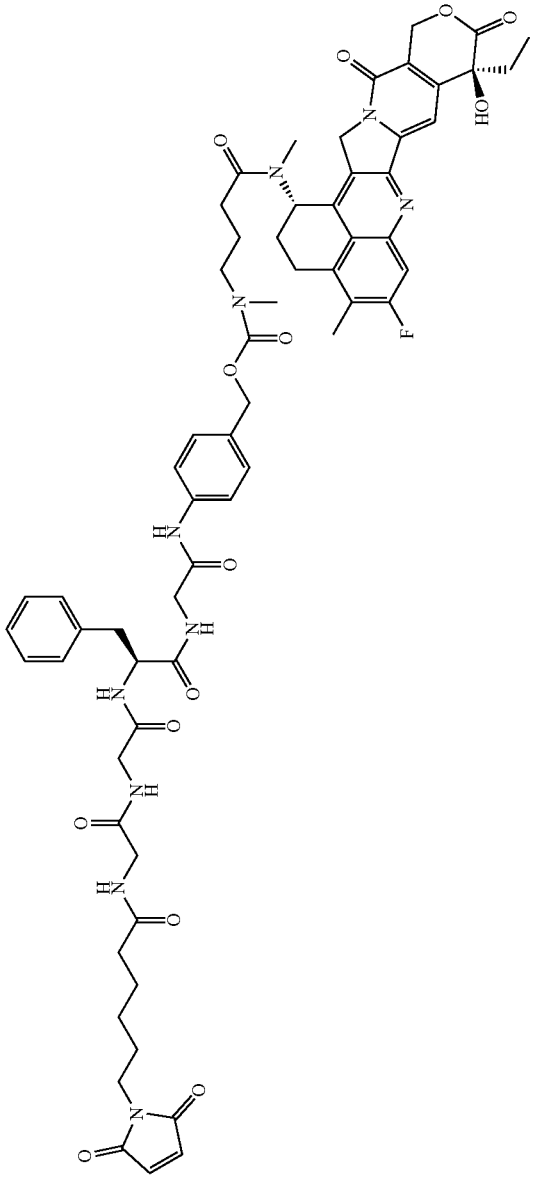 |
| L-I-40 | 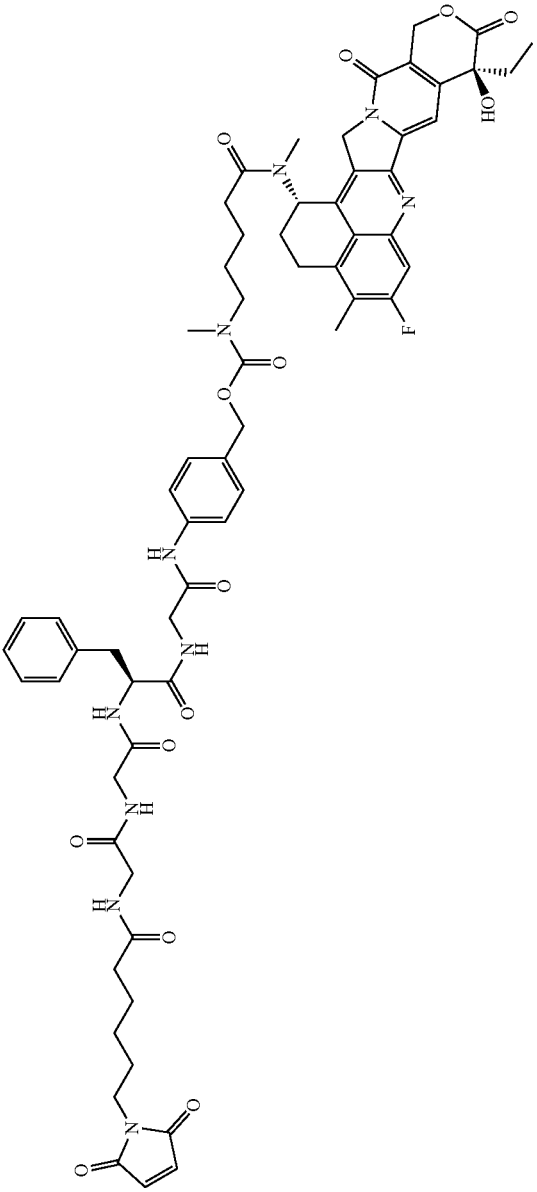 |

| No. | Structure |
|---|---|
| L-I-41 | 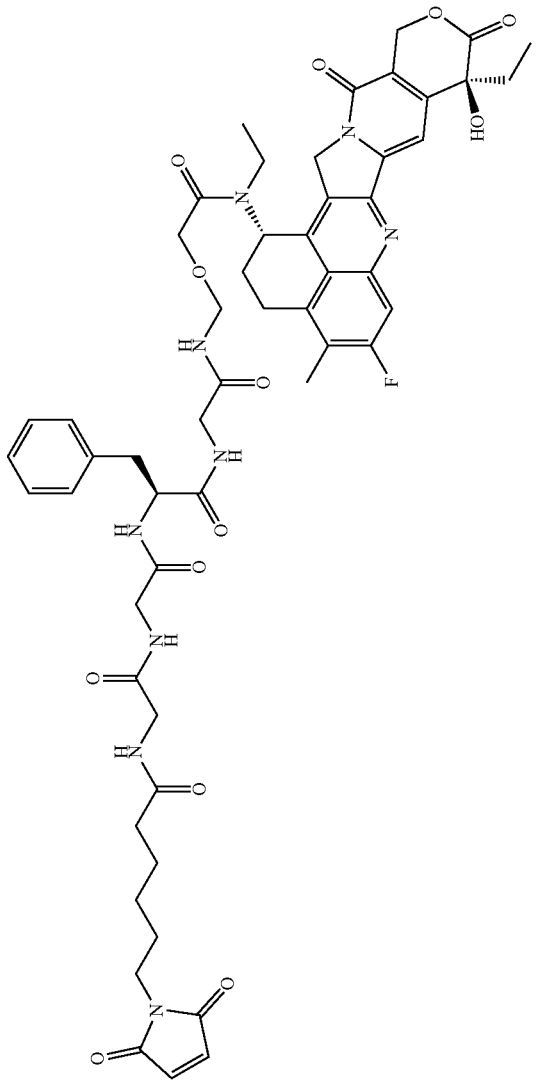 |

-continued
| No. | Structure |
|---|---|
| L-I-42 | 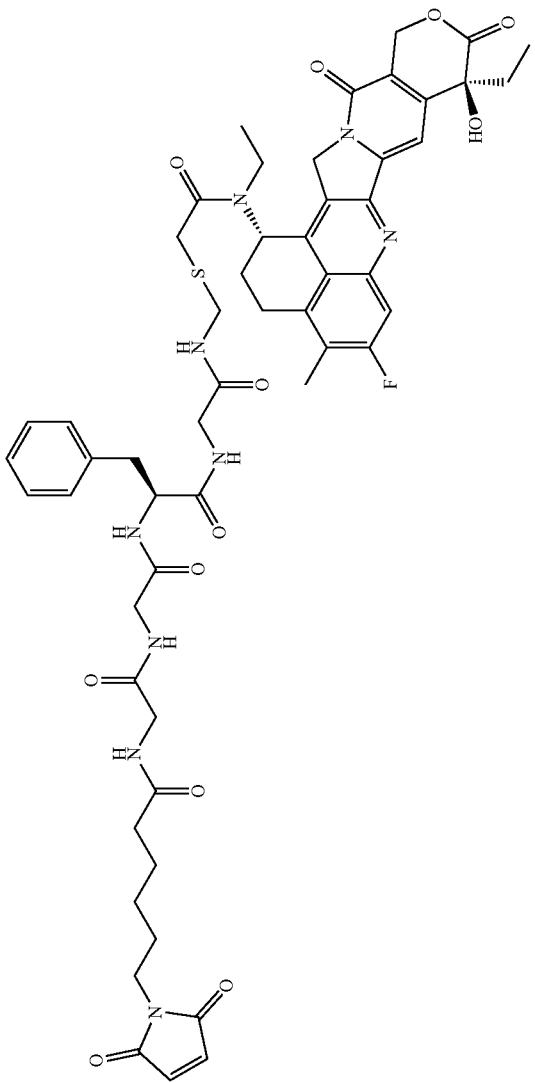 |

| No. | Structure |
|---|---|
| L-I-43 | 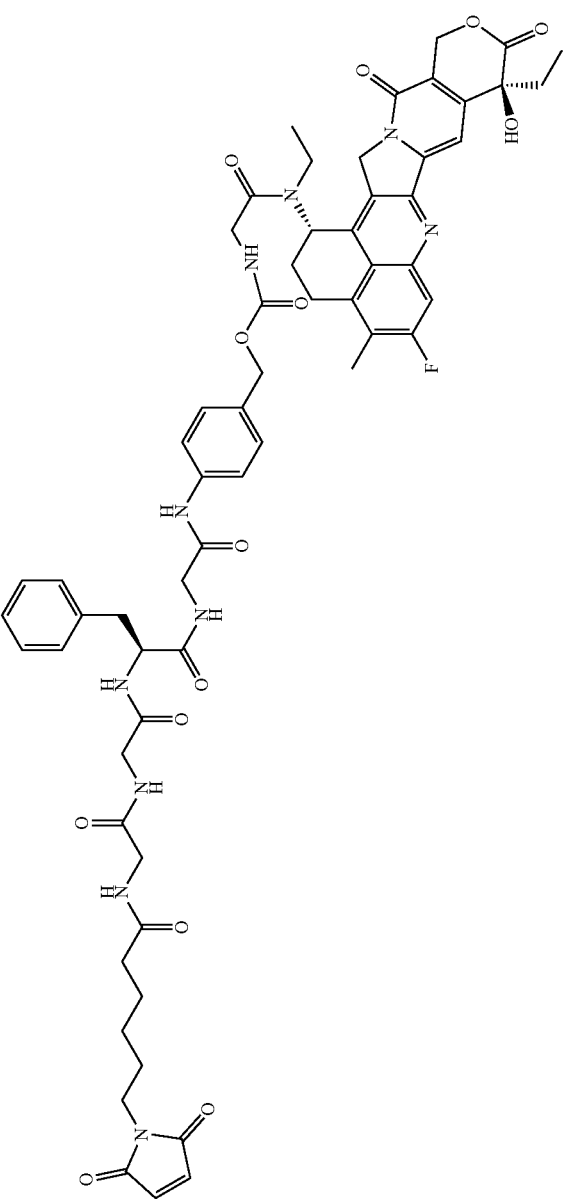 |

-continued
| No. | Structure |
|---|---|
| L-I-44 | 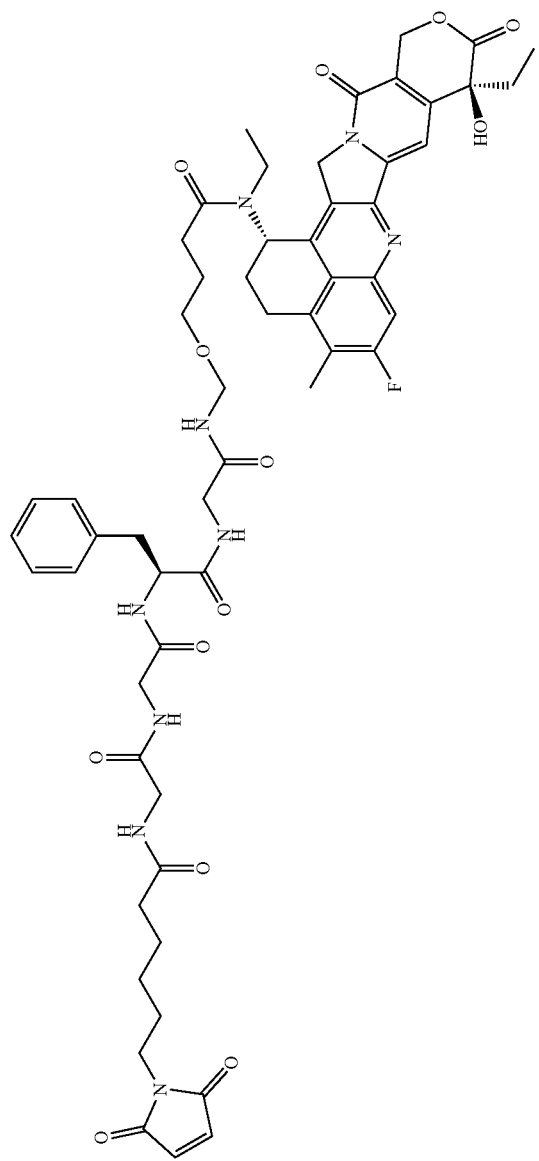 |
| L-I-45 | 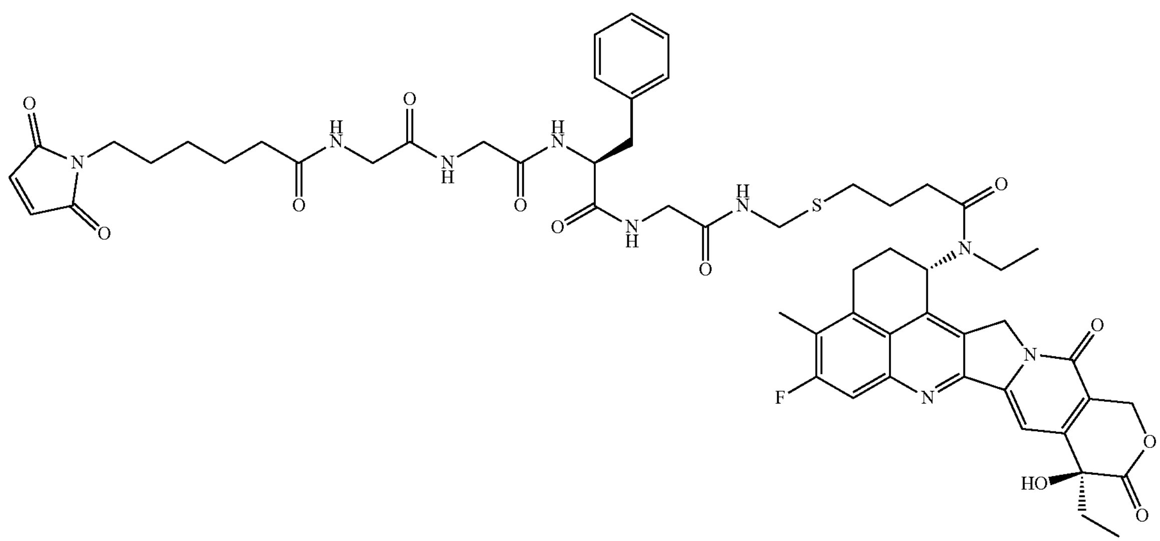 [SMILES: CCN(C(=O)CCCSCNC(=O)CNC(=O)[C@H](Cc1ccccc1)NC(=O)CNC(=O)CNC(=O)CCCCCN1C(=O)C=CC1=O)[C@H]1CCc2c(C)c(F)cc3nc4c(c1c23)Cn1c-4cc2c(c1=O)COC(=O)[C@]2(O)CC] |

| No. | Structure |
|---|---|
| L-I-46 | 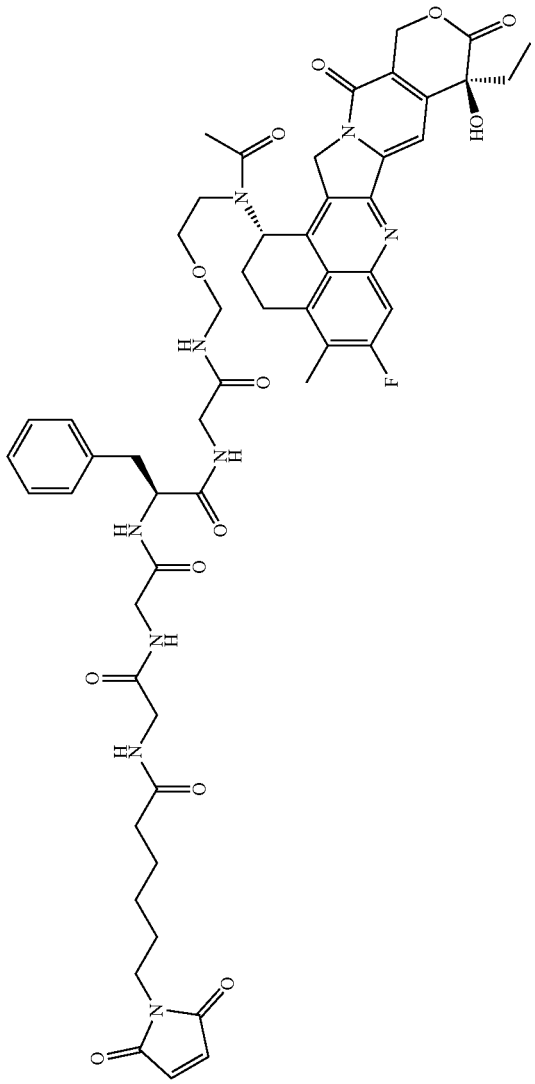 |

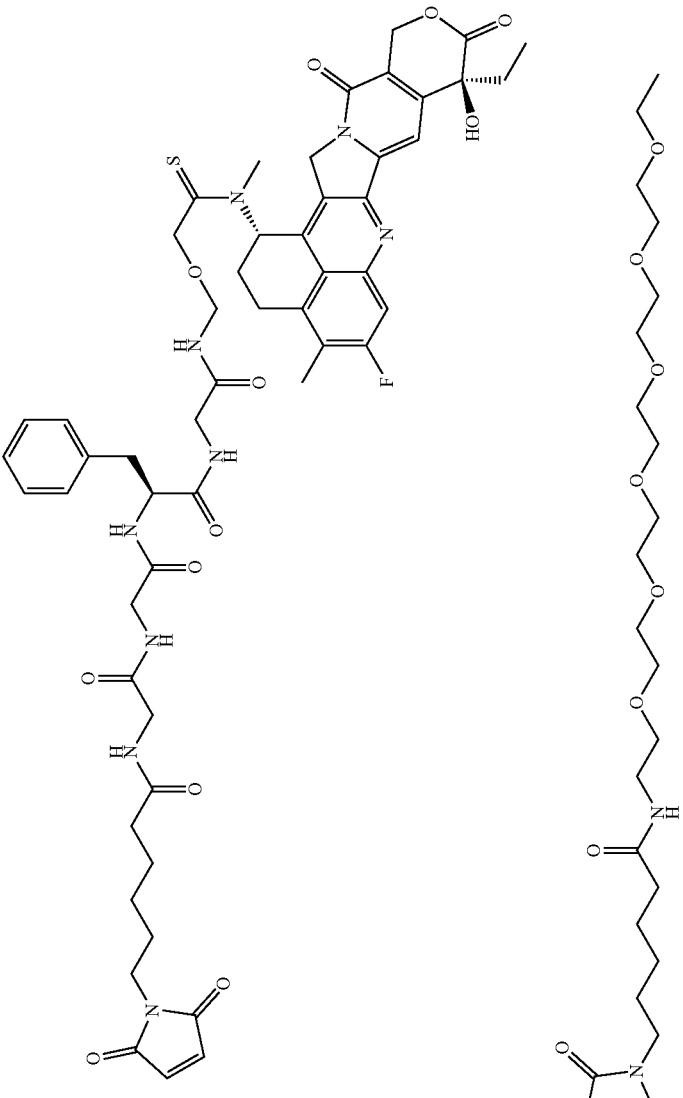

| No. | Structure |
|---|---|
| L-I-49 | 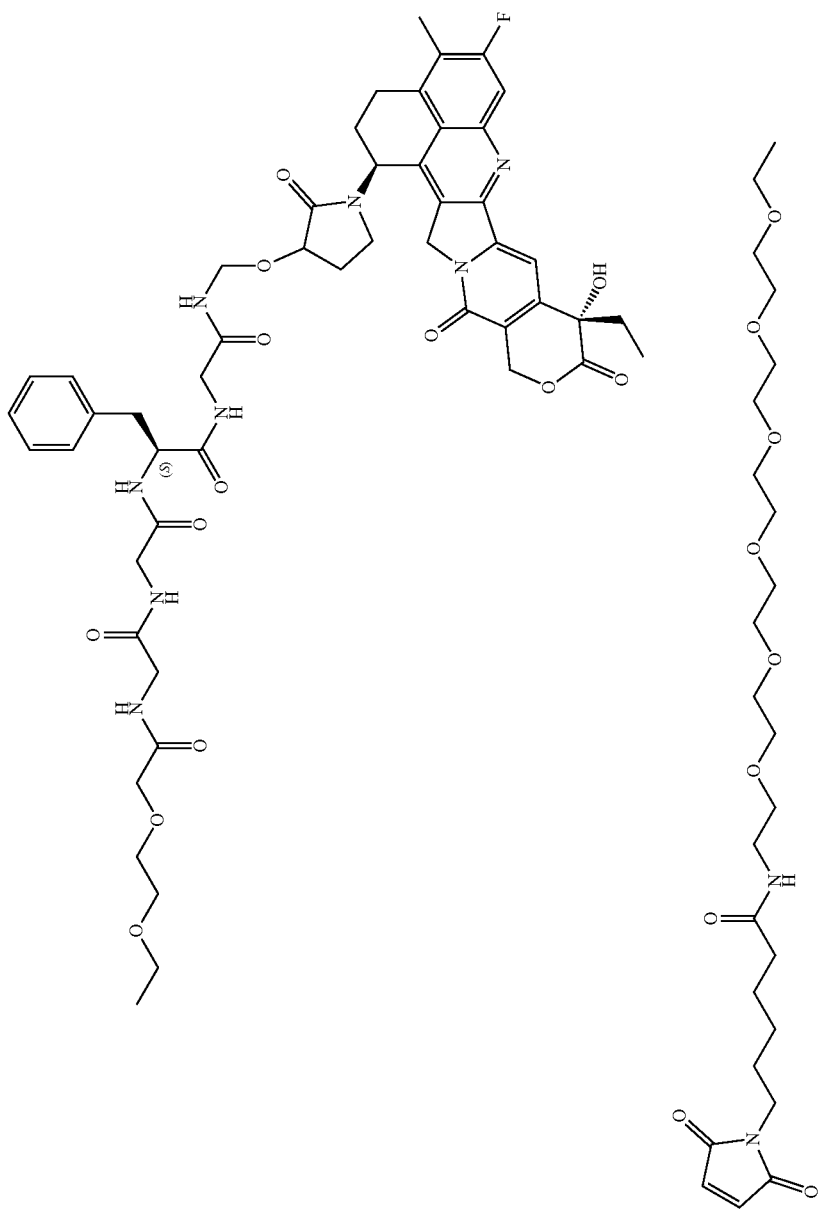 |

-continued
| No. | Structure |
|---|---|
| L-I-50 | 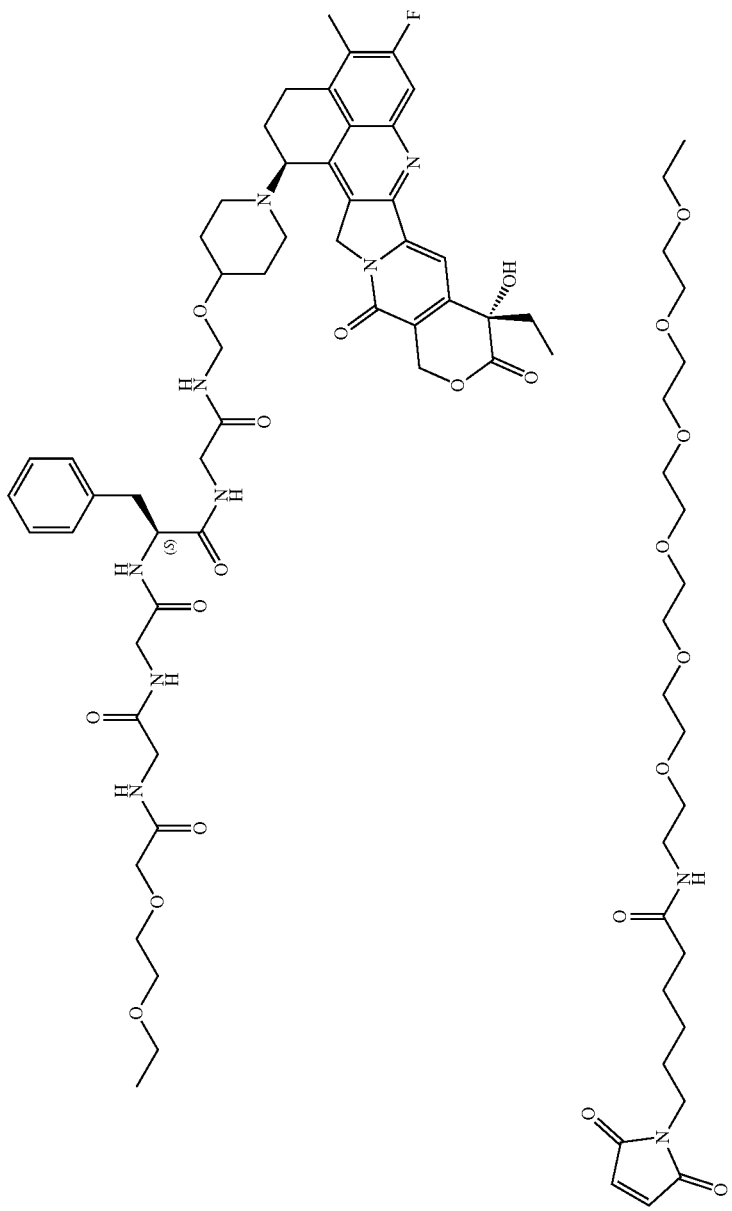 |

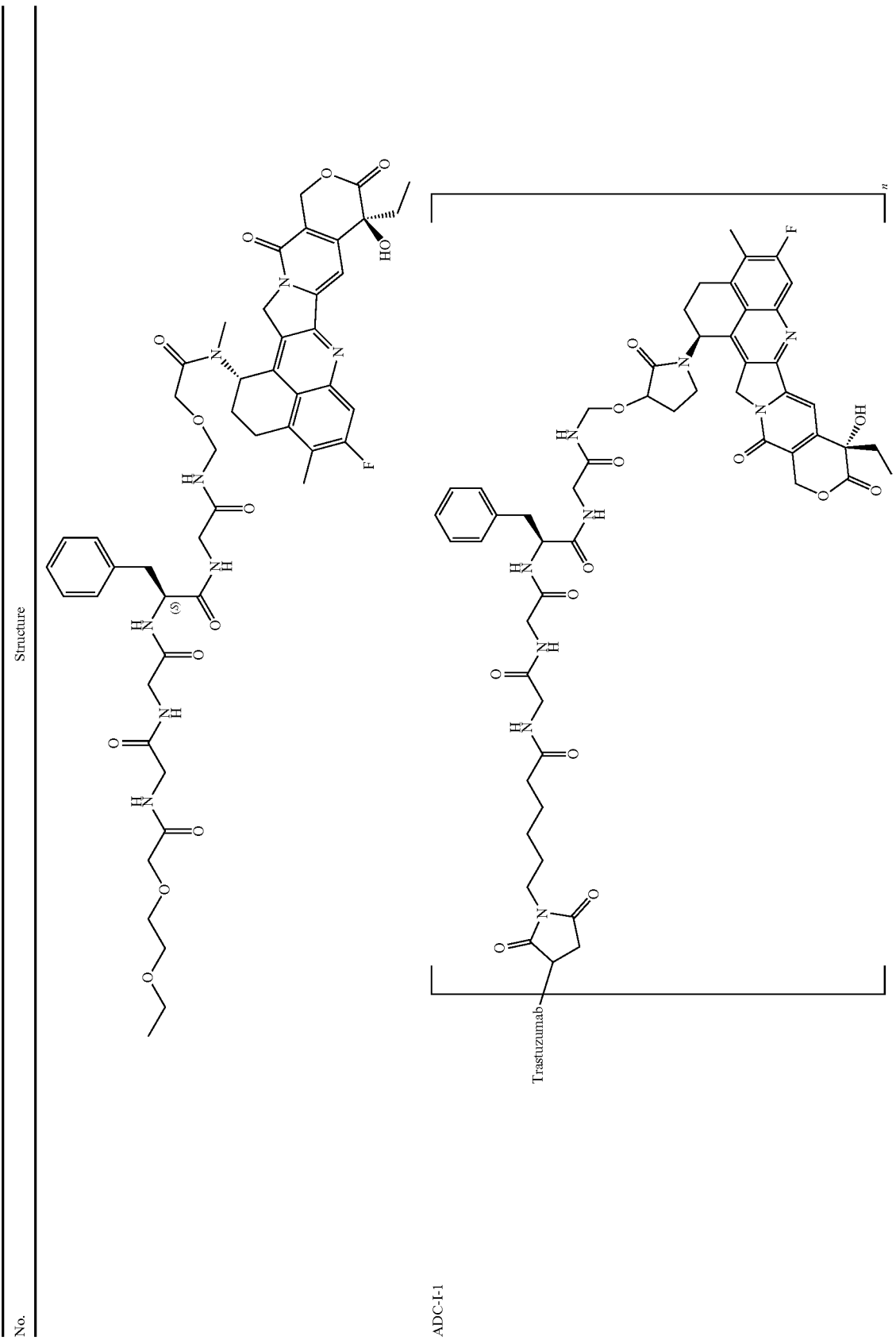

| No. | Structure |
|---|---|
| ADC-I-2 | 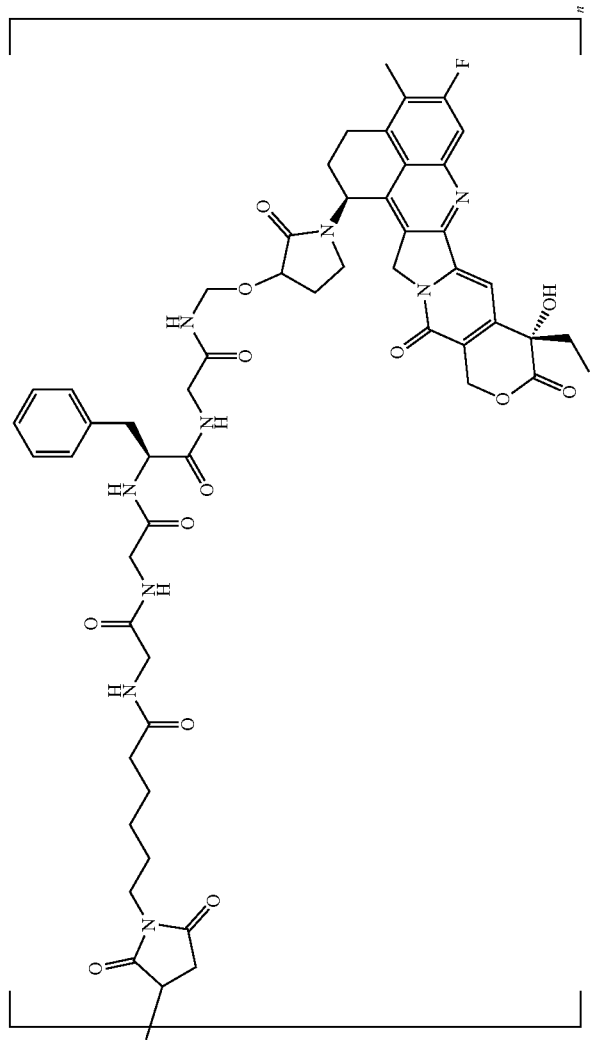 |

-continued
| No. | Structure |
|---|---|
| ADC-I-3 | 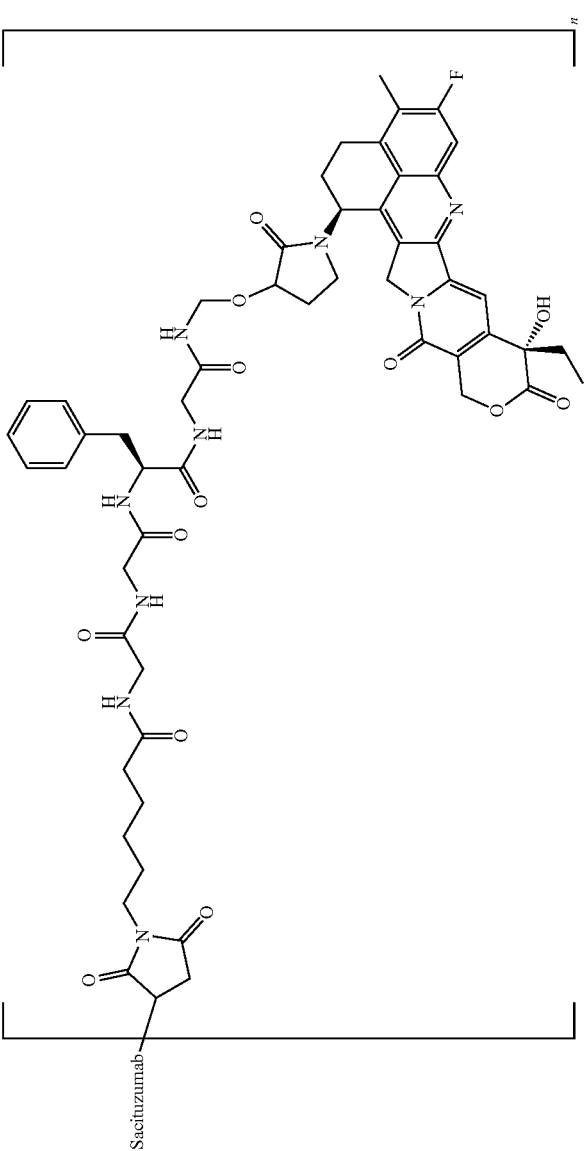 |

-continued
| No. | Structure |
|---|---|
| ADC-I-4 | 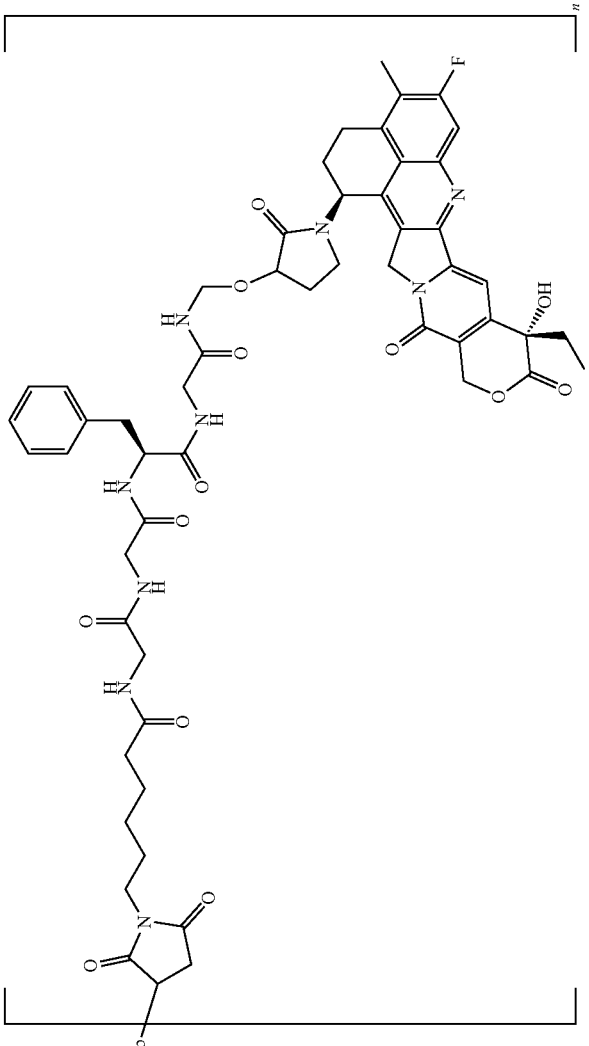 |

| No. | Structure |
|---|---|
| ADC-I-5 | 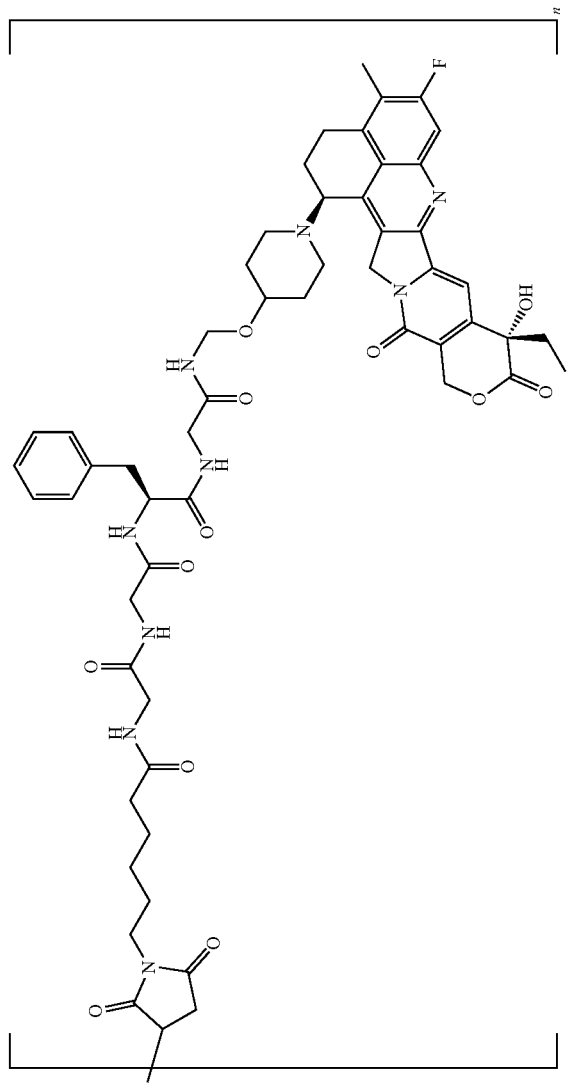 |

| No. | Structure |
|---|---|
| ADC-I-6 | 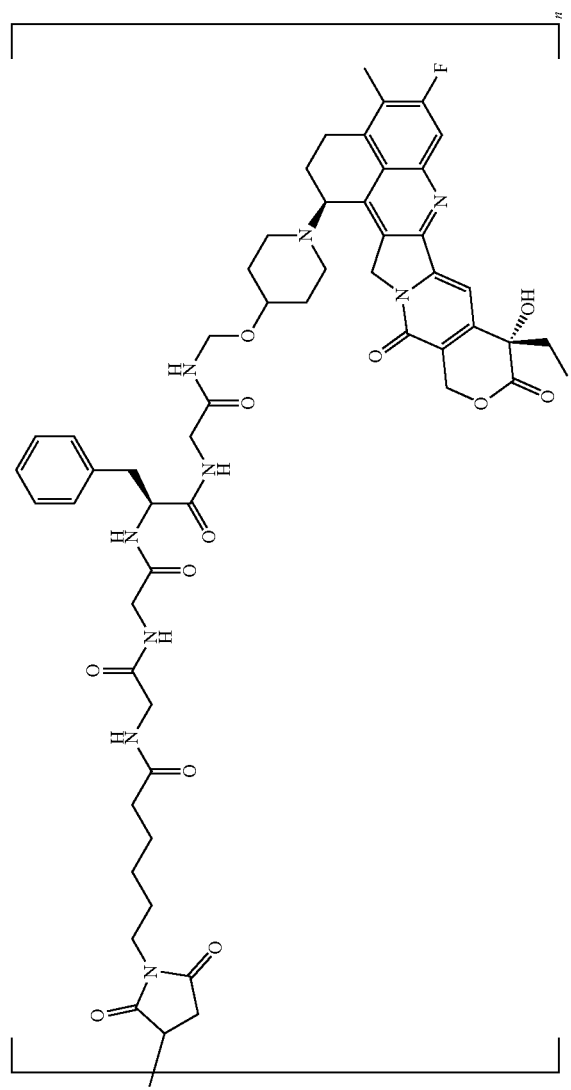 |

-continued
| No. | Structure |
|---|---|
| ADC-I-7 | 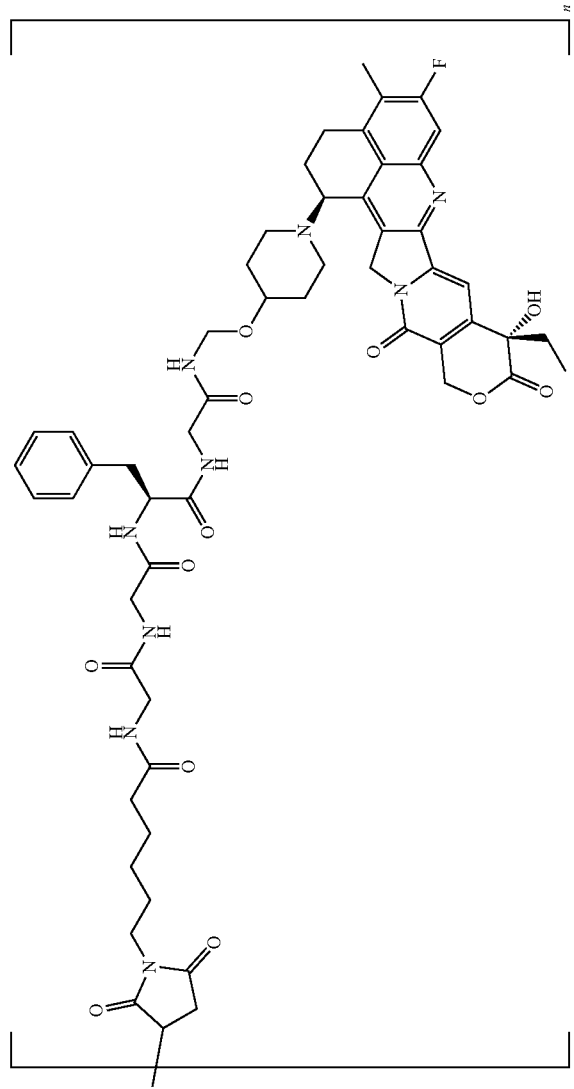 |

| No. | Structure |
|---|---|
| ADC-I-8 | 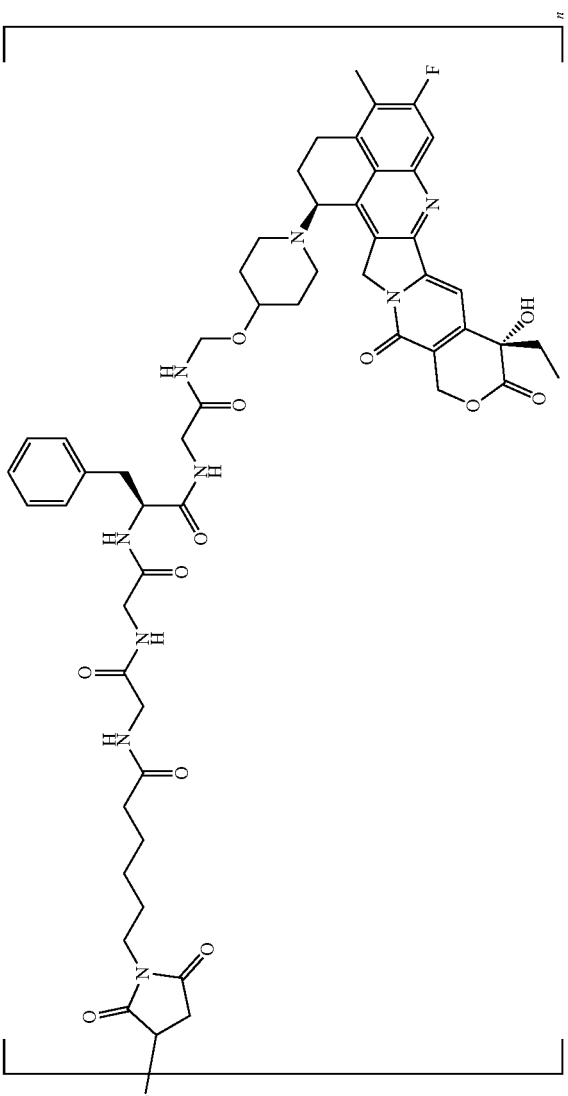 Zolbetuximab |
| ADC-I-9 | 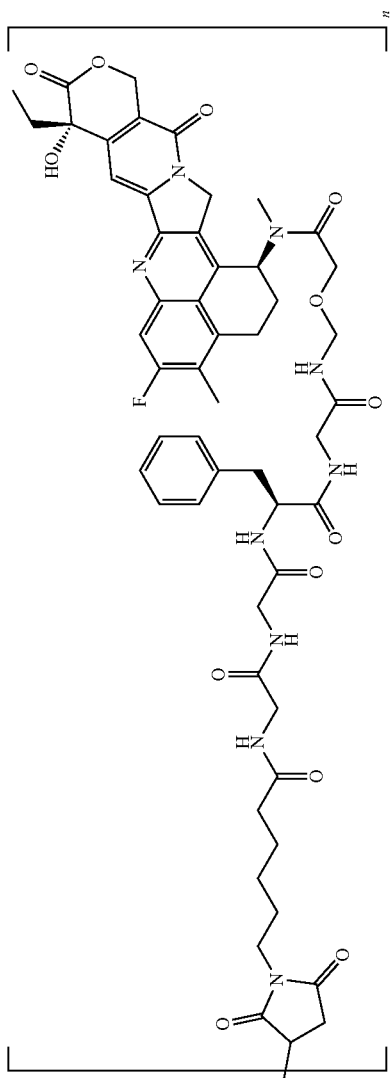 Trastuzumab |

| No. | Structure |
|---|---|
| ADC-I-10 | 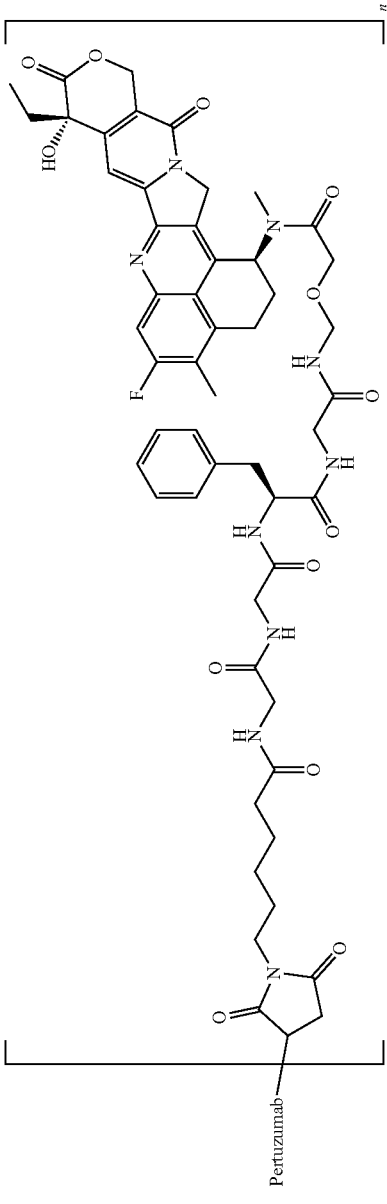 Pertuzumab |
| ADC-I-11 | 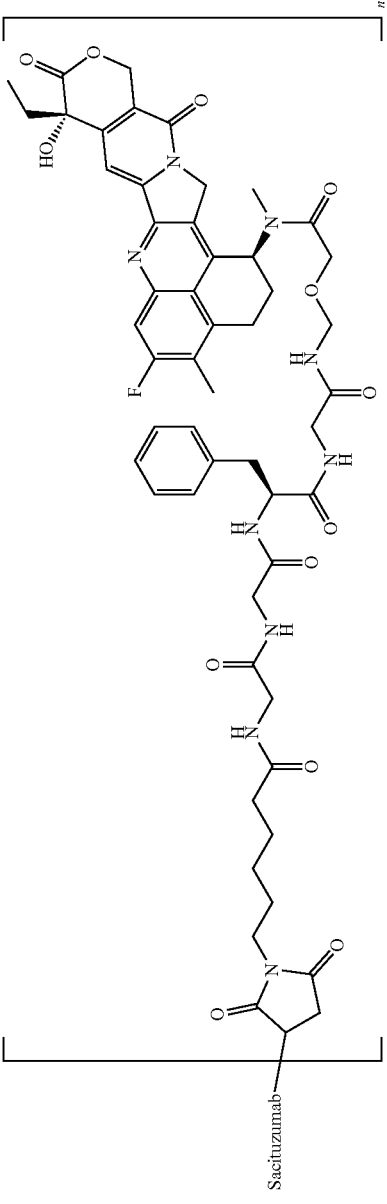 Sacituzumab |

-continued
| No. | Structure |
|---|---|
| ADC-I-12 | 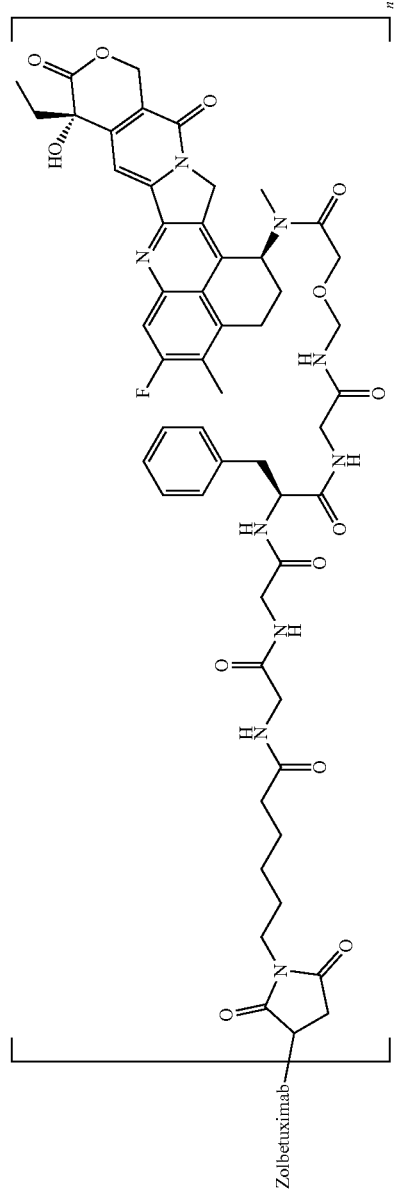 |
| ADC-I-13 | 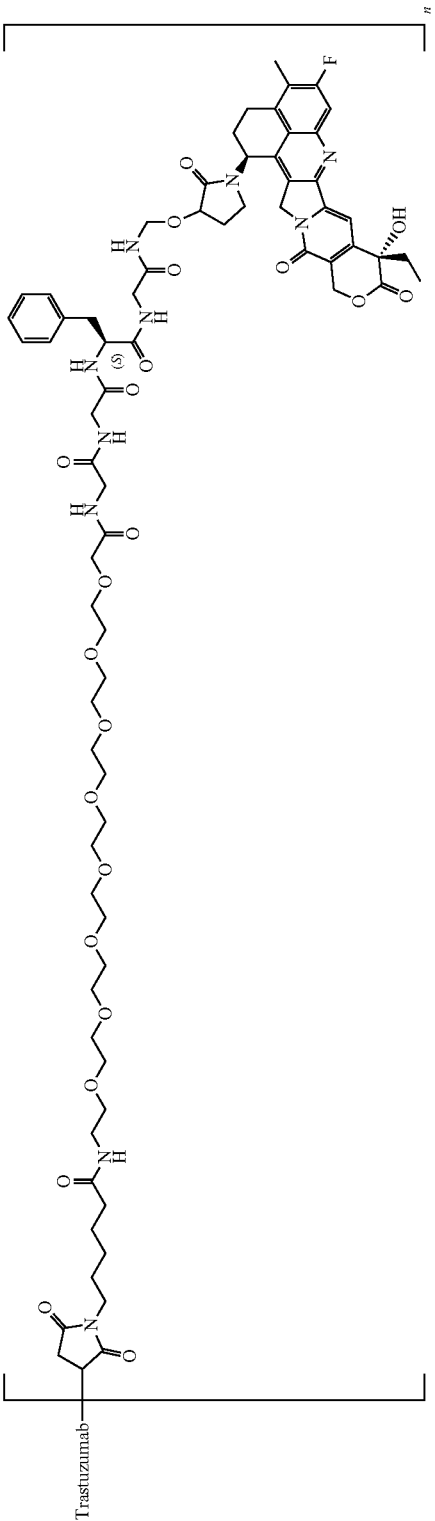 |

| No. | Structure |
|---|---|
| ADC-I-14 | 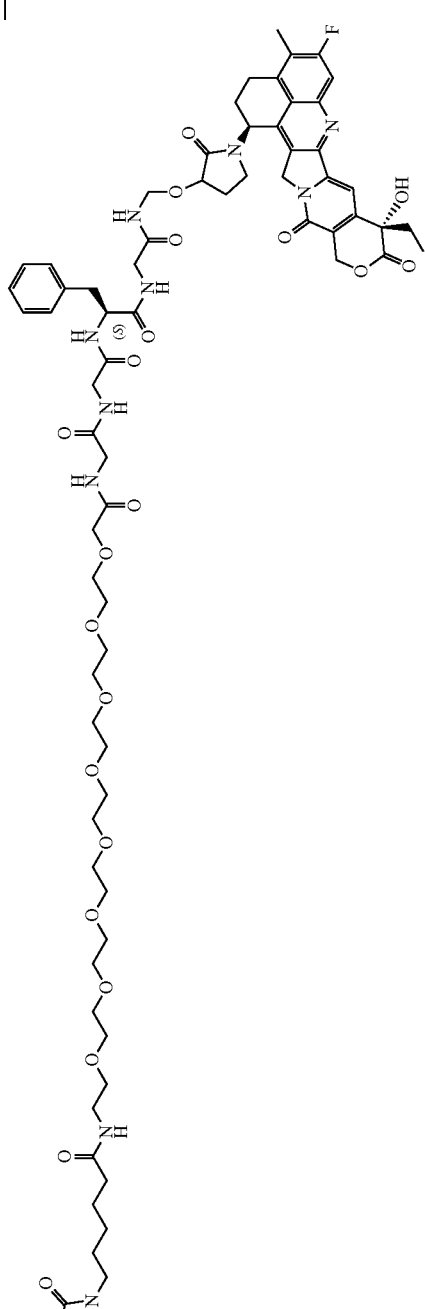 |
| ADC-I-15 | 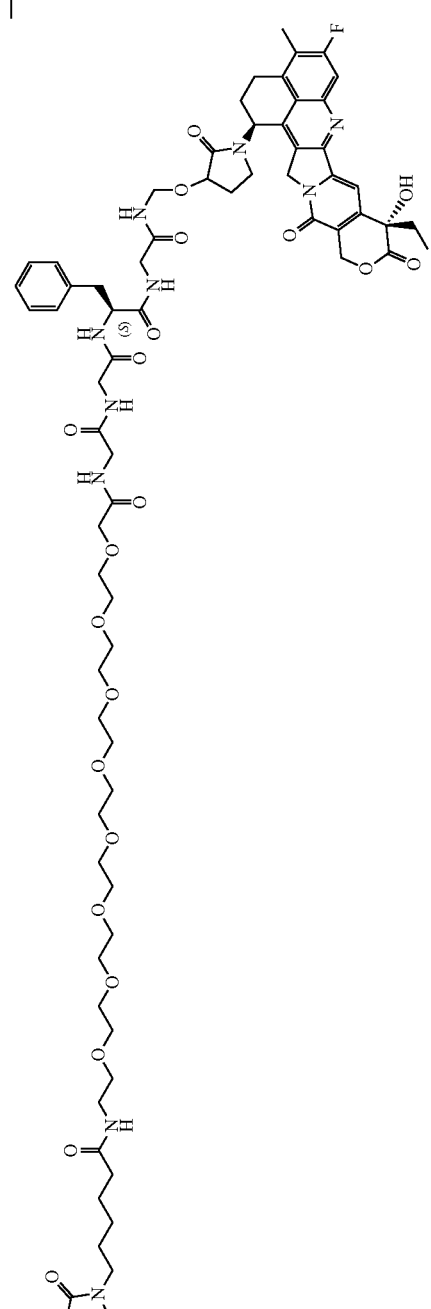 |

| No. | Structure |
|---|---|
| ADC-I-16 | 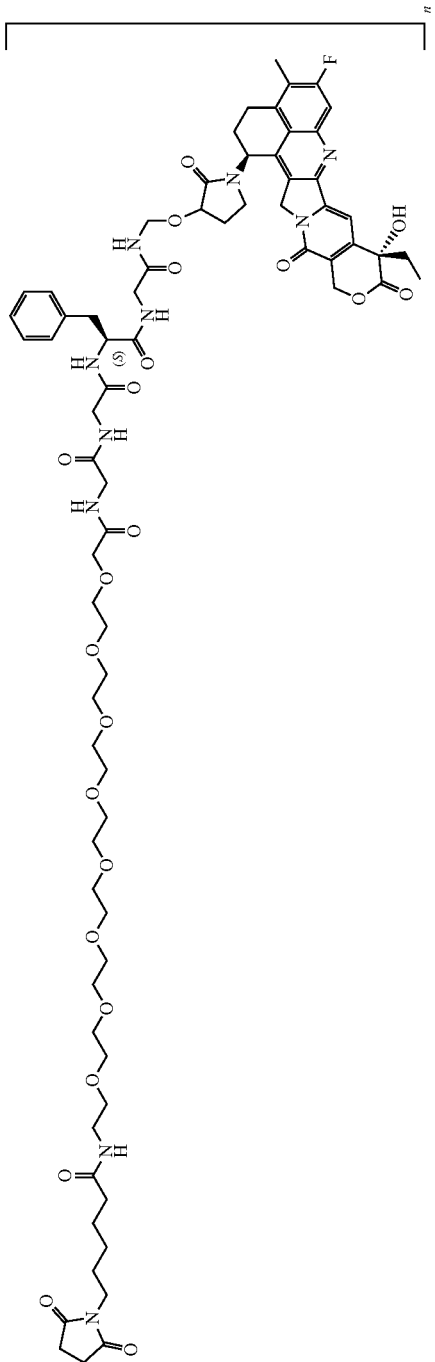 |
| ADC-I-17 | 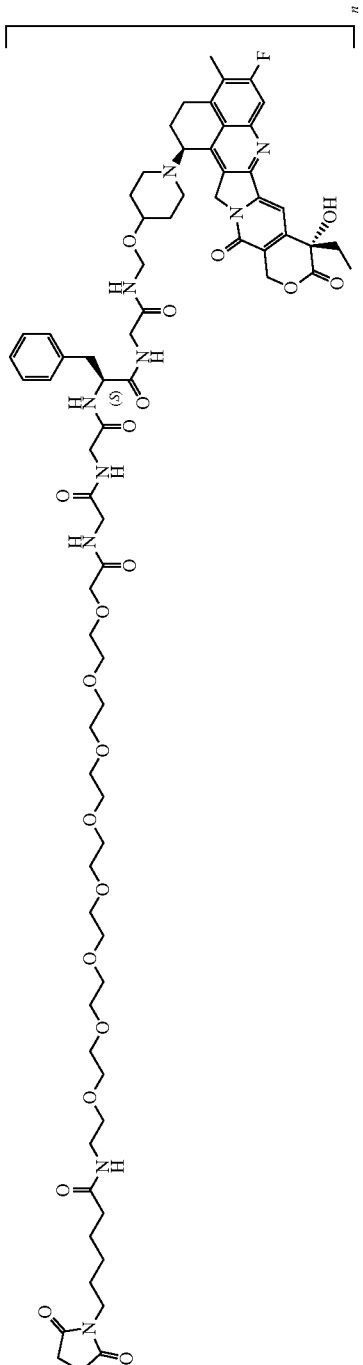 |

| No. | Structure |
|---|---|
| ADC-I-18 | Pertuzumab-[...structure with PEG linker, Gly-Gly-Phe-Gly peptide, and exatecan-like payload...]$_n$ |
| ADC-I-19 | Sacituzumab-[...structure with PEG linker, Gly-Gly-Phe-Gly peptide, and exatecan-like payload...]$_n$ |

| No. | Structure |
|---|---|
| ADC-I-20 | Zolbetuximab-[structure with maleimide-PEG-Gly-Phe-Gly-piperidine-exatecan analog with F and methyl]$_n$ |
| ADC-I-21 | Trastuzumab-[structure with maleimide-PEG-Gly-Phe-Gly-N(Me)-CH2-O-CH2- exatecan analog with F and methyl]$_n$ |
| ADC-I-22 | Pertuzumab-[structure with maleimide-PEG-Gly-Phe-Gly-N(Me)-CH2-O-CH2- exatecan analog with F and methyl]$_n$ |

| No. | Structure |
|---|---|
| ADC-I-23 | 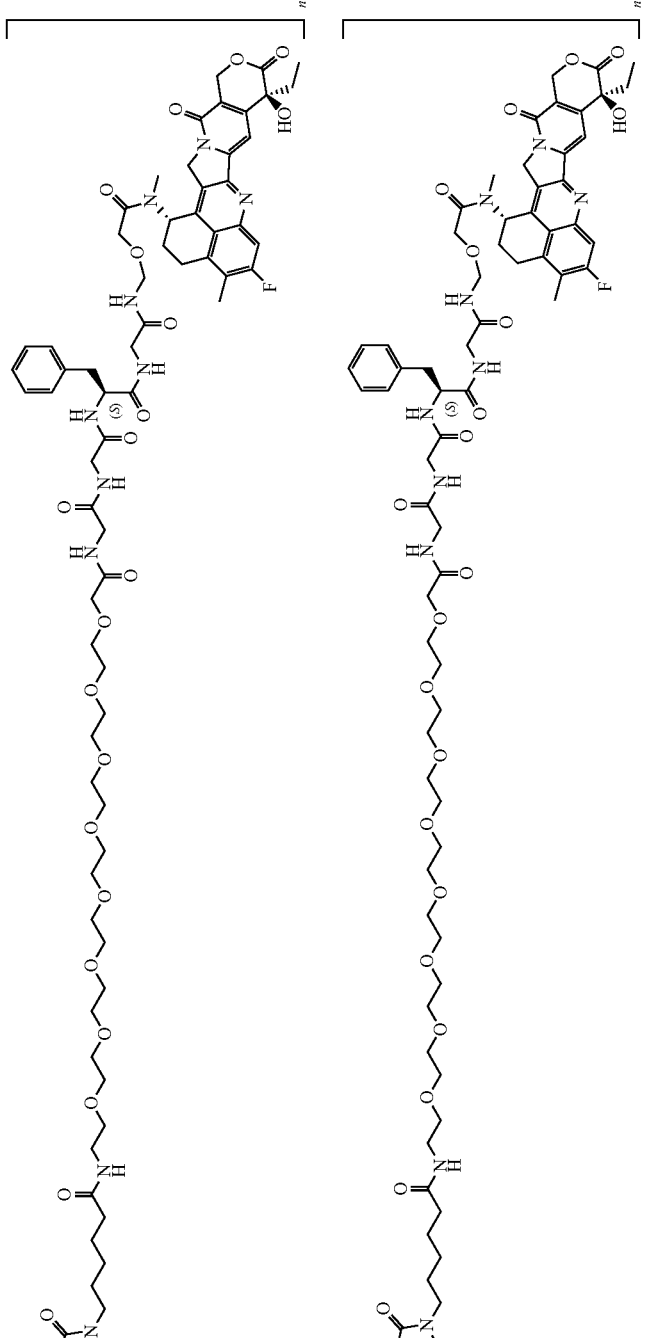 |
| ADC-I-24 | 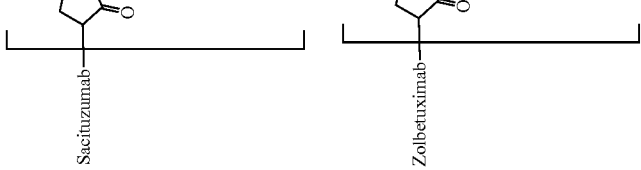 |

| No. | Structure |
|---|---|
| ADC-I-25 | 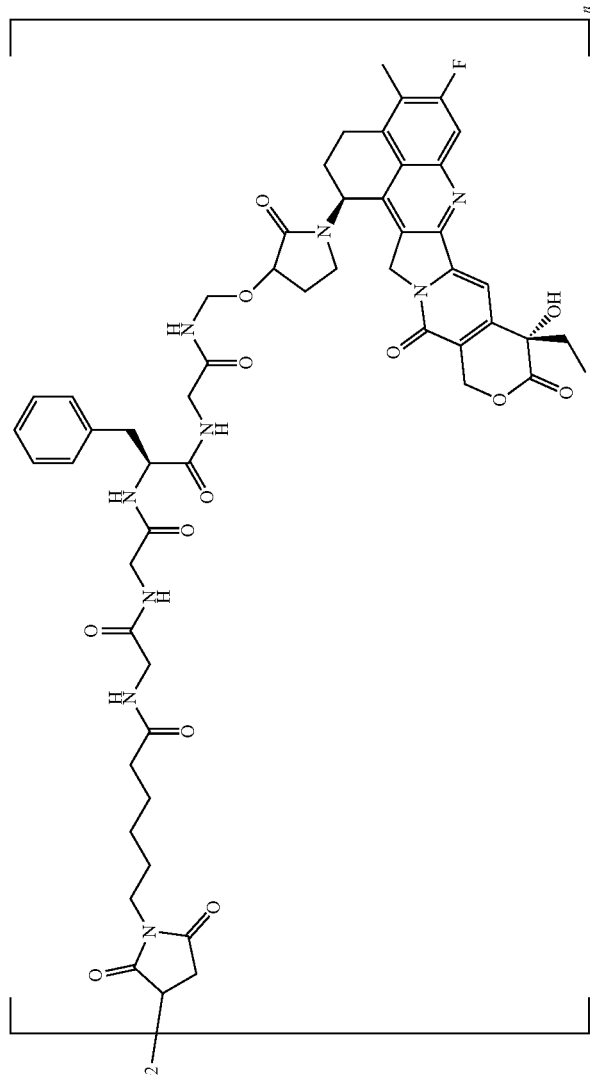 |

| No. | Structure |
|---|---|
| ADC-I-26 | 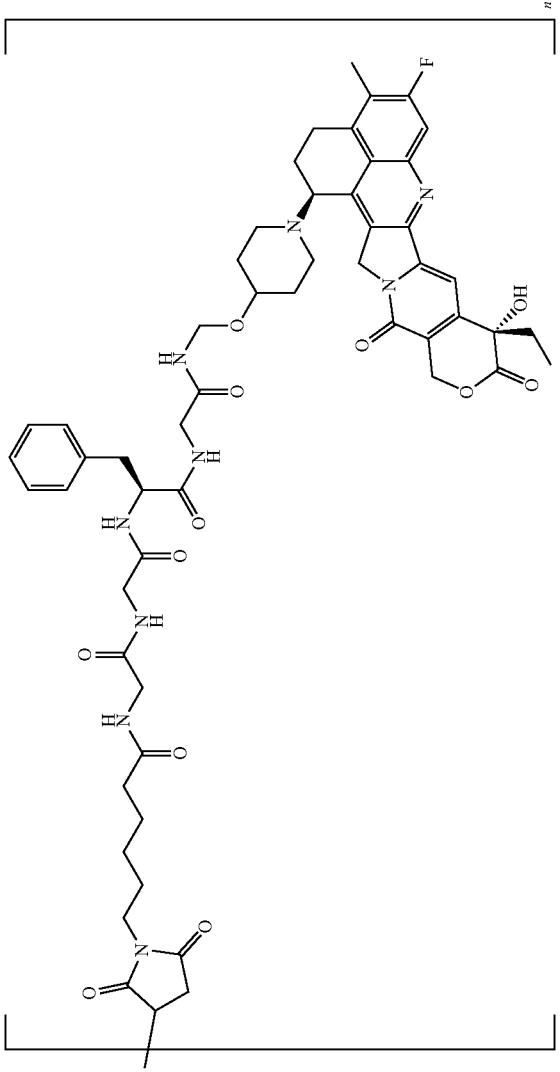 |
| ADC-I-27 | 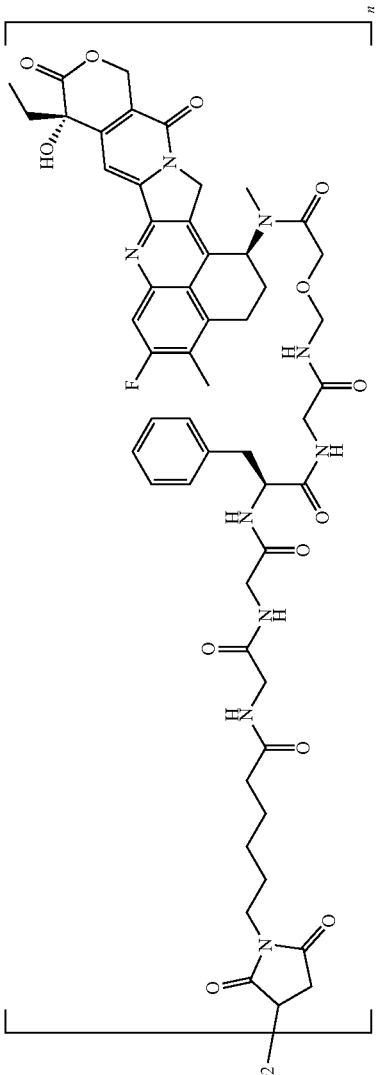 |

| No. | Structure |
|---|---|
| ADC-I-28 | 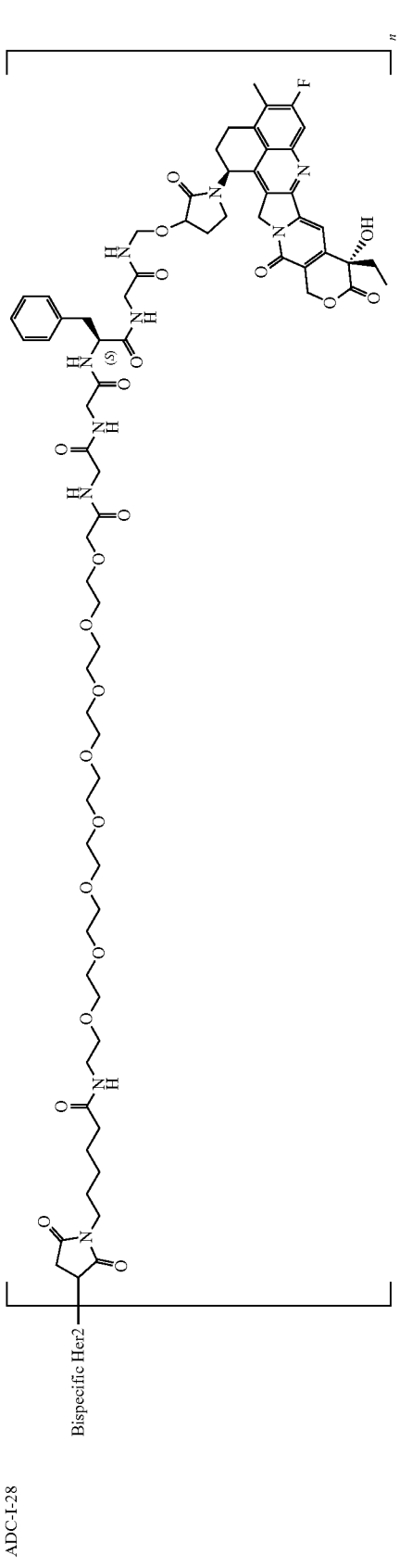 |
| ADC-I-29 | 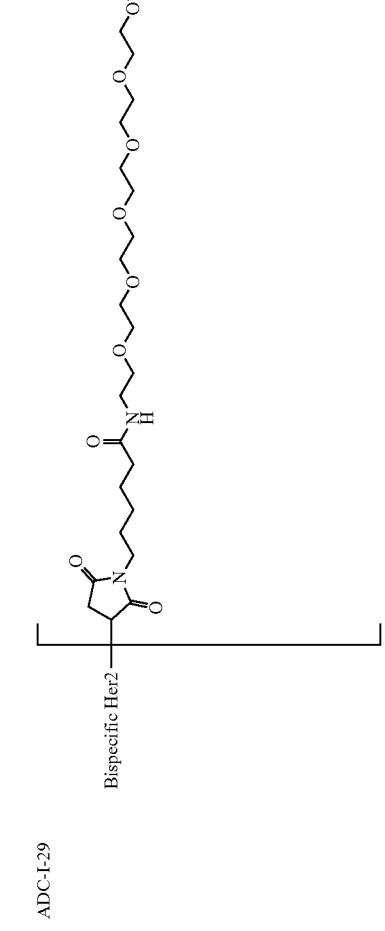 |

| No. | Structure |
|---|---|
| ADC-I-30 | 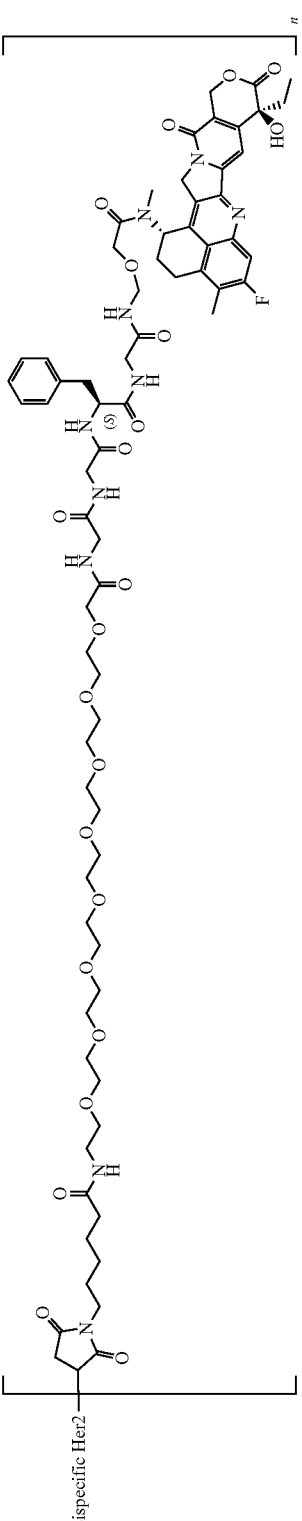 |

The average connection number n in the above list may be an integer or a decimal from 1 to 10. The average connection number n in the above list may be an integer or a decimal from 2 to 8. For example, the average connection number n may be an integer or a decimal from 3 to 8. For example, the average connection number n may be an integer or a decimal from 1 to 2, 2 to 3, 3 to 4, 4 to 5, 5 to 6, 6 to 7, 7 to 8, 8 to 9, or 9 to 10.

In one embodiment, the compounds disclosed herein include, but are not limited to:

| No. | Structure |
|---|---|
| P-II-1 | 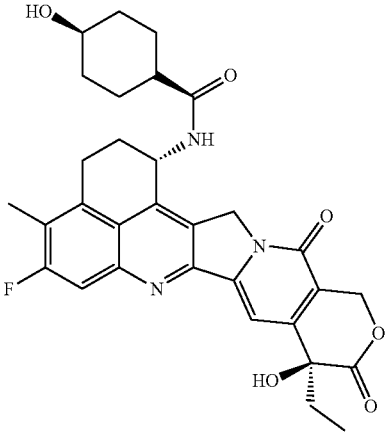 |
| P-II-2 | 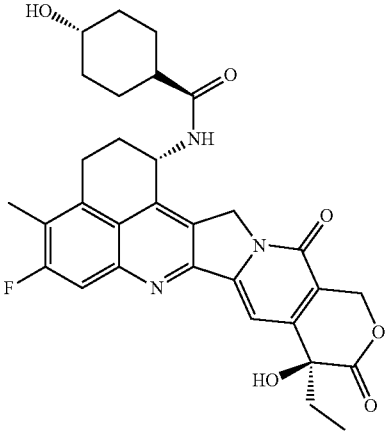 |
| P-II-3 | 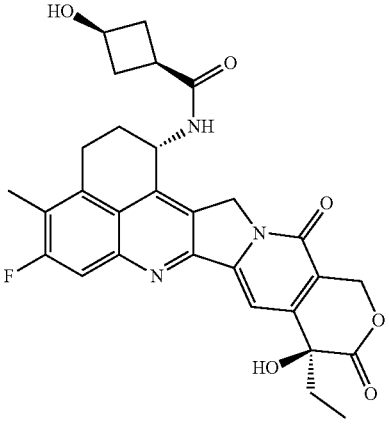 [SMILES: CC[C@@]1(O)C(=O)OCc2c1cc1n(c2=O)Cc2c-1nc1cc(F)c(C)c3c1c2[C@@H](NC(=O)[C@H]1C[C@@H](O)C1)CC3] |

| No. | Structure |
|---|---|
| P-II-4 | 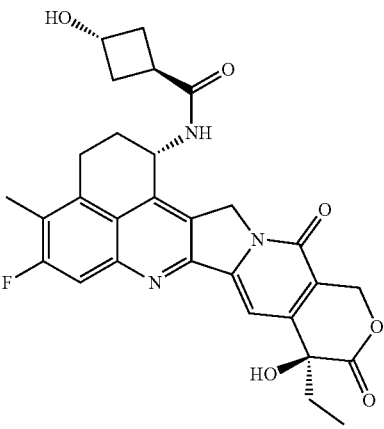 [SMILES: CC[C@@]1(O)C(=O)OCc2c1cc1n(c2=O)Cc2c-1nc1cc(F)c(C)c3c1c2[C@@H](NC(=O)[C@H]1C[C@H](O)C1)CC3] |
| P-II-5 | 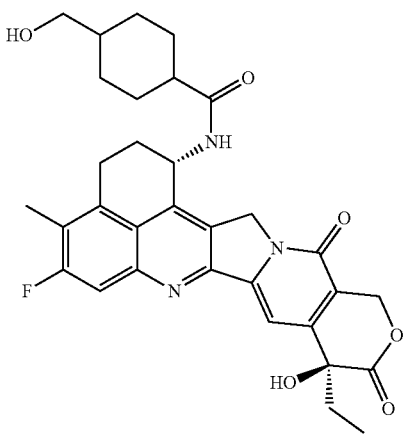 [SMILES: CC[C@@]1(O)C(=O)OCc2c1cc1n(c2=O)Cc2c-1nc1cc(F)c(C)c3c1c2[C@@H](NC(=O)C1CCC(CO)CC1)CC3] |
| P-II-6 | 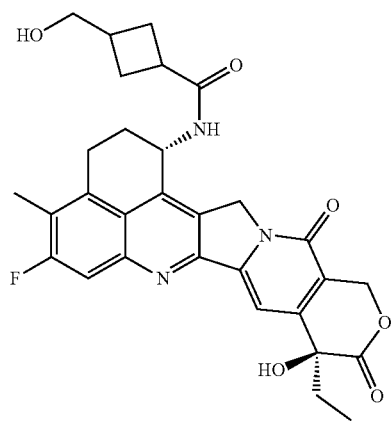 [SMILES: CC[C@@]1(O)C(=O)OCc2c1cc1n(c2=O)Cc2c-1nc1cc(F)c(C)c3c1c2[C@@H](NC(=O)C1CC(CO)C1)CC3] |

| No. | Structure |
|---|---|
| P-II-7 | 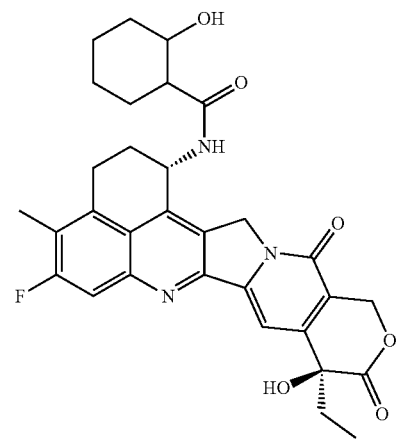 [SMILES: CC[C@@]1(O)C(=O)OCc2c1cc1n(c2=O)Cc2c-1nc1cc(F)c(C)c3c1c2[C@@H](NC(=O)C1CCCCC1O)CC3] |
| P-II-8 | 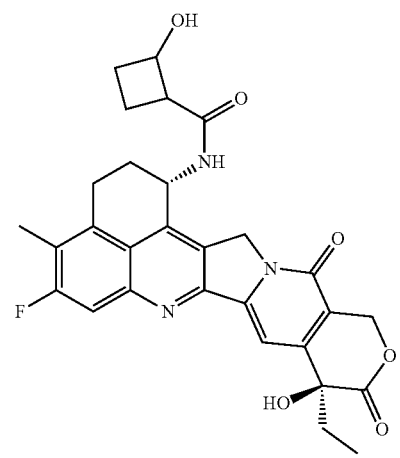 [SMILES: CC[C@@]1(O)C(=O)OCc2c1cc1n(c2=O)Cc2c-1nc1cc(F)c(C)c3c1c2[C@@H](NC(=O)C1CCC1O)CC3] |
| P-II-9 | 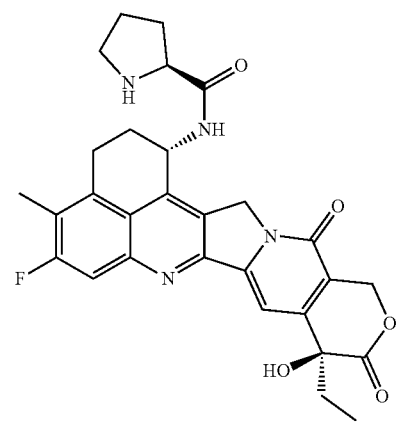 [SMILES: CC[C@@]1(O)C(=O)OCc2c1cc1n(c2=O)Cc2c-1nc1cc(F)c(C)c3c1c2[C@@H](NC(=O)[C@@H]1CCCN1)CC3] |

| No. | Structure |
|---|---|
| P-II-10 | 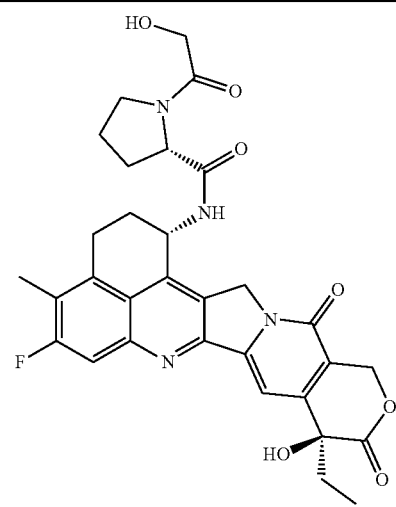 |
| P-II-11 | 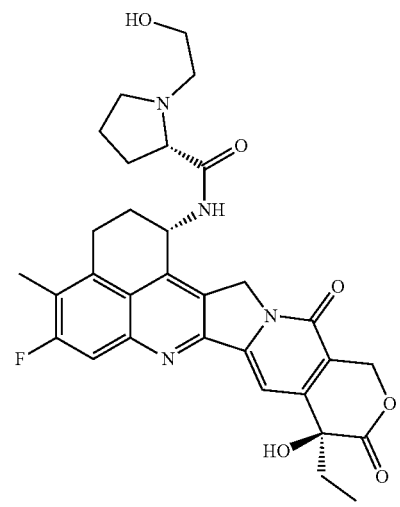 [SMILES: CC[C@@]1(O)C(=O)OCc2c1cc1n(c2=O)Cc2c-1nc1cc(F)c(C)c3c1c2[C@@H](NC(=O)[C@@H]1CCCN1CCO)CC3] |
| P-II-12 | 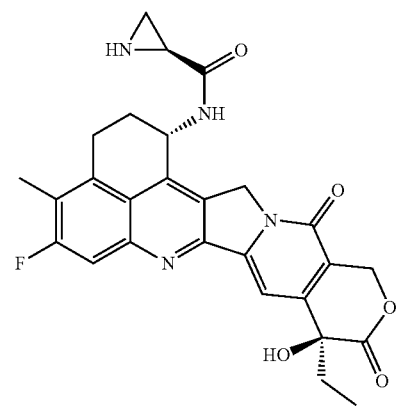 [SMILES: CC[C@@]1(O)C(=O)OCc2c1cc1n(c2=O)Cc2c-1nc1cc(F)c(C)c3c1c2[C@@H](NC(=O)[C@@H]1CN1)CC3] |

| No. | Structure |
|---|---|
| P-II-13 | 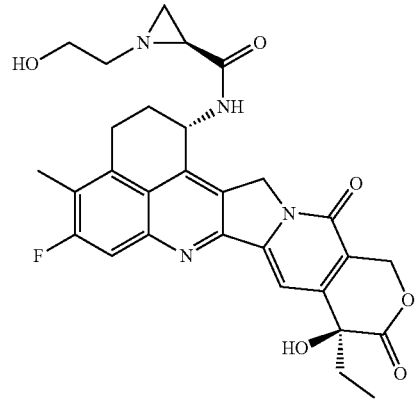 [SMILES: CC[C@@]1(O)C(=O)OCc2c1cc1n(c2=O)Cc2c-1nc1cc(F)c(C)c3c1c2[C@@H](NC(=O)[C@@H]1CN1CCO)CC3] |
| P-II-14 | 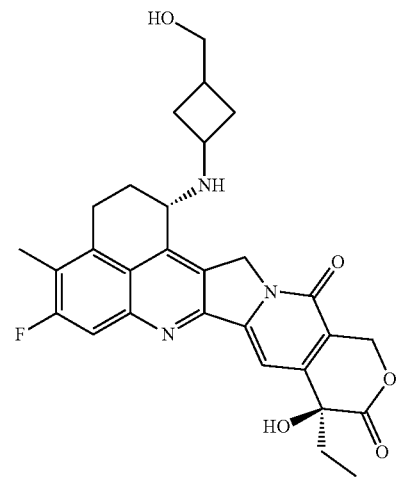 [SMILES: CC[C@@]1(O)C(=O)OCc2c1cc1n(c2=O)Cc2c-1nc1cc(F)c(C)c3c1c2[C@@H](NC1CC(CO)C1)CC3] |
| P-II-15 | 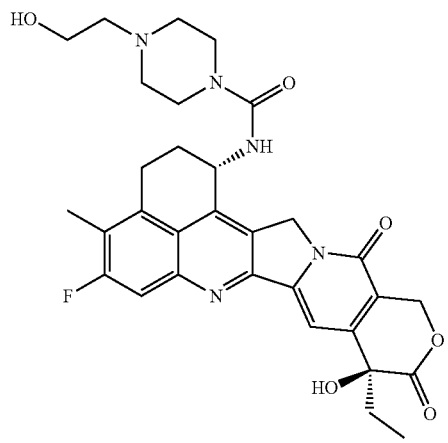 [SMILES: CC[C@@]1(O)C(=O)OCc2c1cc1n(c2=O)Cc2c-1nc1cc(F)c(C)c3c1c2[C@@H](NC(=O)N1CCN(CCO)CC1)CC3] |

| No. | Structure |
|---|---|
| P-II-16 | 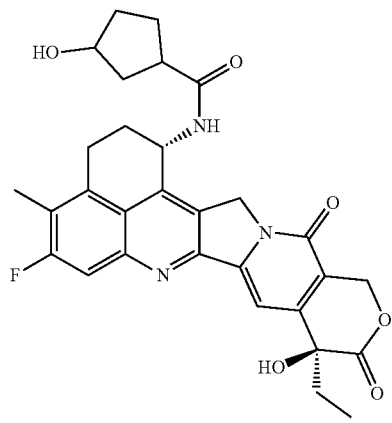 [SMILES: CC[C@@]1(O)C(=O)OCc2c1cc1n(c2=O)Cc2c-1nc1cc(F)c(C)c3c1c2[C@@H](NC(=O)C1CCC(O)C1)CC3] |
| P-II-17 | 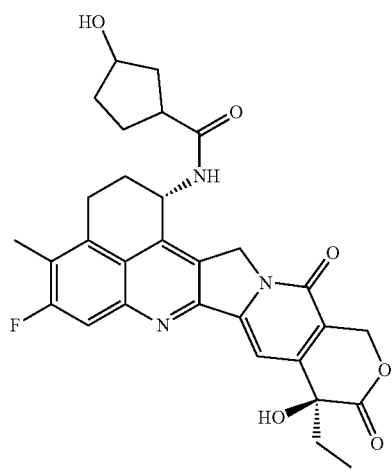 [SMILES: CC[C@@]1(O)C(=O)OCc2c1cc1n(c2=O)Cc2c-1nc1cc(F)c(C)c3c1c2[C@@H](NC(=O)C1CCC(O)C1)CC3] |
| P-II-18 | 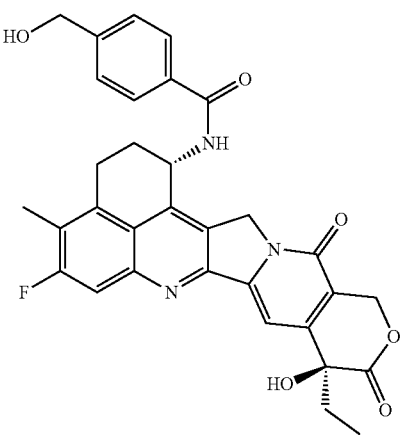 [SMILES: CC[C@@]1(O)C(=O)OCc2c1cc1n(c2=O)Cc2c-1nc1cc(F)c(C)c3c1c2[C@@H](NC(=O)c1ccc(CO)cc1)CC3] |

| No. | Structure |
|---|---|
| P-II-19 | 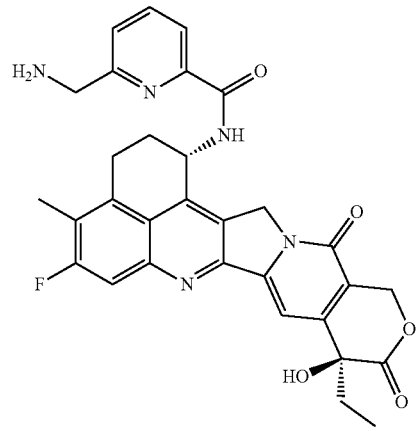 [SMILES: CC[C@@]1(O)C(=O)OCc2c1cc1n(c2=O)Cc2c-1nc1cc(F)c(C)c3c1c2[C@@H](NC(=O)c1cccc(CN)n1)CC3] |
| P-II-20 | 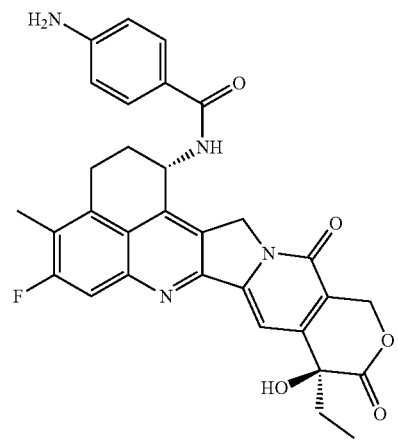 [SMILES: CC[C@@]1(O)C(=O)OCc2c1cc1n(c2=O)Cc2c-1nc1cc(F)c(C)c3c1c2[C@@H](NC(=O)c1ccc(N)cc1)CC3] |
| P-II-21 | 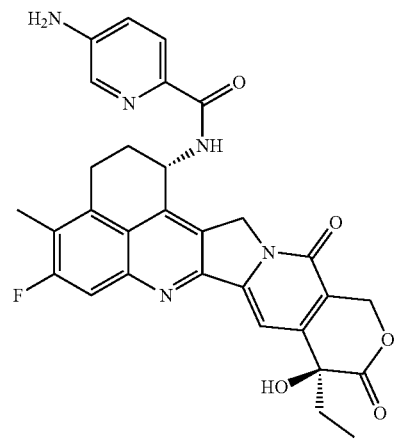 [SMILES: CC[C@@]1(O)C(=O)OCc2c1cc1n(c2=O)Cc2c-1nc1cc(F)c(C)c3c1c2[C@@H](NC(=O)c1ccc(N)cn1)CC3] |

| No. | Structure |
|---|---|
| P-II-22 | 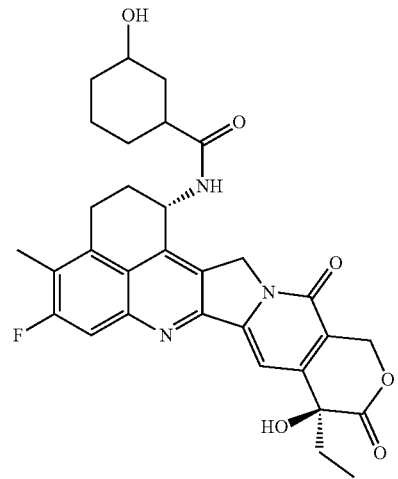 [SMILES: CC[C@@]1(O)C(=O)OCc2c1cc1n(c2=O)Cc2c-1nc1cc(F)c(C)c3c1c2[C@@H](NC(=O)C1CCCC(O)C1)CC3] |
| P-II-23 | 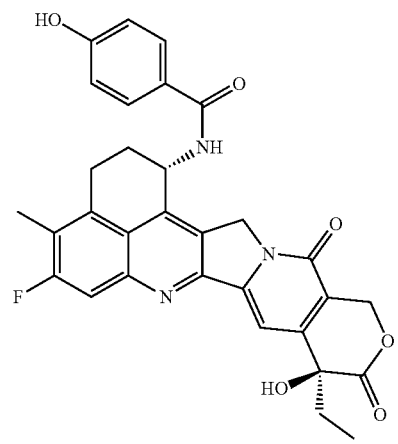 |
| P-II-24 | 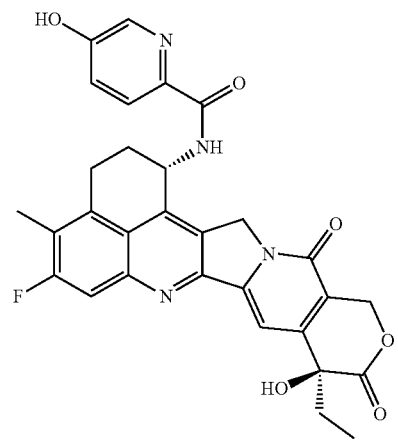 [SMILES: CC[C@@]1(O)C(=O)OCc2c1cc1n(c2=O)Cc2c-1nc1cc(F)c(C)c3c1c2[C@@H](NC(=O)c1ccc(O)cn1)CC3] |

| No. | Structure |
|---|---|
| P-II-25 | 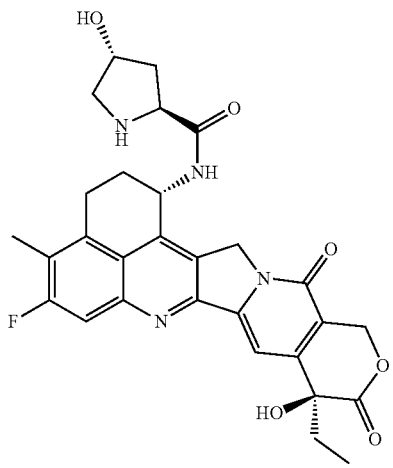 [SMILES: CC[C@@]1(O)C(=O)OCc2c1cc1n(c2=O)Cc2c-1nc1cc(F)c(C)c3c1c2[C@@H](NC(=O)[C@@H]1C[C@@H](O)CN1)CC3] |
| L-II-1 | 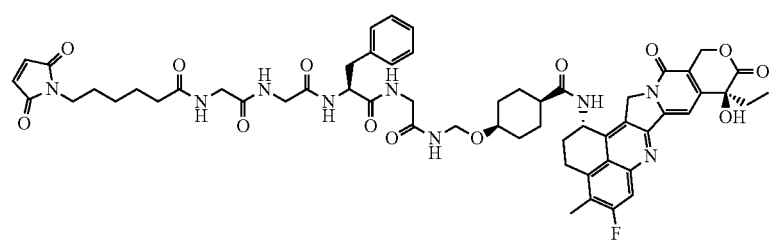 [SMILES: CC[C@@]1(O)C(=O)OCc2c1cc1n(c2=O)Cc2c-1nc1cc(F)c(C)c3c1c2[C@@H](NC(=O)[C@H]1CC[C@@H](OCNC(=O)CNC(=O)[C@H](Cc2ccccc2)NC(=O)CNC(=O)CNC(=O)CCCCCN2C(=O)C=CC2=O)CC1)CC3] |
| L-II-2 | 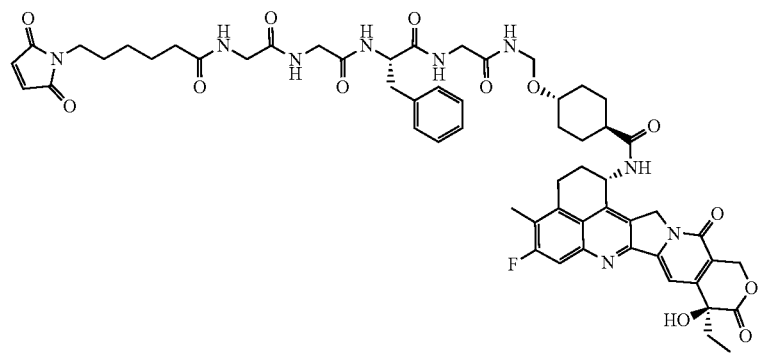 [SMILES: CC[C@@]1(O)C(=O)OCc2c1cc1n(c2=O)Cc2c-1nc1cc(F)c(C)c3c1c2[C@@H](NC(=O)[C@H]1CC[C@H](OCNC(=O)CNC(=O)[C@H](Cc2ccccc2)NC(=O)CNC(=O)CNC(=O)CCCCCN2C(=O)C=CC2=O)CC1)CC3] |
| L-II-3 | 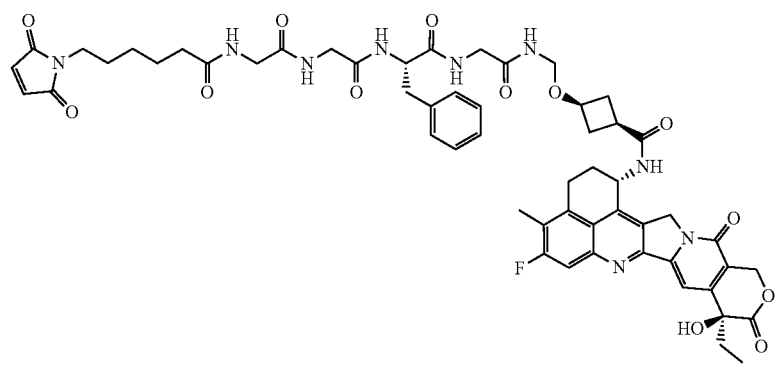 [SMILES: CC[C@@]1(O)C(=O)OCc2c1cc1n(c2=O)Cc2c-1nc1cc(F)c(C)c3c1c2[C@@H](NC(=O)[C@H]1C[C@@H](OCNC(=O)CNC(=O)[C@H](Cc2ccccc2)NC(=O)CNC(=O)CNC(=O)CCCCCN2C(=O)C=CC2=O)C1)CC3] |

-continued

| No. | Structure |
|---|---|
| L-II-4 | 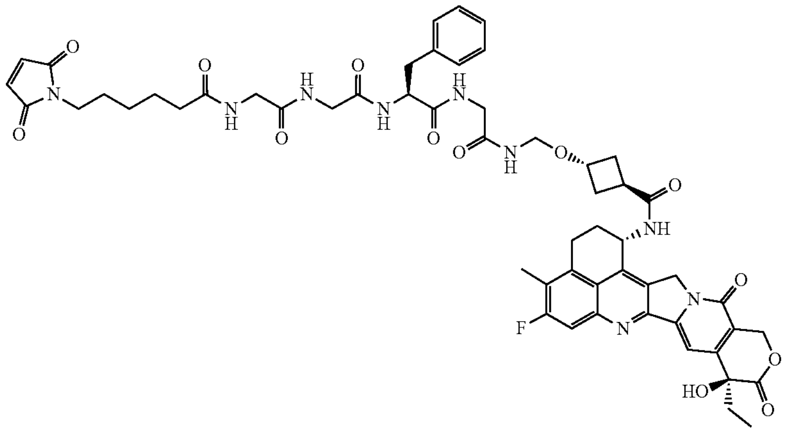 [SMILES: CC[C@@]1(O)C(=O)OCc2c1cc1n(c2=O)Cc2c-1nc1cc(F)c(C)c3c1c2[C@@H](NC(=O)[C@H]1C[C@H](OCNC(=O)CNC(=O)[C@H](Cc2ccccc2)NC(=O)CNC(=O)CNC(=O)CCCCCN2C(=O)C=CC2=O)C1)CC3] |
| L-II-5 | 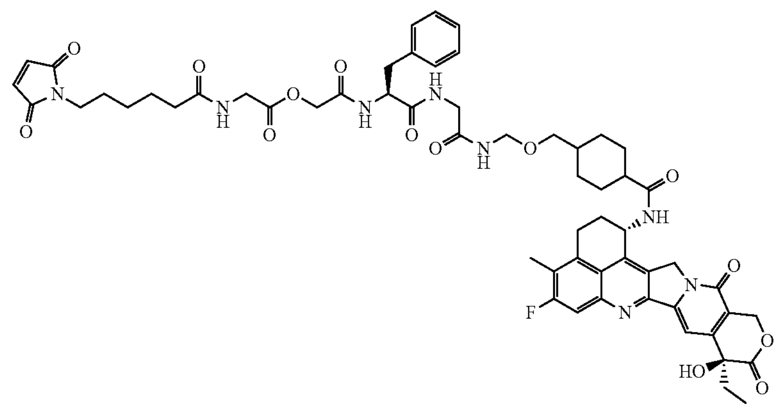 [SMILES: CC[C@@]1(O)C(=O)OCc2c1cc1n(c2=O)Cc2c-1nc1cc(F)c(C)c3c1c2[C@@H](NC(=O)C1CCC(COCNC(=O)CNC(=O)[C@H](Cc2ccccc2)NC(=O)COC(=O)CNC(=O)CCCCCN2C(=O)C=CC2=O)CC1)CC3] |
| L-II-6 | 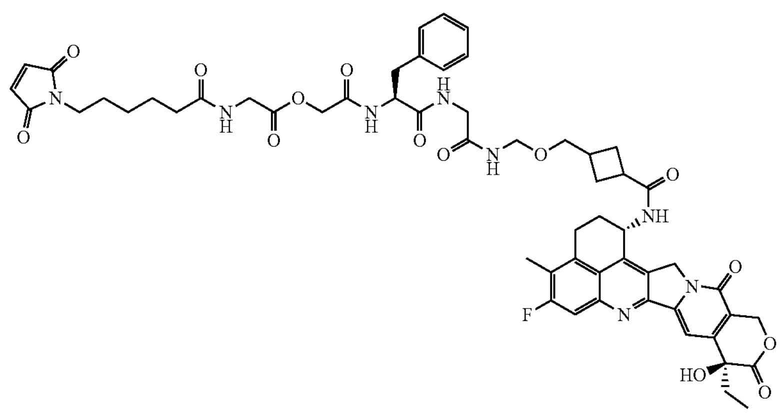 [SMILES: CC[C@@]1(O)C(=O)OCc2c1cc1n(c2=O)Cc2c-1nc1cc(F)c(C)c3c1c2[C@@H](NC(=O)C1CC(COCNC(=O)CNC(=O)[C@H](Cc2ccccc2)NC(=O)COC(=O)CNC(=O)CCCCCN2C(=O)C=CC2=O)C1)CC3] |
| L-II-7 | 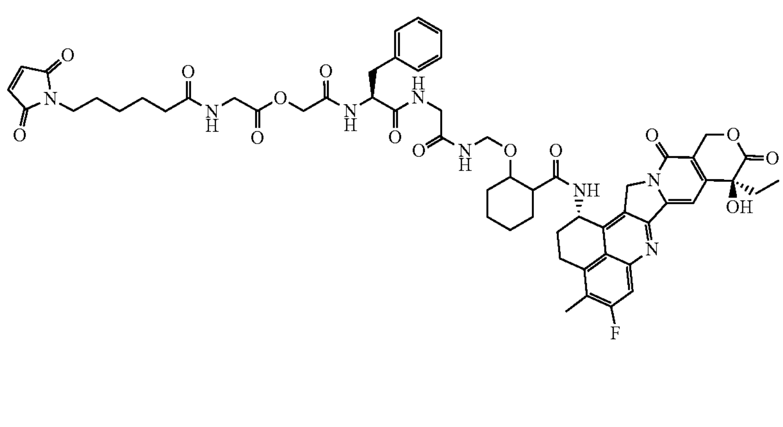 [SMILES: CC[C@@]1(O)C(=O)OCc2c1cc1n(c2=O)Cc2c-1nc1cc(F)c(C)c3c1c2[C@@H](NC(=O)C1CCCCC1OCNC(=O)CNC(=O)[C@H](Cc1ccccc1)NC(=O)COC(=O)CNC(=O)CCCCCN1C(=O)C=CC1=O)CC3] |

-continued

| No. | Structure |
|---|---|
| L-II-8 | 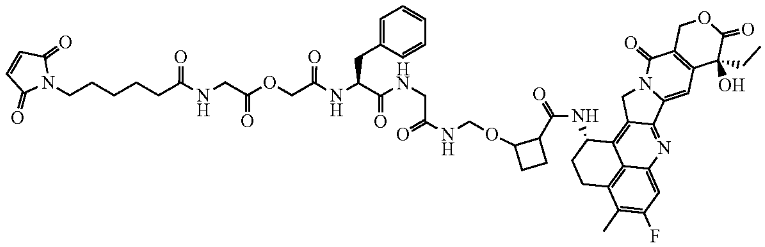 [SMILES: CC[C@@]1(O)C(=O)OCc2c1cc1n(c2=O)Cc2c-1nc1cc(F)c(C)c3c1c2[C@@H](NC(=O)C1CCC1OCNC(=O)CNC(=O)[C@H](Cc1ccccc1)NC(=O)COC(=O)CNC(=O)CCCCCN1C(=O)C=CC1=O)CC3] |
| L-II-9 | 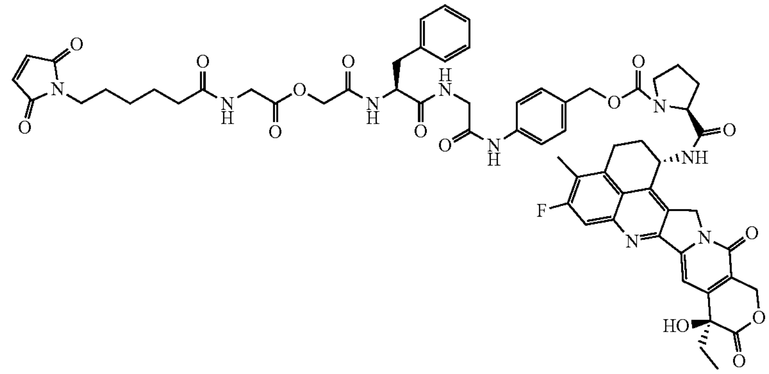 [SMILES: CC[C@@]1(O)C(=O)OCc2c1cc1n(c2=O)Cc2c-1nc1cc(F)c(C)c3c1c2[C@@H](NC(=O)[C@@H]1CCCN1C(=O)OCc1ccc(NC(=O)CNC(=O)[C@H](Cc2ccccc2)NC(=O)COC(=O)CNC(=O)CCCCCN2C(=O)C=CC2=O)cc1)CC3] |
| L-II-10 | 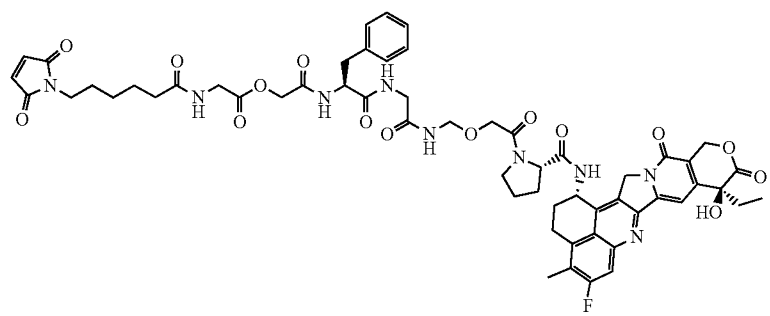 [SMILES: CC[C@@]1(O)C(=O)OCc2c1cc1n(c2=O)Cc2c-1nc1cc(F)c(C)c3c1c2[C@@H](NC(=O)[C@@H]1CCCN1C(=O)COCNC(=O)CNC(=O)[C@H](Cc1ccccc1)NC(=O)COC(=O)CNC(=O)CCCCCN1C(=O)C=CC1=O)CC3] |
| L-II-11 | 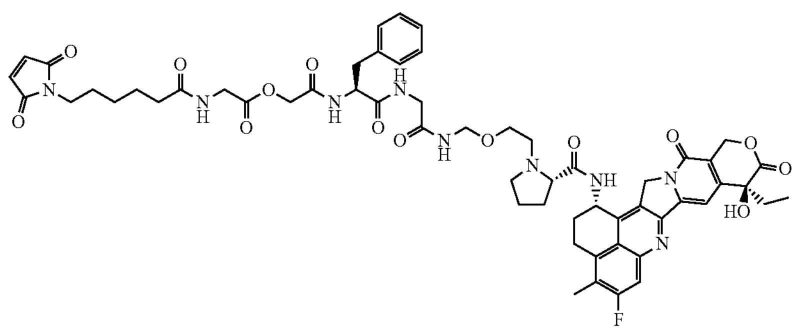 [SMILES: CC[C@@]1(O)C(=O)OCc2c1cc1n(c2=O)Cc2c-1nc1cc(F)c(C)c3c1c2[C@@H](NC(=O)[C@@H]1CCCN1CCOCNC(=O)CNC(=O)[C@H](Cc1ccccc1)NC(=O)COC(=O)CNC(=O)CCCCCN1C(=O)C=CC1=O)CC3] |
| L-II-12 | 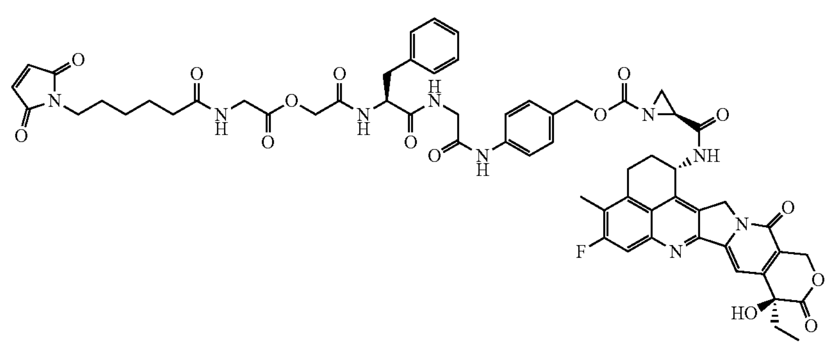 [SMILES: CC[C@@]1(O)C(=O)OCc2c1cc1n(c2=O)Cc2c-1nc1cc(F)c(C)c3c1c2[C@@H](NC(=O)[C@@H]1CN1C(=O)OCc1ccc(NC(=O)CNC(=O)[C@H](Cc2ccccc2)NC(=O)COC(=O)CNC(=O)CCCCCN2C(=O)C=CC2=O)cc1)CC3] |

| No. | Structure |
|---|---|
| L-II-13 | 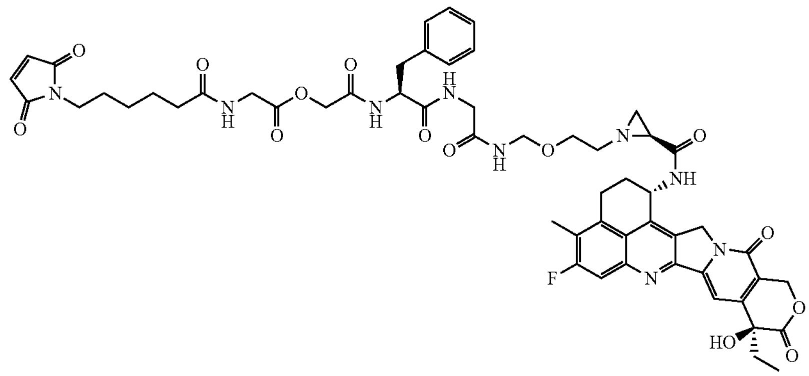 [SMILES: CC[C@@]1(O)C(=O)OCc2c1cc1n(c2=O)Cc2c-1nc1cc(F)c(C)c3c1c2[C@@H](NC(=O)[C@@H]1CN1CCOCNC(=O)CNC(=O)[C@H](Cc1ccccc1)NC(=O)COC(=O)CNC(=O)CCCCCN1C(=O)C=CC1=O)CC3] |
| L-II-14 | 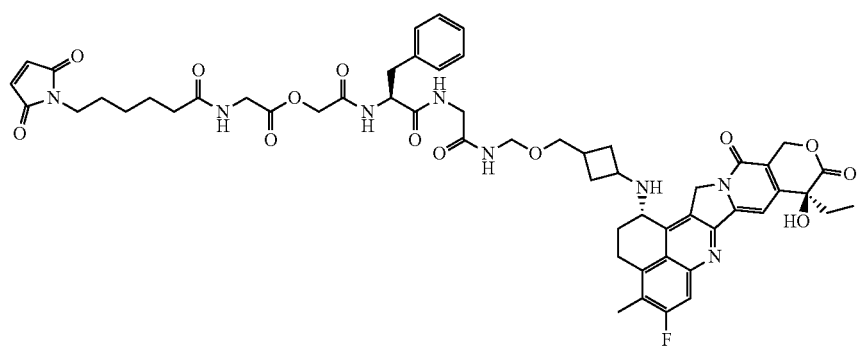 [SMILES: CC[C@@]1(O)C(=O)OCc2c1cc1n(c2=O)Cc2c-1nc1cc(F)c(C)c3c1c2[C@@H](NC1CC(COCNC(=O)CNC(=O)[C@H](Cc2ccccc2)NC(=O)COC(=O)CNC(=O)CCCCCN2C(=O)C=CC2=O)C1)CC3] |
| L-II-15 | 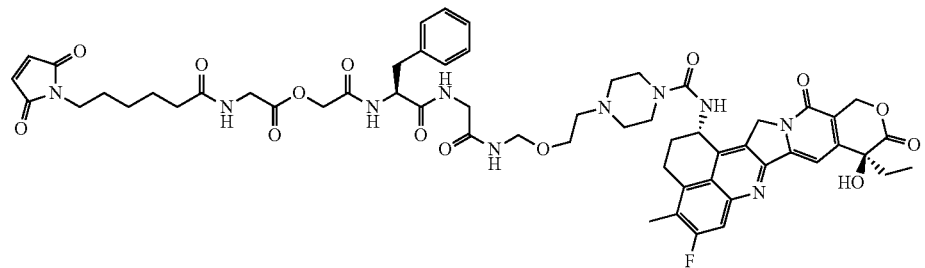 [SMILES: CC[C@@]1(O)C(=O)OCc2c1cc1n(c2=O)Cc2c-1nc1cc(F)c(C)c3c1c2[C@@H](NC(=O)N1CCN(CCOCNC(=O)CNC(=O)[C@H](Cc2ccccc2)NC(=O)COC(=O)CNC(=O)CCCCCN2C(=O)C=CC2=O)CC1)CC3] |
| L-II-16 | 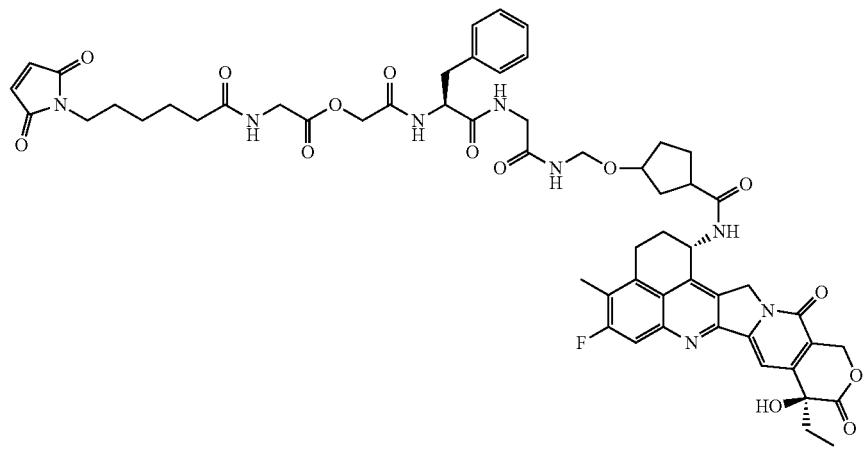 [SMILES: CC[C@@]1(O)C(=O)OCc2c1cc1n(c2=O)Cc2c-1nc1cc(F)c(C)c3c1c2[C@@H](NC(=O)C1CCC(OCNC(=O)CNC(=O)[C@H](Cc2ccccc2)NC(=O)COC(=O)CNC(=O)CCCCCN2C(=O)C=CC2=O)C1)CC3] |

| No. | Structure |
|---|---|
| L-II-17 | 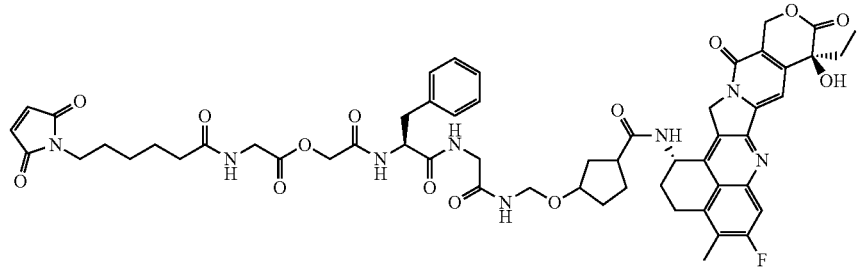 [SMILES: CC[C@@]1(O)C(=O)OCc2c1cc1n(c2=O)Cc2c-1nc1cc(F)c(C)c3c1c2[C@@H](NC(=O)C1CCC(OCNC(=O)CNC(=O)[C@H](Cc2ccccc2)NC(=O)COC(=O)CNC(=O)CCCCCN2C(=O)C=CC2=O)C1)CC3] |
| L-II-18 | 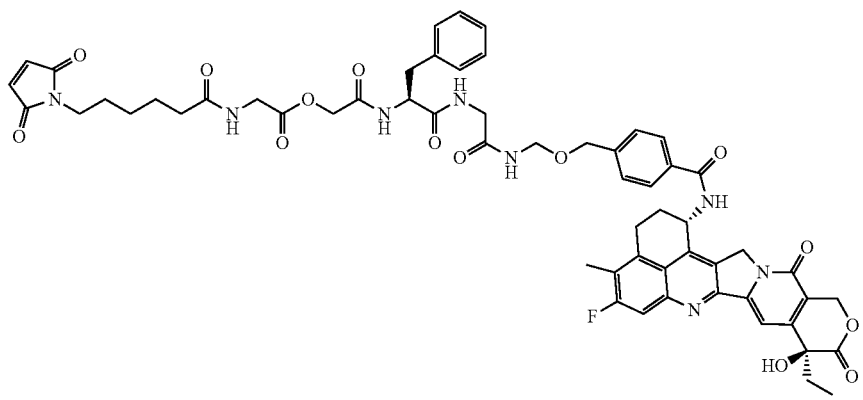 [SMILES: CC[C@@]1(O)C(=O)OCc2c1cc1n(c2=O)Cc2c-1nc1cc(F)c(C)c3c1c2[C@@H](NC(=O)c1ccc(COCNC(=O)CNC(=O)[C@H](Cc2ccccc2)NC(=O)COC(=O)CNC(=O)CCCCCN2C(=O)C=CC2=O)cc1)CC3] |
| L-II-19 | 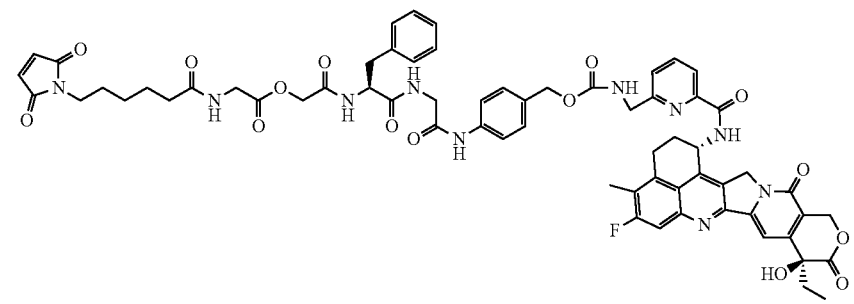 [SMILES: CC[C@@]1(O)C(=O)OCc2c1cc1n(c2=O)Cc2c-1nc1cc(F)c(C)c3c1c2[C@@H](NC(=O)c1cccc(CNC(=O)OCc2ccc(NC(=O)CNC(=O)[C@H](Cc4ccccc4)NC(=O)COC(=O)CNC(=O)CCCCCN4C(=O)C=CC4=O)cc2)n1)CC3] |
| L-II-20 | 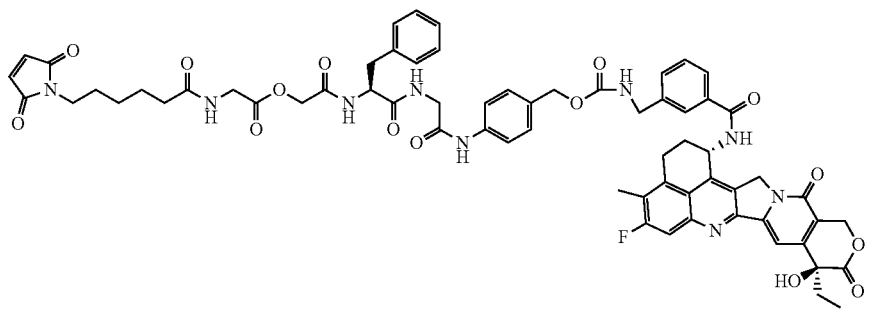 [SMILES: CC[C@@]1(O)C(=O)OCc2c1cc1n(c2=O)Cc2c-1nc1cc(F)c(C)c3c1c2[C@@H](NC(=O)c1cccc(CNC(=O)OCc2ccc(NC(=O)CNC(=O)[C@H](Cc4ccccc4)NC(=O)COC(=O)CNC(=O)CCCCCN4C(=O)C=CC4=O)cc2)c1)CC3] |

| No. | Structure |
|---|---|
| L-II-21 | 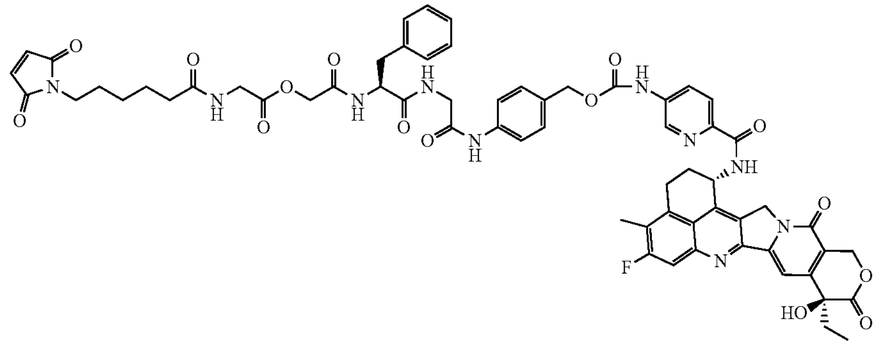 [SMILES: CC[C@@]1(O)C(=O)OCc2c1cc1n(c2=O)Cc2c-1nc1cc(F)c(C)c3c1c2[C@@H](NC(=O)c1ccc(NC(=O)OCc2ccc(NC(=O)CNC(=O)[C@H](Cc4ccccc4)NC(=O)COC(=O)CNC(=O)CCCCCN4C(=O)C=CC4=O)cc2)cn1)CC3] |
| L-II-22 | 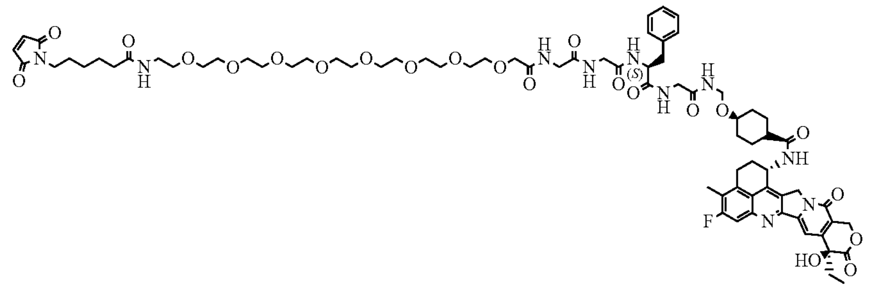 |
| L-II-23 | 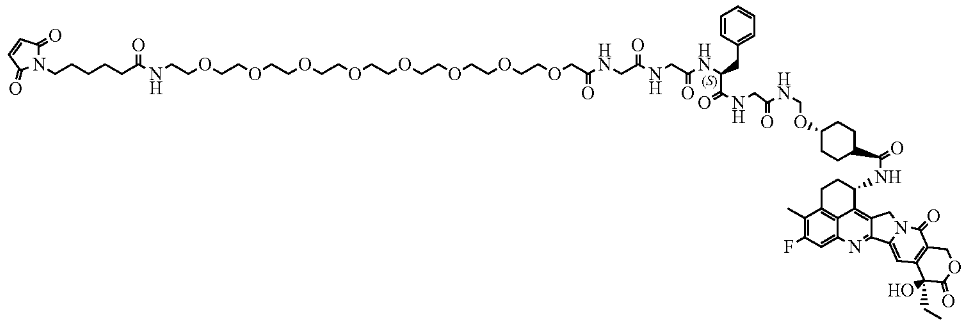 |
| L-II-24 | 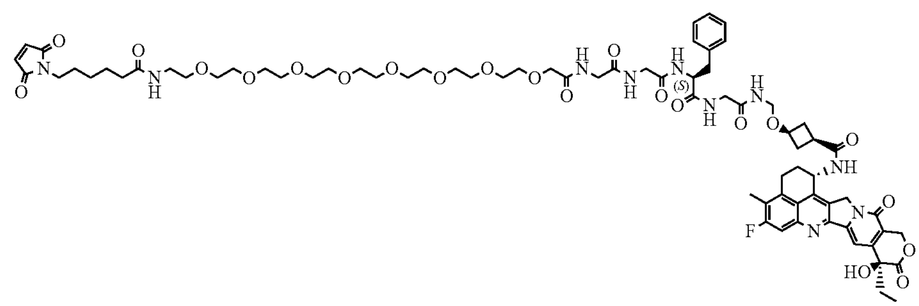 |
| L-II-25 | 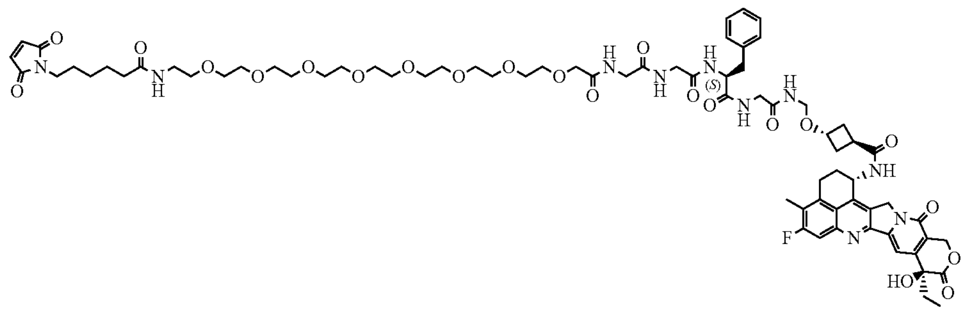 |

| No. | Structure |
|---|---|
| L-II-26 | 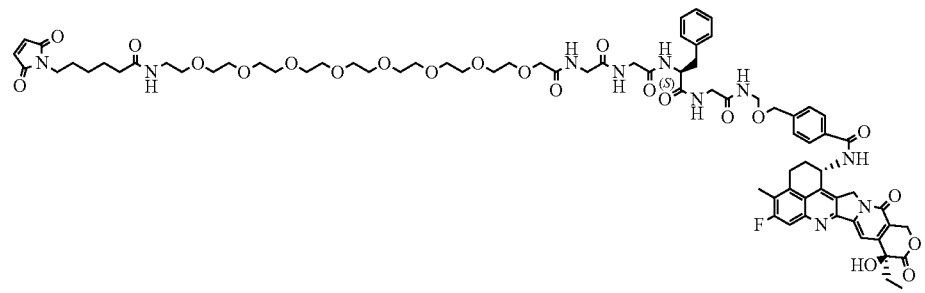 |
| L-II-27 | 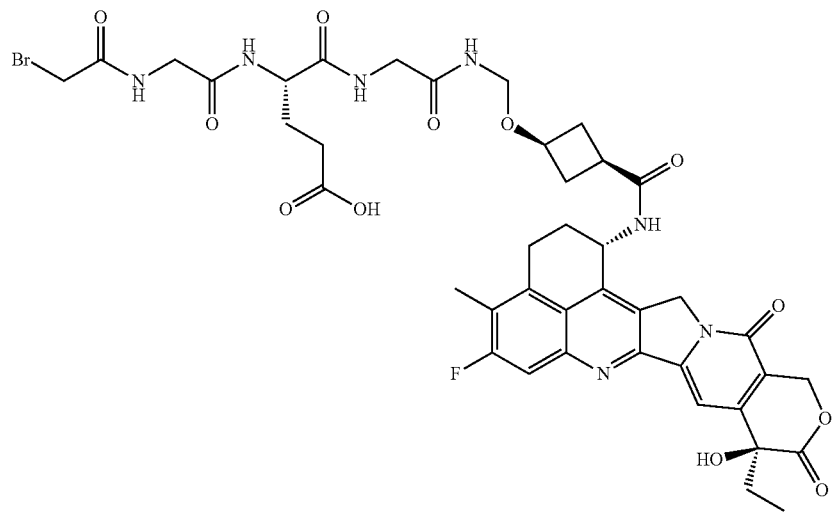 [SMILES: CC[C@@]1(O)C(=O)OCc2c1cc1n(c2=O)Cc2c-1nc1cc(F)c(C)c3c1c2[C@@H](NC(=O)[C@H]1C[C@@H](OCNC(=O)CNC(=O)[C@H](CCC(=O)O)NC(=O)CNC(=O)CBr)C1)CC3] |
| L-II-28 | 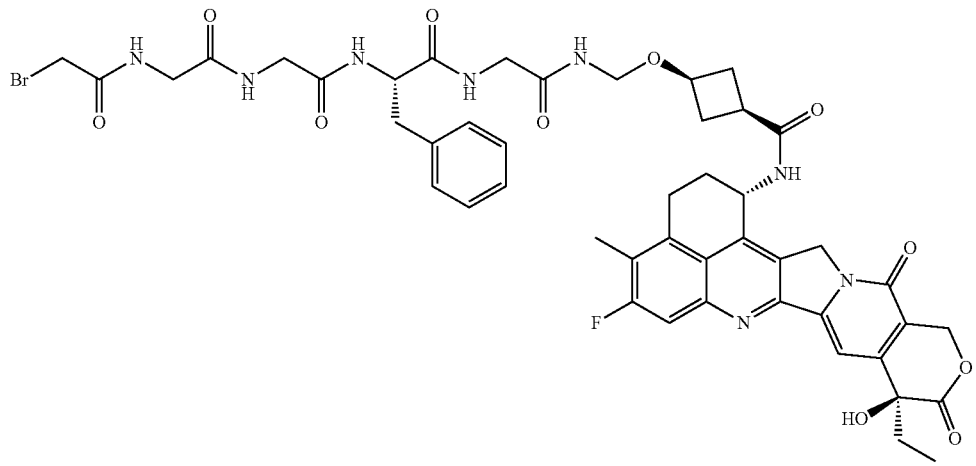 [SMILES: CC[C@@]1(O)C(=O)OCc2c1cc1n(c2=O)Cc2c-1nc1cc(F)c(C)c3c1c2[C@@H](NC(=O)[C@H]1C[C@@H](OCNC(=O)CNC(=O)[C@H](Cc2ccccc2)NC(=O)CNC(=O)CNC(=O)CBr)C1)CC3] |
| ADC-II-1 | 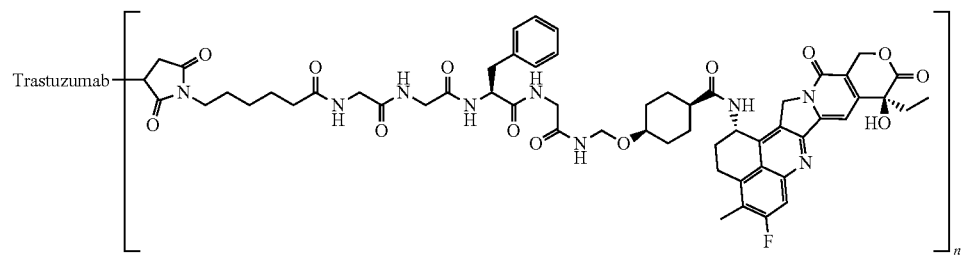 |

-continued
| No. | Structure |
|---|---|
| ADC-II-2 | 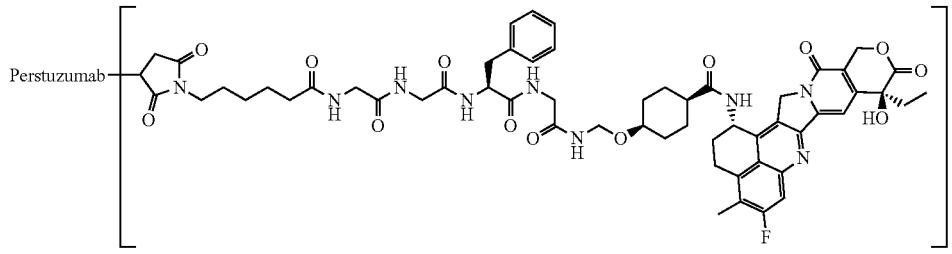 |
| ADC-II-3 | 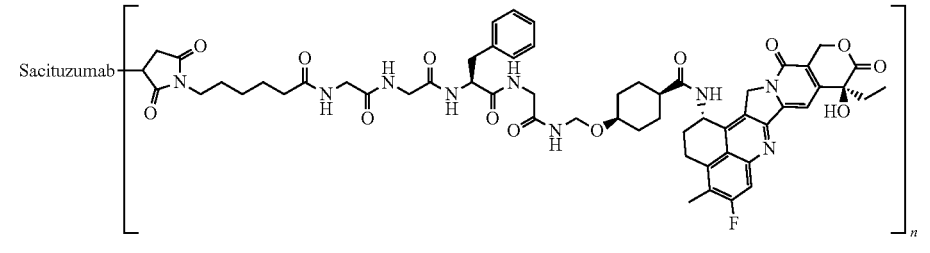 |
| ADC-II-4 | 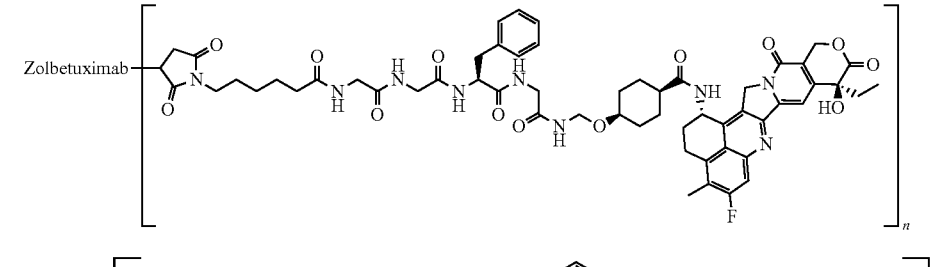 |
| ADC-II-5 | 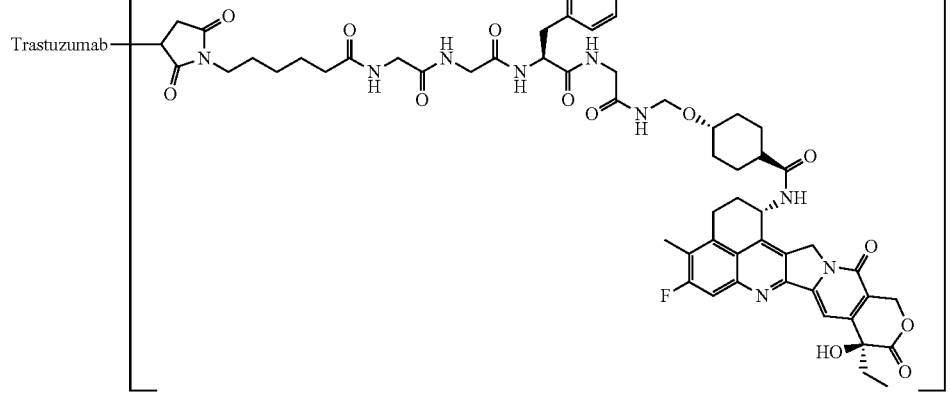 |
| ADC-II-6 | 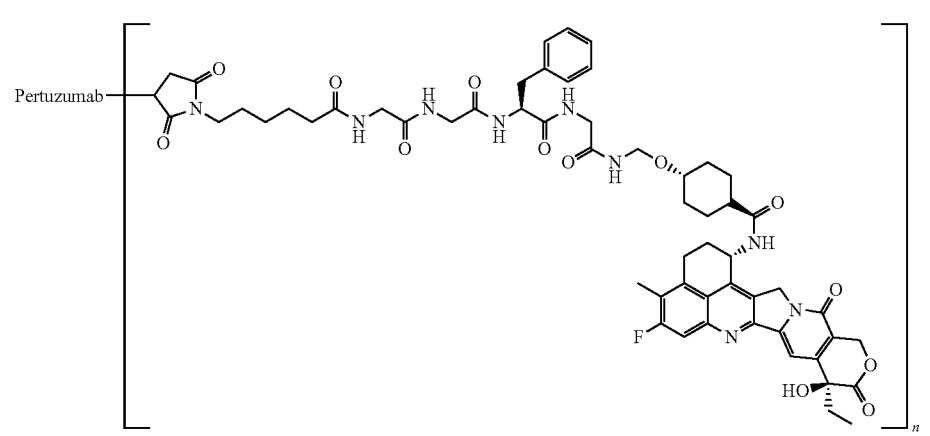 |

-continued
| No. | Structure |
|---|---|
| ADC-II-7 | 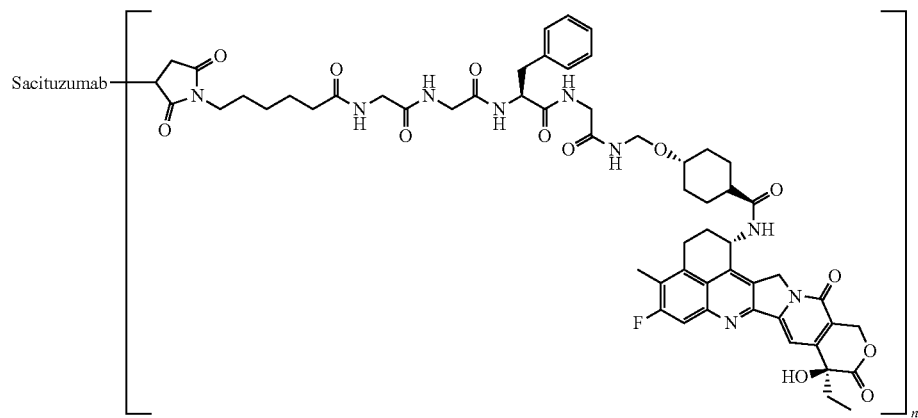 |
| ADC-II-8 | 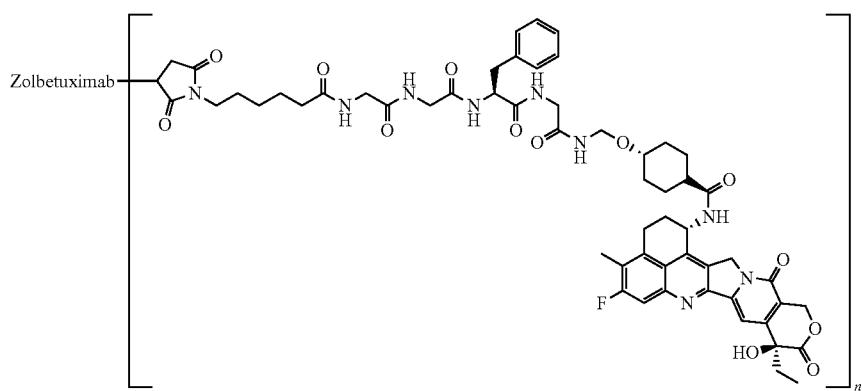 |
| ADC-II-9 | 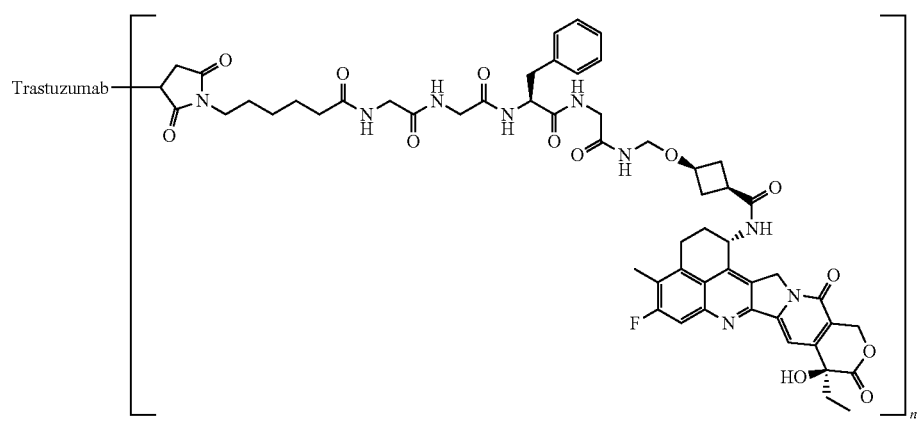 |

-continued
| No. | Structure |
|---|---|
| ADC-II-10 | 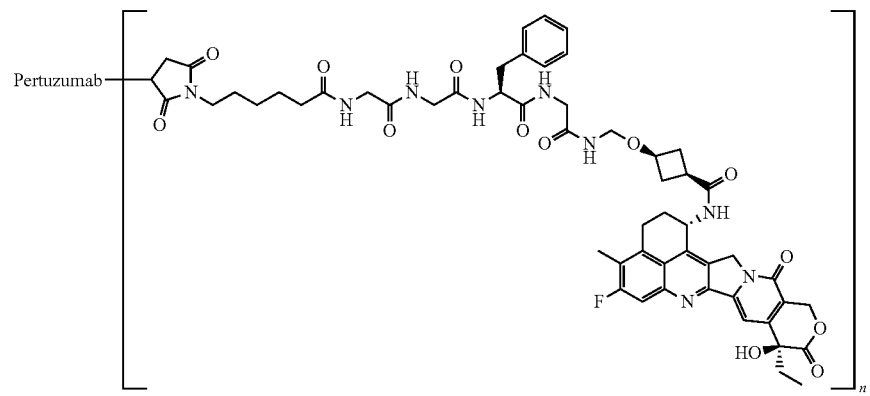 |
| ADC-II-11 | 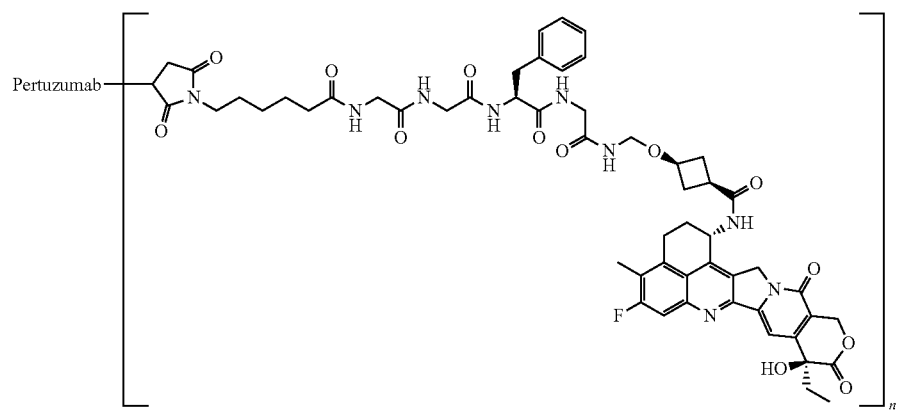 |
| ADC-II-12 | 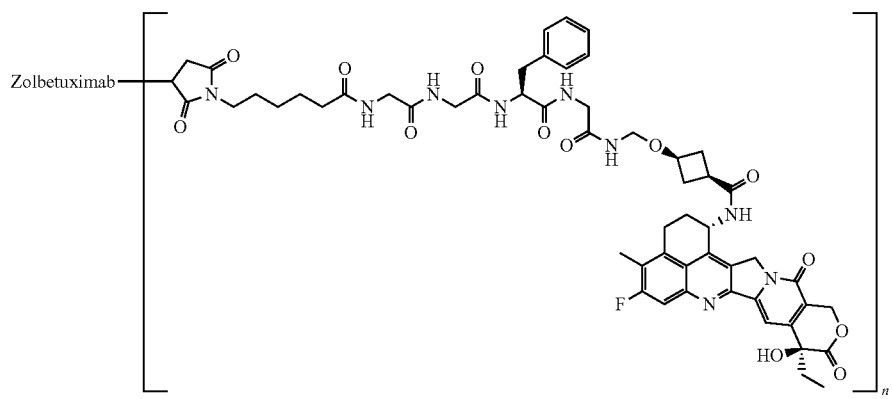 |

| No. | Structure |
|---|---|
| ADC-II-13 | 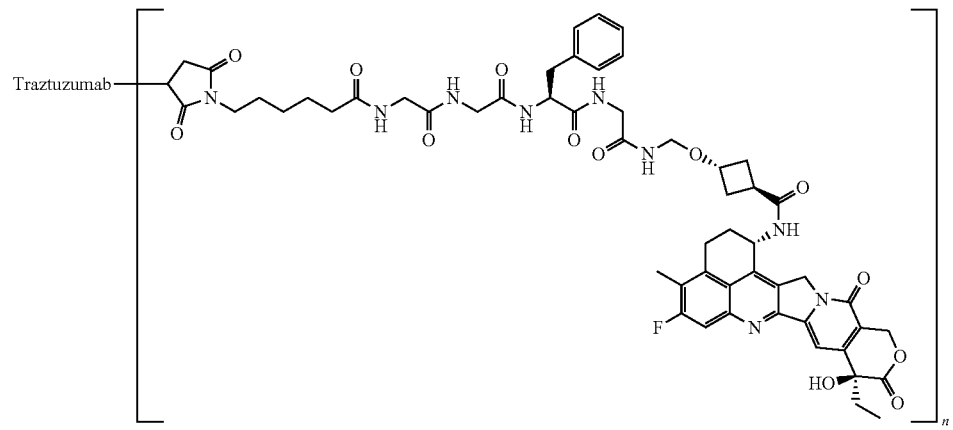 |
| ADC-II-14 | 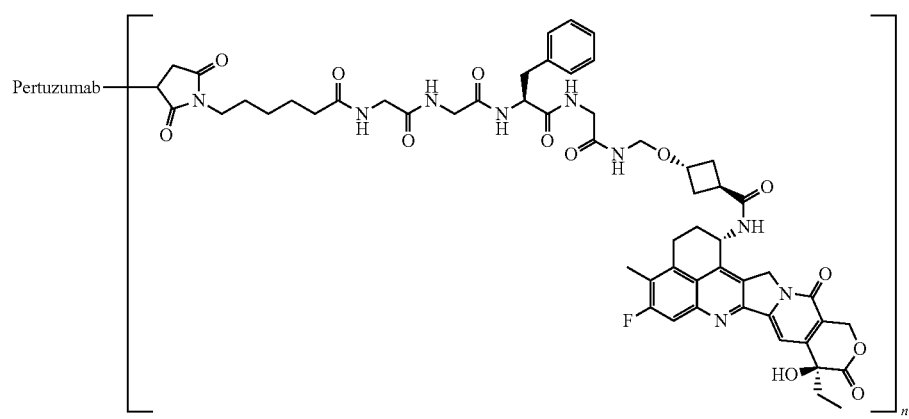 |
| ADC-II-15 | 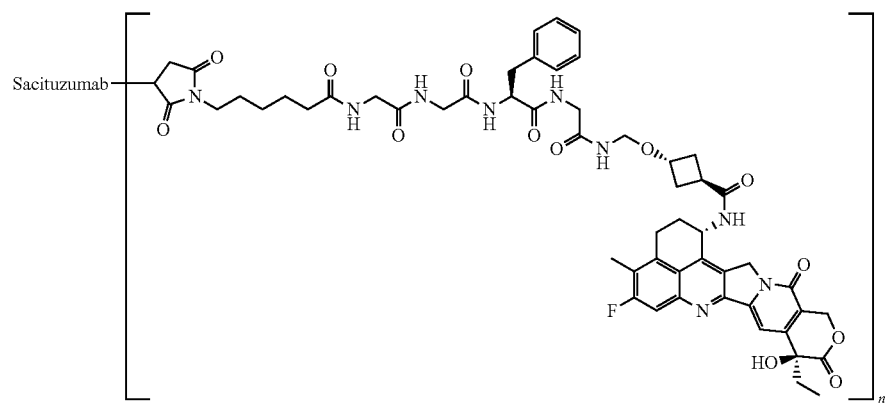 |

| No. | Structure |
|---|---|
| ADC-II-16 | 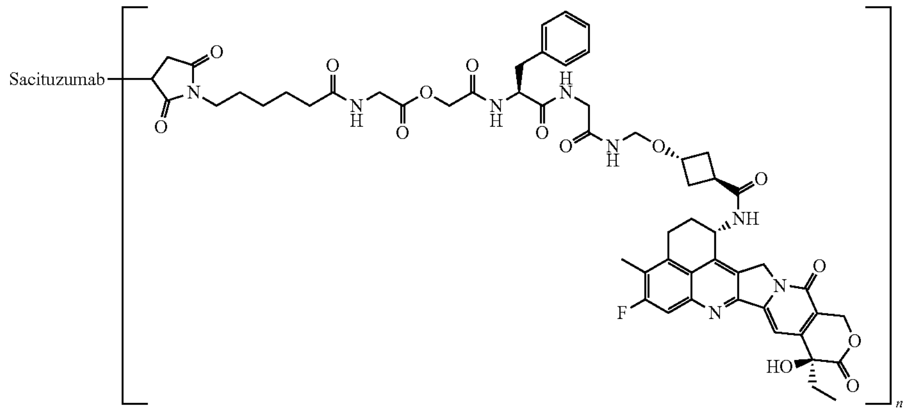 |
| ADC-II-17 | 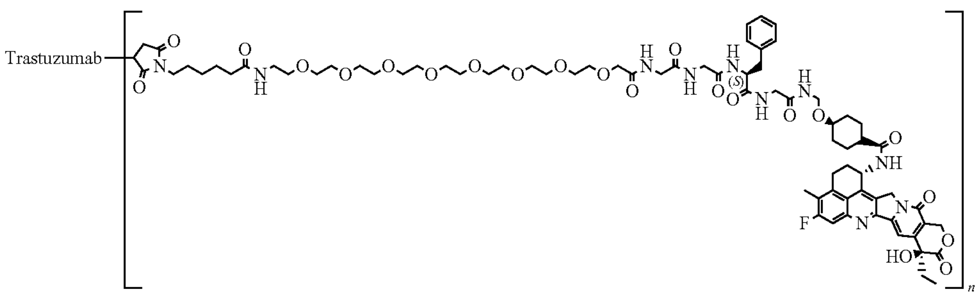 |
| ADC-II-18 | 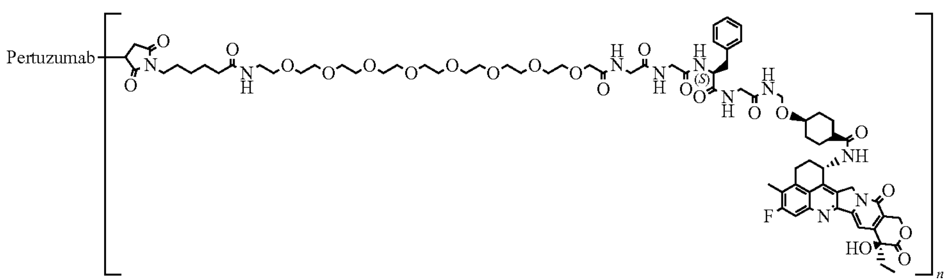 |
| ADC-II-19 | 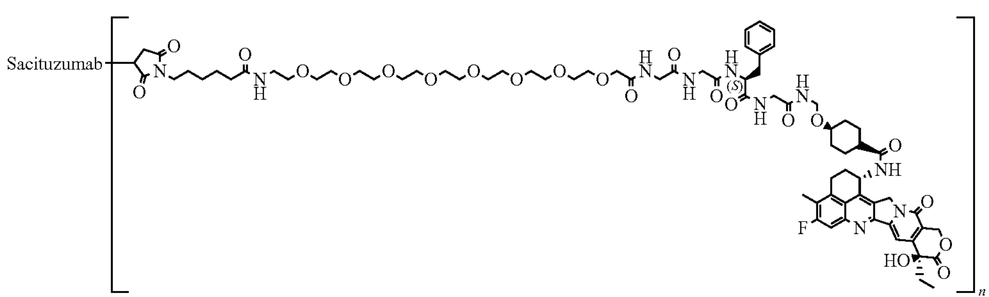 |
| ADC-II-20 | 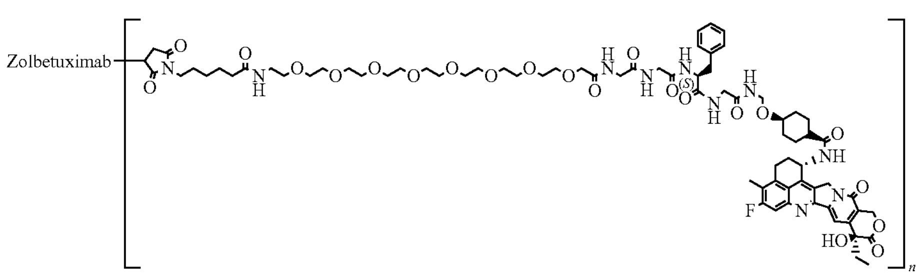 |

| No. | Structure |
|---|---|
| ADC-II-21 | 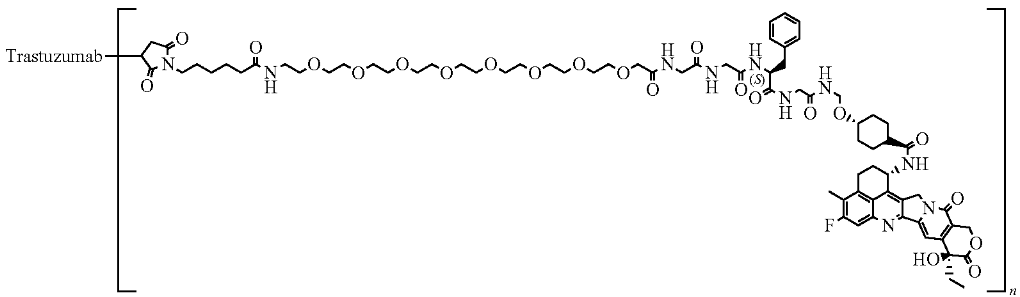 |
| ADC-II-22 | 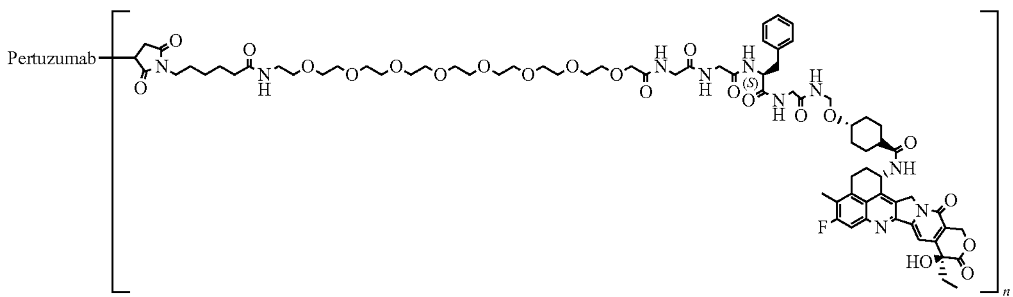 |
| ADC-II-23 | 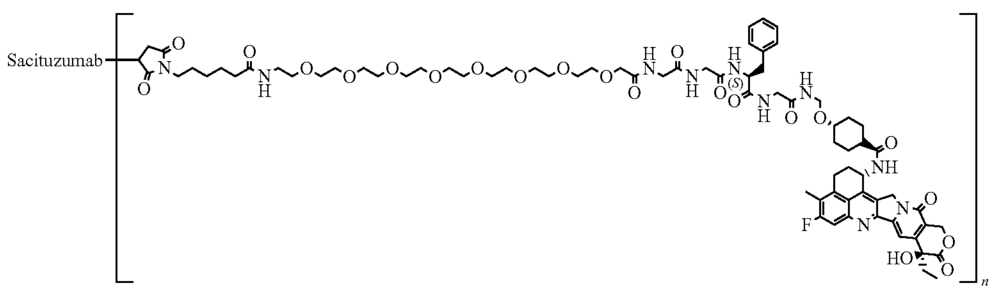 |
| ADC-II-24 | 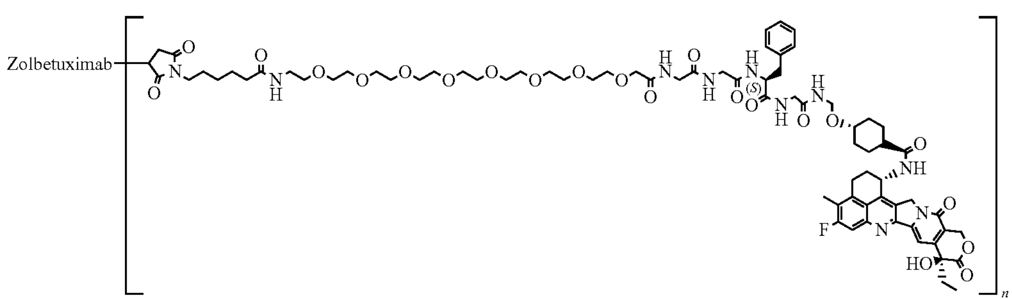 |
| ADC-II-25 | 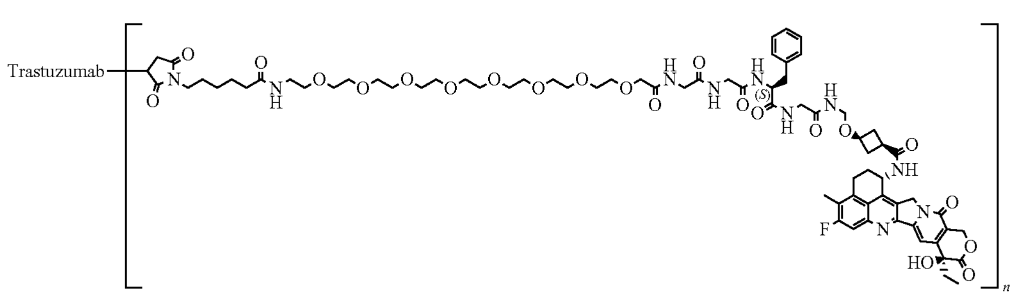 |

-continued

| No. | Structure |
|---|---|
| ADC-II-26 | Pertuzumab—[linker-payload]ₙ |
| ADC-II-27 | Sacituzumab—[linker-payload]ₙ |
| ADC-II-28 | Zolbetuximab—[linker-payload]ₙ |
| ADC-II-29 | Trastuzumab—[linker-payload]ₙ |
| ADC-II-30 | Pertuzumab—[linker-payload]ₙ |

| No. | Structure |
|---|---|
| ADC-II-31 | 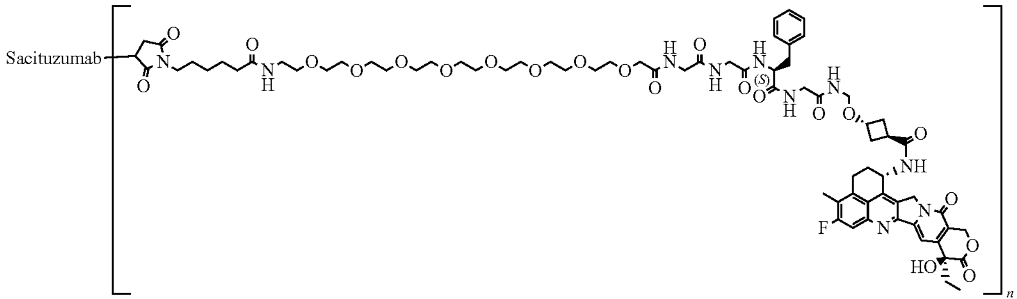 |
| ADC-II-32 | 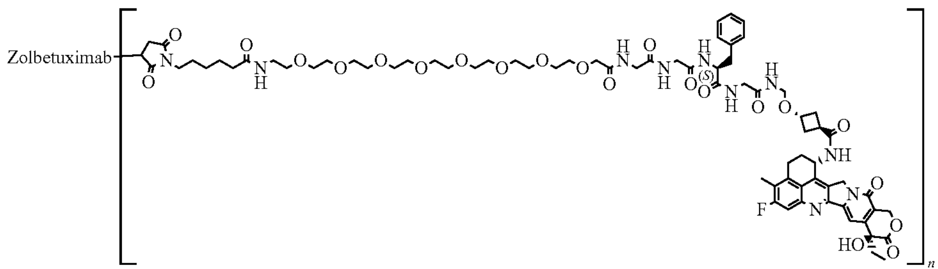 |
| ADC-II-33 | 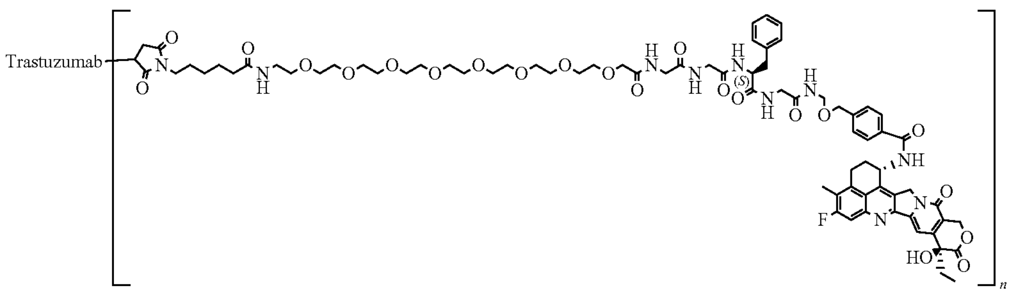 |
| ADC-II-34 | 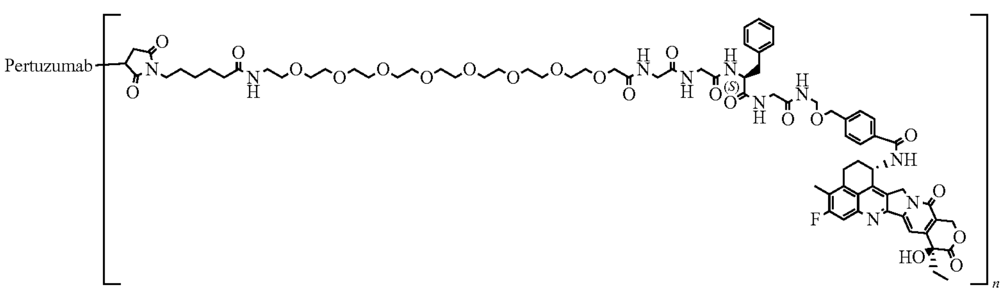 |
| ADC-II-35 | 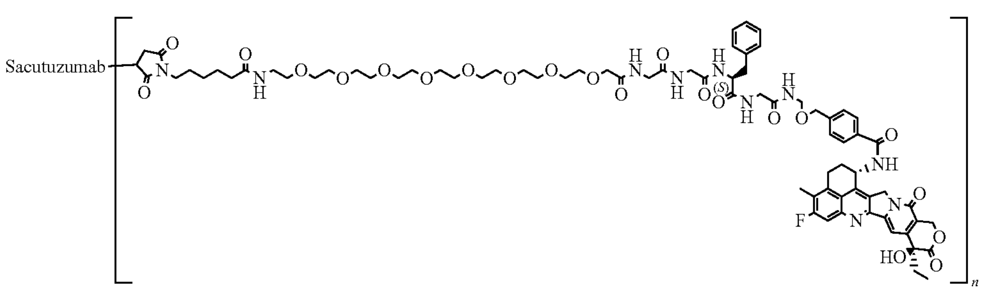 |

| No. | Structure |
|---|---|
| ADC-II-36 | 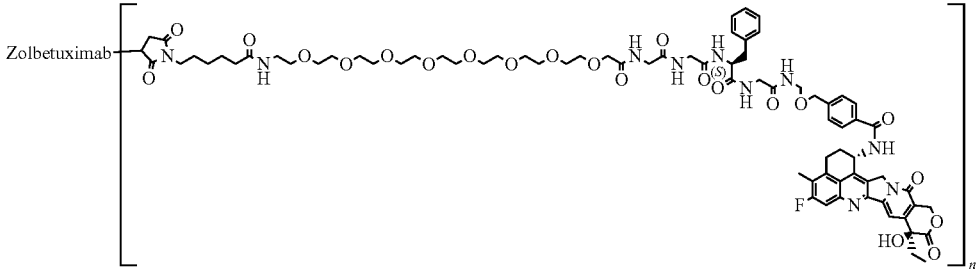 |
| ADC-II-37 | 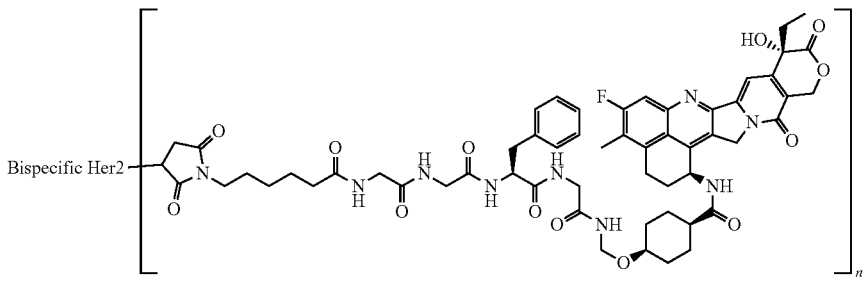 |
| ADC-II-38 | 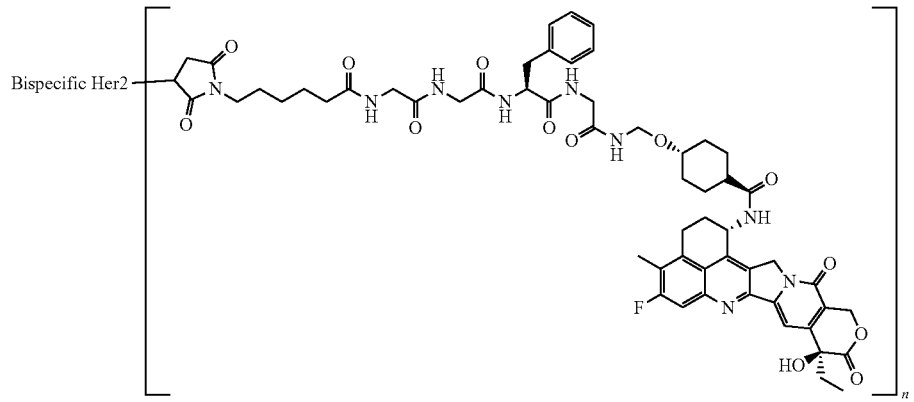 |
| ADC-II-39 | 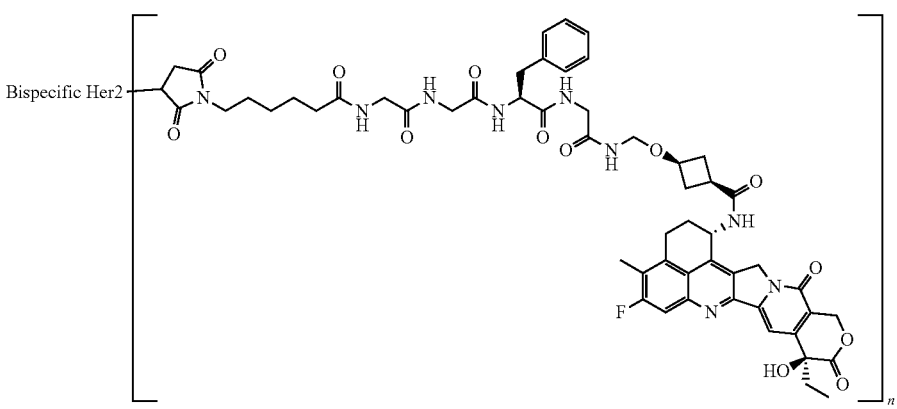 |

| No. | Structure |
|---|---|
| ADC-II-40 | 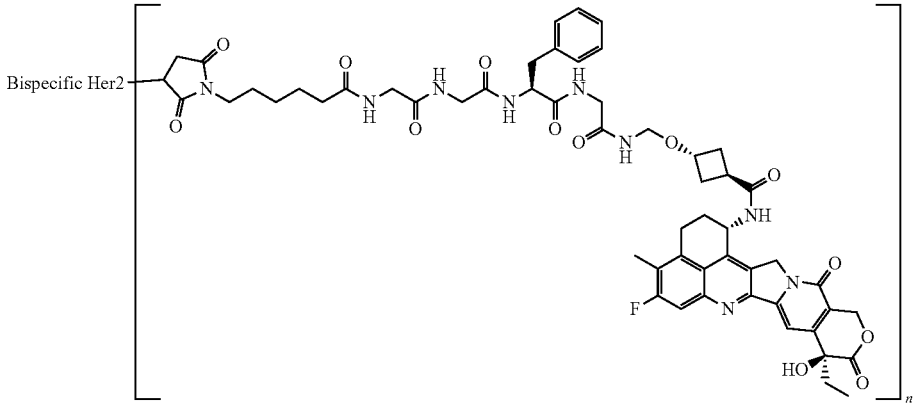 |
| ADC-II-41 | 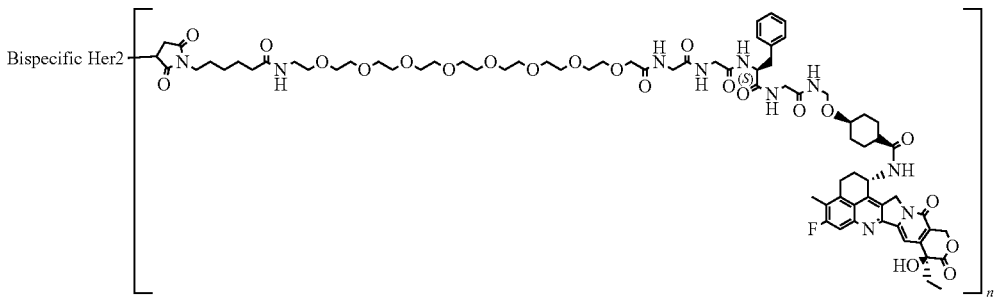 |
| ADC-II-42 | 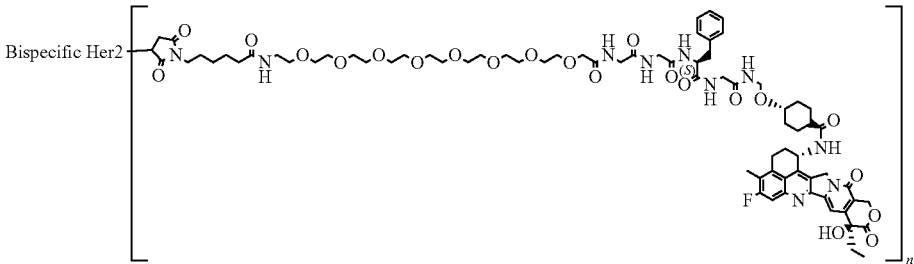 |
| ADC-II-43 | 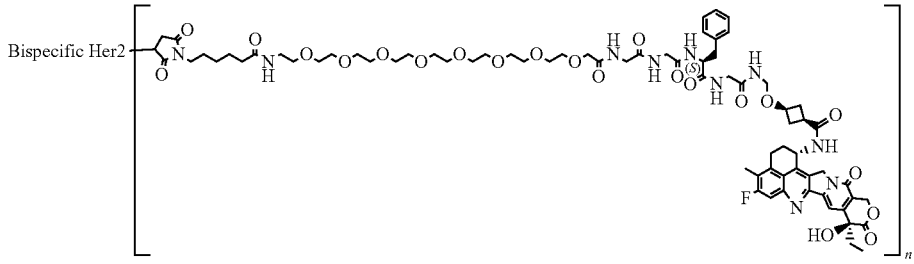 |
| ADC-II-44 | 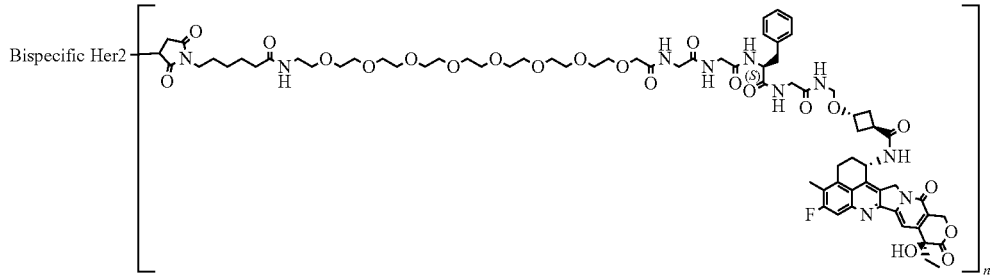 |

| No. | Structure |
|---|---|
| ADC-II-45 | 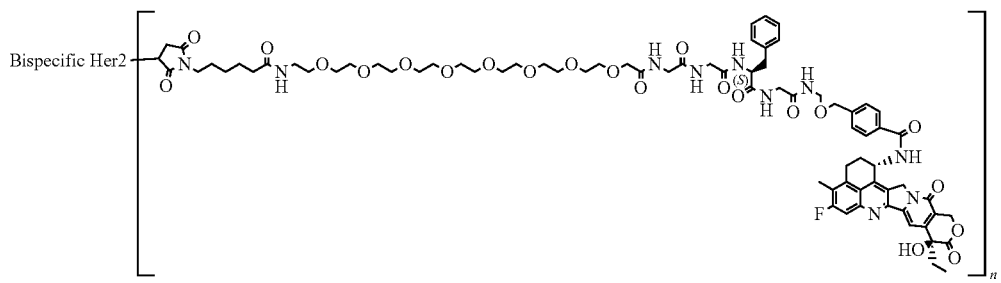 |
| ADC-II-46 | 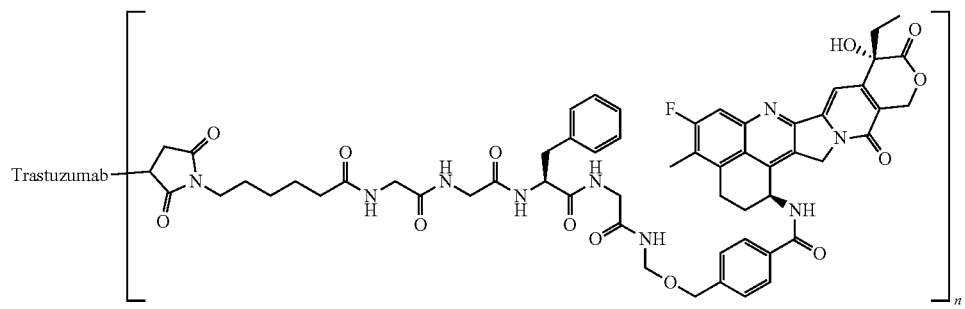 |
| ADC-II-47 | 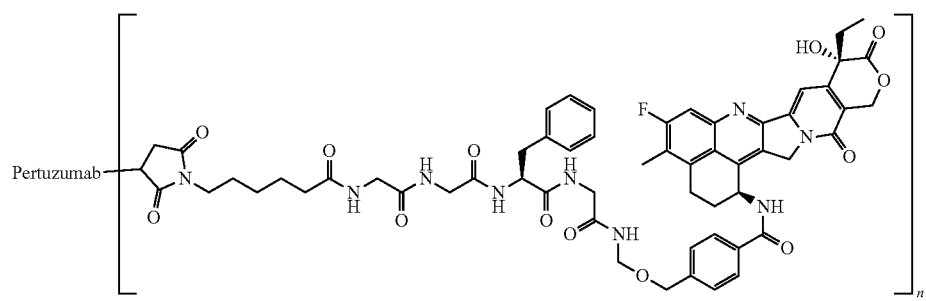 |
| ADC-II-48 | 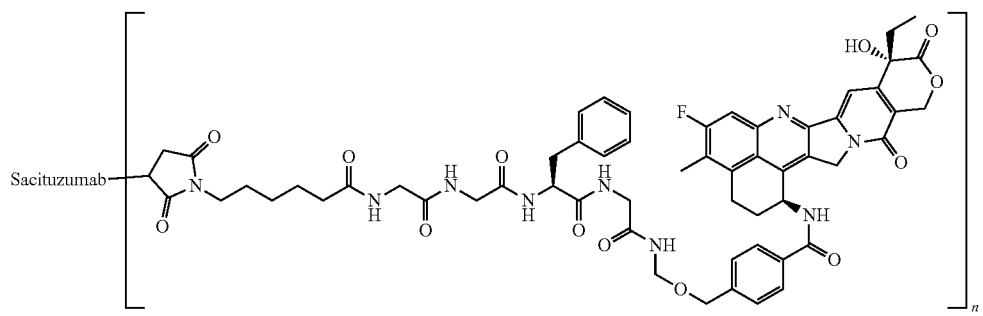 |
| ADC-II-49 | 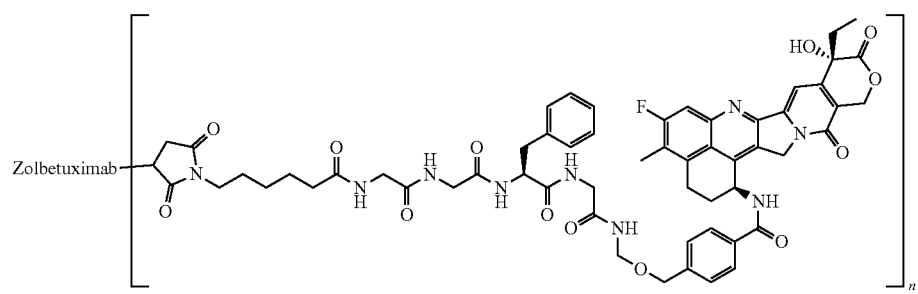 |

| No. | Structure |
|---|---|
| ADC-II-50 | 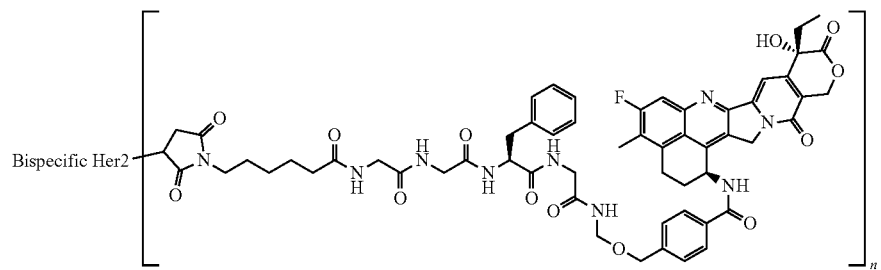 |
| ADC-II-51 | 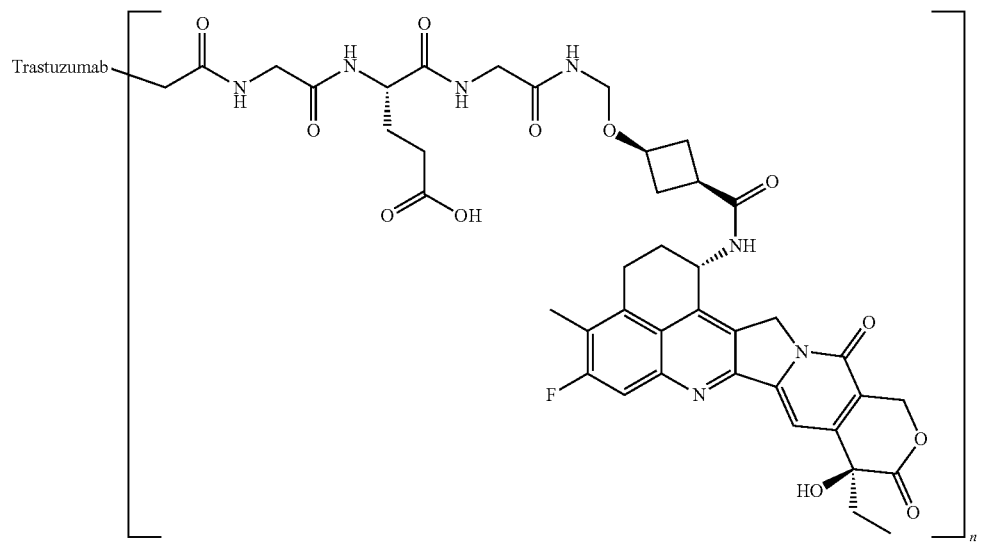 |
| ADC-II-52 | 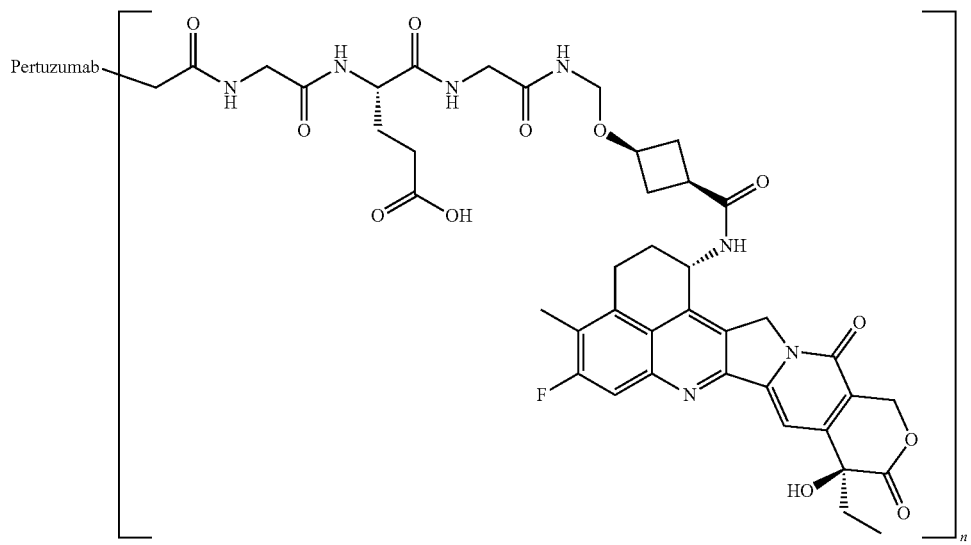 |

| No. | Structure |
|---|---|
| ADC-II-53 | 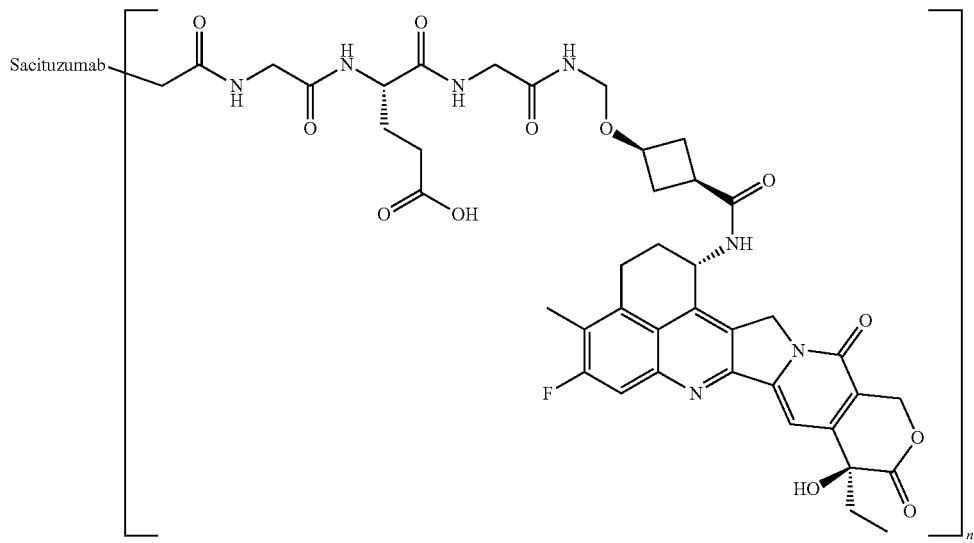 |
| ADC-II-54 | 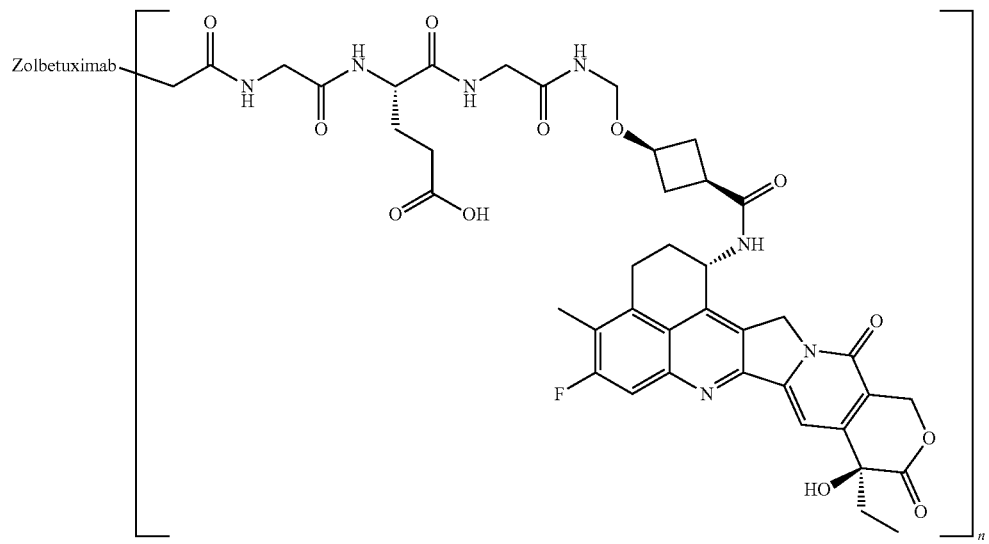 |
| ADC-II-55 | 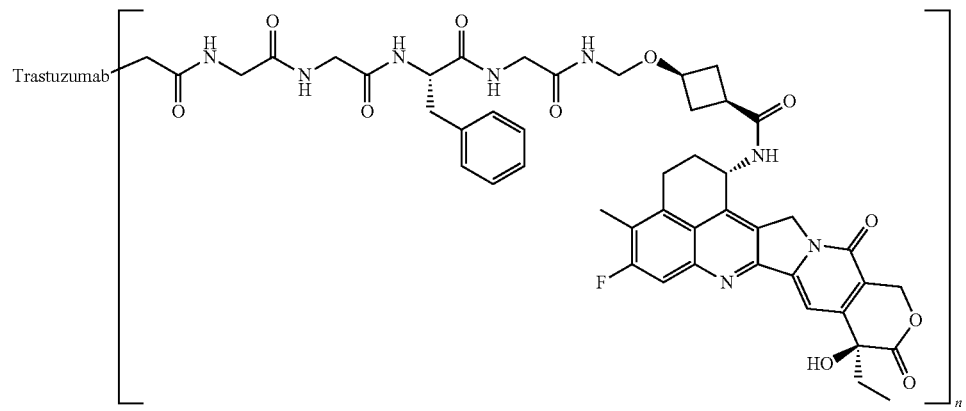 |

| No. | Structure |
|---|---|
| ADC-II-56 | Pertuzumab-[linker-payload structure with fluorinated camptothecin analog]$_n$ |
| ADC-II-57 | Sacituzumab-[linker-payload structure with fluorinated camptothecin analog]$_n$ |
| ADC-II-58 | Zolbetuximab-[linker-payload structure with fluorinated camptothecin analog]$_n$ |

The average connection number n in the above list may be an integer or a decimal from 1 to 10. The average connection number n in the above list may be an integer or a decimal from 2 to 8. For example, the average connection number n may be an integer or a decimal from 3 to 8. For example, the average connection number n may be an integer or a decimal from 1 to 2, 2 to 3, 3 to 4, 4 to 5, 5 to 6, 6 to 7, 7 to 8, 8 to 9, or 9 to 10.

In one embodiment, the compounds disclosed herein include, but are not limited to:

| No. | Structure |
|---|---|
| P-III-1 | 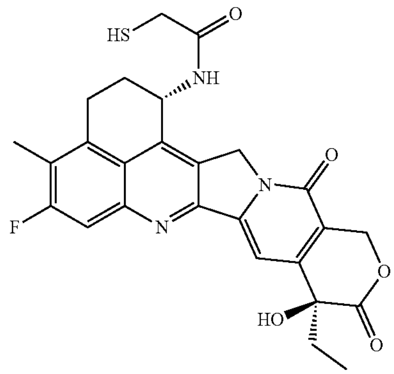 [SMILES: CC[C@@]1(O)C(=O)OCc2c1cc1n(c2=O)Cc2c-1nc1cc(F)c(C)c3c1c2[C@@H](NC(=O)CS)CC3] |
| P-III-2 | 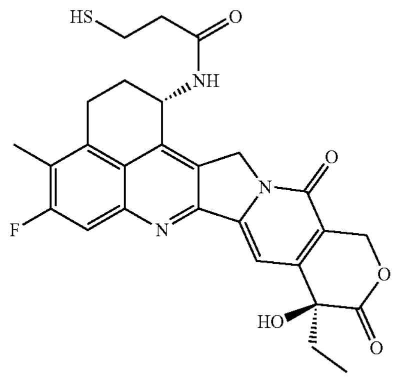 [SMILES: CC[C@@]1(O)C(=O)OCc2c1cc1n(c2=O)Cc2c-1nc1cc(F)c(C)c3c1c2[C@@H](NC(=O)CCS)CC3] |
| P-III-3 | 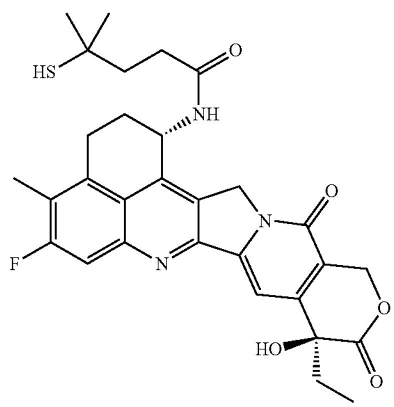 [SMILES: CC[C@@]1(O)C(=O)OCc2c1cc1n(c2=O)Cc2c-1nc1cc(F)c(C)c3c1c2[C@@H](NC(=O)CCC(C)(C)S)CC3] |
| P-III-4 | 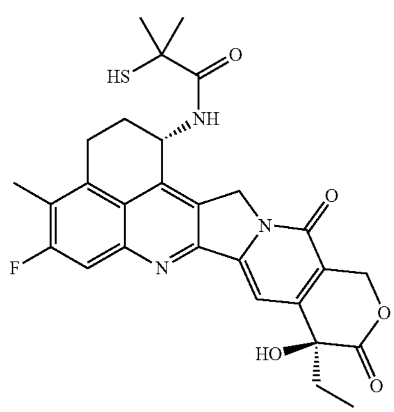 [SMILES: CC[C@@]1(O)C(=O)OCc2c1cc1n(c2=O)Cc2c-1nc1cc(F)c(C)c3c1c2[C@@H](NC(=O)C(C)(C)S)CC3] |

| No. | Structure |
|---|---|
| P-III-5 | 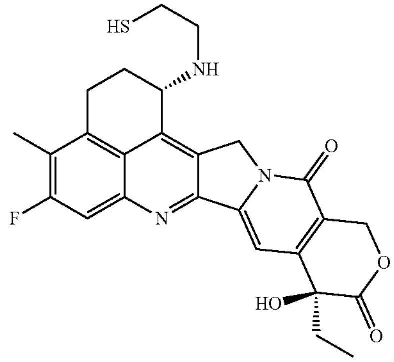 [SMILES: CC[C@@]1(O)C(=O)OCc2c1cc1n(c2=O)Cc2c-1nc1cc(F)c(C)c3c1c2[C@@H](NCCS)CC3] |
| P-III-6 | 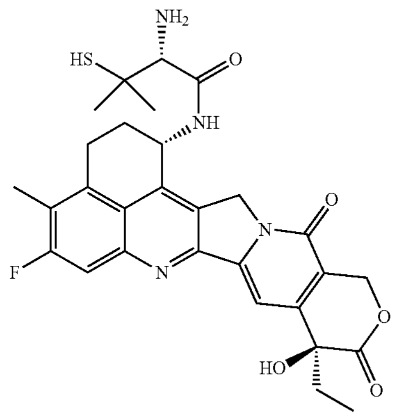 [SMILES: CC[C@@]1(O)C(=O)OCc2c1cc1n(c2=O)Cc2c-1nc1cc(F)c(C)c3c1c2[C@@H](NC(=O)[C@@H](N)C(C)(C)S)CC3] |
| P-III-7 | 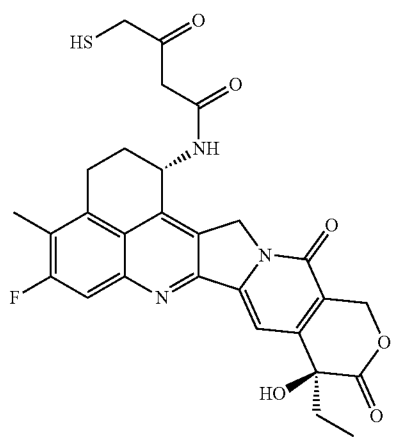 [SMILES: CC[C@@]1(O)C(=O)OCc2c1cc1n(c2=O)Cc2c-1nc1cc(F)c(C)c3c1c2[C@@H](NC(=O)CC(=O)CS)CC3] |
| P-III-8 | 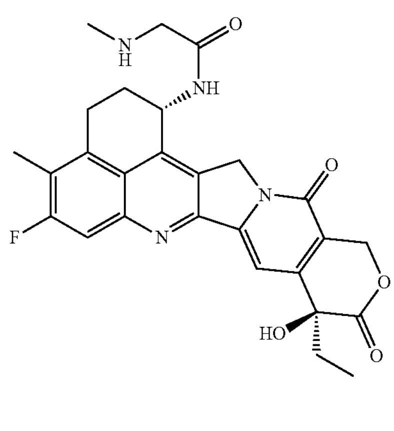 [SMILES: CC[C@@]1(O)C(=O)OCc2c1cc1n(c2=O)Cc2c-1nc1cc(F)c(C)c3c1c2[C@@H](NC(=O)CNC)CC3] |

| No. | Structure |
|---|---|
| P-III-9 | 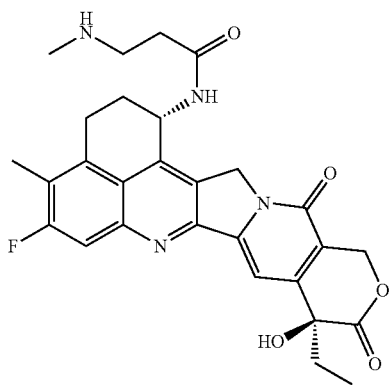 [SMILES: CC[C@@]1(O)C(=O)OCc2c1cc1n(c2=O)Cc2c-1nc1cc(F)c(C)c3c1c2[C@@H](NC(=O)CCNC)CC3] |
| P-III-10 | 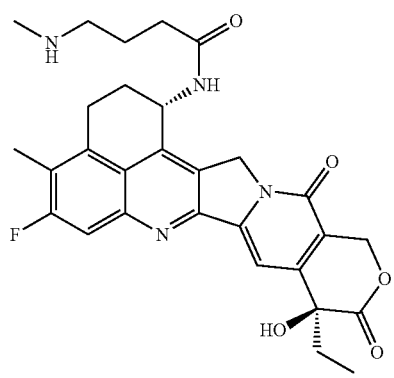 [SMILES: CC[C@@]1(O)C(=O)OCc2c1cc1n(c2=O)Cc2c-1nc1cc(F)c(C)c3c1c2[C@@H](NC(=O)CCCNC)CC3] |
| P-III-11 | 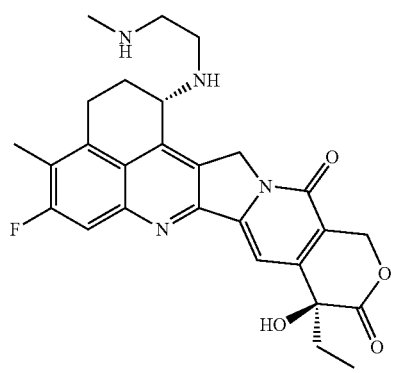 [SMILES: CC[C@@]1(O)C(=O)OCc2c1cc1n(c2=O)Cc2c-1nc1cc(F)c(C)c3c1c2[C@@H](NCCNC)CC3] |
| P-III-12 | 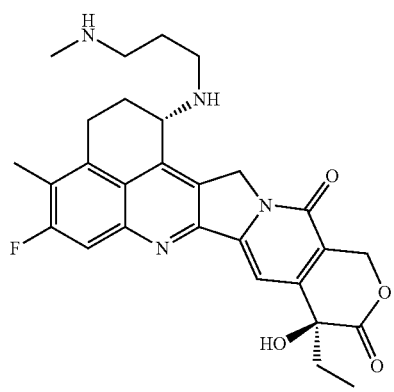 [SMILES: CC[C@@]1(O)C(=O)OCc2c1cc1n(c2=O)Cc2c-1nc1cc(F)c(C)c3c1c2[C@@H](NCCCNC)CC3] |

-continued
| No. | Structure |
|---|---|
| P-III-13 | 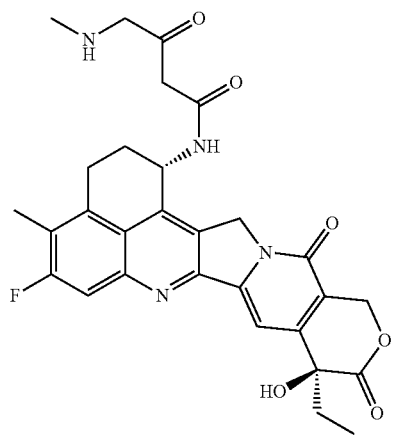 [SMILES: CC[C@@]1(O)C(=O)OCc2c1cc1n(c2=O)Cc2c-1nc1cc(F)c(C)c3c1c2[C@@H](NC(=O)CC(=O)CNC)CC3] |
| P-III-14 | 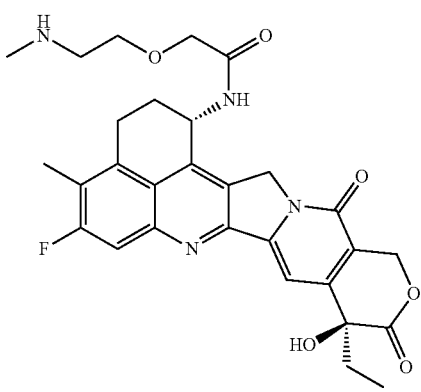 [SMILES: CC[C@@]1(O)C(=O)OCc2c1cc1n(c2=O)Cc2c-1nc1cc(F)c(C)c3c1c2[C@@H](NC(=O)COCCNC)CC3] |
| P-III-15 | 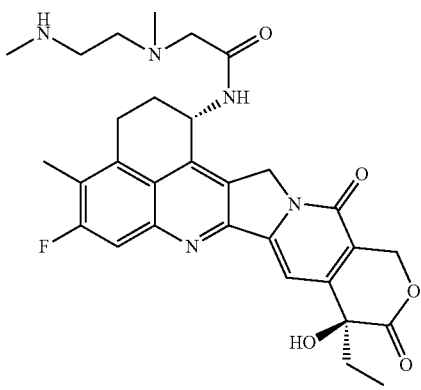 [SMILES: CC[C@@]1(O)C(=O)OCc2c1cc1n(c2=O)Cc2c-1nc1cc(F)c(C)c3c1c2[C@@H](NC(=O)CN(C)CCNC)CC3] |
| P-III-16 | 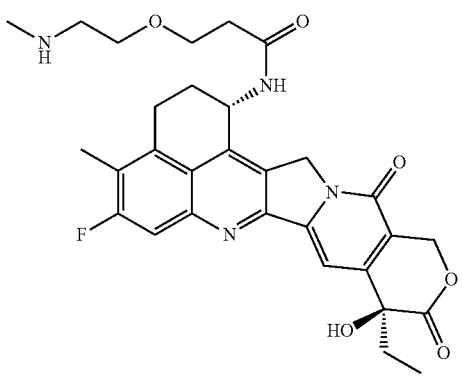 [SMILES: CC[C@@]1(O)C(=O)OCc2c1cc1n(c2=O)Cc2c-1nc1cc(F)c(C)c3c1c2[C@@H](NC(=O)CCOCCNC)CC3] |

| No. | Structure |
|---|---|
| P-III-17 | 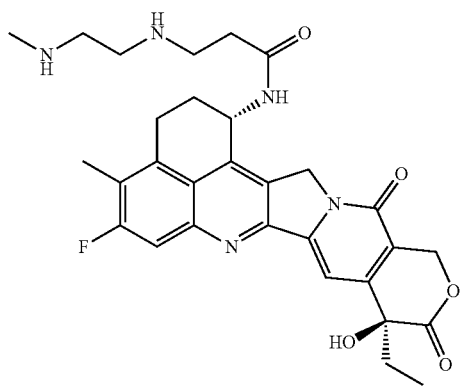 [SMILES: CC[C@@]1(O)C(=O)OCc2c1cc1n(c2=O)Cc2c-1nc1cc(F)c(C)c3c1c2[C@@H](NC(=O)CCNCCNC)CC3] |
| P-III-18 | 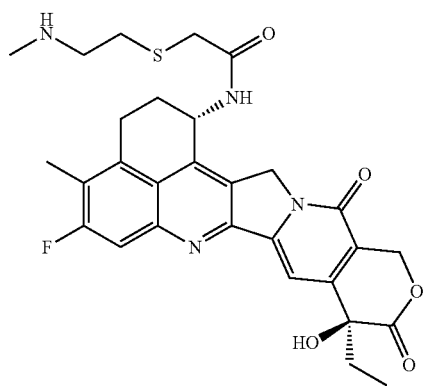 [SMILES: CC[C@@]1(O)C(=O)OCc2c1cc1n(c2=O)Cc2c-1nc1cc(F)c(C)c3c1c2[C@@H](NC(=O)CSCCNC)CC3] |
| P-III-19 | 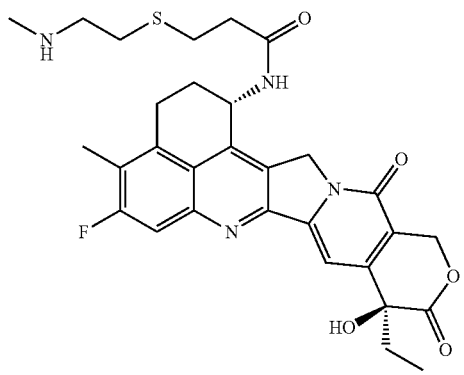 [SMILES: CC[C@@]1(O)C(=O)OCc2c1cc1n(c2=O)Cc2c-1nc1cc(F)c(C)c3c1c2[C@@H](NC(=O)CCSCCNC)CC3] |
| P-III-20 | 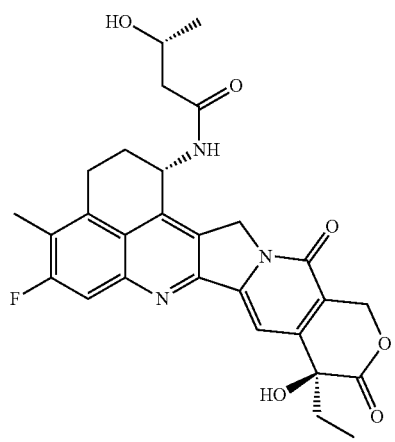 [SMILES: CC[C@@]1(O)C(=O)OCc2c1cc1n(c2=O)Cc2c-1nc1cc(F)c(C)c3c1c2[C@@H](NC(=O)C[C@@H](C)O)CC3] |

| No. | Structure |
|---|---|
| P-III-21 | 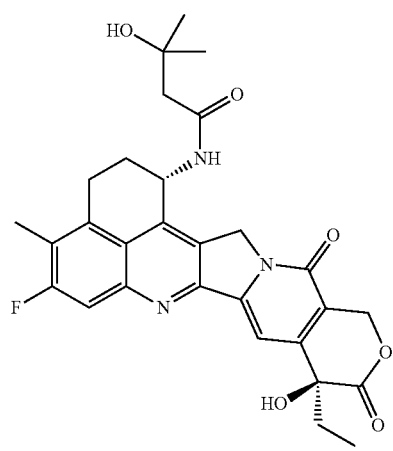 [SMILES: CC[C@@]1(O)C(=O)OCc2c1cc1n(c2=O)Cc2c-1nc1cc(F)c(C)c3c1c2[C@@H](NC(=O)CC(C)(C)O)CC3] |
| P-III-22 | 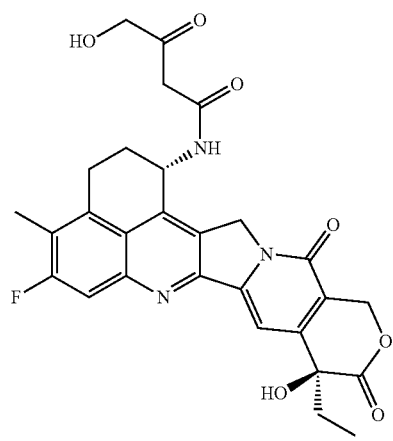 |
| P-III-23 | 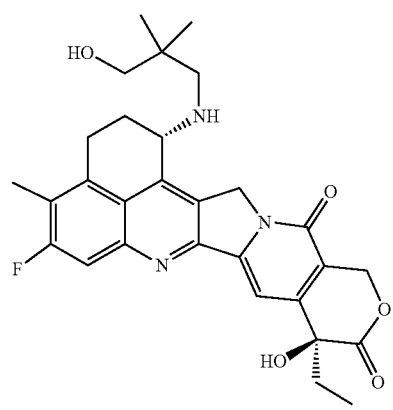 [SMILES: CC[C@@]1(O)C(=O)OCc2c1cc1n(c2=O)Cc2c-1nc1cc(F)c(C)c3c1c2[C@@H](NCC(C)(C)CO)CC3] |

| No. | Structure |
|---|---|
| P-III-24 | 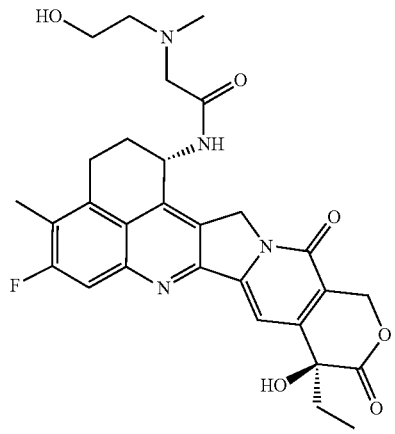 [SMILES: CC[C@@]1(O)C(=O)OCc2c1cc1n(c2=O)Cc2c-1nc1cc(F)c(C)c3c1c2[C@@H](NC(=O)CN(C)CCO)CC3] |
| P-III-25 | 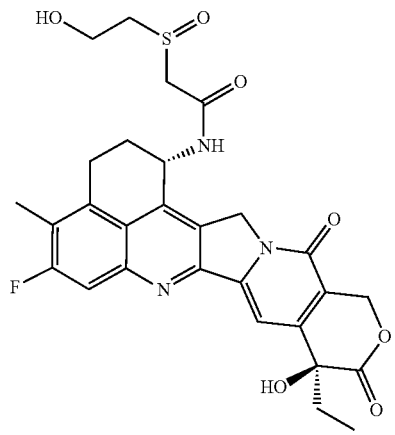 [SMILES: CC[C@@]1(O)C(=O)OCc2c1cc1n(c2=O)Cc2c-1nc1cc(F)c(C)c3c1c2[C@@H](NC(=O)CS(=O)CCO)CC3] |
| P-III-26 | 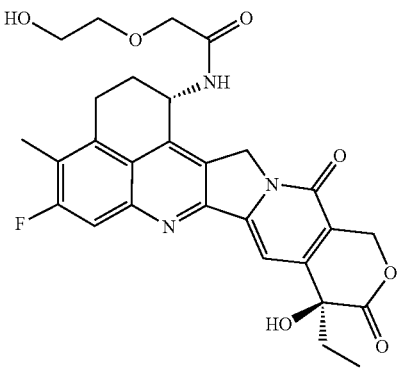 [SMILES: CC[C@@]1(O)C(=O)OCc2c1cc1n(c2=O)Cc2c-1nc1cc(F)c(C)c3c1c2[C@@H](NC(=O)COCCO)CC3] |

| No. | Structure |
|---|---|
| P-III-27 | 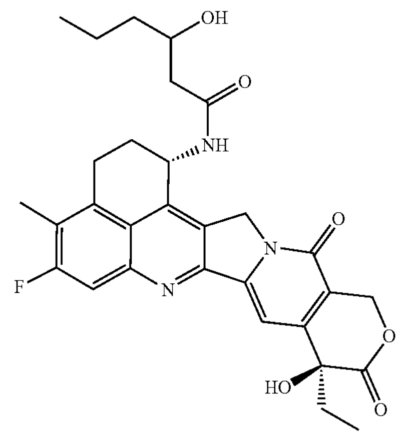 [SMILES: CCCC(O)CC(=O)N[C@H]1CCc2c(C)c(F)cc3nc4c(c1c23)Cn1c-4cc2c(c1=O)COC(=O)[C@]2(O)CC] |
| P-III-28 | 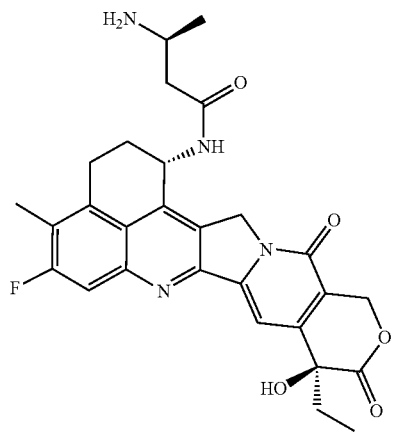 [SMILES: CC[C@@]1(O)C(=O)OCc2c1cc1n(c2=O)Cc2c-1nc1cc(F)c(C)c3c1c2[C@@H](NC(=O)C[C@H](C)N)CC3] |
| P-III-29 | 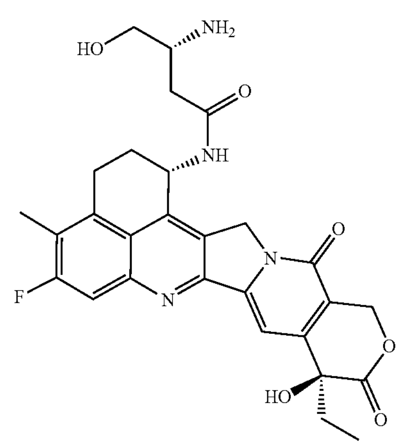 [SMILES: CC[C@@]1(O)C(=O)OCc2c1cc1n(c2=O)Cc2c-1nc1cc(F)c(C)c3c1c2[C@@H](NC(=O)C[C@@H](N)CO)CC3] |

-continued
| No. | Structure |
|---|---|
| P-III-30 | 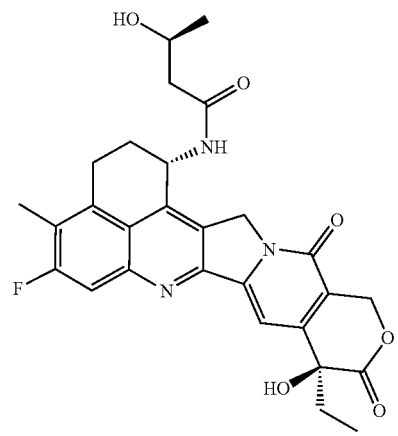 [SMILES: CC[C@@]1(O)C(=O)OCc2c1cc1n(c2=O)Cc2c-1nc1cc(F)c(C)c3c1c2[C@@H](NC(=O)C[C@H](C)O)CC3] |
| P-III-31 | 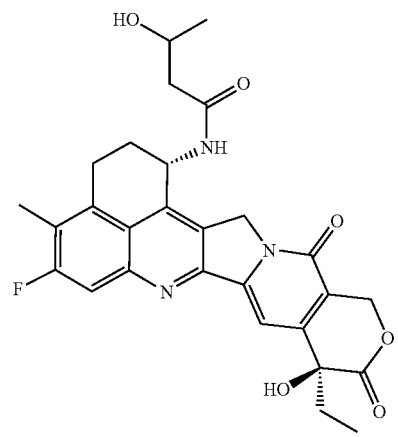 [SMILES: CC[C@@]1(O)C(=O)OCc2c1cc1n(c2=O)Cc2c-1nc1cc(F)c(C)c3c1c2[C@@H](NC(=O)CC(C)O)CC3] |
| L-III-1 | 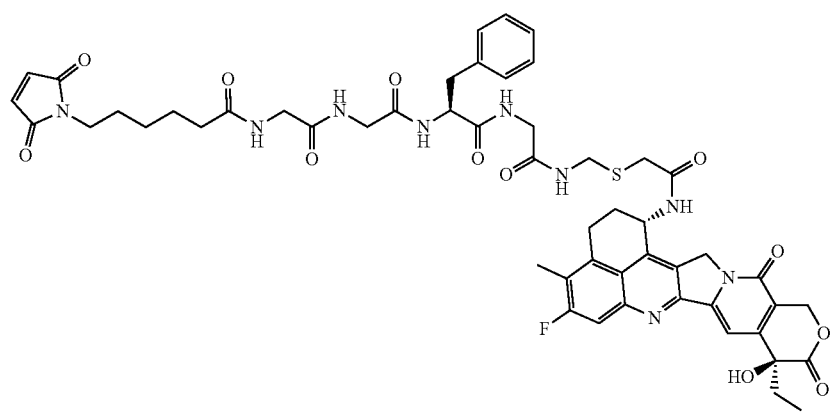 [SMILES: CC[C@@]1(O)C(=O)OCc2c1cc1n(c2=O)Cc2c-1nc1cc(F)c(C)c3c1c2[C@@H](NC(=O)CSCNC(=O)CNC(=O)[C@H](Cc1ccccc1)NC(=O)CNC(=O)CNC(=O)CCCCCN1C(=O)C=CC1=O)CC3] |

| No. | Structure |
|---|---|
| L-III-2 | 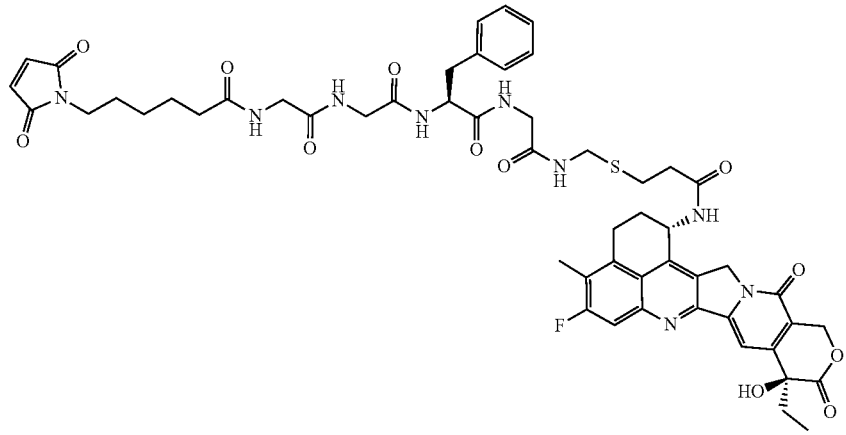 [SMILES: CC[C@@]1(O)C(=O)OCc2c1cc1n(c2=O)Cc2c-1nc1cc(F)c(C)c3c1c2[C@@H](NC(=O)CCSCNC(=O)CNC(=O)[C@H](Cc1ccccc1)NC(=O)CNC(=O)CNC(=O)CCCCCN1C(=O)C=CC1=O)CC3] |
| L-III-3 | 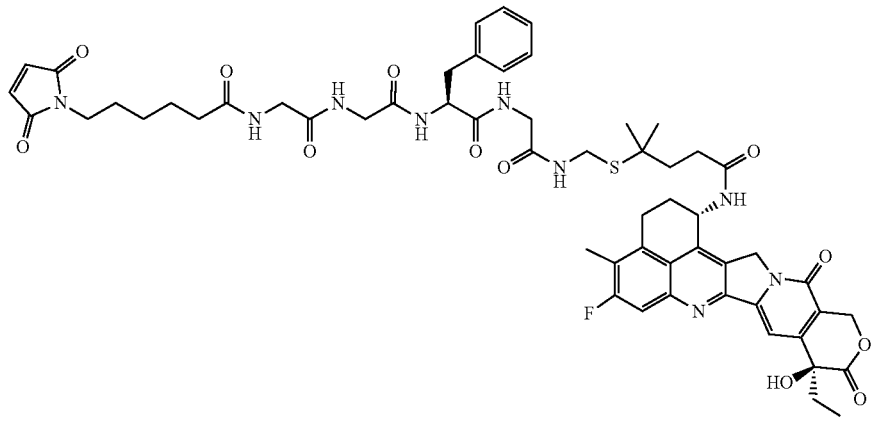 [SMILES: CC[C@@]1(O)C(=O)OCc2c1cc1n(c2=O)Cc2c-1nc1cc(F)c(C)c3c1c2[C@@H](NC(=O)CCC(C)(C)SCNC(=O)CNC(=O)[C@H](Cc1ccccc1)NC(=O)CNC(=O)CNC(=O)CCCCCN1C(=O)C=CC1=O)CC3] |
| L-III-4 | 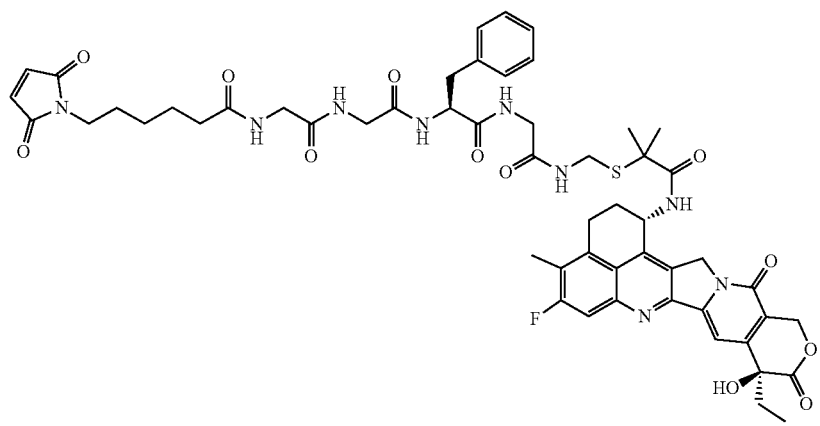 [SMILES: CC[C@@]1(O)C(=O)OCc2c1cc1n(c2=O)Cc2c-1nc1cc(F)c(C)c3c1c2[C@@H](NC(=O)C(C)(C)SCNC(=O)CNC(=O)[C@H](Cc1ccccc1)NC(=O)CNC(=O)CNC(=O)CCCCCN1C(=O)C=CC1=O)CC3] |

| No. | Structure |
|---|---|
| L-III-5 | 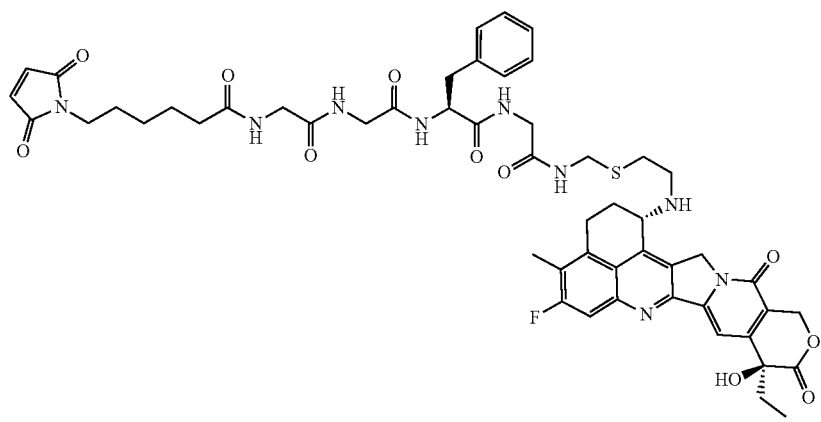 [SMILES: CC[C@@]1(O)C(=O)OCc2c1cc1n(c2=O)Cc2c-1nc1cc(F)c(C)c3c1c2[C@@H](NCCSCNC(=O)CNC(=O)[C@H](Cc1ccccc1)NC(=O)CNC(=O)CNC(=O)CCCCCN1C(=O)C=CC1=O)CC3] |
| L-III-6 | 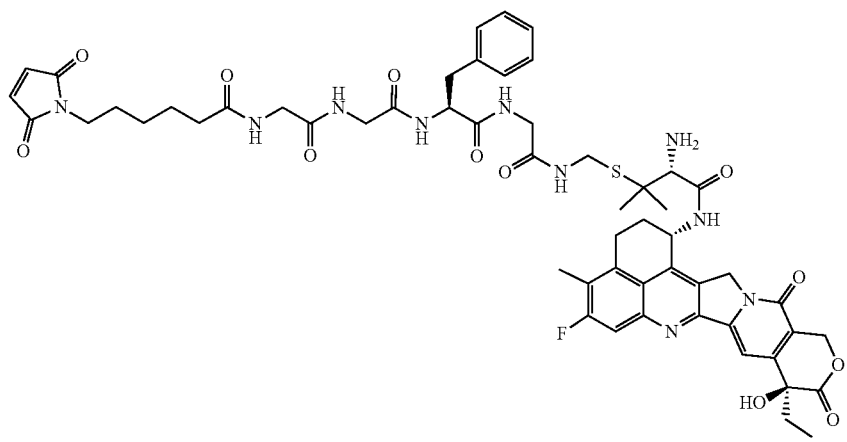 [SMILES: CC[C@@]1(O)C(=O)OCc2c1cc1n(c2=O)Cc2c-1nc1cc(F)c(C)c3c1c2[C@@H](NC(=O)[C@@H](N)C(C)(C)SCNC(=O)CNC(=O)[C@H](Cc1ccccc1)NC(=O)CNC(=O)CNC(=O)CCCCCN1C(=O)C=CC1=O)CC3] |
| L-III-7 | 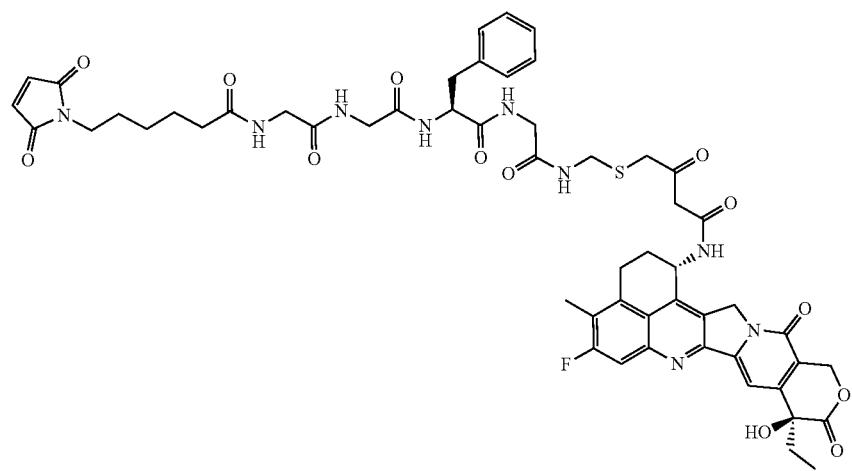 [SMILES: CC[C@@]1(O)C(=O)OCc2c1cc1n(c2=O)Cc2c-1nc1cc(F)c(C)c3c1c2[C@@H](NC(=O)CC(=O)CSCNC(=O)CNC(=O)[C@H](Cc1ccccc1)NC(=O)CNC(=O)CNC(=O)CCCCCN1C(=O)C=CC1=O)CC3] |

| No. | Structure |
|---|---|
| L-III-8 | 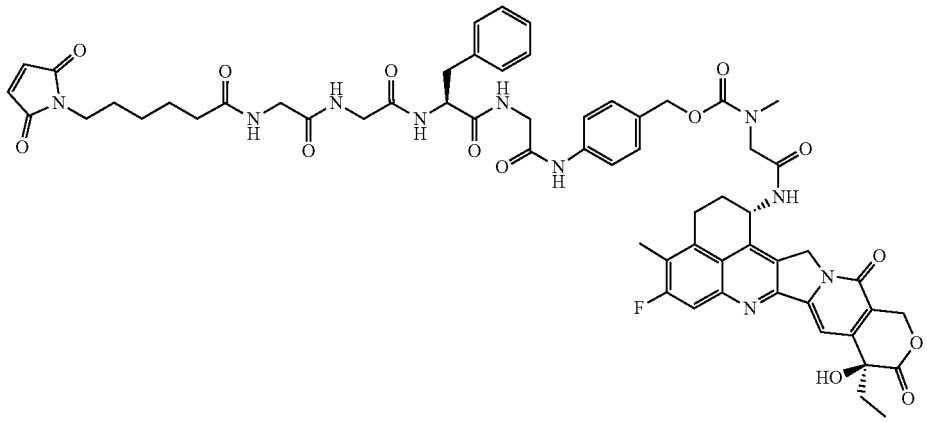 [SMILES: CC[C@@]1(O)C(=O)OCc2c1cc1n(c2=O)Cc2c-1nc1cc(F)c(C)c3c1c2[C@@H](NC(=O)CN(C)C(=O)OCc1ccc(NC(=O)CNC(=O)[C@H](Cc2ccccc2)NC(=O)CNC(=O)CNC(=O)CCCCCN2C(=O)C=CC2=O)cc1)CC3] |
| L-III-9 | 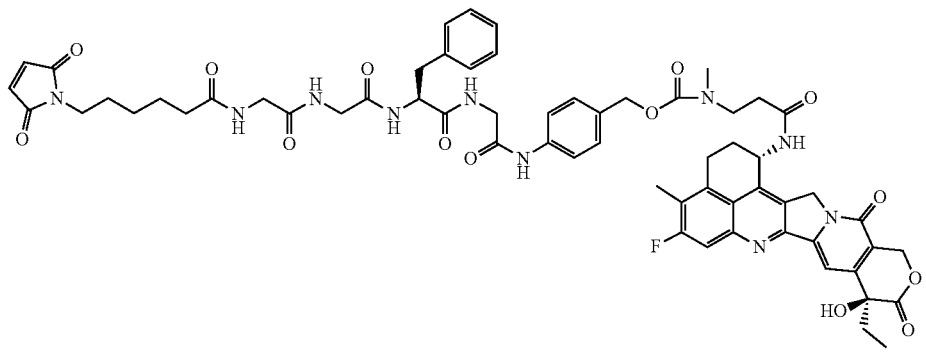 [SMILES: CC[C@@]1(O)C(=O)OCc2c1cc1n(c2=O)Cc2c-1nc1cc(F)c(C)c3c1c2[C@@H](NC(=O)CCN(C)C(=O)OCc1ccc(NC(=O)CNC(=O)[C@H](Cc2ccccc2)NC(=O)CNC(=O)CNC(=O)CCCCCN2C(=O)C=CC2=O)cc1)CC3] |
| L-III-10 | 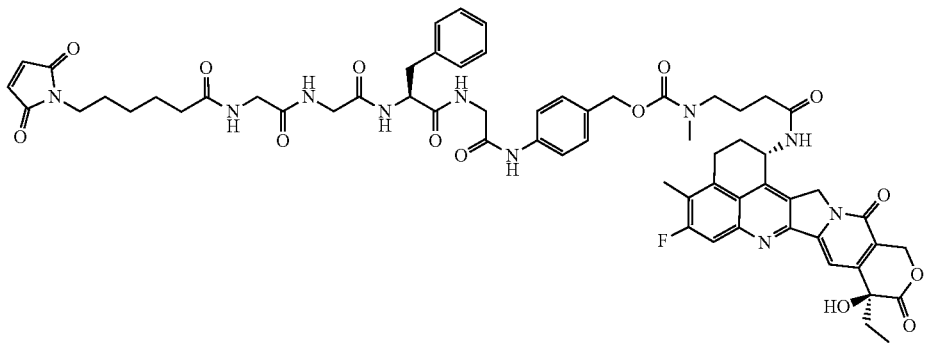 [SMILES: CC[C@@]1(O)C(=O)OCc2c1cc1n(c2=O)Cc2c-1nc1cc(F)c(C)c3c1c2[C@@H](NC(=O)CCCN(C)C(=O)OCc1ccc(NC(=O)CNC(=O)[C@H](Cc2ccccc2)NC(=O)CNC(=O)CNC(=O)CCCCCN2C(=O)C=CC2=O)cc1)CC3] |
| L-III-11 | 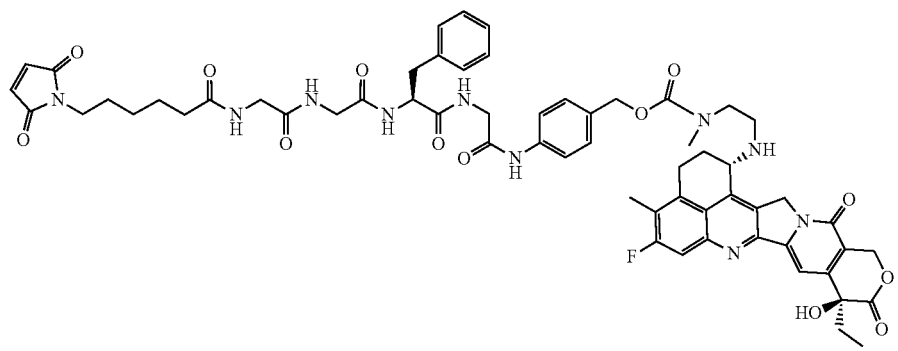 [SMILES: CC[C@@]1(O)C(=O)OCc2c1cc1n(c2=O)Cc2c-1nc1cc(F)c(C)c3c1c2[C@@H](NCCN(C)C(=O)OCc1ccc(NC(=O)CNC(=O)[C@H](Cc2ccccc2)NC(=O)CNC(=O)CNC(=O)CCCCCN2C(=O)C=CC2=O)cc1)CC3] |

| No. | Structure |
|---|---|
| L-III-12 | 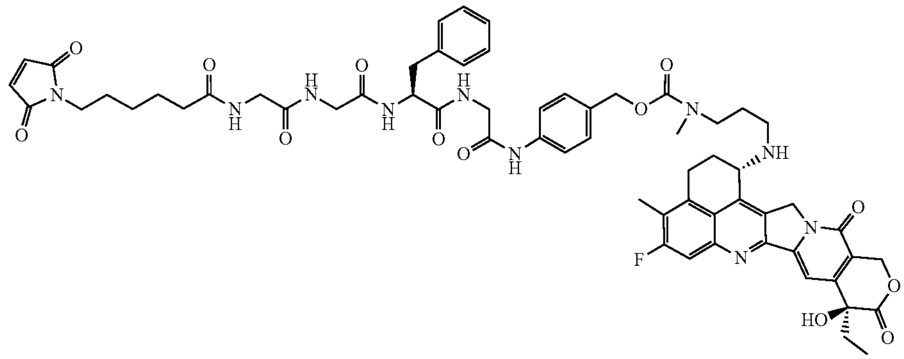 [SMILES: CC[C@@]1(O)C(=O)OCc2c1cc1n(c2=O)Cc2c-1nc1cc(F)c(C)c3c1c2[C@@H](NCCCN(C)C(=O)OCc1ccc(NC(=O)CNC(=O)[C@H](Cc2ccccc2)NC(=O)CNC(=O)CNC(=O)CCCCCN2C(=O)C=CC2=O)cc1)CC3] |
| L-III-13 | 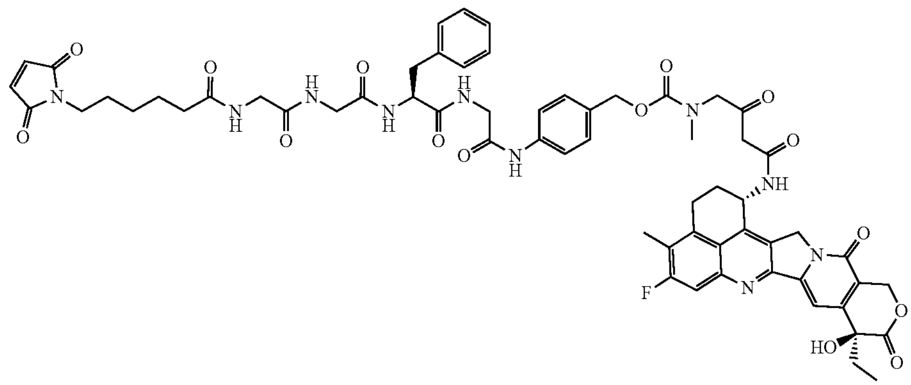 [SMILES: CC[C@@]1(O)C(=O)OCc2c1cc1n(c2=O)Cc2c-1nc1cc(F)c(C)c3c1c2[C@@H](NC(=O)CC(=O)CN(C)C(=O)OCc1ccc(NC(=O)CNC(=O)[C@H](Cc2ccccc2)NC(=O)CNC(=O)CNC(=O)CCCCCN2C(=O)C=CC2=O)cc1)CC3] |
| L-III-14 | 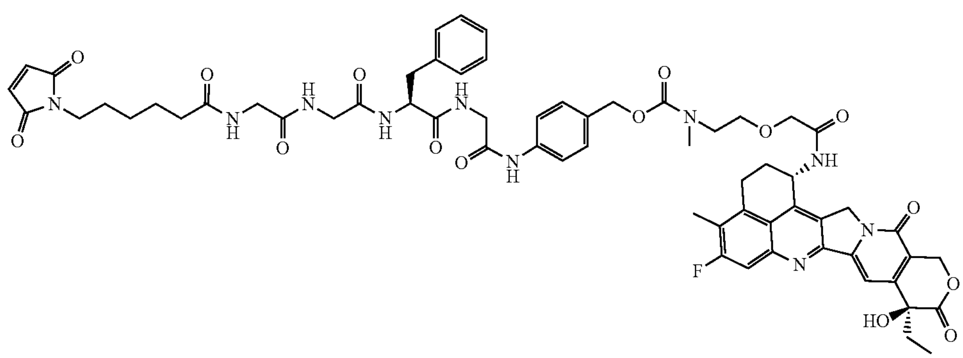 [SMILES: CC[C@@]1(O)C(=O)OCc2c1cc1n(c2=O)Cc2c-1nc1cc(F)c(C)c3c1c2[C@@H](NC(=O)COCCN(C)C(=O)OCc1ccc(NC(=O)CNC(=O)[C@H](Cc2ccccc2)NC(=O)CNC(=O)CNC(=O)CCCCCN2C(=O)C=CC2=O)cc1)CC3] |
| L-III-15 | 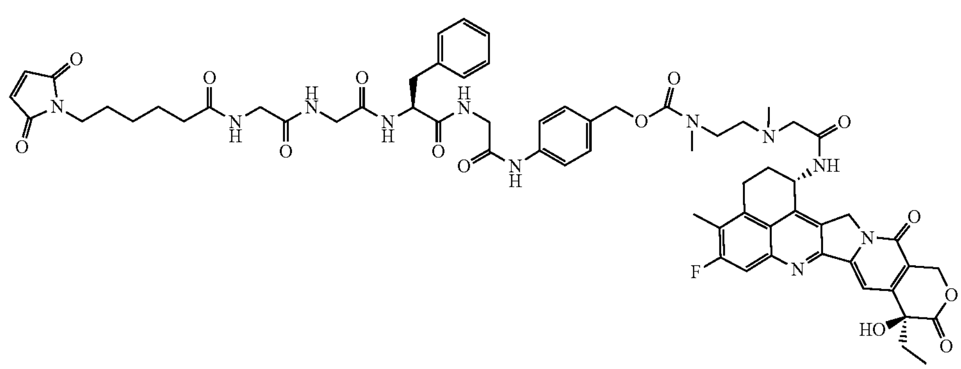 [SMILES: CC[C@@]1(O)C(=O)OCc2c1cc1n(c2=O)Cc2c-1nc1cc(F)c(C)c3c1c2[C@@H](NC(=O)CN(C)CCN(C)C(=O)OCc1ccc(NC(=O)CNC(=O)[C@H](Cc2ccccc2)NC(=O)CNC(=O)CNC(=O)CCCCCN2C(=O)C=CC2=O)cc1)CC3] |

| No. | Structure |
|---|---|
| L-III-16 | 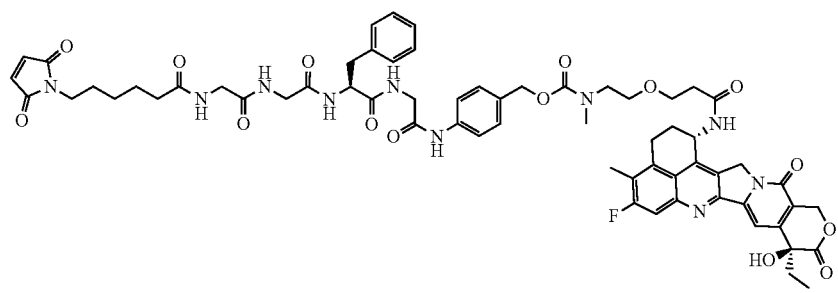 [SMILES: CC[C@@]1(O)C(=O)OCc2c1cc1n(c2=O)Cc2c-1nc1cc(F)c(C)c3c1c2[C@@H](NC(=O)CCOCCN(C)C(=O)OCc1ccc(NC(=O)CNC(=O)[C@H](Cc2ccccc2)NC(=O)CNC(=O)CNC(=O)CCCCCN2C(=O)C=CC2=O)cc1)CC3] |
| L-III-17 | 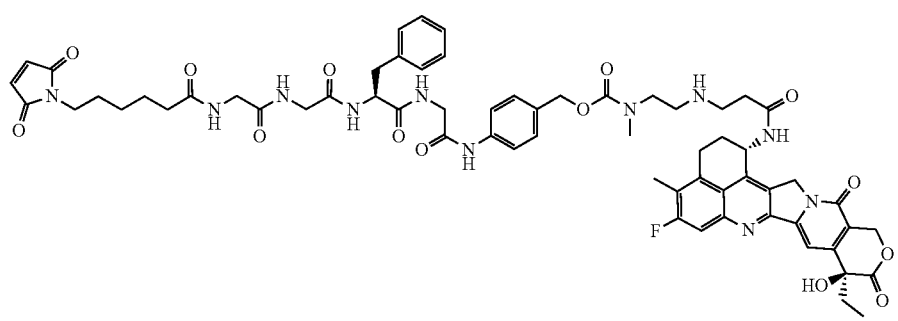 [SMILES: CC[C@@]1(O)C(=O)OCc2c1cc1n(c2=O)Cc2c-1nc1cc(F)c(C)c3c1c2[C@@H](NC(=O)CCNCCN(C)C(=O)OCc1ccc(NC(=O)CNC(=O)[C@H](Cc2ccccc2)NC(=O)CNC(=O)CNC(=O)CCCCCN2C(=O)C=CC2=O)cc1)CC3] |
| L-III-18 | 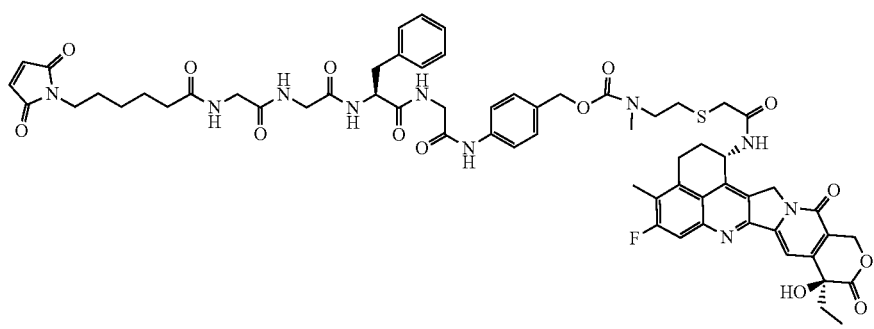 [SMILES: CC[C@@]1(O)C(=O)OCc2c1cc1n(c2=O)Cc2c-1nc1cc(F)c(C)c3c1c2[C@@H](NC(=O)CSCCN(C)C(=O)OCc1ccc(NC(=O)CNC(=O)[C@H](Cc2ccccc2)NC(=O)CNC(=O)CNC(=O)CCCCCN2C(=O)C=CC2=O)cc1)CC3] |
| L-III-19 | 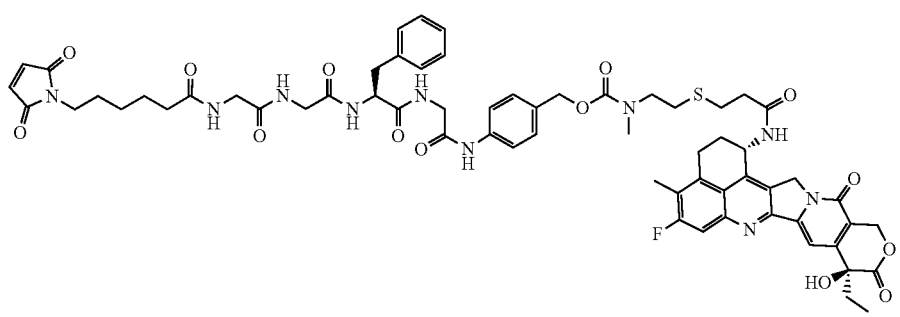 [SMILES: CC[C@@]1(O)C(=O)OCc2c1cc1n(c2=O)Cc2c-1nc1cc(F)c(C)c3c1c2[C@@H](NC(=O)CCSCCN(C)C(=O)OCc1ccc(NC(=O)CNC(=O)[C@H](Cc2ccccc2)NC(=O)CNC(=O)CNC(=O)CCCCCN2C(=O)C=CC2=O)cc1)CC3] |

| No. | Structure |
|---|---|
| L-III-20 | 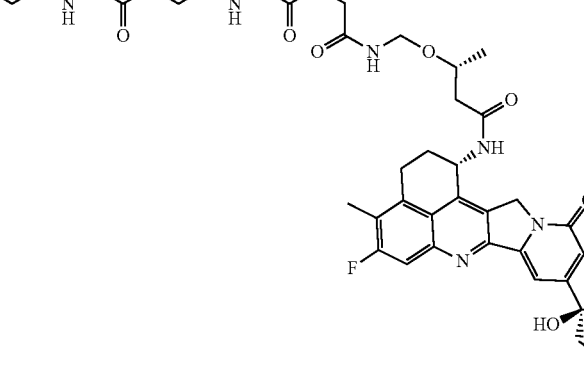 |
| L-III-21 | 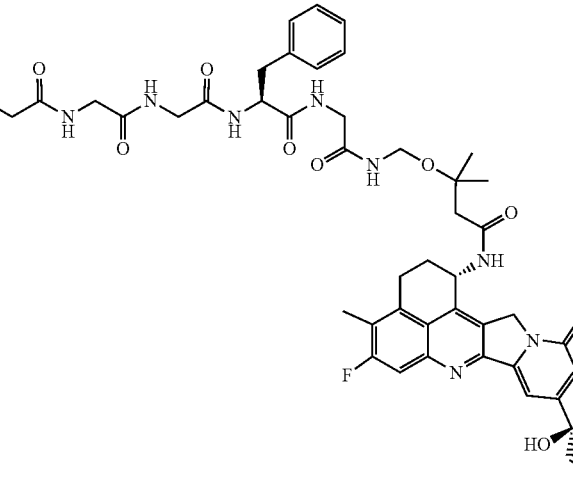 |
| L-III-22 | 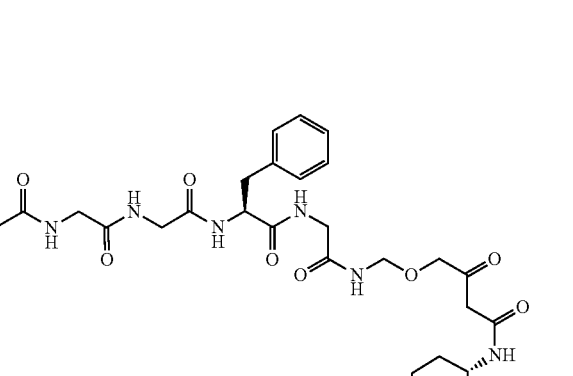 |

| No. | Structure |
|---|---|
| L-III-23 | 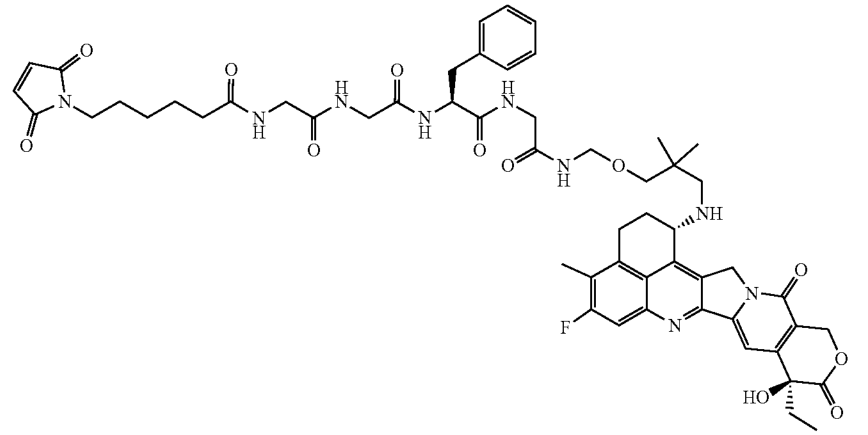 [SMILES: CC[C@@]1(O)C(=O)OCc2c1cc1n(c2=O)Cc2c-1nc1cc(F)c(C)c3c1c2[C@@H](NCC(C)(C)COCNC(=O)CNC(=O)[C@H](Cc1ccccc1)NC(=O)CNC(=O)CNC(=O)CCCCCN1C(=O)C=CC1=O)CC3] |
| L-III-24 | 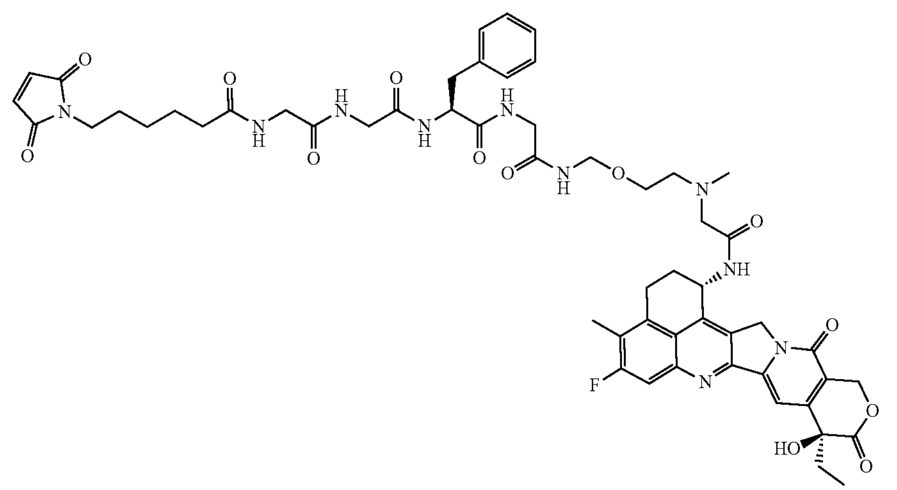 [SMILES: CC[C@@]1(O)C(=O)OCc2c1cc1n(c2=O)Cc2c-1nc1cc(F)c(C)c3c1c2[C@@H](NC(=O)CN(C)CCOCNC(=O)CNC(=O)[C@H](Cc1ccccc1)NC(=O)CNC(=O)CNC(=O)CCCCCN1C(=O)C=CC1=O)CC3] |
| L-III-25 | 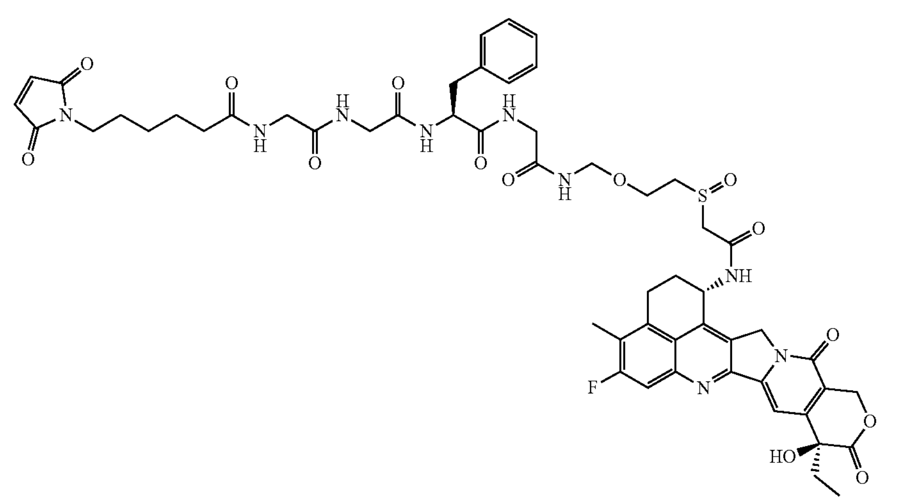 [SMILES: CC[C@@]1(O)C(=O)OCc2c1cc1n(c2=O)Cc2c-1nc1cc(F)c(C)c3c1c2[C@@H](NC(=O)CS(=O)CCOCNC(=O)CNC(=O)[C@H](Cc1ccccc1)NC(=O)CNC(=O)CNC(=O)CCCCCN1C(=O)C=CC1=O)CC3] |

| No. | Structure |
|---|---|
| L-III-26 | 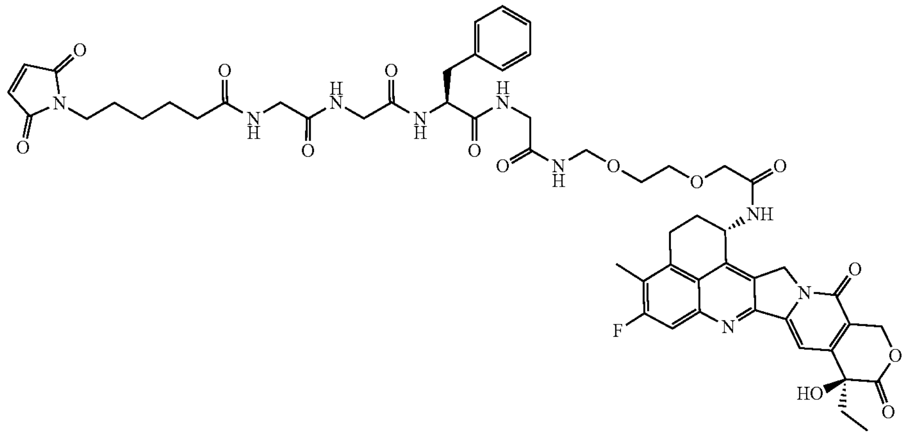 [SMILES: CC[C@@]1(O)C(=O)OCc2c1cc1n(c2=O)Cc2c-1nc1cc(F)c(C)c3c1c2[C@@H](NC(=O)COCCOCNC(=O)CNC(=O)[C@H](Cc1ccccc1)NC(=O)CNC(=O)CNC(=O)CCCCCN1C(=O)C=CC1=O)CC3] |
| L-III-27 | 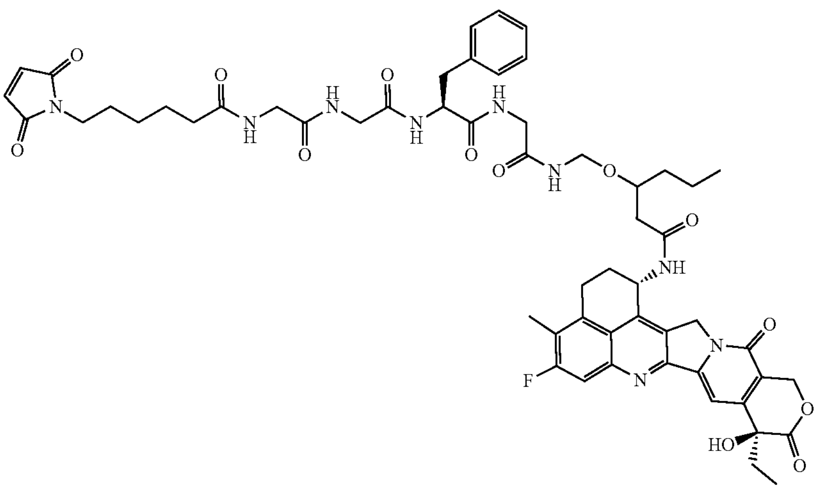 [SMILES: CCCC(CC(=O)N[C@H]1CCc2c(C)c(F)cc3nc4c(c1c23)Cn1c-4cc2c(c1=O)COC(=O)[C@]2(O)CC)OCNC(=O)CNC(=O)[C@H](Cc1ccccc1)NC(=O)CNC(=O)CNC(=O)CCCCCN1C(=O)C=CC1=O] |
| L-III-28 | 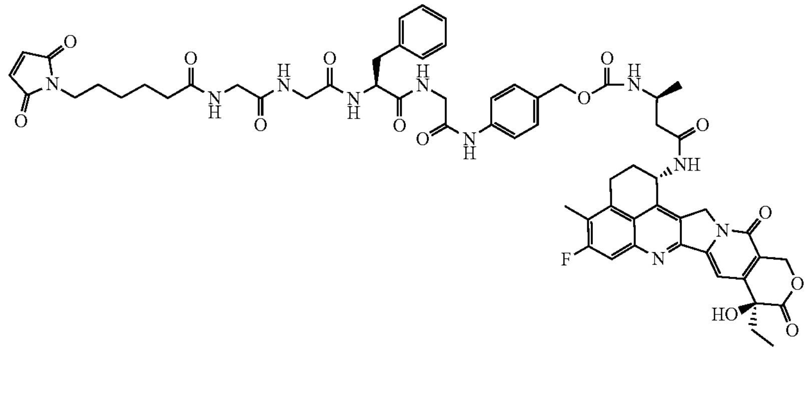 [SMILES: CC[C@@]1(O)C(=O)OCc2c1cc1n(c2=O)Cc2c-1nc1cc(F)c(C)c3c1c2[C@@H](NC(=O)C[C@H](C)NC(=O)OCc1ccc(NC(=O)CNC(=O)[C@H](Cc2ccccc2)NC(=O)CNC(=O)CNC(=O)CCCCCN2C(=O)C=CC2=O)cc1)CC3] |

| No. | Structure |
|---|---|
| L-III-29 | 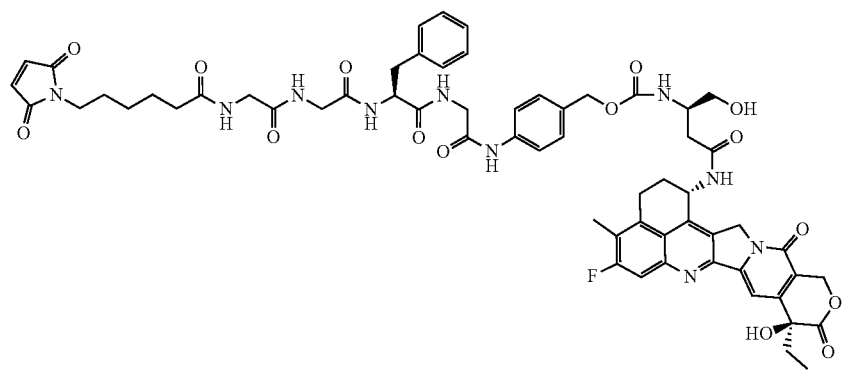 [SMILES: CC[C@@]1(O)C(=O)OCc2c1cc1n(c2=O)Cc2c-1nc1cc(F)c(C)c3c1c2[C@@H](NC(=O)C[C@H](CO)NC(=O)OCc1ccc(NC(=O)CNC(=O)[C@H](Cc2ccccc2)NC(=O)CNC(=O)CNC(=O)CCCCCN2C(=O)C=CC2=O)cc1)CC3] |
| L-III-30 | 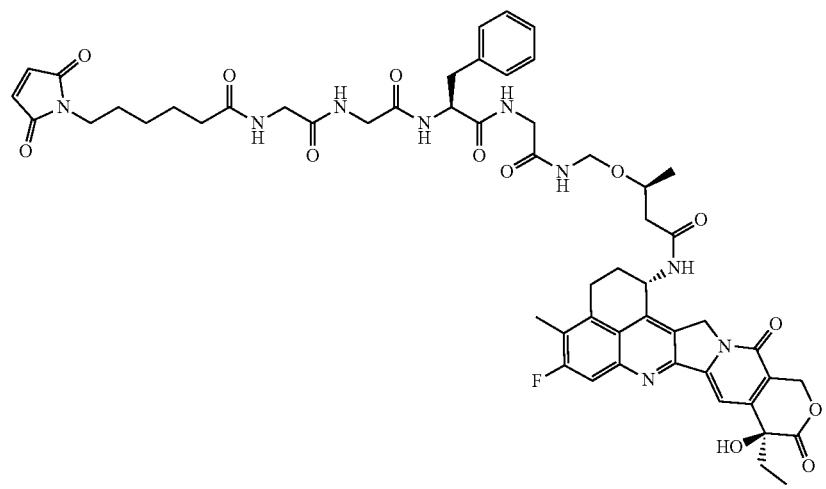 [SMILES: CC[C@@]1(O)C(=O)OCc2c1cc1n(c2=O)Cc2c-1nc1cc(F)c(C)c3c1c2[C@@H](NC(=O)C[C@H](C)OCNC(=O)CNC(=O)[C@H](Cc1ccccc1)NC(=O)CNC(=O)CNC(=O)CCCCCN1C(=O)C=CC1=O)CC3] |
| L-III-31 | 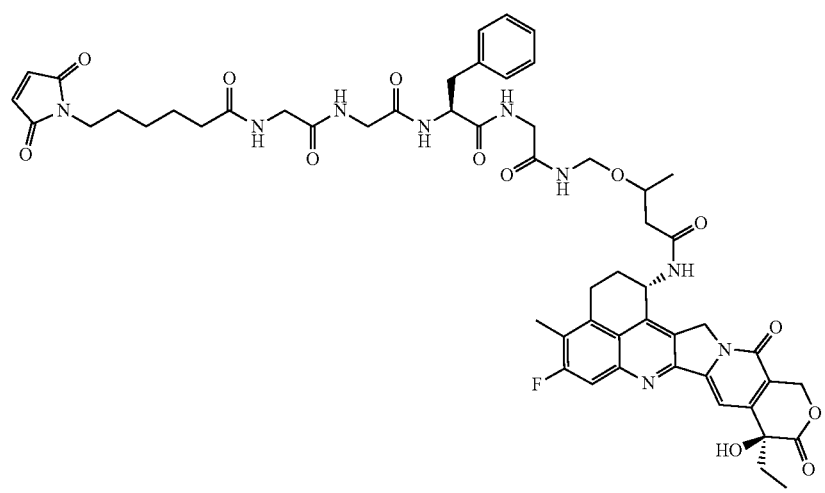 [SMILES: CC[C@@]1(O)C(=O)OCc2c1cc1n(c2=O)Cc2c-1nc1cc(F)c(C)c3c1c2[C@@H](NC(=O)CC(C)OCNC(=O)CNC(=O)[C@H](Cc1ccccc1)NC(=O)CNC(=O)CNC(=O)CCCCCN1C(=O)C=CC1=O)CC3] |

| No. | Structure |
|---|---|
| ADC-III-1 | 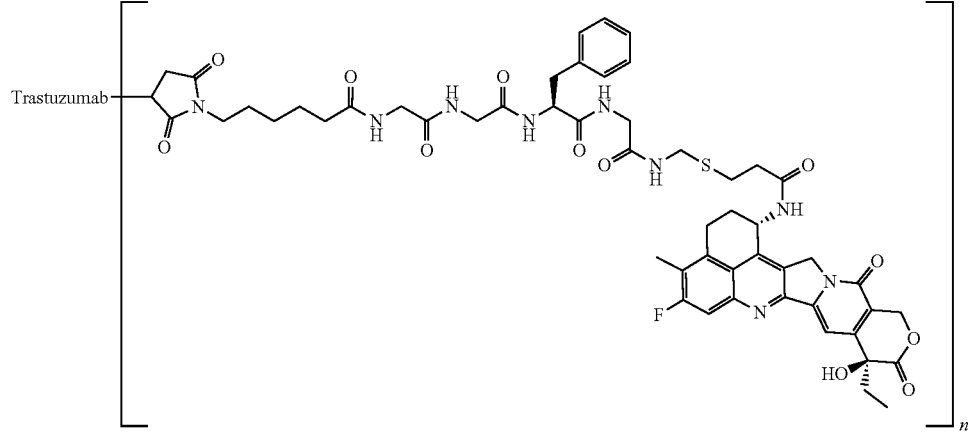 |
| ADC-III-2 | 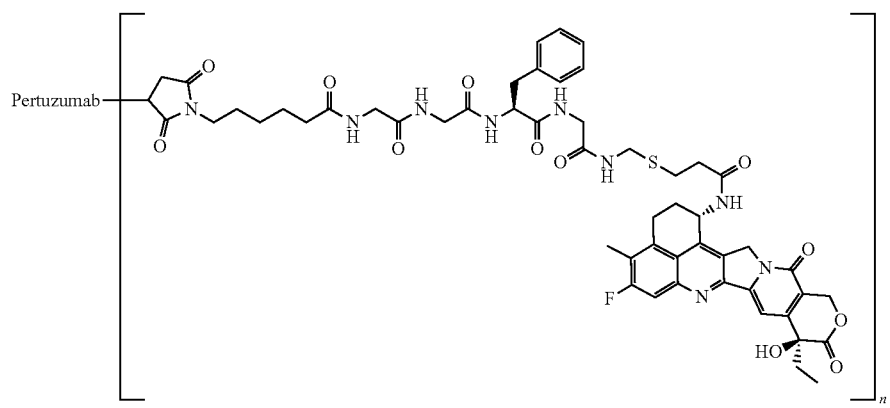 |
| ADC-III-3 | 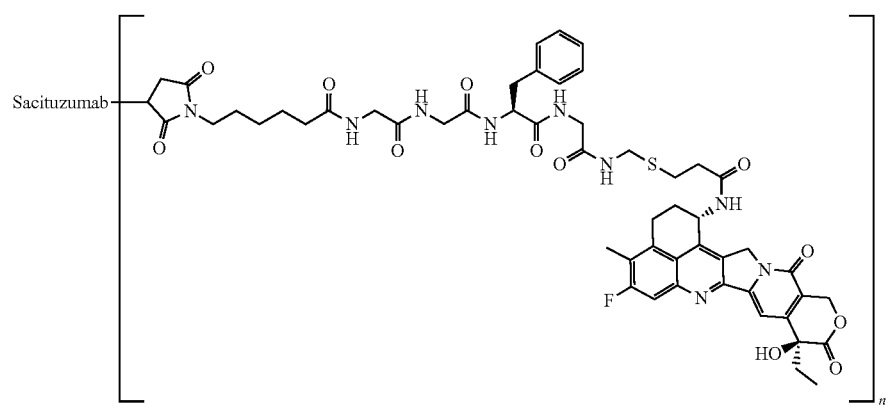 |

| No. | Structure |
|---|---|
| ADC-III-4 | 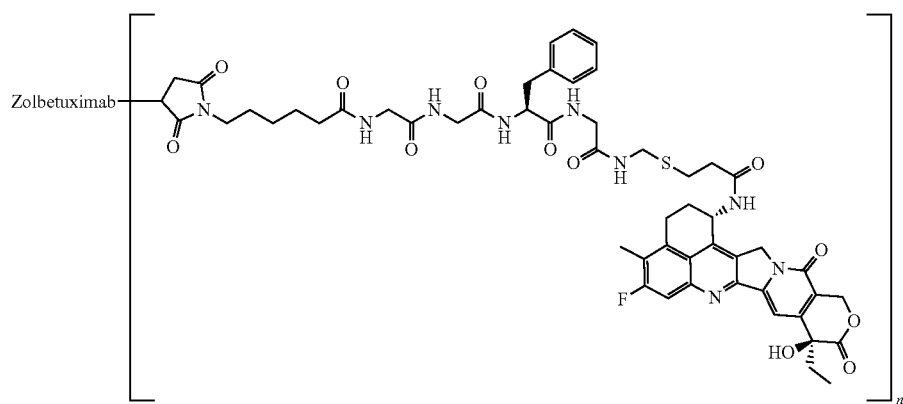 |
| ADC-III-5 | 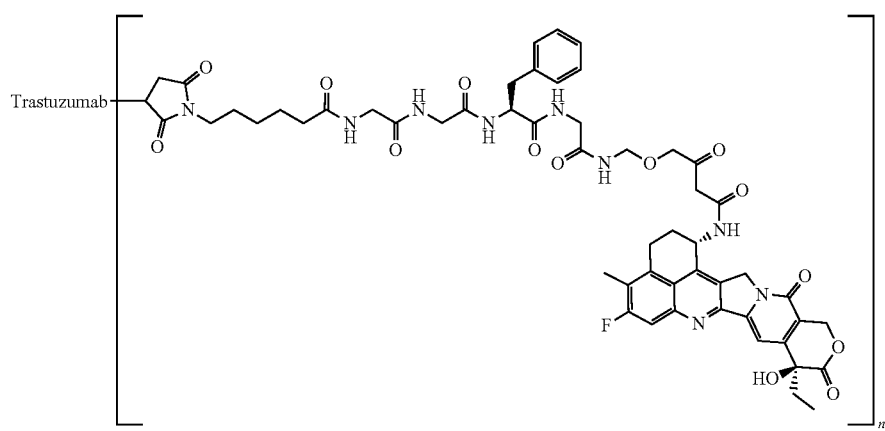 |
| ADC-III-6 | 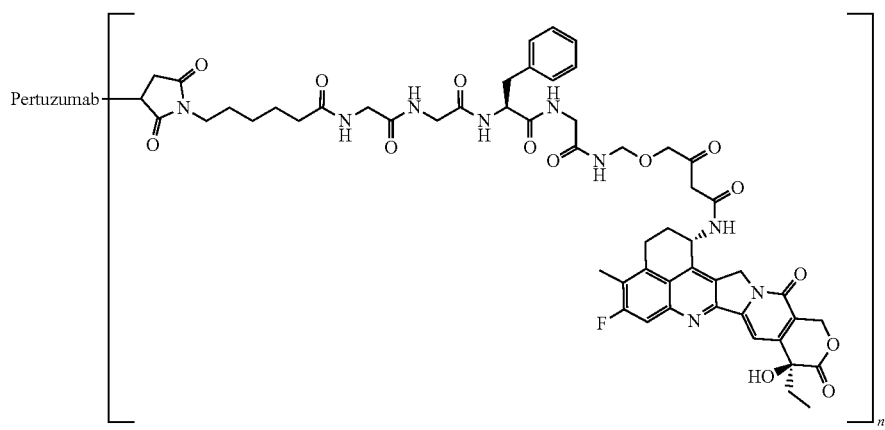 |

| No. | Structure |
|---|---|
| ADC-III-7 | 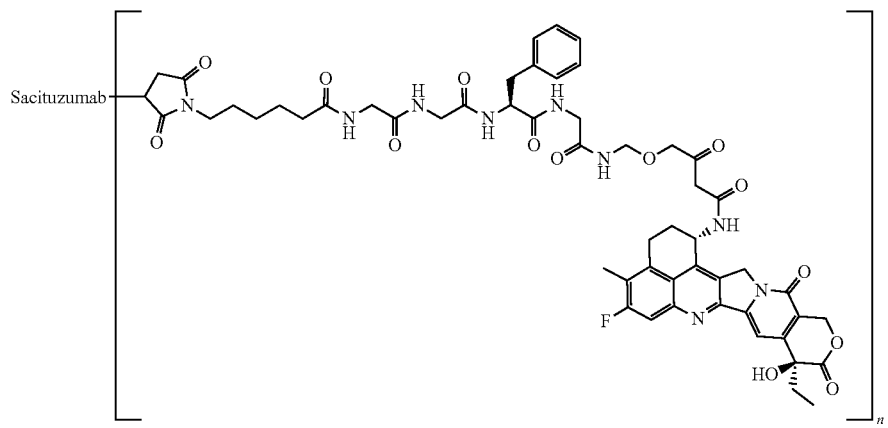 |
| ADC-III-8 | 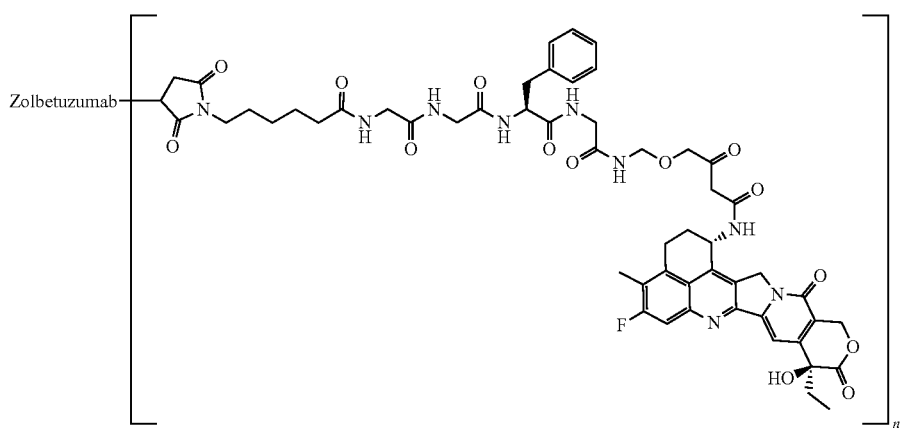 |
| ADC-III-9 | 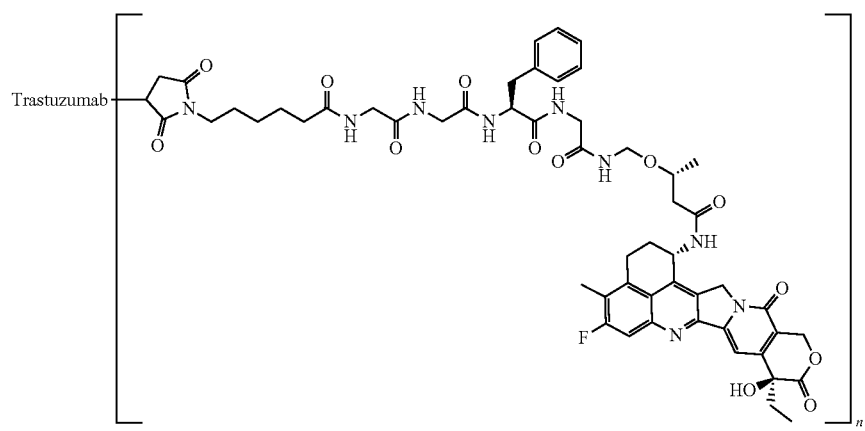 |

| No. | Structure |
|---|---|
| ADC-III-10 | 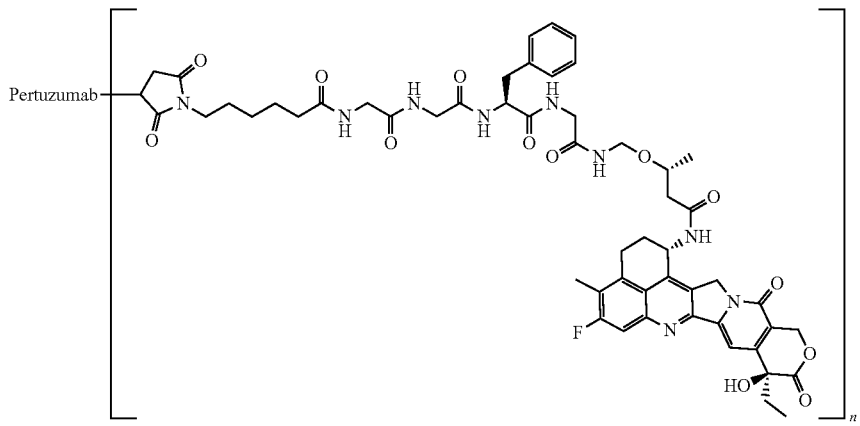 |
| ADC-III-11 | 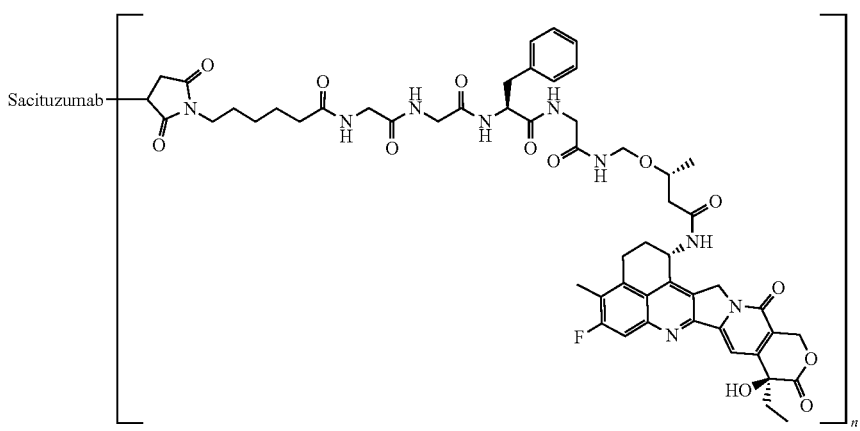 |
| ADC-III-12 | 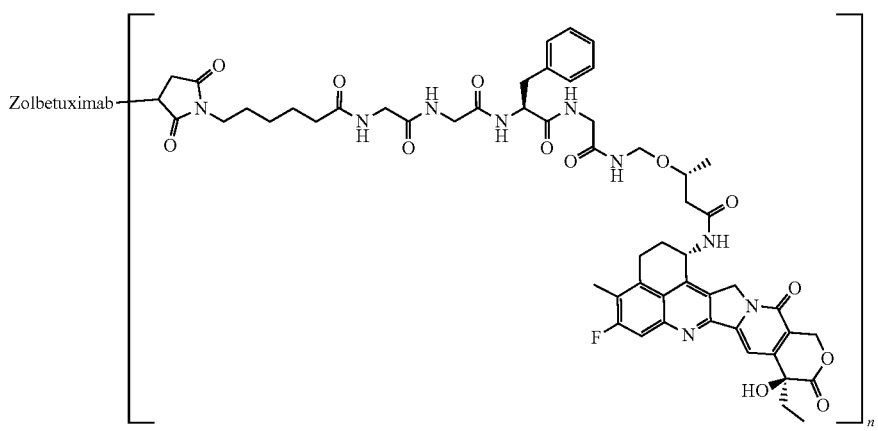 |

| No. | Structure |
|---|---|
| ADC-III-13 | 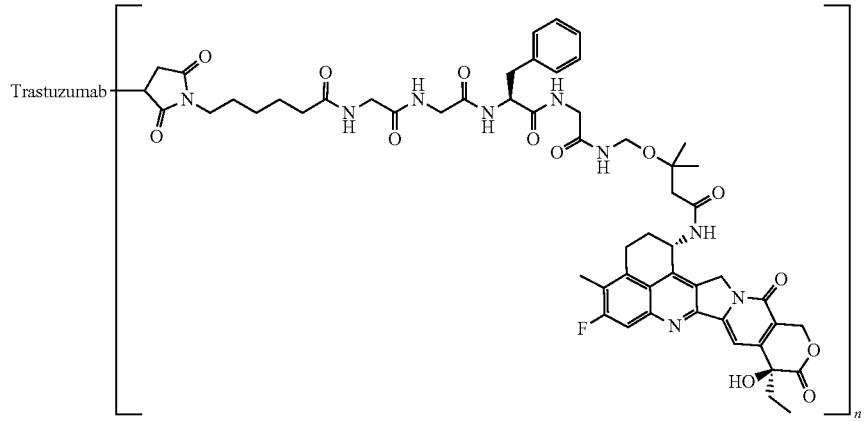 |
| ADC-III-14 | 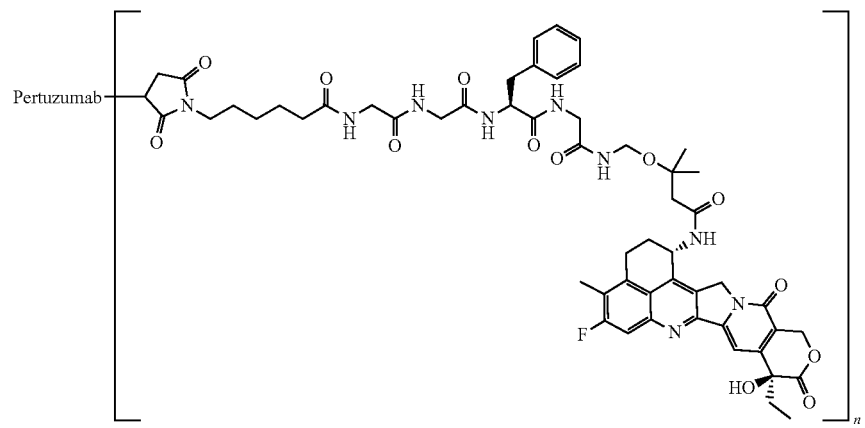 |
| ADC-III-15 | 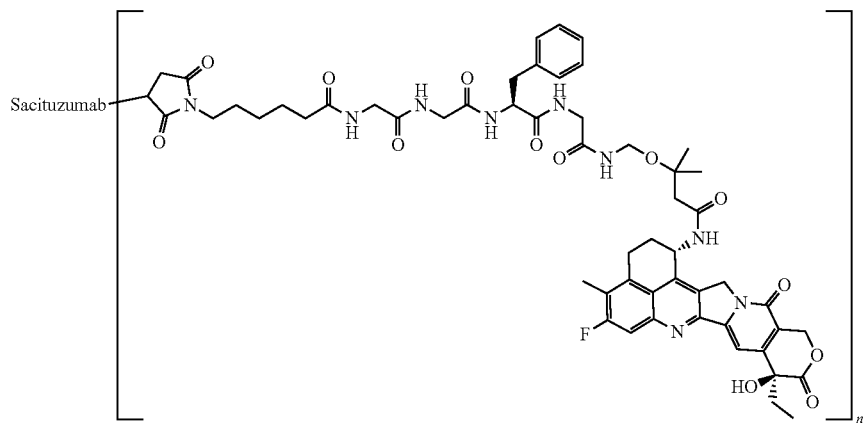 |

| No. | Structure |
|---|---|
| ADC-III-16 | 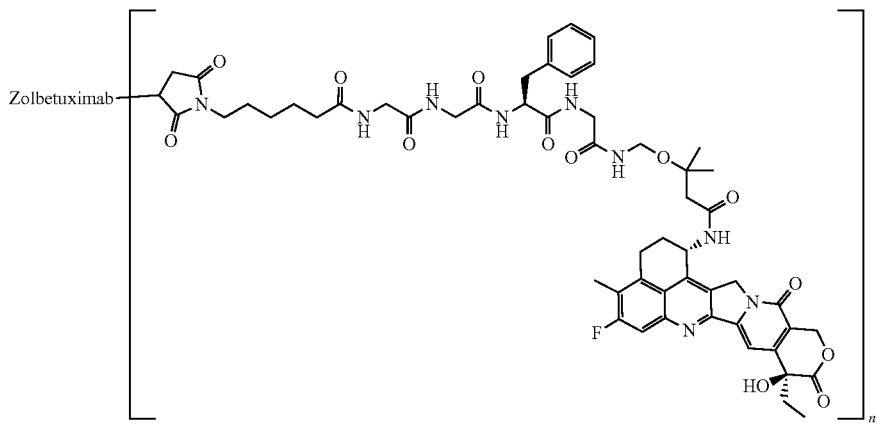 |
| ADC-III-17 | 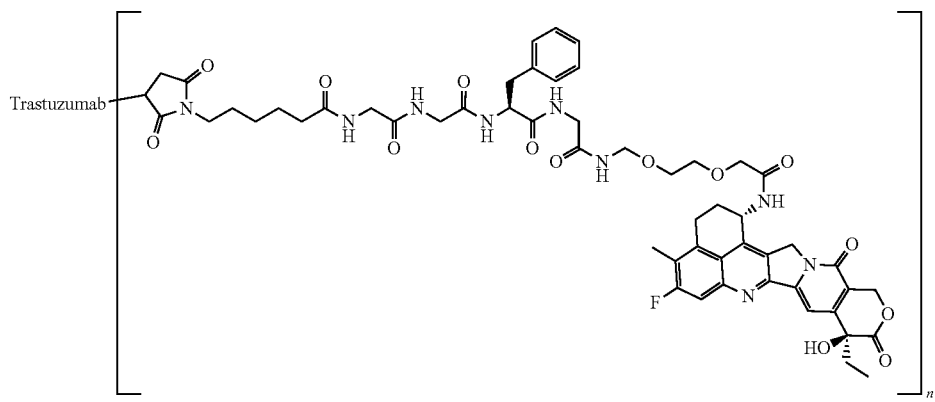 |
| ADC-III-18 | 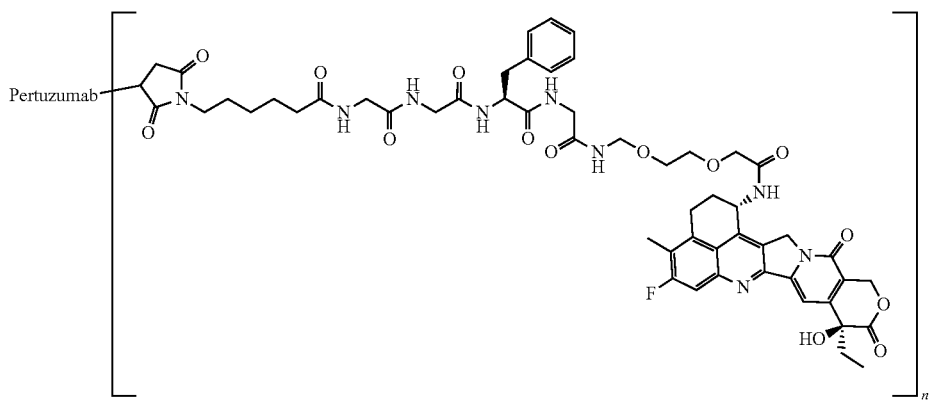 |

| No. | Structure |
|---|---|
| ADC-III-19 | 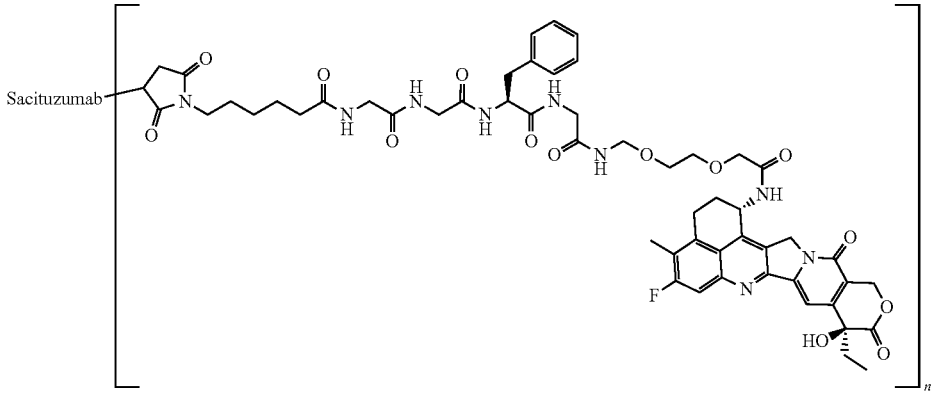 |
| ADC-III-20 | 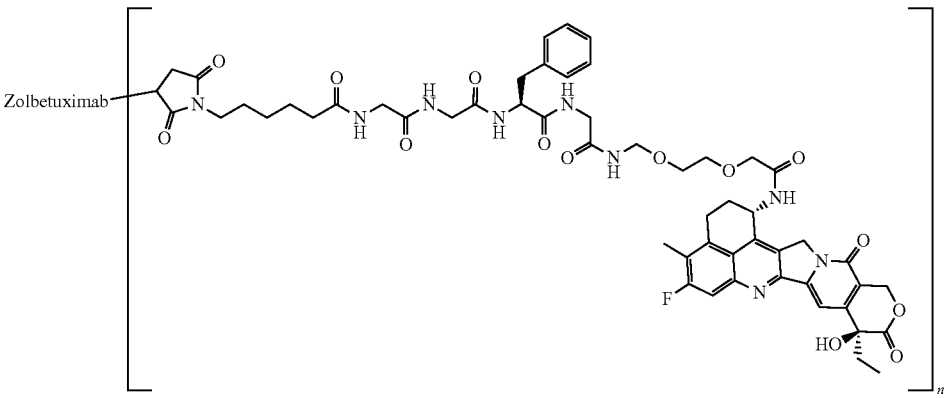 |
| ADC-III-21 | 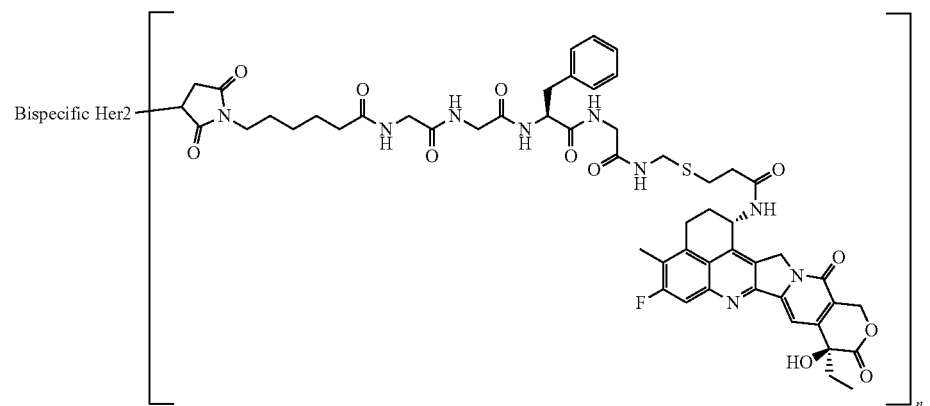 |

| No. | Structure |
|---|---|
| ADC-III-22 | 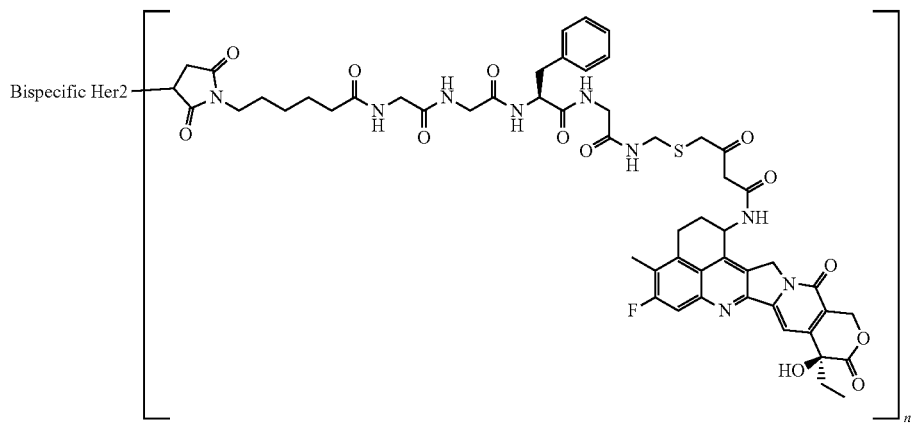 |
| ADC-III-23 | 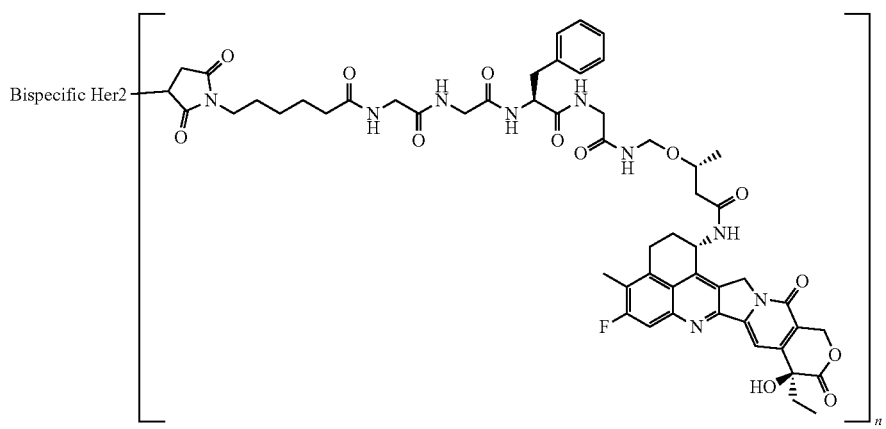 |
| ADC-III-24 | 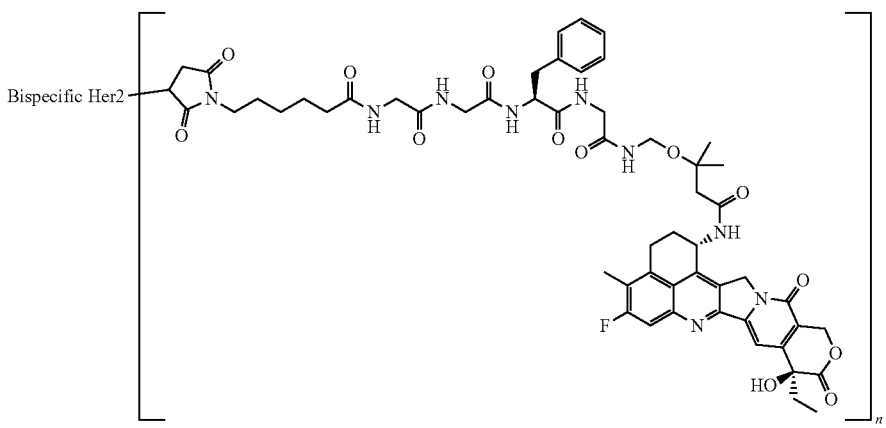 |

| No. | Structure |
|---|---|
| ADC-III-25 | 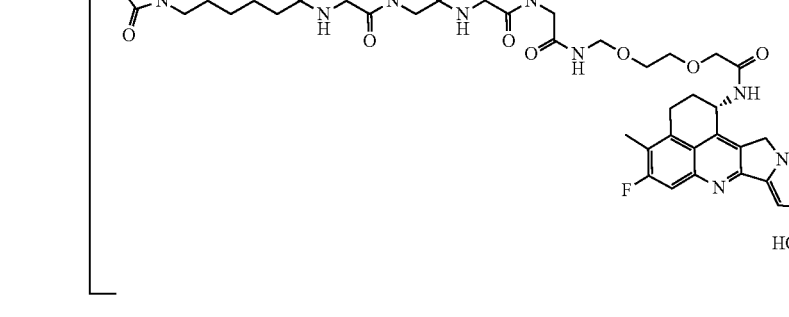 |
| ADC-III-26 | 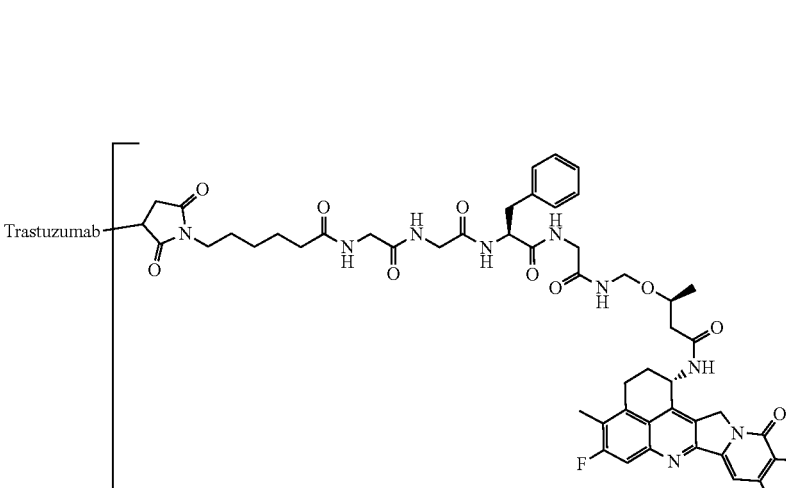 |
| ADC-III-27 | 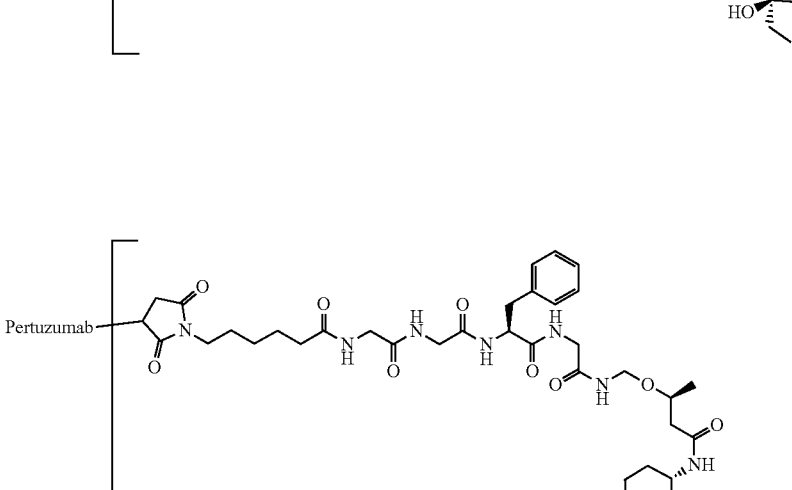 |

| No. | Structure |
|---|---|
| ADC-III-28 | 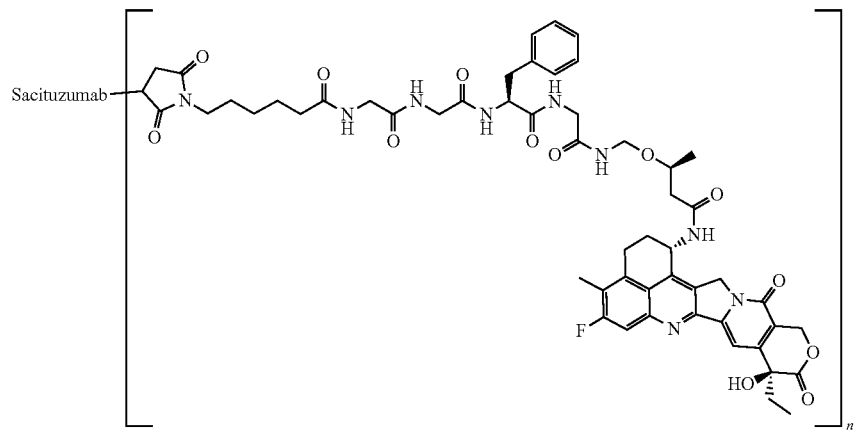 |
| ADC-III-29 | 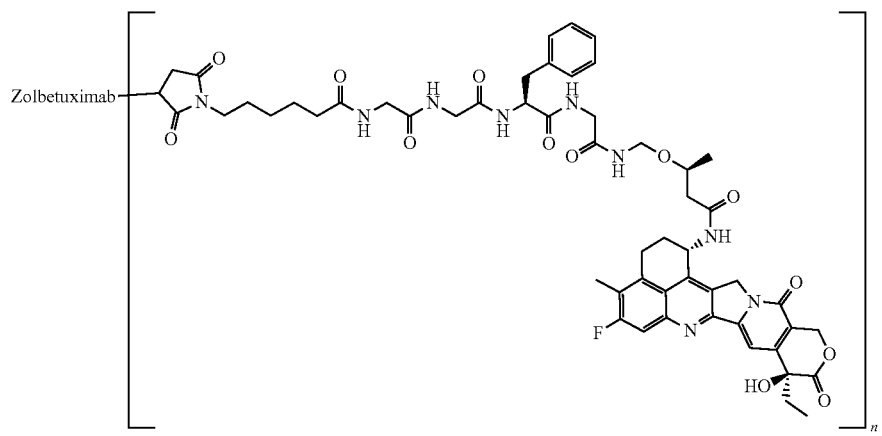 |
| ADC-III-30 | 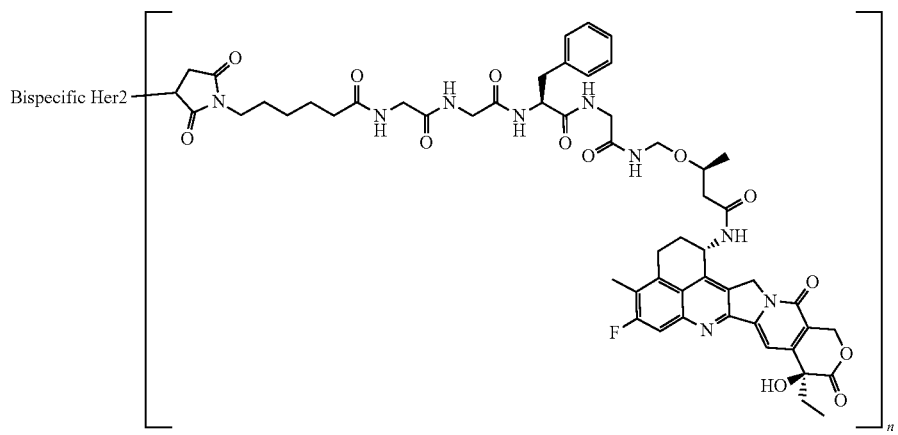 |

| No. | Structure |
|---|---|
| ADC-III-31 | 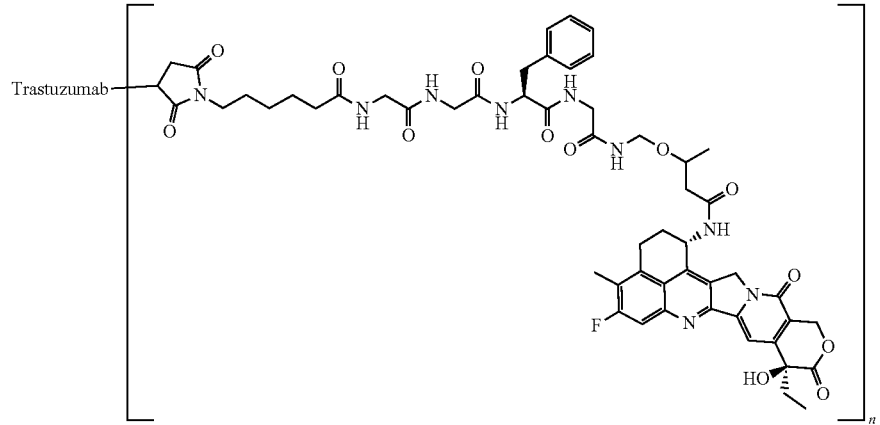 |
| ADC-III-32 | 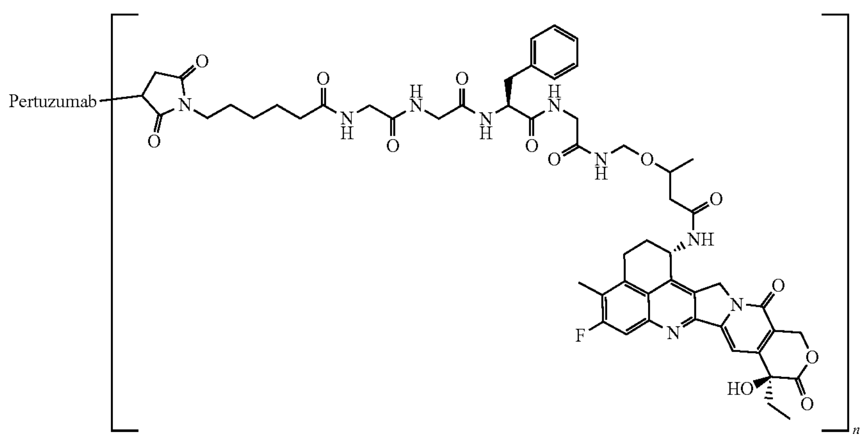 |
| ADC-III-33 | 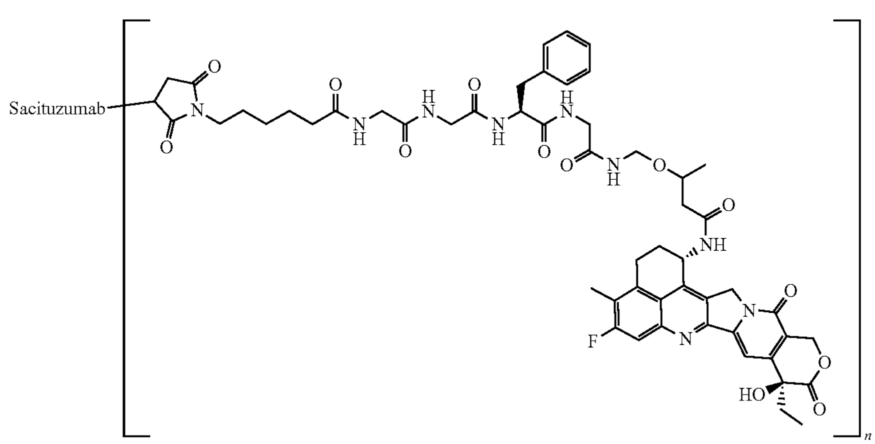 |

| No. | Structure |
|---|---|
| ADC-III-34 | 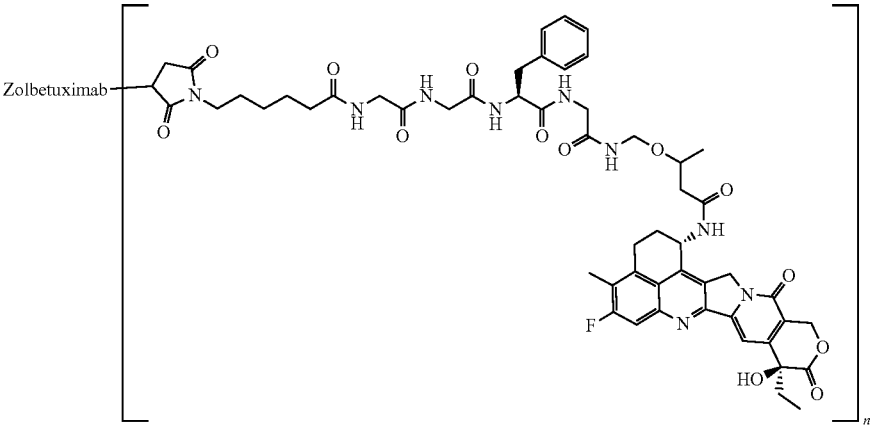 |
| ADC-III-35 | 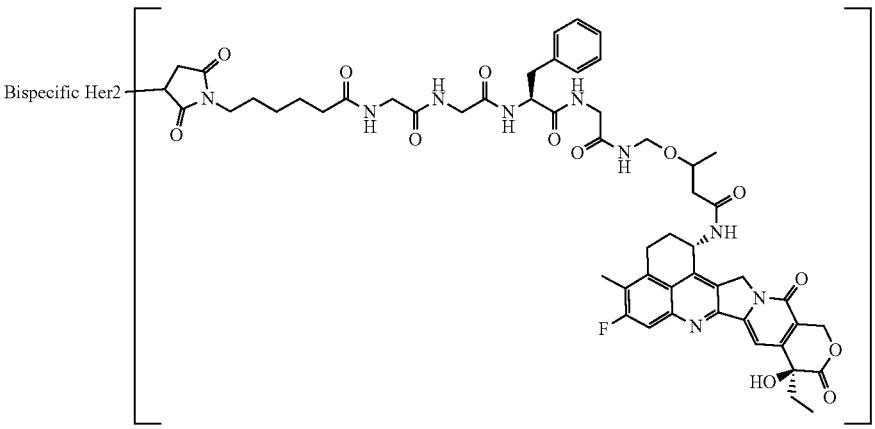 |

The average connection number n in the above list may be an integer or a decimal from 1 to 10. The average connection number n in the above list may be an integer or a decimal from 2 to 8. For example, the average connection number n may be an integer or a decimal from 3 to 8. For example, the average connection number n may be an integer or a decimal from 1 to 2, 2 to 3, 3 to 4, 4 to 5, 5 to 6, 6 to 7, 7 to 8, 8 to 9, or 9 to 10.

Ligands

The ligands described herein may be protein hormones, lectin, growth factors, antibodies, or other molecules capable of binding to a cell, a receptor and/or an antigen. For example, the ligand disclosed herein may be an antibody or an antigen-binding fragment thereof.

In the present application, the ligand may comprise at least one CDR in the light chain variable region VL of an antibody. The CDRs may be defined according to Kabat.

In the present application, the antigen-binding protein may comprise an LCDR1, and the LCDR1 may comprise an amino acid sequence set forth in any one of SEQ ID NOs: 1-4. The CDRs may be defined according to Kabat.

In the present application, the antigen-binding protein may comprise an LCDR2, and the LCDR2 may comprise an amino acid sequence set forth in any one of SEQ ID NOs: 5-8. The CDRs may be defined according to Kabat.

In the present application, the antigen-binding protein may comprise an LCDR3, and the LCDR3 may comprise an amino acid sequence set forth in any one of SEQ ID NOs: 9-12. The CDRs may be defined according to Kabat.

In the present application, the isolated antigen-binding protein may comprise LCDRs 1-3, wherein the LCDR1 may comprise an amino acid sequence set forth in any one of SEQ ID NOs: 1-4, the LCDR2 may comprise an amino acid sequence set forth in any one of SEQ ID NOs: 5-8, and the LCDR3 may comprise an amino acid sequence set forth in any one of SEQ ID NOs: 9-12. The CDRs may be defined according to Kabat.

For example, the antigen-binding protein described herein may comprise the same LCDRs 1-3 as trastuzumab, wherein the LCDR1 may comprise an amino acid sequence set forth in SEQ ID NO: 1, the LCDR2 may comprise an amino acid sequence set forth in SEQ ID NO: 5, and the LCDR3 may comprise an amino acid sequence set forth in SEQ ID NO: 9. For example, the antigen-binding protein described herein may comprise the same LCDRs 1-3 as pertuzumab, wherein the LCDR1 may comprise an amino acid sequence set forth in SEQ ID NO: 2, the LCDR2 may comprise an amino acid sequence set forth in SEQ ID NO: 6, and the LCDR3 may comprise an amino acid sequence set forth in SEQ ID NO: 10. The CDRs may be defined according to Kabat.

For example, the antigen-binding protein described herein may comprise the same LCDRs 1-3 as sacituzumab, wherein the LCDR1 may comprise an amino acid sequence set forth in SEQ ID NO: 3, the LCDR2 may comprise an amino acid sequence set forth in SEQ ID NO: 7, and the LCDR3 may comprise an amino acid sequence set forth in SEQ ID NO: 11. The CDRs may be defined according to Kabat.

For example, the antigen-binding protein described herein may comprise the same LCDRs 1-3 as zolbetuximab, wherein the LCDR1 may comprise an amino acid sequence set forth in SEQ ID NO: 4, the LCDR2 may comprise an amino acid sequence set forth in SEQ ID NO: 8, and the LCDR3 may comprise an amino acid sequence set forth in SEQ ID NO: 12. The CDRs may be defined according to Kabat.

The antigen-binding protein described herein may comprise at least one CDR in the heavy chain variable region VH of an antibody. The CDRs may be defined according to Kabat.

In the present application, the antigen-binding protein may comprise an HCDR1, and the HCDR1 may comprise an amino acid sequence set forth in any one of SEQ ID NOs: 13-16. The CDRs may be defined according to Kabat.

In the present application, the antigen-binding protein may comprise an HCDR2, and the HCDR2 may comprise an amino acid sequence set forth in any one of SEQ ID NOs: 17-20. The CDRs may be defined according to Kabat.

In the present application, the antigen-binding protein may comprise an HCDR3, and the HCDR3 may comprise an amino acid sequence set forth in any one of SEQ ID NOs: 21-24. The CDRs may be defined according to Kabat.

In the present application, the isolated antigen-binding protein may comprise HCDRs 1-3, wherein the HCDR1 may comprise an amino acid sequence set forth in any one of SEQ ID NOs: 13-16, the HCDR2 may comprise an amino acid sequence set forth in any one of SEQ ID NOs: 17-20, and the HCDR3 may comprise an amino acid sequence set forth in any one of SEQ ID NOs: 21-24. The CDRs may be defined according to Kabat.

For example, the antigen-binding protein described herein may comprise the same HCDRs 1-3 as trastuzumab, wherein the HCDR1 may comprise an amino acid sequence set forth in SEQ ID NO: 13, the HCDR2 may comprise an amino acid sequence set forth in SEQ ID NO: 17, and the HCDR3 may comprise an amino acid sequence set forth in SEQ ID NO: 21. The CDRs may be defined according to Kabat.

For example, the antigen-binding protein described herein may comprise the same HCDRs 1-3 as pertuzumab, wherein the HCDR1 may comprise an amino acid sequence set forth in SEQ ID NO: 14, the HCDR2 may comprise an amino acid sequence set forth in SEQ ID NO: 18, and the HCDR3 may comprise an amino acid sequence set forth in SEQ ID NO: 22. The CDRs may be defined according to Kabat.

For example, the antigen-binding protein described herein may comprise the same HCDRs 1-3 as sacituzumab, wherein the HCDR1 may comprise an amino acid sequence set forth in SEQ ID NO: 15, the HCDR2 may comprise an amino acid sequence set forth in SEQ ID NO: 19, and the HCDR3 may comprise an amino acid sequence set forth in SEQ ID NO: 23. The CDRs may be defined according to Kabat.

For example, the antigen-binding protein described herein may comprise the same HCDRs 1-3 as zolbetuximab, wherein the HCDR1 may comprise an amino acid sequence set forth in SEQ ID NO: 16, the HCDR2 may comprise an amino acid sequence set forth in SEQ ID NO: 20, and the HCDR3 may comprise an amino acid sequence set forth in SEQ ID NO: 24. The CDRs may be defined according to Kabat.

In the present application, the isolated antigen-binding protein may comprise LCDRs 1-3 and HCDRs 1-3, wherein The LCDR1 may comprise an amino acid sequence set forth in any one of SEQ ID NOs: 1-4, the LCDR2 may comprise an amino acid sequence set forth in any one of SEQ ID NOs: 5-8, the LCDR3 may comprise an amino acid sequence set forth in any one of SEQ ID NOs: 9-12, the HCDR1 may comprise an amino acid sequence set forth in any one of SEQ ID NOs: 13-16, the HCDR2 may comprise an amino acid sequence set forth in any one of SEQ ID NOs: 17-20, and the HCDR3 may comprise an amino acid sequence set forth in any one of SEQ ID NOs: 21-24. The CDRs may be defined according to Kabat.

For example, the antigen-binding protein described herein may comprise the same LCDRs 1-3 and HCDRs 1-3 as trastuzumab, wherein the LCDR1 may comprise an amino acid sequence set forth in SEQ ID NO: 1, the LCDR2 may comprise an amino acid sequence set forth in SEQ ID NO: 5, the LCDR3 may comprise an amino acid sequence set forth in SEQ ID NO: 9, the HCDR1 may comprise an amino acid sequence set forth in SEQ ID NO: 13, the HCDR2 may comprise an amino acid sequence set forth in SEQ ID NO: 17, and the HCDR3 may comprise an amino acid sequence set forth in SEQ ID NO: 21. The CDRs may be defined according to Kabat.

For example, the antigen-binding protein described herein may comprise the same LCDRs 1-3 and HCDRs 1-3 as pertuzumab, wherein the LCDR1 may comprise an amino acid sequence set forth in SEQ ID NO: 2, the LCDR2 may comprise an amino acid sequence set forth in SEQ ID NO: 6, the LCDR3 may comprise an amino acid sequence set forth in SEQ ID NO: 10, the HCDR1 may comprise an amino acid sequence set forth in SEQ ID NO: 14, the HCDR2 may comprise an amino acid sequence set forth in SEQ ID NO: 18, and the HCDR3 may comprise an amino acid sequence set forth in SEQ ID NO: 22. The CDRs may be defined according to Kabat.

For example, the antigen-binding protein described herein may comprise the same LCDRs 1-3 and HCDRs 1-3 as sacituzumab, wherein the LCDR1 may comprise an amino acid sequence set forth in SEQ ID NO: 3, the LCDR2 may comprise an amino acid sequence set forth in SEQ ID NO: 7, the LCDR3 may comprise an amino acid sequence set forth in SEQ ID NO: 11, the HCDR1 may comprise an amino acid sequence set forth in SEQ ID NO: 15, the HCDR2 may comprise an amino acid sequence set forth in SEQ ID NO: 19, and the HCDR3 may comprise an amino acid sequence set forth in SEQ ID NO: 23. The CDRs may be defined according to Kabat.

For example, the antigen-binding protein described herein may comprise the same LCDRs 1-3 and HCDRs 1-3 as zolbetuximab, wherein the LCDR1 may comprise an amino acid sequence set forth in SEQ ID NO: 4, the LCDR2 may comprise an amino acid sequence set forth in SEQ ID NO: 8, the LCDR3 may comprise an amino acid sequence set forth in SEQ ID NO: 12, the HCDR1 may comprise an amino acid sequence set forth in SEQ ID NO: 16, the HCDR2 may comprise an amino acid sequence set forth in SEQ ID NO: 20, and the HCDR3 may comprise an amino acid sequence set forth in SEQ ID NO: 24. The CDRs may be defined according to Kabat.

In the present application, the antigen-binding protein may comprise a light chain variable region VL, and the VL may comprise an amino acid sequence set forth in any one of SEQ ID NOs: 25-28.

In the present application, the antigen-binding protein may comprise a heavy chain variable region VH, and the VH may comprise an amino acid sequence set forth in any one of SEQ ID NOs: 29-32.

In the present application, the antigen-binding protein may comprise a light chain variable region VL and a heavy chain variable region VH, wherein the VL may comprise an amino acid sequence set forth in any one of SEQ ID NOs: 25-28, and the VH may comprise an amino acid sequence set forth in any one of SEQ ID NOs: 29-32.

For example, the antigen-binding protein described herein may comprise the same light chain variable region VL and heavy chain variable region VH as trastuzumab, wherein the VL may comprise an amino acid sequence set forth in SEQ ID NO: 25, and the VH may comprise an amino acid sequence set forth in SEQ ID NO: 29.

For example, the antigen-binding protein described herein may comprise the same light chain variable region VL and heavy chain variable region VH as pertuzumab, wherein the VL may comprise an amino acid sequence set forth in SEQ ID NO: 26, and the VH may comprise an amino acid sequence set forth in SEQ ID NO: 30.

For example, the antigen-binding protein described herein may comprise the same light chain variable region VL and heavy chain variable region VH as sacituzumab, wherein the VL may comprise an amino acid sequence set forth in SEQ ID NO: 27, and the VH may comprise an amino acid sequence set forth in SEQ ID NO: 31.

For example, the antigen-binding protein described herein may comprise the same light chain variable region VL and heavy chain variable region VH as zolbetuximab, wherein the VL may comprise an amino acid sequence set forth in SEQ ID NO: 28, and the VH may comprise an amino acid sequence set forth in SEQ ID NO: 32.

In the present application, the antigen-binding protein may comprise a light chain, and the light chain may comprise an amino acid sequence set forth in any one of SEQ ID NOs: 33-36.

In the present application, the antigen-binding protein may comprise a heavy chain, and the heavy chain may comprise an amino acid sequence set forth in any one of SEQ ID NOs: 37-40.

In the present application, the antigen-binding protein may comprise an antibody light chain and an antibody heavy chain, wherein the light chain may comprise an amino acid sequence set forth in any one of SEQ ID NOs: 33-36, and the heavy chain may comprise an amino acid sequence set forth in any one of SEQ ID NOs: 37-40.

For example, the antigen-binding protein described herein may comprise the same antibody light chain and antibody heavy chain as trastuzumab, wherein the light chain may comprise an amino acid sequence set forth in SEQ ID NO: 33, and the heavy chain may comprise an amino acid sequence set forth in SEQ ID NO: 37.

For example, the antigen-binding protein described herein may comprise the same antibody light chain and antibody heavy chain as pertuzumab, wherein the light chain may comprise an amino acid sequence set forth in SEQ ID NO: 34, and the heavy chain may comprise an amino acid sequence set forth in SEQ ID NO: 38.

For example, the antigen-binding protein described herein may comprise the same antibody light chain and antibody heavy chain as sacituzumab, wherein the light chain may comprise an amino acid sequence set forth in SEQ ID NO: 35, and the heavy chain may comprise an amino acid sequence set forth in SEQ ID NO: 39.

For example, the antigen-binding protein described herein may comprise the same antibody light chain and antibody heavy chain as zolbetuximab, wherein the light chain may comprise an amino acid sequence set forth in SEQ ID NO: 36, and the heavy chain may comprise an amino acid sequence set forth in SEQ ID NO: 40.

Prevention and/or Prevention of Tumors

In another aspect, the present application provides use of the compound or the tautomer, the mesomer, the racemate, the enantiomer or the diastereoisomer thereof, or the mixture thereof, or the pharmaceutically acceptable salt thereof, or the pharmaceutical composition thereof described herein, in preparing a medicament for treating and/or preventing a tumor. The tumor may be selected from the group consisting of tumors associated with expression of the following: HER2, HER3, B7H3, TROP2, Claudin 18.2, CD30, CD33, CD70 and EGFR. The tumor may be selected from the group consisting of: lung cancer, kidney cancer, urinary tract carcinoma, colorectal cancer, prostatic cancer, glioblastoma multiforme, ovarian cancer, pancreatic cancer, breast cancer, melanoma, liver cancer, bladder cancer, stomach cancer and esophageal cancer.

In another aspect, the present application provides a method for treating and/or preventing a tumor, which comprises administering to a subject in need the compound or the tautomer, the mesomer, the racemate, the enantiomer or the diastereoisomer thereof, or the mixture thereof, or the pharmaceutically acceptable salt thereof described herein, and/or the pharmaceutical composition that may comprise the same. The tumor may be selected from the group consisting of tumors associated with expression of the following: HER2, HER3, B7H3, TROP2, Claudin 18.2, CD30, CD33, CD70 and EGFR. The tumor may be selected from the group consisting of: lung cancer, kidney cancer, urinary tract carcinoma, colorectal cancer, prostatic cancer, glioblastoma multiforme, ovarian cancer, pancreatic cancer, breast cancer, melanoma, liver cancer, bladder cancer, stomach cancer and esophageal cancer.

In another aspect, the present application provides the compound or the tautomer, the mesomer, the racemate, the enantiomer or the diastereoisomer thereof, or the mixture thereof, or the pharmaceutically acceptable salt thereof described herein, and/or the pharmaceutical composition that may comprise the same, for use in treating and/or preventing a tumor. The tumor may be selected from the group consisting of tumors associated with expression of the following: HER2, HER3, B7H3, TROP2, Claudin 18.2, CD30, CD33, CD70 and EGFR. The tumor may be selected from the group consisting of: lung cancer, kidney cancer, urinary tract carcinoma, colorectal cancer, prostatic cancer, glioblastoma multiforme, ovarian cancer, pancreatic cancer, breast cancer, melanoma, liver cancer, bladder cancer, stomach cancer and esophageal cancer.

For example, the tumor may be selected from the group consisting of tumors associated with expression of the following: 5T4, AGS-16, ANGPTL4, ApoE, CD19, CTGF, CXCR5, FGF2, MCPT8, MFI2, MS4A7, NCA, Sema5b, SLITRK6, STC2, TGF, 0772P, 5T4, ACTA2, ADGRE1, AG-7, AIF1, AKR1C1, AKR1C2, ASLG659, Axl, B7H3, BAFF-R, BCMA, BMPR1B, BNIP3, C1QA, C1QB, CA6, CADM1, CCD79b, CCL5, CCR5, CCR7, CD11c, CD123, CD138, CD142, CD147, CD166, CD19, CD19, CD22, CD21, CD20, CD205, CD22, CD223, CD228, CD25, CD30, CD33, CD37, CD38, CD40, CD45, CD45 (PTPRC), CD46, CD47, CD49D (ITGA4), CD56, CD66e, CD70, CD71, CD72, CD74, CD79a, CD79b, CD80, CDCP1, CDH11, CD11b, CEA, CEACAM5, c-Met, COL6A3, COL7A1, CRIPTO, CSF1R, CTSD, CTSS, CXCL11, CXCL10, DDIT4, DLL3, DLL4, DR5, E16, EFNA4, EGFR, EGFRvIII, EGLN, EGLN3, EMR2, ENPP3, EpCAM, EphA2, EphB2R, ETBR, FcRH2, FcRH1, FGFR2, FGFR3, FLT3, FOLR-α, GD2, GEDA, GPC-1, GPNMB, GPR20, GZMB, HER2, HER3, HLA-DOB, HMOX1, IFI6, IFNG, IGF-1R, IGFBP3, IL10RA1, IL-13R, IL-2, IL20Ra, IL-3, IL-4, IL-6, IRTA2, KISS1R, KRT33A, LIV-1, LOX, LRP-1, LRRC15, LUM, LY64, LY6E, Ly86, LYPD3, MDP, MMP10, MMP14, MMP16, MPF, MSG783, MSLN, MUC-1, NaPi2b, Napi3b, Nectin-4, Nectin-4, NOG, P2X5, pCAD, P-Cadherin, PDGFRA, PDK1, PD-L1, PFKFB3, PGF, PGK1, PIK3AP1, PIK3CD, PLOD2, PSCA, PSCAhlg, PSMA, PSMA, PTK7, P-Cadherin, RNF43, NaPi2b, ROR1, ROR2, SERPINE1, SLC39A6, SLTRK6, STAT1, STEAP1, STEAP2, TCF4, TENB2, TGFB1, TGFB2, TGFBR1, TNFRSF21, TNFSF9, Trop-2, TrpM4, Tyro7, UPK1B, VEGFA, WNT5A, epidermal growth factors, brevican, mesothelin, sodium phosphate cotransporter 2B, Claudin 18.2, endothelin receptors, mucins (such as mucin 1 and mucin 16), guanylate cyclase C, integrin a4p7, integrin a5p6, trophoblast glycoprotein, and tissue factors.

The compound described herein may have inhibitory activity against in vitro proliferation of tumor cells. The inhibitory activity may be that: compared with in a culture medium of tumor cells to which a negative control or a control drug is added, the proliferation capacity of the tumor cells is reduced by no less than 1%, no less than 2%, no less than 4%, no less than 5%, no less than 8%, no less than 10%, no less than 15%, no less than 18%, no less than 20%, no less than 25%, no less than 40%, no less than 50%, no less than 60%, no less than 70%, no less than 80%, no less than 90% or no less than 95% in a culture medium to which the compound disclosed herein is added. For example, the inhibitory activity may be an $IC_{50}$ value (nM) for tumor cells of no more than 10000, no more than 5000, no more than 4000, no more than 3000, no more than 2000, no more than 1000, no more than 500, no more than 400, no more than 300, no more than 200, no more than 150, no more than 120, no more than 110, no more than 100, no more than 99, no more than 98, no more than 97, no more than 95, no more than 90, no more than 80, no more than 75, no more than 70, no more than 65, no more than 62, no more than 60, no more than 50, no more than 40, no more than 30, no more than 25, no more than 23, no more than 22, no more than 20, no more than 19, no more than 18, no more than 18.5, no more than 17, no more than 15, no more than 12, no more than 10, no more than 9, no more than 8.5, no more than 7, no more than 6.7, no more than 6, no more than 5.9, no more than 5.5, no more than 5.0, no more than 4.8, no more than 4.5, no more than 4.4, no more than 4, no more than 3.5, no more than 3, no more than 2.5, no more than 2, no more than 1.5, no more than 1.0, no more than 0.5, no more than 0.3, no more than 0.29, no more than 0.25, no more than 0.21, no more than 0.20, no more than 0.18, no more than 0.17, no more than 0.15, no more than 0.12, no more than 0.10, no more than 0.09, no more than 0.08, no more than 0.07, no more than 0.06, no more than 0.05, no more than 0.04, no more than 0.03, no more than 0.02 or no more than 0.01. For example, the tumor cells may include, but are not limited to, solid tumor cells; for example, the tumor cells include, but are not limited to, gastric cancer cells, or breast cancer cells; for example, the tumor cells may include, but are not limited to, NCI-N87 cells, JIMT-1 cells or MBA-MB-231 cells.

The compound described herein may have targeting inhibition. The targeting inhibition may be that: compared with in a culture medium of tumor cells with high expression of a specific target point to which a negative control or a control drug is added, the proliferation capacity of the tumor cells with high expression of a specific target point is reduced by no less than 1%, no less than 2%, no less than 4%, no less than 5%, no less than 8%, no less than 10%, no less than 15%, no less than 18%, no less than 20%, no less than 25%, no less than 40%, no less than 50%, no less than 60%, no less than 70%, no less than 80%, no less than 90% or no less than 95% in a culture medium to which the compound disclosed herein is added. For example, the targeting inhibition may be an $IC_{50}$ value (nM), for tumor cells with high expression of a specific target point, of no more than 10000, no more than 5000, no more than 4000, no more than 3000, no more than 2000, no more than 1000, no more than 500, no more than 400, no more than 300, no more than 200, no more than 185, no more than 150, no more than 120, no more than 110, no more than 100, no more than 99, no more than 98, no more than 97, no more than 95, no more than 91, no more than 80, no more than 74, no more than 70, no more than 65, no more than 62, no more than 60, no more than 50, no more than 40, no more than 30, no more than 25, no more than 23, no more than 22, no more than 20, no more than 19, no more than 18, no more than 18.5, no more than 17, no more than 15, no more than 12, no more than 10, no more than 9, no more than 8.5, no more than 7, no more than 6.7, no more than 6, no more than 5.9, no more than 5.5, no more than 5.0, no more than 4.8, no more than 4.5, no more than 4.4, no more than 4, no more than 3.5, no more than 3, no more than 2.5, no more than 2, no more than 1.5, no more than 1.0, no more than 0.5, no more than 0.3, no more than 0.29, no more than 0.25, no more than 0.21, no more than 0.20, no more than 0.18, no more than 0.17, no more than 0.15, no more than 0.12, no more than 0.10, no more than 0.09, no more than 0.08, no more than 0.07, no more than 0.06, no more than 0.05, no more than 0.04, no more than 0.03, no more than 0.02 or no more than 0.01. For example, the tumor cells with high expression of a specific target point may include, but are not limited to, solid tumor cells; for example, the tumor cells with high expression of a specific target point include, but are not limited to, gastric cancer cells, or breast cancer cells; for example, the tumor cells with high expression of a specific target point may include, but are not limited to, NCI-N87 cells or JIMT-1 cells. The specific target point may include, but is not limited to, HER2 or TROP2.

The compound described herein may have plasma stability. The plasma stability may be that: the compound disclosed herein releases no more than 50%, no more than 40%, no more than 30%, no more than 20%, no more than 10%, no more than 7%, no more than 5%, no more than 4%, no more than 3%, no more than 2%, no more than 1.9%, no more than 1.8%, no more than 1.7%, no more than 1.6%, no more than 1.5%, no more than 1.4%, no more than 1.3%, no more than 1.2%, no more than 1.1%, no more than 1.0%, no more than 0.9%, no more than 0.8%, no more than 0.7%, no more than 0.6%, no more than 0.5%, no more than 0.4%, no more than 0.3%, no more than 0.2% or no more than 0.1% of the cytotoxic drug 1 day, 3 days, 5 days, 7 days, 14 days, 20 days or 30 days after the compound is added to plasma.

The compound described herein may have in vivo tumor-inhibiting effect. The tumor-inhibiting effect may be that: compared with the case where a negative control or a control drug is administered to an animal, the tumor of the animal is reduced in volume by no less than 1%, no less than 2%, no less than 4%, no less than 5%, no less than 8%, no less than 10%, no less than 15%, no less than 18%, no less than 20%, no less than 25%, no less than 40%, no less than 50%, no less than 55%, no less than 60%, no less than 70%, no less than 73%, no less than 75%, no less than 80%, no less than 90% or no less than 95% 1 day, 3 days, 5 days, 7 days, 14 days, 20 days, 21 days or 30 days after the compound disclosed herein is administered, or the tumor of the animal is reduced in volume by no less than 1.1 fold, no less than 1.3 fold, no less than 1.5 fold, no less than 2 fold, no less than 3 fold, no less than 5 fold, no less than 10 fold, no less than 20 fold, no less than 22 fold, no less than 30 fold, no less than 50 fold, no less than 100 fold, no less than 500 fold, no less than 1000 fold or no less than 1500 fold 1 day, 3 days, 5 days, 7 days, 14 days, 20 days, 21 days or 30 days after the compound disclosed herein is administered. The animal may include, but is not limited to, a mammal. For example, the animal may include, but is not limited to, a cat, a dog, a horse, a pig, a cow, a sheep, a rabbit, a mouse, a rat, a monkey or a human. The administration may include, but is not limited to, oral administration, intravenous injection, intravenous drip, intraperitoneal injection or topical administration.

The compound described herein may have a bystander effect. The bystander effect may be that: the compound disclosed herein has no obvious inhibiting effect against cell proliferation of the tumor cells with low expression of a specific target point, but in the co-culturing of the tumor cells with low expression of the specific target point and the tumor cells with high expression of the specific target point, the compound disclosed herein can simultaneously inhibit the cell proliferation of the tumor cells with low expression of the specific target point and the tumor cells with high expression of the specific target point. For example, in the co-culturing of the tumor cells with low expression of the specific target point and the tumor cells with high expression of the specific target point, the inhibiting activity may be an $IC_{50}$ value (nM), for the tumor cells with low expression of the specific target point, of no more than 10000, no more than 5000, no more than 4000, no more than 3000, no more than 2000, no more than 1000, no more than 500, no more than 400, no more than 300, no more than 200, no more than 185, no more than 150, no more than 120, no more than 110, no more than 100, no more than 99, no more than 98, no more than 97, no more than 95, no more than 91, no more than 80, no more than 74, no more than 70, no more than 65, no more than 62, no more than 60, no more than 50, no more than 40, no more than 30, no more than 25, no more than 23, no more than 22, no more than 20, no more than 19, no more than 18, no more than 18.5, no more than 17, no more than 15, no more than 12, no more than 10, no more than 9, no more than 8.5, no more than 7, no more than 6.7, no more than 6, no more than 5.9, no more than 5.5, no more than 5.0, no more than 4.8, no more than 4.5, no more than 4.4, no more than 4, no more than 3.5, no more than 3, no more than 2.5, no more than 2, no more than 1.5, no more than 1.0, no more than 0.5, no more than 0.3, no more than 0.29, no more than 0.25, no more than 0.21, no more than 0.20, no more than 0.18, no more than 0.17, no more than 0.15, no more than 0.12, no more than 0.10, no more than 0.09, no more than 0.08, no more than 0.07, no more than 0.06, no more than 0.05, no more than 0.04, no more than 0.03, no more than 0.02 or no more than 0.01. Compared with in tumor cells with high expression of the specific target point, the expression of the specific target point in tumor cells with low expression of the specific target point may be reduced by no less than 1%, no less than 2%, no less than 4%, no less than 5%, no less than 8%, no less than 10%, no less than 15%, no less than 18%, no less than 20%, no less than 25%, no less than 40%, no less than 50%, no less than 60%, no less than 70%, no less than 80%, no less than 90% or no less than 95%. For example, the tumor cells with high expression of a specific target point may include, but are not limited to, solid tumor cells; for example, the tumor cells with high expression of a specific target point include, but are not limited to, gastric cancer cells, or breast cancer cells; for example, the tumor cells with high expression of a specific target point may include, but are not limited to, NCI-N87 cells or JIMT-1 cells. For example, the tumor cells with low expression of a specific target point may include, but are not limited to, solid tumor cells; for example, the tumor cells with low expression of a specific target point include, but are not limited to, breast cancer cells; for example, the tumor cells with low expression of a specific target point may include, but are not limited to, HCC1187 cells.

The compound described herein may have capacity in inhibiting transport via a transporter. The capacity in inhibiting transport may be a reduction in the efflux ratio of the compound described herein by no less than 1%, no less than 2%, no less than 4%, no less than 5%, no less than 8%, no less than 10%, no less than 15%, no less than 18%, no less than 20%, no less than 25%, no less than 40%, no less than 50%, no less than 60%, no less than 70%, no less than 80%, no less than 90% or no less than 95% compared with a standard of a transport substrate. For example, the testing of the efflux ratio may be a method commonly used by those skilled in the art, or may be described in the examples of the present application.

The compound described herein may have in vivo tumor targeting capability. The in vivo targeting ability may be that: when the compound labeled with a signal substance is administered to an animal, compared with in other tissues and organs of the animal, the distribution of the labeled compound in a tumor tissue may be increased by no less than 1%, no less than 2%, no less than 4%, no less than 5%, no less than 8%, no less than 10%, no less than 15%, no less than 18%, no less than 20%, no less than 25%, no less than 40%, no less than 50%, no less than 60%, no less than 70%, no less than 80%, no less than 90% or no less than 95%, or may be increased by no less than 1.1 fold, no less than 1.3 fold, no less than 1.5 fold, no less than 2 fold, no less than 3 fold, no less than 5 fold, no less than 10 fold, no less than 20 fold, no less than 22 fold, no less than 30 fold, no less than 50 fold, no less than 100 fold, no less than 500 fold, no less than 1000 fold or no less than 1500 fold. The signal substance may be a radioactive material; for example, the signal substance includes, but is not limited to, $^{125}I$. The animal may include, but is not limited to, a mammal. For example, the animal may include, but is not limited to, a cat, a dog, a horse, a pig, a cow, a sheep, a rabbit, a mouse, a rat, a monkey or a human. The administration may include, but is not limited to, oral administration, intravenous injection, intravenous drip, intraperitoneal injection or topical administration. The tissues or organs may include, but are not limited to, heart, liver, spleen, lung, kidney, brain or bone marrow.

The compound described herein may have good in vivo safety. The in vivo safety may be that: after the compound disclosed herein is administered to an animal, the release rate of in vivo free toxin in the animal is no more than 50%, no more than 40%, no more than 30%, no more than 20%, no more than 10%, no more than 7%, no more than 5%, no more than 4%, no more than 3%, no more than 2%, no more than 1.9%, no more than 1.8%, no more than 1.7%, no more than 1.6%, no more than 1.5%, no more than 1.4%, no more than 1.3%, no more than 1.2%, no more than 1.1%, no more than 1.0%, no more than 0.9%, no more than 0.8%, no more than 0.7%, no more than 0.6%, no more than 0.5%, no more than 0.4%, no more than 0.3%, no more than 0.2% or no more than 0.1%. For example, the in vivo safety may be that: the compound described herein may be administered at a concentration of no less than 0.5 mg/kg, no less than 1 mg/kg, no less than 2 mg/kg, no less than 3 mg/kg, no less than 4 mg/kg, no less than 5 mg/kg, no less than 10 mg/kg, no less than 20 mg/kg, no less than 30 mg/kg, no less than 50 mg/kg, no less than 70 mg/kg, no less than 100 mg/kg, no less than 200 mg/kg, no less than 500 mg/kg or no less than 1000 mg/kg without causing toxic manifestation in the animal. For example, the animal may include, but is not limited to, a cat, a dog, a horse, a pig, a cow, a sheep, a rabbit, a mouse, a rat, a monkey or a human. The administration may include, but is not limited to, oral administration, intravenous injection, intravenous drip, intraperitoneal injection or topical administration.

Pharmaceutical Composition

The pharmaceutical composition described herein may contain, in addition to the active compound, one or more adjuvants, which may be selected from the group consisting of the following ingredients: fillers (diluents), binders, wetting agents, disintegrants, excipients, and the like. Depending on the method of administration, the composition may contain 0.1 wt. % to 99% wt. % of the active compound.

The pharmaceutical composition containing the active ingredient may be in a form suitable for oral administration, such as tablet, troche, lozenge, aqueous or oil suspension, dispersible powder or granule, emulsion, hard or soft capsule, or syrup. Oral compositions may be prepared according to any method for preparing pharmaceutical compositions known in the art, and the compositions may contain binders, fillers, lubricants, disintegrants, pharmaceutically acceptable wetting agents, and the like, and may also contain one or more ingredients that may be selected from the group consisting of: sweetening agents, flavouring agents, coloring agents and preservatives.

Aqueous suspensions may contain the active substance in admixture with excipients suitable for the formulation of aqueous suspensions. Aqueous suspensions may also contain one or more preservatives, for example, one or more coloring agents, one or more flavoring agents, and one or more sweetening agents. Oily suspensions may be formulated by suspending the active ingredient in a vegetable oil. These oil suspensions may contain thickening agents. The sweetening agents and the flavoring agents described above may also be added.

The pharmaceutical compositions may also be prepared as follows: dispersible powders or granules for preparing aqueous suspensions provide the active ingredient, and water is added to mix the active ingredient with one or more of dispersing agents, wetting agents, suspending agents or preservatives. Other excipients, such as sweetening agents, flavouring agents and coloring agents, may also be added. These compositions are well preserved by the addition of antioxidants such as ascorbic acid. The pharmaceutical composition disclosed herein may also be in the form of an oil-in-water emulsion.

The pharmaceutical composition may be in the form of a sterile injectable aqueous solution. Available and acceptable vehicles or solvents include water, Ringer's solution and isotonic sodium chloride solution. The sterile injectable formulation may be a sterile injectable oil-in-water microemulsion in which the active ingredient is dissolved in the oil phase. For example, the active ingredient is dissolved in a mixture of soybean oil and lecithin. The oil solution may then be added to a mixture of water and glycerol and treated to form a microemulsion. The injection or microemulsion can be locally injected into the bloodstream of a patient in large quantities. Alternatively, it may be desirable to administer solutions and microemulsions in such a way as to maintain a constant circulating concentration of the compound disclosed herein. To maintain such a constant concentration, a device for continuous intravenous drug delivery may be used. For example, the device may be a Deltec CADD-PLUS™ 5400 intravenous injection pump.

The pharmaceutical composition may be in the form of a sterile injectable aqueous or oily suspension for intramuscular and subcutaneous administration. The suspension may be prepared according to the known art using the suitable dispersing agents or wetting agents and suspending agents described above. The sterile injectable formulation may also be a sterile injection or suspension prepared in a parenterally acceptable non-toxic diluent or solvent. Alternatively, a sterile fixed oil may be conveniently used as a solvent or a suspending medium.

The compound disclosed herein may be administered in the form of a suppository for rectal administration. These pharmaceutical compositions may be prepared by mixing a drug with a suitable non-irritating excipient which may be solid at ordinary temperatures but liquid in the rectum and will therefore melt in the rectum to release the drug. Such materials include cocoa butter, glycerinated gelatin, hydrogenated vegetable oils, and mixtures of polyethylene glycols of various molecular weights and fatty acid esters of polyethylene glycol.

As is well known to those skilled in the art, the dosage of the drug administered depends on a variety of factors, including but not limited to, the activity of the particular compound employed, the age of the patient, the weight of the patient, the health condition of the patient, the behavior of the patient, the diet of the patient, the time of administration, the mode of administration, the rate of excretion, the combination of drugs, and the like. In addition, the optimal treatment regimen, such as the mode of treatment, a compound described herein or a tautomer, a mesomer, a racemate, an enantiomer or a diastereoisomer thereof, or a mixture thereof, or a pharmaceutically acceptable salt thereof, and/or the daily amount of the compound or the tautomer, the mesomer, the racemate, the enantiomer or the diastereoisomer thereof, or the mixture thereof, or the pharmaceutically acceptable salt thereof, or the type of the pharmaceutically acceptable salt thereof, can be verified according to conventional treatment schemes.

Technical Schemes for Synthesis

For the synthesis purpose of the present disclosure, the following technical schemes for synthesis are adopted in the present application:

Scheme I A:

Provided is a method for preparing a compound of general formula (I-E) or a pharmaceutically acceptable salt or a solvate thereof disclosed herein, which comprises:

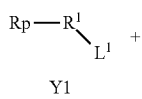

-continued

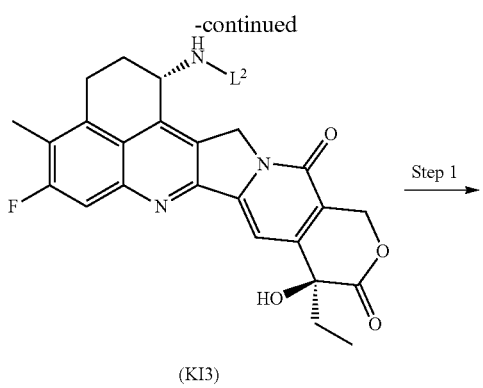

(KI3)

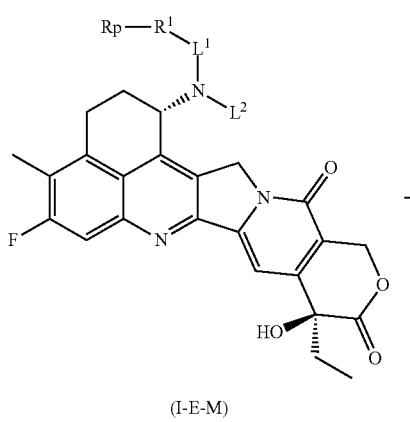

(I-E-M)

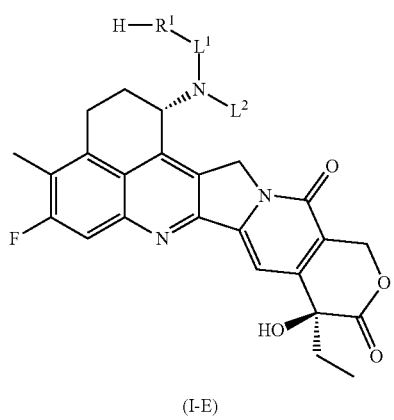

(I-E)

Step 1: reacting a compound of general formula (Y1) with a compound of general formula (KI3) in the presence of a condensing agent, optionally under a basic condition, to obtain a compound of general formula (I-E-M)

Step 2: removing a protecting group of the compound of general formula (I-E-M) to obtain the compound of general formula (I-E)

wherein,

Rp is a hydroxy protecting group;

$R^1$, $L^1$ and $L^2$ are defined as in any formula (I-A) in embodiments of the first aspect.

Reagents that provide basic conditions include organic bases and inorganic bases, wherein the organic bases include, but are not limited to, triethylamine, diethylamine, N-methylmorpholine, pyridine, piperidine, N,N-diisopropylethylamine, n-butyllithium, lithium diisopropylamide, potassium acetate, sodium tert-butoxide, potassium tert-butoxide, and the like, and the inorganic bases include, but are not limited to, sodium hydride, potassium carbonate, sodium carbonate, cesium carbonate, sodium hydroxide, lithium hydroxide, and the like.

The condensing agent may be selected from the group consisting of 4-(4,6-dimethoxy-1,3,5-triazin-2-yl)-4-methylmorpholinium chloride, 1-hydroxybenzotriazole and 1-(3-dimethylaminopropyl)-3-ethylcarbodiimide hydrochloride, N,N'-dicyclohexylcarbodiimide, N,N-diisopropylcarbodiimide, O-benzotriazol-N,N,N',N'-tetramethyluronium tetrafluoroborate, 1-hydroxybenzotriazole, 1-hydroxy-7-azobenzotriazol, O-benzotriazol-N,N,N',N'-tetramethyluronium hexafluorophosphate, 2-(7-azobenzotriazol)-N,N,N',N'-tetramethyluronium hexafluorophosphate, benzotriazol-1-yloxytris(dimethylamino)phosphonium hexafluorophosphate, and benzotriazol-1-yl-oxytripyrrolidinophosphonium hexafluorophosphate, preferably 4-(4,6-dimethoxy-1,3,5-triazin-2-yl)-4-methylmorpholinium chloride, or 1-hydroxybenzotriazole and 1-(3-dimethylaminopropyl)-3-ethylcarbodiimide hydrochloride.

Scheme I B

Provided is a method for preparing a compound of general formula (I-E) or a pharmaceutically acceptable salt or a solvate thereof disclosed herein, which comprises:

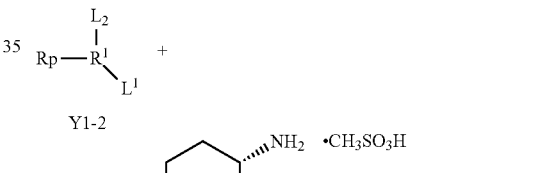

Y1-2

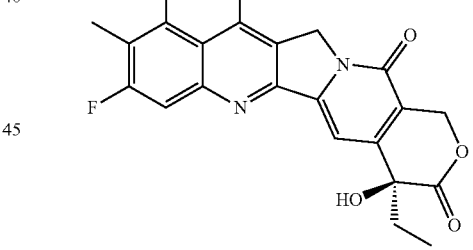

(KI4)

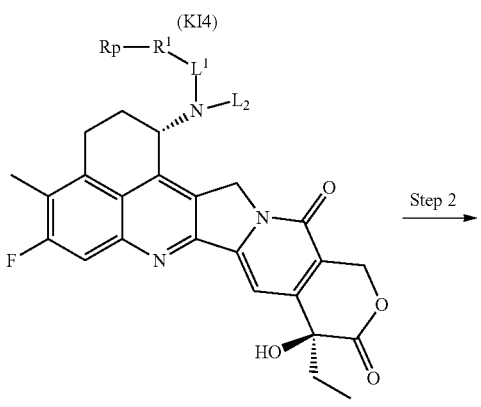

(I-E-M)

-continued

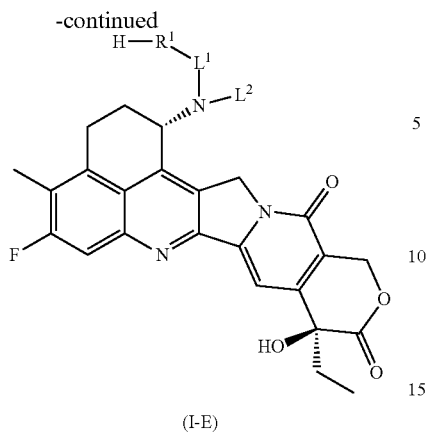

(I-E)

wherein R¹ is selected from the group consisting of: —O—, —(R²)N—, —P(=O)(R²)— and —S—;
L² is —(C(R$^{3a}$)(R$^{3b}$))$_m$—R,
wherein 0 or no less than 1 methylene unit of L² is independently replaced by -Cy-, —N(R⁴)C(O)—, —C(O)N(R⁴)—, —C(O)—, —OC(O)—, —C(O)O—, —NR⁴—, —O—, —S—, —SO—, —SO₂—, —P(R⁴)—, —P(=O)(R⁴)—, —N(R⁴)SO₂—, —SO₂N(R⁴)—, —C(=S)—, —C(=NR⁴)—, —N=N—, —C=N—, —N=C— or —C(=N₂)—;
L¹ is —(C(R$^{5a}$)(R$^{5b}$))$_n$—,
wherein 0 or no less than 1 methylene unit of L' is independently replaced by -Cy-, —N(R⁶)C(O)—, —C(O)N(R⁶)—, —C(O)—, —OC(O)—, —C(O)O—, —NR⁶—, —O—, —S—, —SO—, —SO₂—, —P(R⁶)—, —P(=O)(R⁶)—, —N(R⁶)SO₂—, —SO₂N(R⁶)—, —C(=S)—, —C(=NR⁶)—, —N=N—, —C=N—, —N=C— or —C(=N₂)—;
-Cy- is selected from the group consisting of: 6-10 membered arylene, 5-8 membered heteroarylene, 3-10 membered heterocyclylene, and 3-10 membered saturated or partially unsaturated carbocyclylene, wherein -Cy- is unsubstituted or independently substituted with no less than 1 substituent R⁷;
for example, wherein, R$^{3a}$ and R$^{5a}$ form a ring B together with an atom therebetween, wherein the ring B may be selected from the group consisting of: 5-8 membered heteroarylene and 3-10 membered saturated or partially unsaturated heterocyclylene, and the ring B is unsubstituted or substituted with no less than 1 substituent R⁸; each R$^{3b}$, each R⁴, each R$^{5b}$ and each R⁶ are each independently hydrogen, protium, deuterium, tritium, halogen, —NO₂, —CN, —OR, —SR, —N(R$^a$)(R$^b$), —C(O)R, —CO₂R, —C(O)C(O)R, —C(O)CH₂C(O)R, —S(O)R, —S(O)₂R, —C(O)N(R$^a$)(R$^b$), —SO₂N(R$^a$)(R$^b$), —OC(O)R, —N(R)SO₂R, or a C$_{1-6}$ aliphatic group optionally substituted with R; or R$^{3a}$ and R$^{5a}$, R⁴ and R$^{5a}$, R$^{3a}$ and R⁶ or R⁴ and R⁶ each independently optionally form a ring B together with an atom therebetween, wherein the ring B is selected from the group consisting of: 5-8 membered heteroarylene and 3-10 membered saturated or partially unsaturated heterocyclylene, and the ring B is unsubstituted or substituted with no less than 1 substituent R⁸;
for example, wherein, R⁴ and R$^{5a}$ form a ring B together with an atom therebetween, wherein the ring B is selected from the group consisting of: 5-8 membered heteroarylene and 3-10 membered saturated or partially unsaturated heterocyclylene, and the ring B is unsubstituted or substituted with no less than 1 substituent R⁸; each R$^{3a}$, each R$^{3b}$, each R$^{5b}$ and each R⁶ are each independently hydrogen, protium, deuterium, tritium, halogen, —NO₂, —CN, —OR, —SR, —N(R$^a$)(R$^b$), —C(O)R, —CO₂R, —C(O)C(O)R, —C(O)CH₂C(O)R, —S(O)R, —S(O)₂R, —C(O)N(R$^a$)(R$^b$), —SO₂N(R$^a$)(R$^b$), —OC(O)R, —N(R)SO₂R, or a C$_{1-6}$ aliphatic group optionally substituted with R; or R$^{3a}$ and R$^{5a}$, R⁴ and R$^{5a}$, R$^{3a}$ and R⁶ or R⁴ and R⁶ each independently optionally form a ring B together with an atom therebetween, wherein the ring B is selected from the group consisting of: 5-8 membered heteroarylene and 3-10 membered saturated or partially unsaturated heterocyclylene, and the ring B is unsubstituted or substituted with no less than 1 substituent R⁸;

for example, wherein, R$^{3a}$ and R⁶ form a ring B together with an atom therebetween, wherein the ring B is selected from the group consisting of: 5-8 membered heteroarylene and 3-10 membered saturated or partially unsaturated heterocyclylene, and the ring B is unsubstituted or substituted with no less than 1 substituent R⁸; each R$^{3b}$, each R⁴, each R$^{5a}$ and each R$^{5b}$ are each independently hydrogen, protium, deuterium, tritium, halogen, —NO₂, —CN, —OR, —SR, —N(R$^a$)(R$^b$), —C(O)R, —CO₂R, —C(O)C(O)R, —C(O)CH₂C(O)R, —S(O)R, —S(O)₂R, —C(O)N(R$^a$)(R$^b$), —SO₂N(R$^a$)(R$^b$), —OC(O)R, —N(R)SO₂R, or a C$_{1-6}$ aliphatic group optionally substituted with R; or R$^{3a}$ and R$^{5a}$, R⁴ and R$^{5a}$, R$^{3a}$ and R⁶ or R⁴ and R⁶ each independently optionally form a ring B together with an atom therebetween, wherein the ring B is selected from the group consisting of: 5-8 membered heteroarylene and 3-10 membered saturated or partially unsaturated heterocyclylene, and the ring B is unsubstituted or substituted with no less than 1 substituent R⁸;

for example, wherein, R⁴ and R⁶ independently optionally form a ring B together with an atom therebetween, wherein the ring B is selected from the group consisting of: 5-8 membered heteroarylene and 3-10 membered saturated or partially unsaturated heterocyclylene, and the ring B is unsubstituted or substituted with no less than 1 substituent R⁸; each R$^{3a}$, each R$^{3b}$, each R$^{5a}$ and each R$^{5b}$ are each independently hydrogen, protium, deuterium, tritium, halogen, —NO₂, —CN, —OR, —SR, —N(R$^a$)(R$^b$), —C(O)R, —CO₂R, —C(O)C(O)R, —C(O)CH₂C(O)R, —S(O)R, —S(O)₂R, —C(O)N(R$^a$)(R$^b$), —SO₂N(R$^a$)(R$^b$), —OC(O)R, —N(R)SO₂R, or a C$_{1-6}$ aliphatic group optionally substituted with R; or R$^{3a}$ and R$^{5a}$, R⁴ and R$^{5a}$, R$^{3a}$ and R⁶ or R⁴ and R⁶ each independently optionally form a ring B together with an atom therebetween, wherein the ring B is selected from the group consisting of: 5-8 membered heteroarylene and 3-10 membered saturated or partially unsaturated heterocyclylene, and the ring B is unsubstituted or substituted with no less than 1 substituent R⁸;

wherein each R², each R⁷ and each R⁸ are each independently hydrogen, protium, deuterium, tritium, halogen, —NO₂, —CN, —OR, —SR, —N(R$^a$)(R$^b$), —C(O)R, —CO₂R, —C(O)C(O)R, —C(O)CH₂C(O)R, —S(O)R, —S(O)₂R, —C(O)N(R$^a$)(R$^b$), —SO₂N(R$^a$)(R$^b$), —OC(O)R, —N(R)SO₂R, or a C$_{1-6}$ aliphatic group optionally substituted with R;

wherein each R, each R$^a$ and each R$^b$ are each independently hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)

H, —S(O)₂H, —C(O)NH₂, —SO₂NH₂, —OC(O)H, —N(H)SO₂H or a $C_{1-6}$ aliphatic group;

m and n are each independently selected from the group consisting of integers ≥1.

Step 1: reacting a compound of general formula (Y1-2) with a compound of general formula (KI4) in the presence of or in the absence of a reducing agent under an acidic or basic condition to obtain a compound of general formula (I-E-M)

Step 2: removing a protecting group of the compound of general formula (I-E-M) to obtain the compound of general formula (I-E)

wherein,

Rp is a hydroxy protecting group;

$R^1$, $L^1$ and $L^2$ are defined as in any formula (I-A) in embodiments of the first aspect.

Reducing agents include, but are not limited to, sodium hydride, calcium hydride, lithium hydride, lithium aluminum hydride, sodium borohydride, lithium borohydride, sodium triethylborohydride, sodium triacetoxyborohydride and sodium cyanoborohydride.

Reagents that provide acidic conditions include a protic acid and a Lewis acid, wherein the protic acid includes, but is not limited to, hydrochloric acid, sulfuric acid, nitric acid, nitrous acid, sulfurous acid, phosphoric acid, phosphorous acid, formic acid, acetic acid, propionic acid, butyric acid, citric acid, benzoic acid, p-toluenesulfonic acid, p-nitrobenzoic acid, methanesulfonic acid, trifluoromethanesulfonic acid and trifluoroacetic acid, and the Lewis acid includes, but is not limited to, boron trifluoride, zinc chloride, magnesium chloride, aluminum chloride, stannic chloride and ferric chloride.

Reagents that provide basic conditions include organic bases and inorganic bases, wherein the organic bases include, but are not limited to, triethylamine, diethylamine, N-methylmorpholine, pyridine, piperidine, N,N-diisopropylethylamine, n-butyllithium, lithium diisopropylamide, potassium acetate, sodium tert-butoxide, potassium tert-butoxide, and the like, and the inorganic bases include, but are not limited to, sodium hydride, potassium carbonate, sodium carbonate, cesium carbonate, sodium hydroxide, lithium hydroxide, and the like.

The condensing agent may be selected from the group consisting of 4-(4,6-dimethoxy-1,3,5-triazin-2-yl)-4-methylmorpholinium chloride, 1-hydroxybenzotriazole and 1-(3-dimethylaminopropyl)-3-ethylcarbodiimide hydrochloride, N,N'-dicyclohexylcarbodiimide, N,N-diisopropylcarbodiimide, O-benzotriazol-N,N,N',N'-tetramethyluronium tetrafluoroborate, 1-hydroxybenzotriazole, 1-hydroxy-7-azobenzotriazol, O-benzotriazol-N,N,N',N'-tetramethyluronium hexafluorophosphate, 2-(7-azobenzotriazol)-N,N,N',N'-tetramethyluronium hexafluorophosphate, benzotriazol-1-yloxytris(dimethylamino)phosphonium hexafluorophosphate, and benzotriazol-1-yl-oxytripyrrolidinophosphonium hexafluorophosphate, preferably 4-(4,6-dimethoxy-1,3,5-triazin-2-yl)-4-methylmorpholinium chloride, or 1-hydroxybenzotriazole and 1-(3-dimethylaminopropyl)-3-ethylcarbodiimide hydrochloride.

Scheme II:

Provided is a method for preparing a compound of general formula (II-E) (including a compound of general formula (II-Ex) or general formula (II-Ey)) or a pharmaceutically acceptable salt or a solvate thereof disclosed herein, which comprises:

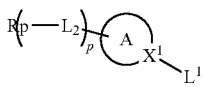

Y2x or +

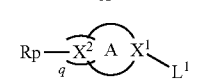

Y2y

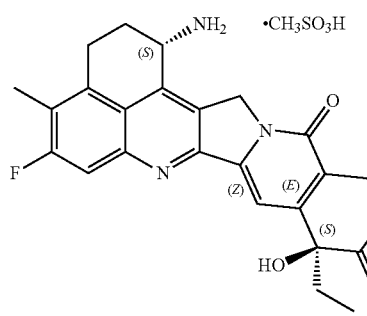

KI4

Step 1 →

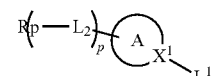

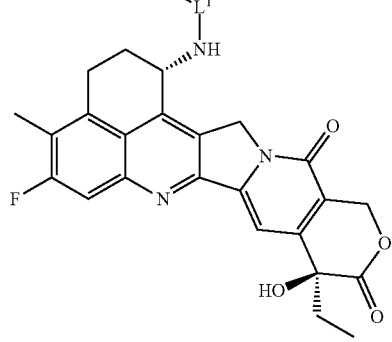

(II-Ex-M)

or

Step 2 →

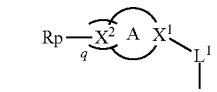

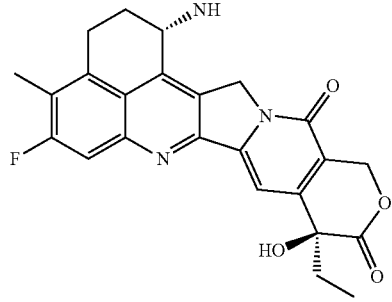

(II-Ey-M)

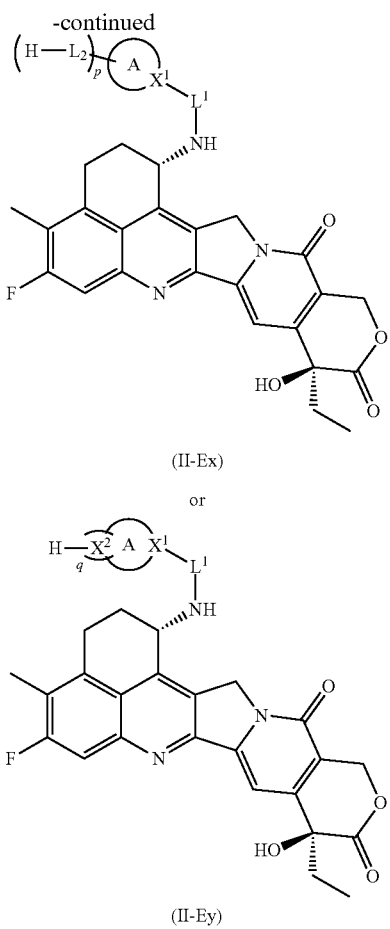

(II-Ex)

or (II-Ey)

Step 1: reacting a compound of general formula (Y2x) or a compound of general formula (Y2y) with a compound of formula (KI4) in the presence of a condensing agent, optionally under a basic condition, to obtain a compound of general formula (II-Ex-M) or general formula (II-Ey-M)

Step 2: removing a protecting group of the compound of general formula (II-Ex-M) or general formula (II-Ey-M) to obtain the compound of general formula (II-Ex) or general formula (II-Ey)

wherein,

Rp is a hydroxy protecting group;

wherein $L^2$, p, ring A, $X^1$ and $L^1$ are defined as in any (II-Ax) in embodiments of the first aspect;

or $X^2$, q, ring A, $X^1$ and $L^1$ are defined as in any (II-Ay) in embodiments of the first aspect.

Reagents that provide basic conditions include organic bases and inorganic bases, wherein the organic bases include, but are not limited to, triethylamine, diethylamine, N-methylmorpholine, pyridine, piperidine, N,N-diisopropylethylamine, n-butyllithium, lithium diisopropylamide, potassium acetate, sodium tert-butoxide, potassium tert-butoxide, and the like, and the inorganic bases include, but are not limited to, sodium hydride, potassium carbonate, sodium carbonate, cesium carbonate, sodium hydroxide, lithium hydroxide, and the like.

The condensing agent may be selected from the group consisting of 4-(4,6-dimethoxy-1,3,5-triazin-2-yl)-4-methylmorpholinium chloride, 1-hydroxybenzotriazole and 1-(3-dimethylaminopropyl)-3-ethylcarbodiimide hydrochloride, N,N'-dicyclohexylcarbodiimide, N,N-diisopropylcarbodiimide, O-benzotriazol-N,N,N',N'-tetramethyluronium tetrafluoroborate, 1-hydroxybenzotriazole, 1-hydroxy-7-azobenzotriazol, O-benzotriazol-N,N,N',N'-tetramethyluronium hexafluorophosphate, 2-(7-azobenzotriazol)-N,N,N',N'-tetramethyluronium hexafluorophosphate, benzotriazol-1-yloxytris(dimethylamino)phosphonium hexafluorophosphate, and benzotriazol-1-yl-oxytripyrrolidinophosphonium hexafluorophosphate, preferably 4-(4,6-dimethoxy-1,3,5-triazin-2-yl)-4-methylmorpholinium chloride, or 1-hydroxybenzotriazole and 1-(3-dimethylaminopropyl)-3-ethylcarbodiimide hydrochloride.

Scheme III:

Provided is a method for preparing a compound of general formula (III-E) or a pharmaceutically acceptable salt or a solvate thereof disclosed herein, which comprises:

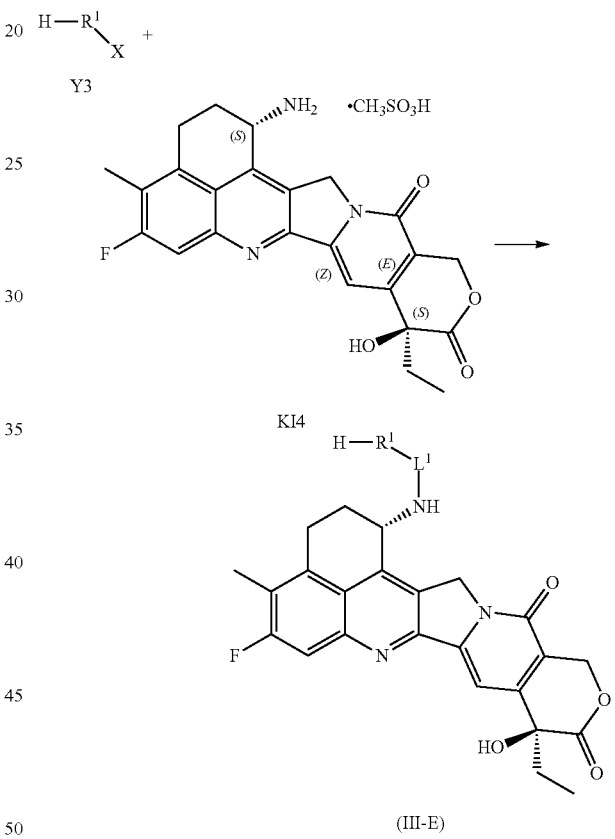

reacting a compound of general formula (Y3) with a compound of general formula (KI4) in the presence of a condensing agent, optionally under a basic condition, to obtain the compound of general formula (III-E-M).

wherein, $R^1$ and X are defined as in any (III-A) in embodiments of the first aspect.

Reagents that provide basic conditions include organic bases and inorganic bases, wherein the organic bases include, but are not limited to, triethylamine, diethylamine, N-methylmorpholine, pyridine, piperidine, N,N-diisopropylethylamine, n-butyllithium, lithium diisopropylamide, potassium acetate, sodium tert-butoxide, potassium tert-butoxide, and the like, and the inorganic bases include, but are not limited to, sodium hydride, potassium carbonate, sodium carbonate, cesium carbonate, sodium hydroxide, lithium hydroxide, and the like.

The condensing agent may be selected from the group consisting of 4-(4,6-dimethoxy-1,3,5-triazin-2-yl)-4-methylmorpholinium chloride, 1-hydroxybenzotriazole and 1-(3-dimethylaminopropyl)-3-ethylcarbodiimide hydrochloride, N,N'-dicyclohexylcarbodiimide, N,N'-diisopropylcarbodiimide, O-benzotriazol-N,N,N',N'-tetramethyluronium tetrafluoroborate, 1-hydroxybenzotriazole, 1-hydroxy-7-azobenzotriazol, O-benzotriazol-N,N,N',N'-tetramethyluronium hexafluorophosphate, 2-(7-azobenzotriazol)-N,N,N',N'-tetramethyluronium hexafluorophosphate, benzotriazol-1-yloxytris(dimethylamino)phosphonium hexafluorophosphate, and benzotriazol-1-yl-oxytripyrrolidinophosphonium hexafluorophosphate, preferably 4-(4,6-dimethoxy-1,3,5-triazin-2-yl)-4-methylmorpholinium chloride, or 1-hydroxybenzotriazole and 1-(3-dimethylaminopropyl)-3-ethylcarbodiimide hydrochloride.

Scheme IV A

Provided is a method for preparing a compound of general formula (I-F) or a pharmaceutically acceptable salt or a solvate thereof disclosed herein, which comprises:

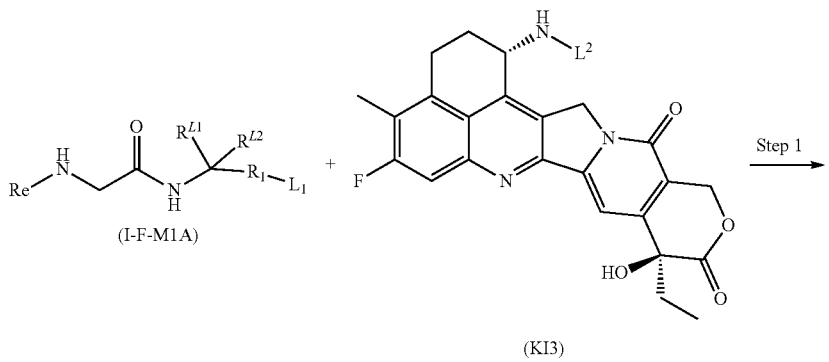

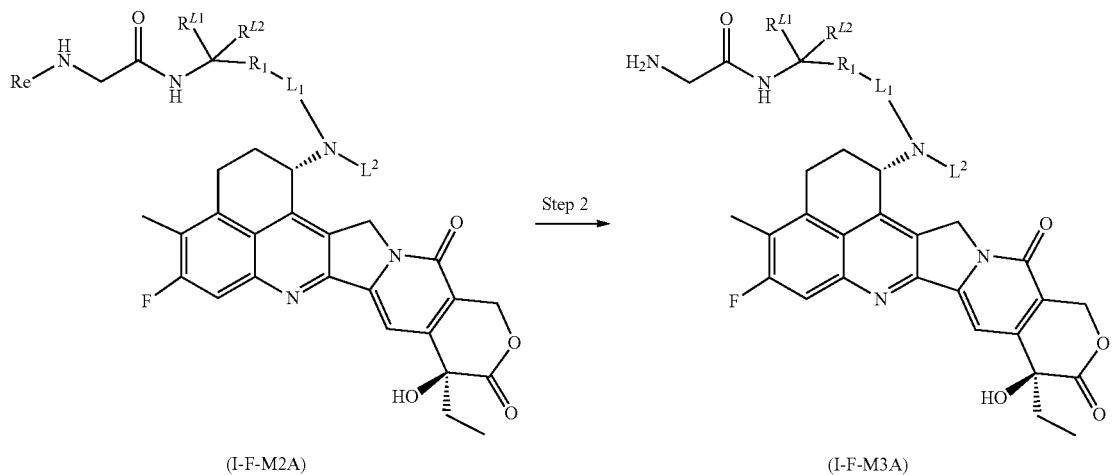

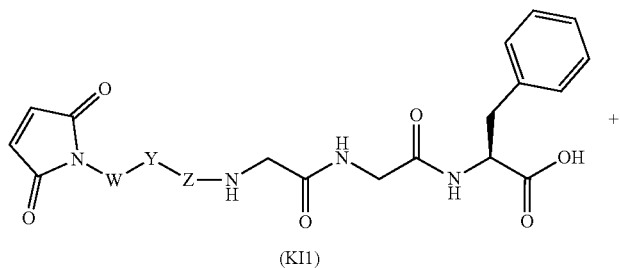

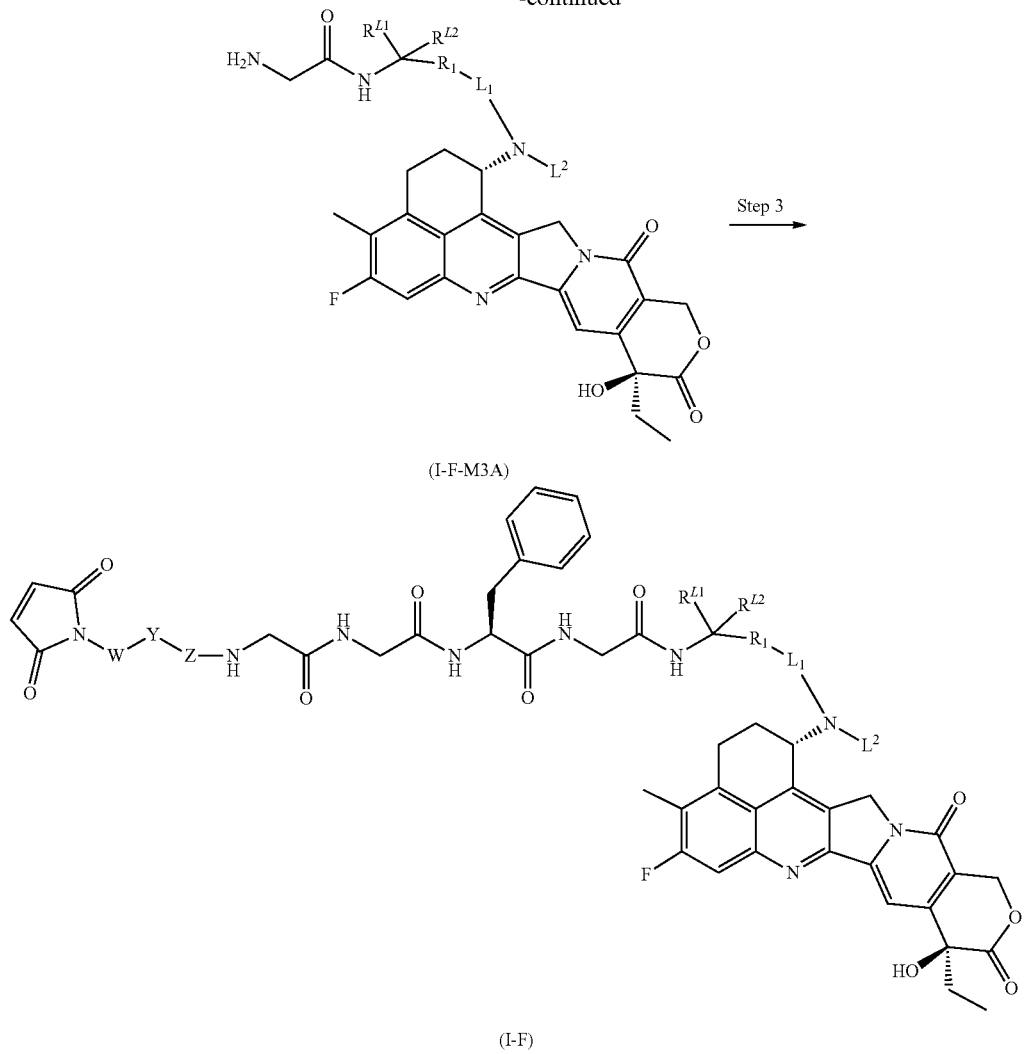

(I-F-M3A)

(I-F)

Step 1: reacting a compound of general formula (I-F-M1A) with a compound of general formula (KI3) in the presence of a condensing agent, optionally under a basic condition, to obtain a compound of general formula (I-F-M2A)

Step 2: removing a protecting group of the compound of general formula (I-F-M2A) to obtain a compound of general formula (I-F-M3A)

Step 3: reacting a compound of general formula (KI1) with the compound of general formula (I-F-M3A) in the presence of a condensing agent, optionally under a basic condition, to obtain the compound of general formula (I-F) wherein, Re is an amino protecting group, preferably Fomc;

W, Y, Z, $R^{L1}$, $R^{L2}$, $R^1$, $L^1$ and $L^2$ are defined as in any formula (I-F) in embodiments of the sixth aspect.

Reagents that provide basic conditions include organic bases and inorganic bases, wherein the organic bases include, but are not limited to, triethylamine, diethylamine, N-methylmorpholine, pyridine, piperidine, N,N-diisopropylethylamine, n-butyllithium, lithium diisopropylamide, potassium acetate, sodium tert-butoxide, potassium tert-butoxide, and the like, and the inorganic bases include, but are not limited to, sodium hydride, potassium carbonate, sodium carbonate, cesium carbonate, sodium hydroxide, lithium hydroxide, and the like.

The condensing agent may be selected from the group consisting of 4-(4,6-dimethoxy-1,3,5-triazin-2-yl)-4-methylmorpholinium chloride, 1-hydroxybenzotriazole and 1-(3-dimethylaminopropyl)-3-ethylcarbodiimide hydrochloride, N,N'-dicyclohexylcarbodiimide, N,N'-diisopropylcarbodiimide, O-benzotriazol-N,N,N',N'-tetramethyluronium tetrafluoroborate, 1-hydroxybenzotriazole, 1-hydroxy-7-azobenzotriazol, O-benzotriazol-N,N,N',N'-tetramethyluronium hexafluorophosphate, 2-(7-azobenzotriazol)-N,N,N',N'-tetramethyluronium hexafluorophosphate, benzotriazol-1-yloxytris(dimethylamino)phosphonium hexafluorophosphate, and benzotriazol-1-yl-oxytripyrrolidinophosphonium hexafluorophosphate, preferably 4-(4,6-dimethoxy-1,3,5-triazin-2-yl)-4-methylmorpholinium chloride, or 1-hydroxybenzotriazole and 1-(3-dimethylaminopropyl)-3-ethylcarbodiimide hydrochloride.

Scheme IV B

Provided is a method for preparing a compound of general formula (I-F) or a pharmaceutically acceptable salt or a solvate thereof disclosed herein, which comprises:

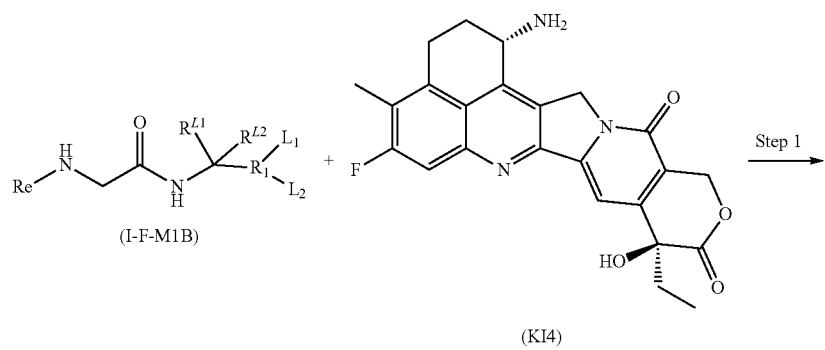
(I-F-M1B) + (KI4) → Step 1
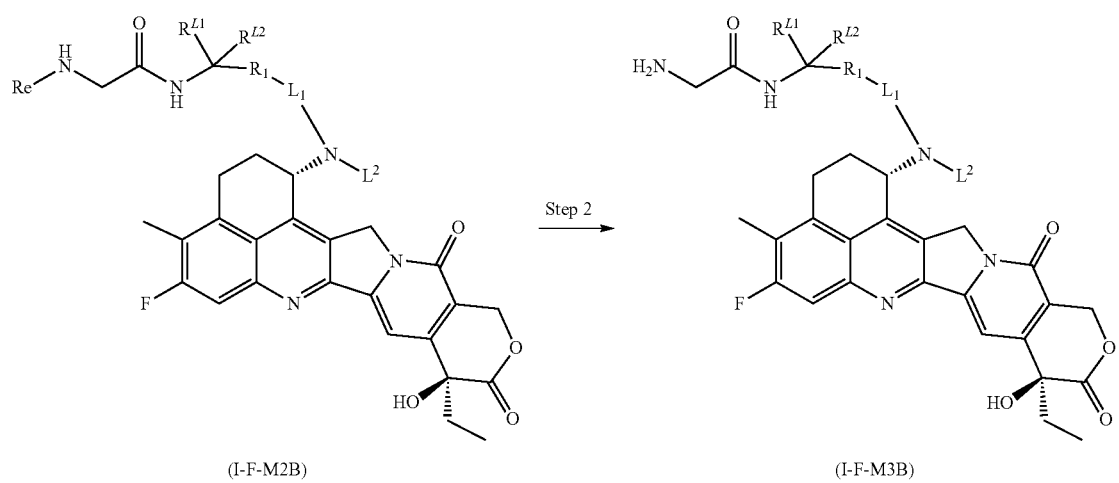
(I-F-M2B) → Step 2 → (I-F-M3B)
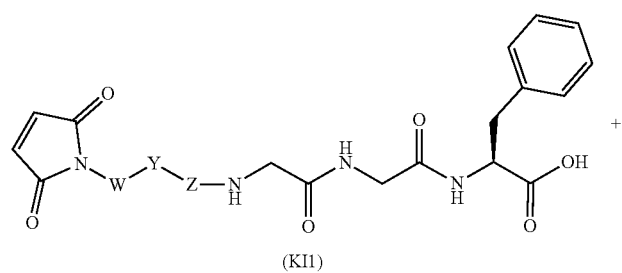
(KI1) +
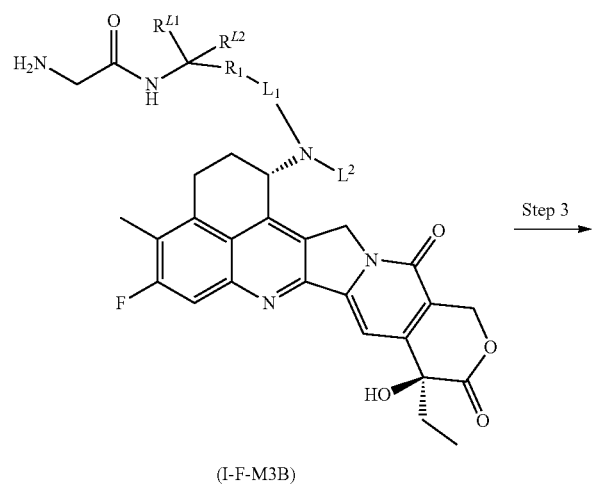
(I-F-M3B) → Step 3

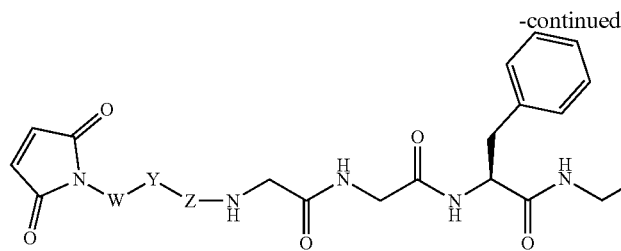

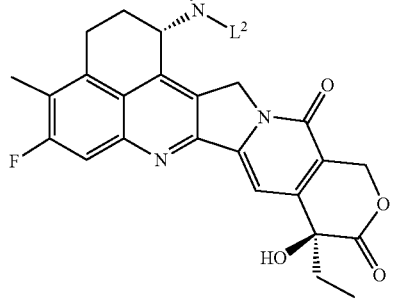

(I-F)

wherein R¹ is selected from the group consisting of: —O—, —(R²)N—, —P(=O)(R²)— and —S—;
L² is —(C(R$^{3a}$)(R$^{3b}$))$_m$—R,
wherein 0 or no less than 1 methylene unit of L² is independently replaced by -Cy-, —N(R⁴)C(O)—, —C(O)N(R⁴)—, —C(O)—, —OC(O)—, —C(O)O—, —NR⁴—, —O—, —S—, —SO—, —SO₂—, —P(R⁴)—, —P(=O)(R⁴)—, —N(R⁴)SO₂—, —SO₂N(R⁴)—, —C(=S)—, —C(=NR⁴)—, —N=N—, —C=N—, —N=C— or —C(=N₂)—;
L¹ is —(C(R$^{5a}$)(R$^{5b}$))$_n$—,
wherein 0 or no less than 1 methylene unit of L¹ is independently replaced by -Cy-, —N(R⁶)C(O)—, —C(O)N(R⁶)—, —C(O)—, —OC(O)—, —C(O)O—, —NR⁶—, —O—, —S—, —SO—, —SO₂—, —P(R⁶)—, —P(=O)(R⁶)—, —N(R⁶)SO₂—, —SO₂N(R⁶)—, —C(=S)—, —C(=NR⁶)—, —N=N—, —C=N—, —N=C— or —C(=N₂)—;
-Cy- is selected from the group consisting of: 6-10 membered arylene, 5-8 membered heteroarylene, 3-10 membered heterocyclylene, and 3-10 membered saturated or partially unsaturated carbocyclylene, wherein -Cy- is unsubstituted or independently substituted with no less than 1 substituent R⁷;
wherein each R$^{3a}$, each R$^{3b}$, each R⁴, each R$^{5a}$, each R$^{5b}$ and each R⁶ are each independently hydrogen, protium, deuterium, tritium, halogen, —NO₂, —CN, —OR, —SR, —N(R$^a$)(R$^b$), —C(O)R, —CO₂R, —C(O)C(O)R, —C(O)CH₂C(O)R, —S(O)R, —S(O)₂R, —C(O)N(R$^a$)(R$^b$), —SO₂N(R$^a$)(R$^b$), —OC(O)R, —N(R)SO₂R, or a C$_{1-6}$ aliphatic group optionally substituted with R;
or, R$^{3a}$ and R$^{5a}$, R⁴ and R$^{5a}$, R$^{3a}$ and R⁶ or R⁴ and R⁶ each independently optionally form a ring B together with an atom therebetween, wherein the ring B is selected from the group consisting of: 5-8 membered heteroarylene and 3-10 membered saturated or partially unsaturated heterocyclylene, and the ring B is unsubstituted or independently substituted with no less than 1 substituent R⁸;
wherein each R², each R⁷ and each R⁸ are each independently hydrogen, protium, deuterium, tritium, halogen, —NO₂, —CN, —OR, —SR, —N(R$^a$)(R$^b$), —C(O)R, —CO₂R, —C(O)C(O)R, —C(O)CH₂C(O)R, —S(O)R, —S(O)₂R, —C(O)N(R$^a$)(R$^b$), —SO₂N(R$^a$)(R$^b$), —OC(O)R, —N(R)SO₂R, or a C$_{1-6}$ aliphatic group optionally substituted with R;
wherein each R, each R$^a$ and each R$^b$ are each independently hydrogen, protium, deuterium, tritium, halogen, —NO₂, —CN, —OH, —SH, —NH₂, —C(O)H, —CO₂H, —C(O)C(O)H, —C(O)CH₂C(O)H, —S(O)H, —S(O)₂H, —C(O)NH₂, —SO₂NH₂, —OC(O)H, —N(H)SO₂H or a C$_{1-6}$ aliphatic group;
m and n are each independently selected from the group consisting of integers ≥1.

Step 1: reacting a compound of general formula (I-F-M1B) with a compound of general formula (KI3) in the presence of or in the absence of a reducing agent, optionally under an acidic or basic condition, to obtain a compound of general formula (I-F-M2B)

Step 2: removing a protecting group of the compound of general formula (I-F-M2B) to obtain a compound of general formula (I-F-M3B)

Step 3: reacting a compound of general formula (KI1) with the compound of general formula (I-F-M3B) in the presence of a condensing agent, optionally under a basic condition, to obtain the compound of general formula (I-F) wherein, Re is an amino protecting group, preferably Fomc;

W, Y, Z, R$^{L1}$, R$^{L2}$, R¹, L¹ and L² are defined as in any formula (I-F) in embodiments of the sixth aspect.

Reducing agents include, but are not limited to, sodium hydride, calcium hydride, lithium hydride, lithium aluminum hydride, sodium borohydride, lithium borohydride, sodium triethylborohydride, sodium triacetoxyborohydride and sodium cyanoborohydride.

Reagents that provide acidic conditions include a protic acid and a Lewis acid, wherein the protic acid includes, but is not limited to, hydrochloric acid, sulfuric acid, nitric acid, nitrous acid, sulfurous acid, phosphoric acid, phosphorous acid, formic acid, acetic acid, propionic acid, butyric acid, citric acid, benzoic acid, p-toluenesulfonic acid, p-nitrobenzoic acid, methanesulfonic acid, trifluoromethanesulfonic acid and trifluoroacetic acid, and the Lewis acid includes, but is not limited to, boron trifluoride, zinc chloride, magnesium chloride, aluminum chloride, stannic chloride and ferric chloride.

Reagents that provide basic conditions include organic bases and inorganic bases, wherein the organic bases include, but are not limited to, triethylamine, diethylamine, N-methylmorpholine, pyridine, piperidine, N,N-diisopropylethylamine, n-butyllithium, lithium diisopropylamide, potassium acetate, sodium tert-butoxide, potassium tert-butoxide, and the like, and the inorganic bases include, but are not limited to, sodium hydride, potassium carbonate, sodium carbonate, cesium carbonate, sodium hydroxide, lithium hydroxide, and the like.

The condensing agent may be selected from the group consisting of 4-(4,6-dimethoxy-1,3,5-triazin-2-yl)-4-methylmorpholinium chloride, 1-hydroxybenzotriazole and 1-(3-dimethylaminopropyl)-3-ethylcarbodiimide hydrochloride, N,N'-dicyclohexylcarbodiimide, N,N'-diisopropylcarbodiimide, O-benzotriazol-N,N,N',N'-tetramethyluronium tetrafluoroborate, 1-hydroxybenzotriazole, 1-hydroxy-7-azobenzotriazol, O-benzotriazol-N,N,N',N'-tetramethyluronium hexafluorophosphate, 2-(7-azobenzotriazol)-N,N,N',N'-tetramethyluronium hexafluorophosphate, benzotriazol-1-yloxytris(dimethylamino)phosphonium hexafluorophosphate, and benzotriazol-1-yl-oxytripyrrolidinophosphonium hexafluorophosphate, preferably 4-(4,6-dimethoxy-1,3,5-triazin-2-yl)-4-methylmorpholinium chloride, or 1-hydroxybenzotriazole and 1-(3-dimethylaminopropyl)-3-ethylcarbodiimide hydrochloride.

Scheme IV C

Provided is a method for preparing a compound of general formula (I-F) or a pharmaceutically acceptable salt or a solvate thereof disclosed herein, which comprises:

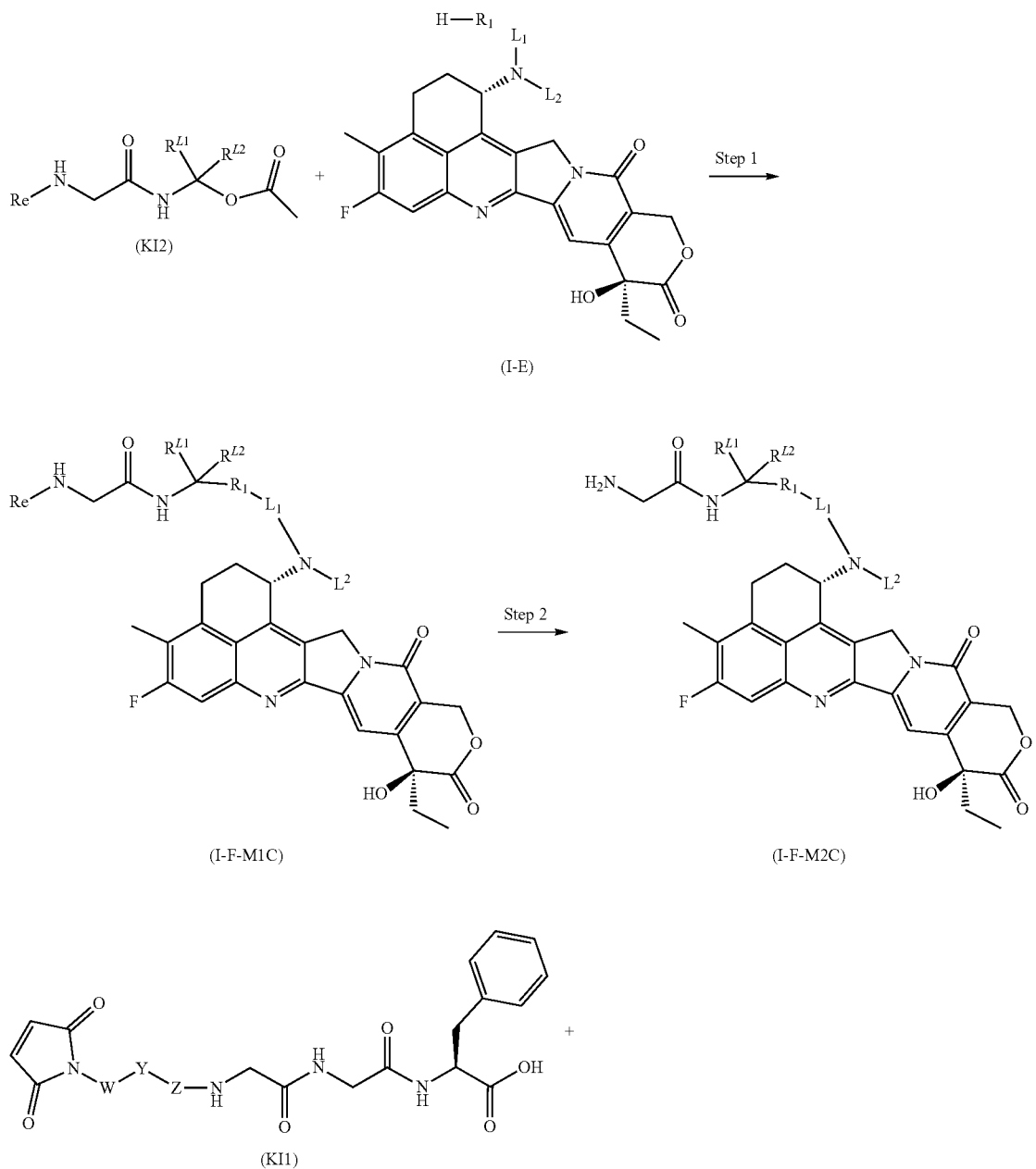

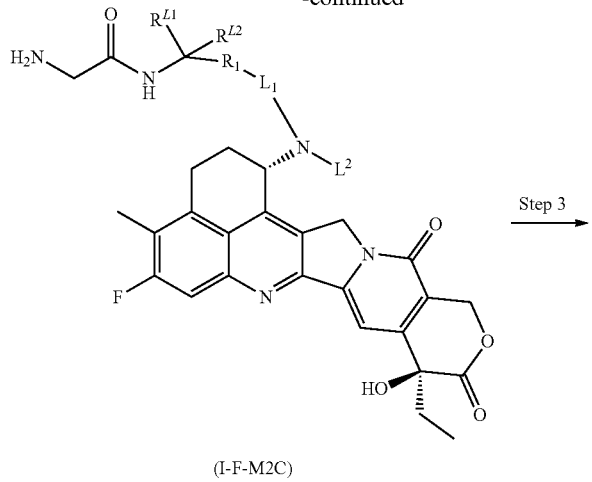

(I-F-M2C)

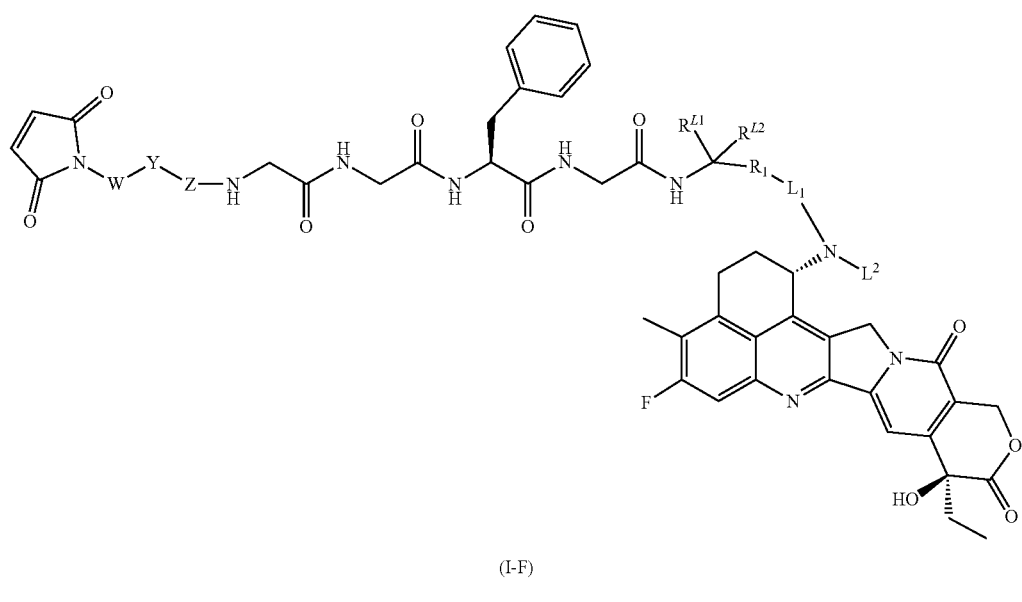

(I-F)

wherein R¹ is selected from the group consisting of: —O—, —(R²)N—, —P(=O)(R²)— and —S—;
L² is —(C(R³ᵃ)(R³ᵇ))ₘ—R,
wherein 0 or no less than 1 methylene unit of L² is independently replaced by -Cy-, —N(R⁴)C(O)—, —C(O)N(R⁴)—, —C(O)—, —OC(O)—, —C(O)O—, —NR⁴—, —O—, —S—, —SO—, —SO₂—, —P(R⁴)—, —P(=O)(R⁴)—, —N(R⁴)SO₂—, —SO₂N(R⁴)—, —C(=S)—, —C(=NR⁴)—, —N=N—, —C=N—, —N=C— or —C(=N₂)—;
L¹ is —(C(R⁵ᵃ)(R⁵ᵇ))ₙ—,
wherein 0 or no less than 1 methylene unit of L¹ is independently replaced by -Cy-, —N(R⁶)C(O)—, —C(O)N(R⁶)—, —C(O)—, —OC(O)—, —C(O)O—, —NR⁶—, —O—, —S—, —SO—, —SO₂—, —P(R⁶)—, —P(=O)(R⁶)—, —N(R⁶)SO₂—, —SO₂N(R⁶)—, —C(=S)—, —C(=NR⁶)—, —N=N—, —C=N—, —N=C— or —C(=N₂)—;

-Cy- is selected from the group consisting of: 6-10 membered arylene, 5-8 membered heteroarylene, 3-10 membered heterocyclylene, and 3-10 membered saturated or partially unsaturated carbocyclylene, wherein -Cy- is unsubstituted or independently substituted with no less than 1 substituent R⁷;

wherein each R³ᵃ, each R³ᵇ, each R⁴, each R⁵ᵃ, each R⁵ᵇ and each R⁶ are each independently hydrogen, protium, deuterium, tritium, halogen, —NO₂, —CN, —OR, —SR, —N(Rᵃ)(Rᵇ), —C(O)R, —CO₂R, —C(O)C(O)

R, —C(O)CH$_2$C(O)R, —S(O)R, —S(O)$_2$R, —C(O)N(R$^a$)(R$^b$), —SO$_2$N(R$^a$)(R$^b$), —OC(O)R, —N(R)SO$_2$R, or a C$_{1-6}$ aliphatic group optionally substituted with R; or, R$^{3a}$ and R$^{5a}$, R$^4$ and R$^{5a}$, R$^{3a}$ and R$^6$ or R$^4$ and R$^6$ each independently optionally form a ring B together with an atom therebetween, wherein the ring B is selected from the group consisting of: 5-8 membered heteroarylene and 3-10 membered saturated or partially unsaturated heterocyclylene, and the ring B is unsubstituted or independently substituted with no less than 1 substituent R$^8$;

wherein each R$^2$, each R$^7$ and each R$^8$ are each independently hydrogen, protium, deuterium, tritium, halogen, —NO$_2$, —CN, —OR, —SR, —N(R$^a$)(R$^b$), —C(O)R, —CO$_2$R, —C(O)C(O)R, —C(O)CH$_2$C(O)R, —S(O)R, —S(O)$_2$R, —C(O)N(R$^a$)(R$^b$), —SO$_2$N(R$^a$)(R$^b$), —OC(O)R, —N(R)SO$_2$R, or a C$_{1-6}$ aliphatic group optionally substituted with R;

wherein each R, each R$^a$ and each R$^b$ are each independently hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group;

m and n are each independently selected from the group consisting of integers ≥1.

Step 1: reacting a compound of general formula (I-E) with a compound of general formula (K12), optionally under an acidic condition, to obtain a compound of general formula (I-F-M1C)

Step 2: removing a protecting group of the compound of general formula (I-F-M1C) to obtain a compound of general formula (I-F-M2C)

Step 3: reacting a compound of general formula (KI1) with the compound of general formula (I-F-M2C) in the presence of a condensing agent, optionally under a basic condition, to obtain the compound of general formula (I-F)

Re is an amino protecting group, preferably Fomc;

W, Y, Z, R$^{L1}$, R$^{L2}$, R$^1$, L$^1$ and L$^2$ are defined as in any general formula (I-F) in embodiments of the sixth aspect.

Reducing agents include, but are not limited to, sodium hydride, calcium hydride, lithium hydride, lithium aluminum hydride, sodium borohydride, lithium borohydride, sodium triethylborohydride, sodium triacetoxyborohydride and sodium cyanoborohydride.

Reagents that provide acidic conditions include a protic acid and a Lewis acid, wherein the protic acid includes, but is not limited to, hydrochloric acid, sulfuric acid, nitric acid, nitrous acid, sulfurous acid, phosphoric acid, phosphorous acid, formic acid, acetic acid, propionic acid, butyric acid, citric acid, benzoic acid, p-toluenesulfonic acid, p-nitrobenzoic acid, methanesulfonic acid, trifluoromethanesulfonic acid and trifluoroacetic acid, and the Lewis acid includes, but is not limited to, boron trifluoride, zinc chloride, magnesium chloride, aluminum chloride, stannic chloride and ferric chloride.

Reagents that provide basic conditions include organic bases and inorganic bases, wherein the organic bases include, but are not limited to, triethylamine, diethylamine, N-methylmorpholine, pyridine, piperidine, N,N-diisopropylethylamine, n-butyllithium, lithium diisopropylamide, potassium acetate, sodium tert-butoxide, potassium tert-butoxide, and the like, and the inorganic bases include, but are not limited to, sodium hydride, potassium carbonate, sodium carbonate, cesium carbonate, sodium hydroxide, lithium hydroxide, and the like.

The condensing agent may be selected from the group consisting of 4-(4,6-dimethoxy-1,3,5-triazin-2-yl)-4-methylmorpholinium chloride, 1-hydroxybenzotriazole and 1-(3-dimethylaminopropyl)-3-ethylcarbodiimide hydrochloride, N,N'-dicyclohexylcarbodiimide, N,N-diisopropylcarbodiimide, O-benzotriazol-N,N,N',N'-tetramethyluronium tetrafluoroborate, 1-hydroxybenzotriazole, 1-hydroxy-7-azobenzotriazol, O-benzotriazol-N,N,N',N'-tetramethyluronium hexafluorophosphate, 2-(7-azobenzotriazol)-N,N,N',N'-tetramethyluronium hexafluorophosphate, benzotriazol-1-yloxytris(dimethylamino)phosphonium hexafluorophosphate, and benzotriazol-1-yl-oxytripyrrolidinophosphonium hexafluorophosphate, preferably 4-(4,6-dimethoxy-1,3,5-triazin-2-yl)-4-methylmorpholinium chloride, or 1-hydroxybenzotriazole and 1-(3-dimethylaminopropyl)-3-ethylcarbodiimide hydrochloride.

Scheme V

Provided is a method for preparing a compound of general formula (II-F) (including general formula (II-Fx) or general formula (II-Fy)) or a pharmaceutically acceptable salt or a solvate thereof disclosed herein, which comprises:

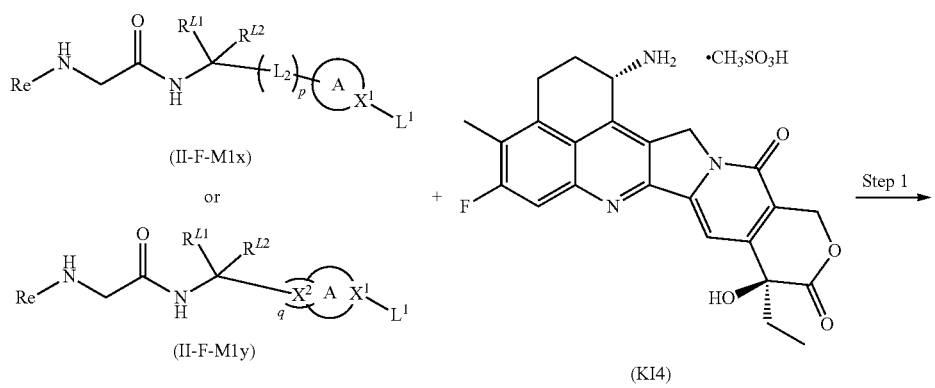

-continued
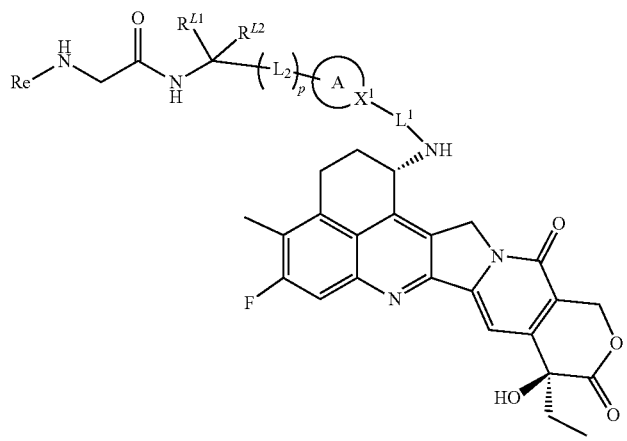
(II-F-M2x)
or
Step 2
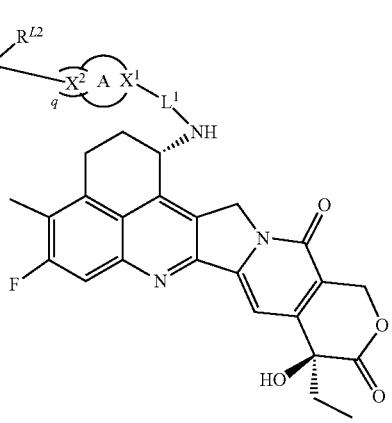
(II-F-M2y)
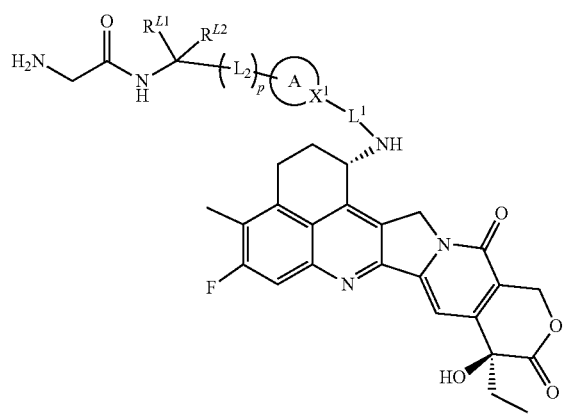
(II-F-M3x)

-continued
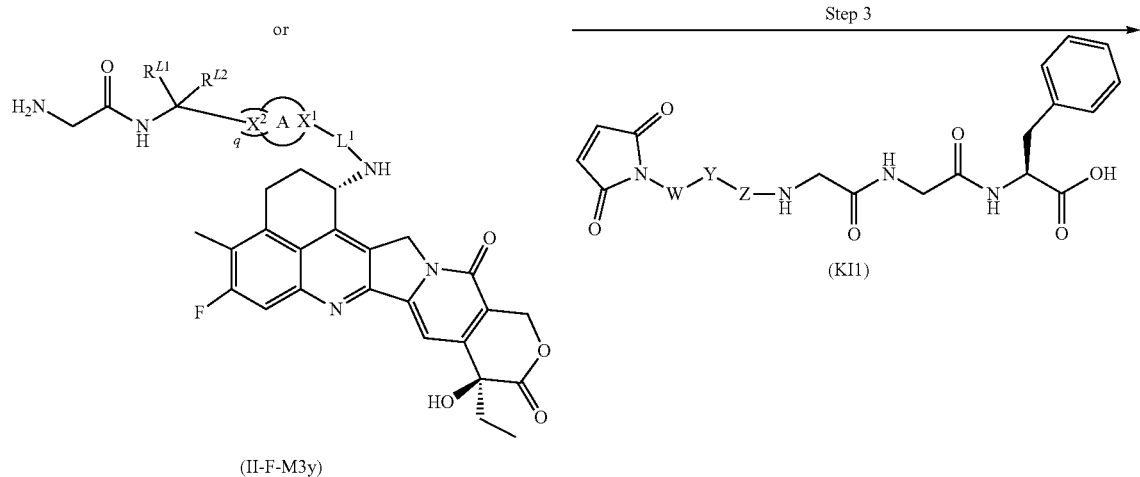
(II-F-M3y)
(KI1)
Step 3 →
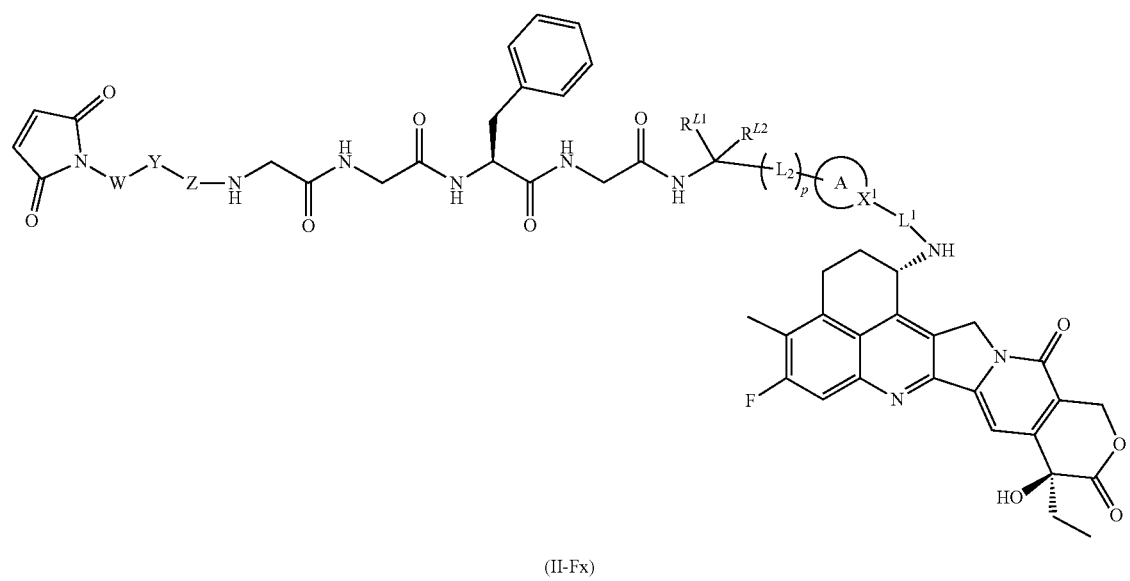
(II-Fx)
or
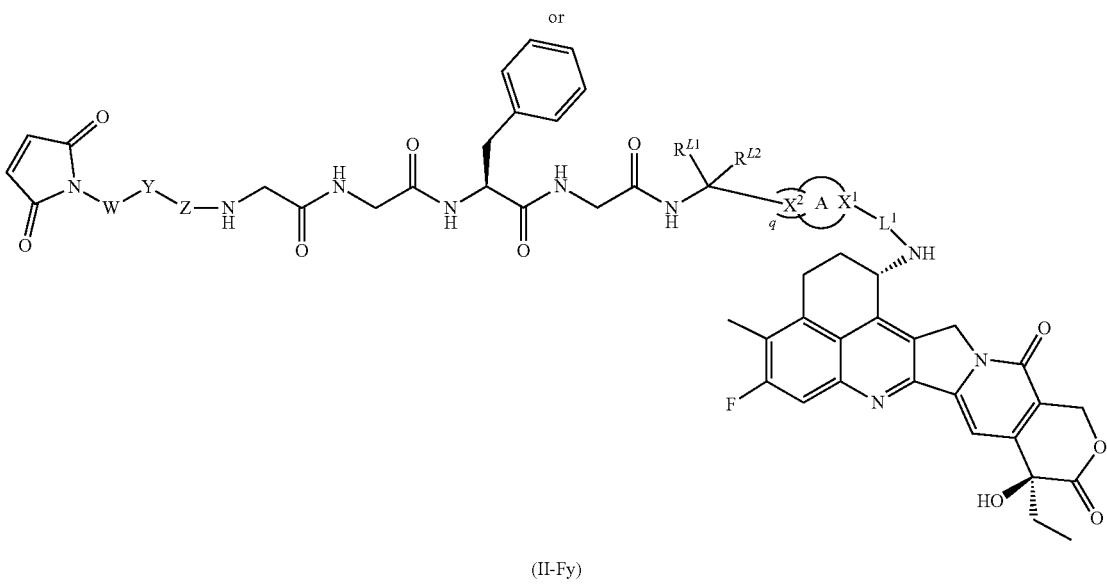
(II-Fy)

Step 1: reacting a compound of general formula (II-F-M1x) or a compound of general formula (II-F-M1y) with a compound of general formula (KI4) in the presence of a condensing agent, optionally under a basic condition, to obtain a compound of general formula (II-F-M2x) or general formula (II-F-M2y)

Step 2: removing a protecting group of the compound of general formula (II-F-M2x) or general formula (II-F-M2y) to obtain a compound of general formula (II-F-M3x) or general formula (II-F-M3y)

Step 3: reacting a compound of general formula (KI1) with the compound of general formula (II-F-M3x) or general formula (II-F-M3y) in the presence of a condensing agent, optionally under a basic condition, to obtain the compound of general formula (II-Fx) or general formula (II-Fy)

wherein,

Re is an amino protecting group, preferably Fomc;

W, Y, Z, $R^{L1}$, $R^{L2}$, A, $X^1$, $L^1$, $L^2$ and p are defined as in any formula (II-Fx) in embodiments of the sixth aspect, or W, Y, Z, $R^{L1}$, $R^{L2}$, A, $X^1$, $L^1$, $X^2$ and q are defined as in any formula (II-Fy) in embodiments of the sixth aspect.

Reagents that provide basic conditions include organic bases and inorganic bases, wherein the organic bases include, but are not limited to, triethylamine, diethylamine, N-methylmorpholine, pyridine, piperidine, N,N-diisopropylethylamine, n-butyllithium, lithium diisopropylamide, potassium acetate, sodium tert-butoxide, potassium tert-butoxide, and the like, and the inorganic bases include, but are not limited to, sodium hydride, potassium carbonate, sodium carbonate, cesium carbonate, sodium hydroxide, lithium hydroxide, and the like.

The condensing agent may be selected from the group consisting of 4-(4,6-dimethoxy-1,3,5-triazin-2-yl)-4-methylmorpholinium chloride, 1-hydroxybenzotriazole and 1-(3-dimethylaminopropyl)-3-ethylcarbodiimide hydrochloride, N,N'-dicyclohexylcarbodiimide, N,N-diisopropylcarbodiimide, O-benzotriazol-N,N,N',N'-tetramethyluronium tetrafluoroborate, 1-hydroxybenzotriazole, 1-hydroxy-7-azobenzotriazol, O-benzotriazol-N,N,N',N'-tetramethyluronium hexafluorophosphate, 2-(7-azobenzotriazol)-N,N,N',N'-tetramethyluronium hexafluorophosphate, benzotriazol-1-yloxytris(dimethylamino)phosphonium hexafluorophosphate, and benzotriazol-1-yl-oxytripyrrolidinophosphonium hexafluorophosphate, preferably 4-(4,6-dimethoxy-1,3,5-triazin-2-yl)-4-methylmorpholinium chloride, or 1-hydroxybenzotriazole and 1-(3-dimethylaminopropyl)-3-ethylcarbodiimide hydrochloride.

Scheme VI

Provided is a method for preparing a compound of general formula (III-F) or a pharmaceutically acceptable salt or a solvate thereof disclosed herein, which comprises:

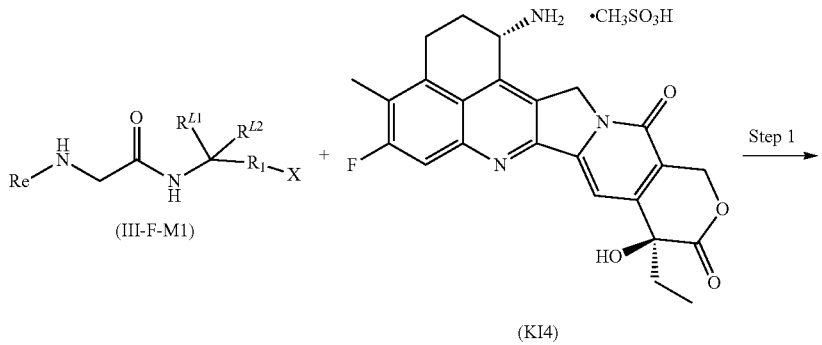

(III-F-M1) + (KI4) → Step 1

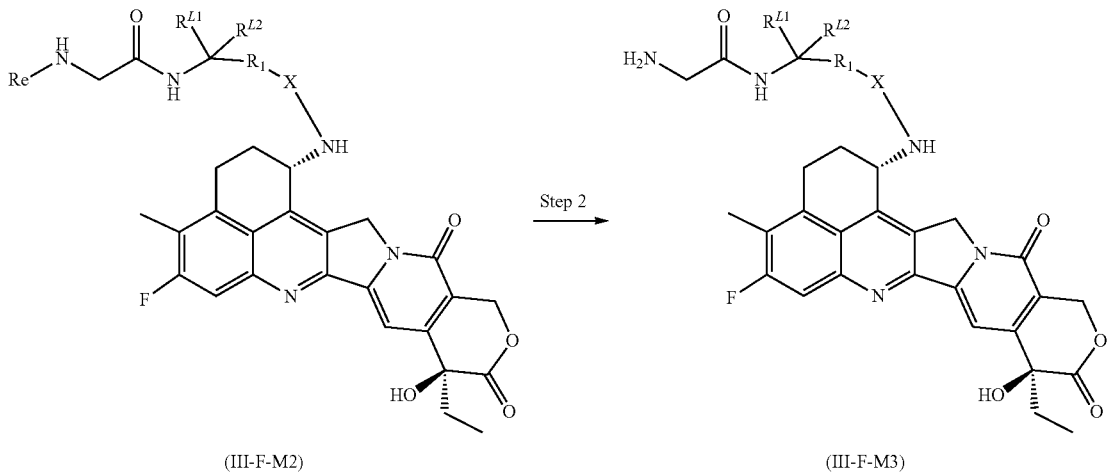

(III-F-M2) → Step 2 → (III-F-M3)

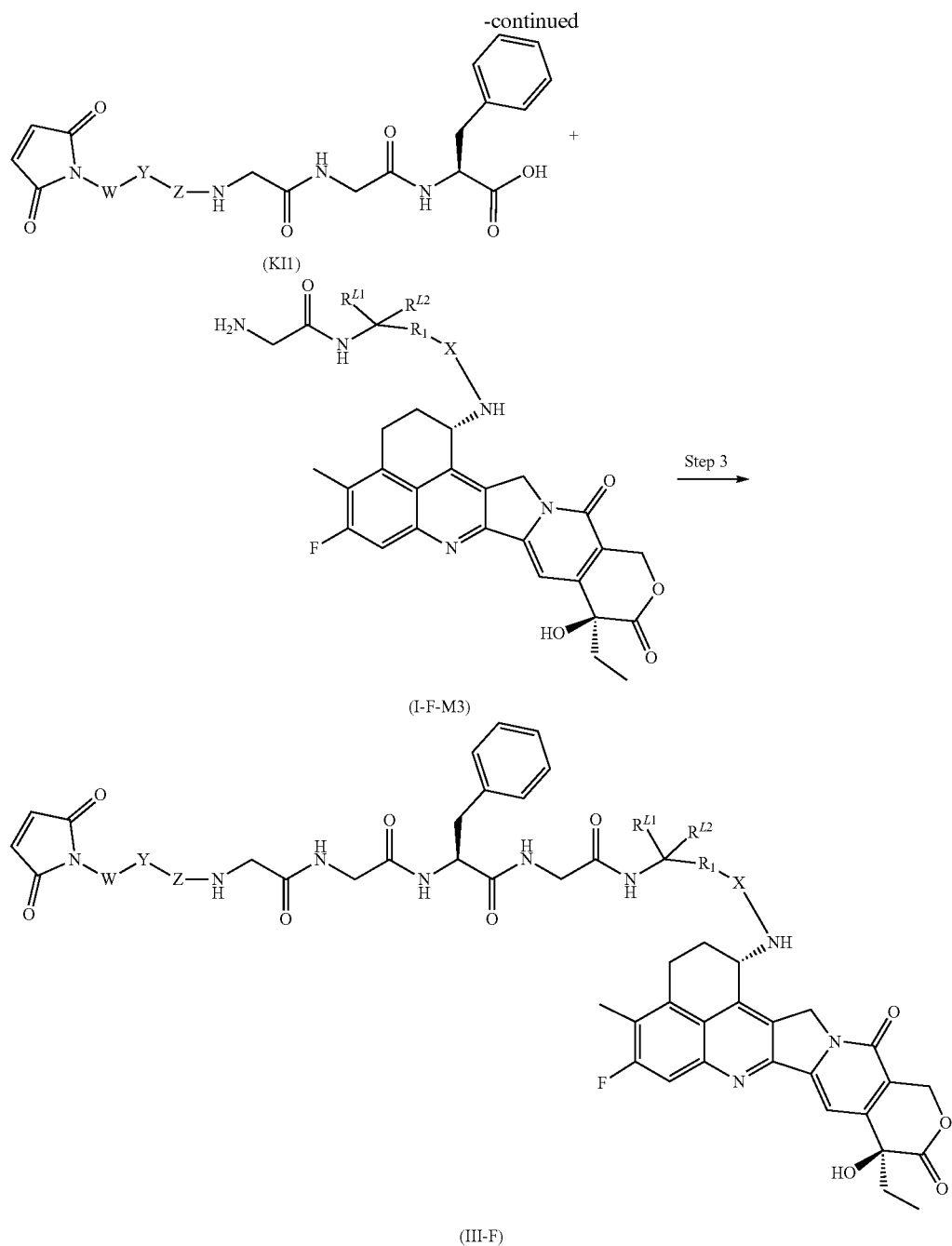

Step 1: reacting a compound of general formula (III-F-M1) with a compound of general formula (KI4) in the presence of a condensing agent, optionally under a basic condition, to obtain a compound of general formula (III-F-M2)

Step 3: reacting a compound of general formula (KI1) with the compound of general formula (III-F-M3) in the presence of a condensing agent, optionally under a basic condition, to obtain the compound of general formula (III-F) wherein, Re is an amino protecting group, preferably Fomc;

W, Y, Z, $R^{L1}$, $R^{L2}$, $R^1$ and X are defined as in any general formula (III-F) in embodiments of the sixth aspect.

Reagents that provide basic conditions include organic bases and inorganic bases, wherein the organic bases include, but are not limited to, triethylamine, diethylamine, N-methylmorpholine, pyridine, piperidine, N,N-diisopropylethylamine, n-butyllithium, lithium diisopropylamide, potassium acetate, sodium tert-butoxide, potassium tert-butoxide, and the like, and the inorganic bases include, but are not limited to, sodium hydride, potassium carbonate, sodium carbonate, cesium carbonate, sodium hydroxide, lithium hydroxide, and the like.

The condensing agent may be selected from the group consisting of 4-(4,6-dimethoxy-1,3,5-triazin-2-yl)-4-methylmorpholinium chloride, 1-hydroxybenzotriazole and 1-(3-dimethylaminopropyl)-3-ethylcarbodiimide hydrochloride, N,N'-dicyclohexylcarbodiimide, N,N-diisopropylcarbodiimide, O-benzotriazol-N,N,N',N'-tetramethyluronium tetrafluoroborate, 1-hydroxybenzotriazole, 1-hydroxy-7-azobenzotriazol, O-benzotriazol-N,N,N',N'-tetramethyluronium hexafluorophosphate, 2-(7-azobenzotriazol)-N,N,N',N'-tetramethyluronium hexafluorophosphate, benzotriazol-1-yloxytris(dimethylamino)phosphonium hexafluorophosphate, and benzotriazol-1-yl-oxytripyrrolidinophosphonium hexafluorophosphate, preferably 4-(4,6-dimethoxy-1,3,5-triazin-2-yl)-4-methylmorpholinium chloride, or 1-hydroxybenzotriazole and 1-(3-dimethylaminopropyl)-3-ethylcarbodiimide hydrochloride.

Scheme VII

Provided is a method for preparing a compound of general formula (I-D), which comprises the following steps:

wherein,

Ab is a ligand, and after being reduced, Ab reacts with the general formula (I-F) to obtain the compound of general formula (I-D);

reducing agents include, but are not limited to, tris(2-carboxyethyl)phosphine, mercaptoethanol, dithiothreitol, cysteine, reduced glutathione, and the like; in particular, disulfide bonds on the antibody are preferably reduced;

W, Y, Z, $R^{L1}$, $R^{L2}$, $R^1$, $L^1$ and $L^2$ are defined as in any formula (I-D) in embodiments of the fourth aspect.

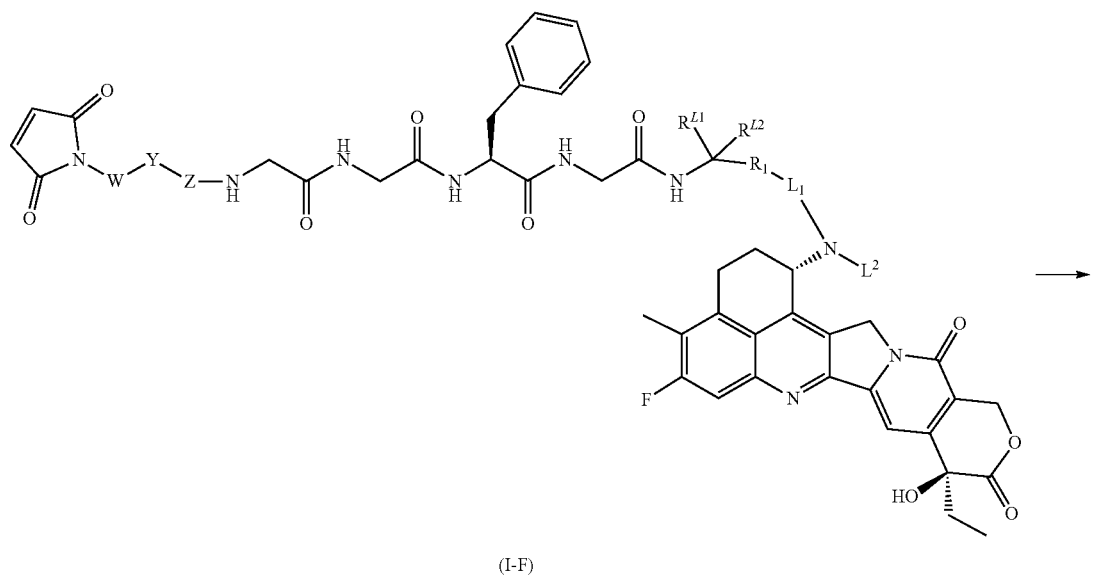

(I-F)

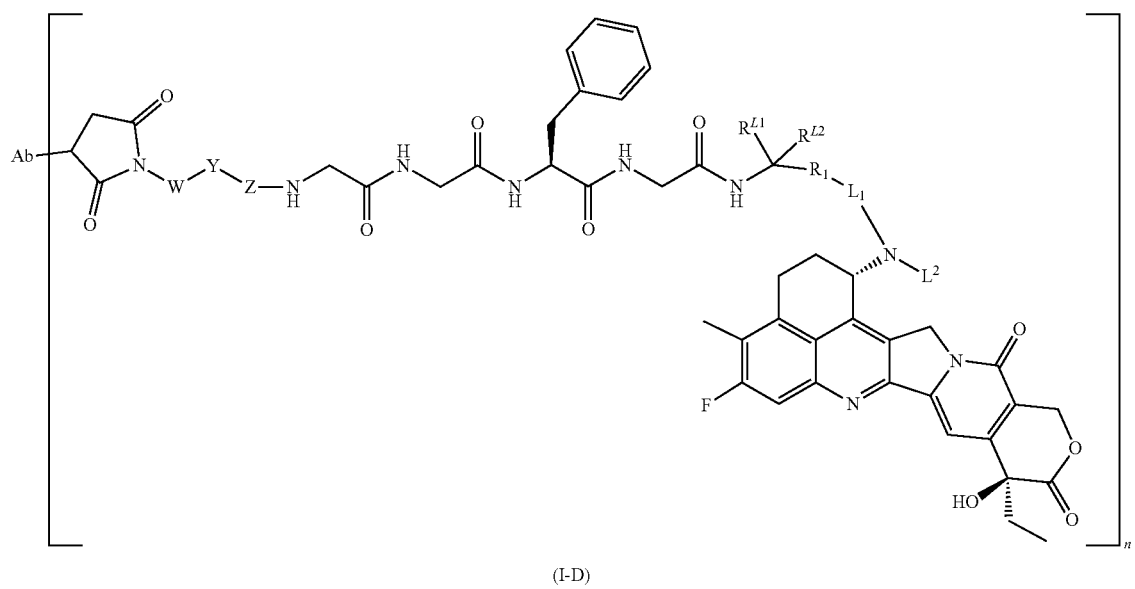

(I-D)

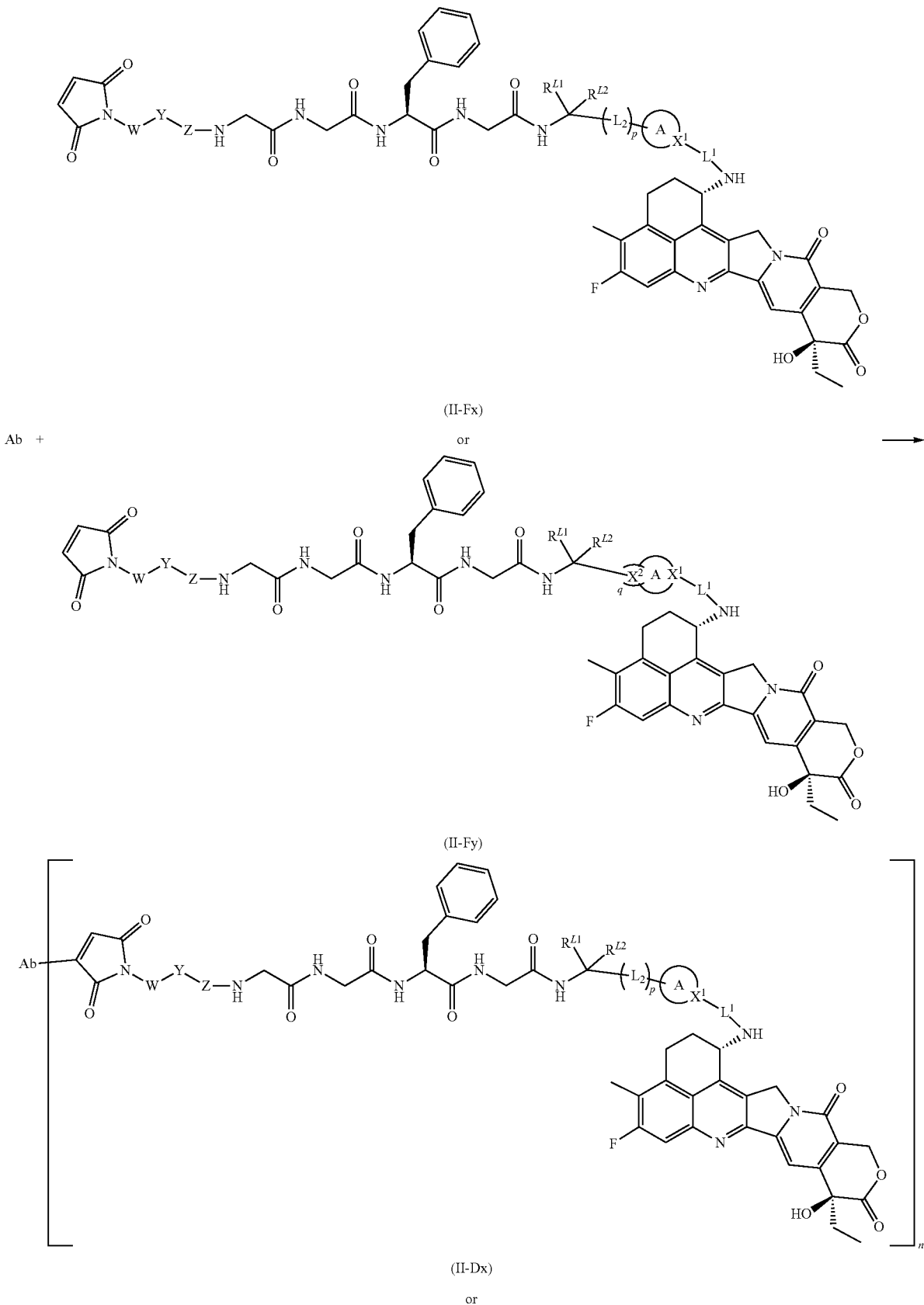

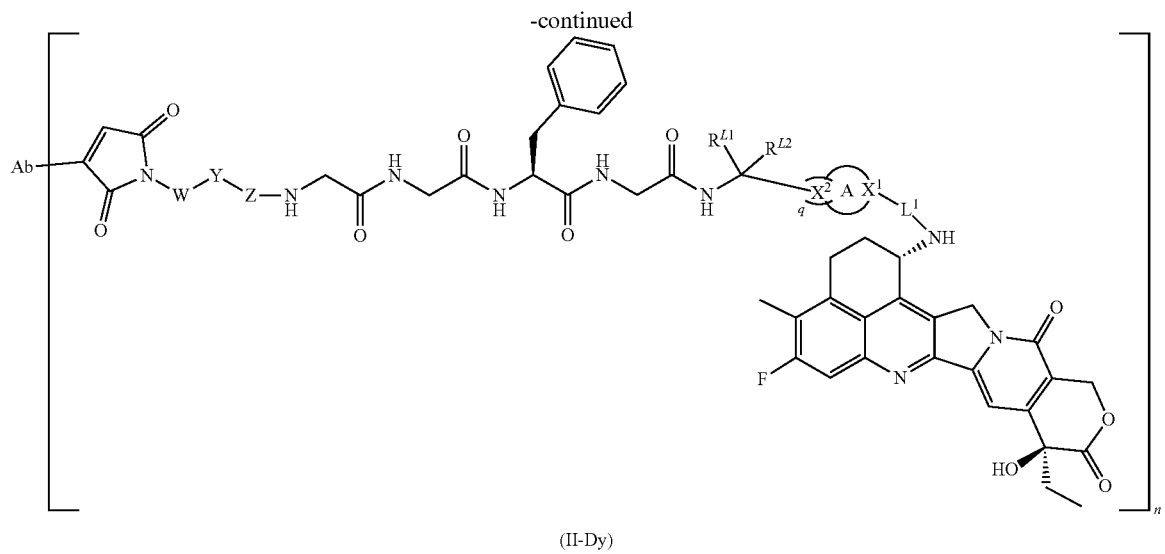

(II-Dy)

wherein,

Ab is a ligand, and after being reduced, Ab reacts with the general formula (II-F), including general formula (II-Fx) or general formula (II-Fy), to obtain the compound of general formula (II-Dx) or general formula (II-Dy);

reducing agents include, but are not limited to, tris(2-carboxyethyl)phosphine, mercaptoethanol, dithiothreitol, cysteine, reduced glutathione, and the like; in particular, disulfide bonds on the antibody are preferably reduced;

W, Y, Z, $R^{L1}$, $R^{L2}$, A, $X^1$, $L^1$, $L^2$ and p are defined as in any formula (II-Dx) in embodiments of the fourth aspect, or W, Y, Z, $R^{L1}$, $R^{L2}$, A, $X^1$, $L^1$, $X^2$ and q are defined as in any formula (II-Dy) in embodiments of the fourth aspect.

Scheme IX

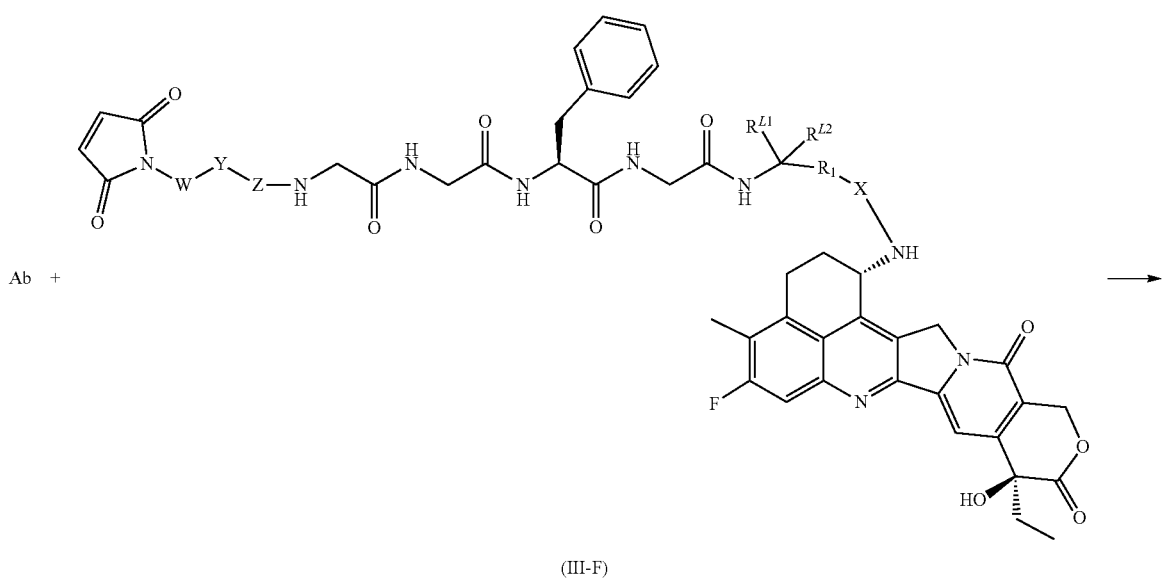

(III-F)

-continued

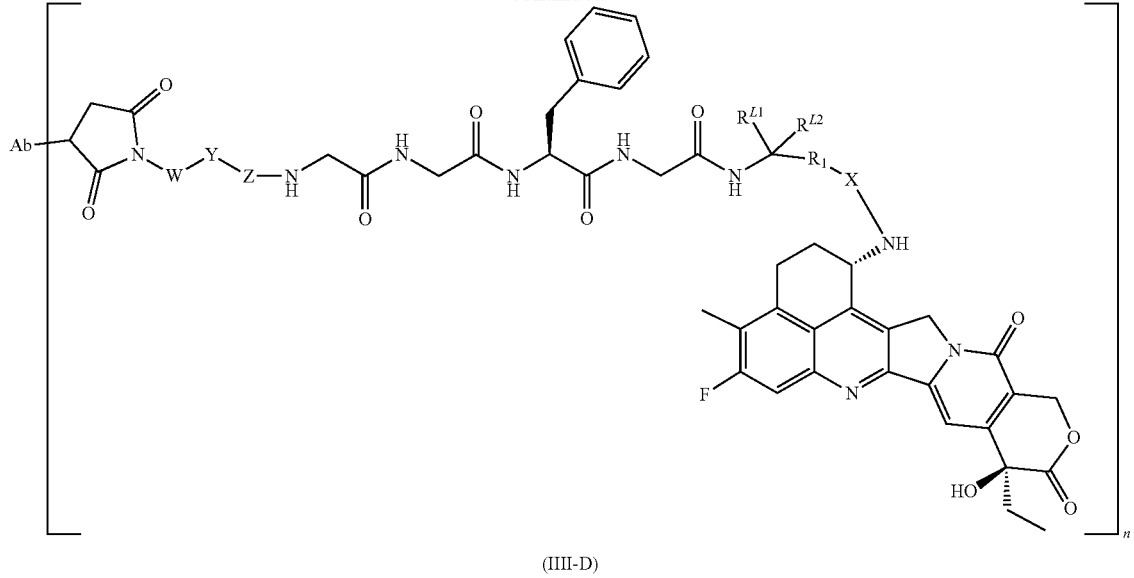

(IIII-D)

wherein,
Ab is a ligand, and after being reduced, Ab reacts with the general formula (II-F) to obtain the compound of general formula (III-D);
reducing agents include, but are not limited to, tris(2-carboxyethyl)phosphine, mercaptoethanol, dithiothreitol, cysteine, reduced glutathione, and the like; in particular, disulfide bonds on the antibody are preferably reduced;
W, Y, Z, $R^{L1}$, $R^{L2}$, $R^1$ and X are defined as in any general formula (III-D) in embodiments of the fourth aspect.

Technical Schemes

1. A compound or a tautomer, a mesomer, a racemate, an enantiomer or a diastereoisomer thereof, or a mixture thereof, or a pharmaceutically acceptable salt thereof, wherein the compound comprises a structure shown as formula (I-A):

(I-A)

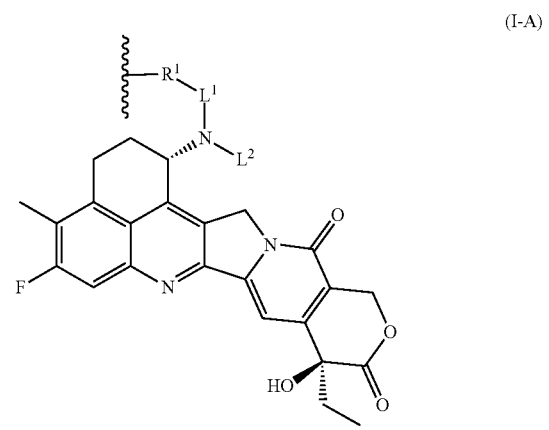

wherein, R1 is selected from the group consisting of: —O—, —(R2)N—, —P(═O)(R2)-, —P(R2)- and —S—;

L2 is —(C(R3a)(R3b))m-R,
wherein 0 or no less than 1 methylene unit of L2 is independently replaced by -Cy-, —N(R4)C(O)—, —C(O)N(R4)-, —C(O)—, —OC(O)—, —C(O)O—, —NR4-, —O—, —S—, —SO—, —SO2-, —P(R4)-, —P(═O)(R4)-, —N(R4)SO2-, —SO2N(R4)-, —C(═S)—, —C(═NR4)-, —N═N—, —C═N—, —N═C— or —C(═N2)-;
L1 is —(C(R5a)(R5b))n-,
wherein 0 or no less than 1 methylene unit of L1 is independently replaced by -Cy-, —N(R6)C(O)—, —C(O)N(R6)-, —C(O)—, —OC(O)—, —C(O)O—, —NR6-, —O—, —S—, —SO—, —SO$_2$—, —P(R6)-, —P(═O)(R6)-, —N(R6)SO$_2$—, —SO2N(R6)-, —C(═S)—, —C(═NR6)-, —N═N—, —C═N—, —N═C— or —C(═N$_2$)—;
-Cy- is selected from the group consisting of: 6-10 membered arylene, 5-8 membered heteroarylene, 3-10 membered heterocyclylene, and 3-10 membered saturated or partially unsaturated carbocyclylene, wherein -Cy- is unsubstituted or independently substituted with no less than 1 substituent R7;
wherein each R3a, each R3b, each R4, each R5a, each R5b and each R6 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R; or, R3a and R5a, R4 and R5a, R3a and R6 or R4 and R6 each independently optionally form a ring B together with an atom therebetween, wherein the ring B is selected from the group consisting of: 5-8 membered heteroarylene and 3-10 membered saturated or partially unsaturated heterocyclylene, and the ring B is unsubstituted or independently substituted with no less than 1 substituent R8;
wherein each R2, each R7 and each R8 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)

R, —S(O)R, —S(O)2R, —C(O)N(Ra)(Rb), —SO2N(Ra)(Rb), —OC(O)R, —N(R)SO2R, or a C1-6 aliphatic group optionally substituted with R;
wherein each R, each Ra and each Rb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;
m and n are each independently selected from the group consisting of integers ≥1.

2. The compound or the tautomer, the mesomer, the racemate, the enantiomer or the diastereoisomer thereof, or the mixture thereof, or the pharmaceutically acceptable salt thereof according to technical scheme 1, wherein each R3a, each R3b, each R4, each R5a, each R5b and each R6 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R.

3. The compound or the tautomer, the mesomer, the racemate, the enantiomer or the diastereoisomer thereof, or the mixture thereof, or the pharmaceutically acceptable salt thereof according to technical scheme 1, wherein R3a and R5a, R4 and R5a, R3a and R6, or R4 and R6 each independently optionally form a ring B together with an atom therebetween, wherein the ring B is selected from the group consisting of: 5-8 membered heteroarylene and 3-10 membered saturated or partially unsaturated heterocyclylene, and the ring B is unsubstituted or substituted with no less than 1 substituent R8.

4. The compound or the tautomer, the mesomer, the racemate, the enantiomer or the diastereoisomer thereof, or the mixture thereof, or the pharmaceutically acceptable salt thereof according to any one of technical schemes 1-3, wherein m is 1 or 2.

5. The compound or the tautomer, the mesomer, the racemate, the enantiomer or the diastereoisomer thereof, or the mixture thereof, or the pharmaceutically acceptable salt thereof according to any one of technical schemes 1-4, wherein m is 1, and L2 is —C(R3a)(R3b)-R.

6. The compound or the tautomer, the mesomer, the racemate, the enantiomer or the diastereoisomer thereof, or the mixture thereof, or the pharmaceutically acceptable salt thereof according to any one of technical schemes 1-5, wherein L2 is —C(R3a)(R3b)-R, and 0 methylene units of L2 are replaced by -Cy-, —N(R4)C(O)—, —C(O)N(R4)-, —C(O)—, —OC(O)—, —C(O)O—, —NR4-, —O—, —S—, —SO—, —SO2-, —P(R4)-, —P(=O)(R4)-, —N(R4)SO2-, —SO2N(R4)-, —C(=S)—, —C(=NR4)—, —N=N—, —C=N—, —N=C— or —C(=N2)-.

7. The compound or the tautomer, the mesomer, the racemate, the enantiomer or the diastereoisomer thereof, or the mixture thereof, or the pharmaceutically acceptable salt thereof according to any one of technical schemes 1-4, wherein m is 2, and L2 is —(C(R3a)(R3b))2-R.

8. The compound or the tautomer, the mesomer, the racemate, the enantiomer or the diastereoisomer thereof, or the mixture thereof, or the pharmaceutically acceptable salt thereof according to any one of technical schemes 1-4 and 7, wherein L2 is —(C(R3a)(R3b))2-R, and 0 methylene units of L2 are replaced by -Cy-, —N(R4)C(O)—, —C(O)N(R4)-, —C(O)—, —OC(O)—, —C(O)O—, —NR4—, —O—, —S—, —SO—, —SO2-, —P(R4)-, —P(=O)(R4)-, —N(R4)SO2-, —SO2N(R4)-, —C(=S)—, —C(=NR4)-, —N=N—, —C=N—, —N=C— or —C(=N2)—.

9. The compound or the tautomer, the mesomer, the racemate, the enantiomer or the diastereoisomer thereof, or the mixture thereof, or the pharmaceutically acceptable salt thereof according to any one of technical schemes 1-4 and 7, wherein L2 is —(C(R3a)(R3b))2-R, and 1 methylene unit of L2 is replaced by -Cy-, —N(R4)C(O)—, —C(O)N(R4)-, —C(O)—, —OC(O)—, —C(O)O—, —NR4-, —O—, —S—, —SO—, —SO2-, —P(R4)-, —P(=O)(R4)-, —N(R4)SO2-, —SO2N(R4)-, —C(=S)—, —C(=NR4)-, —N=N—, —C=N—, —N=C— or —C(=N2)-.

10. The compound or the tautomer, the mesomer, the racemate, the enantiomer or the diastereoisomer thereof, or the mixture thereof, or the pharmaceutically acceptable salt thereof according to any one of technical schemes 1-4, 7 and 9, wherein L2 is —(C(R3a)(R3b))2-R, and 1 methylene unit of L2 is replaced by —C(O)— or -Cy-.

11. The compound or the tautomer, the mesomer, the racemate, the enantiomer or the diastereoisomer thereof, or the mixture thereof, or the pharmaceutically acceptable salt thereof according to any one of technical schemes 1-4, 7 and 9-10, wherein L2 is —(C(R3a)(R3b))2-R, and 1 methylene unit of L2 is replaced by —C(O)—.

12. The compound or the tautomer, the mesomer, the racemate, the enantiomer or the diastereoisomer thereof, or the mixture thereof, or the pharmaceutically acceptable salt thereof according to any one of technical schemes 1-4, 7 and 9-11, wherein L2 is —C(O)—C(R3a)(R3b)-R.

13. The compound or the tautomer, the mesomer, the racemate, the enantiomer or the diastereoisomer thereof, or the mixture thereof, or the pharmaceutically acceptable salt thereof according to any one of technical schemes 1-4, 7 and 9-10, wherein L2 is —(C(R3a)(R3b))2-R, and 1 methylene unit of L2 is replaced by -Cy-.

14. The compound or the tautomer, the mesomer, the racemate, the enantiomer or the diastereoisomer thereof, or the mixture thereof, or the pharmaceutically acceptable salt thereof according to any one of technical schemes 1-4, 7, 9-10 and 13, wherein L2 is —C(R3a)(R3b)-Cy-R.

15. The compound or the tautomer, the mesomer, the racemate, the enantiomer or the diastereoisomer thereof, or the mixture thereof, or the pharmaceutically acceptable salt thereof according to technical scheme 1, wherein 0 methylene units of L2 are replaced by -Cy-, —N(R4)C(O)—, —C(O)N(R4)-, —C(O)—, —OC(O)—, —C(O)O—, —NR4-, —O—, —S—, —SO—, —SO2—, —P(R4)-, —P(=O)(R4)-, —N(R4)SO2-, —SO2N(R4)-, —C(=S)—, —C(=NR4)—, —N=N—, —C=N—, —N=C— or —C(=N2)—.

16. The compound or the tautomer, the mesomer, the racemate, the enantiomer or the diastereoisomer thereof, or the mixture thereof, or the pharmaceutically acceptable salt thereof according to technical scheme 1, wherein 1 methylene unit of L2 is replaced by -Cy-, —N(R4)C(O)—, —C(O)N(R4)-, —C(O)—, —OC(O)—, —C(O)O—, —NR4—, —O—, —S—, —SO—, —SO2—, —P(R4)-, —P(=O)(R4)-, —N(R4)SO2-, —SO2N(R4)-, —C(=S)—, —C(=NR4)—, —N=N—, —C=N—, —N=C— or —C(=N2)—.

17. The compound or the tautomer, the mesomer, the racemate, the enantiomer or the diastereoisomer thereof, or the mixture thereof, or the pharmaceutically acceptable salt thereof according to any one of technical schemes 1 and 16, wherein 1 methylene unit of L2 is replaced by —C(O)— or -Cy-.

18. The compound or the tautomer, the mesomer, the racemate, the enantiomer or the diastereoisomer thereof, or the mixture thereof, or the pharmaceutically acceptable salt thereof according to any one of technical schemes 1 and 16-17, wherein 1 methylene unit of L2 is replaced by —C(O)—.

19. The compound or the tautomer, the mesomer, the racemate, the enantiomer or the diastereoisomer thereof, or the mixture thereof, or the pharmaceutically acceptable salt thereof according to any one of technical schemes 1-18, wherein n is 2, 3 or 5.

20. The compound or the tautomer, the mesomer, the racemate, the enantiomer or the diastereoisomer thereof, or the mixture thereof, or the pharmaceutically acceptable salt thereof according to any one of technical schemes 1-19, wherein n is 2, and L1 is —(C(R5a)(R5b))2-.

21. The compound or the tautomer, the mesomer, the racemate, the enantiomer or the diastereoisomer thereof, or the mixture thereof, or the pharmaceutically acceptable salt thereof according to any one of technical schemes 1-20, wherein L1 is —(C(R5a)(R5b))2-, and 0 methylene units of L1 are replaced by -Cy-, —N(R6)C(O)—, —C(O)N(R6)-, —C(O)—, —OC(O)—, —C(O)O—, —NR6-, —O—, —S—, —SO—, —SO$_2$—, —P(R6)-, —P(=O)(R6)-, —N(R6)SO2-, —SO2N(R6)-, —C(=S)—, —C(=NR6)-, —N=N—, —C=N—, —N=C— or —C(=N2)-.

22. The compound or the tautomer, the mesomer, the racemate, the enantiomer or the diastereoisomer thereof, or the mixture thereof, or the pharmaceutically acceptable salt thereof according to any one of technical schemes 1-19, wherein L1 is —(C(R5a)(R5b))2-, and 1 methylene unit of L1 is replaced by -Cy-, —N(R6)C(O)—, —C(O)N(R6)-, —C(O)—, —OC(O)—, —C(O)O—, —NR6-, —O—, —S—, —SO—, —SO$_2$—, —P(R6)-, —P(=O)(R6)-, —N(R6)SO2-, —SO2N(R6)-, —C(=S)—, —C(=NR6)-, —N=N—, —C=N—, —N=C— or —C(=N$_2$)—.

23. The compound or the tautomer, the mesomer, the racemate, the enantiomer or the diastereoisomer thereof, or the mixture thereof, or the pharmaceutically acceptable salt thereof according to any one of technical schemes 1-19 and 22, wherein L1 is —(C(R5a)(R5b))2-, and 1 methylene unit of L1 is replaced by —C(O)— or —C(=S)—.

24. The compound or the tautomer, the mesomer, the racemate, the enantiomer or the diastereoisomer thereof, or the mixture thereof, or the pharmaceutically acceptable salt thereof according to any one of technical schemes 1-19 and 22-23, wherein L1 is —(C(R5a)(R5b))2-, and 1 methylene unit of L1 is replaced by —C(O)—.

25. The compound or the tautomer, the mesomer, the racemate, the enantiomer or the diastereoisomer thereof, or the mixture thereof, or the pharmaceutically acceptable salt thereof according to any one of technical schemes 1-19 and 22-24, wherein L1 is —C(R5a)(R5b)-C(O)—.

26. The compound or the tautomer, the mesomer, the racemate, the enantiomer or the diastereoisomer thereof, or the mixture thereof, or the pharmaceutically acceptable salt thereof according to any one of technical schemes 1-19 and 22-23, wherein L1 is —(C(R5a)(R5b))2-, and 1 methylene unit of L1 is replaced by —C(=S)—.

27. The compound or the tautomer, the mesomer, the racemate, the enantiomer or the diastereoisomer thereof, or the mixture thereof, or the pharmaceutically acceptable salt thereof according to any one of technical schemes 1-19, 22-23 and 26, wherein L1 is —C(R5a)(R5b)-C(=S)—.

28. The compound or the tautomer, the mesomer, the racemate, the enantiomer or the diastereoisomer thereof, or the mixture thereof, or the pharmaceutically acceptable salt thereof according to any one of technical schemes 1-19, wherein n is 3, and L1 is —(C(R5a)(R5b))3-.

29. The compound or the tautomer, the mesomer, the racemate, the enantiomer or the diastereoisomer thereof, or the mixture thereof, or the pharmaceutically acceptable salt thereof according to any one of technical schemes 1-19 and 28, wherein L1 is —(C(R5a)(R5b))3-, and 0 methylene units of L1 are replaced by -Cy-, —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR$_6$)—, —N=N—, —C=N—, —N=C— or —C(=N$_2$)—.

30. The compound or the tautomer, the mesomer, the racemate, the enantiomer or the diastereoisomer thereof, or the mixture thereof, or the pharmaceutically acceptable salt thereof according to any one of technical schemes 1-19 and 28, wherein L1 is —(C(R5a)(R5b))3-, and 1 methylene unit of L1 is replaced by -Cy-, —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N$_2$)—.

31. The compound or the tautomer, the mesomer, the racemate, the enantiomer or the diastereoisomer thereof, or the mixture thereof, or the pharmaceutically acceptable salt thereof according to any one of technical schemes 1-19, 28 and 30, wherein L1 is —(C(R5a)(R5b))3-, and 1 methylene unit of L1 is replaced by —C(O)—.

32. The compound or the tautomer, the mesomer, the racemate, the enantiomer or the diastereoisomer thereof, or the mixture thereof, or the pharmaceutically acceptable salt thereof according to any one of technical schemes 1-19, 28 and 30-31, wherein L1 is —(C(R5a)(R5b))2-C(O)—.

33. The compound or the tautomer, the mesomer, the racemate, the enantiomer or the diastereoisomer thereof, or the mixture thereof, or the pharmaceutically acceptable salt thereof according to any one of technical schemes 1-19, wherein n is 5, and L1 is —(C(R5a)(R5b))5-.

34. The compound or the tautomer, the mesomer, the racemate, the enantiomer or the diastereoisomer thereof, or the mixture thereof, or the pharmaceutically acceptable salt thereof according to any one of technical schemes 1-19 and 33, wherein L1 is —(C(R5a)(R5b))5-, and 1 methylene unit of L1 is replaced by —NR6- or —O—.

35. The compound or the tautomer, the mesomer, the racemate, the enantiomer or the diastereoisomer thereof, or the mixture thereof, or the pharmaceutically acceptable salt thereof according to any one of technical schemes 1-19 and 33-34, wherein L1 is —(C(R5a)(R5b))5-, and 1 methylene unit of L1 is replaced by —NR6-.

36. The compound or the tautomer, the mesomer, the racemate, the enantiomer or the diastereoisomer thereof, or the mixture thereof, or the pharmaceutically acceptable salt thereof according to any one of technical schemes 1-19 and 33-35, wherein L1 is —(C(R5a)(R5b))2-NR6-(C(R5a)(R5b))2-.

37. The compound or the tautomer, the mesomer, the racemate, the enantiomer or the diastereoisomer thereof, or the mixture thereof, or the pharmaceutically acceptable salt thereof according to any one of technical schemes 1-19 and 33-34, wherein L1 is —(C(R5a)(R5b))5-, and 1 methylene unit of L1 is replaced by —O—.

38. The compound or the tautomer, the mesomer, the racemate, the enantiomer or the diastereoisomer thereof, or the mixture thereof, or the pharmaceutically acceptable salt thereof according to any one of technical schemes 1-19, 33-34 and 37, wherein L1 is —(C(R5a)(R5b))2-O—(C(R5a)(R5b))2-.

39. The compound or the tautomer, the mesomer, the racemate, the enantiomer or the diastereoisomer thereof, or the mixture thereof, or the pharmaceutically acceptable salt thereof according to any one of technical schemes 1-19 and 33, wherein L1 is —(C(R5a)(R5b))5-, and 2 methylene units of L1 are each independently replaced by —C(O)—, —NR6- or —O—.

40. The compound or the tautomer, the mesomer, the racemate, the enantiomer or the diastereoisomer thereof, or the mixture thereof, or the pharmaceutically acceptable salt thereof according to any one of technical schemes 1-19, 33 and 39, wherein L1 is —(C(R5a)(R5b))5-, and 2 methylene units of L1 are each independently replaced by —C(O)— or —NR6-.

41. The compound or the tautomer, the mesomer, the racemate, the enantiomer or the diastereoisomer thereof, or the mixture thereof, or the pharmaceutically acceptable salt thereof according to any one of technical schemes 1-19, 33 and 39-40, wherein L1 is —C(R5a)(R5b)-C(O)—NR6-(C(R5a)(R5b))2-.

42. The compound or the tautomer, the mesomer, the racemate, the enantiomer or the diastereoisomer thereof, or the mixture thereof, or the pharmaceutically acceptable salt thereof according to any one of technical schemes 1-19, 33 and 39-41, wherein L1 is —(C(R5a)(R5b))2-NR6-C(O)—C(R5a)(R5b)-.

43. The compound or the tautomer, the mesomer, the racemate, the enantiomer or the diastereoisomer thereof, or the mixture thereof, or the pharmaceutically acceptable salt thereof according to any one of technical schemes 1-19, 33 and 39, wherein L1 is —(C(R5a)(R5b))5-, and 2 methylene units of L1 are each independently replaced by —C(O)— or —O—.

44. The compound or the tautomer, the mesomer, the racemate, the enantiomer or the diastereoisomer thereof, or the mixture thereof, or the pharmaceutically acceptable salt thereof according to any one of technical schemes 1-19, 33, 39 and 43, wherein L1 is —(C(R5a)(R5b))2-O—C(R5a)(R5b)-C(O)—.

45. The compound or the tautomer, the mesomer, the racemate, the enantiomer or the diastereoisomer thereof, or the mixture thereof, or the pharmaceutically acceptable salt thereof according to any one of technical schemes 1-19 and 33, wherein L1 is —(C(R5a)(R5b))5-, and 3 methylene units of L1 are each independently replaced by —C(O)— or —NR6-.

46. The compound or the tautomer, the mesomer, the racemate, the enantiomer or the diastereoisomer thereof, or the mixture thereof, or the pharmaceutically acceptable salt thereof according to any one of technical schemes 1-19, 33 and 45, wherein L1 is —(C(R5a)(R5b))2-NR6-C(O)—C(O)—.

47. The compound or the tautomer, the mesomer, the racemate, the enantiomer or the diastereoisomer thereof, or the mixture thereof, or the pharmaceutically acceptable salt thereof according to any one of technical schemes 1-18, wherein 0 methylene units of L1 are replaced by -Cy-, —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N₂)—.

48. The compound or the tautomer, the mesomer, the racemate, the enantiomer or the diastereoisomer thereof, or the mixture thereof, or the pharmaceutically acceptable salt thereof according to any one of technical schemes 1-18, wherein 1 methylene unit of L1 is replaced by -Cy-, —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N₂)—.

49. The compound or the tautomer, the mesomer, the racemate, the enantiomer or the diastereoisomer thereof, or the mixture thereof, or the pharmaceutically acceptable salt thereof according to any one of technical schemes 1-18 and 48, wherein 1 methylene unit of L1 is replaced by —C(O)—, —C(=S)—, —NR6- or —O—.

50. The compound or the tautomer, the mesomer, the racemate, the enantiomer or the diastereoisomer thereof, or the mixture thereof, or the pharmaceutically acceptable salt thereof according to any one of technical schemes 1-18 and 48-49, wherein 1 methylene unit of L1 is replaced by —C(O)— or —C(=S)—.

51. The compound or the tautomer, the mesomer, the racemate, the enantiomer or the diastereoisomer thereof, or the mixture thereof, or the pharmaceutically acceptable salt thereof according to any one of technical schemes 1-18 and 48-50, wherein 1 methylene unit of L1 is replaced by —C(O)—.

52. The compound or the tautomer, the mesomer, the racemate, the enantiomer or the diastereoisomer thereof, or the mixture thereof, or the pharmaceutically acceptable salt thereof according to any one of technical schemes 1-18, wherein 2 methylene units of L1 are each independently replaced by -Cy-, —N(R6)C(O)—, —C(O)N(R6)-, —C(O)—, —OC(O)—, —C(O)O—, —NR6-, —O—, —S—, —SO—, —SO₂—, —P(R6)-, —P(=O)(R6)-, —N(R6)SO2-, —SO2N(R6)-, —C(=S)—, —C(=NR6)-, —N=N—, —C=N—, —N=C— or —C(=N₂)—.

53. The compound or the tautomer, the mesomer, the racemate, the enantiomer or the diastereoisomer thereof, or the mixture thereof, or the pharmaceutically acceptable salt thereof according to any one of technical schemes 1-18 and 52, wherein 2 methylene units of L1 are each independently replaced by —C(O)—, —NR6- or —O—.

54. The compound or the tautomer, the mesomer, the racemate, the enantiomer or the diastereoisomer thereof, or the mixture thereof, or the pharmaceutically acceptable salt thereof according to any one of technical schemes 1-18 and 52-53, wherein 2 methylene units of L1 are each independently replaced by —C(O)— or —NR6-.

55. The compound or the tautomer, the mesomer, the racemate, the enantiomer or the diastereoisomer thereof, or the mixture thereof, or the pharmaceutically acceptable salt thereof according to any one of technical schemes 1-18, wherein 3 methylene units of L1 are each independently replaced by -Cy-, —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N₂)—.

56. The compound or the tautomer, the mesomer, the racemate, the enantiomer or the diastereoisomer thereof, or the mixture thereof, or the pharmaceutically acceptable salt thereof according to any one of technical schemes 1-18 and 55, wherein 3 methylene units of L1 are each independently replaced by —C(O)— or —NR6-.

57. The compound or the tautomer, the mesomer, the racemate, the enantiomer or the diastereoisomer thereof, or the mixture thereof, or the pharmaceutically acceptable salt 58. The compound or the tautomer, the mesomer, the racemate, the enantiomer or the diastereoisomer thereof, or the mixture thereof, or the pharmaceutically acceptable salt thereof according to any one of technical schemes 1, 3 and 57, wherein ring B is 3-10 membered saturated or partially unsaturated heterocyclylene.

59. The compound or the tautomer, the mesomer, the racemate, the enantiomer or the diastereoisomer thereof, or the mixture thereof, or the pharmaceutically acceptable salt thereof according to any one of technical schemes 1, 3 and 57-58, wherein ring B is 3-6 membered saturated or partially unsaturated heterocyclylene.

60. The compound or the tautomer, the mesomer, the racemate, the enantiomer or the diastereoisomer thereof, or the mixture thereof, or the pharmaceutically acceptable salt thereof according to any one of technical schemes 1, 3 and 57-59, wherein ring B is 5 membered saturated or partially unsaturated heterocyclylene.

61. The compound or the tautomer, the mesomer, the racemate, the enantiomer or the diastereoisomer thereof, or the mixture thereof, or the pharmaceutically acceptable salt thereof according to any one of technical schemes 1, 3 and 57-60, wherein ring B is 5 membered saturated heterocyclylene.

62. The compound or the tautomer, the mesomer, the racemate, the enantiomer or the diastereoisomer thereof, or the mixture thereof, or the pharmaceutically acceptable salt thereof according to any one of technical schemes 1 and 3, wherein R4 and R5a independently optionally form a ring B together with an atom therebetween.

63. The compound or the tautomer, the mesomer, the racemate, the enantiomer or the diastereoisomer thereof, or the mixture thereof, or the pharmaceutically acceptable salt thereof according to any one of technical schemes 1, 3 and 62, wherein ring B is 3-10 membered saturated or partially unsaturated heterocyclylene.

64. The compound or the tautomer, the mesomer, the racemate, the enantiomer or the diastereoisomer thereof, or the mixture thereof, or the pharmaceutically acceptable salt thereof according to any one of technical schemes 1, 3 and 62-63, wherein ring B is 6 membered saturated or partially unsaturated heterocyclylene.

65. The compound or the tautomer, the mesomer, the racemate, the enantiomer or the diastereoisomer thereof, or the mixture thereof, or the pharmaceutically acceptable salt thereof according to any one of technical schemes 1, 3 and 62-64, wherein ring B is 6 membered saturated heterocyclylene.

66. The compound or the tautomer, the mesomer, the racemate, the enantiomer or the diastereoisomer thereof, or the mixture thereof, or the pharmaceutically acceptable salt thereof according to technical scheme 1, wherein L2 is —C(R3a)(R3b)-R or —(C(R3a)(R3b))2-R, and L1 is —(C(R5a)(R5b))2-, —(C(R5a)(R5b))3- or —(C(R5a)(R5b))5-.

67. The compound or the tautomer, the mesomer, the racemate, the enantiomer or the diastereoisomer thereof, or the mixture thereof, or the pharmaceutically acceptable salt thereof according to any one of technical schemes 1 and 66, wherein L2 is —(C(R3a)(R3b))2-R, and L1 is —(C(R5a)(R5b))2-.

68. The compound or the tautomer, the mesomer, the racemate, the enantiomer or the diastereoisomer thereof, or the mixture thereof, or the pharmaceutically acceptable salt thereof according to any one of technical schemes 1 and 66-67, wherein L2 is —(C(R3a)(R3b))2-R, L1 is —(C(R5a)(R5b))2-, and 1 methylene unit of L1 is replaced by —C(O)—, —C(=S)—, —NR6- or —O—.

69. The compound or the tautomer, the mesomer, the racemate, the enantiomer or the diastereoisomer thereof, or the mixture thereof, or the pharmaceutically acceptable salt thereof according to any one of technical schemes 1 and 66-68, wherein L2 is —(C(R3a)(R3b))2-R, L1 is —(C(R5a)(R5b))2-, and 1 methylene unit of L1 is replaced by —C(O)—.

70. The compound or the tautomer, the mesomer, the racemate, the enantiomer or the diastereoisomer thereof, or the mixture thereof, or the pharmaceutically acceptable salt thereof according to any one of technical schemes 1 and 66-69, wherein L2 is —(C(R3a)(R3b))2-R, and L1 is —C(R5a)(R5b)-C(O)—.

71. The compound or the tautomer, the mesomer, the racemate, the enantiomer or the diastereoisomer thereof, or the mixture thereof, or the pharmaceutically acceptable salt thereof according to any one of technical schemes 1 and 66-70, wherein R3a and R5a independently optionally form a ring B together with an atom therebetween.

72. The compound or the tautomer, the mesomer, the racemate, the enantiomer or the diastereoisomer thereof, or the mixture thereof, or the pharmaceutically acceptable salt thereof according to any one of technical schemes 1 and 66-71, wherein ring B is 3-10 membered saturated or partially unsaturated heterocyclylene.

73. The compound or the tautomer, the mesomer, the racemate, the enantiomer or the diastereoisomer thereof, or the mixture thereof, or the pharmaceutically acceptable salt thereof according to any one of technical schemes 1 and 66-72, wherein ring B is 5 membered saturated heterocyclylene.

74. The compound or the tautomer, the mesomer, the racemate, the enantiomer or the diastereoisomer thereof, or the mixture thereof, or the pharmaceutically acceptable salt thereof according to any one of technical schemes 1 and 66, wherein L2 is —C(R3a)(R3b)-R, and L1 is —(C(R5a)(R5b))2-.

75. The compound or the tautomer, the mesomer, the racemate, the enantiomer or the diastereoisomer thereof, or the mixture thereof, or the pharmaceutically acceptable salt thereof according to any one of technical schemes 1, 66 and 74, wherein L2 is —C(R3a)(R3b)-R, L1 is —(C(R5a)(R5b))2-, and 1 methylene unit of L1 is replaced by —C(O)—, —C(=S)—, —NR6- or —O—.

76. The compound or the tautomer, the mesomer, the racemate, the enantiomer or the diastereoisomer thereof, or the mixture thereof, or the pharmaceutically acceptable salt thereof according to any one of technical schemes 1, 66 and 74-75, wherein L2 is —C(R3a)(R3b)-R, L1 is —(C(R5a)(R5b))2-, and 1 methylene unit of L1 is replaced by —C(O)—.

77. The compound or the tautomer, the mesomer, the racemate, the enantiomer or the diastereoisomer thereof, or the mixture thereof, or the pharmaceutically acceptable salt thereof according to any one of technical schemes 1, 66 and 74-76, wherein L2 is —C(R3a)(R3b)-R, and L1 is —C(R5a)(R5b)-C(O)—.

78. The compound or the tautomer, the mesomer, the racemate, the enantiomer or the diastereoisomer thereof, or the mixture thereof, or the pharmaceutically acceptable salt thereof according to any one of technical schemes 1-77, wherein R1 is selected from the group consisting of: —O—, —(R2)N— and —S—.

79. The compound or the tautomer, the mesomer, the racemate, the enantiomer or the diastereoisomer thereof, or the mixture thereof, or the pharmaceutically acceptable salt thereof according to any one of technical schemes 1-78, wherein R1 is —O—.

80. The compound or the tautomer, the mesomer, the racemate, the enantiomer or the diastereoisomer thereof, or the mixture thereof, or the pharmaceutically acceptable salt thereof according to any one of technical schemes 1-78, wherein R1 is —(R2)N—.

81. The compound or the tautomer, the mesomer, the racemate, the enantiomer or the diastereoisomer thereof, or the mixture thereof, or the pharmaceutically acceptable salt thereof according to any one of technical schemes 1-78 and 80, wherein R2 is hydrogen or a C1-6 aliphatic group.

82. The compound or the tautomer, the mesomer, the racemate, the enantiomer or the diastereoisomer thereof, or the mixture thereof, or the pharmaceutically acceptable salt thereof according to any one of technical schemes 1-78 and 80-81, wherein R1 is —HN—.

83. The compound or the tautomer, the mesomer, the racemate, the enantiomer or the diastereoisomer thereof, or the mixture thereof, or the pharmaceutically acceptable salt thereof according to any one of technical schemes 1-82, wherein -Cy- is 6-10 membered arylene.

84. The compound or the tautomer, the mesomer, the racemate, the enantiomer or the diastereoisomer thereof, or the mixture thereof, or the pharmaceutically acceptable salt thereof according to any one of technical schemes 1-83, wherein -Cy- is phenylene.

85. The compound or the tautomer, the mesomer, the racemate, the enantiomer or the diastereoisomer thereof, or the mixture thereof, or the pharmaceutically acceptable salt thereof according to any one of technical schemes 1-84, wherein R7 is hydrogen.

86. The compound or the tautomer, the mesomer, the racemate, the enantiomer or the diastereoisomer thereof, or the mixture thereof, or the pharmaceutically acceptable salt thereof according to technical scheme 1, wherein R3a and R3b are independently hydrogen, or R3a and R5a independently optionally form a ring B together with an atom therebetween.

87. The compound or the tautomer, the mesomer, the racemate, the enantiomer or the diastereoisomer thereof, or the mixture thereof, or the pharmaceutically acceptable salt thereof according to any one of technical schemes 1 and 86, wherein ring B is 3-10 membered saturated or partially unsaturated heterocyclylene.

88. The compound or the tautomer, the mesomer, the racemate, the enantiomer or the diastereoisomer thereof, or the mixture thereof, or the pharmaceutically acceptable salt thereof according to any one of technical schemes 1 and 86-87, wherein ring B is 5 membered saturated heterocyclylene.

89. The compound or the tautomer, the mesomer, the racemate, the enantiomer or the diastereoisomer thereof, or the mixture thereof, or the pharmaceutically acceptable salt thereof according to technical scheme 1, wherein R4 is hydrogen, or R4 and R5a independently optionally form a ring B together with an atom therebetween.

90. The compound or the tautomer, the mesomer, the racemate, the enantiomer or the diastereoisomer thereof, or the mixture thereof, or the pharmaceutically acceptable salt thereof according to technical scheme 1, wherein R4 is hydrogen, or R4 and R5a independently optionally form a ring B together with an atom therebetween.

91. The compound or the tautomer, the mesomer, the racemate, the enantiomer or the diastereoisomer thereof, or the mixture thereof, or the pharmaceutically acceptable salt thereof according to any one of technical schemes 1 and 86-90, wherein R8 is hydrogen.

92. The compound or the tautomer, the mesomer, the racemate, the enantiomer or the diastereoisomer thereof, or the mixture thereof, or the pharmaceutically acceptable salt thereof according to technical scheme 1, wherein R, Ra and Rb are each independently hydrogen.

93. The compound or the tautomer, the mesomer, the racemate, the enantiomer or the diastereoisomer thereof, or the mixture thereof, or the pharmaceutically acceptable salt thereof according to technical scheme 1, wherein the ligand-drug conjugate comprises the following group of structures:

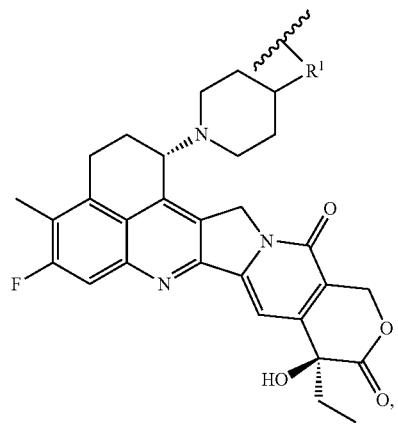

I-A-1

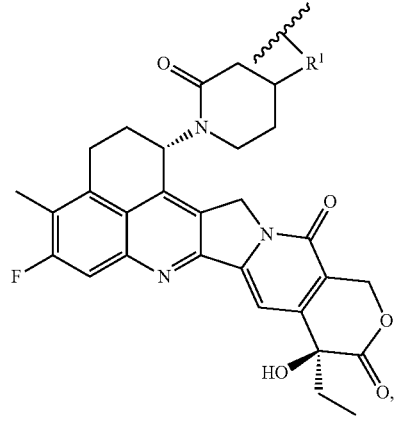

I-A-2

I-A-3
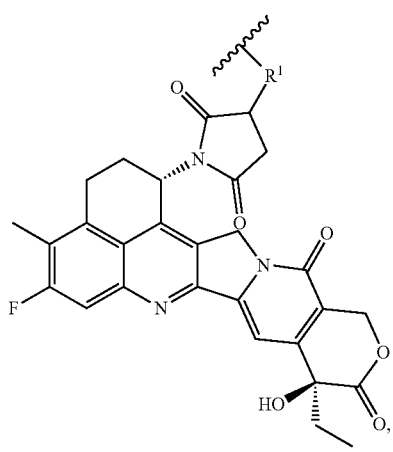
I-A-4
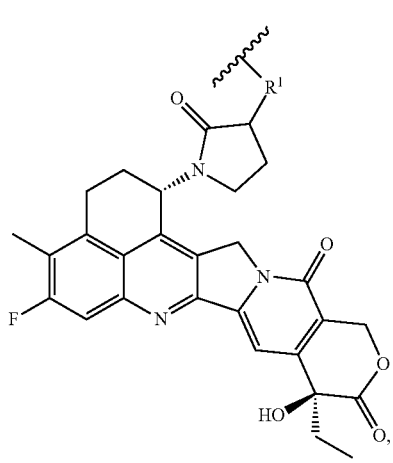
I-A-5
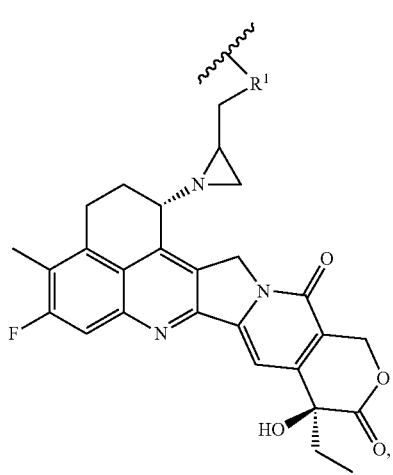
I-A-6
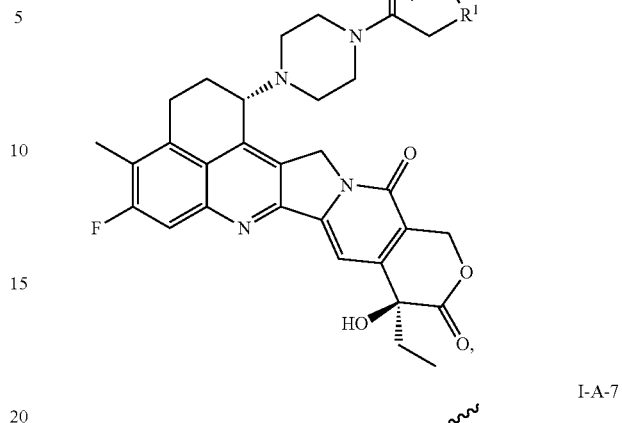
I-A-7
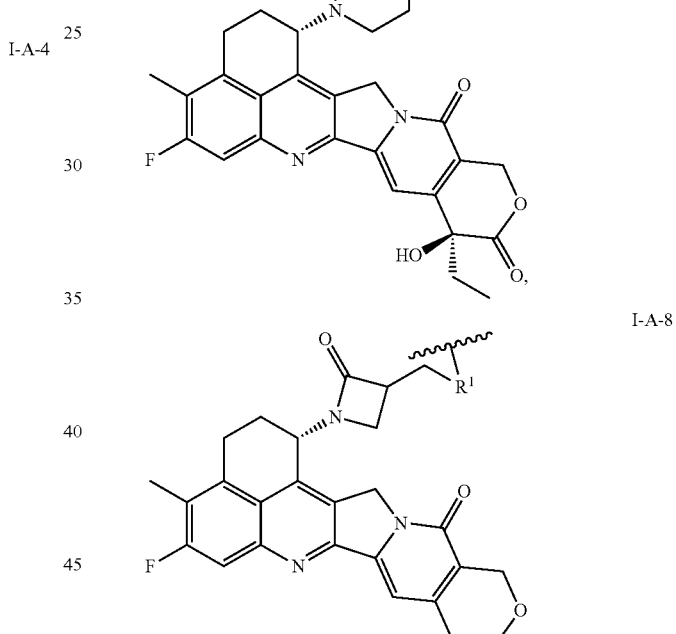
I-A-8
I-A-9
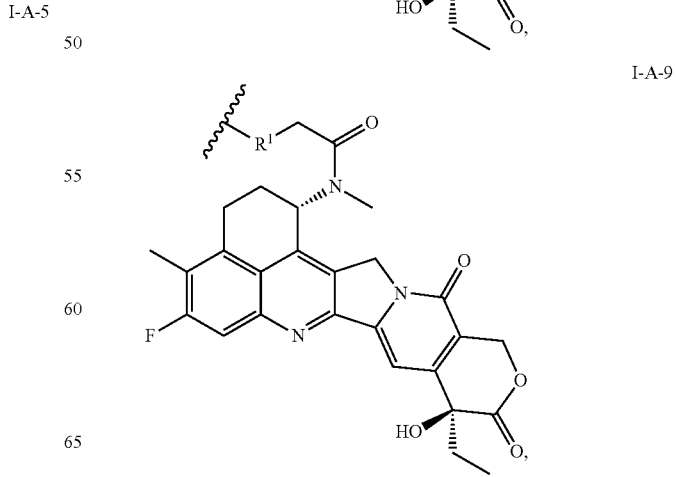

I-A-10
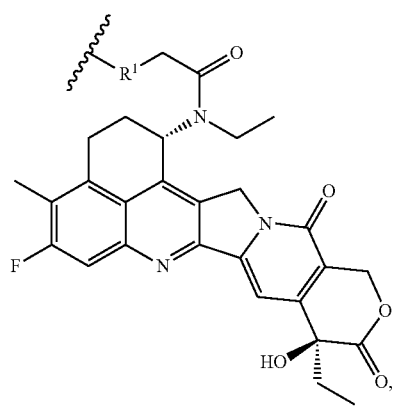
I-A-11
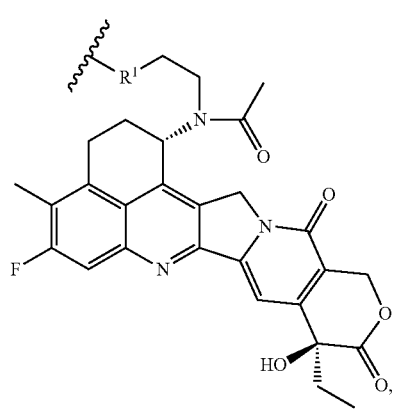
I-A-12
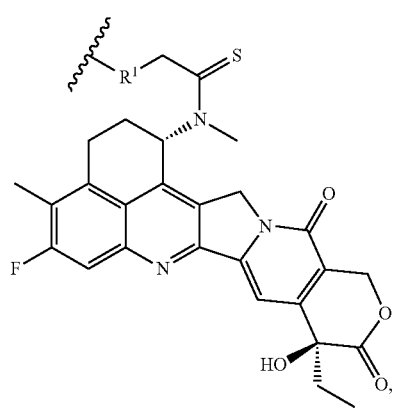
I-A-13
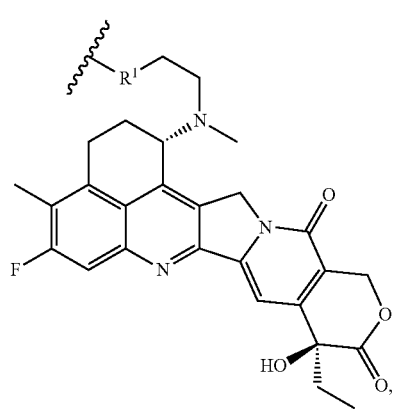
I-A-14
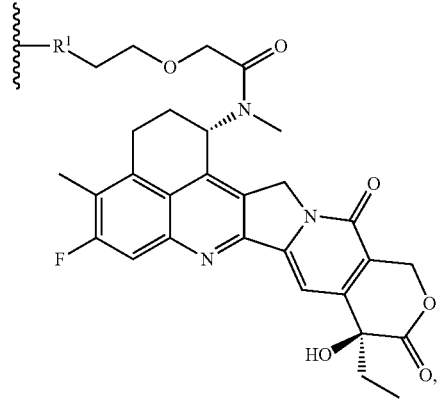
I-A-15
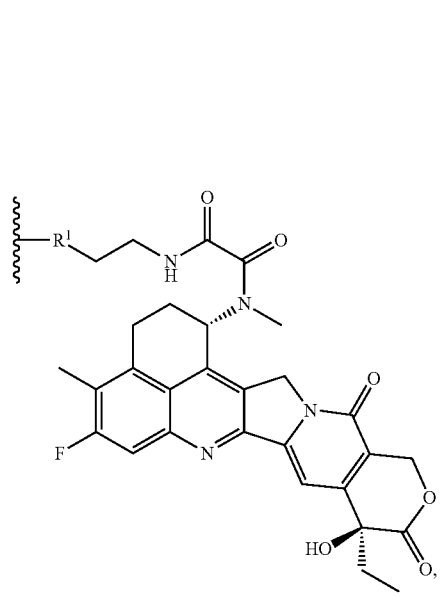
I-A-16
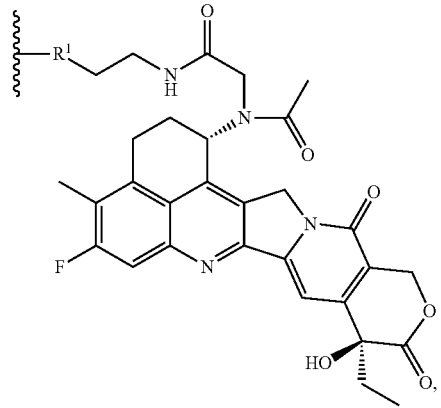

-continued

I-A-17

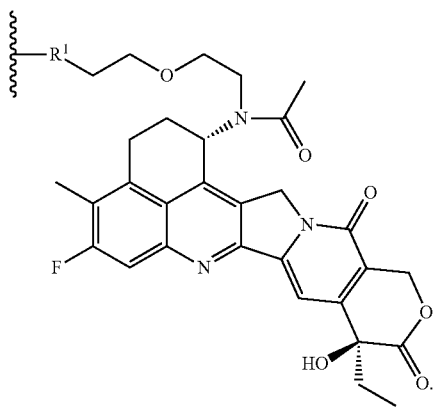

94. A compound or a tautomer, a mesomer, a racemate, an enantiomer or a diastereoisomer thereof, or a mixture thereof, or a pharmaceutically acceptable salt thereof, wherein the compound comprises a structure shown as formula (II-A):

(II-A)

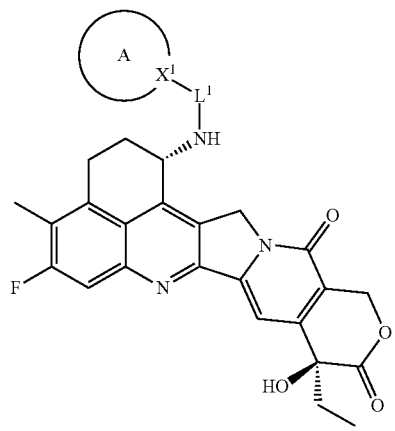

wherein, X1 is selected from the group consisting of: N, P, and saturated or unsaturated C; when X1 is saturated C, X1 is substituted with Rn;
when X1 is saturated C, ring A is selected from the group consisting of: 3-10 membered saturated or partially unsaturated heterocyclyl, and 3-10 membered saturated or partially unsaturated carbocyclyl, wherein ring A is substituted with 0 or no less than 1 substituent R1a;
or, when X1 is unsaturated C, ring A is selected from the group consisting of: 6-10 membered aryl, 5-8 membered heteroaryl, 3-10 membered partially unsaturated heterocyclyl, and 3-10 membered partially unsaturated carbocyclyl, wherein ring A is substituted with 0 or no less than 1 substituent R1b;
or, when X1 is N or P, ring A is selected from the group consisting of: 5-8 membered heteroaryl and 3-10 membered saturated or partially unsaturated heterocyclyl, wherein ring A is substituted with 0 or no less than 1 substituent R1c;
when ring A is selected from the group consisting of: 6-10 membered aryl, 5-8 membered heteroaryl, and 3-10 membered saturated or partially unsaturated carbocyclyl, ring A is substituted with p L2, wherein L2 is not Rn;
or, when ring A is 3-10 membered saturated or partially unsaturated heterocyclyl, ring A is substituted with p L2, or ring A comprises q ring-forming heteroatom X2, and X2 is used for direct or indirect linking of a ligand;
X2 is selected from the group consisting of: N and P;
L2 is —R2-L3-, and R2 is used for direct or indirect linking of a ligand;
L3 is —(C(R3a)(R3b))$_m$—, wherein when L3 comprises a methylene unit, 0 or no less than 1 methylene unit of L3 is independently replaced by —N(R4)C(O)—, —C(O)N(R4)-, —C(O)—, —OC(O)—, —C(O)O—, —NR4-, —O—, —S—, —SO—, —SO$_2$—, —P(R4)-, —P(=O)(R4)-, —N(R4)SO$_2$—, —SO2N(R4)-, —C(=S)—, —C(=NR4)-, —N=N—, —C=N—, —N=C— or —C(=N$_2$)—;
R2 is selected from the group consisting of: —O—, —(R2a)N—, —S— and —P(=O)(R2a)-;
L1 is —(C(R5a)(R5b))$_n$—, wherein when L1 comprises a methylene unit, 0 or no less than 1 methylene unit of L1 is independently replaced by —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N2)-;
wherein each R1a, each R1b, each R1c, each R2a, each R3a, each R3b, each R4, each R5a, each R5b, each R6 and each Rn are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R;
wherein each R, each Ra and each Rb are each independently hydrogen, protium, deuterium, tritium, halogen, —NO2, —CN, —OH, —SH, —NH2, —C(O)H, —CO2H, —C(O)C(O)H, —C(O)CH$_2$C(O)H, —S(O)H, —S(O)2H, —C(O)NH$_2$, —SO2NH2, —OC(O)H, —N(H)SO2H or a C1-6 aliphatic group;
m and n are each independently selected from the group consisting of integers ≥0, and p and q are each independently selected from the group consisting of integers ≥1.

95. The compound or the tautomer, the mesomer, the racemate, the enantiomer or the diastereoisomer thereof, or the mixture thereof, or the pharmaceutically acceptable salt thereof according to technical scheme 94, wherein X1 is saturated C.

96. The compound or the tautomer, the mesomer, the racemate, the enantiomer or the diastereoisomer thereof, or the mixture thereof, or the pharmaceutically acceptable salt thereof according to any one of technical schemes 94-95, wherein ring A is selected from the group consisting of: 3-10 membered saturated heterocyclyl and 3-10 membered saturated carbocyclyl.

97. The compound or the tautomer, the mesomer, the racemate, the enantiomer or the diastereoisomer thereof, or the mixture thereof, or the pharmaceutically acceptable salt thereof according to any one of technical schemes 94-96, wherein ring A is 3-10 membered saturated carbocyclyl.

98. The compound or the tautomer, the mesomer, the racemate, the enantiomer or the diastereoisomer thereof, or the mixture thereof, or the pharmaceutically acceptable salt thereof according to any one of technical schemes 94-97, wherein ring A is 3-6 membered saturated carbocyclyl.

99. The compound or the tautomer, the mesomer, the racemate, the enantiomer or the diastereoisomer thereof, or the mixture thereof, or the pharmaceutically acceptable salt thereof according to any one of technical schemes 94-98, wherein ring A is 4 membered saturated carbocyclyl.

100. The compound or the tautomer, the mesomer, the racemate, the enantiomer or the diastereoisomer thereof, or the mixture thereof, or the pharmaceutically acceptable salt thereof according to any one of technical schemes 94-98, wherein ring A is 6 membered saturated carbocyclyl.

101. The compound or the tautomer, the mesomer, the racemate, the enantiomer or the diastereoisomer thereof, or the mixture thereof, or the pharmaceutically acceptable salt thereof according to any one of technical schemes 94-96, wherein ring A is 3-10 membered saturated heterocyclyl.

102. The compound or the tautomer, the mesomer, the racemate, the enantiomer or the diastereoisomer thereof, or the mixture thereof, or the pharmaceutically acceptable salt thereof according to any one of technical schemes 94-96 and 101, wherein ring A is 3-6 membered saturated heterocyclyl.

103. The compound or the tautomer, the mesomer, the racemate, the enantiomer or the diastereoisomer thereof, or the mixture thereof, or the pharmaceutically acceptable salt thereof according to any one of technical schemes 94-96 and 101-102, wherein ring A is 3 membered saturated heterocyclyl.

104. The compound or the tautomer, the mesomer, the racemate, the enantiomer or the diastereoisomer thereof, or the mixture thereof, or the pharmaceutically acceptable salt thereof according to any one of technical schemes 94-96 and 101-103, wherein ring A comprises 1 heteroatom.

105. The compound or the tautomer, the mesomer, the racemate, the enantiomer or the diastereoisomer thereof, or the mixture thereof, or the pharmaceutically acceptable salt thereof according to any one of technical schemes 94-96 and 101-104, wherein ring A comprises 1 nitrogen atom.

106. The compound or the tautomer, the mesomer, the racemate, the enantiomer or the diastereoisomer thereof, or the mixture thereof, or the pharmaceutically acceptable salt thereof according to any one of technical schemes 94-96 and 101-102, wherein ring A is 5 membered saturated heterocyclyl.

107. The compound or the tautomer, the mesomer, the racemate, the enantiomer or the diastereoisomer thereof, or the mixture thereof, or the pharmaceutically acceptable salt thereof according to any one of technical schemes 94-96, 101-102 and 106, wherein ring A comprises 1 heteroatom.

108. The compound or the tautomer, the mesomer, the racemate, the enantiomer or the diastereoisomer thereof, or the mixture thereof, or the pharmaceutically acceptable salt thereof according to any one of technical schemes 94-96, 101-102 and 106-107, wherein ring A comprises 1 nitrogen atom.

109. The compound or the tautomer, the mesomer, the racemate, the enantiomer or the diastereoisomer thereof, or the mixture thereof, or the pharmaceutically acceptable salt thereof according to any one of technical schemes 94-108, wherein ring A is substituted with 0 substituent $R^{1a}$.

110. The compound or the tautomer, the mesomer, the racemate, the enantiomer or the diastereoisomer thereof, or the mixture thereof, or the pharmaceutically acceptable salt thereof according to technical scheme 94, wherein X1 is unsaturated C.

111. The compound or the tautomer, the mesomer, the racemate, the enantiomer or the diastereoisomer thereof, or the mixture thereof, or the pharmaceutically acceptable salt thereof according to any one of technical schemes 94 and 110, wherein ring A is selected from the group consisting of: 6-10 membered aryl and 5-8 membered heteroaryl.

112. The compound or the tautomer, the mesomer, the racemate, the enantiomer or the diastereoisomer thereof, or the mixture thereof, or the pharmaceutically acceptable salt thereof according to any one of technical schemes 94 and 110-111, wherein ring A is 6-10 membered aryl.

113. The compound or the tautomer, the mesomer, the racemate, the enantiomer or the diastereoisomer thereof, or the mixture thereof, or the pharmaceutically acceptable salt thereof according to any one of technical schemes 94 and 110-112, wherein ring A is phenyl.

114. The compound or the tautomer, the mesomer, the racemate, the enantiomer or the diastereoisomer thereof, or the mixture thereof, or the pharmaceutically acceptable salt thereof according to any one of technical schemes 110-113, wherein ring A is substituted with 0 substituent R1b.

115. The compound or the tautomer, the mesomer, the racemate, the enantiomer or the diastereoisomer thereof, or the mixture thereof, or the pharmaceutically acceptable salt thereof according to technical scheme 94, wherein X1 is N or P.

116. The compound or the tautomer, the mesomer, the racemate, the enantiomer or the diastereoisomer thereof, or the mixture thereof, or the pharmaceutically acceptable salt thereof according to technical scheme 94 or 115, wherein X1 is N.

117. The compound or the tautomer, the mesomer, the racemate, the enantiomer or the diastereoisomer thereof, or the mixture thereof, or the pharmaceutically acceptable salt thereof according to any one of technical schemes 94 and 115-116, wherein ring A is selected from the group consisting of: 5-8 membered heteroaryl and 3-10 membered saturated heterocyclyl.

118. The compound or the tautomer, the mesomer, the racemate, the enantiomer or the diastereoisomer thereof, or the mixture thereof, or the pharmaceutically acceptable salt thereof according to any one of technical schemes 94 and 115-117, wherein ring A is 3-10 membered saturated heterocyclyl.

119. The compound or the tautomer, the mesomer, the racemate, the enantiomer or the diastereoisomer thereof, or the mixture thereof, or the pharmaceutically acceptable salt thereof according to any one of technical schemes 94 and 115-118, wherein ring A is 3-6 membered saturated heterocyclyl.

120. The compound or the tautomer, the mesomer, the racemate, the enantiomer or the diastereoisomer thereof, or the mixture thereof, or the pharmaceutically acceptable salt thereof according to any one of technical schemes 94 and 115-119, wherein ring A is 6 membered saturated heterocyclyl.

121. The compound or the tautomer, the mesomer, the racemate, the enantiomer or the diastereoisomer thereof, or the mixture thereof, or the pharmaceutically acceptable salt thereof according to any one of technical schemes 94 and 115-120, wherein ring A independently comprises 2 heteroatoms.

122. The compound or the tautomer, the mesomer, the racemate, the enantiomer or the diastereoisomer thereof, or the mixture thereof, or the pharmaceutically acceptable salt thereof according to any one of technical schemes 94 and 115-121, wherein ring A independently comprises 2 nitrogen atoms.

123. The compound or the tautomer, the mesomer, the racemate, the enantiomer or the diastereoisomer thereof, or the mixture thereof, or the pharmaceutically acceptable salt thereof according to any one of technical schemes 115-121, wherein ring A is substituted with 0 substituent R1c.

124. The compound or the tautomer, the mesomer, the racemate, the enantiomer or the diastereoisomer thereof, or the mixture thereof, or the pharmaceutically acceptable salt thereof according to technical scheme 94, wherein the formula (II-A) is a structure shown as formula (II-Ax):

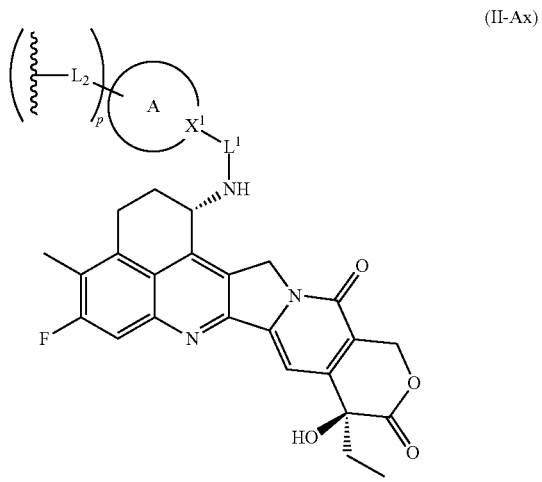

(II-Ax)

wherein, when ring A is selected from the group consisting of: 6-10 membered aryl, 5-8 membered heteroaryl, and 3-10 membered saturated or partially unsaturated carbocyclyl, ring A is substituted with p L2;

or, when ring A is 3-10 membered saturated or partially unsaturated heterocyclyl, ring A is substituted with p L2.

125. The compound or the tautomer, the mesomer, the racemate, the enantiomer or the diastereoisomer thereof, or the mixture thereof, or the pharmaceutically acceptable salt thereof according to technical scheme 94, wherein the formula (II-A) is a structure shown as formula (II-Ay):

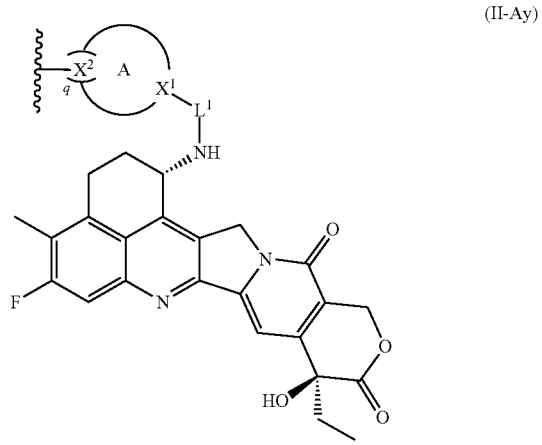

(II-Ay)

wherein ring A is 3-10 membered saturated or partially unsaturated heterocyclyl, ring A comprises q ring-forming heteroatom X2, and X2 is used for direct or indirect linking of a ligand.

126. The compound or the tautomer, the mesomer, the racemate, the enantiomer or the diastereoisomer thereof, or the mixture thereof, or the pharmaceutically acceptable salt thereof according to technical scheme 94, wherein ring A is selected from the group consisting of: 6-10 membered aryl, 5-8 membered heteroaryl, and 3-10 membered saturated carbocyclyl.

127. The compound or the tautomer, the mesomer, the racemate, the enantiomer or the diastereoisomer thereof, or the mixture thereof, or the pharmaceutically acceptable salt thereof according to any one of technical schemes 94 and 126, wherein ring A is selected from the group consisting of: phenyl and 3-6 membered saturated carbocyclyl.

128. The compound or the tautomer, the mesomer, the racemate, the enantiomer or the diastereoisomer thereof, or the mixture thereof, or the pharmaceutically acceptable salt thereof according to any one of technical schemes 94 and 126-127, wherein ring A is 3-6 membered saturated carbocyclyl.

129. The compound or the tautomer, the mesomer, the racemate, the enantiomer or the diastereoisomer thereof, or the mixture thereof, or the pharmaceutically acceptable salt thereof according to any one of technical schemes 94 and 126-128, wherein ring A is 4 membered saturated carbocyclyl or 6 membered saturated carbocyclyl.

130. The compound or the tautomer, the mesomer, the racemate, the enantiomer or the diastereoisomer thereof, or the mixture thereof, or the pharmaceutically acceptable salt thereof according to any one of technical schemes 94 and 126-127, wherein ring A is phenyl.

131. The compound or the tautomer, the mesomer, the racemate, the enantiomer or the diastereoisomer thereof, or the mixture thereof, or the pharmaceutically acceptable salt thereof according to any one of technical schemes 94 and 126-130, wherein ring A is substituted with no less than 1 L2.

132. The compound or the tautomer, the mesomer, the racemate, the enantiomer or the diastereoisomer thereof, or the mixture thereof, or the pharmaceutically acceptable salt thereof according to any one of technical schemes 94 and 126-131, wherein ring A is substituted with 1 L2.

133. The compound or the tautomer, the mesomer, the racemate, the enantiomer or the diastereoisomer thereof, or the mixture thereof, or the pharmaceutically acceptable salt thereof according to any one of technical schemes 94 and 126, wherein ring A is 3-10 membered saturated heterocyclyl.

134. The compound or the tautomer, the mesomer, the racemate, the enantiomer or the diastereoisomer thereof, or the mixture thereof, or the pharmaceutically acceptable salt thereof according to any one of technical schemes 94, 126 and 133, wherein ring A is 3-6 membered saturated heterocyclyl.

135. The compound or the tautomer, the mesomer, the racemate, the enantiomer or the diastereoisomer thereof, or the mixture thereof, or the pharmaceutically acceptable salt thereof according to any one of technical schemes 94, 126 and 133-134, wherein ring A is 3 membered saturated heterocyclyl.

136. The compound or the tautomer, the mesomer, the racemate, the enantiomer or the diastereoisomer thereof, or the mixture thereof, or the pharmaceutically acceptable salt thereof according to any one of technical schemes 94, 126 and 133-134, wherein ring A is 5 membered saturated heterocyclyl.

137. The compound or the tautomer, the mesomer, the racemate, the enantiomer or the diastereoisomer thereof, or the mixture thereof, or the pharmaceutically acceptable salt thereof according to any one of technical schemes 94, 126 and 133-134, wherein ring A is 6 membered saturated heterocyclyl.

138. The compound or the tautomer, the mesomer, the racemate, the enantiomer or the diastereoisomer thereof, or the mixture thereof, or the pharmaceutically acceptable salt thereof according to any one of technical schemes 133-137, wherein ring A is substituted with no less than 1 L2.

139. The compound or the tautomer, the mesomer, the racemate, the enantiomer or the diastereoisomer thereof, or the mixture thereof, or the pharmaceutically acceptable salt thereof according to any one of technical schemes 133-138, wherein ring A is substituted with 1 L2.

140. The compound or the tautomer, the mesomer, the racemate, the enantiomer or the diastereoisomer thereof, or the mixture thereof, or the pharmaceutically acceptable salt thereof according to technical scheme 94, wherein m is 0, 1 or 2.

141. The compound or the tautomer, the mesomer, the racemate, the enantiomer or the diastereoisomer thereof, or the mixture thereof, or the pharmaceutically acceptable salt thereof according to any one of technical schemes 94 and 140, wherein m is 0, and L3 is a covalent bond.

142. The compound or the tautomer, the mesomer, the racemate, the enantiomer or the diastereoisomer thereof, or the mixture thereof, or the pharmaceutically acceptable salt thereof according to any one of technical schemes 94 and 140, wherein m is 1, and L3 is —C(R5a)(R5b)-.

143. The compound or the tautomer, the mesomer, the racemate, the enantiomer or the diastereoisomer thereof, or the mixture thereof, or the pharmaceutically acceptable salt thereof according to any one of technical schemes 94, 140 and 142, wherein 0 methylene units of L3 are replaced by —N(R4)C(O)—, —C(O)N(R4)-, —C(O)—, —OC(O)—, —C(O)O—, —NR4-, —O—, —S—, —SO—, —SO2-, —P(R4)-, —P(=O)(R4)-, —N(R4)SO2-, —SO2N(R4)-, —C(=S)—, —C(=NR4)-, —N=N—, —C=N—, —N=C— or —C(=N2)-.

144. The compound or the tautomer, the mesomer, the racemate, the enantiomer or the diastereoisomer thereof, or the mixture thereof, or the pharmaceutically acceptable salt thereof according to any one of technical schemes 94 and 140, wherein m is 2, and L3 is —(C(R3a)(R3b))2-.

145. The compound or the tautomer, the mesomer, the racemate, the enantiomer or the diastereoisomer thereof, or the mixture thereof, or the pharmaceutically acceptable salt thereof according to any one of technical schemes 94, 140 and 144, wherein 0 methylene units of L3 are replaced by —N(R4)C(O)—, —C(O)N(R4)-, —C(O)—, —OC(O)—, —C(O)O—, —NR4-, —O—, —S—, —SO—, —SO2-, —P(R4)-, —P(=O)(R4)-, —N(R4)SO2-, —SO2N(R4)-, —C(=S)—, —C(=NR4)-, —N=N—, —C=N—, —N=C— or —C(=N2)-.

146. The compound or the tautomer, the mesomer, the racemate, the enantiomer or the diastereoisomer thereof, or the mixture thereof, or the pharmaceutically acceptable salt thereof according to any one of technical schemes 94 and 125, wherein ring A comprises no less than 1 ring-forming heteroatom X2, and X2 is used for direct or indirect linking of a ligand.

147. The compound or the tautomer, the mesomer, the racemate, the enantiomer or the diastereoisomer thereof, or the mixture thereof, or the pharmaceutically acceptable salt thereof according to any one of technical schemes 94, 125 and 146, wherein ring A comprises 1 ring-forming heteroatom X2.

148. The compound or the tautomer, the mesomer, the racemate, the enantiomer or the diastereoisomer thereof, or the mixture thereof, or the pharmaceutically acceptable salt thereof according to any one of technical schemes 94, 125 and 146-147, wherein X2 is N.

149. The compound or the tautomer, the mesomer, the racemate, the enantiomer or the diastereoisomer thereof, or the mixture thereof, or the pharmaceutically acceptable salt thereof according to any one of technical schemes 94-148, wherein n is 0 or 1.

150. The compound or the tautomer, the mesomer, the racemate, the enantiomer or the diastereoisomer thereof, or the mixture thereof, or the pharmaceutically acceptable salt thereof according to any one of technical schemes 94-149, wherein n is 0, and L1 is a covalent bond.

151. The compound or the tautomer, the mesomer, the racemate, the enantiomer or the diastereoisomer thereof, or the mixture thereof, or the pharmaceutically acceptable salt thereof according to any one of technical schemes 94-149, wherein n is 1, and L1 is —C(R5a)(R5b)-.

152. The compound or the tautomer, the mesomer, the racemate, the enantiomer or the diastereoisomer thereof, or the mixture thereof, or the pharmaceutically acceptable salt thereof according to any one of technical schemes 94-149 and 151, wherein 1 methylene unit of L1 is replaced by —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N$_2$)—.

153. The compound or the tautomer, the mesomer, the racemate, the enantiomer or the diastereoisomer thereof, or the mixture thereof, or the pharmaceutically acceptable salt thereof according to any one of technical schemes 94-149 and 151-152, wherein 1 methylene unit of L1 is replaced by —C(O)—.

154. The compound or the tautomer, the mesomer, the racemate, the enantiomer or the diastereoisomer thereof, or the mixture thereof, or the pharmaceutically acceptable salt thereof according to any one of technical schemes 94-153, wherein R2 is selected from the group consisting of: —O—, —(R2a)N— and —S—.

155. The compound or the tautomer, the mesomer, the racemate, the enantiomer or the diastereoisomer thereof, or the mixture thereof, or the pharmaceutically acceptable salt thereof according to any one of technical schemes 94-154, wherein R2 is —O—.

156. The compound or the tautomer, the mesomer, the racemate, the enantiomer or the diastereoisomer thereof, or the mixture thereof, or the pharmaceutically acceptable salt thereof according to any one of technical schemes 94-153, wherein R2 is —(R2A)N—.

157. The compound or the tautomer, the mesomer, the racemate, the enantiomer or the diastereoisomer thereof, or the mixture thereof, or the pharmaceutically acceptable salt thereof according to any one of technical schemes 94-153 and 156, wherein R2a is hydrogen.

158. The compound or the tautomer, the mesomer, the racemate, the enantiomer or the diastereoisomer thereof, or the mixture thereof, or the pharmaceutically acceptable salt thereof according to any one of technical schemes 94-153 and 156-157, wherein R2 is —HN—.

159. The compound or the tautomer, the mesomer, the racemate, the enantiomer or the diastereoisomer thereof, or the mixture thereof, or the pharmaceutically acceptable salt thereof according to any one of technical schemes 94-109, wherein R1a is hydrogen.

160. The compound or the tautomer, the mesomer, the racemate, the enantiomer or the diastereoisomer thereof, or the mixture thereof, or the pharmaceutically acceptable salt thereof according to any one of technical schemes 94 and 110-114, wherein R1b is hydrogen.

161. The compound or the tautomer, the mesomer, the racemate, the enantiomer or the diastereoisomer thereof, or the mixture thereof, or the pharmaceutically acceptable salt thereof according to any one of technical schemes 94 and 115-123, wherein R1c is hydrogen.

162. The compound or the tautomer, the mesomer, the racemate, the enantiomer or the diastereoisomer thereof, or the mixture thereof, or the pharmaceutically acceptable salt thereof according to technical scheme 94, wherein R3a and R3b are each independently hydrogen.

163. The compound or the tautomer, the mesomer, the racemate, the enantiomer or the diastereoisomer thereof, or the mixture thereof, or the pharmaceutically acceptable salt thereof according to technical scheme 94, wherein R4 is hydrogen.

164. The compound or the tautomer, the mesomer, the racemate, the enantiomer or the diastereoisomer thereof, or the mixture thereof, or the pharmaceutically acceptable salt thereof according to technical scheme 94, wherein R5a and R5b are each independently hydrogen.

165. The compound or the tautomer, the mesomer, the racemate, the enantiomer or the diastereoisomer thereof, or the mixture thereof, or the pharmaceutically acceptable salt thereof according to technical scheme 94, wherein R6 is hydrogen.

166. The compound or the tautomer, the mesomer, the racemate, the enantiomer or the diastereoisomer thereof, or the mixture thereof, or the pharmaceutically acceptable salt thereof according to technical scheme 94, wherein R, Ra and Rb are each independently hydrogen.

167. The compound or the tautomer, the mesomer, the racemate, the enantiomer or the diastereoisomer thereof, or the mixture thereof, or the pharmaceutically acceptable salt thereof according to technical scheme 94, wherein the compound comprises the following group of structures:

-continued

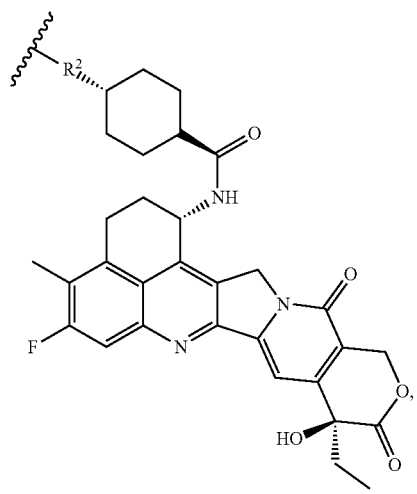

II-A-2

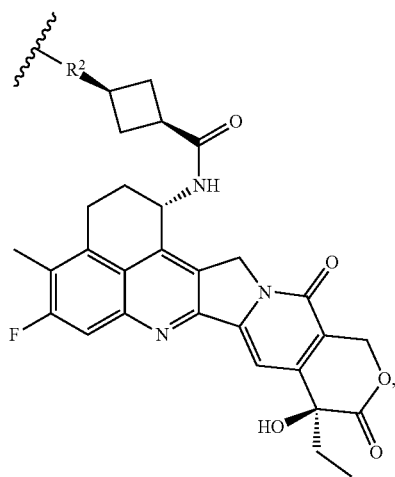

II-A-3

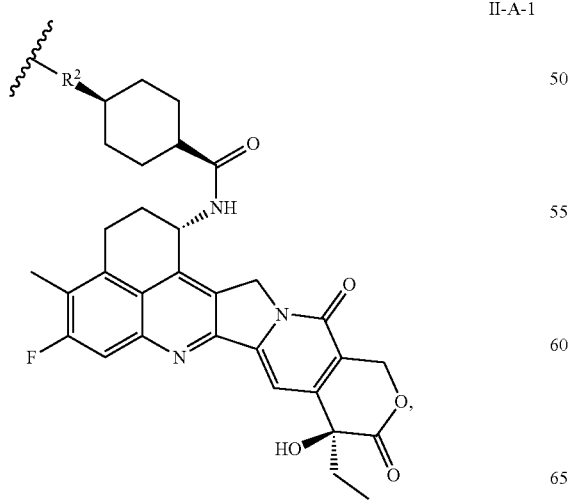

II-A-1

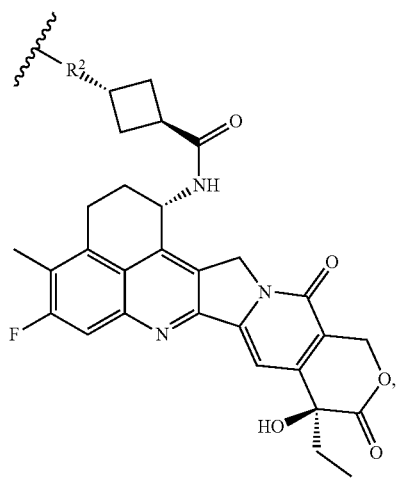

II-A-4

II-A-5
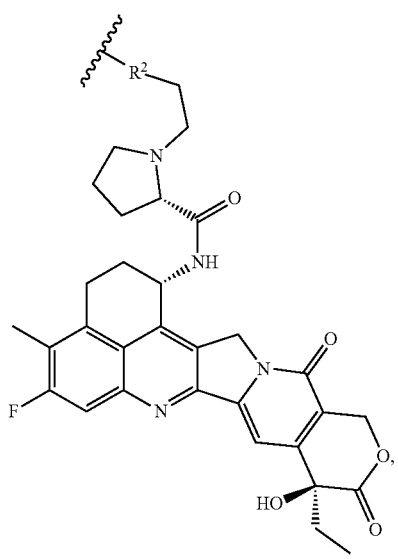
II-A-6
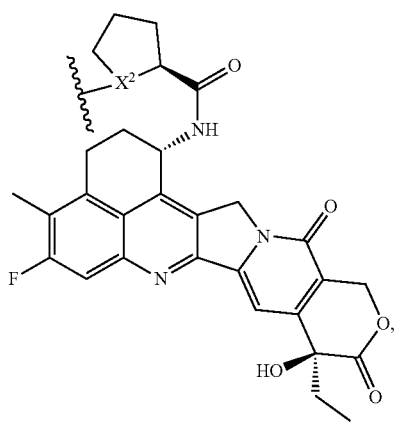
II-A-7
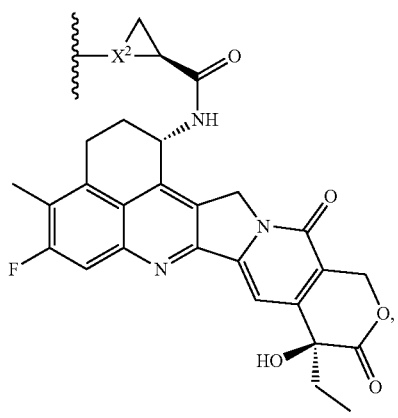
II-A-8
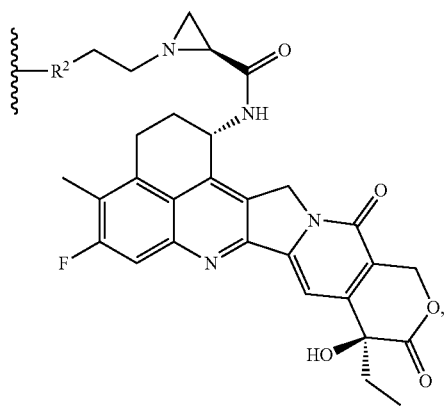
II-A-9
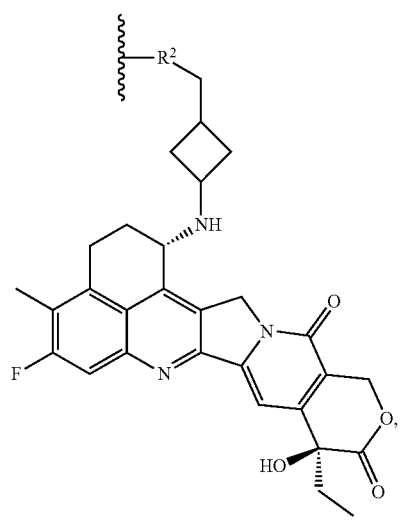
II-A-10
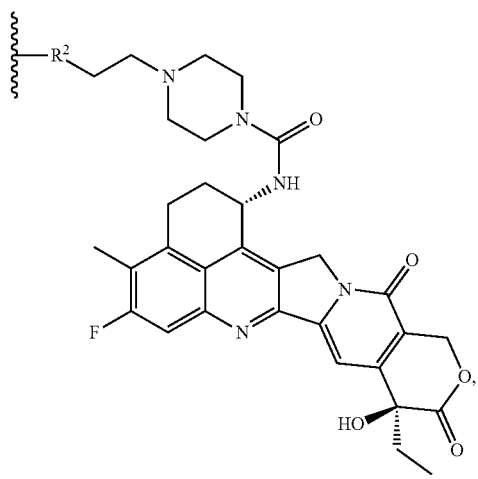

475

-continued

II-A-11

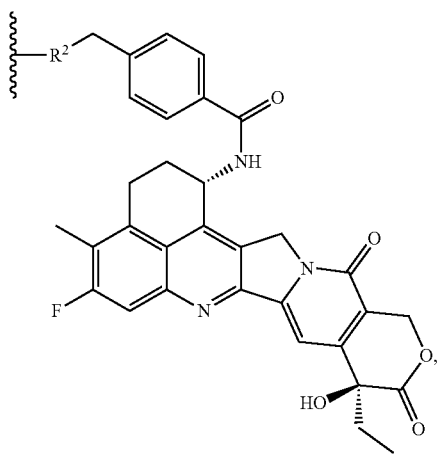

II-A-12

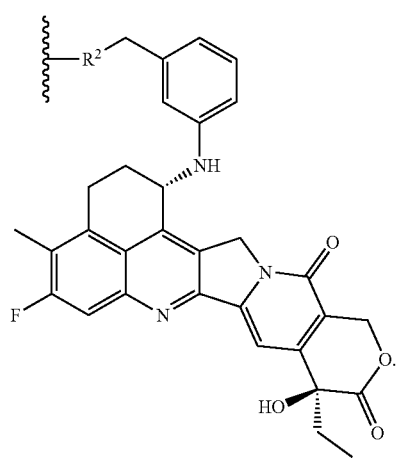

168. A compound or a tautomer, a mesomer, a racemate, an enantiomer or a diastereoisomer thereof, or a mixture thereof, or a pharmaceutically acceptable salt thereof, wherein the compound comprises a structure shown as formula (III-A):

(III-A)

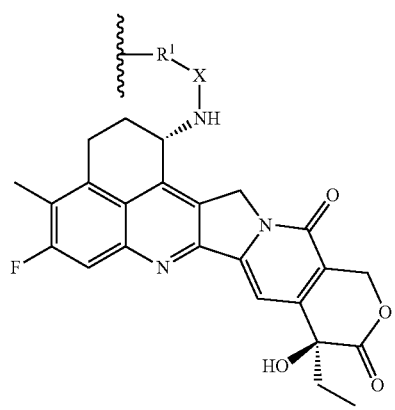

wherein R1 is selected from the group consisting of: —O—, —(R2)N—, —P(=O)(R2)- and —S—;
X is selected from the group consisting of: -L1-C(R1a)(R1b)-C(O)—, -L1-C(R1a)(R1b)-C(S)—, -L1-L0- and -L3-L2-;

476

L1 is —(C(R3a)(R3b))m-, wherein 0 or no less than 1 methylene unit of L1 is independently replaced by —C(O)—, —C(=S)—, —C(=NR4b)- or —C(=N2)-;
L0 is —C(R2a)(R2b)-, or L0 is —C(=S)—, —C(=NR4a)- or —C(=N2)-;
L2 is —C(R5a)(R5b)-, wherein 0 or 1 methylene unit of L2 is replaced by —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N2)-;
L3 is —(C(R7a)(R7b))n-, wherein no less than 1 methylene unit of L3 is independently replaced by —N(R8)C(O)—, —C(O)N(R8)-, —OC(O)—, —C(O)O—, —NR8-, —O—, —S—, —SO—, —SO2-, —P(R8)-, —P(=O)(R8)-, —N(R8)SO2-, —SO2N(R8)-, —N=N—, —C=N— or —N=C—, and 0 or no less than 1 methylene unit of L3 is also independently replaced by —C(O)—, —C(=S)—, —C(=NR8)- or —C(=N2)-;
wherein each R1a, each R1b, each R2, each R2a, each R2b, each R3a, each R3b, each R4a, each R4b, each R5a, each R5b, each R6, each R7a, each R7b and each R8 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R;
wherein each R, each Ra and each Rb are each independently hydrogen, protium, deuterium, tritium, halogen, —NO2, —CN, —OH, —SH, —NH$_2$, —C(O)H, —CO2H, —C(O)C(O)H, —C(O)CH$_2$C(O)H, —S(O)H, —S(O)2H, —C(O)NH$_2$, —SO2NH$_2$, —OC(O)H, —N(H)SO2H or a C1-6 aliphatic group;
m is selected from the group consisting of integers ≥0, and n is selected from the group consisting of integers ≥1;
when R1 is —O— or —HN— and X is -L1-CH$_2$—C(O)—, no less than 1 methylene unit of L1 is independently replaced by —C(O)—, —C(=S)—, —C(=NR4b)- or —C(=N2)-, or each R3a and each R3b are not both hydrogen;
when R1 is —HN—, X is -L1-L0-, and L0 is —CH$_2$—, no less than 1 methylene unit of L1 is independently replaced by —C(O)—, —C(=S)—, —C(=NR4b)- or —C(=N2)-, or each R3a and each R3b are not both hydrogen;
when R1 is —O—, X is -L3-C(O)—, and 1 methylene unit of L3 is replaced by —NR8, R8 is not —CH$_2$—CH$_2$—NH$_2$;
when R1 is —NH—, and X is -L3-C(O)—, no less than 1 methylene unit of L3 is replaced by —N(R8)C(O)—, —OC(O)—, —C(O)O—, —S—, —SO—, —SO2-, —P(R8)-, —P(=O)(R8)-, —N(R8)SO2-, —SO2N(R8)-, —N=N—, —C=N— or —N=C—.

169. The compound or the tautomer, the mesomer, the racemate, the enantiomer or the diastereoisomer thereof, or the mixture thereof, or the pharmaceutically acceptable salt thereof according to technical scheme 168, wherein X is -L1-C(R1a)(R1b)-C(O)—, R1 is —S— or —(R2)N—, and R2 is not hydrogen.

170. The compound or the tautomer, the mesomer, the racemate, the enantiomer or the diastereoisomer thereof, or the mixture thereof, or the pharmaceutically acceptable salt thereof according to any one of technical schemes 168-169, wherein L1 is —(C(R3a)(R3b))$_m$—, and 0 or 1 methylene unit of L1 is replaced by —C(O)—, —C(=S)—, —C(=NR4b)- or —C(=N2)-.

171. The compound or the tautomer, the mesomer, the racemate, the enantiomer or the diastereoisomer thereof, or the mixture thereof, or the pharmaceutically acceptable salt thereof according to any one of technical schemes 168-170, wherein 1 methylene unit of L1 is replaced by —C(O)—.

172. The compound or the tautomer, the mesomer, the racemate, the enantiomer or the diastereoisomer thereof, or the mixture thereof, or the pharmaceutically acceptable salt thereof according to technical scheme 168, wherein X is -L1-C(R1a)(R1b)-C(O)—, R1 is —O— or —HN—, m is not 0, and no less than 1 methylene unit of L1 is replaced by —C(O)—, —C(=S)—, —C(=NR4b)- or —C(=N2)-.

173. The compound or the tautomer, the mesomer, the racemate, the enantiomer or the diastereoisomer thereof, or the mixture thereof, or the pharmaceutically acceptable salt thereof according to any one of technical schemes 168 and 172, wherein 1 methylene unit of L1 is replaced by —C(O)—, —C(=S)—, —C(=NR4b)- or —C(=N2)-.

174. The compound or the tautomer, the mesomer, the racemate, the enantiomer or the diastereoisomer thereof, or the mixture thereof, or the pharmaceutically acceptable salt thereof according to any one of technical schemes 168 and 172-173, wherein 1 methylene unit of L1 is replaced by —C(O)—.

175. The compound or the tautomer, the mesomer, the racemate, the enantiomer or the diastereoisomer thereof, or the mixture thereof, or the pharmaceutically acceptable salt thereof according to technical scheme 168, wherein X is -L1-C(R1a)(R1b)-C(O)—, R1 is —O— or —HN—, L1 is —(C(R3a)(R3b))m-, m is not 0, 0 methylene units of L1 are replaced by —C(O)—, —C(=S)—, —C(=NR4b)- or —C(=N2)-, each R3a and each R3b are not both hydrogen, and R1a and R1b are hydrogen.

176. The compound or the tautomer, the mesomer, the racemate, the enantiomer or the diastereoisomer thereof, or the mixture thereof, or the pharmaceutically acceptable salt thereof according to technical scheme 168, wherein X is -L1-C(R1a)(R1b)-C(O)—, and m is 0, 1 or 2.

177. The compound or the tautomer, the mesomer, the racemate, the enantiomer or the diastereoisomer thereof, or the mixture thereof, or the pharmaceutically acceptable salt thereof according to any one of technical schemes 168 and 176, wherein m is 0, and L1 is a covalent bond.

178. The compound or the tautomer, the mesomer, the racemate, the enantiomer or the diastereoisomer thereof, or the mixture thereof, or the pharmaceutically acceptable salt thereof according to any one of technical schemes 168 and 176-177, wherein R1 is (R2)N- or —S—, and R2 is not hydrogen.

179. The compound or the tautomer, the mesomer, the racemate, the enantiomer or the diastereoisomer thereof, or the mixture thereof, or the pharmaceutically acceptable salt thereof according to any one of technical schemes 168 and 176-178, wherein R1 is —S—.

180. The compound or the tautomer, the mesomer, the racemate, the enantiomer or the diastereoisomer thereof, or the mixture thereof, or the pharmaceutically acceptable salt thereof according to any one of technical schemes 168 and 176, wherein m is 1, and L1 is —C(R3a)(R3b)-.

181. The compound or the tautomer, the mesomer, the racemate, the enantiomer or the diastereoisomer thereof, or the mixture thereof, or the pharmaceutically acceptable salt thereof according to any one of technical schemes 168, 176 and 180, wherein 0 methylene units of L1 are replaced by —C(O)—, —C(=S)—, —C(=NR4b)- or —C(=N2)-.

182. The compound or the tautomer, the mesomer, the racemate, the enantioimer or the diastereoisomer thereof, or the mixture thereof, or the pharmaceutically acceptable salt thereof according to any one of technical schemes 168, 176 and 180-181, wherein R1 is (R2)N- or —S—, and R2 is not hydrogen.

183. The compound or the tautomer, the mesomer, the racemate, the enantiomer or the diastereoisomer thereof, or the mixture thereof, or the pharmaceutically acceptable salt thereof according to any one of technical schemes 168, 176 and 180-182, wherein R1 is —S—.

184. The compound or the tautomer, the mesomer, the racemate, the enantiomer or the diastereoisomer thereof, or the mixture thereof, or the pharmaceutically acceptable salt thereof according to any one of technical schemes 168, 176 and 180-183, wherein R1 is —S—, and R1a and R1b are hydrogen.

185. The compound or the tautomer, the mesomer, the racemate, the enantiomer or the diastereoisomer thereof, or the mixture thereof, or the pharmaceutically acceptable salt thereof according to any one of technical schemes 168, 176 and 180-183, wherein R1 is —S—, and R1a and R1b are each independently —N(Ra)(Rb).

186. The compound or the tautomer, the mesomer, the racemate, the enantiomer or the diastereoisomer thereof, or the mixture thereof, or the pharmaceutically acceptable salt thereof according to any one of technical schemes 168, 176, 180-183 and 185, wherein R1a is —N(Ra)(Rb).

187. The compound or the tautomer, the mesomer, the racemate, the enantiomer or the diastereoisomer thereof, or the mixture thereof, or the pharmaceutically acceptable salt thereof according to any one of technical schemes 168, 176, 180-183 and 185-186, wherein R is hydrogen.

188. The compound or the tautomer, the mesomer, the racemate, the enantiomer or the diastereoisomer thereof, or the mixture thereof, or the pharmaceutically acceptable salt thereof according to any one of technical schemes 168-187, wherein R1 is —(R2)N—, and R2 is a C1-6 aliphatic group.

189. The compound or the tautomer, the mesomer, the racemate, the enantiomer or the diastereoisomer thereof, or the mixture thereof, or the pharmaceutically acceptable salt thereof according to any one of technical schemes 168-188, wherein R2 is methyl.

190. The compound or the tautomer, the mesomer, the racemate, the enantiomer or the diastereoisomer thereof, or the mixture thereof, or the pharmaceutically acceptable salt thereof according to any one of technical schemes 168-187, wherein L1 is —C(R3a)(R3b)-, R1 is —O— or —HN—, 0 methylene units of L1 are replaced by —C(O)—, —C(=S)—, —C(=NR4b)- or —C(=N2)-, and R3a and R3b are not both hydrogen.

191. The compound or the tautomer, the mesomer, the racemate, the enantiomer or the diastereoisomer thereof, or the mixture thereof, or the pharmaceutically acceptable salt thereof according to any one of technical schemes 168-187 and 190, wherein R1 is —O—.

192. The compound or the tautomer, the mesomer, the racemate, the enantiomer or the diastereoisomer thereof, or the mixture thereof, or the pharmaceutically acceptable salt thereof according to any one of technical schemes 168-187 and 190-191, wherein R3a is a C1-6 aliphatic group.

193. The compound or the tautomer, the mesomer, the racemate, the enantiomer or the diastereoisomer thereof, or the mixture thereof, or the pharmaceutically acceptable salt thereof according to any one of technical schemes 168-187

194. The compound or the tautomer, the mesomer, the racemate, the enantiomer or the diastereoisomer thereof, or the mixture thereof, or the pharmaceutically acceptable salt thereof according to any one of technical schemes 168-187 and 190-193, wherein R3a is a C1-6 aliphatic group, and R3b is hydrogen.

195. The compound or the tautomer, the mesomer, the racemate, the enantiomer or the diastereoisomer thereof, or the mixture thereof, or the pharmaceutically acceptable salt thereof according to any one of technical schemes 168-187 and 190-194, wherein R3a is methyl, and R3b is hydrogen.

196. The compound or the tautomer, the mesomer, the racemate, the enantiomer or the diastereoisomer thereof, or the mixture thereof, or the pharmaceutically acceptable salt thereof according to technical scheme 168, wherein R3a is a C1-6 aliphatic group, and R3b is a C1-6 aliphatic group.

197. The compound or the tautomer, the mesomer, the racemate, the enantiomer or the diastereoisomer thereof, or the mixture thereof, or the pharmaceutically acceptable salt thereof according to any one of technical schemes 168 and 196, wherein R3a is methyl, and R3b is a C1-6 aliphatic group.

198. The compound or the tautomer, the mesomer, the racemate, the enantiomer or the diastereoisomer thereof, or the mixture thereof, or the pharmaceutically acceptable salt thereof according to any one of technical schemes 168 and 196-197, wherein R3a is methyl, and R3b is methyl.

199. The compound or the tautomer, the mesomer, the racemate, the enantiomer or the diastereoisomer thereof, or the mixture thereof, or the pharmaceutically acceptable salt thereof according to any one of technical schemes 168 and 176, wherein m is 2, and L1 is —(C(R3a)(R3b))2-.

200. The compound or the tautomer, the mesomer, the racemate, the enantiomer or the diastereoisomer thereof, or the mixture thereof, or the pharmaceutically acceptable salt thereof according to any one of technical schemes 168, 176 and 199, wherein 1 methylene unit of L1 is replaced by —C(O)—, —C(=S)—, —C(=NR4b)- or —C(=N2)-.

201. The compound or the tautomer, the mesomer, the racemate, the enantiomer or the diastereoisomer thereof, or the mixture thereof, or the pharmaceutically acceptable salt thereof according to any one of technical schemes 168, 176 and 199-200, wherein 1 methylene unit of L1 is replaced by —C(O)—.

202. The compound or the tautomer, the mesomer, the racemate, the enantiomer or the diastereoisomer thereof, or the mixture thereof, or the pharmaceutically acceptable salt thereof according to any one of technical schemes 168, 176 and 199-201, wherein R1 is selected from the group consisting of: —O—, —(R2)N—, —P(=O)(R2)- and —S—.

203. The compound or the tautomer, the mesomer, the racemate, the enantiomer or the diastereoisomer thereof, or the mixture thereof, or the pharmaceutically acceptable salt thereof according to any one of technical schemes 168, 176 and 199-202, wherein R1 is —O—.

204. The compound or the tautomer, the mesomer, the racemate, the enantiomer or the diastereoisomer thereof, or the mixture thereof, or the pharmaceutically acceptable salt thereof according to any one of technical schemes 168, 176 and 199-202, wherein R1 is —S—.

205. The compound or the tautomer, the mesomer, the racemate, the enantiomer or the diastereoisomer thereof, or the mixture thereof, or the pharmaceutically acceptable salt thereof according to any one of technical schemes 168, 176 and 199-202, wherein R1 is —(R2)N—.

206. The compound or the tautomer, the mesomer, the racemate, the enantiomer or the diastereoisomer thereof, or the mixture thereof, or the pharmaceutically acceptable salt thereof according to any one of technical schemes 168, 176, 199-202 and 205, wherein R2 is a C1-6 aliphatic group.

207. The compound or the tautomer, the mesomer, the racemate, the enantiomer or the diastereoisomer thereof, or the mixture thereof, or the pharmaceutically acceptable salt thereof according to any one of technical schemes 168, 176, 199-202 and 205-206, wherein R2 is methyl.

208. The compound or the tautomer, the mesomer, the racemate, the enantiomer or the diastereoisomer thereof, or the mixture thereof, or the pharmaceutically acceptable salt thereof according to technical scheme 168, wherein X is -L1-L0-, R1 is —O—, —S— or —(R2)N—, and R2 is not hydrogen.

209. The compound or the tautomer, the mesomer, the racemate, the enantiomer or the diastereoisomer thereof, or the mixture thereof, or the pharmaceutically acceptable salt thereof according to any one of technical schemes 168 and 208, wherein L1 is —C(R3a)(R3b), and 0 or 1 methylene unit of L1 is replaced by —C(O)—, —C(=S)—, —C(=NR4b)- or —C(=N2)-.

210. The compound or the tautomer, the mesomer, the racemate, the enantiomer or the diastereoisomer thereof, or the mixture thereof, or the pharmaceutically acceptable salt thereof according to any one of technical schemes 168 and 208-209, wherein 1 methylene unit of L1 is replaced by —C(O)—.

211. The compound or the tautomer, the mesomer, the racemate, the enantiomer or the diastereoisomer thereof, or the mixture thereof, or the pharmaceutically acceptable salt thereof according to technical scheme 168, wherein X is -L1-L0-, R1 is —HN—, m is not 0, and L0 is —C(=S)—, —C(=NR4a)- or —C(=N2)-.

212. The compound or the tautomer, the mesomer, the racemate, the enantiomer or the diastereoisomer thereof, or the mixture thereof, or the pharmaceutically acceptable salt thereof according to technical scheme 168, wherein X is -L1-L0-, R1 is —HN—, m is not 0, L0 is —C(R2a)(R2b)-, L1 is —(C(R3a)(R3b))m-, and each R3a and each R3b are not both hydrogen.

213. The compound or the tautomer, the mesomer, the racemate, the enantiomer or the diastereoisomer thereof, or the mixture thereof, or the pharmaceutically acceptable salt thereof according to technical scheme 168, wherein X is -L1-L0-, and m is 1 or 2.

214. The compound or the tautomer, the mesomer, the racemate, the enantiomer or the diastereoisomer thereof, or the mixture thereof, or the pharmaceutically acceptable salt thereof according to any one of technical schemes 168 and 213, wherein m is 1, and L1 is —C(R3a)(R3b)-.

215. The compound or the tautomer, the mesomer, the racemate, the enantiomer or the diastereoisomer thereof, or the mixture thereof, or the pharmaceutically acceptable salt thereof according to any one of technical schemes 168 and 213-214, wherein 0 methylene units of L1 are replaced by —C(O)—, —C(=S)—, —C(=NR4b)- or —C(=N2)-.

216. The compound or the tautomer, the mesomer, the racemate, the enantiomer or the diastereoisomer thereof, or the mixture thereof, or the pharmaceutically acceptable salt thereof according to any one of technical schemes 168 and 213-215, wherein R1 is (R2)N- or —S—, and R2 is not hydrogen.

217. The compound or the tautomer, the mesomer, the racemate, the enantiomer or the diastereoisomer thereof, or the mixture thereof, or the pharmaceutically acceptable salt thereof according to any one of technical schemes 168 and 213-216, wherein R1 is —S—.

218. The compound or the tautomer, the mesomer, the racemate, the enantiomer or the diastereoisomer thereof, or the mixture thereof, or the pharmaceutically acceptable salt thereof according to any one of technical schemes 168 and 213, wherein m is 2, and L1 is —(C(R3a)(R3b))2-.

219. The compound or the tautomer, the mesomer, the racemate, the enantiomer or the diastereoisomer thereof, or the mixture thereof, or the pharmaceutically acceptable salt thereof according to any one of technical schemes 168, 213 and 218, wherein 0 methylene units of L1 are replaced by —C(O)—, —C(=S)—, —C(=NR4b)- or —C(=N2)-.

220. The compound or the tautomer, the mesomer, the racemate, the enantiomer or the diastereoisomer thereof, or the mixture thereof, or the pharmaceutically acceptable salt thereof according to any one of technical schemes 168, 213 and 218-219, wherein R1 is —O—, —S— or (R2)N—, and R2 is not hydrogen.

221. The compound or the tautomer, the mesomer, the racemate, the enantiomer or the diastereoisomer thereof, or the mixture thereof, or the pharmaceutically acceptable salt thereof according to any one of technical schemes 168, 213 and 218-220, wherein R1 is —(R2)N—, and R2 is not hydrogen.

222. The compound or the tautomer, the mesomer, the racemate, the enantiomer or the diastereoisomer thereof, or the mixture thereof, or the pharmaceutically acceptable salt thereof according to any one of technical schemes 168, 213 and 218-221, wherein R2 is a C1-6 aliphatic group.

223. The compound or the tautomer, the mesomer, the racemate, the enantiomer or the diastereoisomer thereof, or the mixture thereof, or the pharmaceutically acceptable salt thereof according to any one of technical schemes 168, 213 and 218-222, wherein R2 is methyl.

224. The compound or the tautomer, the mesomer, the racemate, the enantiomer or the diastereoisomer thereof, or the mixture thereof, or the pharmaceutically acceptable salt thereof according to any one of technical schemes 168, 213 and 218-220, wherein R1 is —O—.

225. The compound or the tautomer, the mesomer, the racemate, the enantiomer or the diastereoisomer thereof, or the mixture thereof, or the pharmaceutically acceptable salt thereof according to any one of technical schemes 168, 213, 218-220 and 224, wherein R3a is a C1-6 aliphatic group.

226. The compound or the tautomer, the mesomer, the racemate, the enantiomer or the diastereoisomer thereof, or the mixture thereof, or the pharmaceutically acceptable salt thereof according to any one of technical schemes 168, 213, 218-220 and 224-225, wherein R3a is a C1-6 aliphatic group, and R3b is hydrogen or a C1-6 aliphatic group.

227. The compound or the tautomer, the mesomer, the racemate, the enantiomer or the diastereoisomer thereof, or the mixture thereof, or the pharmaceutically acceptable salt thereof according to any one of technical schemes 168, 213, 218-220 and 224-226, wherein R3a is a C1-6 aliphatic group, and R3b is a C1-6 aliphatic group.

228. The compound or the tautomer, the mesomer, the racemate, the enantiomer or the diastereoisomer thereof, or the mixture thereof, or the pharmaceutically acceptable salt thereof according to any one of technical schemes 168, 213, 218-220 and 224-227, wherein R3a is methyl, and R3b is a C1-6 aliphatic group.

229. The compound or the tautomer, the mesomer, the racemate, the enantiomer or the diastereoisomer thereof, or the mixture thereof, or the pharmaceutically acceptable salt thereof according to any one of technical schemes 168, 213, 218-220 and 224-228, wherein R3a is methyl, and R3b is methyl.

230. The compound or the tautomer, the mesomer, the racemate, the enantiomer or the diastereoisomer thereof, or the mixture thereof, or the pharmaceutically acceptable salt thereof according to any one of technical schemes 168, 213, 218-220 and 224-229, wherein L1 is —C(R3a)(R3b)-C(CH3)2-.

231. The compound or the tautomer, the mesomer, the racemate, the enantiomer or the diastereoisomer thereof, or the mixture thereof, or the pharmaceutically acceptable salt thereof according to technical scheme 168, wherein X is -L3-L2-, wherein L2 is —C(R5a)(R5b)-, L3 is —(C(R7a)(R7b))n-, R1 is —S— or —(R2)N—, and R2 is not hydrogen.

232. The compound or the tautomer, the mesomer, the racemate, the enantiomer or the diastereoisomer thereof, or the mixture thereof, or the pharmaceutically acceptable salt thereof according to technical scheme 168, wherein X is -L3-L2-, wherein L2 is —C(O)—, R1 is —O—, L3 is —(C(R7a)(R7b))n-, and when 1 methylene unit of L3 is replaced by —NR8, R8 is not a C1-6 aliphatic group substituted with —NH₂.

233. The compound or the tautomer, the mesomer, the racemate, the enantiomer or the diastereoisomer thereof, or the mixture thereof, or the pharmaceutically acceptable salt thereof according to any one of technical schemes 168 and 232, wherein 1 methylene unit of L3 is replaced by —NR8-, —O— or —SO—.

234. The compound or the tautomer, the mesomer, the racemate, the enantiomer or the diastereoisomer thereof, or the mixture thereof, or the pharmaceutically acceptable salt thereof according to any one of technical schemes 168 and 232-233, wherein R8 is a C1-6 aliphatic group, and R8 is optionally substituted with hydrogen, protium, deuterium, tritium, halogen, —NO2, —CN, —OH, —SH, —C(O)H, —CO2H, —C(O)C(O)H, —C(O)CH₂C(O)H, —S(O)H, —S(O)2H, —C(O)NH₂, —SO2NH₂, —OC(O)H, —N(H)SO2H or a C1-6 aliphatic group.

235. The compound or the tautomer, the mesomer, the racemate, the enantiomer or the diastereoisomer thereof, or the mixture thereof, or the pharmaceutically acceptable salt thereof according to any one of technical schemes 168 and 232-234, wherein R8 is a C1-3 aliphatic group, and R8 is unsubstituted.

236. The compound or the tautomer, the mesomer, the racemate, the enantiomer or the diastereoisomer thereof, or the mixture thereof, or the pharmaceutically acceptable salt thereof according to technical scheme 168, wherein X is -L3-L2-, wherein when L2 is —C(O)—, R1 is —HN—, and L3 is —(C(R7a)(R7b))$_n$—, at least 1 methylene unit of L3 is replaced by —N(R8)C(O)—, —OC(O)—, —C(O)O—, —S—, —SO—, —SO2-, —P(R8)-, —P(=O)(R8)-, —N(R8)SO₂—, —SO2N(R8)-, —N=N—, —C=N— or —N=C—.

237. The compound or the tautomer, the mesomer, the racemate, the enantiomer or the diastereoisomer thereof, or the mixture thereof, or the pharmaceutically acceptable salt thereof according to technical scheme 168, wherein X is -L3-L2-, n is 4, and L3 is —(C(R7a)(R7b))4-.

238. The compound or the tautomer, the mesomer, the racemate, the enantiomer or the diastereoisomer thereof, or the mixture thereof, or the pharmaceutically acceptable salt thereof according to any one of technical schemes 168 and 237, wherein L2 is —C(R5a)(R5b)-, wherein 1 methylene unit of L2 is replaced by —N(R6)C(O)—, —C(O)N(R6)-, —C(O)—, —OC(O)—, —C(O)O—, —NR6-, —O—, —S—, —SO—, —SO$_2$—, —P(R6)-, —P(=O)(R6)-, —N(R6)SO2-, —SO2N(R6)-, —C(=S)—, —C(=NR6)-, —N=N—, —C=N—, —N=C— or —C(=N2)-.

239. The compound or the tautomer, the mesomer, the racemate, the enantiomer or the diastereoisomer thereof, or the mixture thereof, or the pharmaceutically acceptable salt thereof according to any one of technical schemes 168 and 237-238, wherein L2 is —C(R5a)(R5b)-, wherein 1 methylene unit of L2 is replaced by —C(O)—, and L2 is —C(O)—.

240. The compound or the tautomer, the mesomer, the racemate, the enantiomer or the diastereoisomer thereof, or the mixture thereof, or the pharmaceutically acceptable salt thereof according to any one of technical schemes 168 and 237-239, wherein 1 methylene unit of L3 is replaced by —N(R8)C(O)—, —C(O)N(R8)-, —OC(O)—, —C(O)O—, —NR8-, —O—, —S—, —SO—, —SO2-, —P(R8)-, —P(=O)(R8)-, —N(R8)SO$_2$—, —SO2N(R8)-, —N=N—, —C=N— or —N=C—.

241. The compound or the tautomer, the mesomer, the racemate, the enantiomer or the diastereoisomer thereof, or the mixture thereof, or the pharmaceutically acceptable salt thereof according to any one of technical schemes 168 and 237-240, wherein 1 methylene unit of L3 is replaced by —NR8-, —O— or —SO—.

242. The compound or the tautomer, the mesomer, the racemate, the enantiomer or the diastereoisomer thereof, or the mixture thereof, or the pharmaceutically acceptable salt thereof according to any one of technical schemes 168 and 237-241, wherein 1 methylene unit of L3 is replaced by —NR8-.

243. The compound or the tautomer, the mesomer, the racemate, the enantiomer or the diastereoisomer thereof, or the mixture thereof, or the pharmaceutically acceptable salt thereof according to any one of technical schemes 168 and 237-242, wherein R8 is a C1-6 aliphatic group.

244. The compound or the tautomer, the mesomer, the racemate, the enantiomer or the diastereoisomer thereof, or the mixture thereof, or the pharmaceutically acceptable salt thereof according to any one of technical schemes 168 and 237-243, wherein R8 is methyl.

245. The compound or the tautomer, the mesomer, the racemate, the enantiomer or the diastereoisomer thereof, or the mixture thereof, or the pharmaceutically acceptable salt thereof according to any one of technical schemes 168 and 237-244, wherein X is —(C(R7a)(R7b))2-N(CH$_3$)—C(R7a)(R7b)-C(O)—.

246. The compound or the tautomer, the mesomer, the racemate, the enantiomer or the diastereoisomer thereof, or the mixture thereof, or the pharmaceutically acceptable salt thereof according to any one of technical schemes 168 and 237-241, wherein 1 methylene unit of L3 is replaced by —SO—.

247. The compound or the tautomer, the mesomer, the racemate, the enantiomer or the diastereoisomer thereof, or the mixture thereof, or the pharmaceutically acceptable salt thereof according to any one of technical schemes 168 and 237-238, wherein X is —(C(R7a)(R7b))2-SO—C(R7a)(R7b)-C(O)—.

248. The compound or the tautomer, the mesomer, the racemate, the enantiomer or the diastereoisomer thereof, or the mixture thereof, or the pharmaceutically acceptable salt thereof according to technical scheme 168, wherein 1 methylene unit of L3 is replaced by —O—.

249. The compound or the tautomer, the mesomer, the racemate, the enantiomer or the diastereoisomer thereof, or the mixture thereof, or the pharmaceutically acceptable salt thereof according to any one of technical schemes 168 and 248, wherein X is —(C(R7a)(R7b))2-O—C(R7a)(R7b)-C(O)—.

250. The compound or the tautomer, the mesomer, the racemate, the enantiomer or the diastereoisomer thereof, or the mixture thereof, or the pharmaceutically acceptable salt thereof according to technical scheme 168, wherein R1a and R1b are each independently hydrogen or —N(Ra)(Rb).

251. The compound or the tautomer, the mesomer, the racemate, the enantiomer or the diastereoisomer thereof, or the mixture thereof, or the pharmaceutically acceptable salt thereof according to technical scheme 168, wherein R2 is a C1-6 aliphatic group.

252. The compound or the tautomer, the mesomer, the racemate, the enantiomer or the diastereoisomer thereof, or the mixture thereof, or the pharmaceutically acceptable salt thereof according to any one of technical schemes 168 and 251, wherein R2 is a C1-3 aliphatic group.

253. The compound or the tautomer, the mesomer, the racemate, the enantiomer or the diastereoisomer thereof, or the mixture thereof, or the pharmaceutically acceptable salt thereof according to any one of technical schemes 168 and 251-252, wherein R2 is methyl.

254. The compound or the tautomer, the mesomer, the racemate, the enantiomer or the diastereoisomer thereof, or the mixture thereof, or the pharmaceutically acceptable salt thereof according to technical scheme 168, wherein R3a and R3b are each independently hydrogen or a C1-6 aliphatic group.

255. The compound or the tautomer, the mesomer, the racemate, the enantiomer or the diastereoisomer thereof, or the mixture thereof, or the pharmaceutically acceptable salt thereof according to any one of technical schemes 168 and 254, wherein R3a and R3b are each independently a C1-3 aliphatic group.

256. The compound or the tautomer, the mesomer, the racemate, the enantiomer or the diastereoisomer thereof, or the mixture thereof, or the pharmaceutically acceptable salt thereof according to any one of technical schemes 168 and 254-255, wherein R3a and R3b are methyl.

257. The compound or the tautomer, the mesomer, the racemate, the enantiomer or the diastereoisomer thereof, or the mixture thereof, or the pharmaceutically acceptable salt thereof according to technical scheme 168, wherein R4a and R4b are hydrogen.

258. The compound or the tautomer, the mesomer, the racemate, the enantiomer or the diastereoisomer thereof, or the mixture thereof, or the pharmaceutically acceptable salt thereof according to technical scheme 168, wherein R5a and R5b are hydrogen.

259. The compound or the tautomer, the mesomer, the racemate, the enantiomer or the diastereoisomer thereof, or the mixture thereof, or the pharmaceutically acceptable salt thereof according to technical scheme 168, wherein R6 is hydrogen.

260. The compound or the tautomer, the mesomer, the racemate, the enantiomer or the diastereoisomer thereof, or the mixture thereof, or the pharmaceutically acceptable salt thereof according to technical scheme 168, wherein R7a and R7b are hydrogen.

261. The compound or the tautomer, the mesomer, the racemate, the enantiomer or the diastereoisomer thereof, or the mixture thereof, or the pharmaceutically acceptable salt thereof according to technical scheme 168, wherein R8 is a C1-6 aliphatic group.

262. The compound or the tautomer, the mesomer, the racemate, the enantiomer or the diastereoisomer thereof, or the mixture thereof, or the pharmaceutically acceptable salt thereof according to any one of technical schemes 168 and 261, wherein R8 is a C1-3 aliphatic group.

263. The compound or the tautomer, the mesomer, the racemate, the enantiomer or the diastereoisomer thereof, or the mixture thereof, or the pharmaceutically acceptable salt thereof according to any one of technical schemes 168 and 261-262, wherein R8 is methyl.

264. The compound or the tautomer, the mesomer, the racemate, the enantiomer or the diastereoisomer thereof, or the mixture thereof, or the pharmaceutically acceptable salt thereof according to technical scheme 168, wherein R, Ra and Rb are hydrogen.

265. The compound or the tautomer, the mesomer, the racemate, the enantiomer or the diastereoisomer thereof, or the mixture thereof, or the pharmaceutically acceptable salt thereof according to technical scheme 168, wherein the ligand-drug conjugate comprises the following group of structures:

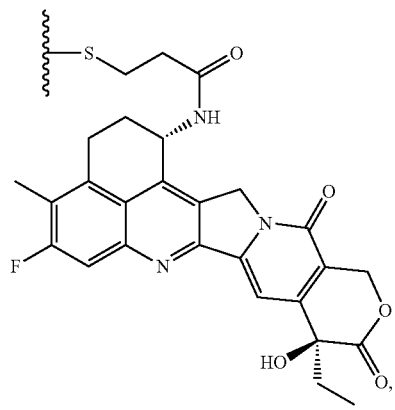

III-A-1

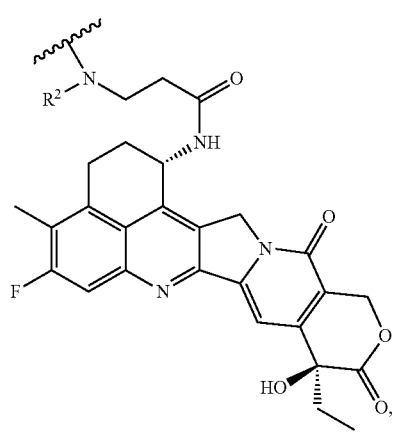

III-A-2

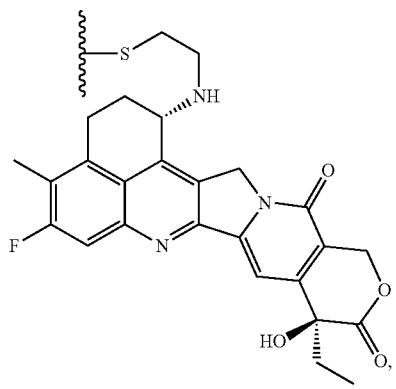

III-A-3

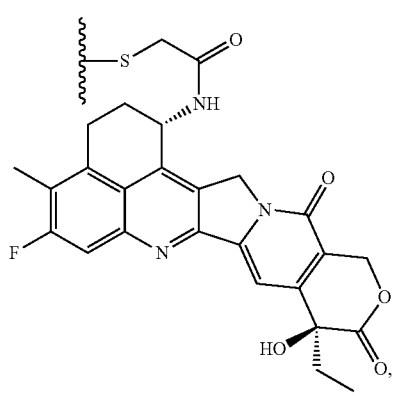

III-A-4

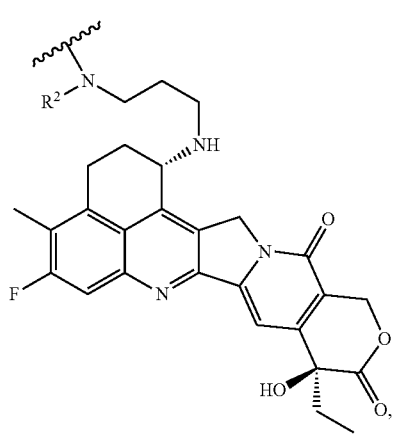

III-A-5

III-A-6
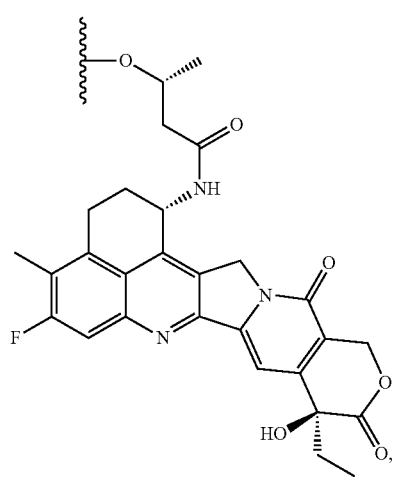
III-A-9
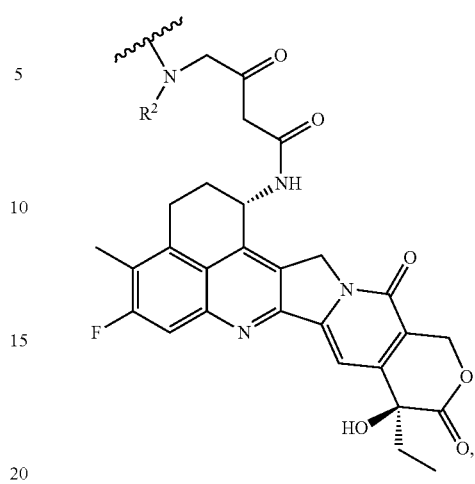
III-A-7
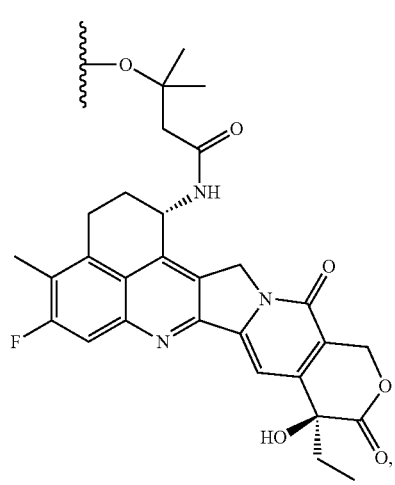
III-A-10
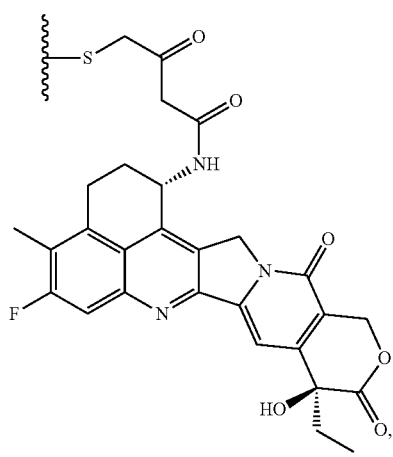
III-A-8
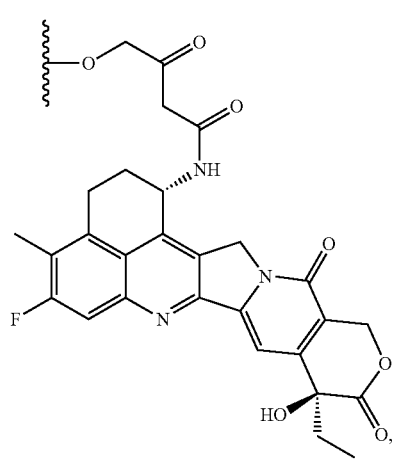
III-A-11
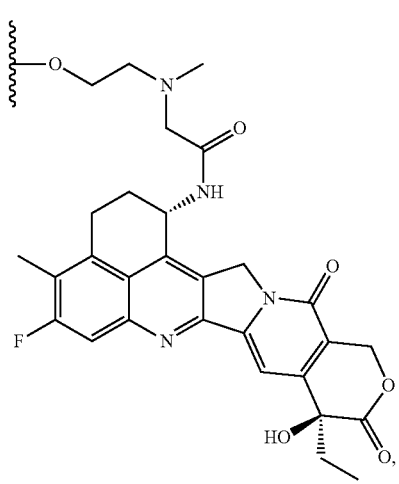

III-A-12
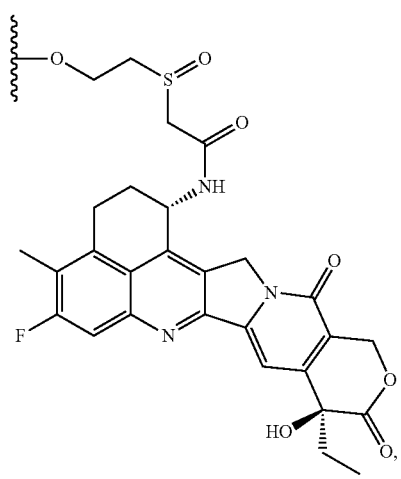
III-A-13
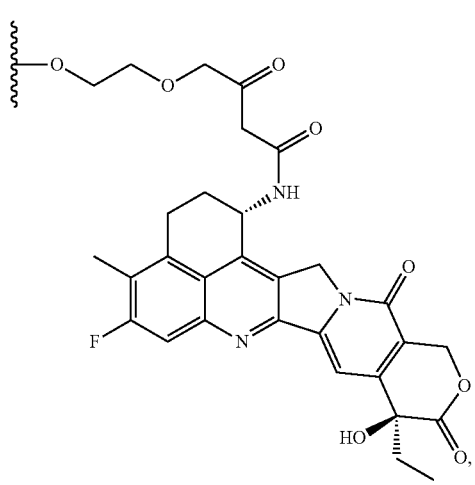
III-A-14
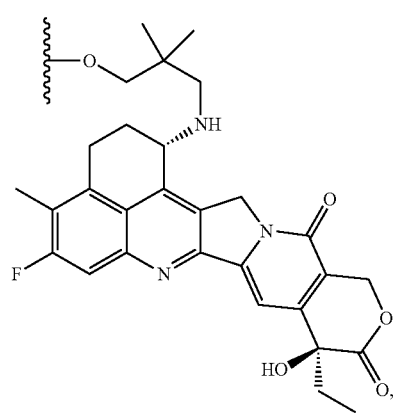
III-A-15
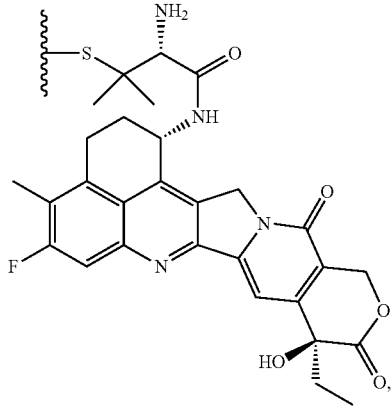
III-A-16
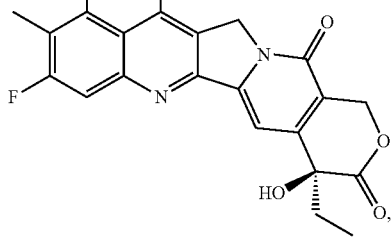
III-A-17
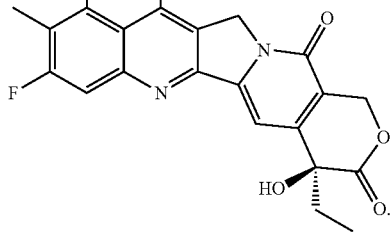
266. A compound or a tautomer, a mesomer, a racemate, an enantiomer or a diastereoisomer thereof, or a mixture thereof, or a pharmaceutically acceptable salt thereof, wherein the compound comprises a structure shown as formula (I-B):

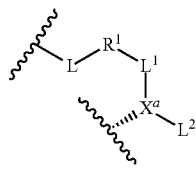
(I-B)

wherein, Xa is nitrogen generated by removal of two hydrogen atoms from an amino group of a cytotoxic drug;

L is -La-Lb-Lc-;

-La- is selected from the group consisting of:

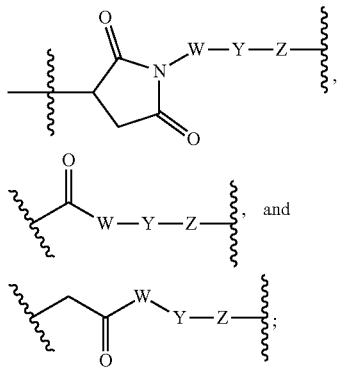

wherein W is —(C(Rwa)(Rwb))wn-, Y is —(OCH2CH2)yn-Oyp-, and Z is —(C(Rza)(Rzb))zn;

wherein wn is selected from the group consisting of integers ≥0, and 0 or no less than 1 methylene unit of W is independently replaced by -Cyr-, —N(Rwx)C(O)—, —C(O)N(Rwx)-, —C(O)—, —OC(O)—, —C(O)O—, —NRwx-, —O—, —S—, —SO—, —SO2-, —P(Rwx)-, —P(=O)(Rwx)-, —N(Rwx)SO2-, —SO2N(Rwx)-, —C(=S)—, —C(=NRwx)-, —N=N—, —C=N—, —N=C— or —C(=N2)-;

wherein yn is selected from the group consisting of integers ≥0, and yp is 0 or 1;

wherein zn is selected from the group consisting of integers ≥0, and 0 or no less than 1 methylene unit of Z is independently replaced by -Cyr-, —N(Rzx)C(O)—, —C(O)N(Rzx)-, —C(O)—, —OC(O)—, —C(O)O—, —NRzx-, —O—, —S—, —SO—, —SO2-, —P(Rzx)-, —P(=O)(Rzx)-, —N(Rzx)SO2-, —SO2N(Rzx)-, —C(=S)—, —C(=NRzx)-, —N=N—, —C=N—, —N=C— or —C(=N2)-;

Cyr- is selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or independently substituted with no less than 1 substituent Rcx;

wherein each Rwa, each Rwb, each Rza, each Rzb, each Rwx, each Rzx and each Rcx are each independently hydrogen, protium, deuterium, tritium, halogen, —NO2, —CN, —ORr, —SRr, —N(Rra)(Rrb), —C(O)Rr, —CO2Rr, —C(O)C(O)Rr, —C(O)CH2C(O)Rr, —S(O)Rr, —S(O)2Rr, —C(O)N(Rra)(Rrb), —SO2N(Rra)(Rrb), —OC(O)Rr, —N(R)SO2Rr, or a C1-6 aliphatic group optionally substituted with Rr;

wherein each Rr, each Rra and each Rrb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

-Lb- represents a peptide residue consisting of 2 to 7 amino acids;

-Lc- is selected from the group consisting of:

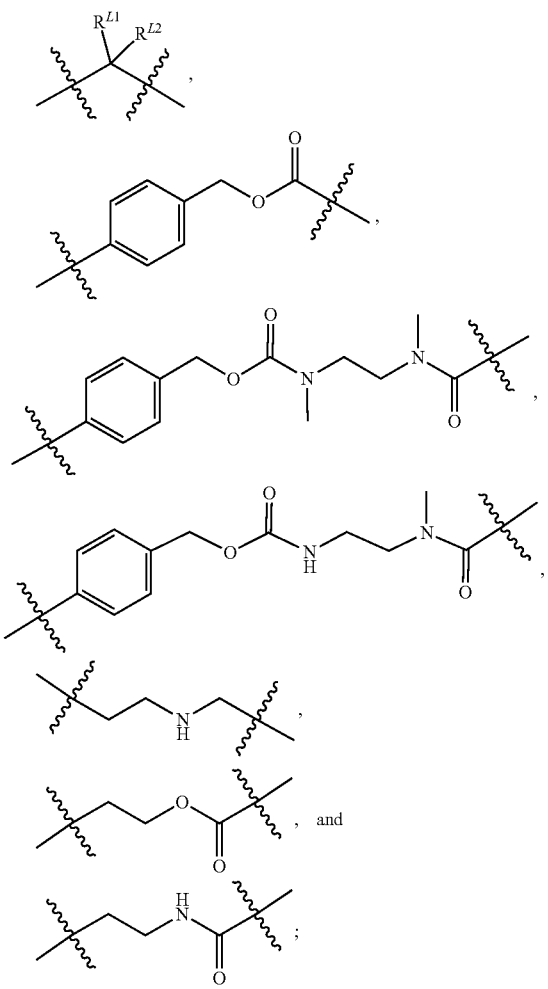

wherein RL1 and RL2 are each independently selected from the group consisting of: hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H and a C1-6 aliphatic group;

wherein R1 is selected from the group consisting of: —O—, —(R2)N—, —P(=O)(R2)- and —S—;

L2 is —(C(R3a)(R3b))m-R, wherein 0 or no less than 1 methylene unit of L2 is independently replaced by -Cy-, —N(R4)C(O)—, —C(O)N(R4)-, —C(O)—, —OC(O)—, —C(O)O—, —NR4-, —O—, —S—, —SO—, —SO2-, —P(R4)-, —P(=O)(R4)-, —N(R4)SO2-, —SO2N(R4)-, —C(=S)—, —C(=NR4)-, —N=N—, —C=N—, —N=C— or —C(=N2)-;

L1 is —(C(R5a)(R5b))n-, wherein 0 or no less than 1 methylene unit of L1 is independently replaced by -Cy-, —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N2)-;

-Cy- is selected from the group consisting of: 6-10 membered arylene, 5-8 membered heteroarylene, 3-10 membered heterocyclylene, and 3-10 membered saturated or partially unsaturated carbocyclylene, wherein -Cy- is unsubstituted or independently substituted with no less than 1 substituent R7;

wherein each R3a, each R3b, each R4, each R5a, each R5b and each R6 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R; or, R3a and R5a, R4 and R5a, R3a and R6 or R4 and R6 each independently optionally form a ring B together with an atom therebetween, wherein the ring B is selected from the group consisting of: 5-8 membered heteroarylene and 3-10 membered saturated or partially unsaturated heterocyclylene, and the ring B is unsubstituted or substituted with no less than 1 substituent R8;

wherein each R2, each R7 and each R8 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R;

wherein each R, each Ra and each Rb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

m and n are each independently selected from the group consisting of integers ≥1.

267. A compound or a tautomer, a mesomer, a racemate, an enantiomer or a diastereoisomer thereof, or a mixture thereof, or a pharmaceutically acceptable salt thereof, wherein the compound comprises a structure shown as formula (II-Bx) or formula (II-By):

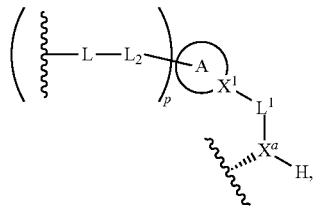
(II-Bx)

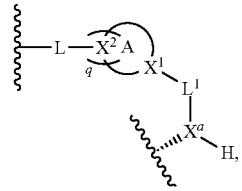
(II-By)

wherein, Xa is nitrogen generated by removal of two hydrogen atoms from an amino group of a cytotoxic drug;

L is -La-Lb-Lc-;

La- is selected from the group consisting of:

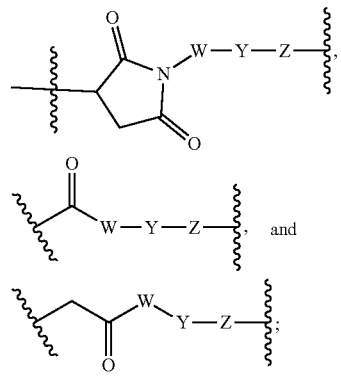

wherein W is —(C(Rwa)(Rwb))wn-, Y is —(OCH2CH2)yn-Oyp-, and Z is —(C(Rza)(Rzb))zn;

wherein wn is selected from the group consisting of integers ≥0, and 0 or no less than 1 methylene unit of W is independently replaced by -Cyr-, —N(Rwx)C(O)—, —C(O)N(Rwx)-, —C(O)—, —OC(O)—, —C(O)O—, —NRwx-, —O—, —S—, —SO—, —SO2-, —P(Rwx)-, —P(=O)(Rwx)-, —N(Rwx)SO2-, —SO2N(Rwx)-, —C(=S)—, —C(=NRwx)-, —N=N—, —C=N—, —N=C— or —C(=N2)-;

wherein yn is selected from the group consisting of integers ≥0, and yp is 0 or 1;

wherein zn is selected from the group consisting of integers ≥0, and 0 or no less than 1 methylene unit of Z is independently replaced by -Cyr-, —N(Rzx)C(O)—, —C(O)N(Rzx)-, —C(O)—, —OC(O)—, —C(O)O—, —NRzx-, —O—, —S—, —SO—, —SO2-, —P(Rzx)-, —P(=O)(Rzx)-, —N(Rzx)SO2-, —SO2N(Rzx)-, —C(=S)—, —C(=NRzx)-, —N=N—, —C=N—, —N=C— or —C(=N2)-;

Cyr- is selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or independently substituted with no less than 1 substituent Rex;

wherein each Rwa, each Rwb, each Rza, each Rzb, each Rwx, each Rzx and each Rcx are each independently hydrogen, protium, deuterium, tritium, halogen, —NO2, —CN, —ORr, —SRr, —N(Rra)(Rrb), —C(O)Rr, —CO2Rr, —C(O)C(O)Rr, —C(O)CH2C(O)Rr, —S(O)Rr, —S(O)2Rr, —C(O)N(Rra)(Rrb), —SO2N (Rra)(Rrb), —OC(O)Rr, —N(R)SO2Rr, or a C1-6 aliphatic group optionally substituted with Rr;
wherein each Rr, each Rra and each Rrb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;
-Lb- represents a peptide residue consisting of 2 to 7 amino acids;
-Lc- is selected from the group consisting of:

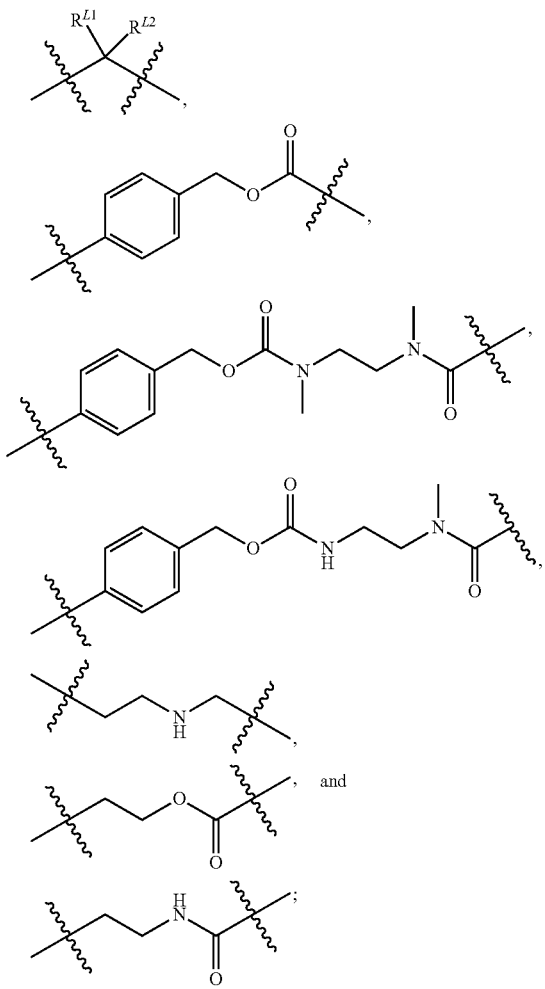

wherein RL1 and RL2 are each independently selected from the group consisting of: hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H and a C1-6 aliphatic group;
wherein, X1 is selected from the group consisting of: N, P, and saturated or unsaturated C; when X1 is saturated C, X1 is substituted with Rn;
when X1 is saturated C, ring A is selected from the group consisting of: 3-10 membered saturated or partially unsaturated heterocyclyl, and 3-10 membered saturated or partially unsaturated carbocyclyl, wherein ring A is unsubstituted or substituted with no less than 1 substituent R1a;

or, when X1 is unsaturated C, ring A is selected from the group consisting of: 6-10 membered aryl, 5-8 membered heteroaryl, 3-10 membered partially unsaturated heterocyclyl, and 3-10 membered partially unsaturated carbocyclyl, wherein ring A is unsubstituted or substituted with no less than 1 substituent R1b;

or, when X1 is N or P, ring A is selected from the group consisting of: 5-8 membered heteroaryl and 3-10 membered saturated or partially unsaturated heterocyclyl, wherein ring A is unsubstituted or substituted with no less than 1 substituent R1c;

when ring A is selected from the group consisting of: 6-10 membered aryl, 5-8 membered heteroaryl, and 3-10 membered saturated or partially unsaturated carbocyclyl, ring A is substituted with p L2, wherein L2 is not Rn;

or, when ring A is 3-10 membered saturated or partially unsaturated heterocyclyl, ring A is substituted with p L2, or ring A comprises q ring-forming heteroatom X2, and X2 is used for direct or indirect linking of a ligand;

X2 is selected from the group consisting of: N and P;

L2 is —R2-L3-, and R2 is used for direct or indirect linking of a ligand;

L3 is —(C(R3a)(R3b))$_m$—, wherein 0 or no less than 1 methylene unit of L3 is independently replaced by —N(R4)C(O)—, —C(O)N(R4)-, —C(O)—, —OC(O)—, —C(O)O—, —NR4-, —O—, —S—, —SO—, —SO2-, —P(R4)-, —P(=O)(R4)-, —N(R4)SO2-, —SO2N(R4)-, —C(=S)—, —C(=NR4)-, —N=N—, —C=N—, —N=C— or —C(=N2)-;

R2 is selected from the group consisting of: —O—, —(R2a)N—, —S— and —P(=O)(R2a)-;

L1 is —(C(R5a)(R5b))$_n$—, wherein 0 or no less than 1 methylene unit of L1 is independently replaced by —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N2)-;

wherein each R1a, each R1b, each R1c, each R2a, each R3a, each R3b, each R4, each R5a, each R5b, each R6 and each Rn are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R;

wherein each R, each Ra and each Rb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

m and n are each independently selected from the group consisting of integers ≥0, and p and q are each independently selected from the group consisting of integers ≥1.

268. A compound or a tautomer, a mesomer, a racemate, an enantiomer or a diastereoisomer thereof, or a mixture thereof, or a pharmaceutically acceptable salt thereof, wherein the compound comprises a structure shown as formula (III-B):

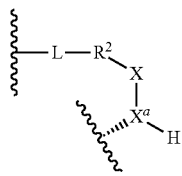
(III-B)

wherein, Xa is nitrogen generated by removal of two hydrogen atoms from an amino group of a cytotoxic drug;

L is -La-Lb-Lc-;

-La- is selected from the group consisting of:

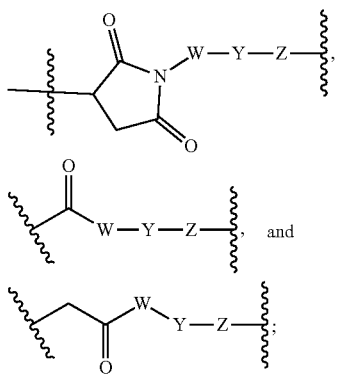

wherein W is —(C(Rwa)(Rwb))wn-, Y is —(OCH2CH2)yn-Oyp, and Z is —(C(Rza)(Rzb))zn;

wherein wn is selected from the group consisting of integers ≥0, and 0 or no less than 1 methylene unit of W is independently replaced by -Cyr-, —N(Rwx)C(O)—, —C(O)N(Rwx)-, —C(O)—, —OC(O)—, —C(O)O—, —NRwx-, —O—, —S—, —SO—, —SO2-, —P(Rwx)-, —P(=O)(Rwx)-, —N(Rwx)SO2-, —SO2N(Rwx)-, —C(=S)—, —C(=NRwx)-, —N=N—, —C=N—, —N=C— or —C(=N2)-;

wherein yn is selected from the group consisting of integers ≥0, and yp is 0 or 1;

wherein zn is selected from the group consisting of integers ≥0, and 0 or no less than 1 methylene unit of Z is independently replaced by -Cyr-, —N(Rzx)C(O)—, —C(O)N(Rzx)-, —C(O)—, —OC(O)—, —C(O)O—, —NRzx-, —O—, —S—, —SO—, —SO2-, —P(Rzx)-, —P(=O)(Rzx)-, —N(Rzx)SO2-, —SO2N(Rzx)-, —C(=S)—, —C(=NRzx)-, —N=N—, —C=N—, —N=C— or —C(=N2)-;

Cyr- is selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or independently substituted with no less than 1 substituent Rcx;

wherein each Rwa, each Rwb, each Rza, each Rzb, each Rwx, each Rzx and each Rcx are each independently hydrogen, protium, deuterium, tritium, halogen, —NO2, —CN, —ORr, —SRr, —N(Rra)(Rrb), —C(O)Rr, —CO2Rr, —C(O)C(O)Rr, —C(O)CH2C(O)Rr, —S(O)Rr, —S(O)2Rr, —C(O)N(Rra)(Rrb), —SO2N(Rra)(Rrb), —OC(O)Rr, —N(R)SO2Rr, or a C1-6 aliphatic group optionally substituted with Rr;

wherein each Rr, each Rra and each Rrb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

-Lb- represents a peptide residue consisting of 2 to 7 amino acids;

-Lc- is selected from the group consisting of:

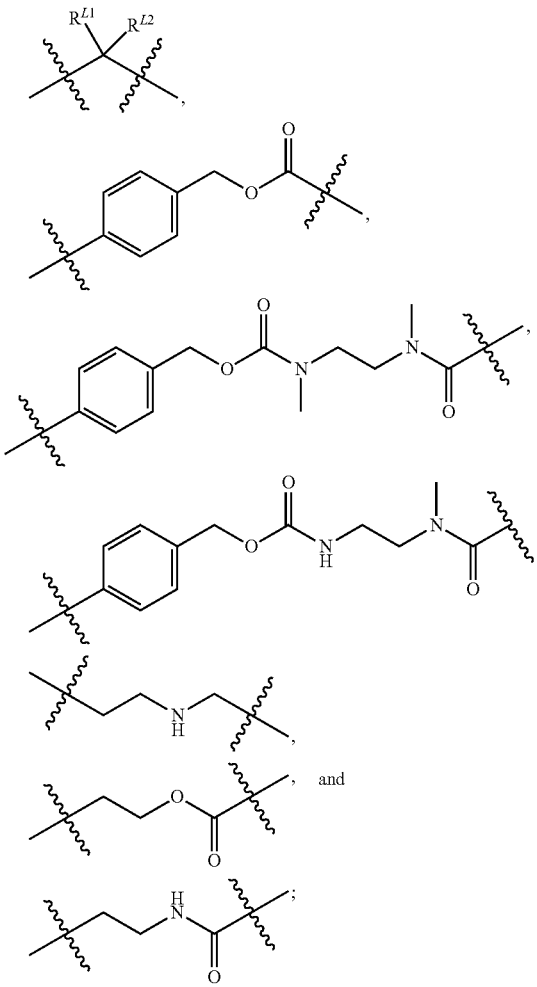

wherein RL1 and RL2 are each independently selected from the group consisting of: hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H and a C1-6 aliphatic group;

wherein R1 is selected from the group consisting of: —O—, —(R2)N—, —P(=O)(R2)- and —S—;

X is selected from the group consisting of: -L1-C(R1a)(R1b)-C(O)—, -L1-C(R1a)(R1b)-C(S)—, -L1-L0- and -L3-L2-;

L1 is —(C(R3a)(R3b))m-, wherein 0 or no less than 1 methylene unit of L1 is independently replaced by —C(O)—, —C(=S)—, —C(=NR4b)- or —C(=N2)-;

L0 is —C(R2a)(R2b)-, or L0 is —C(=S)—, —C(=NR4a)- or —C(=N2)-;

L2 is —C(R5a)(R5b)-, wherein 0 or 1 methylene unit of L2 is replaced by —N(R6)C(O)—, —C(O)N(R6)-, —C(O)—, —OC(O)—, —C(O)O—, —NR6-, —O—, —S—, —SO—, —SO$_2$—, —P(R6)-, —P(=O)(R6)-, —N(R6)SO2-, —SO2N(R6)-, —C(=S)—, —C(=NR6)-, —N=N—, —C=N—, —N=C— or —C(=N2)-;

L3 is —(C(R7a)(R7b))$_n$—, wherein no less than 1 methylene unit of L3 is independently replaced by —N(R8)C(O)—, —C(O)N(R8)-, —OC(O)—, —C(O)O—, —NR8-, —O—, —S—, —SO—, —SO2-, —P(R8)-, —P(=O)(R8)-, —N(R8)SO$_2$—, —SO2N(R8)-, —N=N—, —C=N— or —N=C—, and 0 or no less than 1 methylene unit of L3 is also independently replaced by —C(O)—, —C(=S)—, —C(=NR8)- or —C(=N2)-;

wherein each R1a, each R1b, each R2, each R2a, each R2b, each R3a, each R3b, each R4a, each R4b, each R5a, each R5b, each R6, each R7a, each R7b and each R8 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R;

wherein each R, each Ra and each Rb are each independently hydrogen, protium, deuterium, tritium, halogen, —NO2, —CN, —OH, —SH, —NH$_2$, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

m is selected from the group consisting of integers ≥0, and n is selected from the group consisting of integers ≥1;

when R1 is —O— or —HN— and X is -L1-CH$_2$—C(O)—, no less than 1 methylene unit of L1 is independently replaced by —C(O)—, —C(=S)—, —C(=NR4b)- or —C(=N2)-, or each R3a and each R3b are not both hydrogen;

when R1 is —HN—, X is -L1-L0-, and L0 is —CH$_2$—, no less than 1 methylene unit of L1 is independently replaced by —C(O)—, —C(=S)—, —C(=NR4b)- or —C(=N2)-, or each R3a and each R3b are not both hydrogen;

when R1 is —O—, X is -L3-C(O)—, and 1 methylene unit of L3 is replaced by —NR8, R8 is not —CH2—CH$_2$—NH$_2$;

when R1 is —NH—, and X is -L3-C(O)—, no less than 1 methylene unit of L3 is replaced by —N(R8)C(O)—, —OC(O)—, —C(O)O—, —S—, —SO—, —SO2-, —P(R8)-, —P(=O)(R8)-, —N(R8)SO$_2$—, —SO2N(R8)-, —N=N—, —C=N— or —N=C—.

269. The compound or the tautomer, the mesomer, the racemate, the enantiomer or the diastereoisomer thereof, or the mixture thereof, or the pharmaceutically acceptable salt thereof according to any one of technical schemes 266-268, wherein La- is selected from the group consisting of:

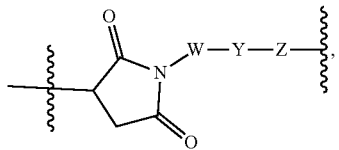

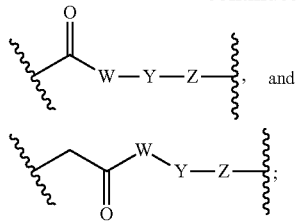 and wherein W is —(C(Rwa)(Rwb))wn-, Y is —(OCH2CH2)yn-Oyp-, and Z is —(C(Rza)(Rzb))zn;

wherein wn is selected from the group consisting of integers from 2 to 6, and 0 or 1 methylene unit of W is independently replaced by -Cyr-, —N(Rwx)C(O)—, —C(O)N(Rwx)-, —C(O)—, —NRwx- or —O—;

wherein yn is selected from the group consisting of integers from 0 to 12, and yp is 0 or 1;

wherein zn is selected from the group consisting of integers from 0 to 10, and 0 or 1 methylene unit of Z is independently replaced by -Cyr-, —N(Rzx)C(O)—, —C(O)N(Rzx)- or —C(O)—;

Cyr- is selected from the group consisting of: 6-10 membered arylene and 3-10 membered saturated or partially unsaturated carbocyclylene, wherein -Cyr- is unsubstituted or independently substituted with 1 to 3 substituent Rcx;

wherein each Rwa, each Rwb, each Rza, each Rzb, each Rwx, each Rzx and each Rcx are each independently hydrogen, protium, deuterium, tritium, halogen, —NO2, —CN, —ORr, —SRr, —N(Rra)(Rrb), —C(O)Rr, —CO2Rr, —C(O)C(O)Rr, —C(O)CH$_2$C(O)Rr, —S(O)Rr, —S(O)2Rr, —C(O)N(Rra)(Rrb), —SO2N(Rra)(Rrb), —OC(O)Rr, —N(R)SO2Rr, or a C1-6 aliphatic group optionally substituted with Rr;

wherein each Rr, each Rra and each Rrb are each independently hydrogen, protium, deuterium, tritium, halogen, —NO2, —CN, —OH, —SH, —NH$_2$, —C(O)H, —CO2H, —C(O)C(O)H, —C(O)CH2C(O)H, —S(O)H, —S(O)2H, —C(O)NH2, —SO2NH$_2$, —OC(O)H, —N(H)SO2H or a C1-6 aliphatic group;

-Lb- represents a peptide residue consisting of 2 to 7 amino acids, and the peptide residue of -Lb- is a peptide residue formed of amino acids selected from the group consisting of: phenylalanine, glycine, alanine, valine, citrulline, lysine, serine, glutamic acid and aspartic acid;

-Lc- is selected from the group consisting of:

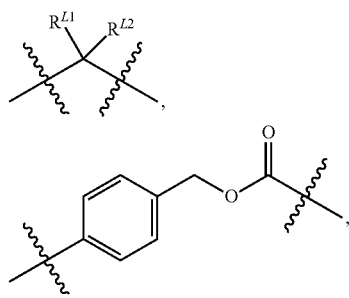

-continued

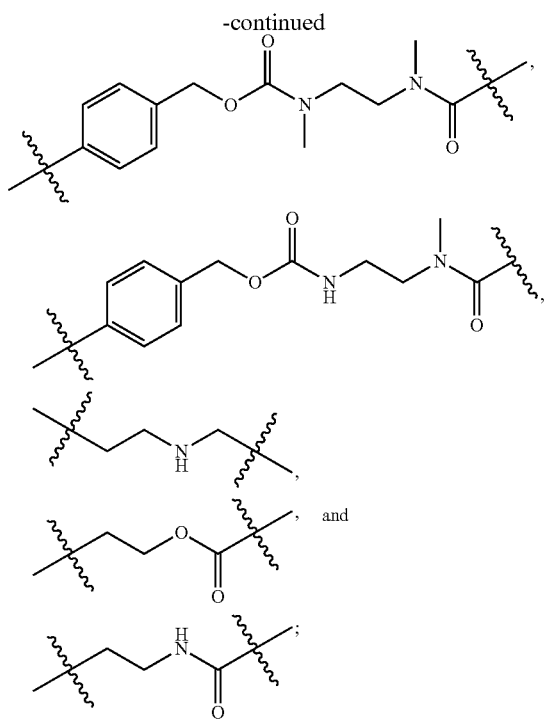

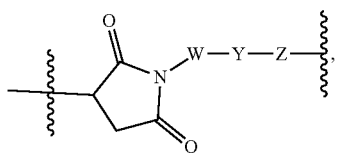

wherein RL1 and RL2 are each independently selected from the group consisting of: hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH$_2$, —OC(O)H, —N(H)SO2H and a C1-6 aliphatic group.

270. The compound or the tautomer, the mesomer, the racemate, the enantiomer or the diastereoisomer thereof, or the mixture thereof, or the pharmaceutically acceptable salt thereof according to any one of technical schemes 266-269, wherein
La- is

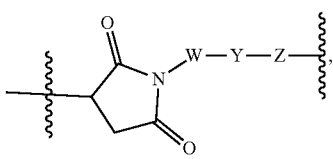

wherein W is —(C(Rwa)(Rwb))wn-, Y is —(OCH2CH2)yn-Oyp-, and Z is —(C(Rza)(Rzb))zn;
wherein wn is 1, 2, 3 or 6, and
1 methylene unit of W is independently replaced by -Cyr-, —N(Rwx)C(O)—, —C(O)N(Rwx)- or —C(O)—;
wherein yn is 0, 4 or 8, and yp is 0 or 1;
wherein zn is 1, 2 or 3, and
1 methylene unit of Z is independently replaced by -Cyr-, —N(Rzx)C(O)—, —C(O)N(Rzx)- or —C(O)—;
Cyr- is 3-10 membered saturated carbocyclylene, wherein -Cyr- is unsubstituted or independently substituted with 1 to 3 substituent Rex;
wherein each Rwa, each Rwb, each Rza, each Rzb, each Rwx, each Rzx and each Rcx are each independently hydrogen, halogen, —ORr, or a C1-6 aliphatic group optionally substituted with Rr;
wherein each Rr is independently hydrogen, halogen or a C1-6 aliphatic group;
-Lb- represents a peptide residue consisting of 2 to 4 amino acids, and the peptide residue of -Lb- is a peptide residue formed of amino acids selected from the group consisting of: phenylalanine, glycine, alanine, valine, citrulline and lysine;
-Lc- is selected from the group consisting of:

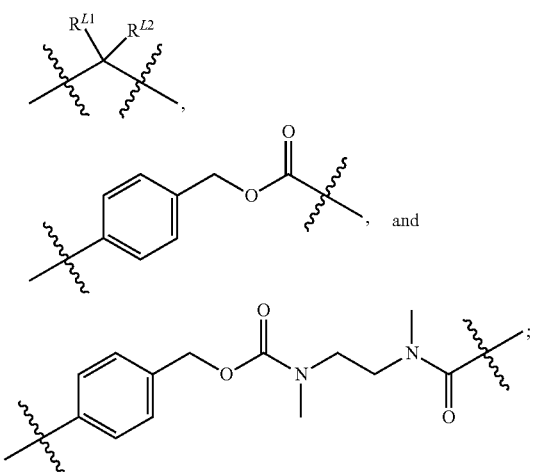

wherein RL1 and RL2 are each independently selected from the group consisting of: hydrogen, halogen, —OH and a C1-6 aliphatic group.

271. The compound or the tautomer, the mesomer, the racemate, the enantiomer or the diastereoisomer thereof, or the mixture thereof, or the pharmaceutically acceptable salt thereof according to any one of technical schemes 266-270, wherein
La- is

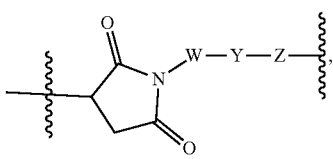

wherein W is —(C(Rwa)(Rwb))wn-, Y is —(OCH2CH2)yn-Oyp-, and Z is —(C(Rza)(Rzb))zn;
wherein wn is 1, 2, 3 or 6, and
1 methylene unit of W is independently replaced by -Cyr-, —N(Rwx)C(O)—, —C(O)N(Rwx)- or —C(O)—;
wherein yn is 0, 4 or 8, and yp is 0 or 1;
wherein zn is 1, 2 or 3, and
1 methylene unit of Z is independently replaced by -Cyr-, —N(Rzx)C(O)—, —C(O)N(Rzx)- or —C(O)—;
Cyr- is 3-10 membered saturated carbocyclylene, wherein -Cyr- is unsubstituted or independently substituted with 1 to 3 substituent Rex;
wherein each Rwa, each Rwb, each Rza, each Rzb, each Rwx, each Rzx and each Rcx are each independently hydrogen, halogen, —ORr, or a C1-6 aliphatic group optionally substituted with Rr;
wherein each Rr is independently hydrogen, halogen or a C1-6 aliphatic group;

$L_b$- is selected from the group consisting of:

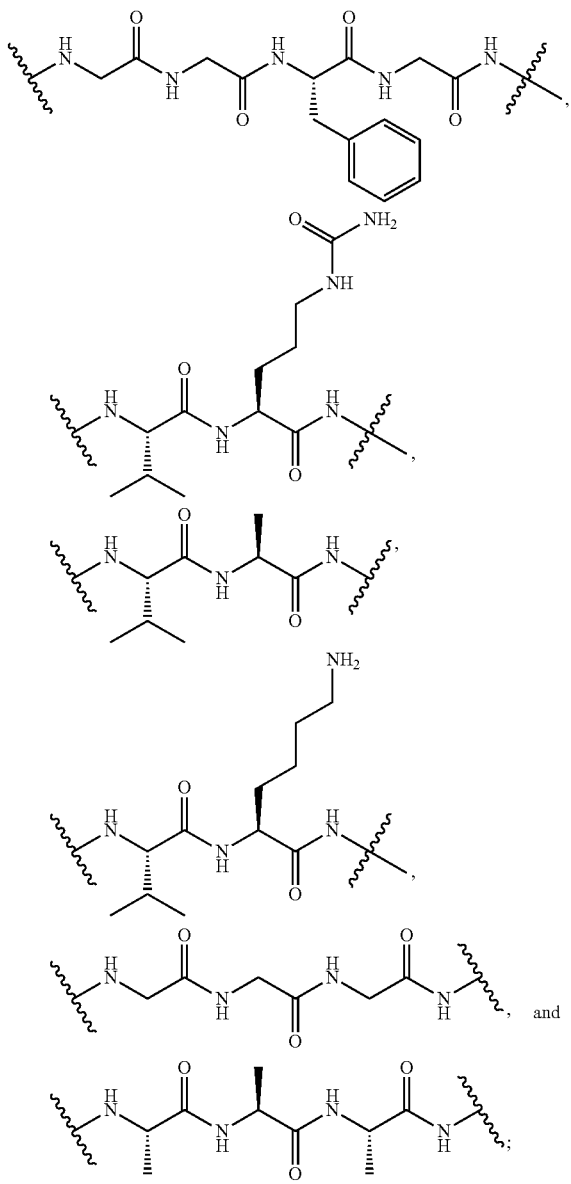

$L_c$- is

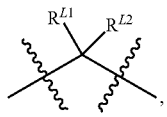

wherein RL1 and RL2 are each independently selected from the group consisting of: hydrogen, halogen, —OH and a C1-6 aliphatic group.

272. The compound or the tautomer, the mesomer, the racemate, the enantiomer or the diastereoisomer thereof, or the mixture thereof, or the pharmaceutically acceptable salt thereof according to any one of technical schemes 266-271, wherein La- is

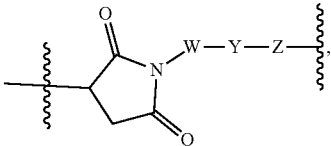

wherein W is —(C(Rwa)(Rwb))wn-, Y is —(OCH2CH2)yn-Oyp-, and Z is —(C(Rza)(Rzb))zn;
wherein wn is 1, 2, 3 or 6, and
1 methylene unit of W is independently replaced by -Cyr-, —N(Rwx)C(O)—, —C(O)N(Rwx)- or —C(O)—;
wherein yn is 0, 4 or 8, and yp is 0 or 1;
wherein zn is 1, 2 or 3, and
1 methylene unit of Z is independently replaced by -Cyr-, —N(Rzx)C(O)—, —C(O)N(Rzx)- or —C(O)—;
Cyr- is 3-10 membered saturated carbocyclylene, wherein -Cyr- is unsubstituted or independently substituted with 1 to 3 substituent Rcx;
wherein each Rwa, each Rwb, each Rza, each Rzb, each Rwx, each Rzx and each Rcx are each independently hydrogen, halogen, —ORr, or a C1-6 aliphatic group optionally substituted with Rr;
wherein each Rr is independently hydrogen, halogen or a C1-6 aliphatic group;
$L_b$- is

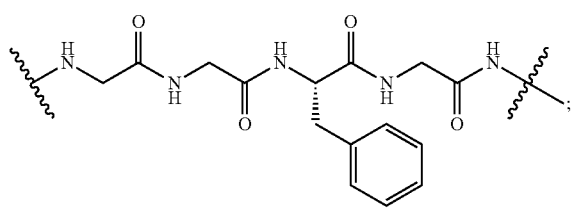 [SMILES: *NCC(=O)NCC(=O)N[C@@H](Cc1ccccc1)C(=O)NCC(=O)N*]

$L_c$- is

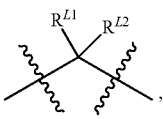

wherein RL1 and RL2 are each independently selected from the group consisting of: hydrogen, halogen, —OH and a C1-6 aliphatic group.

273. The compound or the tautomer, the mesomer, the racemate, the enantiomer or the diastereoisomer thereof, or the mixture thereof, or the pharmaceutically acceptable salt thereof according to any one of technical schemes 266-272, wherein La- is

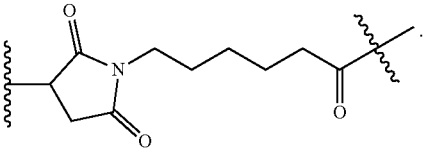 [SMILES: *C(=O)CCCCCN1C(=O)CC(*)C1=O]

274. The compound or the tautomer, the mesomer, the racemate, the enantiomer or the diastereoisomer thereof, or the mixture thereof, or the pharmaceutically acceptable salt thereof according to any one of technical schemes 266-273, wherein
 -Lb- is:

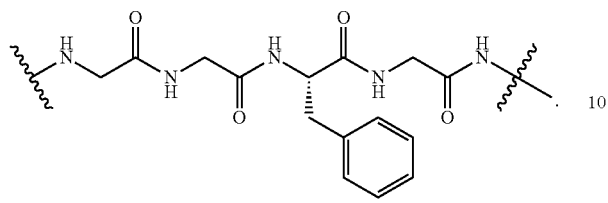

275. The compound or the tautomer, the mesomer, the racemate, the enantiomer or the diastereoisomer thereof, or the mixture thereof, or the pharmaceutically acceptable salt thereof according to any one of technical schemes 266-274, wherein
 -Lc- is

276. The compound or the tautomer, the mesomer, the racemate, the enantiomer or the diastereoisomer thereof, or the mixture thereof, or the pharmaceutically acceptable salt thereof according to any one of technical schemes 266-275, wherein
 -La-Lb-Lc- is

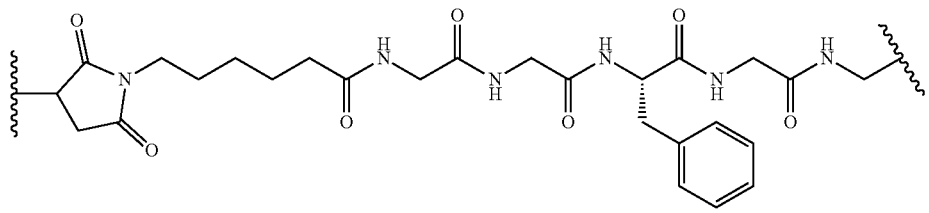 [SMILES: *CNC(=O)CNC(=O)[C@H](Cc1ccccc1)NC(=O)CNC(=O)CNC(=O)CCCCCN1C(=O)CC(*)C1=O]

277. The compound or the tautomer, the mesomer, the racemate, the enantiomer or the diastereoisomer thereof, or the mixture thereof, or the pharmaceutically acceptable salt thereof according to any one of technical schemes 266-276, wherein the cytotoxic drug is shown as formula (EXA):

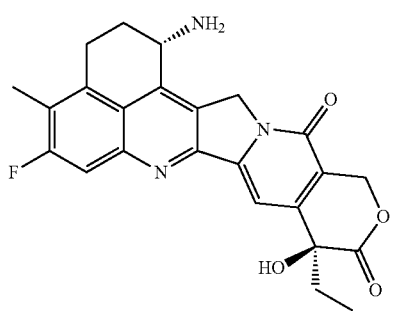

(EXA)

278. A compound or a tautomer, a mesomer, a racemate, an enantiomer or a diastereoisomer thereof, or a mixture thereof, or a pharmaceutically acceptable salt thereof, wherein the compound comprises a structure shown as formula (I-C):

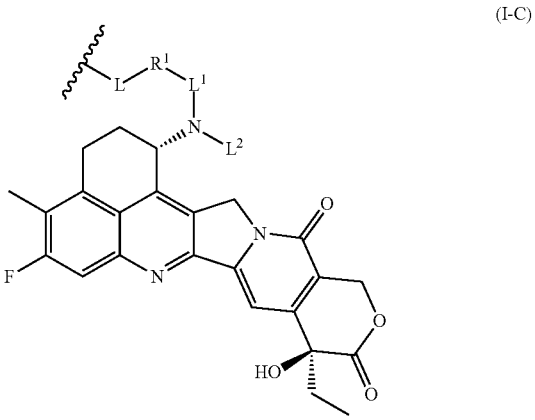

(I-C)

wherein, L is -La-Lb-Lc-;

La- is selected from the group consisting of:

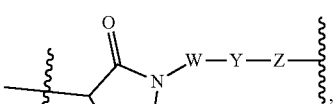

,

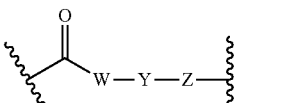

, and

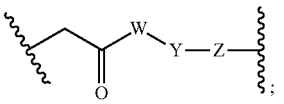

;

wherein W is —(C(Rwa)(Rwb))wn-, Y is —(OCH2CH2)yn-Oyp-, and Z is —(C(Rza)(Rzb))zn;

wherein wn is selected from the group consisting of integers ≥0, and 0 or no less than 1 methylene unit of W is independently replaced by -Cyr-, —N(Rwx)C(O)—, —C(O)N(Rwx)-, —C(O)—, —OC(O)—, —C(O)O—, —NRwx-, —O—, —S—, —SO—, —SO2-, —P(Rwx)-, —P(=O)(Rwx)-, —N(Rwx)SO₂—, —SO2N(Rwx)-, —C(=S)—, —C(=NRwx)-, —N=N—, —C=N—, —N=C— or —C(=N2)-;

wherein yn is selected from the group consisting of integers ≥0, and yp is 0 or 1;

wherein zn is selected from the group consisting of integers ≥0, and 0 or no less than 1 methylene unit of Z is independently replaced by -Cyr-, —N(Rzx)C(O)—, —C(O)N(Rzx)-, —C(O)—, —OC(O)—, —C(O)O—, —NRzx-, —O—, —S—, —SO—, —SO2-, —P(Rzx)-, —P(=O)(Rzx)-, —N(Rzx)SO2-, —SO2N(Rzx)-, —C(=S)—, —C(=NRzx)-, —N=N—, —C=N—, —N=C— or —C(=N2)-;

Cyr- is selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or independently substituted with no less than 1 substituent Rex;

wherein each Rwa, each Rwb, each Rza, each Rzb, each Rwx, each Rzx and each Rcx are each independently hydrogen, protium, deuterium, tritium, halogen, —NO2, —CN, —ORr, —SRr, —N(Rra)(Rrb), —C(O)Rr, —CO2Rr, —C(O)C(O)Rr, —C(O)CH2C(O)Rr, —S(O)Rr, —S(O)2Rr, —C(O)N(Rra)(Rrb), —SO2N(Rra)(Rrb), —OC(O)Rr, —N(R)SO2Rr, or a C1-6 aliphatic group optionally substituted with Rr;

wherein each Rr, each Rra and each Rrb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

-Lb- represents a peptide residue consisting of 2 to 7 amino acids;

-Lc- is selected from the group consisting of:

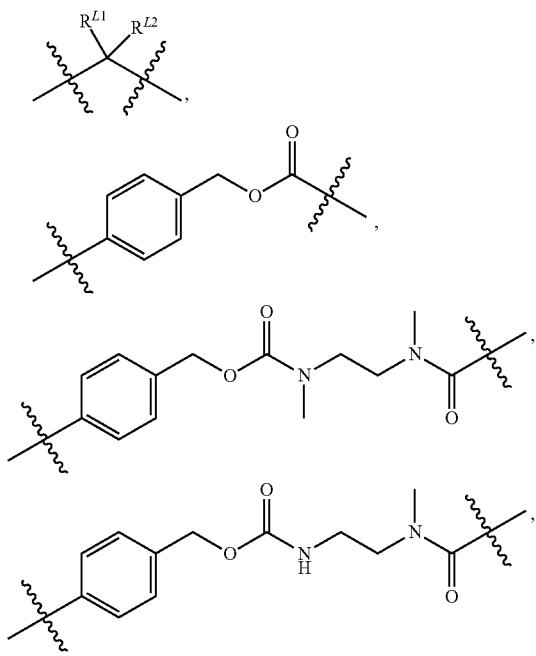

wherein RL1 and RL2 are each independently selected from the group consisting of: hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H and a C1-6 aliphatic group;

wherein R1 is selected from the group consisting of: —O—, —(R2)N—, —P(=O)(R2)- and —S—;

L2 is —(C(R3a)(R3b))m-R, wherein 0 or no less than 1 methylene unit of L2 is independently replaced by -Cy-, —N(R4)C(O)—, —C(O)N(R4)-, —C(O)—, —OC(O)—, —C(O)O—, —NR4-, —O—, —S—, —SO—, —SO2-, —P(R4)-, —P(=O)(R4)-, —N(R4)SO2-, —SO2N(R4)-, —C(=S)—, —C(=NR4)-, —N=N—, —C=N—, —N=C— or —C(=N2)-;

L1 is —(C(R5a)(R5b))$_n$—, wherein 0 or no less than 1 methylene unit of L1 is independently replaced by -Cy-, —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N2)-;

-Cy- is selected from the group consisting of: 6-10 membered arylene, 5-8 membered heteroarylene, 3-10 membered heterocyclylene, and 3-10 membered saturated or partially unsaturated carbocyclylene, wherein -Cy- is unsubstituted or independently substituted with no less than 1 substituent R7;

wherein each R3a, each R3b, each R4, each R5a, each R5b and each R6 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R; or, R3a and R5a, R4 and R5a, R3a and R6 or R4 and R6 each independently optionally form a ring B together with an atom therebetween, wherein the ring B is selected from the group consisting of: 5-8 membered heteroarylene and 3-10 membered saturated or partially unsaturated heterocyclylene, and the ring B is unsubstituted or substituted with no less than 1 substituent R8;

wherein each R2, each R7 and each R8 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N (Ra)(Rb), —OC(O)R, —N(R)SO2R, or a C1-6 aliphatic group optionally substituted with R;
wherein each R, each Ra and each Rb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

m and n are each independently selected from the group consisting of integers ≥1.

279. A compound or a tautomer, a mesomer, a racemate, an enantiomer or a diastereoisomer thereof, or a mixture thereof, or a pharmaceutically acceptable salt thereof, wherein the compound comprises a structure shown as formula (II-C$_x$) or formula (II-Cy):

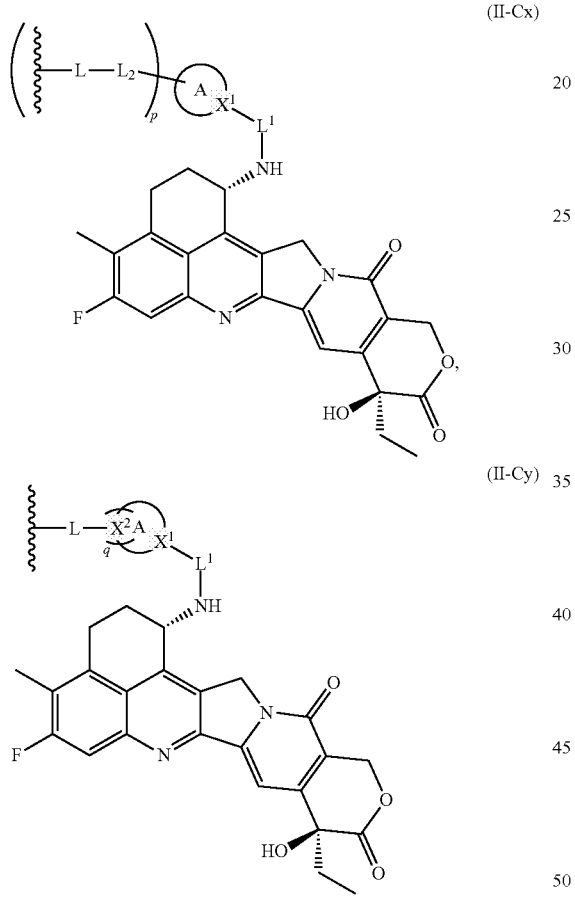

wherein, L is -La-Lb-Lc-;
La- is selected from the group consisting of:

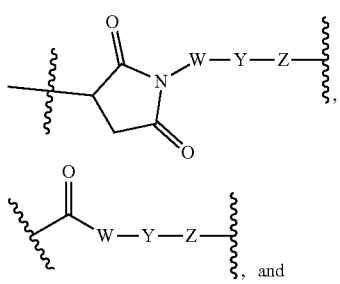, and

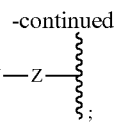;

wherein W is —(C(Rwa)(Rwb))wn-, Y is —(OCH2CH2)yn-Oyp-, and Z is —(C(Rza)(Rzb))zn;
wherein wn is selected from the group consisting of integers ≥0, and
0 or no less than 1 methylene unit of W is independently replaced by -Cyr-, —N(Rwx)C(O)—, —C(O)N(Rwx)-, —C(O)—, —OC(O)—, —C(O)O—, —NRwx-, —O—, —S—, —SO—, —SO2-, —P(Rwx)-, —P(=O)(Rwx)-, —N(Rwx)SO2-, —SO2N(Rwx)-, —C(=S)—, —C(=NRwx)-, —N=N—, —C=N—, —N=C— or —C(=N2)-;
wherein yn is selected from the group consisting of integers ≥0, and yp is 0 or 1;
wherein zn is selected from the group consisting of integers ≥0, and
0 or no less than 1 methylene unit of Z is independently replaced by -Cyr-, —N(Rzx)C(O)—, —C(O)N(Rzx)-, —C(O)—, —OC(O)—, —C(O)O—, —NRzx-, —O—, —S—, —SO—, —SO2-, —P(Rzx)-, —P(=O)(Rzx)-, —N(Rzx)SO2-, —SO2N(Rzx)-, —C(=S)—, —C(=NRzx)-, —N=N—, —C=N—, —N=C— or —C(=N2)-;
Cyr- is selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or independently substituted with no less than 1 substituent Rcx;
wherein each Rwa, each Rwb, each Rza, each Rzb, each Rwx, each Rzx and each Rcx are each independently hydrogen, protium, deuterium, tritium, halogen, —NO2, —CN, —ORr, —SRr, —N(Rra)(Rrb), —C(O)Rr, —CO2Rr, —C(O)C(O)Rr, —C(O)CH$_2$C(O)Rr, —S(O)Rr, —S(O)2Rr, —C(O)N(Rra)(Rrb), —SO2N(Rra)(Rrb), —OC(O)Rr, —N(R)SO2Rr, or a C1-6 aliphatic group optionally substituted with Rr;
wherein each Rr, each Rra and each Rrb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;
-Lb- represents a peptide residue consisting of 2 to 7 amino acids;
-Lc- is selected from the group consisting of:

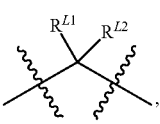,

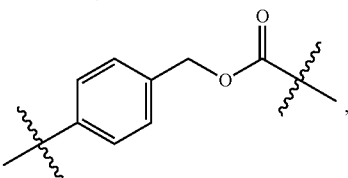,

-continued

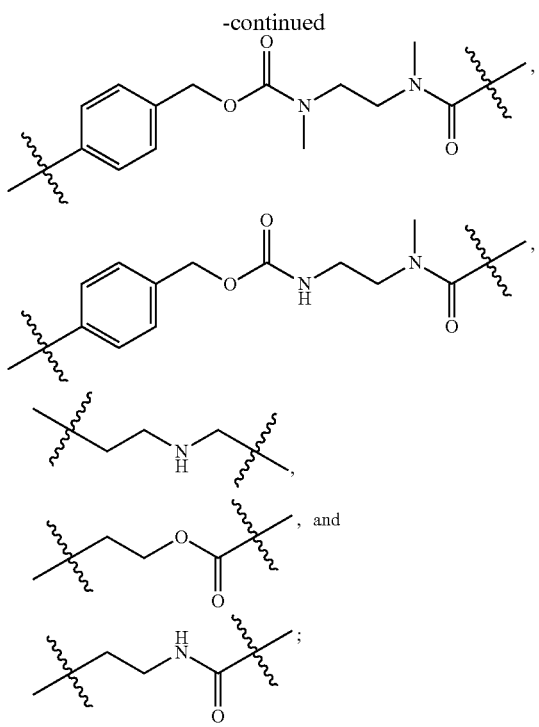

wherein RL1 and RL2 are each independently selected from the group consisting of: hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H and a C1-6 aliphatic group;

wherein, X1 is selected from the group consisting of: N, P, and saturated or unsaturated C; when X1 is saturated C, X1 is substituted with Rn;

when X1 is saturated C, ring A is selected from the group consisting of: 3-10 membered saturated or partially unsaturated heterocyclyl, and 3-10 membered saturated or partially unsaturated carbocyclyl, wherein ring A is unsubstituted or substituted with no less than 1 substituent R1a;

or, when X1 is unsaturated C, ring A is selected from the group consisting of: 6-10 membered aryl, 5-8 membered heteroaryl, 3-10 membered partially unsaturated heterocyclyl, and 3-10 membered partially unsaturated carbocyclyl, wherein ring A is unsubstituted or substituted with no less than 1 substituent R1b;

or, when X1 is N or P, ring A is selected from the group consisting of: 5-8 membered heteroaryl and 3-10 membered saturated or partially unsaturated heterocyclyl, wherein ring A is unsubstituted or substituted with no less than 1 substituent R1c;

when ring A is selected from the group consisting of: 6-10 membered aryl, 5-8 membered heteroaryl, and 3-10 membered saturated or partially unsaturated carbocyclyl, ring A is substituted with p L2, wherein L2 is not Rn;

or, when ring A is 3-10 membered saturated or partially unsaturated heterocyclyl, ring A is substituted with p L2, or ring A comprises q ring-forming heteroatom X2, and X2 is used for direct or indirect linking of a ligand; X2 is selected from the group consisting of: N and P;

L2 is —R2-L3-, and R2 is used for direct or indirect linking of a ligand;

L3 is —(C(R3a)(R3b))m-, wherein 0 or no less than 1 methylene unit of L3 is independently replaced by —N(R4)C(O)—, —C(O)N(R4)-, —C(O)—, —OC(O)—, —C(O)O—, —NR4-, —O—, —S—, —SO—, —SO2-, —P(R4)-, —P(=O)(R4)-, —N(R4)SO2-, —SO2N(R4)-, —C(=S)—, —C(=NR4)-, —N=N—, —C=N—, —N=C— or —C(=N2)-;

R2 is selected from the group consisting of: —O—, —(R2a)N—, —S— and —P(=O)(R2a)-;

L1 is —(C(R5a)(R5b))n-, wherein 0 or no less than 1 methylene unit of L1 is independently replaced by —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N2)-;

wherein each R1a, each R1b, each R1c, each R2a, each R3a, each R3b, each R4, each R5a, each R5b, each R6 and each Rn are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R;

wherein each R, each Ra and each Rb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

m and n are each independently selected from the group consisting of integers ≥0, and p and q are each independently selected from the group consisting of integers ≥1.

280. A compound or a tautomer, a mesomer, a racemate, an enantiomer or a diastereoisomer thereof, or a mixture thereof, or a pharmaceutically acceptable salt thereof, wherein the compound comprises a structure shown as formula (III-C):

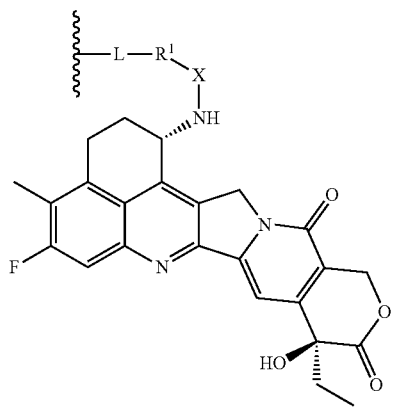

(III-C)

wherein, L is -La-Lb-Lc-;
-La- is selected from the group consisting of:

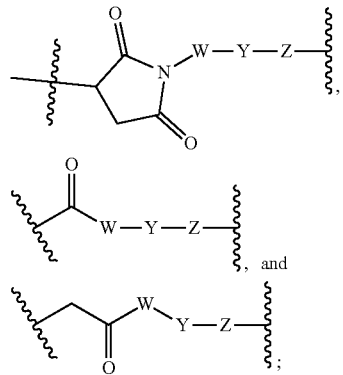

wherein W is —(C(Rwa)(Rwb))wn-, Y is —(OCH2CH2)yn-Oyp, and Z is —(C(Rza)(Rzb))zn;
wherein wn is selected from the group consisting of integers ≥0, and
0 or no less than 1 methylene unit of W is independently replaced by -Cyr-, —N(Rwx)C(O)—, —C(O)N(Rwx)-, —C(O)—, —OC(O)—, —C(O)O—, -NRwx-, —O—, —S—, —SO—, —SO2-, —P(Rwx)-, —P(=O)(Rwx)-, —N(Rwx)SO2-, —SO2N(Rwx)-, —C(=S)—, —C(=NRwx)-, —N=N—, —C=N—, —N=C— or —C(=N2)-;
wherein yn is selected from the group consisting of integers ≥0, and yp is 0 or 1;
wherein zn is selected from the group consisting of integers ≥0, and
0 or no less than 1 methylene unit of Z is independently replaced by -Cyr-, —N(Rzx)C(O)—, —C(O)N(Rzx)-, —C(O)—, —OC(O)—, —C(O)O—, —NRzx-, —O—, —S—, —SO—, —SO2-, —P(Rzx)-, —P(=O)(Rzx)-, —N(Rzx)SO2-, —SO2N(Rzx)-, —C(=S)—, —C(=NRzx)-, —N=N—, —C=N—, —N=C— or —C(=N2)-;
Cyr- is selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or independently substituted with no less than 1 substituent Rcx;
wherein each Rwa, each Rwb, each Rza, each Rzb, each Rwx, each Rzx and each Rcx are each independently hydrogen, protium, deuterium, tritium, halogen, —NO2, —CN, —ORr, —SRr, —N(Rra)(Rrb), —C(O)Rr, —CO2Rr, —C(O)C(O)Rr, —C(O)CH2C(O)Rr, —S(O)Rr, —S(O)2Rr, —C(O)N(Rra)(Rrb), —SO2N(Rra)(Rrb), —OC(O)Rr, —N(R)SO2Rr, or a C1-6 aliphatic group optionally substituted with Rr;
wherein each Rr, each Rra and each Rrb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;
-Lb- represents a peptide residue consisting of 2 to 7 amino acids;
-Lc- is selected from the group consisting of:

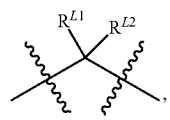

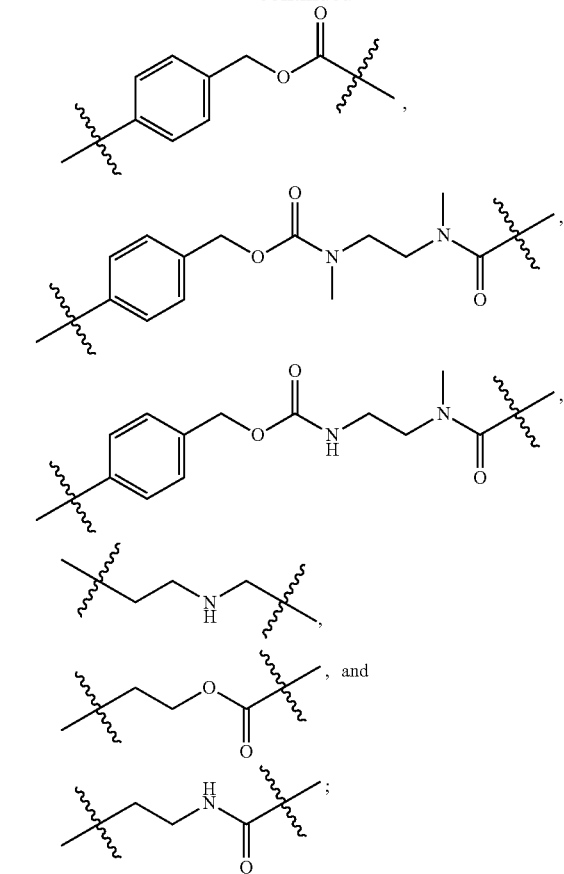

wherein RL1 and RL2 are each independently selected from the group consisting of: hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H and a C1-6 aliphatic group;
wherein R1 is selected from the group consisting of: —O—, —(R2)N—, —P(=O)(R2)- and —S—;
X is selected from the group consisting of: -L1-C(R1a)(R1b)-C(O)—, -L1-C(R1a)(R1b)-C(S)—, -L1-L0- and -L3-L2-;
L1 is —(C(R3a)(R3b))m—, wherein 0 or no less than 1 methylene unit of L1 is independently replaced by —C(O)—, —C(=S)—, —C(=NR4b)- or —C(=N2)-;
L0 is —C(R2a)(R2b)-, or L0 is —C(=S)—, —C(=NR4a)- or —C(=N2)-;
L2 is —C(R5a)(R5b)-, wherein 0 or 1 methylene unit of L2 is replaced by —N(R6)C(O)—, —C(O)N(R6)-, —C(O)—, —OC(O)—, —C(O)O—, —NR6-, —O—, —S—, —SO—, —SO$_2$—, —P(R6)-, —P(=O)(R6)-, —N(R6)SO2-, —SO2N(R6)-, —C(=S)—, —C(=NR6)-, —N=N—, —C=N—, —N=C— or —C(=N2)-;
L3 is —(C(R7a)(R7b))n-, wherein no less than 1 methylene unit of L3 is independently replaced by —N(R8)C(O)—, —C(O)N(R8)-, —OC(O)—, —C(O)O—, —NR8-, —O—, —S—, —SO—, —SO2-, —P(R8)-, —P(=O)(R8)-, —N(R8)SO2—, —SO2N(R8)-, —N=N—, —C=N— or —N=C—, and 0 or no less than 1 methylene unit of L3 is also independently replaced by —C(O)—, —C(=S)—, —C(=NR8)- or —C(=N2)-;
wherein each R1a, each R1b, each R2, each R2a, each R2b, each R3a, each R3b, each R4a, each R4b, each R5a, each R5b, each R6, each R7a, each R7b and each R8 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R;
wherein each R, each Ra and each Rb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;
m is selected from the group consisting of integers ≥0, and n is selected from the group consisting of integers ≥1;
when R1 is —O— or —HN— and X is -L1-CH2-C(O)—, no less than 1 methylene unit of L1 is independently replaced by —C(O)—, —C(=S)—, —C(=NR4b)- or —C(=N2)-, or each R3a and each R3b are not both hydrogen;
when R1 is —HN—, X is -L1-L0-, and L0 is —CH2—, no less than 1 methylene unit of L1 is independently replaced by —C(O)—, —C(=S)—, —C(=NR4b)- or —C(=N2)-, or each R3a and each R3b are not both hydrogen;
when R1 is —O—, X is -L3-C(O)—, and 1 methylene unit of L3 is replaced by —NR8, R8 is not —CH2-CH2-NH2;
when R1 is —NH—, and X is -L3-C(O)—, no less than 1 methylene unit of L3 is replaced by —N(R8)C(O)—, —OC(O)—, —C(O)O—, —S—, —SO—, —SO2-, —P(R8)-, —P(=O)(R8)-, —N(R8)SO2-, —SO2N(R8)-, —N=N—, —C=N— or —N=C—.

281. A compound or a tautomer, a mesomer, a racemate, an enantiomer or a diastereoisomer thereof, or a mixture thereof, or a pharmaceutically acceptable salt thereof, wherein the compound comprises a structure shown as formula (I-D):

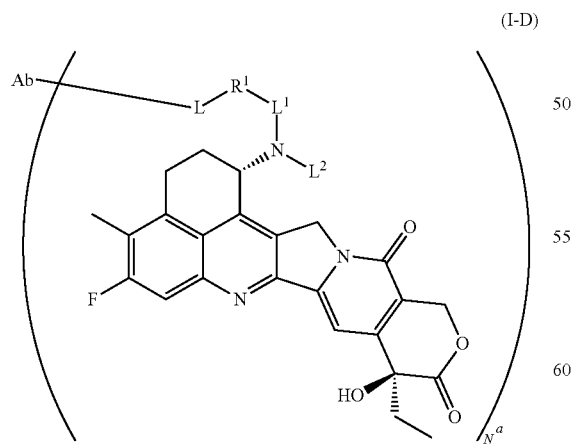

(I-D)

wherein, Ab is a ligand, and an average connection number Na is an integer or a decimal from 1 to 10;
L is -La-Lb-Lc-;

La- is selected from the group consisting of:

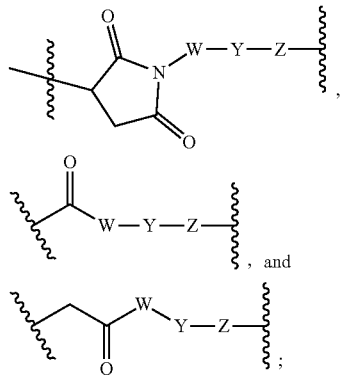

wherein W is —(C(Rwa)(Rwb))wn-, Y is —(OCH2CH2)yn-Oyp-, and Z is —(C(Rza)(Rzb))zn;
wherein wn is selected from the group consisting of integers ≥0, and
0 or no less than 1 methylene unit of W is independently replaced by -Cyr-, —N(Rwx)C(O)—, —C(O)N(Rwx)-, —C(O)—, —OC(O)—, —C(O)O—, —NRwx-, —O—, —S—, —SO—, —SO2-, —P(Rwx)-, —P(=O)(Rwx)-, —N(Rwx)SO2-, —SO2N(Rwx)-, —C(=S)—, —C(=NRwx)-, —N=N—, —C=N—, —N=C— or —C(=N2)-;
wherein yn is selected from the group consisting of integers ≥0, and yp is 0 or 1;
wherein zn is selected from the group consisting of integers ≥0, and
0 or no less than 1 methylene unit of Z is independently replaced by -Cyr-, —N(Rzx)C(O)—, —C(O)N(Rzx)-, —C(O)—, —OC(O)—, —C(O)O—, —NRzx-, —O—, —S—, —SO—, —SO2-, —P(Rzx)-, —P(=O)(Rzx)-, —N(Rzx)SO2-, —SO2N(Rzx)-, —C(=S)—, —C(=NRzx)-, —N=N—, —C=N—, —N=C— or —C(=N2)-;
Cyr- is selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or independently substituted with no less than 1 substituent Rcx;
wherein each Rwa, each Rwb, each Rza, each Rzb, each Rwx, each Rzx and each Rcx are each independently hydrogen, protium, deuterium, tritium, halogen, —NO2, —CN, —ORr, —SRr, —N(Rra)(Rrb), —C(O)Rr, —CO2Rr, —C(O)C(O)Rr, —C(O)CH2C(O)Rr, —S(O)Rr, —S(O)2Rr, —C(O)N(Rra)(Rrb), —SO2N(Rra)(Rrb), —OC(O)Rr, —N(R)SO2Rr, or a C1-6 aliphatic group optionally substituted with Rr;
wherein each Rr, each Rra and each Rrb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;
-Lb- represents a peptide residue consisting of 2 to 7 amino acids;

-Lc- is selected from the group consisting of:

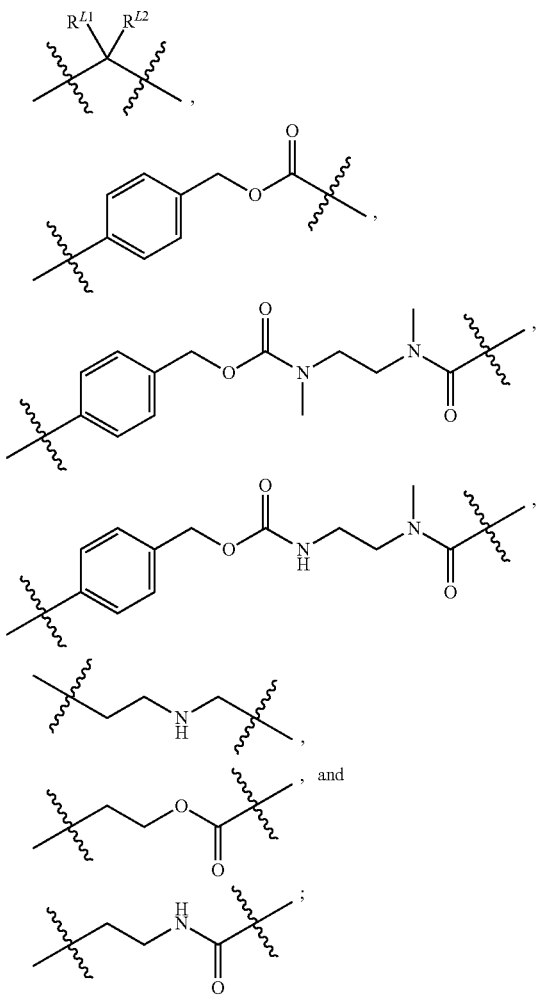

, and wherein RL1 and RL2 are each independently selected from the group consisting of: hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H and a C1-6 aliphatic group;

wherein R1 is selected from the group consisting of: —O—, —(R2)N—, —P(=O)(R2)- and —S—;

L2 is —(C(R3a)(R3b))m-R, wherein 0 or no less than 1 methylene unit of L2 is independently replaced by -Cy-, —N(R4)C(O)—, —C(O)N(R4)-, —C(O)—, —OC(O)—, —C(O)O—, —NR4-, —O—, —S—, —SO—, —SO2-, —P(R4)-, —P(=O)(R4)-, —N(R4)SO2-, —SO2N(R4)-, —C(=S)—, —C(=NR4)-, —N=N—, —C=N—, —N=C— or —C(=N2)-;

L1 is —(C(R5a)(R5b))n-, wherein 0 or no less than 1 methylene unit of L1 is independently replaced by -Cy-, —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N2)-;

-Cy- is selected from the group consisting of: 6-10 membered arylene, 5-8 membered heteroarylene, 3-10 membered heterocyclylene, and 3-10 membered saturated or partially unsaturated carbocyclylene, wherein -Cy- is unsubstituted or independently substituted with no less than 1 substituent R7;

wherein each R3a, each R3b, each R4, each R5a, each R5b and each R6 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R; or, R3a and R5a, R4 and R5a, R3a and R6 or R4 and R6 each independently optionally form a ring B together with an atom therebetween, wherein the ring B is selected from the group consisting of: 5-8 membered heteroarylene and 3-10 membered saturated or partially unsaturated heterocyclylene, and the ring B is unsubstituted or substituted with no less than 1 substituent R8;

wherein each R2, each R7 and each R8 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R;

wherein each R, each Ra and each Rb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

m and n are each independently selected from the group consisting of integers ≥1.

282. A compound or a tautomer, a mesomer, a racemate, an enantiomer or a diastereoisomer thereof, or a mixture thereof, or a pharmaceutically acceptable salt thereof, wherein the compound comprises a structure shown as formula (II-Dx) or formula (II-Dy):

(II-Dx)

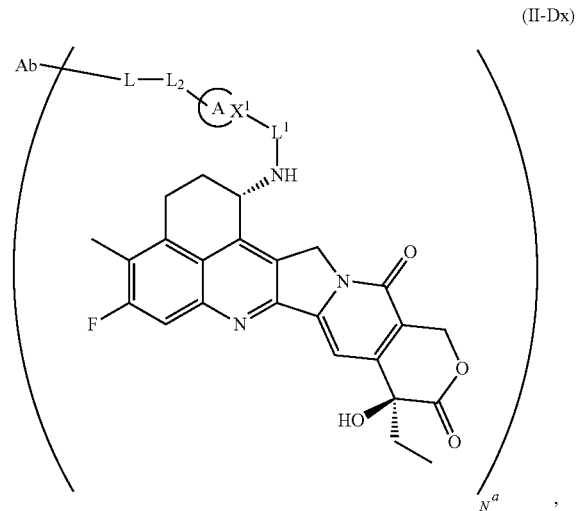

-continued (II-Dy)

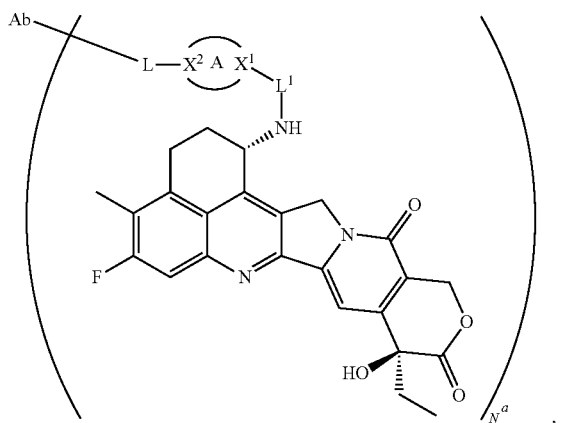

wherein, Ab is a ligand, and an average connection number Na is an integer or a decimal from 1 to 10;
L is -La-Lb-Lc-;
La- is selected from the group consisting of:

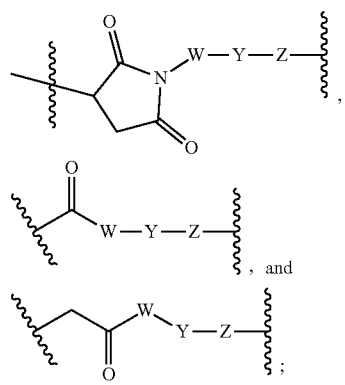

wherein W is —(C(Rwa)(Rwb))wn-, Y is —(OCH2CH2)yn-Oyp-, and Z is —(C(Rza)(Rzb))zn;
wherein wn is selected from the group consisting of integers ≥0, and
0 or no less than 1 methylene unit of W is independently replaced by -Cyr-, —N(Rwx)C(O)—, —C(O)N(Rwx)-, —C(O)—, —OC(O)—, —C(O)O—, —NRwx-, —O—, —S—, —SO—, —SO2-, —P(Rwx)-, —P(=O)(Rwx)-, —N(Rwx)SO2-, —SO2N(Rwx)-, —C(=S)—, —C(=NRwx)-, —N=N—, —C=N—, —N=C— or —C(=N2)-;
wherein yn is selected from the group consisting of integers ≥0, and yp is 0 or 1;
wherein zn is selected from the group consisting of integers ≥0, and
0 or no less than 1 methylene unit of Z is independently replaced by -Cyr-, —N(Rzx)C(O)—, —C(O)N(Rzx)-, —C(O)—, —OC(O)—, —C(O)O—, —NRzx-, —O—, —S—, —SO—, —SO2-, —P(Rzx)-, —P(=O)(Rzx)-, —N(Rzx)SO2-, —SO2N(Rzx)-, —C(=S)—, —C(=NRzx)-, —N=N—, —C=N—, —N=C— or —C(=N2)-;
Cyr- is selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or independently substituted with no less than 1 substituent Rcx;
wherein each Rwa, each Rwb, each Rza, each Rzb, each Rwx, each Rzx and each Rcx are each independently hydrogen, protium, deuterium, tritium, halogen, —NO2, —CN, —ORr, —SRr, —N(Rra)(Rrb), —C(O)Rr, —CO2Rr, —C(O)C(O)Rr, —C(O)CH2C(O)Rr, —S(O)Rr, —S(O)2Rr, —C(O)N(Rra)(Rrb), —SO2N(Rra)(Rrb), —OC(O)Rr, —N(R)SO2Rr, or a C1-6 aliphatic group optionally substituted with Rr;
wherein each Rr, each Rra and each Rrb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;
-Lb- represents a peptide residue consisting of 2 to 7 amino acids;
-Lc- is selected from the group consisting of:

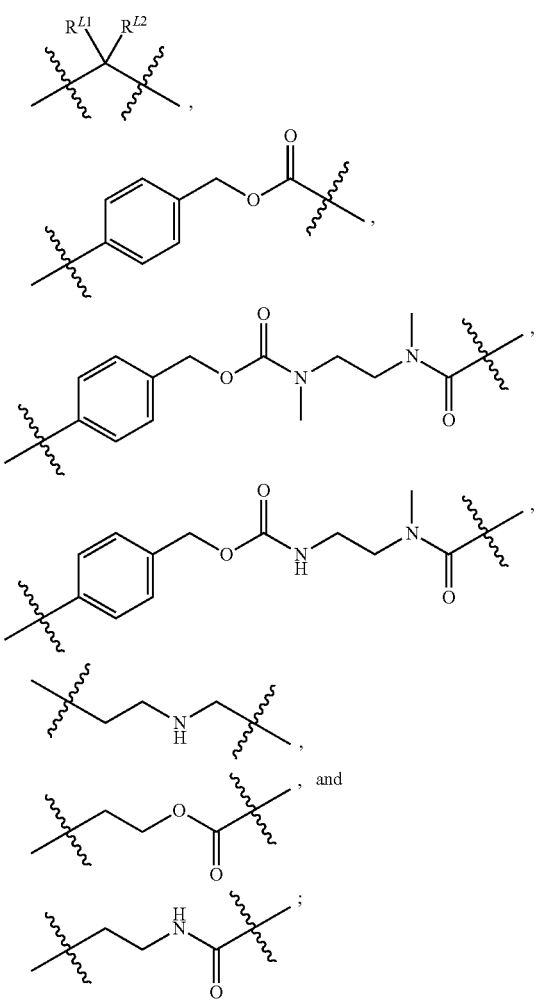

wherein RL1 and RL2 are each independently selected from the group consisting of: hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H and a C1-6 aliphatic group;

wherein, X1 is selected from the group consisting of: N, P, and saturated or unsaturated C; when X1 is saturated C, X1 is substituted with Rn;

when X1 is saturated C, ring A is selected from the group consisting of: 3-10 membered saturated or partially unsaturated heterocyclyl, and 3-10 membered saturated or partially unsaturated carbocyclyl, wherein ring A is unsubstituted or substituted with no less than 1 substituent R1a;

or, when X1 is unsaturated C, ring A is selected from the group consisting of: 6-10 membered aryl, 5-8 membered heteroaryl, 3-10 membered partially unsaturated heterocyclyl, and 3-10 membered partially unsaturated carbocyclyl, wherein ring A is unsubstituted or substituted with no less than 1 substituent R1b;

or, when X1 is N or P, ring A is selected from the group consisting of: 5-8 membered heteroaryl and 3-10 membered saturated or partially unsaturated heterocyclyl, wherein ring A is unsubstituted or substituted with no less than 1 substituent R1c;

when ring A is selected from the group consisting of: 6-10 membered aryl, 5-8 membered heteroaryl, and 3-10 membered saturated or partially unsaturated carbocyclyl, ring A is substituted with p L2, wherein L2 is not Rn;

or, when ring A is 3-10 membered saturated or partially unsaturated heterocyclyl, ring A is substituted with p L2, or ring A comprises q ring-forming heteroatom X2, and X2 is used for direct or indirect linking of a ligand;

X2 is selected from the group consisting of: N and P;

L2 is —R2-L3-, and R2 is used for direct or indirect linking of a ligand;

L3 is —(C(R3a)(R3b))m-, wherein 0 or no less than 1 methylene unit of L3 is independently replaced by —N(R4)C(O)—, —C(O)N(R4)-, —C(O)—, —OC(O)—, —C(O)O—, —NR4-, —O—, —S—, —SO—, —SO2-, —P(R4)-, —P(=O)(R4)-, —N(R4)SO2-, —SO2N(R4)-, —C(=S)—, —C(=NR4)-, —N=N—, —C=N—, —N=C— or —C(=N2)-;

R2 is selected from the group consisting of: —O—, —(R2a)N—, —S— and —P(=O)(R2a)-;

L1 is —(C(R5a)(R5b))n—, wherein 0 or no less than 1 methylene unit of L1 is independently replaced by —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N2)-;

wherein each R1a, each R1b, each R1c, each R2a, each R3a, each R3b, each R4, each R5a, each R5b, each R6 and each Rn are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R;

wherein each R, each Ra and each Rb are each independently hydrogen, protium, deuterium, tritium, halogen, —NO2, —CN, —OH, —SH, —NH$_2$, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

m and n are each independently selected from the group consisting of integers ≥0, and p and q are each independently selected from the group consisting of integers ≥1.

283. A compound or a tautomer, a mesomer, a racemate, an enantiomer or a diastereoisomer thereof, or a mixture thereof, or a pharmaceutically acceptable salt thereof, wherein the compound comprises a structure shown as formula (III-D):

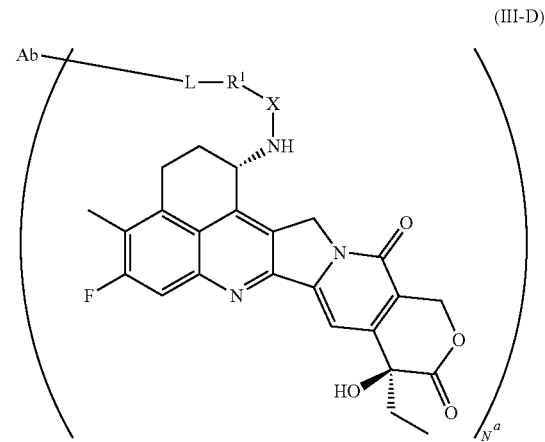

(III-D)

wherein, Ab is a ligand, and an average connection number Na is an integer or a decimal from 1 to 10;

L is -La-Lb-Lc-;

La- is selected from the group consisting of:

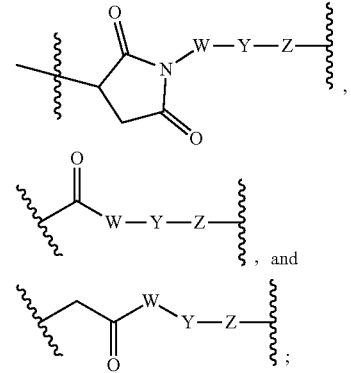

, and

;

wherein W is —(C(Rwa)(Rwb))wn-, Y is —(OCH2CH2)yn-Oyp, and Z is —(C(Rza)(Rzb))zn;

wherein wn is selected from the group consisting of integers ≥0, and 0 or no less than 1 methylene unit of W is independently replaced by -Cyr-, —N(Rwx)C(O)—, —C(O)N(Rwx)-, —C(O)—, —OC(O)—, —C(O)O—, —NRwx-, —O—, —S—, —SO—, —SO2-, —P(Rwx)-, —P(=O)(Rwx)-, —N(Rwx)SO2-, —SO2N(Rwx)-, —C(=S)—, —C(=NRwx)-, —N=N—, —C=N—, —N=C— or —C(=N2)-;

wherein yn is selected from the group consisting of integers ≥0, and yp is 0 or 1;

wherein zn is selected from the group consisting of integers ≥0, and 0 or no less than 1 methylene unit of Z is independently replaced by -Cyr-, —N(Rzx)C(O)—, —C(O)N(Rzx)-, —C(O)—, —OC(O)—, —C(O)O—, —NRzx-, —O—, —S—, —SO—, —SO2-, —P(Rzx)-, —P(=O)(Rzx)-, —N(Rzx)SO2-, —SO2N(Rzx)-, —C(=S)—, —C(=NRzx)-, —N=N—, —C=N—, —N=C— or —C(=N2)-;

Cyr- is selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or independently substituted with no less than 1 substituent Rcx;

wherein each Rwa, each Rwb, each Rza, each Rzb, each Rwx, each Rzx and each Rcx are each independently hydrogen, protium, deuterium, tritium, halogen, —NO2, —CN, —ORr, —SRr, —N(Rra)(Rrb), —C(O)Rr, —CO2Rr, —C(O)C(O)Rr, —C(O)CH2C(O)Rr, —S(O)Rr, —S(O)2Rr, —C(O)N(Rra)(Rrb), —SO2N(Rra)(Rrb), —OC(O)Rr, —N(R)SO2Rr, or a C1-6 aliphatic group optionally substituted with Rr;

wherein each Rr, each Rra and each Rrb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

-Lb- represents a peptide residue consisting of 2 to 7 amino acids;

-Lc- is selected from the group consisting of:

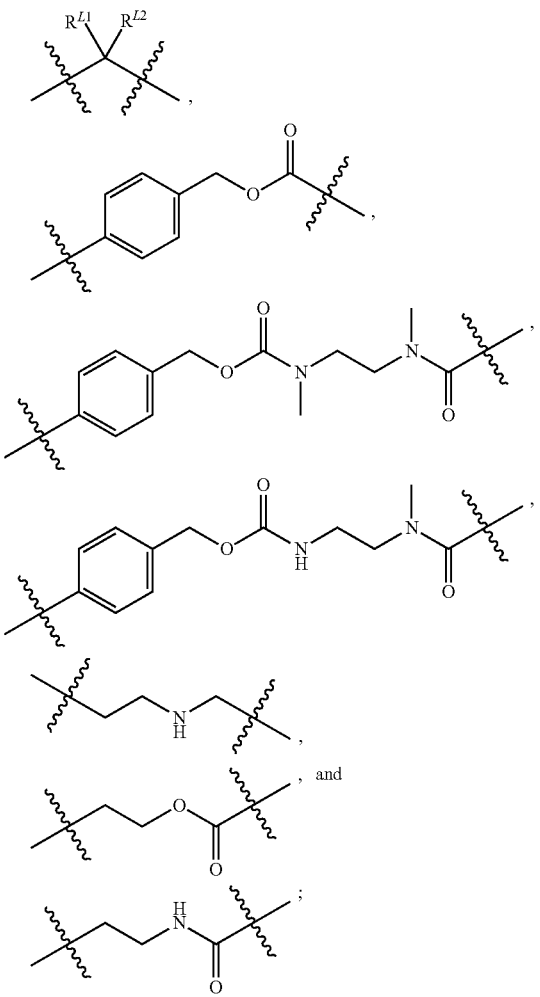

wherein RL1 and RL2 are each independently selected from the group consisting of: hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H and a C1-6 aliphatic group;

wherein R1 is selected from the group consisting of: —O—, —(R2)N—, —P(=O)(R2)- and —S—;

X is selected from the group consisting of: -L1-C(R1a)(R1b)-C(O)—, -L1-C(R1a)(R1b)-C(S)—, -L1-L0- and -L3-L2-;

L1 is —(C(R3a)(R3b))m-, wherein 0 or no less than 1 methylene unit of L1 is independently replaced by —C(O)—, —C(=S)—, —C(=NR4b)- or —C(=N2)-;

L0 is —C(R2a)(R2b)-, or L0 is —C(=S)—, —C(=NR4a)- or —C(=N2)-;

L2 is —C(R5a)(R5b)-, wherein 0 or 1 methylene unit of L2 is replaced by —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N2)-;

L3 is —(C(R7a)(R7b))n-, wherein no less than 1 methylene unit of L3 is independently replaced by —N(R8)C(O)—, —C(O)N(R8)-, —OC(O)—, —C(O)O—, —NR8-, —O—, —S—, —SO—, —SO2-, —P(R8)-, —P(=O)(R8)-, —N(R8)SO2-, —SO2N(R8)-, —N=N—, —C=N— or —N=C—, and 0 or no less than 1 methylene unit of L3 is also independently replaced by —C(O)—, —C(=S)—, —C(=NR8)- or —C(=N2)-;

wherein each R1a, each R1b, each R2, each R2a, each R2b, each R3a, each R3b, each R4a, each R4b, each R5a, each R5b, each R6, each R7a, each R7b and each R8 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R;

wherein each R, each Ra and each Rb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

m is selected from the group consisting of integers ≥0, and n is selected from the group consisting of integers ≥1;

when R1 is —O— or —HN— and X is -L1-CH2-C(O)—, no less than 1 methylene unit of L1 is independently replaced by —C(O)—, —C(=S)—, —C(=NR4b)- or —C(=N2)-, or each R3a and each R3b are not both hydrogen;

when R1 is —HN—, X is -L1-L0-, and L0 is —CH2-, no less than 1 methylene unit of L1 is independently replaced by —C(O)—, —C(=S)—, —C(=NR4b)- or —C(=N2)-, or each R3a and each R3b are not both hydrogen;

when R1 is —O—, X is -L3-C(O)—, and 1 methylene unit of L3 is replaced by —NR8, R8 is not —CH2-CH2-NH2;

when R1 is —NH—, and X is -L3-C(O)—, no less than 1 methylene unit of L3 is replaced by —N(R8)C(O)—, —OC(O)—, —C(O)O—, —S—, —SO—, —SO2-, —P(R8)-, —P(=O)(R8)-, —N(R8)SO2-, —SO2N(R8)-, —N=N—, —C=N— or —N=C—.

284. The compound or the tautomer, the mesomer, the racemate, the enantiomer or the diastereoisomer thereof, or the mixture thereof, or the pharmaceutically acceptable salt thereof according to any one of technical schemes 281-283, wherein the ligand Ab is an antibody or an antigen-binding fragment thereof.

285. The compound or the tautomer, the mesomer, the racemate, the enantiomer or the diastereoisomer thereof or the mixture thereof, or the pharmaceutically acceptable salt thereof according to any one of technical schemes 281-284, wherein the ligand Ab is selected from the group consisting of: a chimeric antibody, a humanized antibody and a fully humanized antibody.

286. The compound or the tautomer, the mesomer, the racemate, the enantiomer or the diastereoisomer thereof, or the mixture thereof, or the pharmaceutically acceptable salt thereof according to any one of technical schemes 281-285, wherein the ligand Ab targets the following: HER2, HER3, B7H3, TROP2, Claudin 18.2, CD30, CD33, CD70 or EGFR.

287. A compound of general formula (I-E) or a tautomer, a mesomer, a racemate, an enantiomer or a diastereoisomer thereof, or a mixture thereof, or a pharmaceutically acceptable salt thereof,

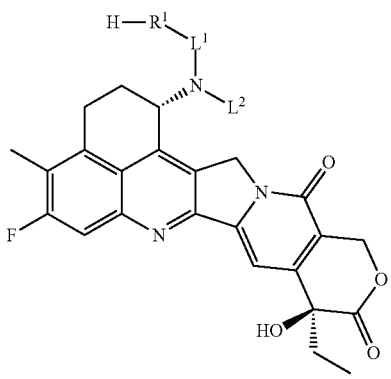

(I-E)

wherein R1 is selected from the group consisting of: —O—, —(R2)N—, —P(=O)(R2)- and —S—;
L2 is —(C(R3a)(R3b))m-R,
wherein 0 or no less than 1 methylene unit of L2 is independently replaced by -Cy-, —N(R4)C(O)—, —C(O)N(R4)-, —C(O)—, —OC(O)—, —C(O)O—, —NR4-, —O—, —S—, —SO—, —SO2-, —P(R4)-, —P(=O)(R4)-, —N(R4)SO2-, —SO2N(R4)-, —C(=S)—, —C(=NR4)-, —N=N—, —C=N—, —N=C— or —C(=N2)-;
L1 is —(C(R5a)(R5b))n-,
wherein 0 or no less than 1 methylene unit of L1 is independently replaced by -Cy-, —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N2)-;

-Cy- is selected from the group consisting of: 6-10 membered arylene, 5-8 membered heteroarylene, 3-10 membered heterocyclylene, and 3-10 membered saturated or partially unsaturated carbocyclylene, wherein -Cy- is unsubstituted or independently substituted with no less than 1 substituent R7;

wherein each R3a, each R3b, each R4, each R5a, each R5b and each R6 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R; or, R3a and R5a, R4 and R5a, R3a and R6 or R4 and R6 each independently optionally form a ring B together with an atom therebetween, wherein the ring B is selected from the group consisting of: 5-8 membered heteroarylene and 3-10 membered saturated or partially unsaturated heterocyclylene, and the ring B is unsubstituted or independently substituted with no less than 1 substituent R8;

wherein each R2, each R7 and each R8 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R;

wherein each R, each Ra and each Rb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

m and n are each independently selected from the group consisting of integers ≥1.

288. A compound of general formula (II-Ex) or (II-Ey), or a tautomer, a mesomer, a racemate, an enantiomer or a diastereoisomer thereof, or a mixture thereof, or a pharmaceutically acceptable salt thereof,

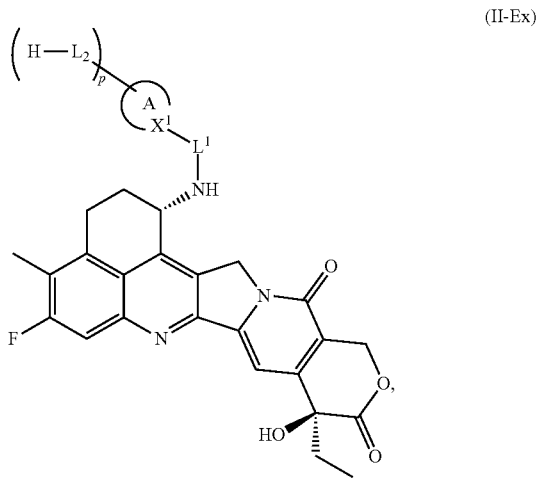

(II-Ex)

-continued (II-Ey)

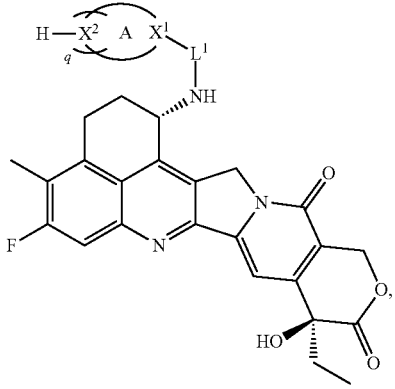

wherein, X1 is selected from the group consisting of: N, P, and saturated or unsaturated C; when X1 is saturated C, X1 is substituted with Rn;
when X1 is saturated C, ring A is selected from the group consisting of: 3-10 membered saturated or partially unsaturated heterocyclyl, and 3-10 membered saturated or partially unsaturated carbocyclyl, wherein ring A is unsubstituted or independently substituted with no less than 1 substituent R1a;
or, when X1 is unsaturated C, ring A is selected from the group consisting of: 6-10 membered aryl, 5-8 membered heteroaryl, 3-10 membered partially unsaturated heterocyclyl, and 3-10 membered partially unsaturated carbocyclyl, wherein ring A is unsubstituted or independently substituted with no less than 1 substituent R1b;
or, when X1 is N or P, ring A is selected from the group consisting of: 5-8 membered heteroaryl and 3-10 membered saturated or partially unsaturated heterocyclyl, wherein ring A is unsubstituted or independently substituted with no less than 1 substituent R1c;
when ring A is selected from the group consisting of: 6-10 membered aryl, 5-8 membered heteroaryl, and 3-10 membered saturated or partially unsaturated carbocyclyl, ring A is substituted with p L2, wherein L2 is not Rn;
or, when ring A is 3-10 membered saturated or partially unsaturated heterocyclyl, ring A is substituted with p L2, or ring A comprises q ring-forming heteroatom X2, and X2 is used for direct or indirect linking of a ligand;
X2 is selected from the group consisting of: N and P;
L2 is —R2-L3-, and R2 is used for direct or indirect linking of a ligand;
L3 is —(C(R3a)(R3b))m-, wherein 0 or no less than 1 methylene unit of L3 is independently replaced by —N(R4)C(O)—, —C(O)N(R4)-, —C(O)—, —OC(O)—, —C(O)O—, —NR4-, —O—, —S—, —SO—, —SO2-, —P(R4)-, —P(=O)(R4)-, —N(R4)SO2-, —SO2N(R4)-, —C(=S)—, —C(=NR4)-, —N=N—, —C=N—, —N=C— or —C(=N2)-;
R2 is selected from the group consisting of: —O—, —(R2a)N—, —S— and —P(=O)(R2a)-;
L1 is —(C(R5a)(R5b))n-, wherein 0 or no less than 1 methylene unit of L1 is independently replaced by —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N2)-;

wherein each R1a, each R1b, each R1c, each R2a, each R3a, each R3b, each R4, each R5a, each R5b, each R6 and each Rn are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R;
wherein each R, each Ra and each Rb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;
m and n are each independently selected from the group consisting of integers ≥0, and p and q are each independently selected from the group consisting of integers ≥1.

289. A compound of general formula (III-E) or a tautomer, a mesomer, a racemate, an enantiomer or a diastereoisomer thereof, or a mixture thereof, or a pharmaceutically acceptable salt thereof,

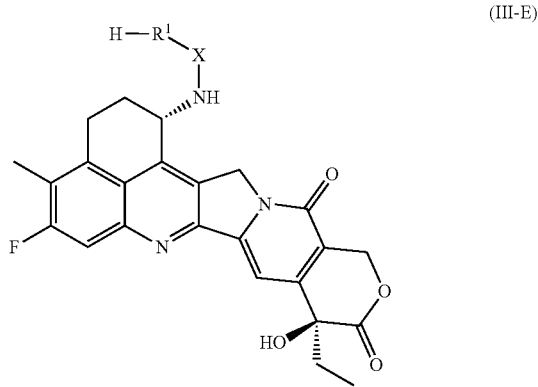

(III-E)

wherein R1 is selected from the group consisting of: —O—, —(R2)N—, —P(=O)(R2)- and —S—;
X is selected from the group consisting of: -L1-C(R1a)(R1b)-C(O)—, -L1-C(R1a)(R1b)-C(S)—, -L1-L0- and -L3-L2-;
L1 is —(C(R3a)(R3b))m-, wherein 0 or no less than 1 methylene unit of L1 is independently replaced by —C(O)—, —C(=S)—, —C(=NR4b)- or —C(=N2)-;
L0 is —C(R2a)(R2b)-, or L0 is —C(=S)—, —C(=NR4a)- or —C(=N2)-;
L2 is —C(R5a)(R5b)-, wherein 0 or 1 methylene unit of L2 is replaced by —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N2)-;
L3 is —(C(R7a)(R7b))n-, wherein no less than 1 methylene unit of L3 is independently replaced by —N(R8)C(O)—, —C(O)N(R8)-, —OC(O)—, —C(O)O—, —NR8-, —O—, —S—, —SO—, —SO2-, —P(R8)-, —P(=O)(R8)-, —N(R8)SO2-, —SO2N(R8)-, —N=N—, —C=N— or —N=C—, and 0 or no less than 1 methylene unit of L3 is also independently replaced by —C(O)—, —C(=S)—, —C(=NR8)- or —C(=N2)-;

wherein each R1a, each R1b, each R2, each R2a, each R2b, each R3a, each R3b, each R4a, each R4b, each R5a, each R5b, each R6, each R7a, each R7b and each R8 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R;

wherein each R, each Ra and each Rb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

m is selected from the group consisting of integers ≥0, and n is selected from the group consisting of integers ≥1;

when R1 is —O— or —HN— and X is -L1-CH2-C(O)—, no less than 1 methylene unit of L1 is independently replaced by —C(O)—, —C(=S)—, —C(=NR4b)- or —C(=N2)-, or each R3a and each R3b are not both hydrogen;

when R1 is —HN—, X is -L1-L0-, and L0 is —CH2-, no less than 1 methylene unit of L1 is independently replaced by —C(O)—, —C(=S)—, —C(=NR4b)- or —C(=N2)-, or each R3a and each R3b are not both hydrogen;

when R1 is —O—, X is -L3-C(O)—, and 1 methylene unit of L3 is replaced by —NR8, R8 is not —CH2-CH2-NH$_2$;

when R1 is —NH—, and X is -L3-C(O)—, no less than 1 methylene unit of L3 is replaced by —N(R8)C(O)—, —OC(O)—, —C(O)O—, —S—, —SO—, —SO$_2$—, —P(R8)-, —P(=O)(R8)-, —N(R8)SO2-, —SO2N(R8)-, —N=N—, —C=N— or —N=C—.

290. A compound of general formula (I-F) or a tautomer, a mesomer, a racemate, an enantiomer or a diastereoisomer thereof, or a mixture thereof, or a pharmaceutically acceptable salt thereof,

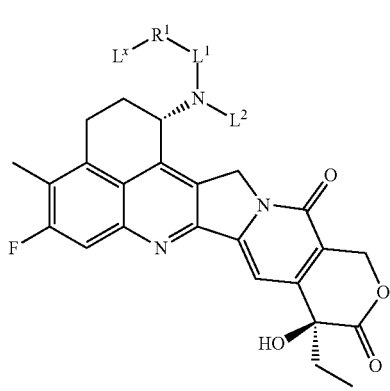
(I-F)

wherein, Lx is Lax-Lb-Lc-;

Lax- is selected from the group consisting of:

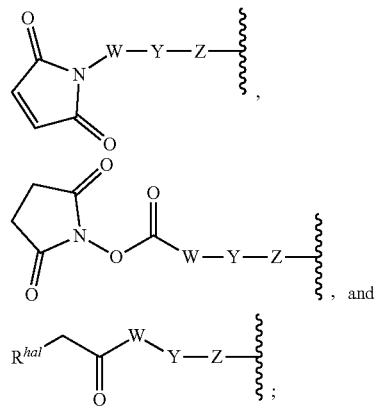

wherein Rhal is iodine or bromine;

wherein W is —(C(Rwa)(Rwb))wn-, Y is —(OCH2CH2)yn-Oyp-, and Z is —(C(Rza)(Rzb))zn;

wherein wn is selected from the group consisting of integers ≥0, and 0 or no less than 1 methylene unit of W is independently replaced by -Cyr-, —N(Rwx)C(O)—, —C(O)N(Rwx)-, —C(O)—, —OC(O)—, —C(O)O—, —NRwx-, —O—, —S—, —SO—, —SO2-, —P(Rwx)-, —P(=O)(Rwx)-, —N(Rwx)SO2-, —SO2N(Rwx)-, —C(=S)—, —C(=NRwx)-, —N=N—, —C=N—, —N=C— or —C(=N2)-;

wherein yn is selected from the group consisting of integers ≥0, and yp is 0 or 1;

wherein zn is selected from the group consisting of integers ≥0, and 0 or no less than 1 methylene unit of Z is independently replaced by -Cyr-, —N(Rzx)C(O)—, —C(O)N(Rzx)-, —C(O)—, —OC(O)—, —C(O)O—, —NRzx-, —O—, —S—, —SO—, —SO2-, —P(Rzx)-, —P(=O)(Rzx)-, —N(Rzx)SO2-, —SO2N(Rzx)-, —C(=S)—, —C(=NRzx)-, —N=N—, —C=N—, —N=C— or —C(=N2)-;

Cyr- is selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or independently substituted with no less than 1 substituent Rcx;

wherein each Rwa, each Rwb, each Rza, each Rzb, each Rwx, each Rzx and each Rcx are each independently hydrogen, protium, deuterium, tritium, halogen, —NO2, —CN, —ORr, —SRr, —N(Rra)(Rrb), —C(O)Rr, —CO2Rr, —C(O)C(O)Rr, —C(O)CH2C(O)Rr, —S(O)Rr, —S(O)2Rr, —C(O)N(Rra)(Rrb), —SO2N(Rra)(Rrb), —OC(O)Rr, —N(R)SO2Rr, or a C1-6 aliphatic group optionally substituted with Rr;

wherein each Rr, each Rra and each Rrb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

-Lb- represents a peptide residue consisting of 2 to 7 amino acids;

-Lc- is selected from the group consisting of:

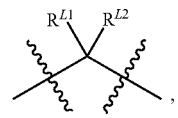,

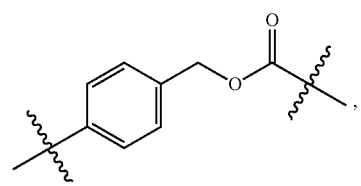,

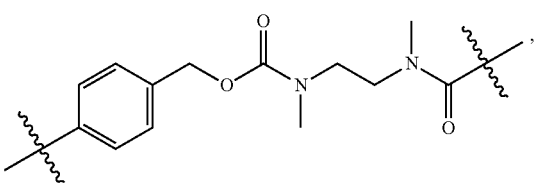,

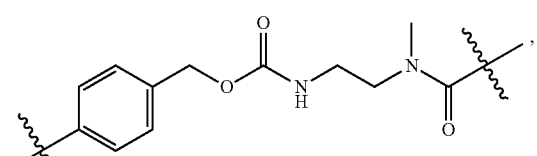,

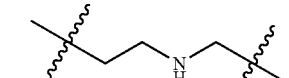,

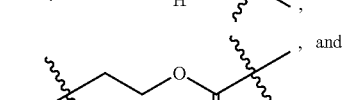, and

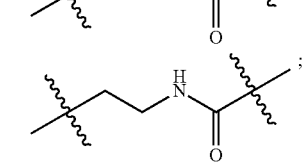;

wherein RL1 and RL2 are each independently selected from the group consisting of: hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H and a C1-6 aliphatic group;

wherein R1 is selected from the group consisting of: —O—, —(R2)N—, —P(=O)(R2)- and —S—;

L2 is —(C(R3a)(R3b))m-R, wherein 0 or no less than 1 methylene unit of L2 is independently replaced by -Cy-, —N(R4)C(O)—, —C(O)N(R4)-, —C(O)—, —OC(O)—, —C(O)O—, —NR4-, —O—, —S—, —SO—, —SO2-, —P(R4)-, —P(=O)(R4)-, —N(R4)SO2-, —SO2N(R4)-, —C(=S)—, —C(=NR4)-, —N=N—, —C=N—, —N=C— or —C(=N2)-;

L1 is —(C(R5a)(R5b))n-, wherein 0 or no less than 1 methylene unit of L1 is independently replaced by -Cy-, —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N2)-;

-Cy- is selected from the group consisting of: 6-10 membered arylene, 5-8 membered heteroarylene, 3-10 membered heterocyclylene, and 3-10 membered saturated or partially unsaturated carbocyclylene, wherein -Cy- is unsubstituted or independently substituted with no less than 1 substituent R7;

wherein each R3a, each R3b, each R4, each R5a, each R5b and each R6 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R; or, R3a and R5a, R4 and R5a, R3a and R6 or R4 and R6 each independently optionally form a ring B together with an atom therebetween, wherein the ring B is selected from the group consisting of: 5-8 membered heteroarylene and 3-10 membered saturated or partially unsaturated heterocyclylene, and the ring B is unsubstituted or substituted with no less than 1 substituent R8;

wherein each R2, each R7 and each R8 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R;

wherein each R, each Ra and each Rb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

m and n are each independently selected from the group consisting of integers ≥1.

291. A compound of general formula (II-Fx) or (II-Fy), or a tautomer, a mesomer, a racemate, an enantiomer or a diastereoisomer thereof, or a mixture thereof, or a pharmaceutically acceptable salt thereof, (II-Fx)

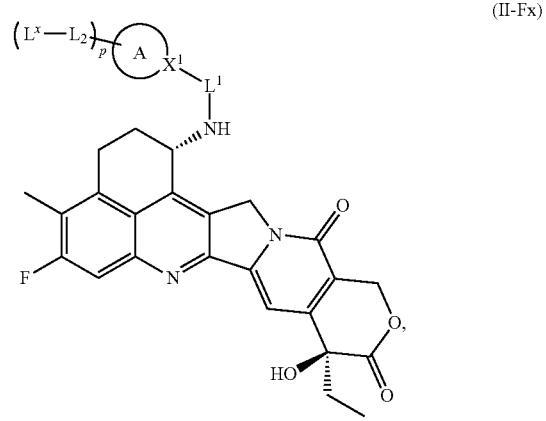

(II-Fy)

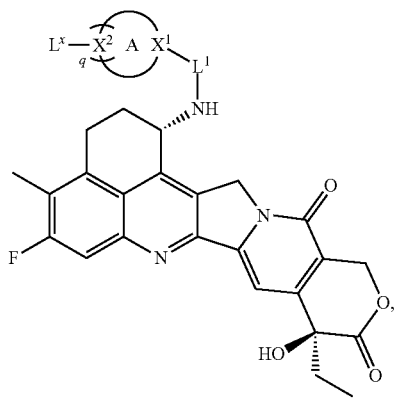

wherein, Lx is Lax-Lb-Lc-;
Lax- is selected from the group consisting of:

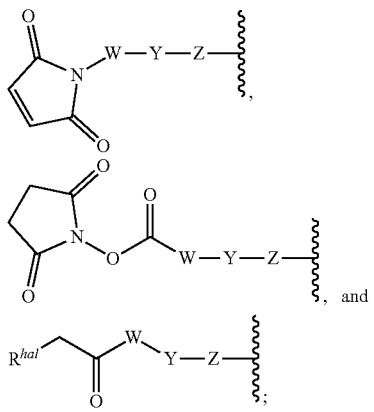

wherein Rhal is iodine or bromine;
wherein W is —(C(Rwa)(Rwb))wn-, Y is —(OCH2CH2)yn-Oyp-, and Z is —(C(Rza)(Rzb))zn;
wherein wn is selected from the group consisting of integers ≥0, and
0 or no less than 1 methylene unit of W is independently replaced by -Cyr-, —N(Rwx)C(O)—, —C(O)N(Rwx)-, —C(O)—, —OC(O)—, —C(O)O—, —NRwx-, —O—, —S—, —SO—, —SO2-, —P(Rwx)-, —P(=O)(Rwx)-, —N(Rwx)SO2-, —SO2N(Rwx)-, —C(=S)—, —C(=NRwx)-, —N=N—, —C=N—, —N=C— or —C(=N2)-;
wherein yn is selected from the group consisting of integers ≥0, and yp is 0 or 1;
wherein zn is selected from the group consisting of integers ≥0, and
0 or no less than 1 methylene unit of Z is independently replaced by -Cyr-, —N(Rzx)C(O)—, —C(O)N(Rzx)-, —C(O)—, —OC(O)—, —C(O)O—, —NRzx-, —O—, —S—, —SO—, —SO2-, —P(Rzx)-, —P(=O)(Rzx)-, —N(Rzx)SO2-, —SO2N(Rzx)-, —C(=S)—, —C(=NRzx)-, —N=N—, —C=N—, —N=C— or —C(=N2)-;
Cyr- is selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or independently substituted with no less than 1 substituent Rcx;
wherein each Rwa, each Rwb, each Rza, each Rzb, each Rwx, each Rzx and each Rcx are each independently hydrogen, protium, deuterium, tritium, halogen, —NO2, —CN, —ORr, —SRr, —N(Rra)(Rrb), —C(O)Rr, —CO2Rr, —C(O)C(O)Rr, —C(O)CH2C(O)Rr, —S(O)Rr, —S(O)2Rr, —C(O)N(Rra)(Rrb), —SO2N(Rra)(Rrb), —OC(O)Rr, —N(R)SO2Rr, or a C1-6 aliphatic group optionally substituted with Rr;
wherein each Rr, each Rra and each Rrb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;
-Lb- represents a peptide residue consisting of 2 to 7 amino acids;
-Lc- is selected from the group consisting of:

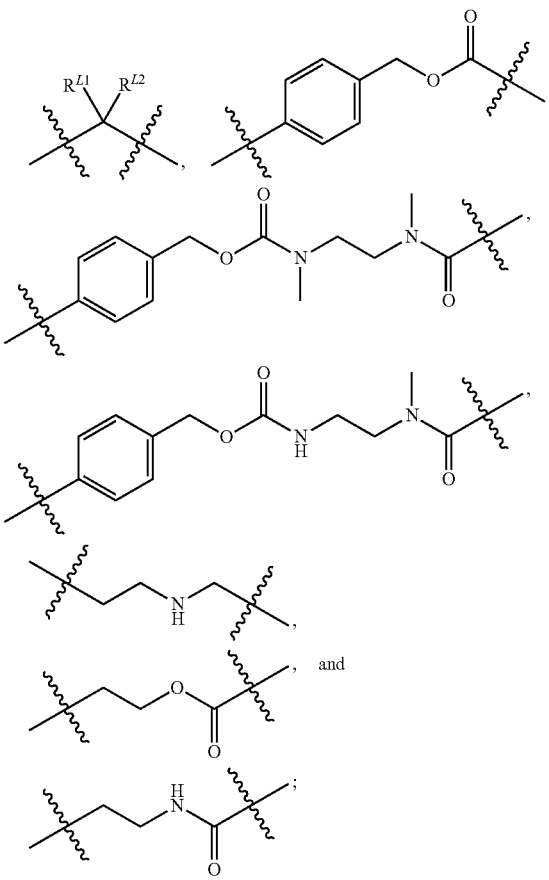

wherein RL1 and RL2 are each independently selected from the group consisting of hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H and a C1-6 aliphatic group;
wherein, X1 is selected from the group consisting of: N, P, and saturated or unsaturated C; when X1 is saturated C, X1 is substituted with Rn;
when X1 is saturated C, ring A is selected from the group consisting of: 3-10 membered saturated or partially unsaturated heterocyclyl, and 3-10 membered saturated or partially unsaturated carbocyclyl, wherein ring A is unsubstituted or substituted with no less than 1 substituent R1a;

or, when X1 is unsaturated C, ring A is selected from the group consisting of: 6-10 membered aryl, 5-8 membered heteroaryl, 3-10 membered partially unsaturated heterocyclyl, and 3-10 membered partially unsaturated carbocyclyl, wherein ring A is unsubstituted or substituted with no less than 1 substituent R1b;

or, when X1 is N or P, ring A is selected from the group consisting of: 5-8 membered heteroaryl and 3-10 membered saturated or partially unsaturated heterocyclyl, wherein ring A is unsubstituted or substituted with no less than 1 substituent R1c;

when ring A is selected from the group consisting of: 6-10 membered aryl, 5-8 membered heteroaryl, and 3-10 membered saturated or partially unsaturated carbocyclyl, ring A is substituted with p L2, wherein L2 is not Rn;

or, when ring A is 3-10 membered saturated or partially unsaturated heterocyclyl, ring A is substituted with p L2, or ring A comprises q ring-forming heteroatom X2, and X2 is used for direct or indirect linking of a ligand;

X2 is selected from the group consisting of: N and P;

L2 is —R2-L3-, and R2 is used for direct or indirect linking of a ligand;

L3 is —(C(R3a)(R3b))m-, wherein 0 or no less than 1 methylene unit of L3 is independently replaced by —N(R4)C(O)—, —C(O)N(R4)-, —C(O)—, —OC(O)—, —C(O)O—, —NR4-, —O—, —S—, —SO—, —SO2-, —P(R4)-, —P(=O)(R4)-, —N(R4)SO2-, —SO2N(R4)-, —C(=S)—, —C(=NR4)-, —N=N—, —C=N—, —N=C— or —C(=N2)-;

R2 is selected from the group consisting of: —O—, —(R2a)N—, —S— and —P(=O)(R2a)-;

L1 is —(C(R5a)(R5b))n-, wherein 0 or no less than 1 methylene unit of L1 is independently replaced by —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N2)-;

wherein each R1a, each R1b, each R1c, each R2a, each R3a, each R3b, each R4, each R5a, each R5b, each R6 and each Rn are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R;

wherein each R, each Ra and each Rb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

m and n are each independently selected from the group consisting of integers ≥0, and p and q are each independently selected from the group consisting of integers ≥1.

292. A compound of general formula (III-F) or a tautomer, a mesomer, a racemate, an enantiomer or a diastereoisomer thereof, or a mixture thereof, or a pharmaceutically acceptable salt thereof,

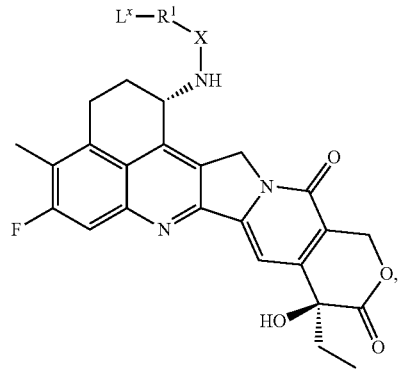

(III-F)

wherein, Lx is Lax-Lb-Lc-;
Lax- is selected from the group consisting of:

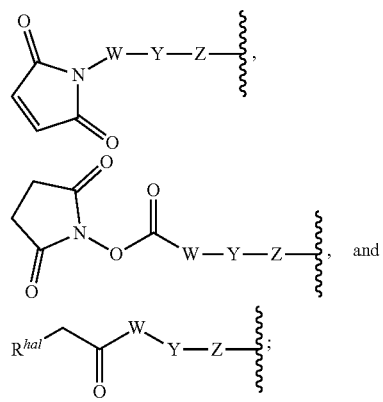

wherein Rhal is iodine or bromine;
wherein W is —(C(Rwa)(Rwb))wn-, Y is —(OCH2CH2)yn-Oyp, and Z is —(C(Rza)(Rzb))zn;
wherein wn is selected from the group consisting of integers ≥0, and 0 or no less than 1 methylene unit of W is independently replaced by -Cyr-, —N(Rwx)C(O)—, —C(O)N(Rwx)-, —C(O)—, —OC(O)—, —C(O)O—, —NRwx-, —O—, —S—, —SO—, —SO2-, —P(Rwx)-, —P(=O)(Rwx)-, —N(Rwx)SO2-, —SO2N(Rwx)-, —C(=S)—, —C(=NRwx)-, —N=N—, —C=N—, —N=C— or —C(=N2)-;

wherein yn is selected from the group consisting of integers ≥0, and yp is 0 or 1;

wherein zn is selected from the group consisting of integers ≥0, and 0 or no less than 1 methylene unit of Z is independently replaced by -Cyr-, —N(Rzx)C(O)—, —C(O)N(Rzx)-, —C(O)—, —OC(O)—, —C(O)O—, —NRzx-, —O—, —S—, —SO—, —SO2-, —P(Rzx)-, —P(=O)(Rzx)-, —N(Rzx)SO2-, —SO2N(Rzx)-, —C(=S)—, —C(=NRzx)-, —N=N—, —C=N—, —N=C— or —C(=N2)-;

Cyr- is selected from the group consisting of: 6-10 membered arylene, 5-8 membered heteroarylene, 3-10 membered heterocyclylene, and 3-10 membered saturated or partially unsaturated carbocyclylene, wherein -Cyr- is unsubstituted or independently substituted with no less than 1 substituent Rcx;

wherein each Rwa, each Rwb, each Rza, each Rzb, each Rwx, each Rzx and each Rcx are each independently hydrogen, protium, deuterium, tritium, halogen, —NO2, —CN, —ORr, —SRr, —N(Rra)(Rrb), —C(O)Rr, —CO2Rr, —C(O)C(O)Rr, —C(O)CH2C(O)Rr, —S(O)Rr, —S(O)2Rr, —C(O)N(Rra)(Rrb), —SO2N(Rra)(Rrb), —OC(O)Rr, —N(R)SO2Rr, or a C1-6 aliphatic group optionally substituted with Rr;

wherein each Rr, each Rra and each Rrb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

-Lb- represents a peptide residue consisting of 2 to 7 amino acids;

-Lc- is selected from the group consisting of:

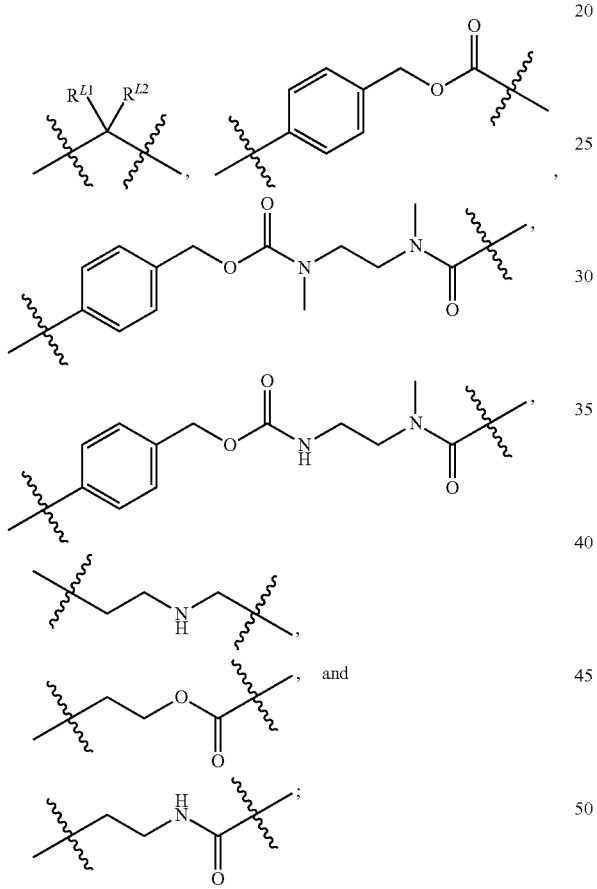

wherein RL1 and RL2 are each independently selected from the group consisting of: hydrogen, protium, deuterium, tritium, halogen, —NO2, —CN, —OH, —SH, —NH$_2$, —C(O)H, —CO2H, —C(O)C(O)H, —C(O)CH2C(O)H, —S(O)H, —S(O)2H, —C(O)NH2, —SO2NH2, —OC(O)H, —N(H)SO2H and a C1-6 aliphatic group;

wherein R1 is selected from the group consisting of: —O—, —(R2)N—, —P(=O)(R2)- and —S—;

X is selected from the group consisting of: -L1-C(R1a)(R1b)-C(O)—, -L1-C(R1a)(R1b)-C(S)—, -L1-L0- and -L3-L2-;

L1 is —(C(R3a)(R3b))m-, wherein 0 or no less than 1 methylene unit of L1 is independently replaced by —C(O)—, —C(=S)—, —C(=NR4b)- or —C(=N2)-;

L0 is —C(R2a)(R2b)-, or L0 is —C(=S)—, —C(=NR4a)- or —C(=N2)-;

L2 is —C(R5a)(R5b)-, wherein 0 or 1 methylene unit of L2 is replaced by —N(R6)C(O)—, —C(O)N(R6)-, —C(O)—, —OC(O)—, —C(O)O—, —NR6-, —O—, —S—, —SO—, —SO2-, —P(R6)-, —P(=O)(R6)-, —N(R6)SO2-, —SO2N(R6)-, —C(=S)—, —C(=NR6)-, —N=N—, —C=N—, —N=C— or —C(=N2)-;

L3 is —(C(R7a)(R7b))n-, wherein no less than 1 methylene unit of L3 is independently replaced by —N(R8)C(O)—, —C(O)N(R8)-, —OC(O)—, —C(O)O—, —NR8-, —O—, —S—, —SO—, —SO2-, —P(R8)-, —P(=O)(R8)-, —N(R8)SO$_2$—, —SO2N(R8)-, —N=N—, —C=N— or —N=C—, and 0 or no less than 1 methylene unit of L3 is also independently replaced by —C(O)—, —C(=S)—, —C(=NR8)- or —C(=N2)-;

wherein each R1a, each R1b, each R2, each R2a, each R2b, each R3a, each R3b, each R4a, each R4b, each R5a, each R5b, each R6, each R7a, each R7b and each R8 are each independently hydrogen, protium, deuterium, tritium, halogen, —NO2, —CN, —OR, —SR, —N(Ra)(Rb), —C(O)R, —CO2R, —C(O)C(O)R, —C(O)CH2C(O)R, —S(O)R, —S(O)2R, —C(O)N(Ra)(Rb), —SO2N(Ra)(Rb), —OC(O)R, —N(R)SO2R, or a C1-6 aliphatic group optionally substituted with R;

wherein each R, each Ra and each Rb are each independently hydrogen, protium, deuterium, tritium, halogen, —NO2, —CN, —OH, —SH, —NH2, —C(O)H, —CO2H, —C(O)C(O)H, —C(O)CH2C(O)H, —S(O)H, —S(O)2H, —C(O)NH2, —SO2NH2, —OC(O)H, —N(H)SO2H or a C1-6 aliphatic group;

m is selected from the group consisting of integers ≥0, and n is selected from the group consisting of integers ≥1;

when R1 is —O— or —HN— and X is -L1-CH2-C(O)—, no less than 1 methylene unit of L1 is independently replaced by —C(O)—, —C(=S)—, —C(=NR4b)- or —C(=N2)-, or each R3a and each R3b are not both hydrogen;

when R1 is —HN—, X is -L1-L0-, and L0 is —CH2-, no less than 1 methylene unit of L1 is independently replaced by —C(O)—, —C(=S)—, —C(=NR4b)- or —C(=N2)-, or each R3a and each R3b are not both hydrogen;

when R1 is —O—, X is -L3-C(O)—, and 1 methylene unit of L3 is replaced by —NR8, R8 is not —CH2-CH2-NH$_2$;

when R1 is —NH—, and X is -L3-C(O)—, no less than 1 methylene unit of L3 is replaced by —N(R8)C(O)—, —OC(O)—, —C(O)O—, —S—, —SO—, —SO2-, —P(R8)-, —P(=O)(R8)-, —N(R8)SO2-, —SO2N(R8)-, —N=N—, —C=N— or —N=C—.

293. The compound or the tautomer, the mesomer, the racemate, the enantiomer or the diastereoisomer thereof, or the mixture thereof, or the pharmaceutically acceptable salt thereof according to any one of technical schemes 290-292, wherein Lax- is

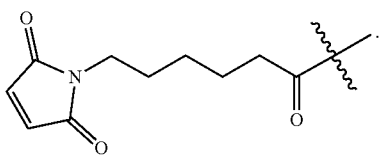

294. The compound or the tautomer, the mesomer, the racemate, the enantiomer or the diastereoisomer thereof, or the mixture thereof, or the pharmaceutically acceptable salt thereof according to any one of technical schemes 290-293, wherein Lax-Lb-Lc- is selected from the group consisting of:

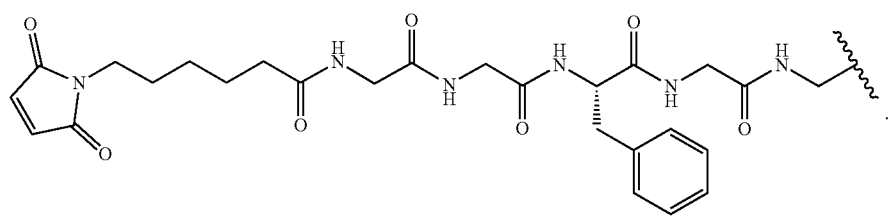 [SMILES: *CNC(=O)CNC(=O)[C@H](Cc1ccccc1)NC(=O)CNC(=O)CNC(=O)CCCCCN1C(=O)C=CC1=O]

295. The compound of formula (I-B) according to any one of technical schemes 266 and 269-277, the compound of formula (I-C) according to technical scheme 278, the compound of formula (I-D) according to any one of technical schemes 281 and 284-286, the compound of formula (I-E) according to technical scheme 287 or the compound of formula (I-F) according to any one of technical schemes 290 and 293-294, or the tautomer, the mesomer, the racemate, the enantiomer or the diastereoisomer thereof, or the mixture thereof, or the pharmaceutically acceptable salt thereof, wherein in a structure

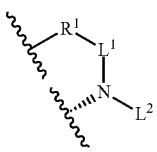

comprised therein, L1, L2 and R1 are L1, L2 and R1, respectively, of the compound according to any one of technical schemes 1-93.

296. The compound of formula (II-Bx) or (II-By) according to any one of technical schemes 267 and 269-277, the compound of formula (II-Cx) or (II-Cy) according to technical scheme 279, the compound of formula (II-Dx) or (II-Dy) according to any one of technical schemes 282 and 284-286, the compound of formula (II-Ex) or (II-Ey) according to technical scheme 288, or the compound of formula (II-Fx) or (II-Fy) according to any one of technical schemes 291 and 293-294, or the tautomer, the mesomer, the racemate, the enantiomer or the diastereoisomer thereof, or the mixture thereof, or the pharmaceutically acceptable salt thereof, wherein in a structure

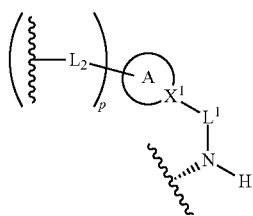

comprised therein, L1, X1, A and L2 are L1, X1, A and L2, respectively, of the compound according to any one of technical schemes 94-167, or in a structure

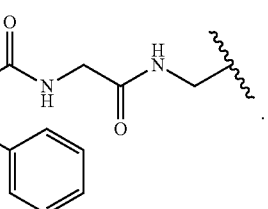

comprised therein, L1, X1, A and X2 are L1, X1, A and X2, respectively, of the compound according to any one of technical schemes 94-167.

297. The compound of formula (III-B) according to any one of technical schemes 268-277, the compound of formula (III-C) according to technical scheme 280, the compound of formula (III-D) according to any one of technical schemes 283-286, the compound of formula (III-E) according to technical scheme 289, or the compound of formula (III-F) according to any one of technical schemes 292-294, or the tautomer, the mesomer, the racemate, the enantiomer or the diastereoisomer thereof, or the mixture thereof, or the pharmaceutically acceptable salt thereof, wherein in a structure

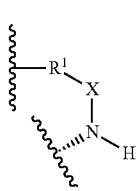

comprised therein, R1 and X1 are R1 and X1, respectively, of the compound according to any one of technical schemes 168-265.

298. The compound of formula (I-C) according to any one of technical schemes 278 and 295 or the compound of formula (I-D) according to any one of technical schemes 281, 284-286 and 295, or the tautomer, the mesomer, the racemate, the enantiomer or the diastereoisomer thereof, or the mixture thereof, or the pharmaceutically acceptable salt thereof, wherein in a structure -L- comprised therein, L is L of the compound according to any one of technical schemes 266 and 269-277.

299. The compound of formula (II-Cx) or (II-Cy) according to any one of technical schemes 279 and 296 or the compound of formula (II-Dx) or (II-Dy) according to any one of technical schemes 282, 284-286 and 296, or the tautomer, the mesomer, the racemate, the enantiomer or the diastereoisomer thereof, or the mixture thereof, or the pharmaceutically acceptable salt thereof, wherein in a structure -L- comprised therein, L is L of the compound according to any one of technical schemes 267 and 269-277.

300. The compound of formula (III-C) according to any one of technical schemes 280 and 297 or the compound of formula (III-D) according to any one of technical schemes 283-286 and 297, or the tautomer, the mesomer, the racemate, the enantiomer or the diastereoisomer thereof, or the mixture thereof, or the pharmaceutically acceptable salt thereof, wherein in a structure -L- comprised therein, L is L of the compound according to any one of technical schemes 268-277.

301. The compound of formula (I-F) according to any one of technical schemes 290, 293-294 and 295, or the tautomer, the mesomer, the racemate, the enantiomer or the diastereoisomer thereof, or the mixture thereof, or the pharmaceutically acceptable salt thereof, wherein Lb and Lc are Lb and Lc, respectively, of the compound according to any one of technical schemes 266 and 269-277.

302. The compound of formula (II-Fx) or (II-Fy) according to any one of technical schemes 291, 293-294 and 296, or the tautomer, the mesomer, the racemate, the enantiomer or the diastereoisomer thereof, or the mixture thereof, or the pharmaceutically acceptable salt thereof, wherein Lb and Lc are Lb and Lc, respectively, of the compound according to any one of technical schemes 267 and 269-277.

303. The compound of formula (III-F) according to any one of technical schemes 292-294 and 297, or the tautomer, the mesomer, the racemate, the enantiomer or the diastereoisomer thereof, or the mixture thereof, or the pharmaceutically acceptable salt thereof, wherein Lb and Lc are Lb and Lc, respectively, of the compound according to any one of technical schemes 268-277.

304. The compound or the tautomer, the mesomer, the racemate, the enantiomer or the diastereoisomer thereof, or the mixture thereof, or the pharmaceutically acceptable salt thereof according to any one of technical schemes 1-303, comprising the ligand-drug conjugate or a pharmaceutically acceptable salt or a solvate thereof.

305. A method for preparing the compound or the tautomer, the mesomer, the racemate, the enantiomer or the diastereoisomer thereof, or the mixture thereof, or the pharmaceutically acceptable salt thereof according to any one of technical schemes 1-304, comprising linking a cytotoxic drug to a ligand Ab via the structure of formula (I-B) according to any one of technical schemes 266, 269-277 and 295.

306. A method for preparing the compound or the tautomer, the mesomer, the racemate, the enantiomer or the diastereoisomer thereof, or the mixture thereof, or the pharmaceutically acceptable salt thereof according to any one of technical schemes 1-304, comprising linking a cytotoxic drug to a ligand Ab via the structure of formula (II-Bx) or (II-By) according to any one of technical schemes 267, 269-277 and 296.

307. A method for preparing the compound or the tautomer, the mesomer, the racemate, the enantiomer or the diastereoisomer thereof, or the mixture thereof, or the pharmaceutically acceptable salt thereof according to any one of technical schemes 1-304, comprising linking a cytotoxic drug to a ligand Ab via the structure of formula (III-B) according to any one of technical schemes 268, 269-277 and 297.

308. A pharmaceutical composition, comprising the compound or the tautomer, the mesomer, the racemate, the enantiomer or the diastereoisomer thereof, or the mixture thereof, or the pharmaceutically acceptable salt thereof according to any one of technical schemes 1-304, and a pharmaceutically acceptable carrier.

309. Use of the compound or the tautomer, the mesomer, the racemate, the enantiomer or the diastereoisomer thereof, or the mixture thereof, or the pharmaceutically acceptable salt thereof according to any one of technical schemes 1-304, and/or the pharmaceutical composition according to technical scheme 308, in preparing a medicament for treating and/or preventing a tumor.

310. The use according to technical scheme 309, wherein the tumor is selected from the group consisting of tumors associated with expression of the following: HER2, HER3, B7H3, TROP2, Claudin 18.2, CD30, CD33, CD70 and EGFR.

311. The use according to any one of technical schemes 309-310, wherein the tumor is selected from the group consisting of: lung cancer, kidney cancer, urinary tract carcinoma, colorectal cancer, prostatic cancer, glioblastoma multiforme, ovarian cancer, pancreatic cancer, breast cancer, melanoma, liver cancer, bladder cancer, stomach cancer and esophageal cancer.

Without being bound by any theory, the following examples are intended only to illustrate the compounds, preparation methods, use, etc., of the present application, and are not intended to limit the scope of the present application.

EXAMPLES

The structure of the compounds is determined by nuclear magnetic resonance (NMR) or mass spectrometry (MS). NMR is performed using a Quantum-I NMR spectrometer with deuterated dimethyl sulfoxide (DMSO-D), deuterated chloroform (CDCl3), and deuterated methanol (CD30D) as solvents, and tetramethylsilane (TMS) as an internal standard, and chemical shifts are given in units of 10_6 (ppm).

MS is performed using an Angilent 6230 ESI-TOF mass spectrometer (manufacturer: Agilent, type c: 6230)

UPLC is performed using a Waters AcquityUPLCSQD liquid chromatograph-mass spectrometer (Poroshell 120 EC-C18, 2.1 mm×50 mm, 1.9 m column).

HPLC is performed using an Agilent 1260 high-performance liquid chromatograph (TOSOH G3000 SW SEC column).

UV is measured using a Thermo Nanodrop 2000 spectrophotometer.

The proliferation inhibition rate and the IC5Q value are measured using an EnVision microplate reader (PerkinElmer).

Yantai Yellow Sea HSGF254 or Qingdao GF254 silica gel plate is adopted as a thin layer chromatography (TLC) silica gel plate. The specification adopted by the TLC is 0.15-0.20 mm, and the specification adopted by the thin layer chromatography for the separation and purification of products is 0.4-0.5 mm.

Yantai Yellow Sea silica gel of 200-300 mesh is generally utilized as a carrier in column chromatography.

543

Known starting materials of the present disclosure can be synthesized using or according to methods known in the art, or can be purchased from companies such as ABCR GMBH & Co. KG, Acros Organnics, Aldrich Chemical Company, Accela ChemBio Inc., and Darui Chemicals.

In the examples, all reactions are carried out under an argon atmosphere or a nitrogen atmosphere unless otherwise stated.

The argon atmosphere or nitrogen atmosphere is created by connecting the reaction flask to an argon or nitrogen balloon with a volume of about 1 L.

The hydrogen atmosphere is created by connecting a reaction flask to a hydrogen balloon with a volume of about 1 L.

In the examples, the solution in the reaction is an aqueous solution unless otherwise stated.

In the examples, the reaction temperature is room temperature unless otherwise stated. The room temperature is the optimum reaction temperature, which ranges from 20° C. to 30° C.

The system of eluents for column chromatography and the system of developing agents for thin layer chromatography used for purifying compounds include: A: dichloromethane and isopropanol system, B: dichloromethane and methanol system, and C: petroleum ether and ethyl acetate system. The volume ratio of solvents is regulated according to different polarities of the compound, and can also be regulated by adding a small amount of triethylamine and acidic or alkaline reagent.

Some of the compounds of the present disclosure are characterized by TOF-LC/MS. TOF-LC/MS is performed using Agilent 6230 time-of-flight mass spectrometer and Agilent 1290-Infinity ultra high performance liquid chromatograph.

Example 1 Preparation of Compounds

Preparation Example 1.1. (1s,4R)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-4-hydroxycyclohexane-1-carboxamide

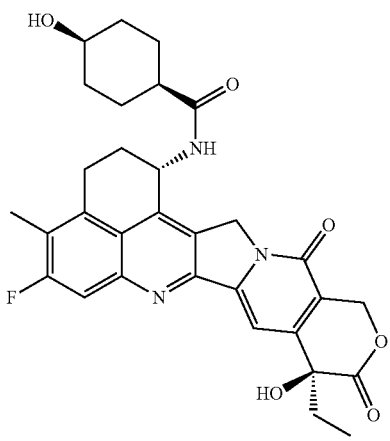

P-II-1

544

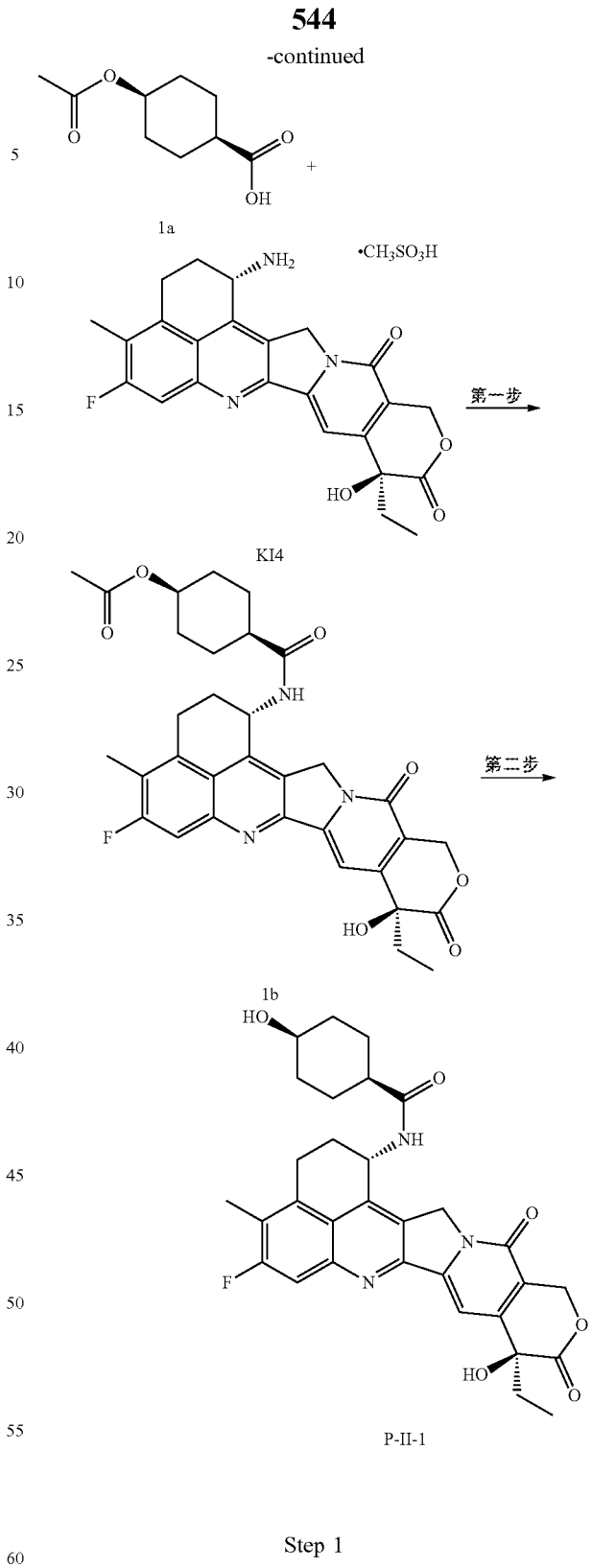

Step 1

DIEA (486 mg, 3.76 mmol) was added to a solution of KI4 (1.00 g, 1.88 mmol), HATU (691 mg, 1.88 mmol) and 1a (350 mg, 1.88 mmol) in DMF (18 mL) at 0° C. under nitrogen atmosphere, and the mixture was stirred at 25° C. for 3 h. After the starting material was consumed completely as detected by TLC (EA), the reaction solution was added dropwise to deionized water (320 mL) and filtered to give a gray solid (1.02 g, yield 90%).

Step 2

NaHCO₃ (417 mg, 5.00 mmol) as a solid was added to a solution of 1b (100 mg, 0.166 mmol) in MeOH/DCM (1/1, 5 mL), and the mixture was stirred at 25° C. for 3 h. After the reaction was completed as detected by TLC (EA), the reaction solution was filtered, dried by rotary evaporation at low temperature, slurried with aq. HCl (0.5 M, 10 mL), filtered and purified by prep-HPLC (0.1% TFA) to give a yellow solid (14 mg).

MS m/z (ESI): 562 [M+1]

H-NMR (400 MHz, DMSO-D): 8.37 (d, 1H), 7.81 (d, 1H), 7.32 (s, 1H), 5.57-5.55 (m, 1H), 5.43 (s, 2H), 5.18 (dd, 2H), 3.79 (m, 1H), 3.19-3.17 (m, 2H), 2.41 (s, 3H), 2.30-2.12 (m, 3H), 1.95-1.80 (m, 4H), 1.73-1.62 (m, 2H), 1.59-1.32 (m, 4H), 0.89 (t, 3H)

Preparation Example 1.2. (1r,4S)-N((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-4-hydroxycyclohexane-1-carboxamide

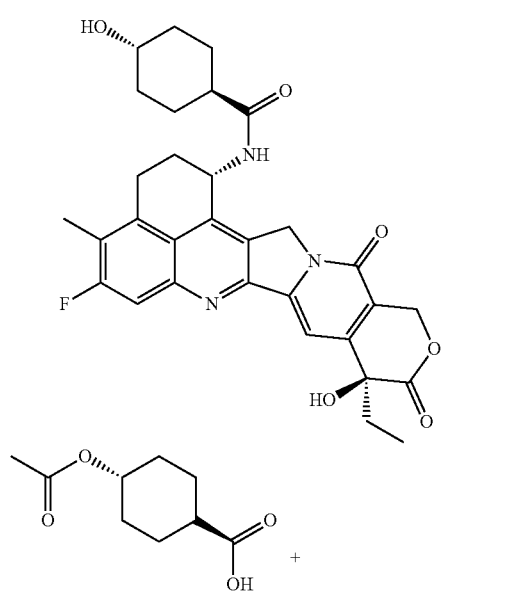

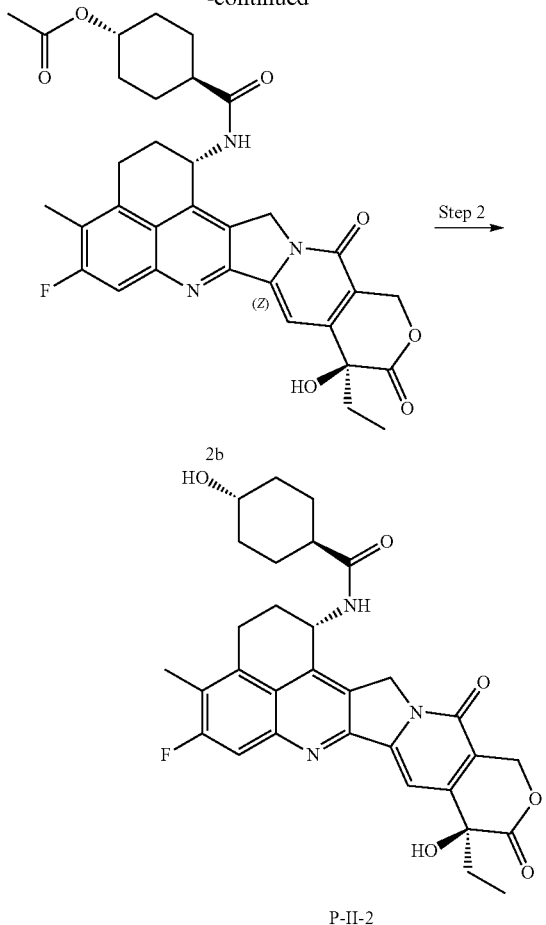

Step 1

DIEA (486 mg, 3.76 mmol) was added to a solution of KI4 (1.00 g, 1.88 mmol), HATU (691 mg, 1.88 mmol) and 2a (390 mg, 2.07 mmol) in DMF (18 mL) at 0° C. under nitrogen atmosphere, and the mixture was stirred at 25° C. for 3 h. After the starting material was consumed completely as detected by TLC (EA), the reaction solution was added dropwise to deionized water (320 mL) and filtered to give a gray solid (913 mg, yield 81%).

Step 2

NaHCO₃ (42 mg, 0.50 mmol) as a solid was added to a solution of 2b (100 mg, 0.166 mmol) in MeOH/DCM (1/1, 3 mL), and the mixture was stirred at 25° C. for 3 h. After the reaction was completed as detected by TLC (EA), the reaction solution was filtered, dried by rotary evaporation at low temperature, slurried with aq. HCl (0.5 M, 10 mL), filtered and purified by prep-HPLC (0.1% TFA) to give a gray solid (18 mg, yield 20%).

MS m/z (ESI): 562 [M+1]

H-NMR (400 MHz, DMSO-D): 8.39 (d, 1H), 7.78 (d, 1H), 7.29 (s, 1H), 6.52 (s, 1H), 5.53-5.51 (m, 1H), 5.41 (s, 2H), 5.12 (dd, 2H), 4.57 (d, 1H), 3.17-3.14 (m, 2H), 2.38 (s, 3H), 2.13-2.07 (m, 3H), 1.90-1.70 (m, 6H), 1.52-1.41 (m, 2H), 1.18-1.01 (m, 2H), 0.86 (t, 3H)

547

Preparation Example 1.3. (1s,3R)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3-hydroxycyclobutane-1-carboxamide

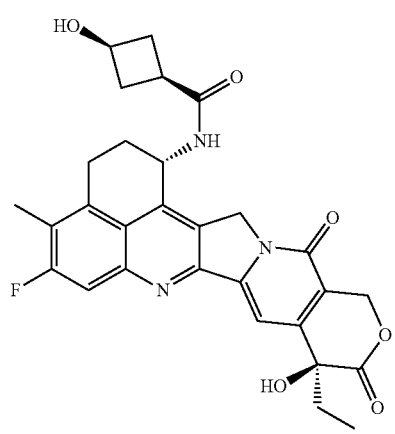

P-II-3

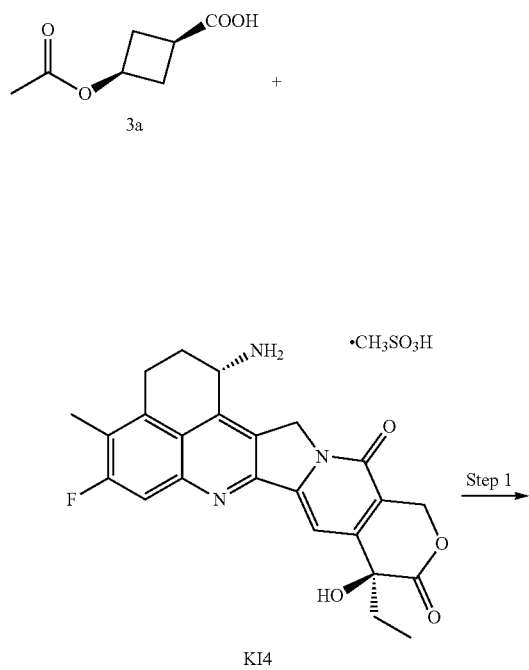

548

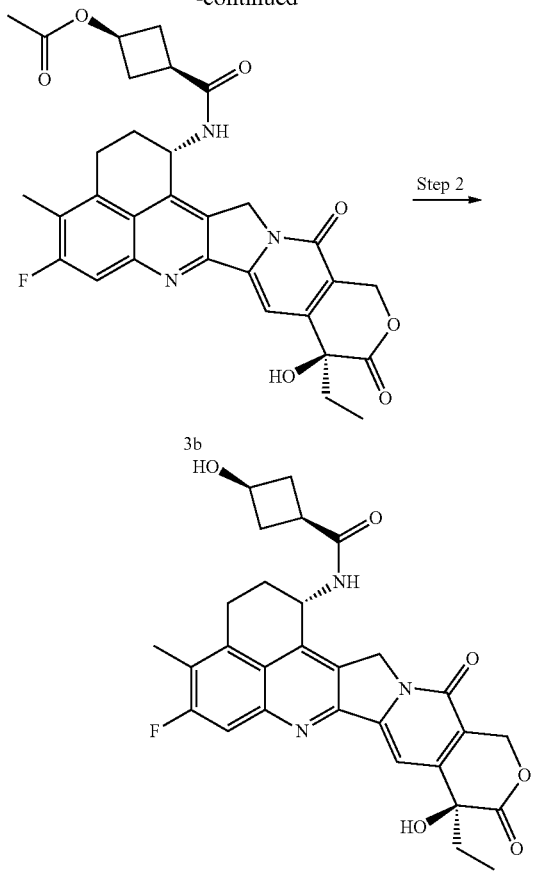

Step 1

DIEA (500 mg, 3.87 mmol) was added to a solution of KI4 (900 mg, 1.69 mmol), HATU (691 mg, 1.88 mmol) and 3a (320 mg, 2.00 mmol) in DMF (18 mL) at 0° C. under nitrogen atmosphere, and the mixture was stirred at 25° C. for 3 h. After the starting material was consumed completely as detected by TLC (EA), the reaction solution was added dropwise to deionized water (320 mL) and filtered to give a gray solid (850 mg, yield 87%).

Step 2

NaHCO$_3$ (42 mg, 0.50 mmol) as a solid was added to a solution of 3b (100 mg, 0.174 mmol) in MeOH/DCM (1/1, 3 mL), and the mixture was stirred at 25° C. for 3 h. After the reaction was completed as detected by TLC (EA), the reaction solution was filtered, dried by rotary evaporation at low temperature, slurried with aq. HCl (0.5 M, 10 mL), filtered and purified by prep-HPLC (0.1% TFA), and then lyophilized to give a gray solid (15 mg, yield 16%).

MS m/z (ESI): 534 [M+1]

H-NMR (400 MHz, DMSO-D): 8.45 (d, 1H), 7.81 (d, 1H), 7.32 (s, 1H), 6.52 (m, 1H), 5.58-5.56 (m, 1H), 5.44 (s, 2H), 5.14 (dd, 2H), 3.96 (m, 1H), 3.48 (m, 1H), 3.19 (m, 2H), 2.53-2.28 (m, 3H), 2.48 (s, 3H), 2.20-2.00 (m, 4H), 1.95-1.80 (m, 2H), 0.89 (t, 3H)

549

Preparation Example 1.4. (1r,3S)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3-hydroxycyclobutane-1-carboxamide

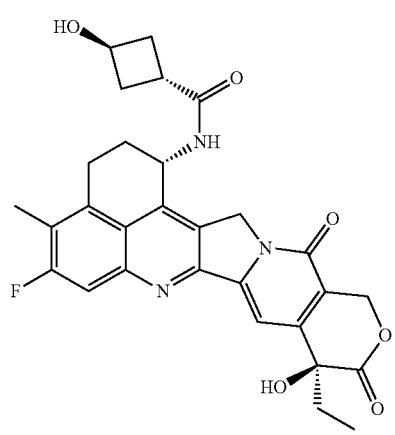

P-II-4

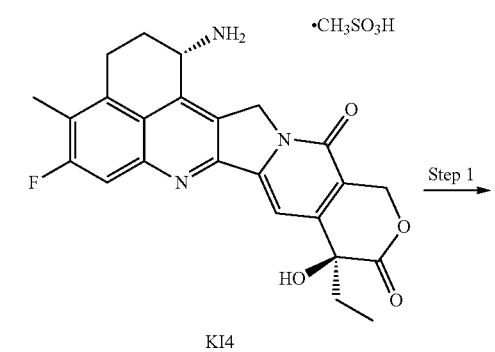

550

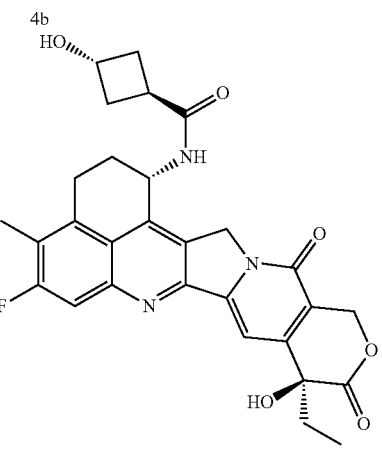

Step 1

DIEA (486 mg, 3.76 mmol) was added to a solution of KI4 (1.00 g, 1.88 mmol), HATU (691 mg, 1.88 mmol) and 4a (310 mg, 1.88 mmol) in DMF (18 mL) at 0° C. under nitrogen atmosphere, and the mixture was stirred at 25° C. for 3 h. After the starting material was consumed completely as detected by TLC (EA), the reaction solution was added dropwise to deionized water (320 mL) and filtered to give a gray solid (910 mg, yield 84%).

Step 2

NaHCO$_3$ (42 mg, 0.50 mmol) as a solid was added to a solution of 4b (100 mg, 1.58 mmol) in MeOH/DCM (1/1, 3 mL), and the mixture was stirred at 25° C. for 3 h. After the reaction was completed as detected by TLC (EA), the reaction solution was filtered, dried by rotary evaporation at low temperature, slurried with aq. HCl (0.5 M, 10 mL), filtered and purified by prep-HPLC (0.1% TFA), and then lyophilized to give a yellow solid (13 mg, yield 14%).

MS m/z (ESI): 534 [M+1]

H-NMR (400 MHz, DMSO-D): 8.39 (d, 1H), 7.77 (d, 1H), 7.29 (s, 1H), 6.52 (m, 1H), 5.58-5.54 (m, 1H), 5.41 (s, 2H), 5.18-5.06 (m, 3H), 4.39-4.33 (m, 1H), 3.19-3.07 (m, 2H), 2.97-2.82 (m, 1H), 2.49-2.36 (m, 2H), 2.38 (s, 3H), 2.20-1.96 (m, 4H), 1.93-1.79 (m, 2H), 0.87 (t, 3H)

Preparation Example 1.5
(1S,9S)-9-ethyl-5-fluoro-9-hydroxy-1-((R)-3-hydroxy-2-oxopyrrolidin-1-yl)-4-methyl-1,2,3,9,12,15-hexahydro-10H,13H-benzo[de]pyrano[3',4':6,7]indolizino[[1,2-b]quinoline-10,13-dione]
(1S,9S)-9-ethyl-5-fluoro-9-hydroxy-1-((S)-3-hydroxy-2-oxopyrrolidin-1-yl)-4-methyl-1,2,3,9,12,15-hexahydro-10H,13H-benzo[de]pyrano[3',4':6,7]indolizino[[1,2-b]quinoline-10,13-dione]
P-I-1 A
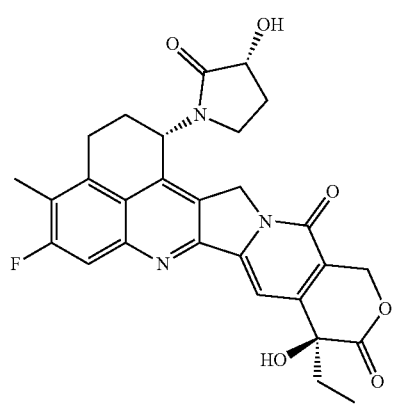
P-I-1 B
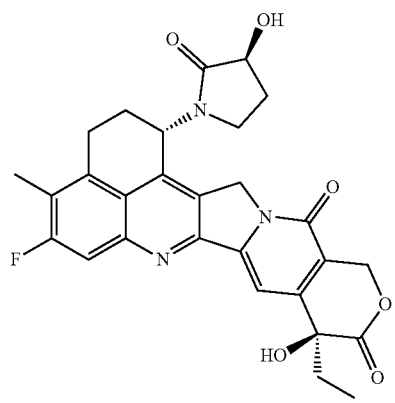
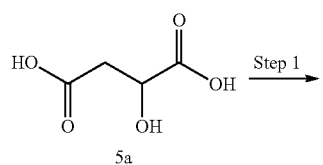
5a
Step 1
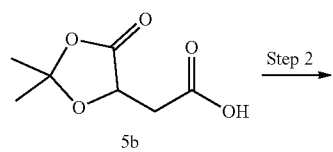
5b
Step 2
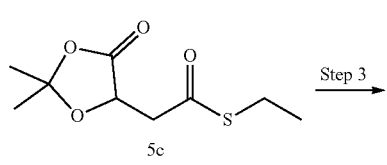
5c
Step 3
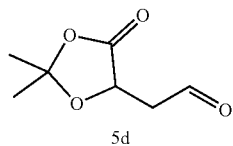
5d
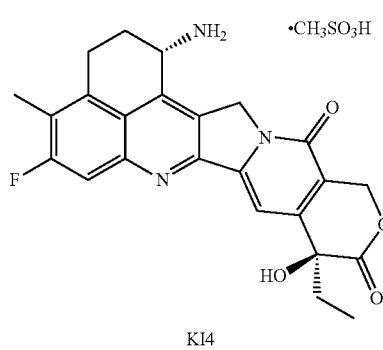
KI4
Step 4
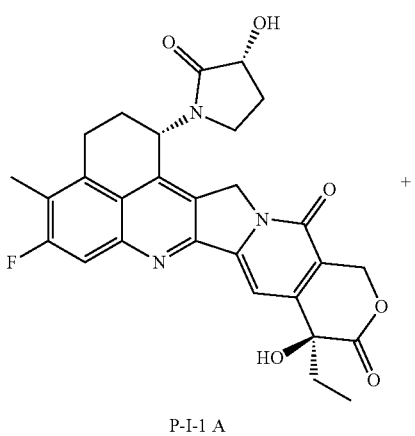
P-I-1 A
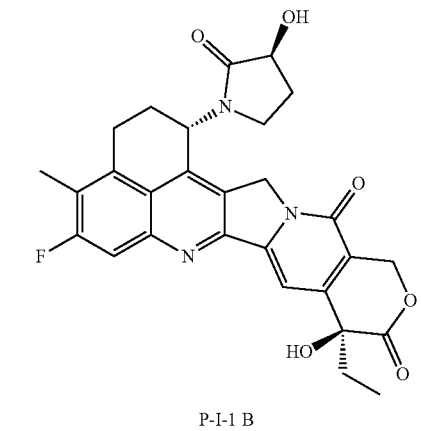
P-I-1 B

Step 1

TsOH (300 mg, 7.46 mmol) was added slowly to a solution of 5a (20.0 g, 149 mmol) in 2,2-dimethoxypropane (500 mL) at 25° C., and the mixture was stirred for 17 h. After the reaction was completed as detected by TLC (EA), the reaction solution was directly purified by column chromatography (PE:EA=1:0 to 1:1) to give a white solid (20 g, yield 77%).

Step 2

Ethanethiol (6.40 g, 103 mmol), DCC (30.9 g, 149 mmol) and DMAP (280 mg, 2.30 mmol) were added to a solution of 5b (20.0 g, 115 mmol) in DCM (500 mL) at 0° C. After the addition was completed, the reaction solution was warmed to 25° C. and stirred for 17 h. After the reaction was completed as detected by TLC (PE/EA=2/1), the reaction solution was filtered and washed with saturated brine (100 mL). The organic phase was dried, filtered, concentrated and purified by column chromatography (PE:EA=1:0 to 10:1) to give a pale yellow oil (20 g, yield 80%).

Step 3

Pd(OAc)$_2$ (1.00 g, 4.58 mmol) and Et$_3$SiH (5.33 g, 45.8 mmol) were added to a solution of 5c (5.00 g, 22.9 mmol) in acetone (100 mL) at 0° C., and the mixture was stirred at 25° C. for 3 h. After the reaction was completed as detected by TLC (PE/EA=2/1), the reaction solution was filtered, concentrated and purified by column chromatography (PE:EA=1:0 to 1:1) to give a yellow oil (3.6 g, yield 82%).

Step 4

HOAc (6.8 mg, 0.11 mmol) was added to a solution of 5d (15 mg, 71 μmol), a solution of KI4 (40 mg, 71 μmol) in DCE (4 mL), and DMA (1 mL), and the mixture was stirred at 25° C. for 20 min. Sodium borohydride acetate (24 mg, 0.11 mmol) was added to the above reaction solution, and the mixture was stirred at 25° C. for 4 h. After the reaction was completed as detected by LCMS, the reaction solution was added with saturated brine, extracted with DCM/MeOH (5:1, 20 mL) three times, washed with saturated aqueous sodium chloride solution (30 mL), dried over anhydrous sodium sulfate, dried by rotary evaporation, and purified by prep-HPLC (0.1% TFA) to give two products: P10A (8 mg, RT: 0.895 min, yield 20%) as a yellow solid and P10B (9 mg, RT: 0.917 min, yield 23%) as a yellow solid.

P-I-1 A MS m/z (ESI): 520 [M+1]

P-I-1 A H-NMR (400 MHz, DMSO-D): 7.83 (d, 1H), 7.33 (s, 1H), 6.55 (m, 1H), 5.60-5.58 (m, 1H), 5.44 (s, 2H), 5.01 (dd, 2H), 4.29 (t, 1H), 3.31-3.11 (m, 4H), 2.96-2.82 (m, 1H), 2.42 (s, 3H), 2.29-2.12 (m, 2H), 1.99-1.81 (m, 3H), 0.89 (t, 3H)

P-I-1 B MS m/z (ESI): 520 [M+1]

P-I-1 B H-NMR (400 MHz, DMSO-D): 7.84 (d, 1H), 7.33 (s, 1H), 6.55 (m, 1H), 5.67-5.65 (m, 1H), 5.44 (s, 2H), 5.17 (dd, 2H), 4.28 (t, 1H), 3.30-3.11 (m, 4H), 2.87 (t, 1H), 2.32-2.12 (m, 2H), 2.41 (s, 3H), 1.95-1.82 (m, 2H), 1.78-1.65 (m, 1H), 0.90 (t, 3H)

Preparation Example 1.6. N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3-mercaptopropanamide

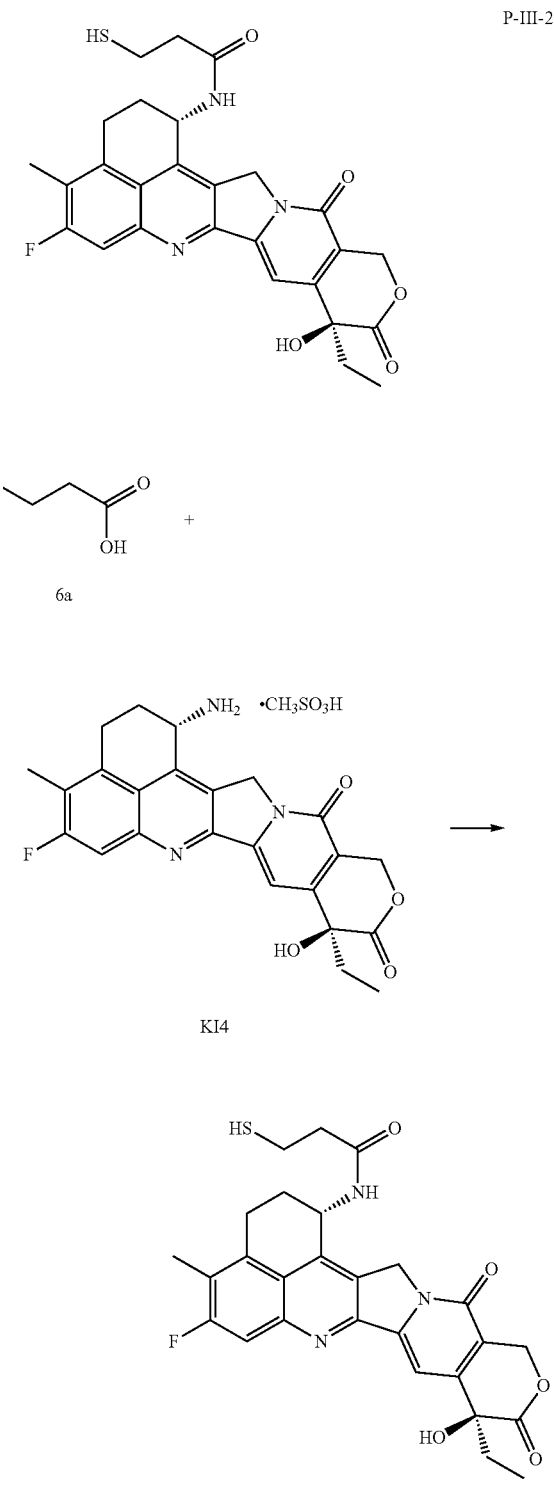

DIEA (122 mg, 0.943 mmol) was added to a solution of KI4 (200 mg, 0.377 mmol), HATU (214.7 mg, 0.565 mmol) and 6a (60 mg, 0.565 mmol) in DMF (6 mL) under nitrogen atmosphere, and the mixture was stirred at 25° C. for 3 h. After the starting material was consumed completely as detected by LCMS, the reaction solution was added dropwise to water (90 mL) and filtered to give a yellow solid (326 mg), which was prepared by prep-HPLC (0.5% TFA) to give a yellow solid (19 mg, yield 9.6%).

MS m/z (ESI): 524 [M+1]

H-NMR (400 MHz, DMSO-D): 8.55 (d, 1H), 7.83 (d, 1H), 7.33 (s, 1H), 6.54 (m, 1H), 5.65-5.55 (m, 1H), 5.45 (s, 2H), 5.26 (dd, 2H), 3.23-3.17 (m, 2H), 2.80-2.71 (dd, 2H), 2.70-2.66 (m, 2H), 2.43 (s, 3H), 2.19-2.14 (m, 1H), 1.92-1.83 (m, 2H), 0.89 (t, 3H)

Preparation Example 1.7. (R)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3-hydroxybutanamide

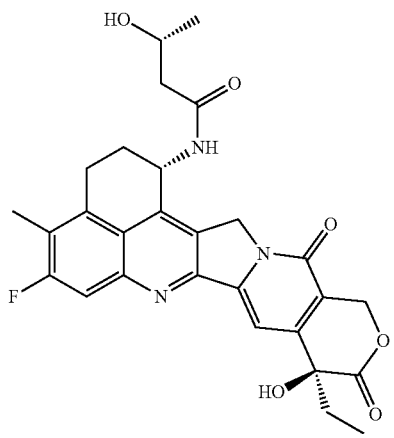

P-III-20

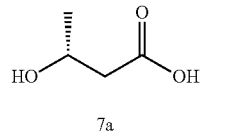

7a

+

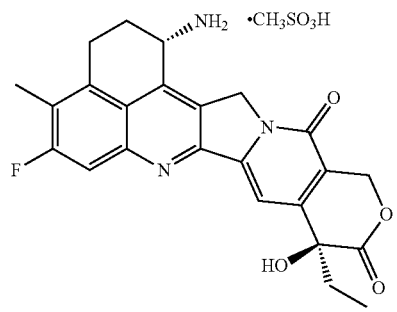

KI4

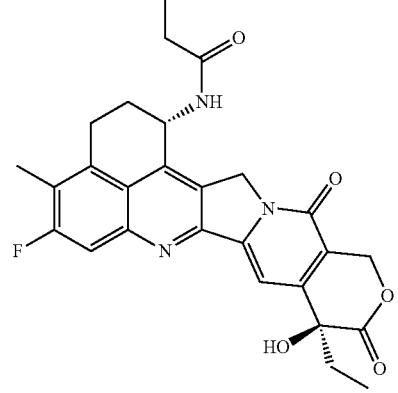

P-III-2O

DIEA (61 mg, 0.47 mmol) was added to a solution of KI4 (100 mg, 0.188 mmol), HATU (86 mg, 0.23 mmol) and 7a (22 mg, 0.21 mmol) in DMF (2 mL) under nitrogen atmosphere. After the addition was completed, the mixture was reacted at 25° C. for 2.5 h. After the starting material was consumed completely as detected by LCMS, the reaction solution was added to water (20 mL), and a solid was precipitated. The resulting mixture was filtered to give the product (13 mg, yield 11%).

MS m/z (ESI): 522 [M+1]

H-NMR (400 MHz, DMSO-D): 8.44 (d, 1H), 7.80 (d, 1H), 7.32 (s, 1H), 6.54 (m, 1H), 5.60-5.50 (m, 1H), 5.44 (s, 2H), 5.22 (dd, 2H), 4.10-4.00 (m, 1H), 3.30-3.17 (m, 2H), 2.41 (s, 3H), 2.38-2.10 (m, 4H), 1.96-1.80 (m, 2H), 1.11 (d, 3H), 0.89 (t, 3H)

Preparation Example 1.8. N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3-hydroxy-3-methylbutanamide

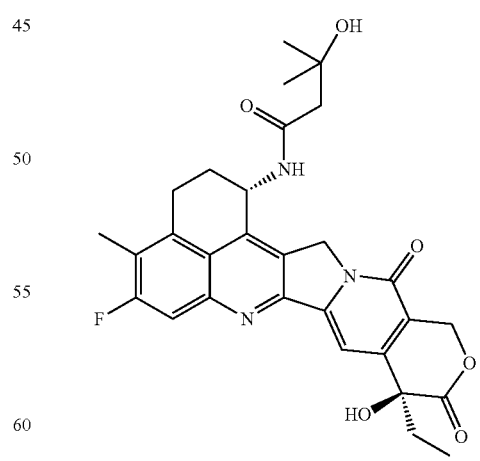

P-III-21

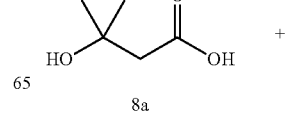

8a

+

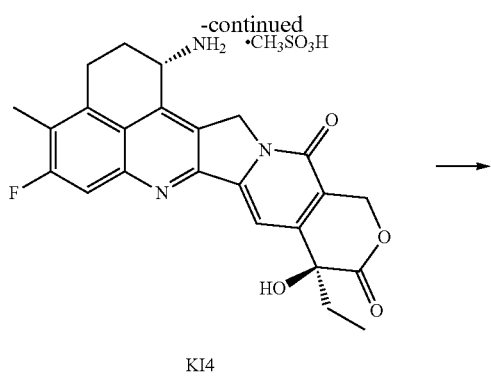

KI4

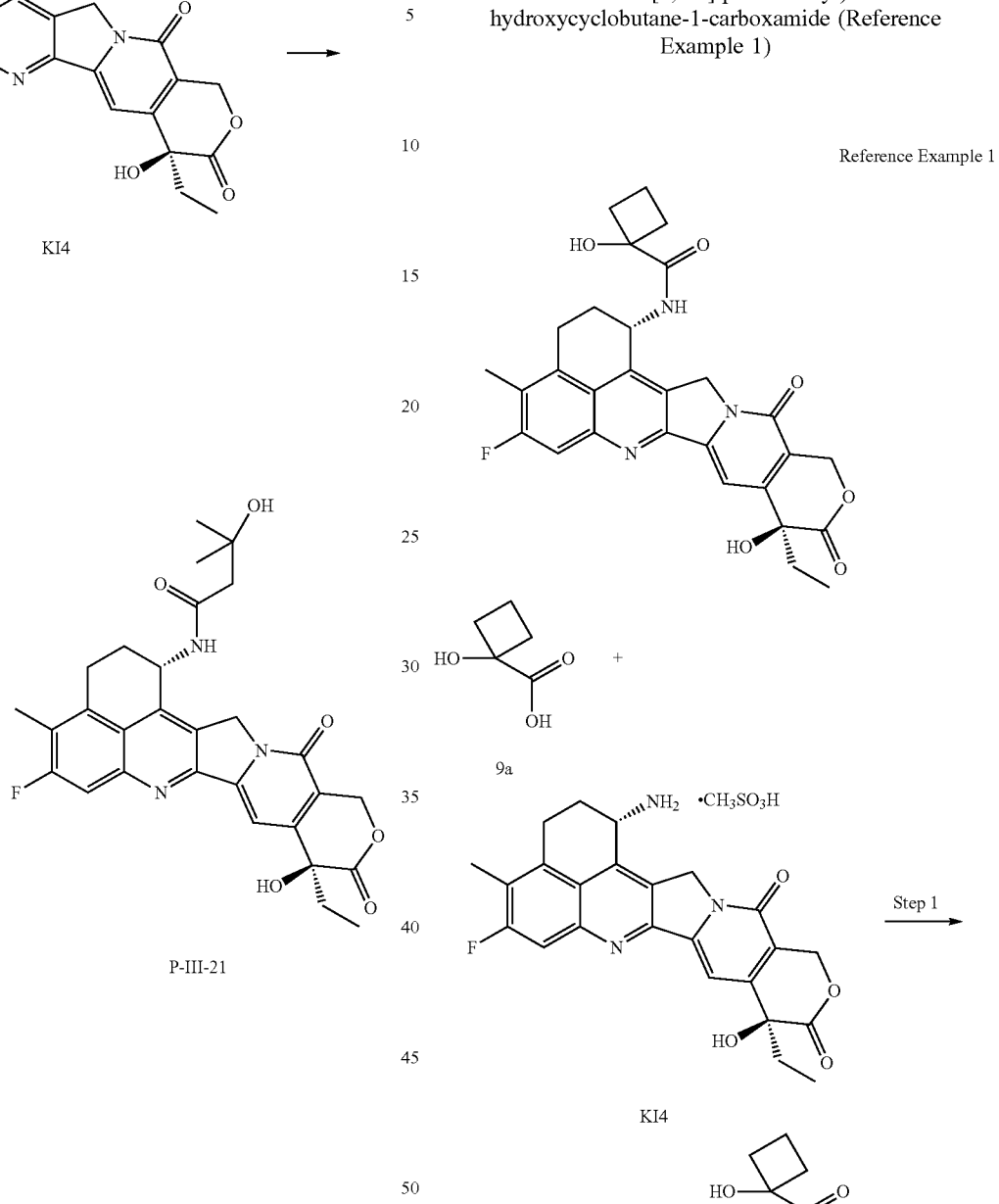

P-III-21

A solution of DIEA (61 mg, 0.47 mmol) in DMF (1 mL) was added to a solution of KI4 (100 mg, 0.188 mmol), HATU (86 mg, 0.23 mmol) and 8a (24 mg, 0.21 mmol) in DMF (1 mL) under nitrogen atmosphere. After the addition was completed, the mixture was reacted at 25° C. for 3 h. After the starting material was consumed completely as detected by TLC (EA), the reaction solution was purified by preparative chromatography to give a yellow solid (17 mg, yield 17%).

MS m/z (ESI): 536 [M+1]

H-NMR (400 MHz, DMSO-D): 8.42 (d, 1H), 7.79 (d, 1H), 7.30 (s, 1H), 6.53 (m, 1H), 5.59-5.55 (m, 1H), 5.42 (s, 2H), 5.22 (dd, 2H), 4.69 (s, 1H), 3.20-3.11 (m, 2H), 2.39 (sc, 3H), 2.29 (s, 2H), 2.20-2.08 (m, 2H), 1.19 (d, 6H), 0.87 (t, 3H)

Preparation Example 1.9. N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-1-hydroxycyclobutane-1-carboxamide (Reference Example 1)

Reference Example 1

Reference Example 1

Step 1

KI4 (50 mg, 0.094 mmol), 25a (11 mg, 0.094 mmol) and HATU (39 mg, 0.103 mmol) were added to DMF (3 mL), and DIEA (30 mg, 0.235 mmol) was added after purging with nitrogen. The mixture was reacted at 25° C. for 1.5 h. After the reaction was completed as detected by LCMS, the reaction solution was added dropwise to water (50 mL) with stirring. After the addition was completed, the reaction solution was left to stand for 5 min and filtered, and the filter cake was lyophilized to give 25 (20 mg, yield 40%) as a gray solid.

MS-ESI: m/z 534.3 [M+H]+.

1H NMR (400 MHz, DMSO-d6) δ 8.26 (d, J=9.1 Hz, 1H), 7.72 (d, J=10.9 Hz, 1H), 7.28 (s, 1H), 6.51 (s, 1H), 6.12 (s, 1H), 5.59-5.50 (m, 1H), 5.40 (s, 2H), 5.15 (d, J=18.8 Hz, 1H), 4.98 (d, J=19.0 Hz, 1H), 3.28-3.16 (m, 1H), 3.15-3.02 (m, 1H), 2.74-2.52 (m, 2H), 2.36 (s, 3H), 2.24-2.04 (m, 4H), 1.92-1.79 (m, 4H), 0.86 (t, J=7.3 Hz, 3H).

Preparation Example 1.10. N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolino[1,2-b]quinolin-1-yl)-3-aminopropionamide (Reference Example 2)

Reference Example 2

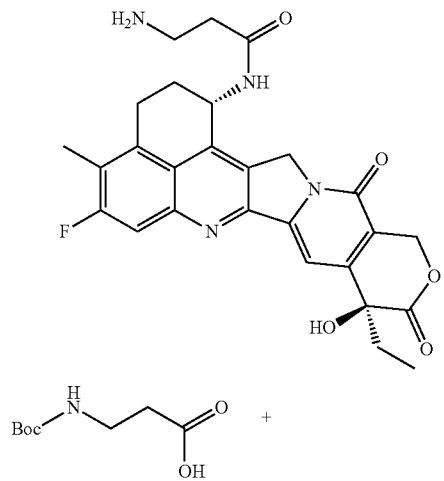

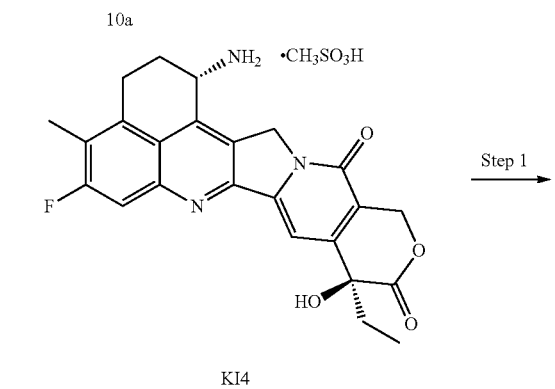

KI4

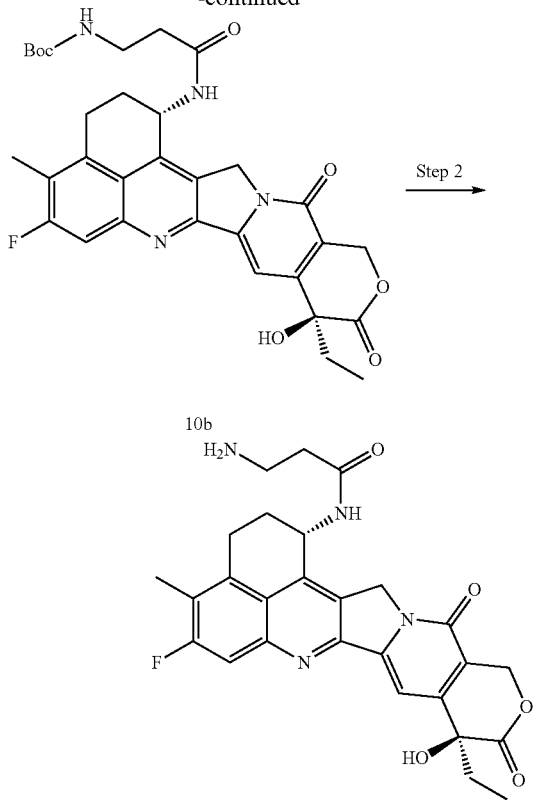

10b

Reference Example 2

Step 1

KI4 (50 mg, 0.094 mmol), 26a (18 mg, 0.094 mmol) and HATU (39 mg, 0.103 mmol) were added to DMF (3 mL), and DIEA (48 mg, 0.376 mmol) was added after purging with nitrogen. The mixture was reacted at 25° C. for 1.5 h. After the reaction was completed as detected by LCMS, the reaction solution was added dropwise to water (50 mL) with stirring. After the addition was completed, the reaction solution was left to stand for 5 min and filtered, and the filter cake was lyophilized to give a gray solid 26b, (30 mg, yield 52%). MS-ESI: m/z 607.4 [M+H]+.

Step 2

26b (30 mg, 0.049 mmol) was dissolved in DCM (2 mL), and the solution was purged with N₂, cooled to 0° C. and added with TFA (0.5 mL). The mixture was reacted at 0° C. for 1.5 h. After the reaction was completed as detected by LCMS, the reaction solution was dried by rotary evaporation at low temperature, washed with DCM once, added with acetonitrile and water and lyophilized to give a yellow solid (20 mg, yield 80%).

MS-ESI: m/z 507.1 [M+H]+.

1H NMR (400 MHz, DMSO-d6) δ 8.67 (d, J=8.6 Hz, 1H), 7.86-7.66 (m, 4H), 7.32 (s, 1H), 6.56 (brs, 1H), 5.63-5.54 (m, 1H), 5.43 (s, 2H), 5.29 (d, J=18.9 Hz, 1H), 5.22 (d, J=18.9 Hz, 1H), 3.23-3.15 (m, 2H), 3.13-3.03 (m, 2H), 2.57-2.51 (m, 2H), 2.43-2.38 (m, 3H), 2.27-2.08 (m, 2H), 1.94-1.78 (m, 2H), 0.87 (t, J=7.3 Hz, 3H).

Preparation example 1.11. N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3-hydroxypropanamide (Reference Example 3)

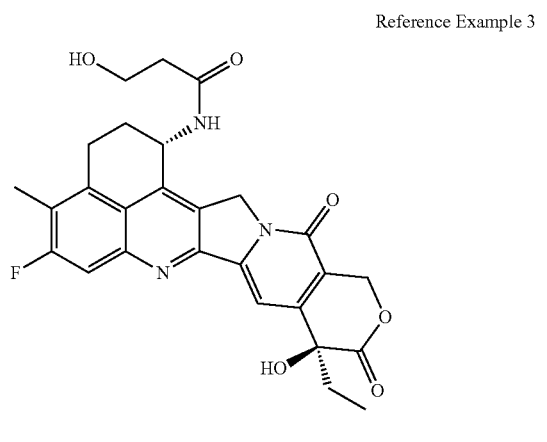

Reference Example 3

11a

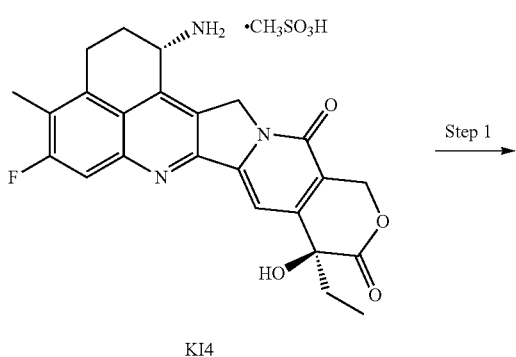

KI4

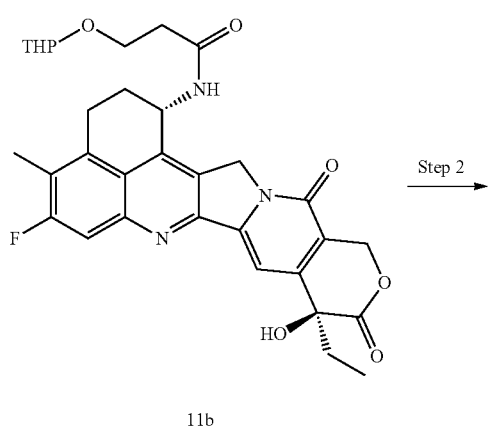

11b

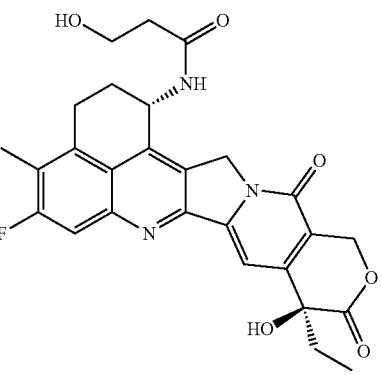

Reference Example 3

Step 1

KI4 (100 mg, 0.188 mmol), 11a (33 mg, 0.188 mmol) and HATU (77 mg, 0.203 mmol) were added to DMF (3 mL), and DIEA (73 mg, 0.564 mmol) was added after purging with nitrogen. The mixture was reacted at 25° C. for 1.5 h. After the reaction was completed as detected by LCMS, the reaction solution was added dropwise to water (50 mL) with stirring. After the addition was completed, the reaction solution was left to stand for 5 min and filtered, and the filter cake was lyophilized to give a gray solid 11b, (80 mg, yield 72%). MS-ESI: m/z 592.4 [M+H]+.

Step 2

27b (80 mg, 0.135 mmol) was dissolved in DCM (2 mL), and the solution was purged with N2, cooled to 0° C. and added with TFA (0.5 mL). The mixture was reacted at 0° C. for 1.5 h. After the reaction was completed as detected by LCMS, the reaction solution was dried by rotary evaporation at low temperature, purified by PTLC, added with acetonitrile and water and lyophilized to give a white solid (25 mg, yield 36%).

MS-ESI: m/z 508.3 [M+H]+.

1H NMR (400 MHz, DMSO-d6) δ 8.44 (d, J=8.6 Hz, 1H), 7.79 (d, J=11.0 Hz, 1H), 7.30 (s, 1H), 6.53 (s, 1H), 5.60-5.53 (m, 1H), 5.42 (s, 2H), 5.28-5.15 (m, 2H), 4.59 (t, J=5.1 Hz, 1H), 3.72-3.63 (m, 2H), 3.21-3.12 (m, 2H), 2.40 (s, 3H), 2.32 (t, J=6.4 Hz, 2H), 2.21-2.06 (m, 2H), 1.92-1.79 (m, 2H), 0.87 (t, J=7.3 Hz, 3H).

Preparation Example 1.12. N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3-hydroxy-2-methylbutanamide (Reference Example 4)

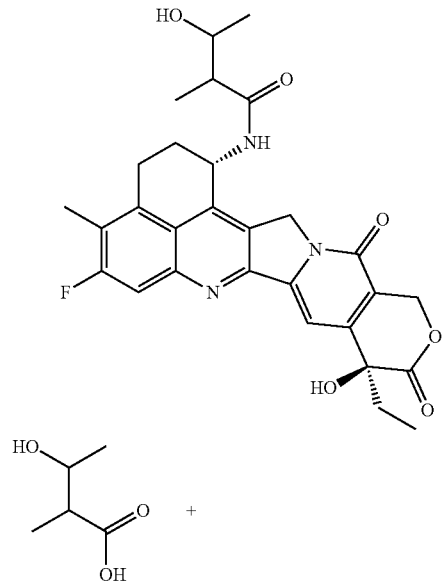

Reference Example 4

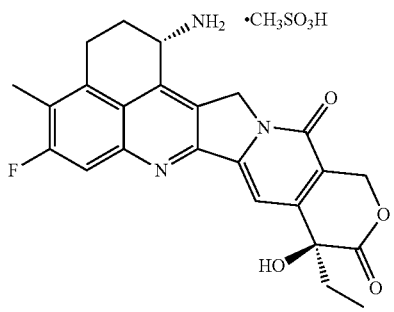

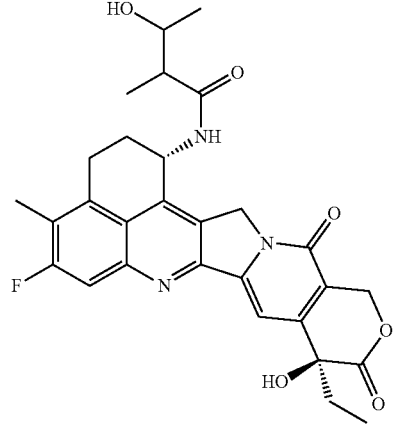

Step 1

12a (13 mg, 0.113 mmol), KI4 (60 mg, 0.113 mmol) and HATU (50 mg, 0.135 mmol) were added to a 25 mL three-necked flask and dissolved with DMF (2 mL), followed by the slow addition of DIEA (44 mg, 0.339 mmol). After the reaction was completed as detected by LCMS, the reaction solution was purified by reverse-phase column chromatography to give a yellow powder (37.2 mg, yield 62%).

MS-ESI: m/z 536.3 [M+H]+.

1H NMR (400 MHz, DMSO-d6) δ 8.50-8.23 (m, 1H), 7.82-7.75 (m, 1H), 7.32-7.28 (m, 1H), 6.66-6.38 (m, 1H), 5.61-5.50 (m, 1H), 5.42 (s, 2H), 5.31-5.10 (m, 2H), 3.77-3.61 (m, 2H), 3.22-3.12 (m, 2H), 2.56-2.52 (m, 1H), 2.42-2.37 (m, 3H), 2.31-2.02 (m, 3H), 1.93-1.78 (m, 2H), 1.28-0.96 (m, 7H), 0.91-0.84 (m, 3H).

Preparation Example 1.13. N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3-hydroxycyclohexane-1-carboxamide

P-II-22

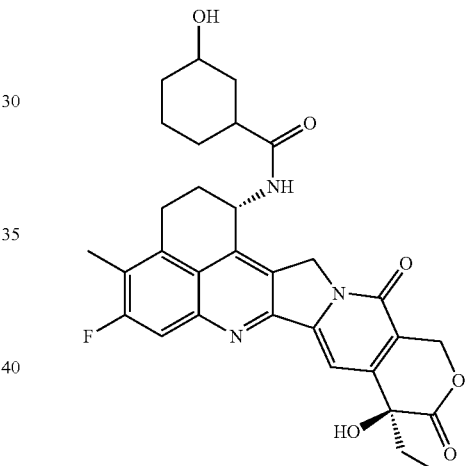

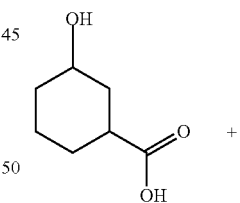

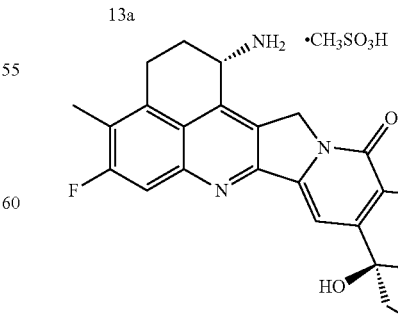

-continued

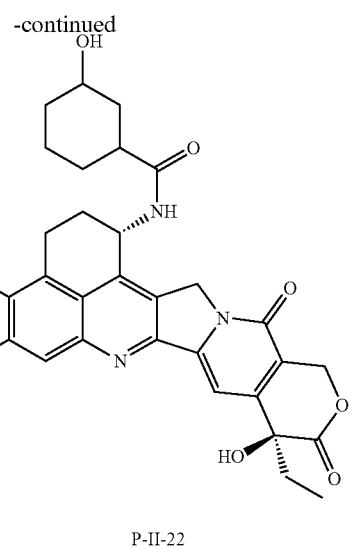

P-II-22

Step 1

13a (22 mg, 0.15 mmol), KI4 (90 mg, 0.17 mmol) and HATU (68 mg, 0.18 mmol) were added to a 25 mL three-necked flask and dissolved with DMF (2 mL), followed by the slow addition of DIEA (58 mg, 0.45 mmol). After the reaction was completed as detected by LCMS, the reaction solution was purified by reverse-phase column chromatography to give the compound P-II-22 (52 mg, yield 55%).

MS-ESI: m/z 562.3 [M+H]+.

1H NMR (400 MHz, DMSO-d6) δ 8.45-8.32 (m, 1H), 7.78 (dd, J=11.0, 3.5 Hz, 1H), 7.29 (d, J=2.2 Hz, 1H), 6.52 (s, 1H), 5.59-5.49 (m, 1H), 5.42 (s, 2H), 5.27-5.01 (m, 2H), 3.24-3.08 (m, 2H), 2.71-2.54 (m, 1H), 2.39 (s, 3H), 2.29-2.04 (m, 3H), 1.95-1.61 (m, 6H), 1.48-0.98 (m, 4H), 0.87 (t, J=7.3 Hz, 3H).

Preparation Example 1.14. N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-4-hydroxybenzamide-1-carboxamide

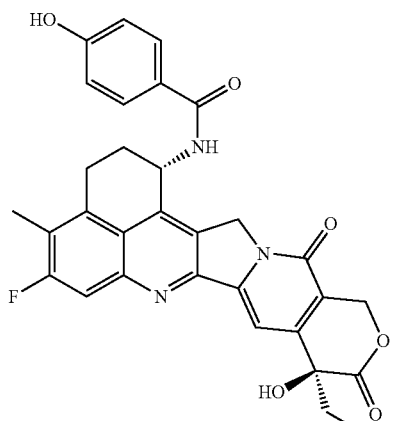

P-II-23

-continued

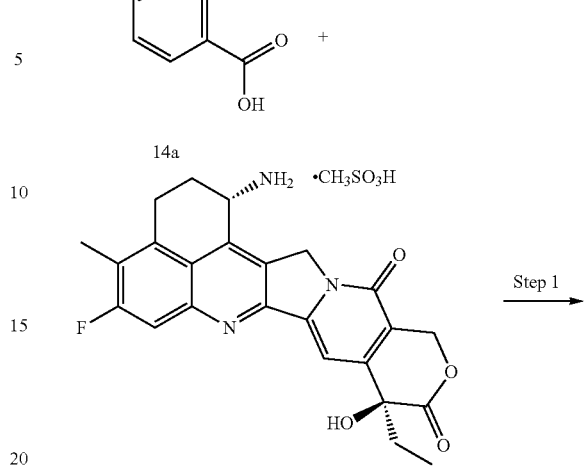

Step 1

14a (31 mg, 0.169 mmol), KI4 (100 mg, 0.188 mmol) and HATU (78 mg, 0.206 mmol) were added to a 25 mL three-necked flask and dissolved with DMF (4 mL), followed by the slow addition of DIEA (67 mg, 0.516 mmol). After the reaction was completed as detected by LCMS, the reaction solution was purified by reverse-phase column chromatography to give the compound 14b (40 mg, yield 35%). MS-ESI: m/z 600.2 [M+H]+.

Step 2

14b (40 mg, 0.067 mmol) was added to a 25 mL three-necked flask, and found to be insoluble after the addition of ethyl acetate (30 mL) purged with hydrochloric acid gas, and then dissolved after the dropwise addition of methanol (2 mL). The solution was stirred for 1 h, and dried by rotary evaporation in vacuum under a water pump. After the reaction was completed as detected by LCMS, the reaction solution was purified by reverse-phase column chromatography to give the compound P-II-23 (9 mg, yield 24%).

MS-ESI: m/z 556.3 [M+H]+.

1H NMR (400 MHz, DMSO-d6) δ 10.03 (s, 1H), 8.76 (d, J=8.5 Hz, 1H), 7.85-7.77 (m, 3H), 7.30 (s, 1H), 6.80 (d, J=8.8 Hz, 2H), 6.52 (s, 1H), 5.78-5.72 (m, 1H), 5.37 (s, 2H), 5.19 (d, J=18.8 Hz, 1H), 5.09 (d, J=19.0 Hz, 1H), 3.27-3.10 (m, 2H), 2.43-2.38 (m, 3H), 2.30-2.18 (m, 2H), 1.90-1.77 (m, 2H), 0.85 (t, J=7.3 Hz, 3H).

Preparation Example 1.15. N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-5-hydroxypicolinamide

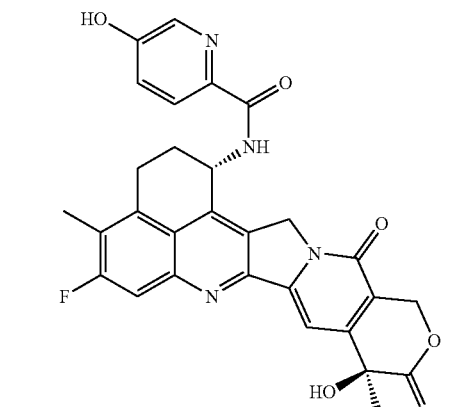

P-II-24

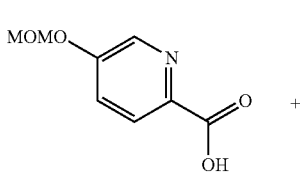

15a

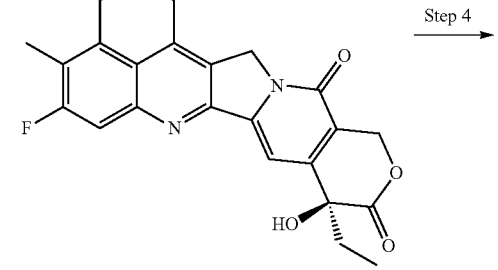

15b

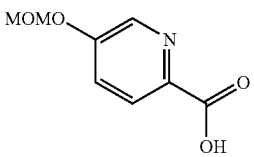

15c

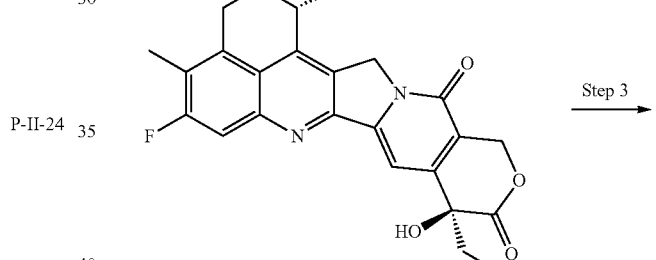

15c

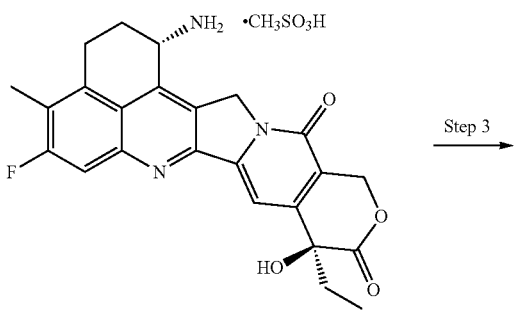

KI4

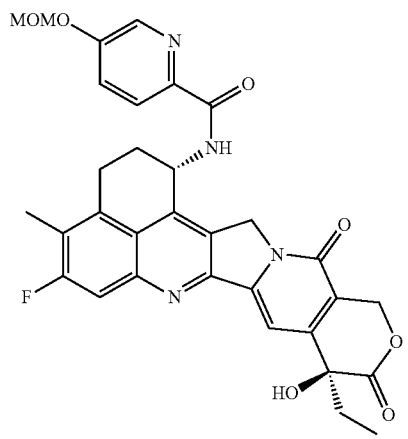

15d

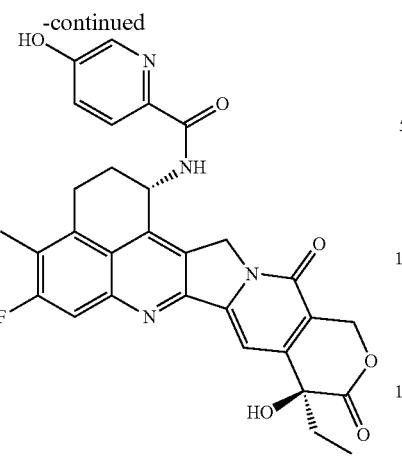

P-II-24

Step 1

MOMBr (195 mg, 1.6 mmol) was added to an ice bath-cooled solution of 15a (200 mg, 1.3 mmol) and DIEA (336 mg, 2.6 mmol) in THF (6.5 mL) under $N_2$ atmosphere. The reaction solution was stirred at 0° C. for 3 h. After the reaction was completed, the reaction solution was added with MeOH (10 mL) at 0° C. and stirred for 20 min. The reaction solution was concentrated to give a pale yellow oil, which was purified by silica gel column chromatography (PE/EA=20/1-10/1) to give 15b (240 mg, yield 93%) as a pale yellow solid.

Step 2

NaOH (1 M in water, 2.2 mL, 2.2 mmol) was added dropwise to a solution of 15b (220 mg, 1.1 mmol) in THF (5.0 mL) in an ice-water bath under $N_2$ atmosphere, and the reaction solution was stirred at the same temperature for 1.5 h. After the reaction was completed, the reaction solution was adjusted to pH 2-3 at 0° C. with diluted hydrochloric acid (1 M in water), and concentrated to give a yellow oil, which was dissolved with DCM (10 mL) and filtered and the filter cake was washed with DCM (15 mL). The filtrate was concentrated to give 15c (205 mg) as a pale yellow oil, which was directly used in the next step.

Step 3

HATU (173 mg, 0.46 mmol) was added to a suspension of 15c (76 mg, 0.42 mmol), KI4 (185 mg, 0.35 mmol) and DIEA (136 mg, 1.05 mmol) in DMF (4.0 mL) at 0° C. under $N_2$ atmosphere. The reaction solution was stirred for 3 h to give a clear reaction solution. After the reaction was completed as detected by TLC, the reaction was added dropwise into water (10 mL), and a large amount of yellow solid was precipitated. The resulting mixture was filtered to give 15d (85 mg, yield 40%) as a yellow solid.

Step 4

31d (80 mg, 0.13 mmol) was dissolved in a mixed solution of TFA/DCM (2/1) in an ice-water bath under $N_2$ atmosphere, and the reaction solution was stirred for 0.5 h, concentrated, separated by prep-HPLC, and lyophilized to give P-II-24 (22 mg, yield 31%) as a yellow powder.

MS-ESI: m/z 557.3 [M+H]+.

1H NMR (400 MHz, DMSO-d6) δ 10.75 (brs, 1H), 9.24 (d, J=9.1 Hz, 1H), 8.14 (d, J=2.7 Hz, 1H), 8.02 (d, J=8.6 Hz, 1H), 7.77 (d, J=10.9 Hz, 1H), 7.37 (dd, J=8.6, 2.7 Hz, 1H), 7.28 (s, 1H), 5.76-5.66 (m, 1H), 5.34 (s, 2H), 5.18 (d, J=19.1 Hz, 1H), 5.04 (d, J=19.0 Hz, 1H), 3.32-3.24 (m, 1H), 3.19-3.08 (m, 1H), 2.38 (s, 3H), 2.36-2.20 (m, 2H), 1.92-1.75 (m, 2H), 0.85 (t, J=7.3 Hz, 3H).

Preparation Example 1.16. N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3-methylaminopropanamide

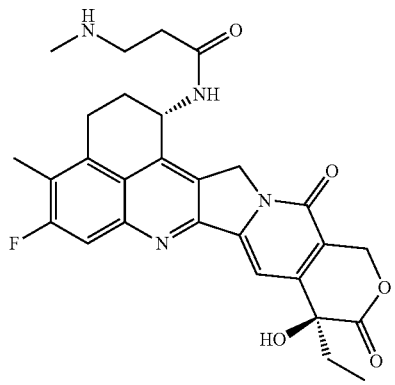

P-III-9

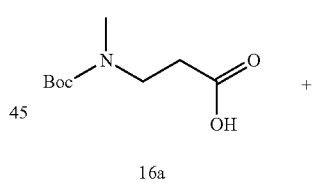

16a

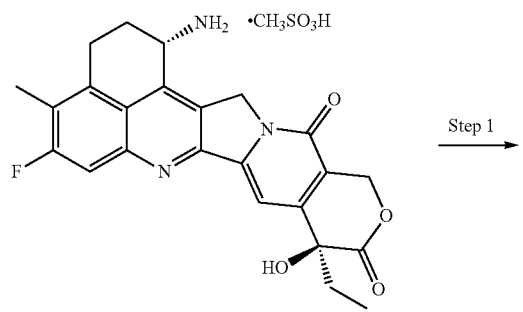

KI4

Step 1

-continued

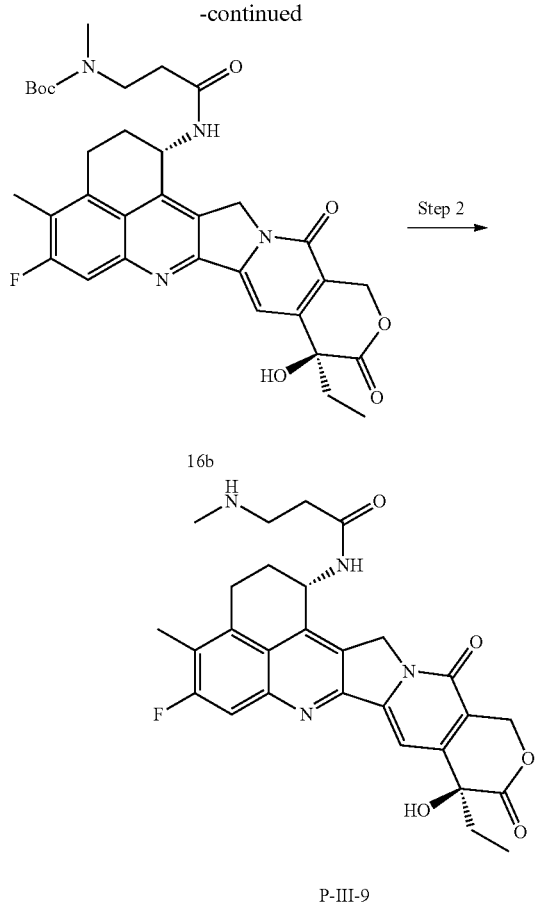

16b

P-III-9

Step 1

KI4 (100 mg, 0.188 mmol), 16a (42 mg, 0.207 mmol) and HATU (86 mg, 0.226 mmol) were added to DMF (2 mL), followed by the addition of DIEA (73 mg, 0.564 mmol), and the mixture was reacted at room temperature for 1 h. After the reaction was completed as detected by LCMS, the reaction was added dropwise to water (20 mL), and a solid was precipitated. The resulting mixture was filtered, and the filter cake was washed with water (20 mL×2) and lyophilized to give 32b (100 mg, yield 86%) as a gray powder. MS-ESI: m/z 621.3 [M+H]+.

Step 2

16b (25 mg, 0.040 mmol) was added to DCM (2 mL), and the mixture was cooled to 0° C., added with TFA (0.5 mL) and reacted at 0° C. for 1.5 h. After the reaction was completed as detected by LCMS, the reaction solution was dried by rotary evaporation at low temperature to remove DCM and TFA, and the residue was added with water (10 mL) and MeCN (2 mL) and lyophilized to give P-III-9 (23 mg, yield 90%) as a yellow powder.
MS-ESI: m/z 521.3 [M+H]+.
1H NMR (400 MHz, DMSO-d6) δ 8.71 (d, J=8.6 Hz, 1H), 8.43 (brs, 2H), 7.81 (d, J=11.0 Hz, 1H), 7.31 (s, 1H), 6.55 (brs, 1H), 5.58 (dt, J=8.8, 4.5 Hz, 1H), 5.42 (s, 2H), 5.28 (d, J=18.9 Hz, 1H), 5.21 (d, J=18.9 Hz, 1H), 3.25-3.12 (m, 4H), 2.62-2.53 (m, 5H), 2.40 (s, 3H), 2.26-2.06 (m, 2H), 1.94-1.78 (m, 2H), 0.87 (t, J=7.3 Hz, 3H).

Preparation Example 1.17. N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-2-mercaptoacetamide

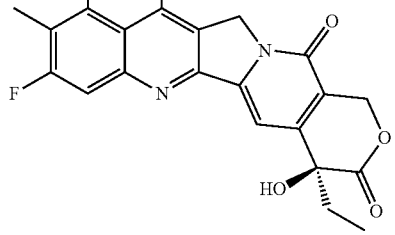

P-III-1

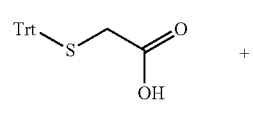

17a

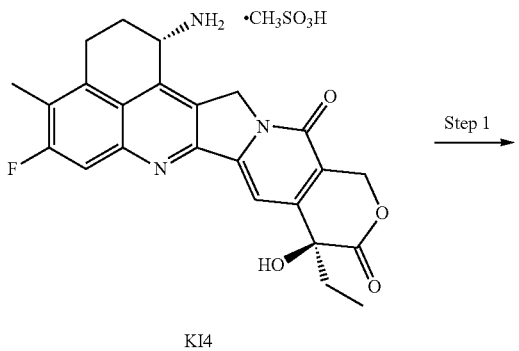

KI4

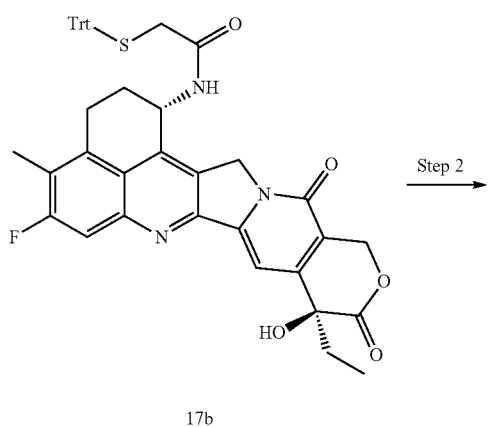

17b

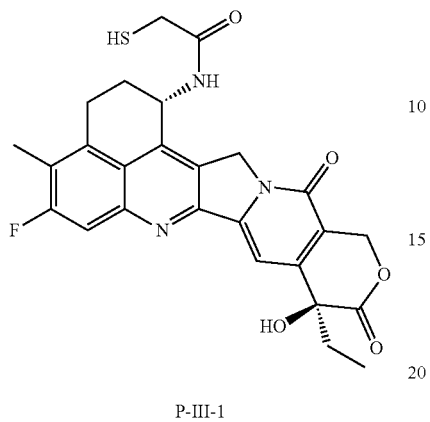

P-III-1

Step 1

17a (118 mg, 0.353 mmol), KI4 (200 mg, 0.376 mmol) and HATU (160 mg, 0.421 mmol) were added to a 25 mL three-necked flask and dissolved with DMF (6 mL), followed by the slow addition of DIEA (133 mg, 1.03 mmol). After the reaction was completed as detected by LCMS, the reaction solution was slowly poured into water (50 mL), and the resulting mixture was filtered to give a white solid, which was dried in vacuum to give the product 17b (200 mg, yield 71%). MS-ESI: m/z 752.4 [M+H]+.

Step 2

17b (200 mg, 0.266 mmol) was added to a 25 mL three-necked flask, and found to be insoluble after the addition of ethyl acetate (50 mL) purged with hydrochloric acid gas, and then dissolved after the dropwise addition of methanol (5 mL). The solution was stirred for 1 h, and dried by rotary evaporation in vacuum under a water pump. After the reaction was completed as detected by LCMS, the reaction solution was purified by reverse-phase column chromatography to give the compound P-III-1 (14 mg, yield 10%).

MS-ESI: m/z 510.1 [M+H]+.

1H NMR (400 MHz, DMSO-d6) δ 8.67-8.59 (m, 1H), 7.81 (d, J=11.0 Hz, 1H), 7.33-7.29 (m, 1H), 6.53 (brs, 1H), 5.54 (dt, J=8.7, 4.5 Hz, 1H), 5.43 (s, 2H), 5.30 (d, J=19.0 Hz, 1H), 5.20 (d, J=19.0 Hz, 1H), 3.20-3.09 (m, 4H), 2.86 (t, J=8.1 Hz, 1H), 2.41 (s, 3H), 2.25-2.05 (m, 2H), 1.93-1.77 (m, 2H), 0.91-0.83 (m, 3H).

Preparation Example 1.18. N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3-hydroxyhexanamide

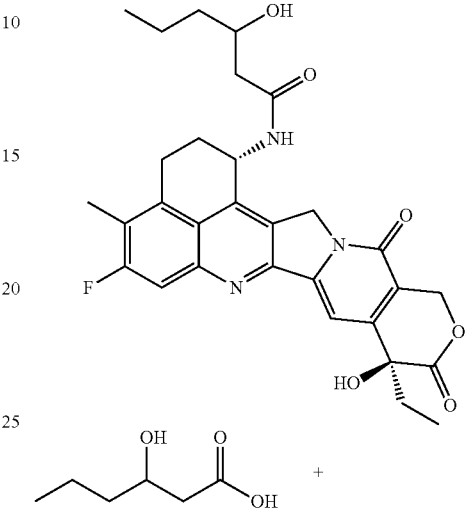

P-III-27

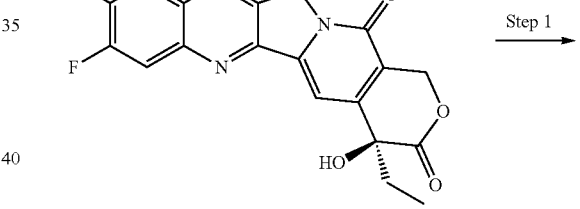

18a

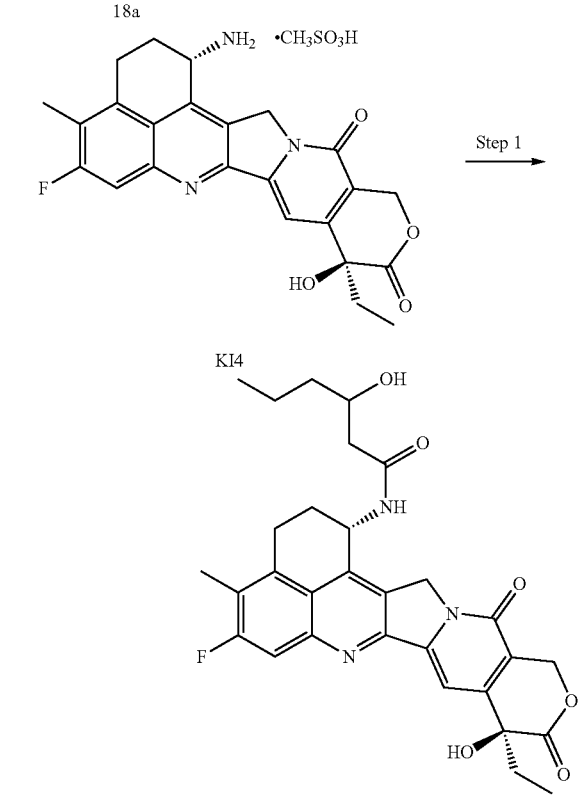

KI4

P-III-27

Step 1

KI4 (50 mg, 0.094 mmol), 18a (14 mg, 0.106 mmol) and HATU (43 mg, 0.113 mmol) were added to DMF (1 mL), followed by the addition of DIEA (36 mg, 0.278 mmol), and the mixture was reacted at room temperature for 1 h. After the reaction was completed as detected by LCMS, the reaction solution was added dropwise to water (10 mL), and a solid was precipitated. The resulting mixture was filtered, purified by preparative chromatography and lyophilized to give P-III-27 (18 mg, yield 35%) as a yellow solid.

MS-ESI: m/z 550.3 [M+H]+.

1H NMR (400 MHz, DMSO-d6) δ 8.40 (dd, J=8.7, 2.5 Hz, 1H), 7.79 (d, J=10.7 Hz, 1H), 7.30 (d, J=1.2 Hz, 1H), 6.53 (brs, 1H), 5.60-5.52 (m, 1H), 5.42 (s, 2H), 5.30-5.15 (m, 2H), 3.92-3.83 (m, 1H), 3.23-3.10 (m, 2H), 2.44-2.36 (m, 3H), 2.23 (t, J=6.6 Hz, 2H), 2.20-2.03 (m, 2H), 1.94-1.78 (m, 2H), 1.41-1.19 (m, 4H), 0.92-0.77 (m, 6H).

Preparation Example 1.19. N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-4-hydroxy-3-oxobutanamide

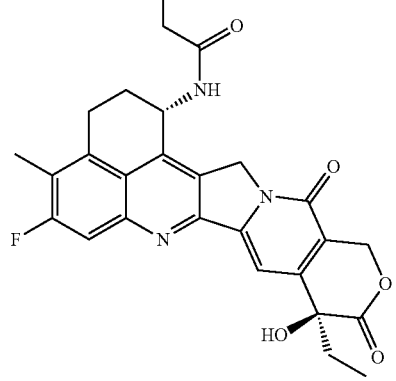

P-III-22

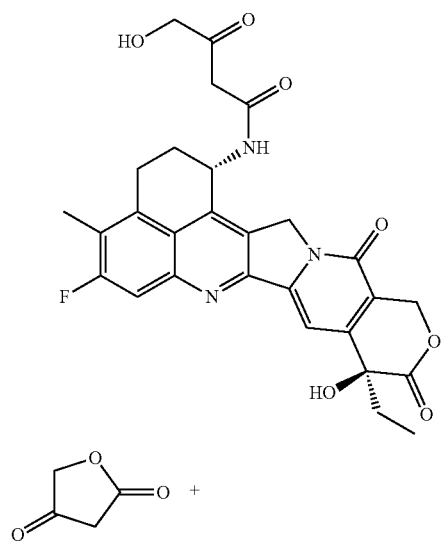

P-III-22

Step 1

KI4 (50 mg, 0.094 mmol) and 19a (28.2 mg, 0.282 mmol) were dissolved in DMA (4 mL), followed by the addition of DIEA (60.7 mg, 0.470 mmol). The mixture was reacted at 20° C. for 1 h under nitrogen atmosphere, and then warmed to 80° C. and reacted for 17 h. After the reaction was completed as detected by LCMS, the product MS-18 was obtained, which was then purified by preparative chromatography to give P-III-22 (10 mg, yield 20%) as a yellow solid.

MS-ESI: m/z 518.2 [M+H-H$_2$O]+.

1H NMR (400 MHz, DMSO-d6) δ 7.97 (s, 1H), 7.82 (d, J=10.9 Hz, 1H), 7.32 (s, 1H), 6.54 (brs, 1H), 5.42 (s, 2H), 5.36 (d, J=19.0 Hz, 1H), 5.24-5.11 (m, 2H), 5.03 (s, 1H), 4.66 (s, 2H), 3.31-3.06 (m, 3H), 2.43-2.37 (m, 3H), 2.35-2.23 (m, 1H), 2.22-2.08 (m, 1H), 1.93-1.79 (m, 2H), 0.87 (t, J=7.3 Hz, 3H).

Preparation Example 1.20. (S)-3-amino-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)butanamide

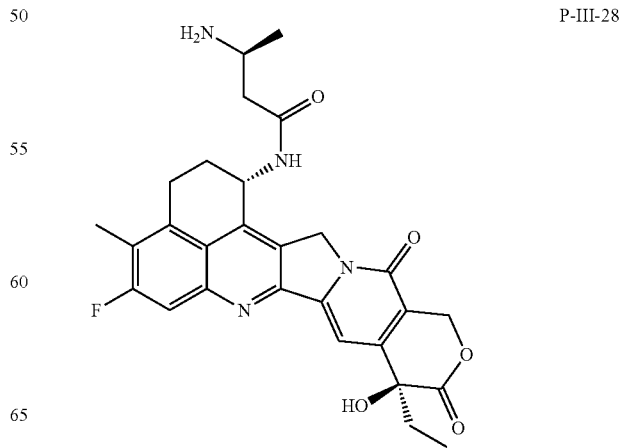

P-III-28

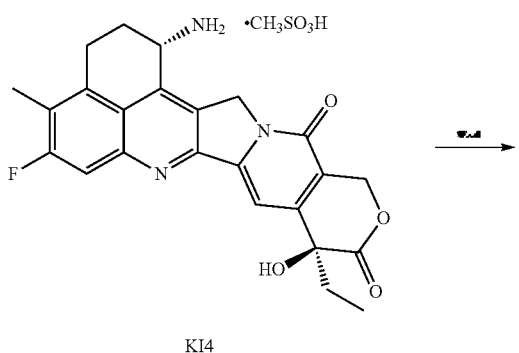

KI4

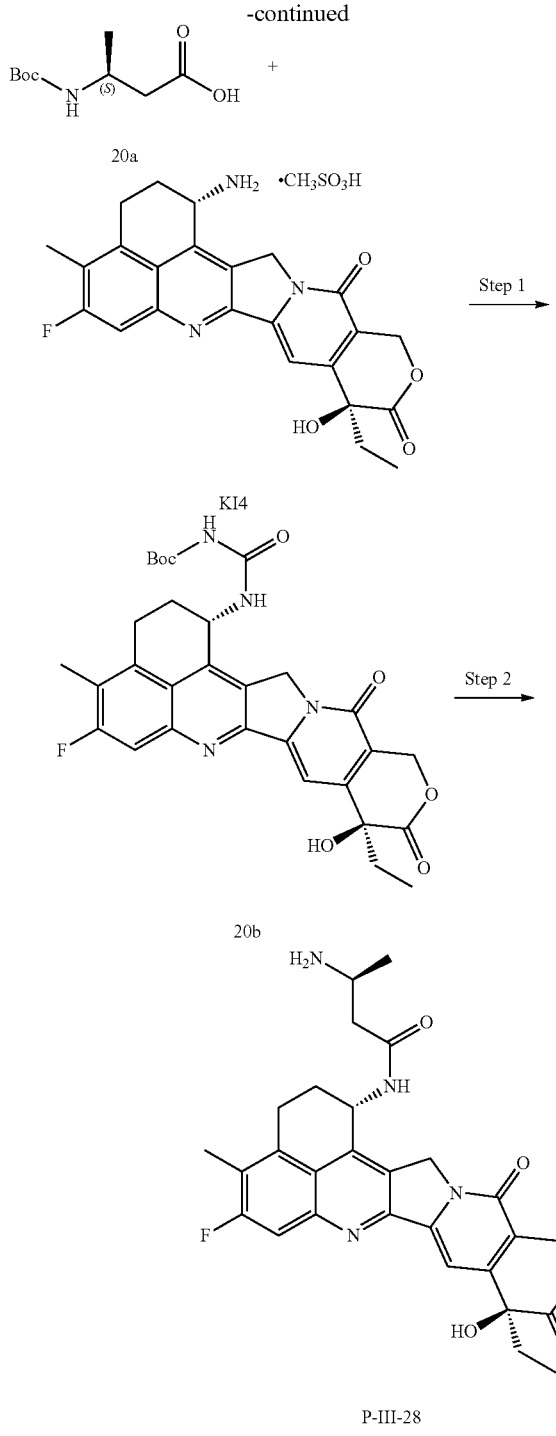

20a

KI4

20b

P-III-28 was filtered, and the solid was lyophilized to give 20b (89 mg, yield 76%) as a yellow solid. MS-ESI: m/z 621.3 [M+H]+.

Step 2

20b (40 mg, 0.0644 mmol) was dissolved in DCM (2 mL), and the mixture was cooled to 0° C. under nitrogen atmosphere, added dropwise with TFA (0.5 mL) and reacted at 0° C. for 1.5 h after the addition was completed. After the starting material was consumed completely as detected by LCMS, the reaction solution was dried by rotary evaporation, added with acetonitrile and water and lyophilized to give P-III-28 (28.8 mg, yield 86%) as a yellow solid.

MS-ESI: m/z 521.3 [M+H]+.

1H NMR (400 MHz, DMSO-d6) δ 8.74 (d, J=8.5 Hz, 1H), 7.90-7.77 (m, 4H), 7.32 (s, 1H), 6.54 (brs, 1H), 5.57 (dt, J=9.0, 4.6 Hz, 1H), 5.42 (s, 2H), 5.28 (d, J=18.9 Hz, 1H), 5.19 (d, J=18.9 Hz, 1H), 3.62-3.53 (m, 2H), 3.24-3.12 (m, 2H), 2.48-2.38 (m, 4H), 2.25-2.07 (m, 2H), 1.94-1.79 (m, 2H), 1.28-1.18 (m, 4H), 0.87 (t, J=7.3 Hz, 3H).

Preparation Example 1.21. (2S,4R)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-4-hydroxypyrrolidine-2-carboxamide

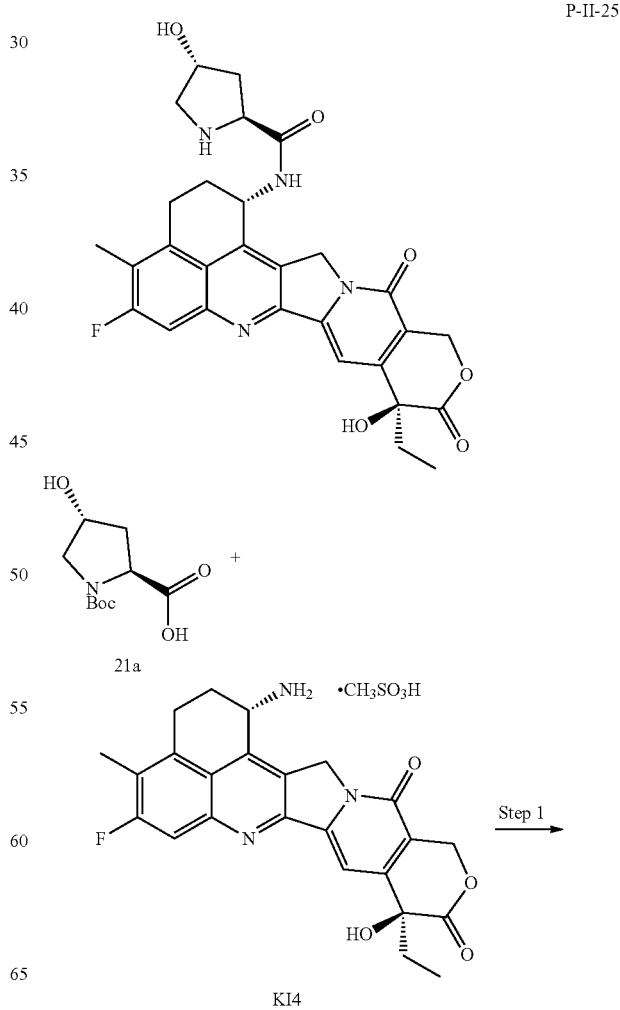

P-II-25

21a

KI4

Step 1

KI4 (100 mg, 0.188 mmol) and 20a (42 mg, 0.207 mmol) were dissolved in DMF (5 mL), followed by the addition of DIEA (73 mg, 0.564 mmol). The mixture was cooled to 0° C. under nitrogen atmosphere, added with HATU (93 mg, 0.244 mmol) and reacted at 0° C. for 2 h. After the starting material was consumed completely as detected by TLC (EA/MeOH=10/1), the reaction solution was added to water (60 mL), and a solid was precipitated. The resulting mixture -continued

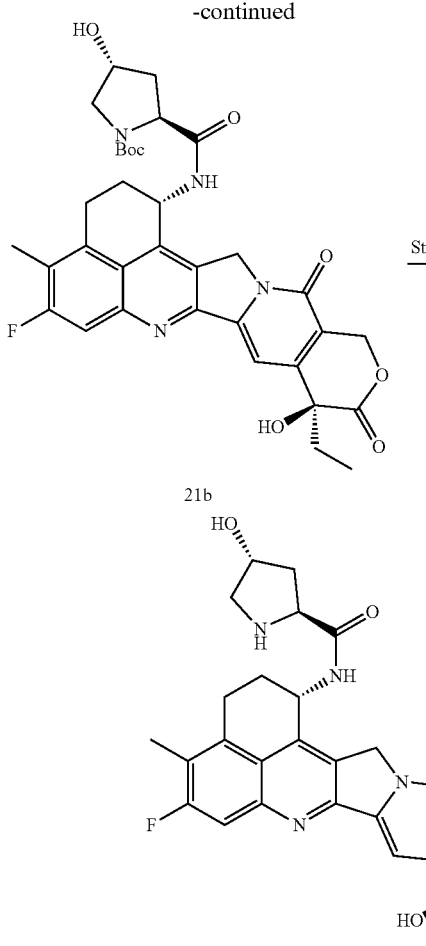

21b

P-II-25

Step 1

KI4 (100 mg, 0.188 mmol) and 21a (48 mg, 0.207 mmol) were dissolved in DMF (5 mL), followed by the addition of DIEA (73 mg, 0.564 mmol). The mixture was cooled to 0° C. under nitrogen atmosphere, added with HATU (93 mg, 0.244 mmol) and reacted at 0° C. for 2 h. After the reaction was completed as detected by TLC (EA/MeOH=10/1), the reaction was added to water (60 mL), and a solid was precipitated. The resulting mixture was filtered, and the solid was lyophilized to give 21b (72 mg, yield 59%) as a yellow solid. MS-ESI: m/z 649.3 [M+H]+.

Step 2

21b (60 mg, 0.0925 mmol) was dissolved in DCM (2 mL), and the mixture was cooled to 0° C. under nitrogen atmosphere, added dropwise with TFA (0.5 mL) and reacted at 0° C. for 1.5 h after the addition was completed. After the starting material was consumed completely as detected by LCMS, the reaction solution was dried by rotary evaporation, added with acetonitrile and water and lyophilized to give P-II-25 (45.8 mg, yield 90%) as a yellow solid.
MS-ESI: m/z 5493 [M+H]+.
1H NMR (400 MHz, DMSO-d6) δ 9.65 (brs, 1H), 9.14 (d, J=8.6 Hz, 1H), 8.85 (brs, 1H), 7.82 (d, J=10.9 Hz, 1H), 7.32 (s, 1H), 6.54 (brs, 1H), 5.62 (dt, J=9.0, 4.7 Hz, 1H), 5.42 (s, 2H), 5.27 (d, J=18.7 Hz, 1H), 5.09 (d, J=18.7 Hz, 1H), 4.48-4.41 (m, 1H), 4.39-4.27 (m, 1H), 3.26-3.08 (m, 3H), 2.41 (s, 3H), 2.31-2.13 (m, 3H), 2.02-1.92 (m, 1H), 1.92-1.79 (m, 2H), 1.30-1.20 (m, 2H), 0.88 (t, J=7.3 Hz, 3H).

Preparation Example 1.22. (R)-3-amino-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-4-hydroxybutanamide

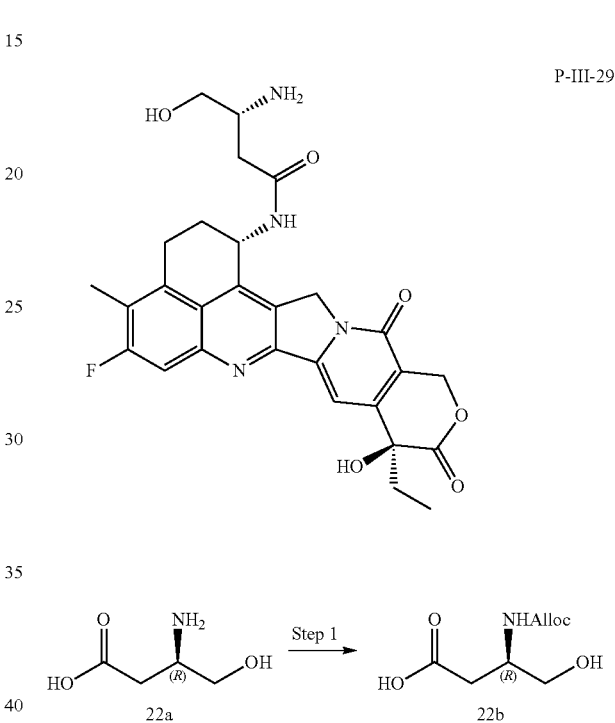

P-III-29

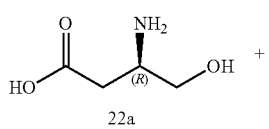

22a     22b

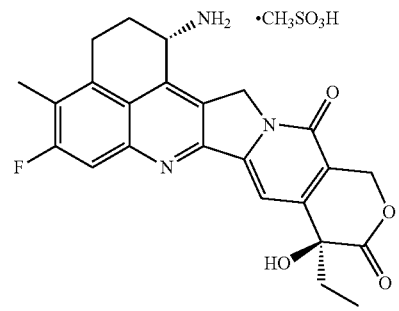

KI4

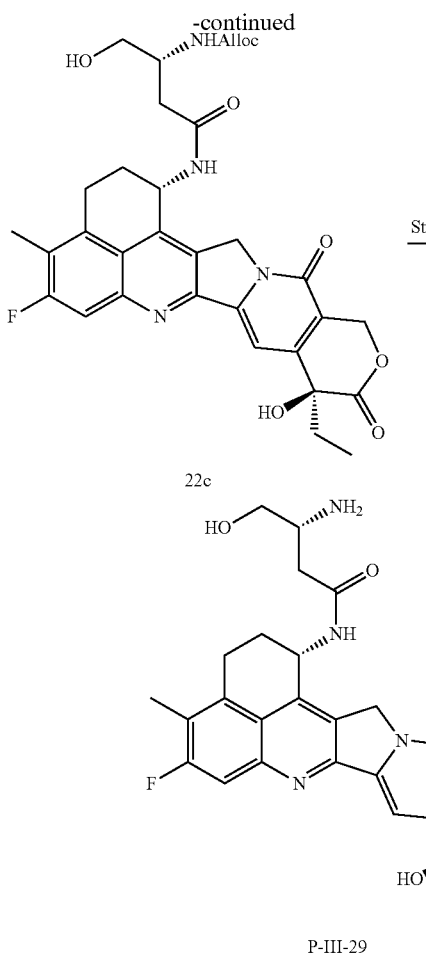

22c

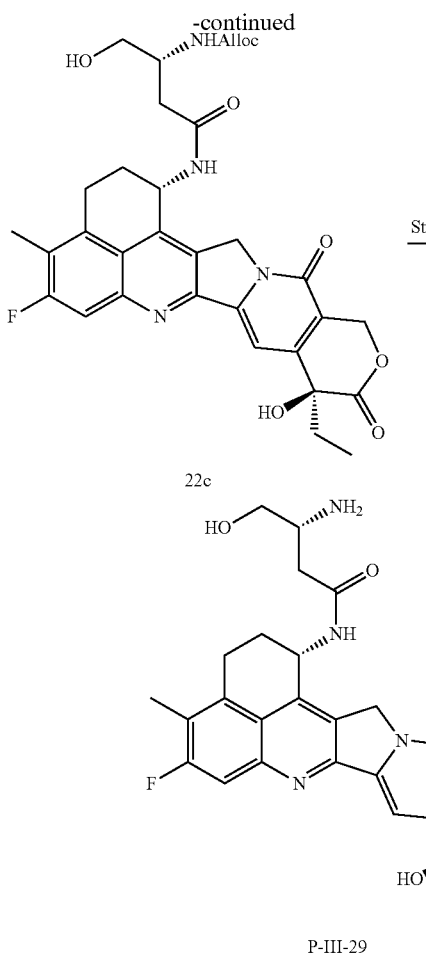

P-III-29

Step 1

22a (200 mg, 1.68 mmol) was dissolved in saturated NaHCO₃ solution (4 mL) and THF (1 mL). The solution was reacted overnight. After the product was generated as detected by LCMS, the product was purified by reverse-phase column chromatography and lyophilized to give 22b (200 mg, 59%) as a white solid. MS-ESI: m/z 203.6 [M+H]+.

Step 2

22b (76 mg, 0.375 mmol), KI4 (200 mg, 0.375 mmol) and HATU (170 mg, 0.450 mmol) were added to a 25 mL three-necked flask and dissolved with DMF (4 mL), followed by the slow addition of DIEA (145 mg, 1.125 mmol). After the reaction was completed as detected by LCMS, the reaction solution was purified by reverse-phase column chromatography and lyophilized to give the compound 22c (40 mg, yield 17%). MS-ESI: m/z 621.2 [M+H]+.

Step 3

Compound 22c (40 mg, 0.0645 mmol) and Pd(PPh₃)₄ (22 mg, 0.0194 mmol) were added to a 25 mL three-necked flask and dissolved with THF (4 mL). The solution was added dropwise with N-methylmorpholine (0.2 mL) under nitrogen atmosphere, and reacted for 0.5 h. After the reaction was completed as detected by LCMS, the reaction solution was purified by reverse-phase column chromatography (ACN in water from 30%-70%), and lyophilized to give P-III-29 (14.3 mg, yield 41%) as a yellow powder.

MS-ESI: m/z 537.2 [M+H]+.

1H NMR (400 MHz, DMSO-d6) δ 8.68 (d, J=8.5 Hz, 1H), 7.95-7.82 (m, 3H), 7.81 (d, J=10.9 Hz, 1H), 7.32 (s, 1H), 6.55 (s, 1H), 5.56 (dt, J=8.8, 4.5 Hz, 1H), 5.42 (s, 2H), 5.30 (d, J=18.9 Hz, 1H), 5.22 (d, J=18.9 Hz, 1H), 3.60 (dd, J=10.6, 3.6 Hz, 1H), 3.55-3.45 (m, 3H), 3.22-3.13 (m, 2H), 2.56-2.52 (m, 1H), 2.48-2.44 (m, 1H), 2.44-2.37 (m, 3H), 2.26-2.05 (m, 2H), 1.95-1.77 (m, 2H), 0.87 (t, J=7.3 Hz, 3H).

Preparation Example 1.23. (S)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3-hydroxybutanamide

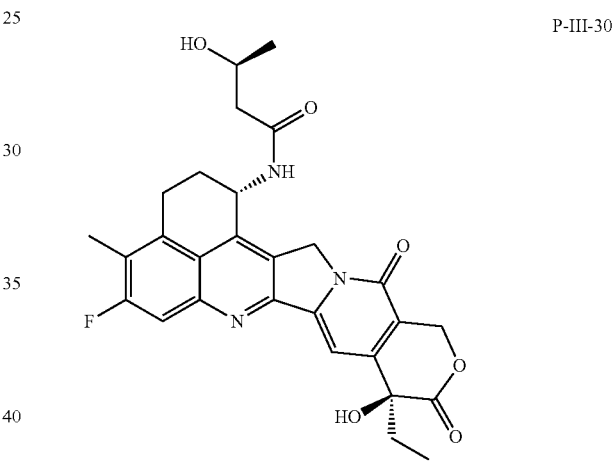

P-III-30

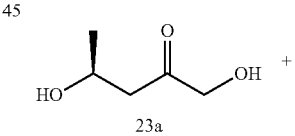

23a

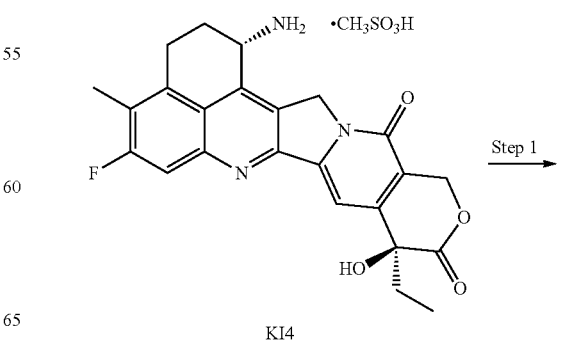

KI4

-continued

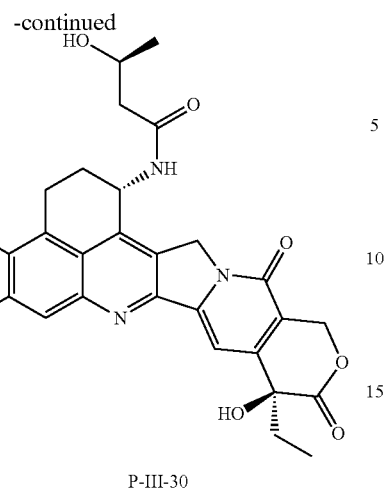

P-III-30

Step 1

DIEA (60.6 mg, 0.47 mmol) was added dropwise to a solution of KI4 (100 mg, 0.19 mmol), HATU (85.7 mg, 0.23 mmol) and 23a (21.5 mg, 0.21 mmol) in DMF (2 mL) under nitrogen atmosphere. After the addition was completed, the mixture was stirred at 0° C. for 2 h. After the starting material was consumed completely as detected by LCMS, the reaction solution was added dropwise to water (20 mL) and stirred, and a solid was precipitated. The resulting mixture was filtered to give P-III-30 (60.2 mg, yield 61%) as a gray solid. MS-ESI: m/z 522.2 [M+H]+.

1H NMR (400 MHz, DMSO-d6) δ 8.42 (d, J=8.7 Hz, 1H), 7.79 (d, J=11.0 Hz, 1H), 7.30 (s, 1H), 6.53 (s, 1H), 5.62-5.53 (m, 1H), 5.42 (s, 2H), 5.30-5.16 (m, 2H), 4.63 (d, J=4.6 Hz, 1H), 4.09-3.99 (m, 1H), 3.22-3.11 (m, 2H), 2.40 (s, 3H), 2.28 (dd, J=13.7, 7.2 Hz, 1H), 2.22-2.08 (m, 3H), 1.94-1.78 (m, 2H), 1.08 (d, J=6.1 Hz, 3H), 0.87 (t, J=7.3 Hz, 3H).

Preparation Example 1.24. N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3-hydroxybutanamide

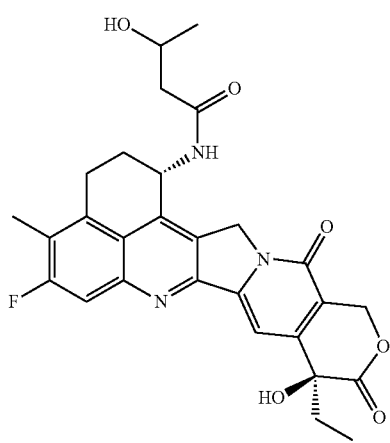

P-III-31

-continued

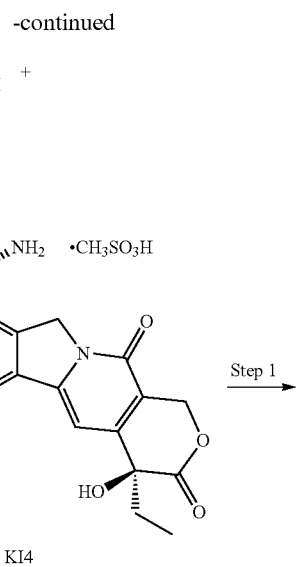

24a

KI4

Step 1

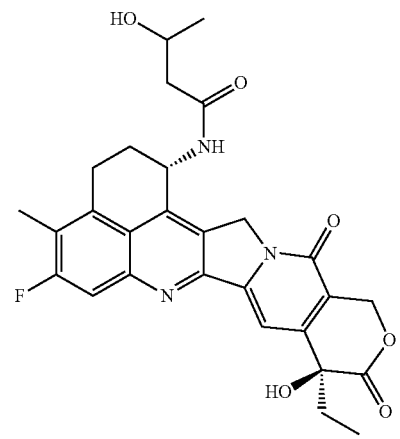

P-III-31

Step 1

24a (19.6 mg, 0.188 mmol), KI4 (100 mg, 0.188 mmol) and DIEA (60.7 mg, 0.47 mmol) were added to a three-necked flask (100 mL), and dissolved with DMF (2 mL). The solution was purged with N₂ three times, added with HATU (85.9 mg, 0.226 mmol) with stirring at 0° C. and reacted at 0° C. for 2 hours. After the reaction was completed as detected by TLC (DCM:MeOH=10:1), the reaction solution was added to water (20 mL), and a gray solid was precipitated, lyophilized and purified on a preparation plate (EA:MeOH=10:1) to give P-III-31 (54.5 mg, yield 56%) as a pale yellow solid. MS-ESI: m/z 522.5 [M+H]+.

1H NMR (400 MHz, DMSO-d6) δ 8.44 (dd, J=8.7, 2.9 Hz, 1H), 7.78 (dd, J=10.9, 2.6 Hz, 1H), 7.30 (s, 1H), 6.53 (s, 1H), 5.60-5.51 (m, 1H), 5.42 (s, 2H), 5.21 (dd, J=10.9, 3.4 Hz, 1H), 4.66 (dd, J=13.1, 4.7 Hz, 1H), 4.10-3.98 (m, 1H), 3.21-3.10 (m, 2H), 2.39 (s, 3H), 2.34-2.05 (m, 4H), 1.93-1.77 (m, 2H), 1.08 (dd, J=6.2, 1.6 Hz, 3H), 0.87 (t, J=7.3 Hz, 3H).

Preparation Example 1.25. (1R,4R)-4-(((S)-7-benzyl-20-(2,5-dioxo-2,5-dihydro-1H-pyrrol-1-yl)-3,6,9,12,15-pentaoxo-2,5,8,11,14-pentaazaicosyl)oxy)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclohexane-1-carboxamide
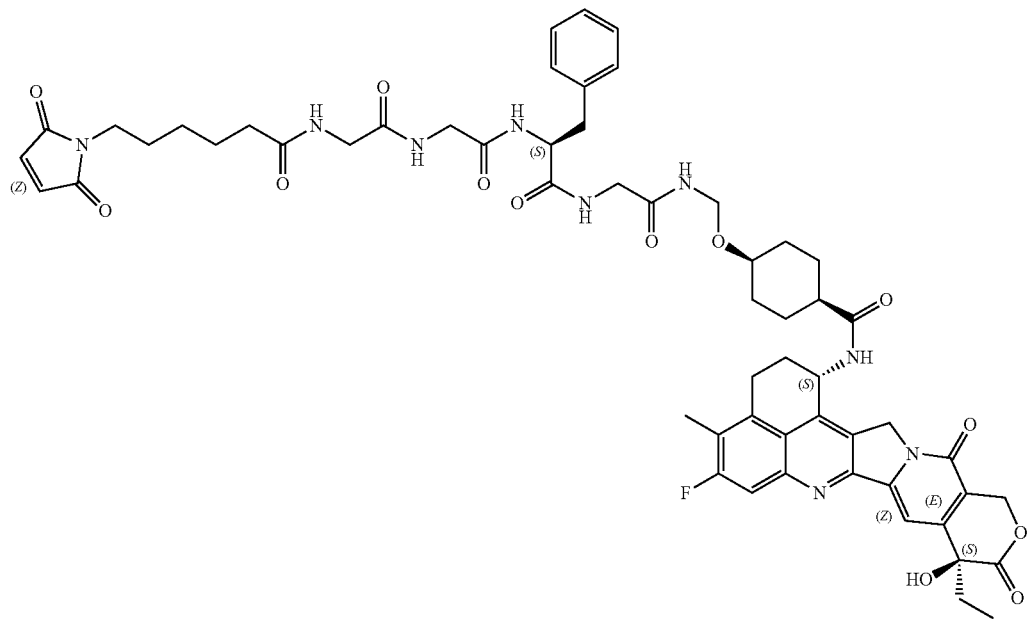
L-II-1
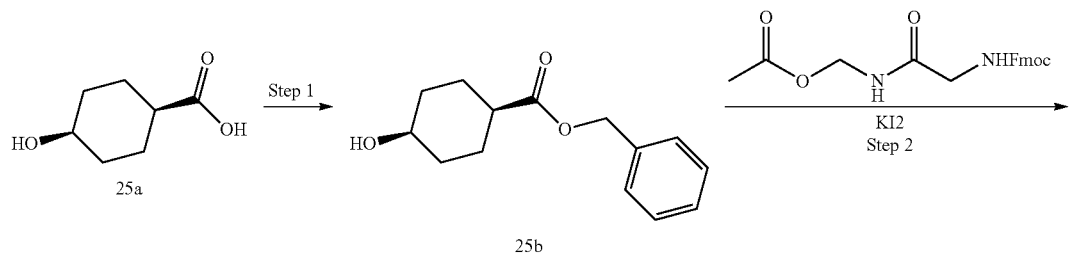
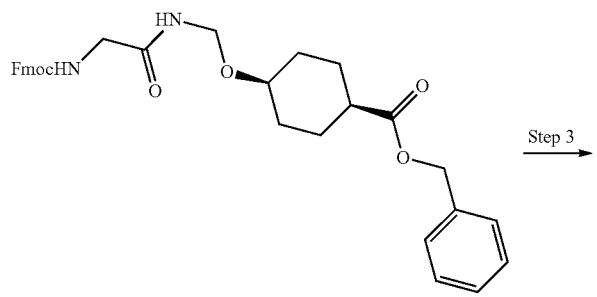

-continued
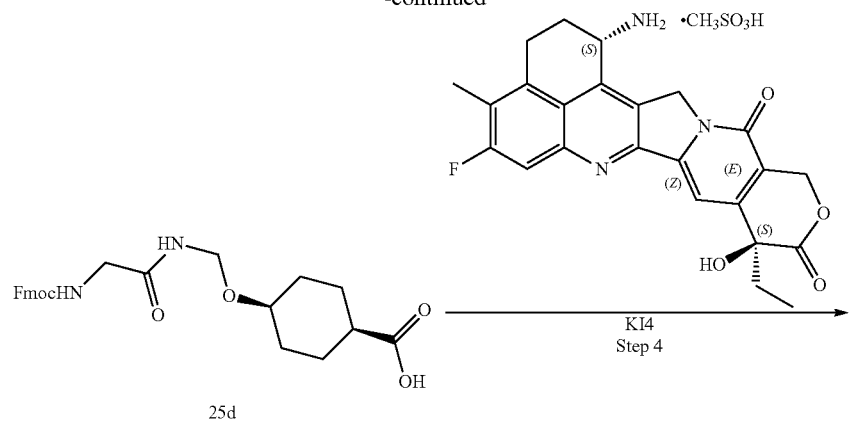
25d
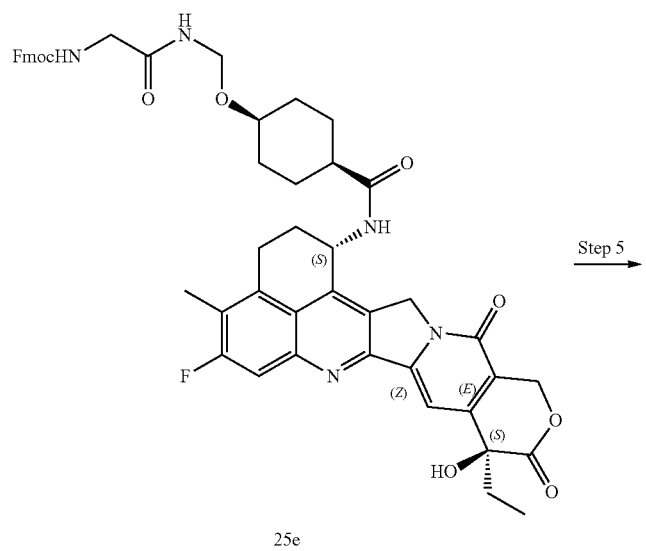
25e
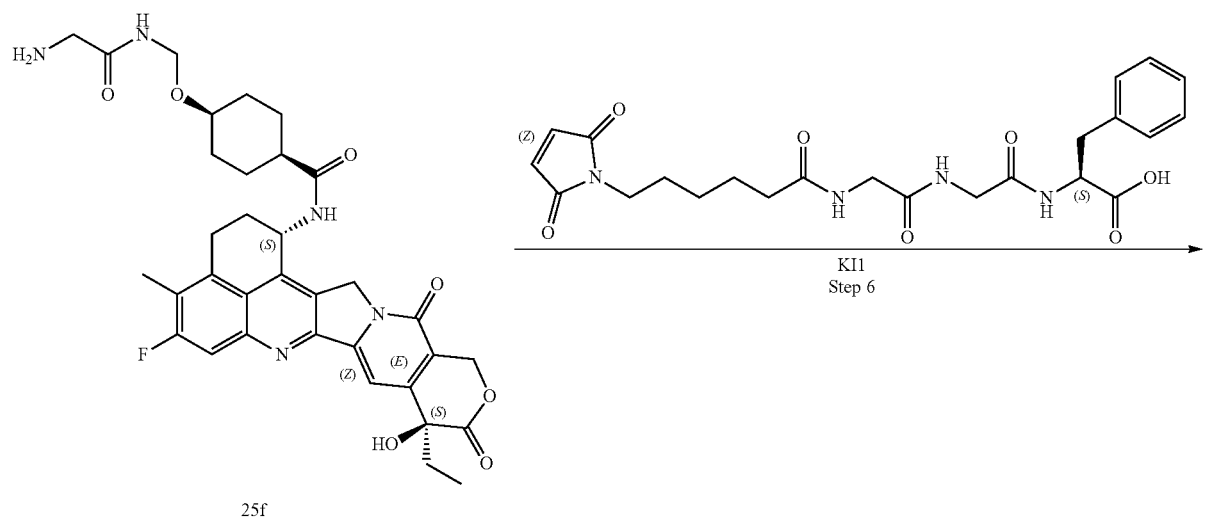
25f

-continued

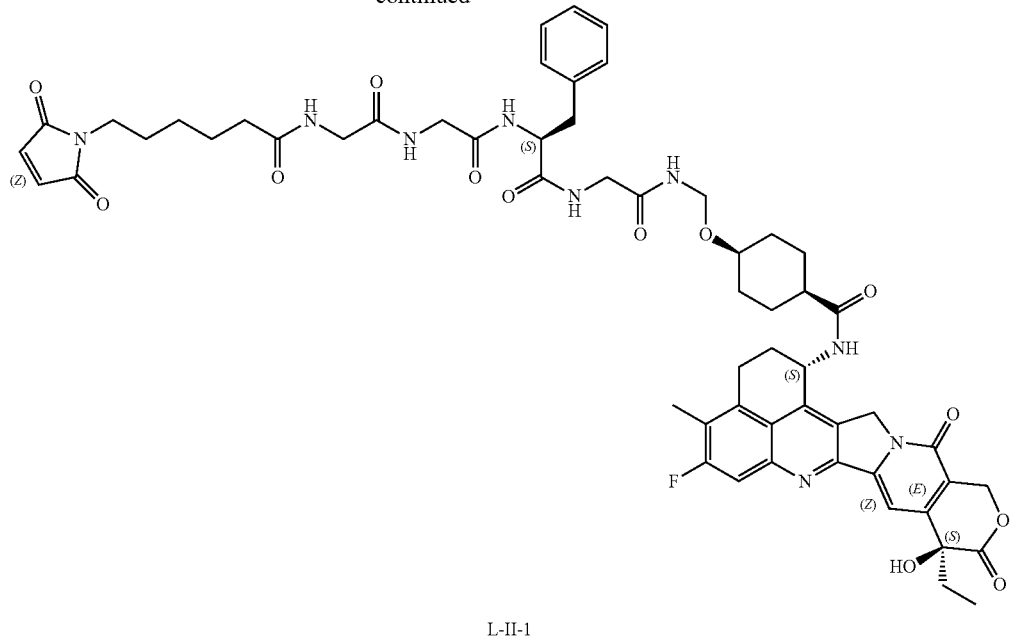

L-II-1

Step 1

Benzyl bromide (8.90 g, 52.1 mmol) was added dropwise to a solution of 25a (5.00 g, 34.7 mmol) and NaHCO$_3$ (8.74 g, 105 mmol) in DMF (50 mL) under nitrogen atmosphere, and the mixture was reacted at 25° C. for 17 h. After the reaction was completed as detected by TLC (PE/EA=3/1), the reaction solution was added to water (250 mL), extracted with EA (150 mL) separated, and washed with saturated aqueous sodium chloride solution (200 mL). The organic phase was dried over anhydrous Na$_2$SO$_4$, concentrated and purified by column chromatography (PE:EA=7:1) to give a colorless liquid (4.60 g, yield 56.6%).

Step 2

A solution of 25b (3.00 g, 1.00 mmol) in THF (5 mL) was added dropwise to a solution of K12 (2.36 g, 6.41 mmol) and TsOH (472 mg, 2.48 mmol) in THF (15 mL) at 0° C. under nitrogen atmosphere, and the mixture was reacted at 25° C. for 2 h. After the reaction was completed as detected by TLC (PE/EA=1/1), the reaction solution was added to water (100 mL), extracted with EA (60 mL) twice and separated. The organic phase was dried over anhydrous Na$_2$SO$_4$, concentrated and purified by column chromatography (PE:EA=2:1) to give a white solid (4.00 g, yield 57.6%).

Step 3

Pd/C (340 mg) was added to a mixed solution of 25c (1.70 g, 3.14 mmol) in MeOH (20 mL) and EA (20 mL) at 0° C. under hydrogen atmosphere, and the mixture was reacted at 0° C. for 2 h. After the reaction was completed as detected by LCMS, the reaction solution was filtered through celite, and the filter cake was washed with EA (100 mL). The filtrate was concentrated, and washed with THF (10 mL) three times to remove MeOH to give a gray solid (530 mg, yield 21%).

Step 4

DIEA (130 mg, 1.01 mmol) was added to a solution of 25d (200 mg, 0.443 mmol), HY-13631A (214 mg, 0.402 mmol) and HATU (183 mg, 0.481 mmol) in DMF (4 mL) at 0° C. under nitrogen atmosphere, and the mixture was reacted at 0° C. for 2 h. After the reaction was completed as detected by LCMS, the reaction solution was added to a saturated aqueous citric acid solution (100 mL), and a brown solid was precipitated. The resulting mixture was filtered, and the filter cake was washed with water (100 mL) twice, dried by filtration, and dried with an oil pump to give a brown solid (300 mg, yield 78%).

Step 5

DIEA (9 mL) was added dropwise to a solution of 25e (300 mg, 0.345 mmol) in DCM (40 mL) at 0° C. under nitrogen atmosphere, and the mixture was reacted at 0° C. for 6 h. When there was 3% starting material left as detected by LCMS, the reaction solution was added to a petroleum ether solution (600 mL) at 0° C., and a solid was precipitated. The resulting mixture was left to stand until the solid was adsorbed on the bottom of the flask, and the solution was poured out, washed with petroleum ether (50 mL) twice, and dried with an oil pump to give a brown solid (178 mg, 80%).

Step 6

HATU (70.4 mg, 0.185 mmol) was added to a solution of 25f (80.0 mg, 0.123 mmol), KI-1 (87.6 mg, 0.185 mmol) and DIEA (47.8 mg, 0.370 mmol) in DMF (2 mL) at 0° C. under nitrogen atmosphere, and the mixture was reacted at 0° C. for 2 h. After the reaction was completed as detected by LCMS, the reaction solution was added to an aqueous citric acid solution (30 mL) at pH 4 at 0° C., and a flocculent solid was precipitated but could not be filtered off. The resulting solution was extracted with DCM/MeOH (10/1, 100 mL)

solution, separated and washed with a saturated aqueous sodium chloride solution (50 mL). The organic phase was dried over anhydrous sodium sulfate, concentrated and purified on a preparation plate (DCM/MeOH=10/1) to give a pale yellow solid (17 mg, yield 12.5%).

MS m/z (ESI): 1102 [M+1]

H-NMR (400 MHz, DMSO-D): 8.04 (m, 1H), 7.81 (d, 1H), 7.32 (s, 1H), 7.01 (s, 2H), 6.54 (s, 1H), 5.61-5.51 (m, 1H), 5.48-5.40 (m, 2H), 5.18 (dd, 2H), 4.65-4.59 (m, 4H), 3.80-3.68 (m, 8H), 3.23-3.17 (m, 2H), 2.42 (s, 3H), 2.29-2.19 (m, 1H), 2.19-2.09 (m, 4H), 1.94-1.71 (m, 6H), 1.63-1.35 (m, 10H), 1.25-1.18 (m, 2H), 0.89 (t, 3H)

Preparation Example 1.26. (1S,4S)-4-(((S)-7-benzyl-20-(2,5-dioxo-2,5-dihydro-1H-pyrrol-1-yl)-3,6,9,12,15-pentaoxo-2,5,8,11,14-pentaazaicosyl)oxy)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclohexane-1-carboxamide

L-II-2

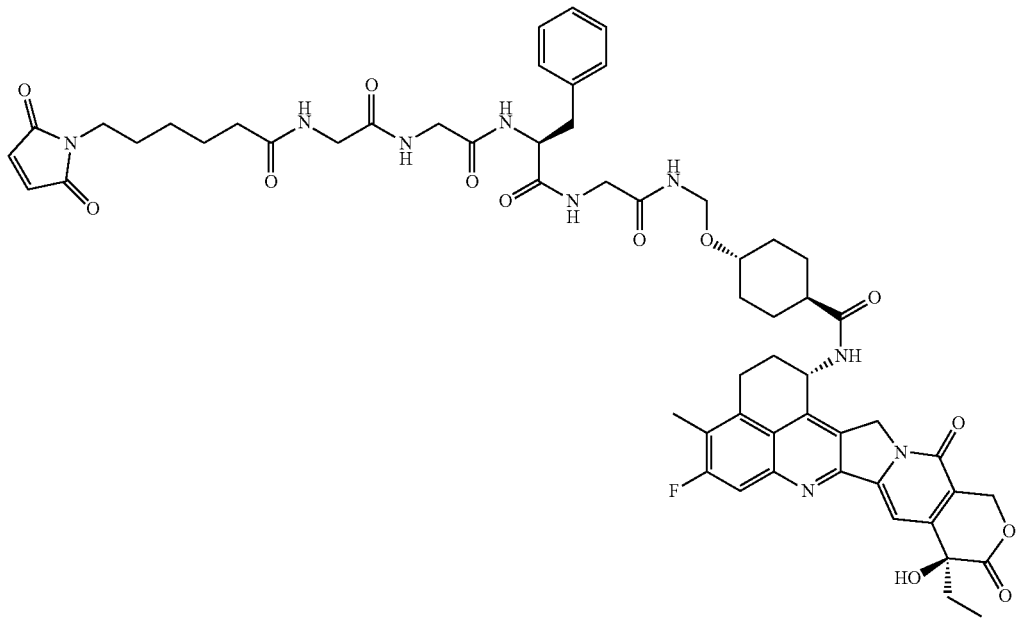

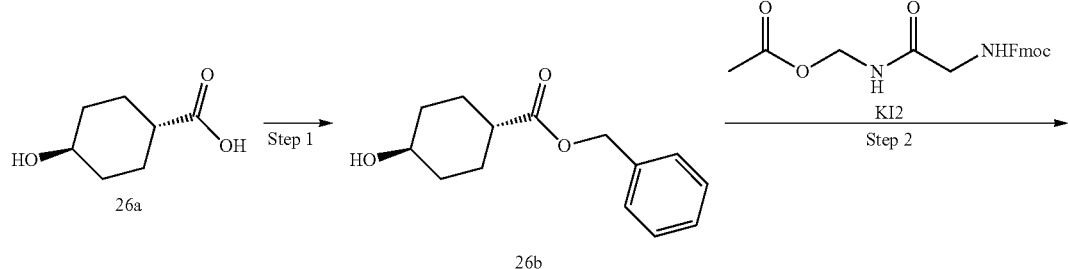

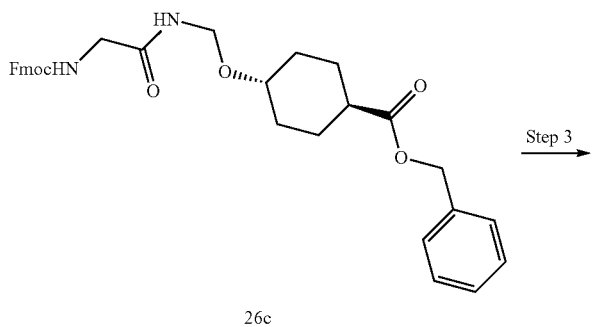

-continued
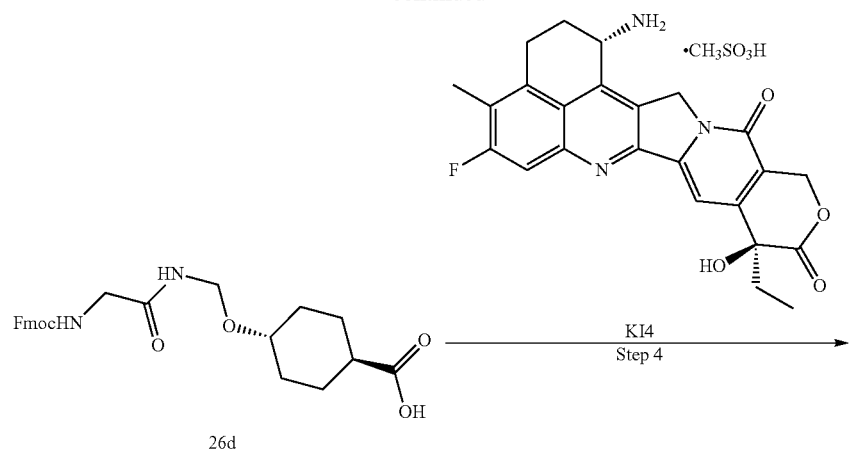
26d
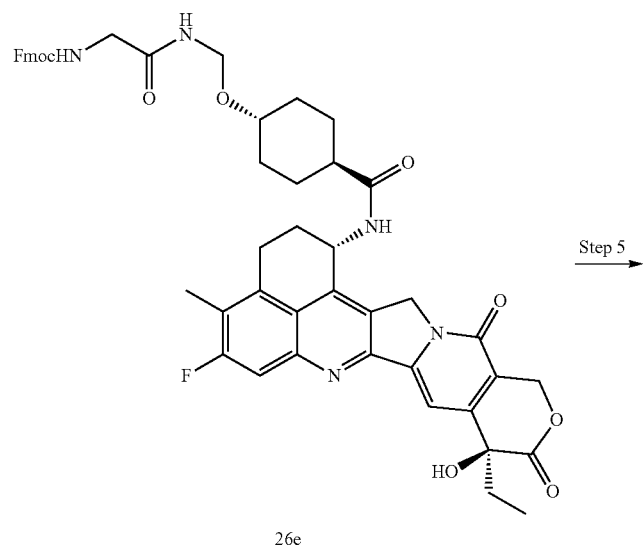
26e
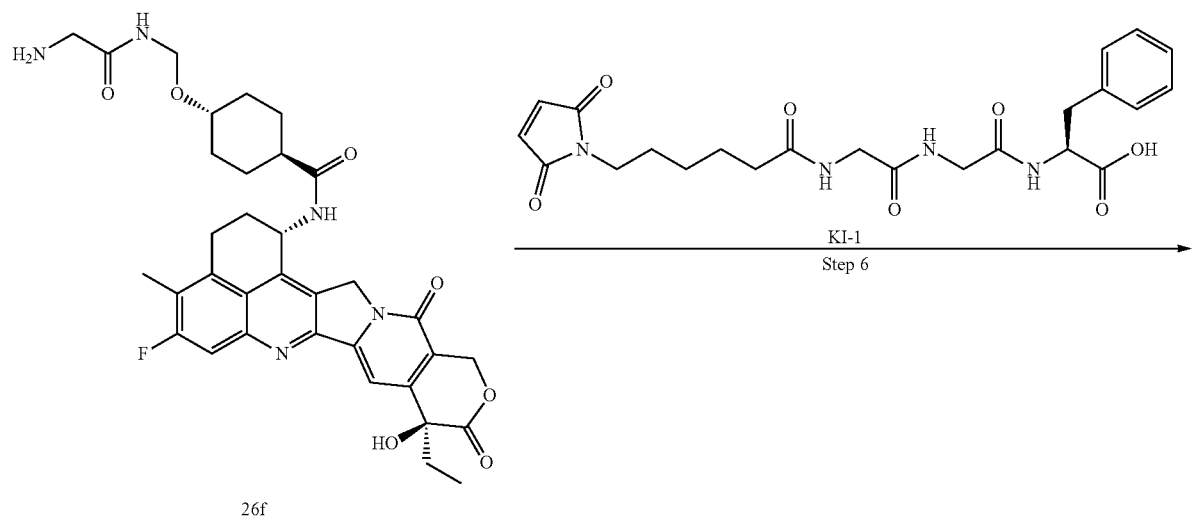
26f

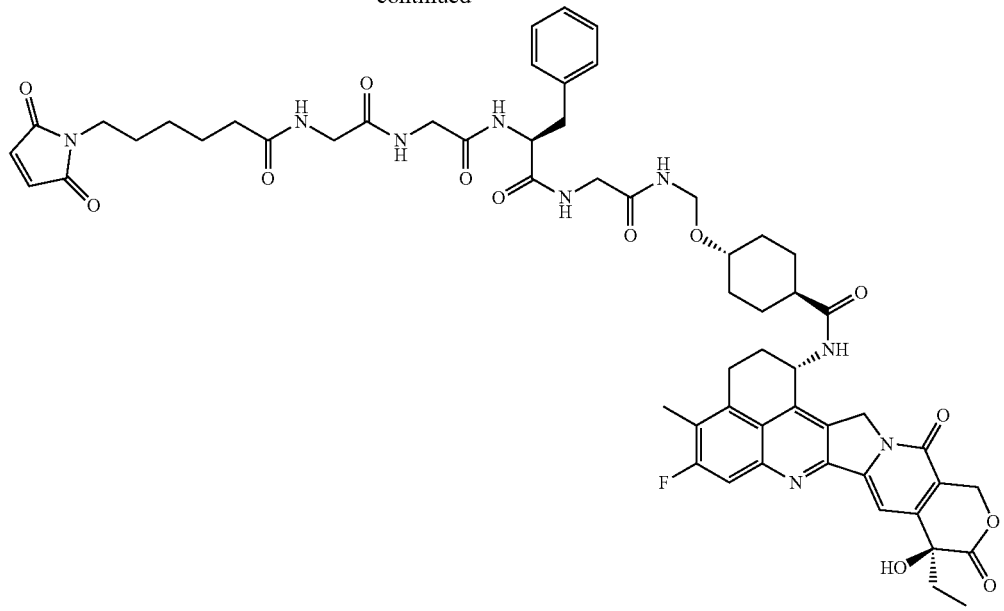

L-II-2

Step 1

Benzyl bromide (8.90 g, 52.1 mmol) was added dropwise to a solution of 26a (5.00 g, 34.7 mmol) and NaHCO$_3$ (8.74 g, 105 mmol) in DMF (50 mL) under nitrogen atmosphere, and the mixture was reacted at 25° C. for 17 h. After the reaction was completed as detected by TLC (PE/EA=3/1), the reaction solution was added to water (250 mL), extracted with EA (150 mL) separated and washed with saturated aqueous sodium chloride solution (200 mL). The organic phase was dried over anhydrous Na$_2$SO$_4$, concentrated and purified by column chromatography (PE:EA=7:1) to give a colorless liquid (4.60 g, yield 62.4%).

Step 2

A solution of 26b (2.25 g, 9.62 mmol) in THF (5 mL) was added dropwise to a solution of K12 (1.77 g, 4.81 mmol) and TsOH (354 mg, 1.86 mmol) in THF (20 mL) at 0° C. under nitrogen atmosphere, and the mixture was reacted at 25° C. for 2 h. After the reaction was completed as detected by TLC (PE/EA=1/1), the reaction solution was added to water (100 mL), extracted with EA (60 mL) twice and separated. The organic phase was dried over anhydrous Na$_2$SO$_4$, concentrated and purified by column chromatography (PE:EA=2:1) to give a white solid (1.2 g, yield 23%).

Step 3

Pd/C (120 mg) was added to a mixed solution of 26c (600 mg, 3.14 mmol) in MeOH (15 mL) and EA (15 mL) at 0° C. under hydrogen atmosphere, and the mixture was reacted at 0° C. for 2 h. After the reaction was completed as detected by LCMS, the reaction solution was filtered through celite, and the filter cake was washed with EA (50 mL). The filtrate was concentrated, and washed with THF (10 mL) three times to remove MeOH to give a gray solid (260 mg, yield 52%).

Step 4

DIEA (121 mg, 0.940 mmol) was added to a solution of 26d (187 mg, 0.414 mmol), HY-13631A (200 mg, 0.376 mmol) and HATU (171 mg, 0.451 mmol) in DMF (4 mL) at 0° C. under nitrogen atmosphere, and the mixture was reacted at 0° C. for 2 h. After the reaction was completed as detected by LCMS, the reaction solution was added to a saturated aqueous citric acid solution (200 mL), and a brown solid was precipitated. The resulting mixture was filtered, and the filter cake was washed with water (100 mL) twice, dried by filtration, and dried with an oil pump to give a brown solid (230 mg, yield 70%).

Step 5

Diethylamine (1.5 mL) was added dropwise to a solution of 26e (110 mg, 0.126 mmol) in DCM (3 mL) at 0° C. under nitrogen atmosphere, and the mixture was reacted at 0° C. for 6 h. When there was 3% starting material left as detected by LCMS, the reaction solution was added to a petroleum ether solution (500 mL) at 0° C., and a solid was precipitated. The resulting mixture was left to stand until the solid was adsorbed on the bottom of the flask, and the solution was poured out, washed with petroleum ether (50 mL) twice, and dried with an oil pump to give a brown solid (65 mg, 79%).

Step 6

A solution of HATU (70.4 mg, 0.185 mmol) in DMF (1 mL) was added to a solution of 26f (60 mg, 0.093 mmol), KI-1 (66 mg, 0.14 mmol) and DIEA (36 mg, 0.28 mmol) in DMF (1 mL) at 0° C. under nitrogen atmosphere, and the mixture was reacted at 0° C. for 2 h. After the reaction was completed as detected by LCMS, the reaction solution was added to an aqueous citric acid solution (30 mL) at pH 4 at 0° C., and a flocculent solid was precipitated but could not be filtered off. The resulting solution was extracted with DCM/MeOH (10/1, 100 mL) solution, separated and washed with a saturated aqueous sodium chloride solution (50 mL). The organic phase was dried over anhydrous sodium sulfate, concentrated and purified on a preparation plate (DCM/MeOH=10/1) to give a pale yellow solid (12 mg, yield 11.7%).
MS m/z (ESI): 1102 [M+1]
H-NMR (400 MHz, MeOD): 7.70 (d, 1H), 7.66 (s, 1H), 7.35-7.20 (m, 5H), 6.79 (s, 2H), 5.68-5.54 (m, 2H), 5.42-5.38 (m, 2H), 5.25 (dd, 2H), 5.01-4.97 (m, 3H), 4.58-4.52 (m, 1H), 3.97-3.73 (m, 6H), 3.51-3.46 (m, 3H), 3.28-3.01 (m, 3H), 2.47 (s, 3H), 2.31-2.26 (m, 4H), 2.20-2.12 (m, 2H), 2.09-1.95 (m, 4H), 1.71-1.57 (m, 8H), 1.47-1.39 (m, 2H), 1.02 (t, 3H)
Example 1.27
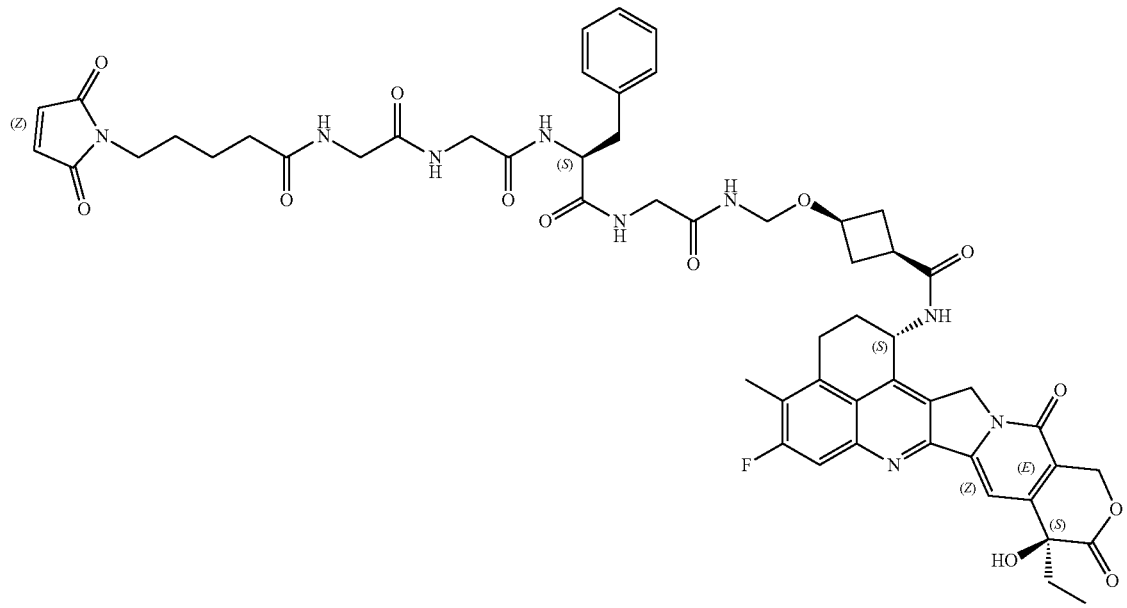
L-II-3
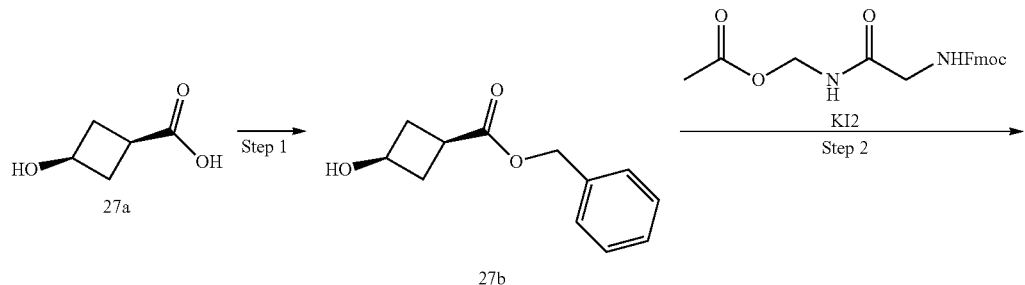
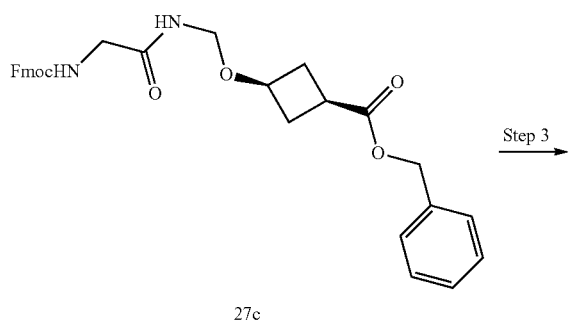

-continued
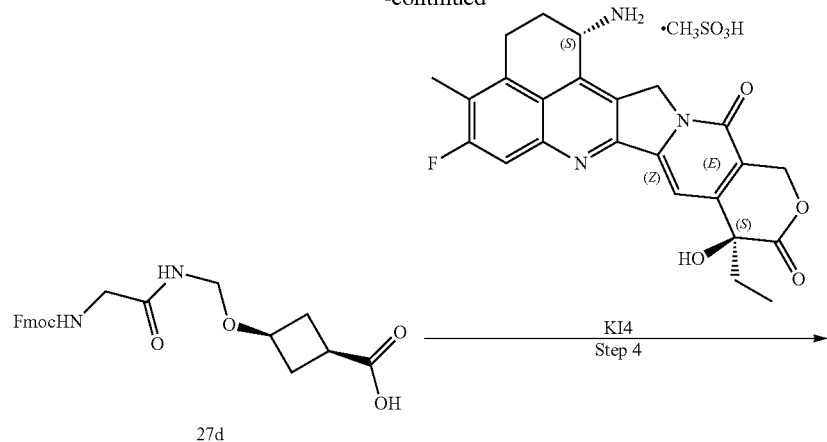
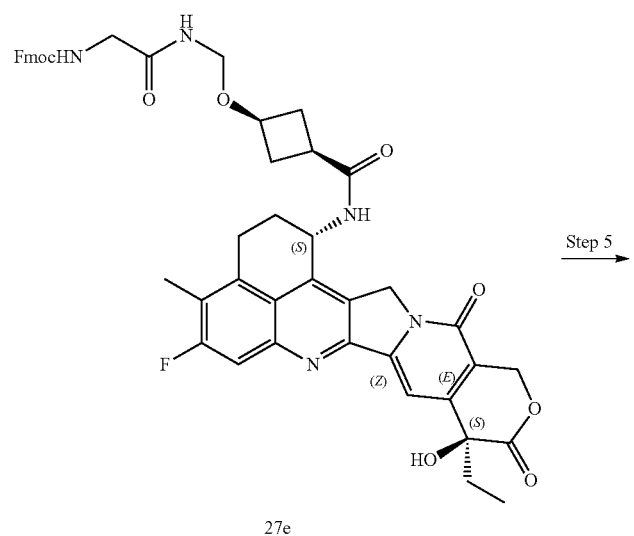
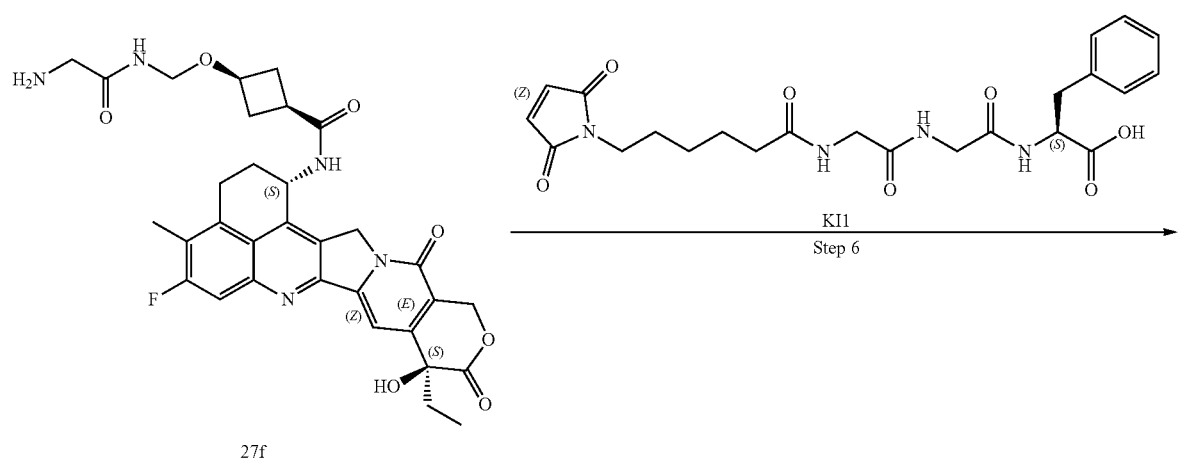

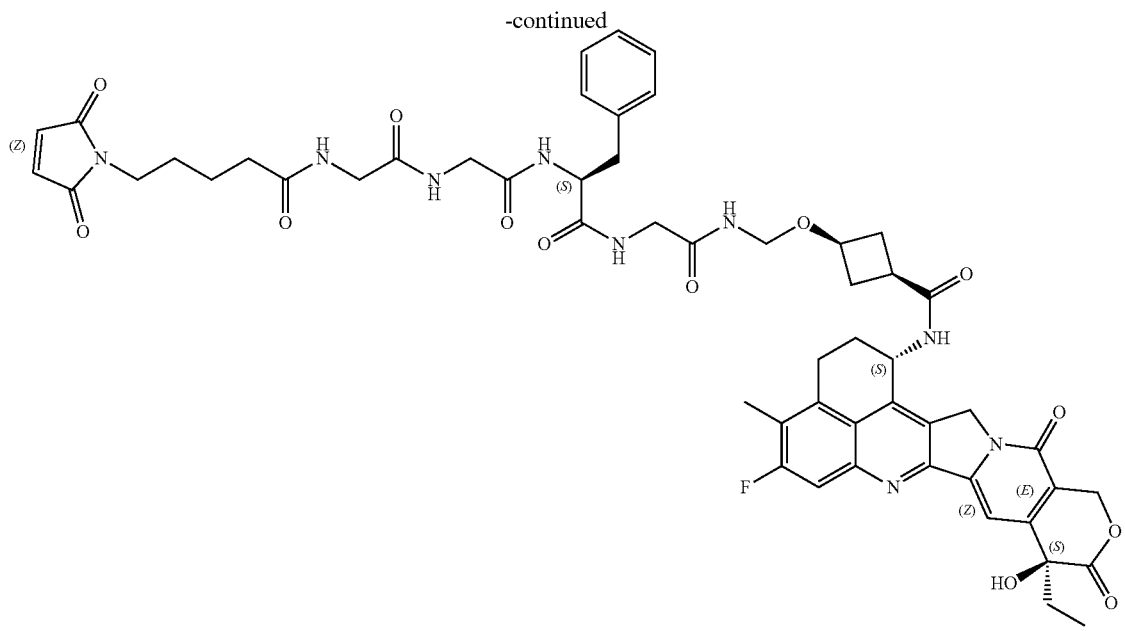

L-II-3

Step 1

Benzyl bromide (11.0 g, 64.6 mmol) was added dropwise to a solution of 27a (5.00 g, 43.0 mmol) and NaHCO₃ (10.9 g, 129 mmol) in DMF (50 mL) under nitrogen atmosphere, and the mixture was reacted at 25° C. for 17 h. After the reaction was completed as detected by TLC (PE/EA=2/1), the reaction solution was added to water (500 mL), extracted with EA (250 mL) twice, separated and washed with saturated aqueous sodium chloride solution (500 mL). The organic phase was dried over anhydrous Na₂SO₄, concentrated and purified by column chromatography (PE:EA=3:2) to give a colorless liquid (5.1 g, yield 57.1%).

Step 2

A solution of 27b (4.50 g, 21.8 mmol) in THF (10 mL) was added dropwise to a solution of K12 (4.00 g, 10.9 mmol) and TsOH (800 mg, 4.65 mmol) in THF (30 mL) at 0° C. under nitrogen atmosphere, and the mixture was reacted at 25° C. for 2 h. After the reaction was completed as detected by TLC (PE/EA=1/2), the reaction solution was added to water (200 mL), extracted with EA (200 mL) twice and separated. The organic phase was dried over anhydrous Na₂SO₄, concentrated and purified by column chromatography (PE/EA=3/2) to give a white solid (1.56 g, yield 26%).

Step 3

Pd/C (80 mg) was added to a mixed solution of 27c (800 mg, 1.55 mmol) in EtOH (8 mL) and EA (8 mL) at 0° C. under hydrogen atmosphere, and the mixture was stirred at 0° C. for 2.5 h. After the reaction was completed as detected by LCMS, the reaction solution was filtered through celite, and the filter cake was washed with EA (200 mL). The filtrate was concentrated, dissolved with THF (20 mL) and dried by rotary evaporation to give a white solid (600 mg, yield 91%).

Step 4

DIEA (152 mg, 1.18 mmol) was added to a solution of 27d (220 mg, 0.515 mmol), HY-13631A (250 mg, 0.47 mmol) and HATU (214 mg, 0.56 mmol) in DMF (6 mL) at 0° C. under nitrogen atmosphere, and the mixture was reacted at 0° C. for 2 h. After the reaction was completed as detected by LCMS, the reaction solution was added to an aqueous citric acid solution (pH=4) (150 mL), and filtered. The filter cake was washed with water (175 mL), dried by filtration, and dried with an oil pump to give a brown solid (260 mg, yield 66%).

Step 5

Diethylamine (8 mL) was added dropwise to a solution of 27e (260 mg, 0.309 mmol) in DCM (30 mL) at 0° C. under nitrogen atmosphere, and the mixture was reacted at 0° C. for 3 h. After the reaction was completed as detected by LCMS, the reaction solution was added to a petroleum ether solution (600 mL) at 0° C., and a solid was precipitated. The resulting mixture was left to stand until the solid was adsorbed on the bottom of the flask, and the solution was poured out and dried with an oil pump to give a brown solid (90 mg, yield 47.1%).

Step 6

HATU (74 mg, 0.19 mmol) was added to a solution of 27f (90 mg, 0.13 mmol), KI-1 (92 mg, 0.19 mmol) and DIEA (50 mg, 0.39 mmol) in DMF (2.5 mL) at 0° C. under nitrogen atmosphere, and the mixture was reacted at 0° C. for 2 h. After the reaction was completed as detected by LCMS, the reaction mixture was added to an aqueous citric acid solution (30 mL) at pH 4 at 0° C., and a flocculent solid was precipitated. The resulting mixture was filtered, and purified on a preparation plate (DCM/MeOH=10/1) to give a pale yellow solid (9.2 mg, yield 6%).

MS m/z (ESI): 1074 [M+1]

H-NMR (400 MHz, MeOD): 7.65 (d, 1H), 7.62 (s, 1H), 7.30-7.21 (m, 5H), 6.79 (s, 2H), 5.69-5.65 (m, 1H), 5.57 (d, 1H), 5.43-5.10 (m, 3H), 4.70 (d, 2H), 4.48-4.39 (m, 2H), 4.10-4.05 (m, 1H), 4.01-3.75 (m, 5H), 3.46 (t, 2H), 3.22-3.15 (m, 2H), 3.07-3.00 (m, 1H), 2.75 (m, 1H), 2.62 (m, 1H), 2.45 (s, 3H), 2.37-2.20 (m, 6H), 2.10-2.02 (m, 2H), 2.00-1.92 (m, 2H) 1.68-1.57 (m, 6H), 1.01 (t, 3H)
Example 1.28
L-II-4
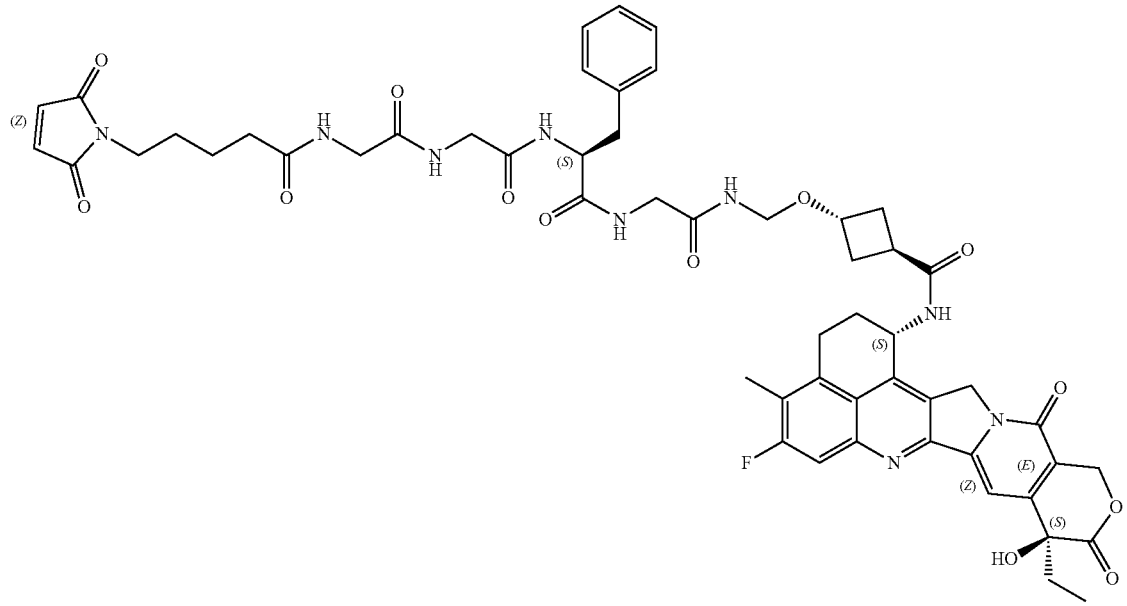
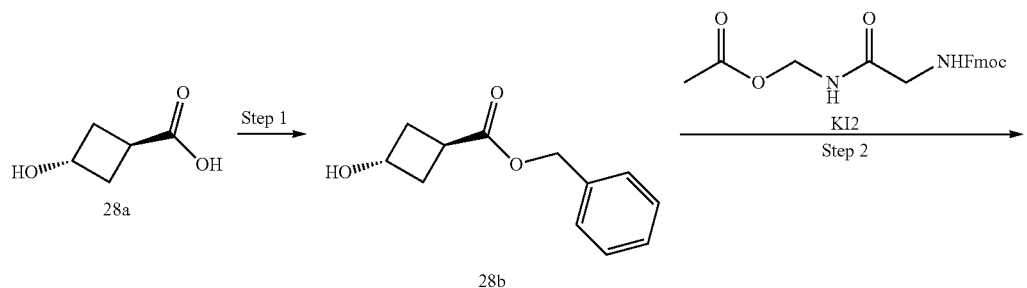
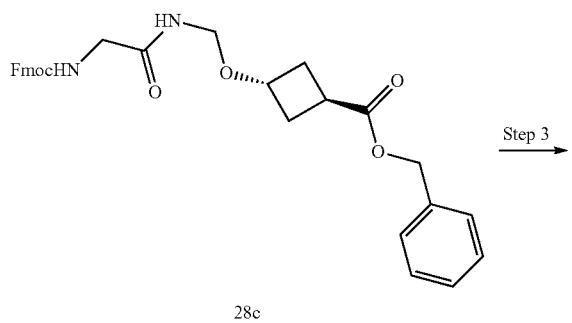

-continued
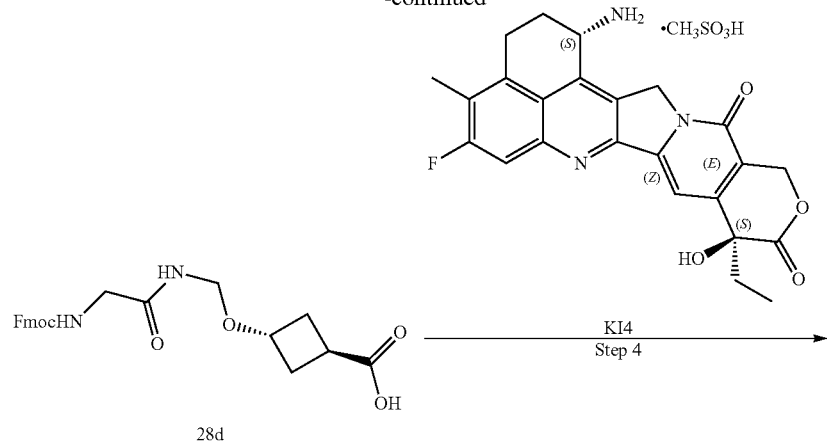
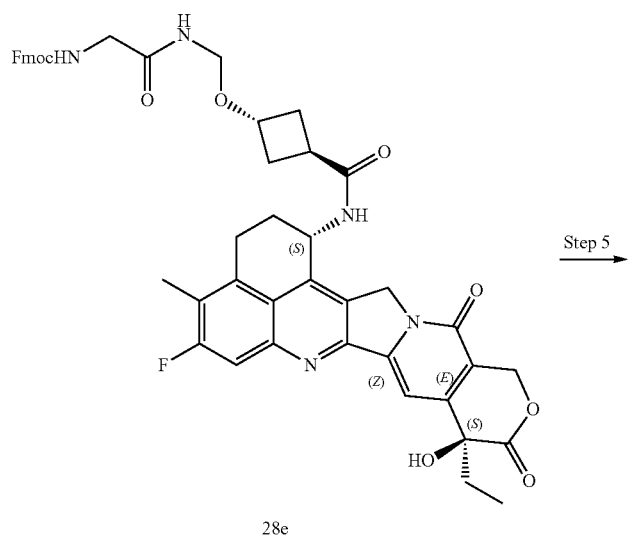
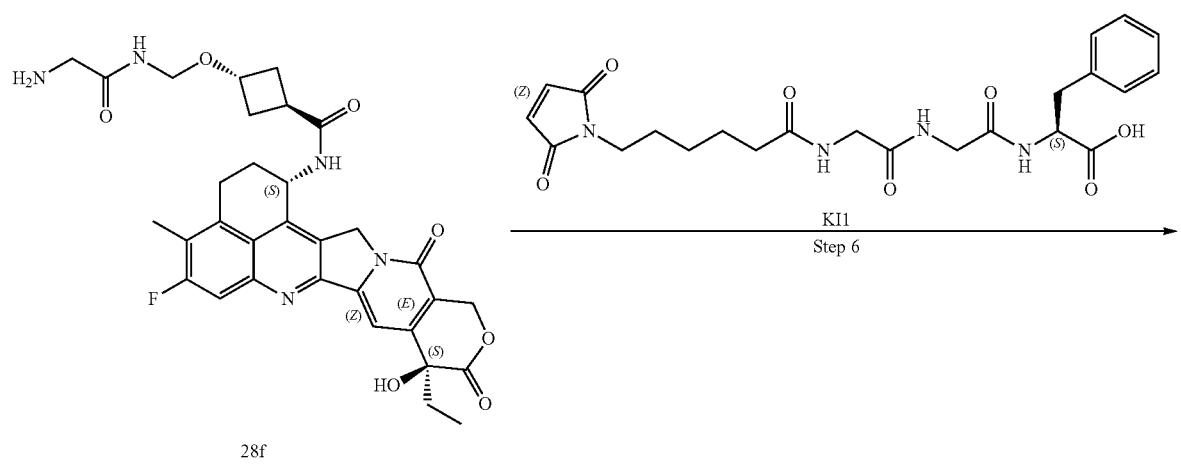

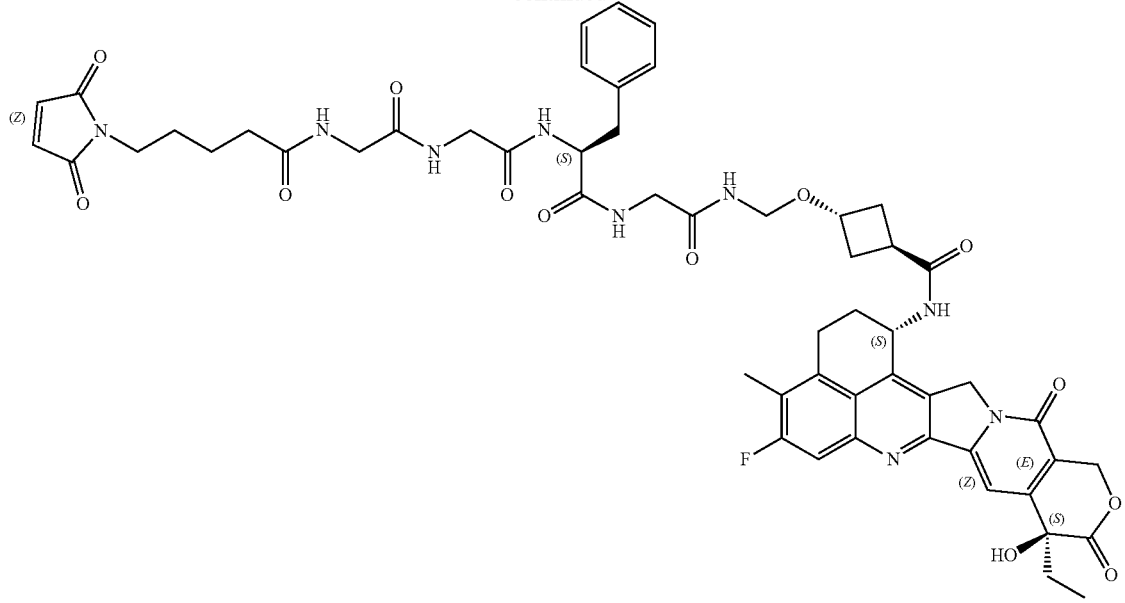

L-II-4

Step 1

Benzyl bromide (5.52 g, 32.0 mmol) was added dropwise to a solution of 28a (2.50 g, 21.0 mmol) and NaHCO$_3$ (5.43 g, 64.0 mmol) in DMF (25 mL) under nitrogen atmosphere, and the mixture was reacted at 25° C. for 12 h. After the reaction was completed as detected by TLC (PE/EA=2/1), the reaction solution was added to water (250 mL), extracted with EA (500 mL), separated and washed with saturated aqueous sodium chloride solution (500 mL). The organic phase was dried over anhydrous Na$_2$SO$_4$, concentrated and purified by column chromatography (PE:EA=3:2) to give a colorless liquid (2.50 g, yield 56.3%).

Step 2

A solution of 28b (2.5 g, 12.1 mmol) in THF (1 mL) was added dropwise to a solution of K12 (2.23 g, 6.05 mmol) and TsOH (446 mg, 2.59 mmol) in THF (19 mL) at 0° C. under nitrogen atmosphere, and the mixture was reacted at 25° C. for 2 h. After the reaction was completed as detected by LCMS, the reaction solution was added to water (50 mL), extracted with DCM (20 mL) three times and separated. The organic phase was dried over anhydrous Na$_2$SO$_4$, concentrated and purified by column chromatography (PE/EA=3/2) to give a white solid (1.60 g, yield 43%).

Step 3

Pd/C (80 mg) was added to a mixed solution of 28c (800 mg, 1.56 mmol) in MeOH (8 mL) and EA (8 mL) at 0° C. under hydrogen atmosphere, and the mixture was stirred at 0° C. for 7 h. After the reaction was completed as detected by LCMS, the reaction solution was filtered through celite, and the filter cake was washed with EA (200 mL). The filtrate was concentrated to give a white solid (600 mg, yield 91%).

Step 4

DIEA (122 mg, 0.940 mmol) was added to a solution of 28d (176 mg, 0.414 mmol), HY-13631A (200 mg, 0.377 mmol) and HATU (172 mg, 0.450 mmol) in DMF (7 mL) at 0° C. under nitrogen atmosphere, and the mixture was reacted at 0° C. for 2 h. After the reaction was completed as detected by LCMS, the reaction solution was added to a saturated aqueous citric acid solution (120 mL). The resulting mixture was filtered, and the filter cake was washed with water (120 mL) once, dried by filtration, and dried with an oil pump to give a brown solid (280 mg, yield 88%).

Step 5

DIEA (4.2 mL) was added dropwise to a solution of 28e (140 mg, 0.166 mmol) in DCM (14 mL) at 0° C. under nitrogen atmosphere, and the mixture was reacted at 0° C. for 7 h. When there was 2% starting material left as detected by LCMS, the reaction solution was added to a petroleum ether solution (420 mL) at 0° C., and a solid was precipitated. The resulting mixture was left to stand until the solid was adsorbed on the bottom of the flask, and the solution was poured out, washed with petroleum ether (50 mL) three times, and dried with an oil pump to give a brown solid (97 mg, yield 68%).

Step 6

HATU (91.2 mg, 0.240 mmol) was added to a solution of 28f (82.0 mg, 0.130 mmol), KI-1 (113 mg, 0.240 mmol) and DIEA (51 mg, 0.39 mmol) in DMF (5 mL) at 0° C. under nitrogen atmosphere, and the mixture was reacted at 0° C. for 2 h. After the reaction was completed as detected by LCMS, the reaction mixture was added to an aqueous citric acid solution (30 mL) at pH 4 at 0° C., and a flocculent solid was precipitated. The resulting mixture was filtered, and purified on a preparation plate (DCM/MeOH=10/1) to give a pale yellow solid (24 mg, yield 17%).

MS m/z (ESI): 1074 [M+1]

H-NMR (400 MHz, MeOD): 7.66 (d, 1H), 7.62 (s, 1H), 7.27-7.20 (m, 5H), 6.76 (s, 2H), 5.70-5.62 (m, 1H), 5.58 (d, 1H), 5.38-5.17 (m, 3H), 4.73 (d, 1H), 4.62-4.52 (m, 2H), 4.50-4.39 (m, 2H), 3.90-3.83 (d, 4H), 3.72-3.67 (d, 1H), 3.49-3.41 (m, 1H), 3.25-3.11 (m, 3H), 3.07-2.98 (m, 2H), 2.61-2.52 (m, 2H), 2.43 (s, 3H), 2.31-2.20 (m, 6H), 2.01-1.90 (m, 2H), 2.00-1.92 (m, 2H), 1.65-1.52 (m, 4H), 1.30-1.25 (m, 2H), 1.00 (t, 3H)
Preparation Example 1.29. N-((7S)-7-benzyl-1-((1-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-2-oxopyrrolidin-3-yl)oxy)-3,6,9,12-tetraoxo-2,5,8,11-tetraazatridecan-13-yl)-6-(2,5-dioxo-2,5-dihydro-1H-pyrrol-1-yl)hexanamide
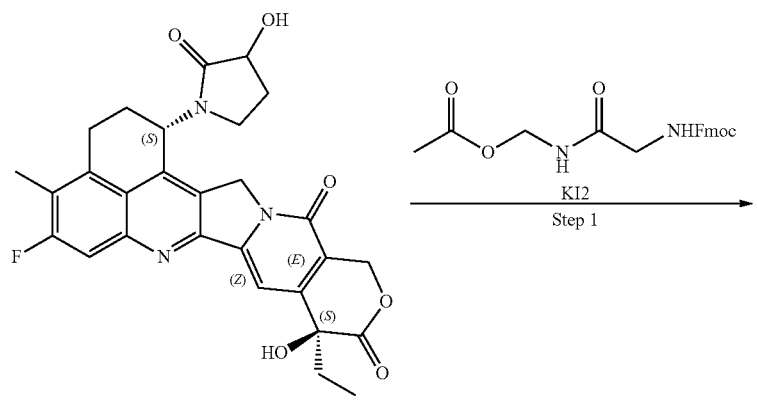
29a
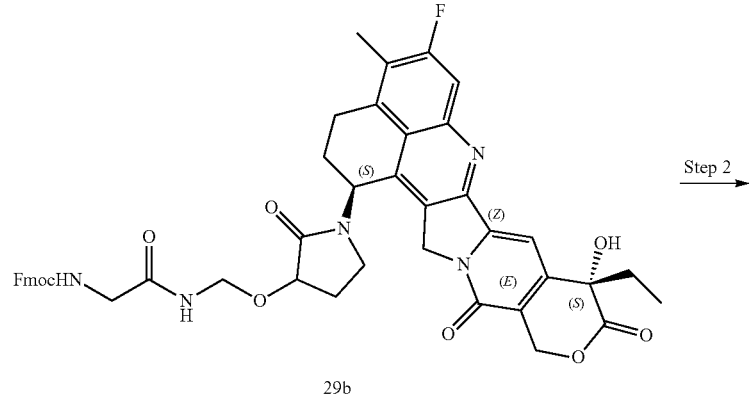
29b
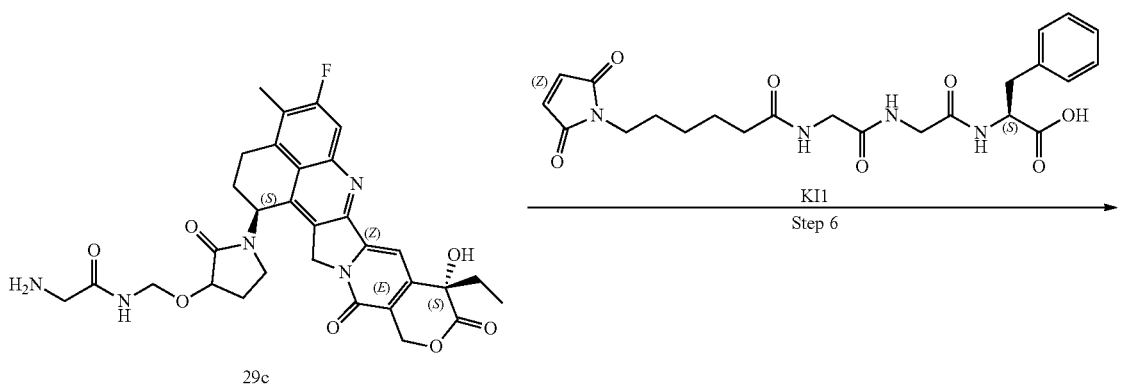
29c

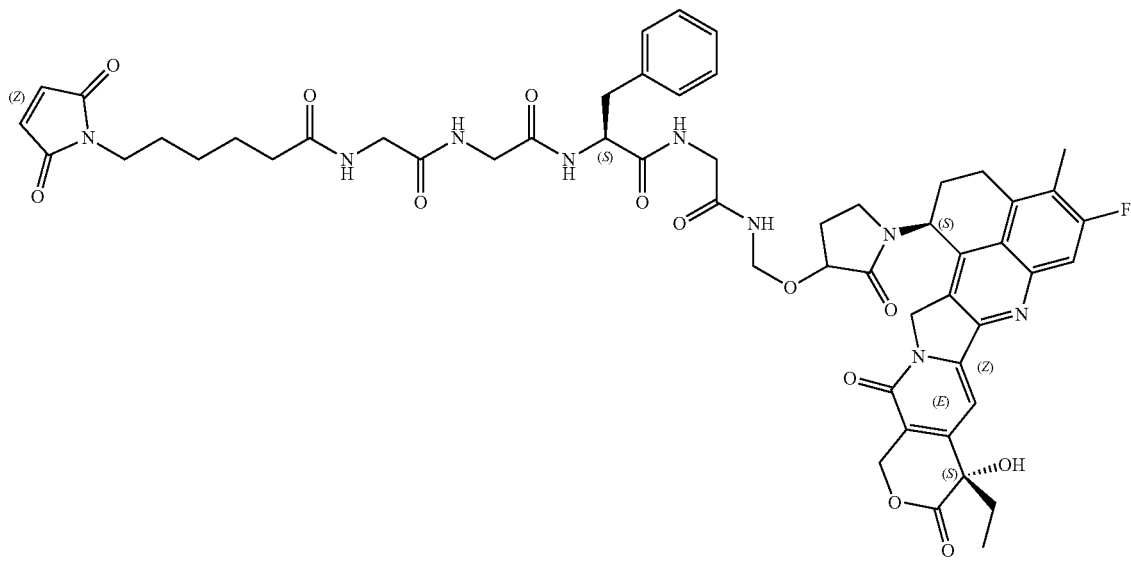

L-I-1

Step 1

K12 (638 mg, 1.73 mmol) and TsOH (50 mg, 0.29 mmol) were added to a solution of 29a (300 mg, 0.577 mmol) in DMA (30 mL) sequentially, and the mixture was stirred at 50° C. for 3 h. The reaction solution was cooled to room temperature, supplemented with KI2 (1.28 g, 3.46 mmol) and stirred at 50° C. for 17 h. When there was about 50% product generated as detected by LCMS, the reaction solution was cooled to room temperature, added to ice water, extracted with DCM/MeOH (5:1, 30 mL) three times, washed with a saturated aqueous sodium chloride solution (50 mL), and separated. The organic phase was dried over anhydrous sodium sulfate, concentrated, and purified by column chromatography to give an impure product, which was separated by prep-HPLC (10 mmol/L NH$_4$OAc) to give a white solid (70 mg, yield 12%).

Step 2

Diethylamine (3.0 mL) was added to a solution of 29b (70 mg, 0.085 mmol) in DCM (9 mL) at 0° C., and the mixture was stirred at 0° C. for 9 h. After the reaction was completed as detected by LCMS, the reaction solution was added to petroleum ether (250 mL) at 0° C., and a solid was precipitated. The mixture was stirred for 10 min, and petroleum ether was poured out. A three-necked flask was washed with petroleum ether (50 mL) and dried with a pump, and the product was transferred to a single-necked flask with tetrahydrofuran (20 mL) and dried by rotary evaporation to give a yellow solid (40 mg, yield 78%).

Step 3

HATU (45 mg, 0.012 mmol) and DIEA (26 mg, 0.20 mmol) were added to a solution of 29c (40 mg, 0.066 mmol) and KI1 (56 mg, 0.012 mmol) in DMF (2 mL) at 0° C., and the mixture was stirred for 1 h. After the reaction was completed as detected by LCMS, the reaction solution was poured into a citric acid solution (20 mL) at pH 4-5, extracted with DCM/MeOH (5/1, 30 mL), and washed with saturated brine (10 mL). The organic phase was dried over anhydrous sodium sulfate, concentrated, and purified by prep-TLC (DCM:MeOH=10:1) to give a yellow solid (15 mg, yield 21%).

MS m/z (ESI): 1060 [M+1]

H-NMR (400 MHz, DMSO-D): 7.81 (d, 1H), 7.32 (s, 1H), 7.24 (m, 5H), 7.00 (s, 2H), 6.55 (s, 1H), 5.45 (dd, 2H), 5.11-4.80 (m, 4H), 4.60-4.50 (m, 1H), 4.40-4.30 (m, 1H), 3.80-3.71 (m, 3H), 3.70-3.66 (m, 2H), 3.65-3.60 (m, 1H), 3.30-2.79 (m, 6H), 2.46-2.35 (m, 6H), 2.25-2.17 (m, 3H), 1.94-1.80 (m, 3H), 1.50-1.40 (m, 4H), 1.28-1.20 (m, 2H), 1.00 (t, 3H)

Preparation Example 1.30. N-((S)-7-benzyl-17-
(((1S,9S)-9-ethyl-5-fluoro-9-hydroxy-4-methyl-10,
13-dioxo-2,3,9,10,13,15-hexahydro-1H,12H-benzo
[de]pyrano[3',4':6,7]indolizino[1,2-b]quinolin-1-yl)
amino)-2,5,8,11,17-pentaoxo-14-thia-3,6,9,12-
tetraazaheptadecyl)-6-(2,5-dioxo-2,5-dihydro-1H-
pyrrol-1-yl)hexanamide
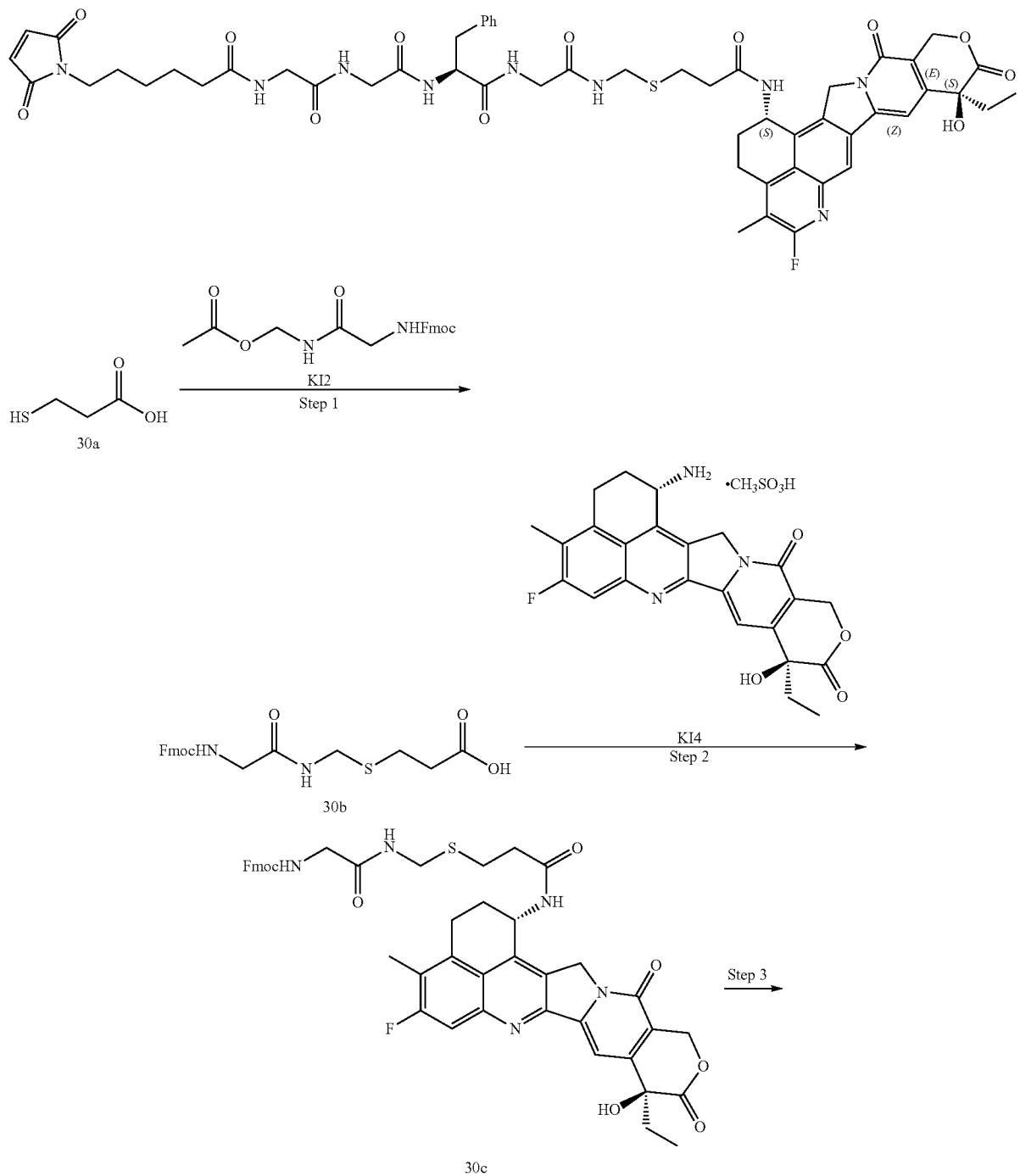

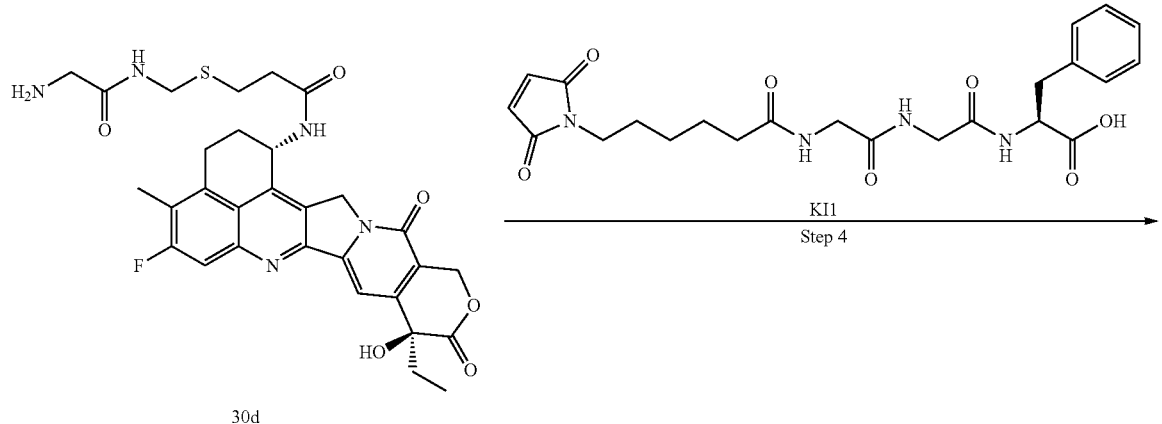

30d

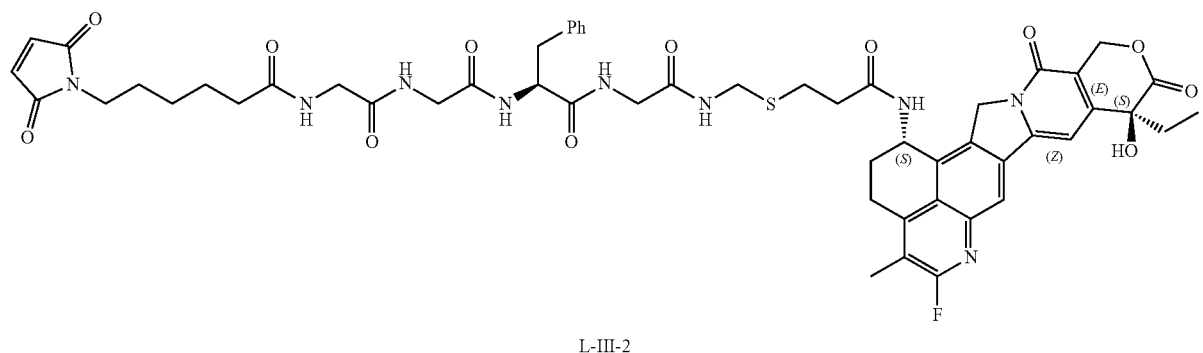

L-III-2

TsOH (52 mg, 0.272 mmol) and P12-3 (288 mg, 2.72 mmol) were added to a solution of 30a (1.00 g, 2.72 mmol) in THF (10 mL) at 0° C. under nitrogen atmosphere. After the addition was completed, the mixture was slowly warmed to 25° C. and reacted for 1 h. The reaction solution was directly mixed with silica gel and purified by column chromatography (DCM/MeOH=80/1) to give a white solid (760 mg, yield 67%).

Step 2

DIEA (181 mg, 1.40 mmol) was added to a solution of 30b (321 mg, 0.620 mmol), HY-13631A (300 mg, 0.560 mmol) and HATU (255 mg, 0.670 mmol) in DMF (12 mL) under nitrogen atmosphere. After the addition was completed, the mixture was reacted at 25° C. for 2 h. After the reaction was completed as detected by TLC (DCM/MeOH=20/1), the reaction solution was added dropwise to water (180 mL), filtered and purified on a preparation plate (DCM/MeOH=20/1) to give a yellow solid (320 mg, yield 68%).

Step 3

Diethylamine (4 mL) was added dropwise to a solution of 30c (115 mg, 0.138 mmol) in DCM (12 mL) under nitrogen atmosphere, and the mixture was stirred at 0° C. for 3 h. After the starting material was consumed completely as detected by LCMS, the reaction solution was added dropwise into PE (345 mL) at 0° C. under nitrogen atmosphere, and stirred for 3 min. The resulting mixture was left to stand at 0° C. for 1 h until the solid was gathered at the bottom of the flask, and the supernatant was poured out, and dried with a pump to give a yellow solid (56 mg, yield 67%).

Step 4

HATU (57 mg, 0.15 mmol) was added to a solution of 30d (51 mg, 0.084 mmol), KI1 (71.1 mg, 0.151 mmol) and DIEA (33 mg, 0.25 mmol) in DMF (2.5 mL) at 0° C. under nitrogen atmosphere, and the mixture was reacted at 0° C. for 2 h. After the starting material was consumed completely as detected by LCMS, the reaction solution was added dropwise into citric acid (30 mL) at pH 4 at 0° C. The resulting mixture was filtered to give a yellow solid (130 mg), which was purified by prep-HPLC (10 mmol/L $NH_4OAc$) to give a white solid (22 mg, yield 25%).

MS m/z (ESI): 1064 [M+1]

H-NMR (400 MHz, MeOD): 7.70 (d, 1H), 7.65 (s, 1H), 7.21 (m, 3H), 7.07 (d, 2H), 6.80 (s, 1H), 5.70 (m, 1H), 5.47 (dd, 4H), 4.66 (m, 2H), 4.33 (m, 3H), 3.82 (m, 5H), 3.61 (m, 1H), 3.52 (m, 3H), 3.25 (m, 1H), 3.06-2.75 (m, 4H), 2.62 (m, 2H), 2.47 (s, 3H), 2.30 (m, 2H), 2.25 (m, 2H), 1.60 (m, 4H), 1.25 (m, 2H), 0.99 (t, 3H)

Preparation Example 1.31. N-((7S,15R)-7-benzyl-17-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-15-methyl-2,5,8,11,17-pentaoxo-14-oxa-3,6,9,12-tetraazaheptadecyl)-6-(2,5-dioxo-2,5-dihydro-1H-pyrrol-1-yl)hexanamide
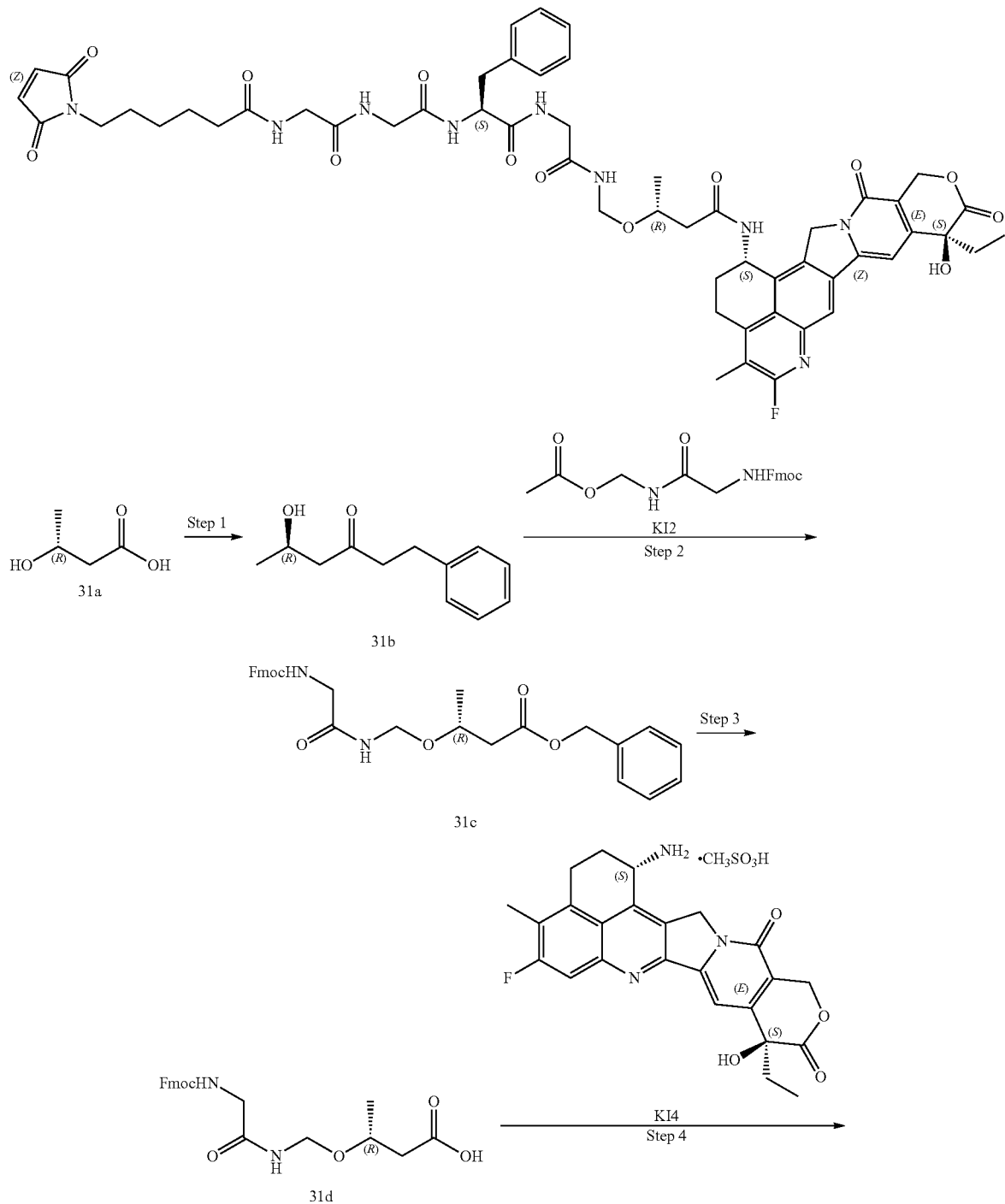

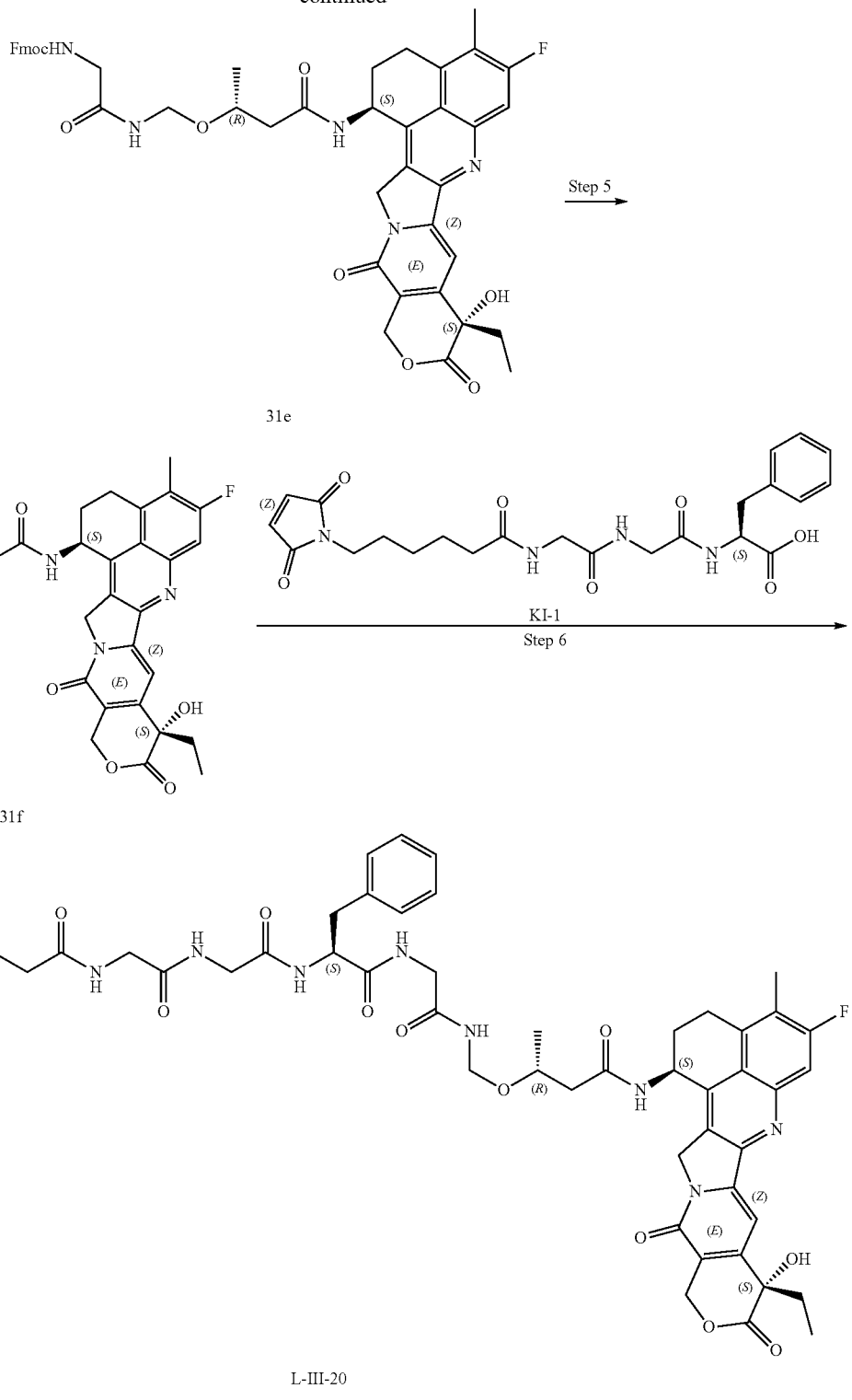

Step 1

Benzyl bromide (24.6 g, 144 mmol) was added dropwise to a solution of 31a (10.0 g, 96.0 mmol) and NaHCO₃ (24.1 g, 288 mmol) in DMF (50 mL) under nitrogen atmosphere, and the mixture was reacted at 25° C. for 17 h. After the reaction was completed as detected by TLC (PE/EA=1/1), the reaction solution was added to water (500 mL), extracted with EA (200 mL) twice, separated and washed with saturated aqueous sodium chloride solution (200 mL). The organic phase was dried over anhydrous Na₂SO₄, concentrated and purified by column chromatography (PE:EA=3:2) to give a pale yellow oily liquid (9.5 g, yield 57.1%).

Step 2

A solution of 31b (6.30 g, 32.5 mmol) in THF (10 mL) was added dropwise to a solution of K12 (4.00 g, 10.9 mmol) and TsOH (800 mg, 4.65 mmol) in THF (30 mL) at 0° C. under nitrogen atmosphere, and the mixture was reacted at 25° C. for 2 h. After the reaction was completed as detected by TLC (PE/EA=1/1), the reaction solution was added to water (400 mL), extracted with EA (200 mL) twice, separated and washed with saturated aqueous sodium chloride solution (200 mL) once. The organic phase was dried over anhydrous $Na_2SO_4$, concentrated and purified by column chromatography (PE/EA=3/2) to give a white sticky solid (850 mg, yield 15.5%).

Step 3

Pd/C (200 mg) was added to a mixed solution of 31c (500 mg, 0.990 mmol) in EtOH (5 mL) and EA (5 mL) at 0° C. under hydrogen atmosphere, and the mixture was reacted at 0° C. for 2.5 h. After the reaction was completed as detected by LCMS, the reaction solution was filtered through celite, and the filter cake was washed with EA (200 mL). The filtrate was concentrated, and dissolved with THF (20 mL) and dried by rotary evaporation, which was repeated three times, to give a gray solid (350 mg, yield 85%).

Step 4

DIEA (152 mg, 1.18 mmol) was added to a solution of 31d (213 mg, 0.515 mmol), HY-13631A (250 mg, 0.470 mmol) and HATU (214 mg, 0.560 mmol) in DMF (6 mL) at 0° C. under nitrogen atmosphere, and the mixture was reacted at 0° C. for 2 h. After the reaction was completed as detected by LCMS, the reaction solution was added to a saturated aqueous citric acid solution (150 mL), and a brown solid was precipitated. The resulting mixture was filtered, and the filter cake was washed with water (175 mL), dried by filtration, and dried with an oil pump to give a brown solid (150 mg, yield 38.5%).

Step 5

Diethylamine (10 mL) was added dropwise to a solution of 31e (100 mg, 0.120 mmol) in DCM (30 mL) at 0° C. under nitrogen atmosphere, and the mixture was reacted at 0° C. for 6 h. After the reaction was completed as detected by LCMS, the reaction solution was added to a petroleum ether solution (600 mL) at 0° C., and a solid was precipitated. The resulting mixture was left to stand until the solid was adsorbed on the bottom of the flask, and the solution was poured out and dried with an oil pump to give a gray solid (95 mg, yield not counted, impure product).

Step 6

A solution of HATU (74 mg, 0.19 mmol) in DMF (1 mL) was added to a solution of 31f (90 mg, 0.15 mmol), KI1 (140 mg, 0.296 mmol) and DIEA (57 mg, 0.44 mmol) in DMF (2 mL) at 0° C. under nitrogen atmosphere, and the mixture was reacted at 0° C. for 2 h. After the reaction was completed as detected by LCMS, the reaction mixture was added to an aqueous citric acid solution (30 mL) at pH 4 at 0° C., and a flocculent solid was precipitated. The resulting mixture was filtered, and purified by prep-TLC (DCM/MeOH=10/1) to give a pale yellow solid (18.7 mg, yield 3% over two steps).

MS m/z (ESI): 1062 [M+1]

H-NMR (400 MHz, MeOD): 7.65 (m, 2H), 7.21 (m, 5H), 6.80 (s, 1H), 5.60 (m, 2H), 5.41 (m, 2H), 5.19 (m, 1H), 4.72 (s, 2H), 4.47 (m, 1H), 4.25 (m, 1H), 3.84 (m, 5H), 3.65 (m, 1H), 3.48 (m, 2H), 3.06 (m, 1H), 2.95 (m, 1H), 2.50 (m, 5H), 2.27 (m, 5H), 1.98 (m, 2H), 1.60 (m, 5H), 1.33 (m, 2H), 1.03 (t, 3H)

Preparation Example 1.32. N-((7S,15S)-7-benzyl-17-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-15-methyl-2,5,8,11,17-pentaoxo-14-oxa-3,6,9,12-tetraazaheptadecyl)-6-(2,5-dioxo-2,5-dihydro-1H-pyrrol-1-yl)hexanamide

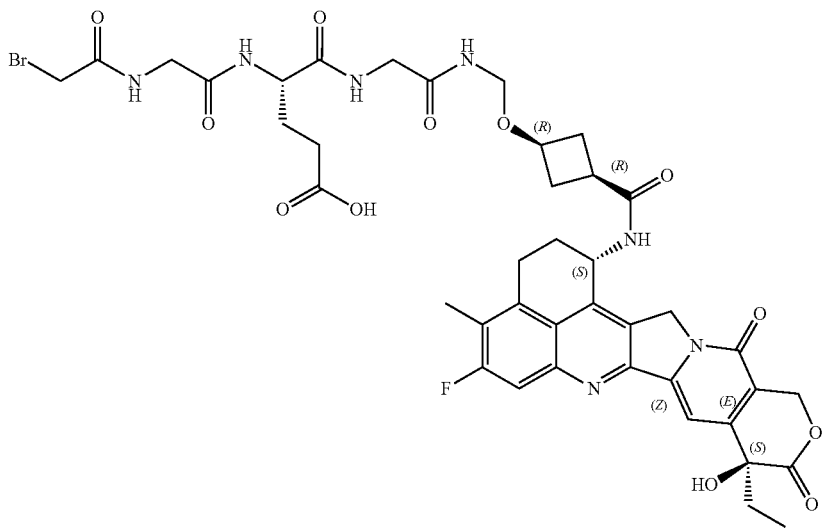

L-II-27

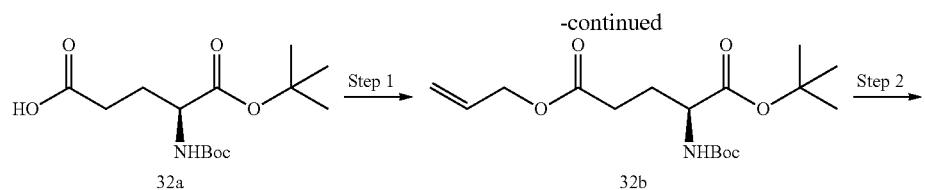
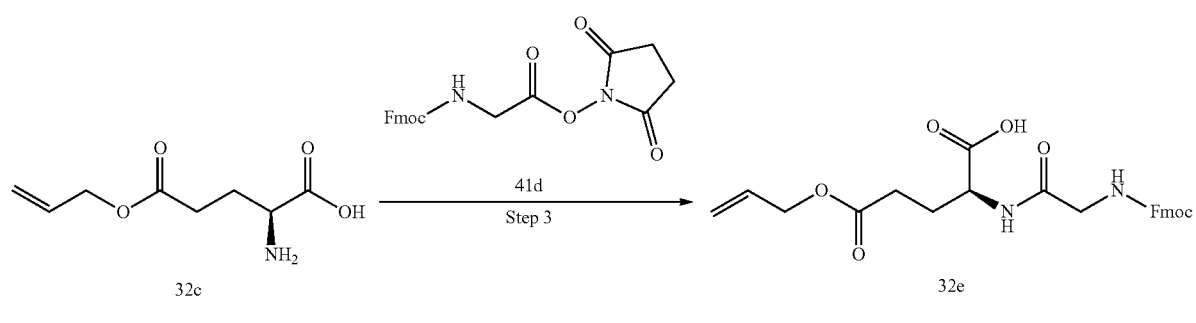
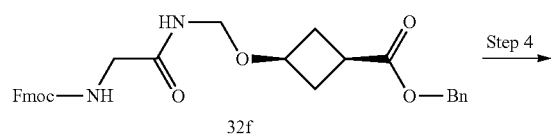
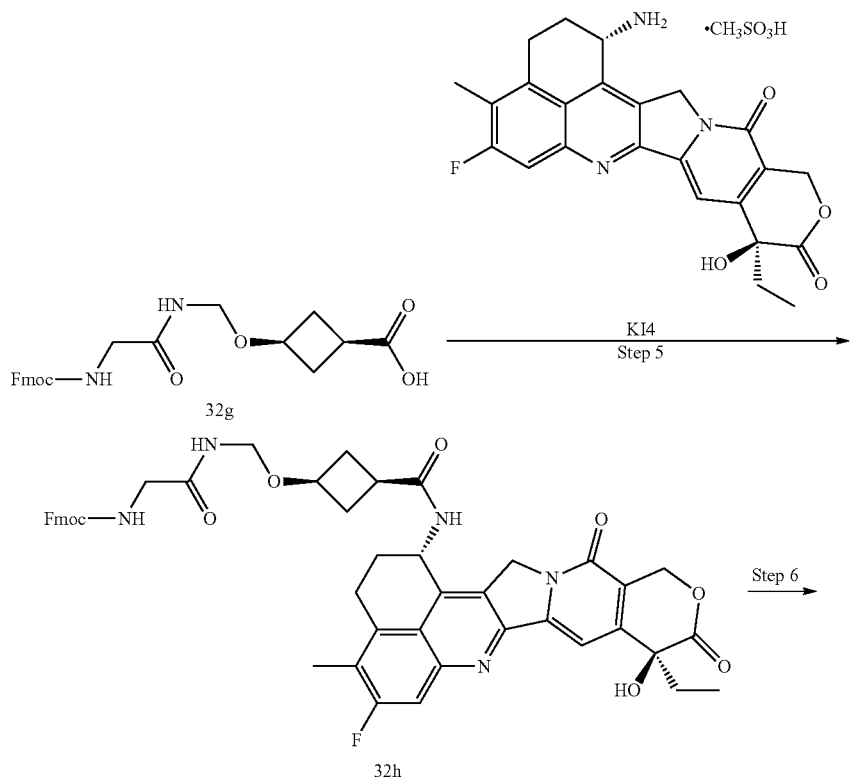

-continued
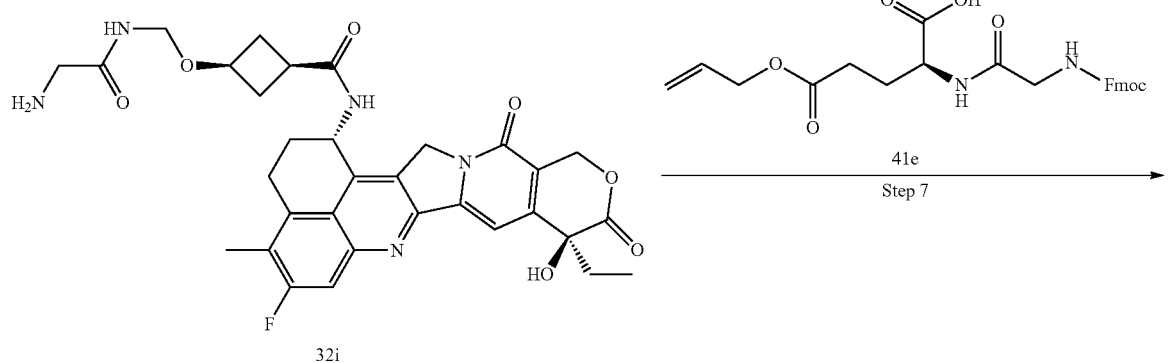
32i
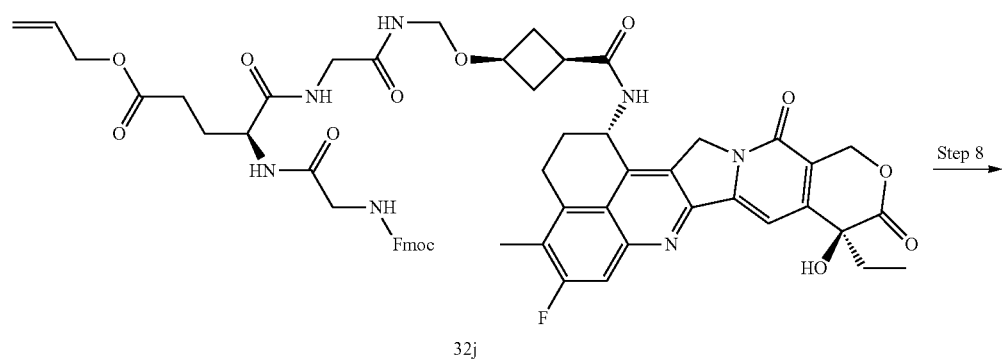
32j
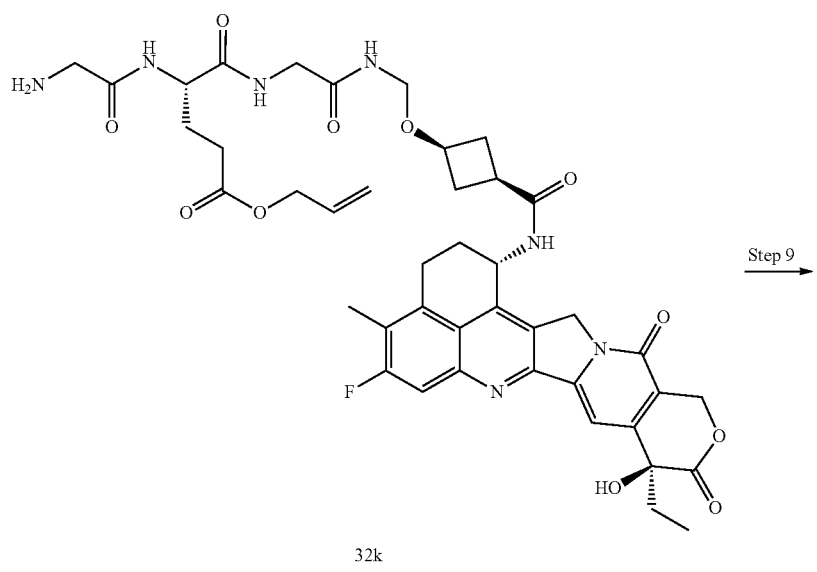
32k

-continued

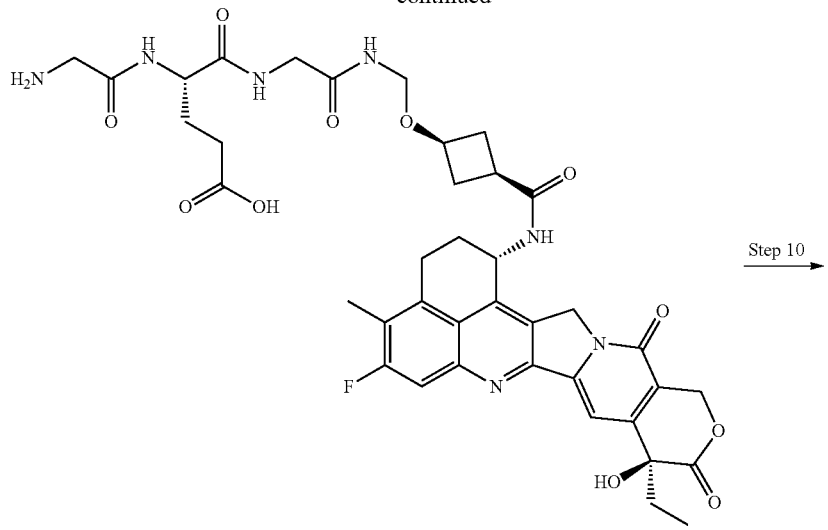

321

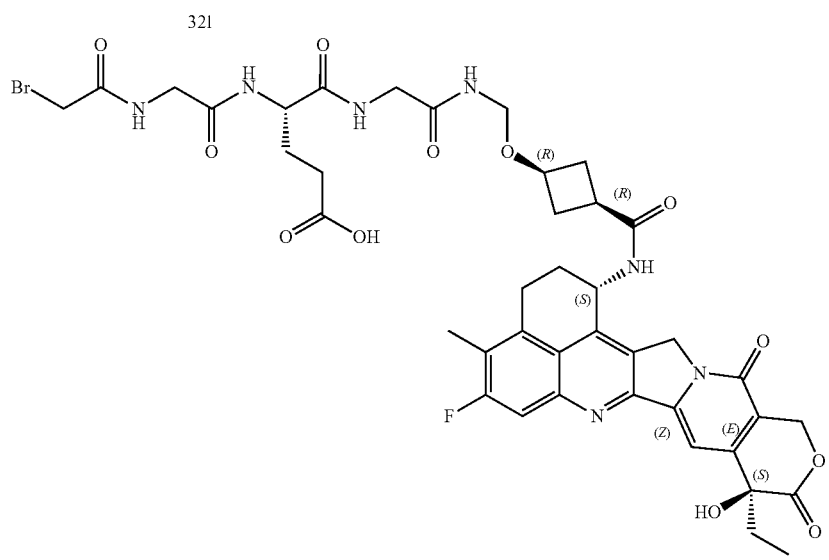

L-II-27

Step 1

Bromopropene (960 mg, 7.92 mmol) was added to a solution of 32a (2.00 g, 6.6 mmol) and K$_2$CO$_3$ (1.82 g, 13.2 mmol) in MeCN (20 mL), and the mixture was stirred at 20° C. for 5 h. After the reaction was completed as detected by TLC (PE/EA=1/2), the reaction solution was poured into water (100 mL), adjusted to pH 5 and extracted with EA (100 mL) three times. The organic phase was dried over anhydrous sodium sulfate, dried by rotary evaporation, and purified by column chromatography (PE/EA=2/1) to give 32b (1.83 g, yield 81%) as a white solid.

Step 2

TFA (10 mL) was added to a solution of 32b (1.38 g, 4.02 mmol) in DCM (10 mL), and the mixture was stirred at 25° C. for 17 h. After the reaction was completed as detected by TLC (PE/EA=1/3), the reaction solution was dried by rotary evaporation to give 32c (0.91 g, yield not counted) as a yellow sticky substance.

Step 3

41d (1.92 g, 4.87 mmol) was added to a solution of 32c (910 mg, 4.87 mmol) and NaHCO$_3$ (613 mg, 7.3 mmol) in DME/H$_2$O (20 mL/10 mL), and the mixture was stirred at 25° C. for 3 h. After the reaction was completed as detected by TLC (DCM/MeOH=1/1), the reaction solution was poured into water (100 mL), adjusted to pH 5 with aq. HCl (1 N) and extracted with EA (150 mL) twice. The organic phase was dried over anhydrous sodium sulfate, dried by rotary evaporation, and purified by column chromatography (DCM/MeOH=20/1) to give 32e (1.53 g, yield 67%) as a white solid. MS-ESI: m/z 467.4 [M+H]+.

Step 4

Pd/C (600 mg) was added to a solution of 32f (3 g, 5.83 mmol) in MeOH (50 mL), and the mixture was stirred under hydrogen atmosphere at 25° C. for 5 h. After the reaction was completed as detected by TLC (EA), the reaction solution was filtered and dried by rotary evaporation to give 32 g (1.9 g, yield 77%) as a white solid.

Step 5

HATU (707 mg, 1.86 mmol) was added to a solution of 32 g (789 mg, 1.86 mmol), KI4 (900 mg, 1.69 mmol) and triethylamine (342 mg, 3.38 mmol) in DMF (10 mL), and the mixture was stirred at 0° C. for 3.5 h. After the reaction was completed as detected by TLC (EA), the reaction solution was poured into H₂O (80 mL), and extracted with EA (100 mL) twice. The organic phase was dried over anhydrous sodium sulfate, dried by rotary evaporation, and purified by column chromatography (EA) to give 32h (1.186 g, yield 83%) as a white solid. MS-ESI: m/z 842.3 [M+H]+.

Step 6

A solution of 32h (1.186 g, 1.41 mmol) in DCM/diethylamine (20 mL, 20/1) was stirred at 25° C. for 17 h. After the reaction was completed as detected by TLC (DCM/MeOH=10/1), the reaction solution was poured into petroleum ether (200 mL), and the resulting mixture was filtered to give 32i (768 mg, yield 88%) as a white solid. MS-ESI: m/z 620.3 [M+H]+.

Step 7

HATU (414 mg, 1.09 mmol) was added to a solution of 32 g (676 mg, 1.09 mmol), 41e (508 mg, 1.09 mmol) and DIEA (423 mg, 3.27 mmol) in DMF (10 mL), and the mixture was stirred at 20° C. for 17 h. After the reaction was completed as detected by TLC (PE/EA=1/5), the reaction solution was poured into water (30 mL). The resulting mixture was filtered, and the filter cake was purified by column chromatography (DCM/MeOH=50/1) to give 32j (511 mg, yield 44%) as a white solid. MS-ESI: m/z 1068.3 [M+H]+.

Step 8

A solution of 32j (482 mg, 0.451 mmol) in diethylamine/DCM (10 mL, 1/5) was stirred at 10° C. for 17 h. After the reaction was completed as detected by TLC (EA), the reaction solution was poured into PE (300 mL), and the resulting mixture was filtered to give 32k (301 mg, yield not counted) as a white solid.

Step 9

Morpholine (93 mg, 1.07 mmol) was added to a solution of 32k (301 mg, 0.356 mmol) and Pd(PPh₃)₄ (82 mg, 0.071 mmol) in THF (5 mL), and the mixture was stirred at 25° C. for 5 h. After the reaction was completed as detected by LCMS, the reaction solution was purified by preparative chromatography to give 32l (108 mg, yield 38%) as a white solid. MS-ESI: m/z 806.3 [M+H]+.

Step 10

Bromoacetyl bromide (27 mg, 0.134 mmol) was added to a solution of 32l (108 mg, 0.134 mmol) and triethylamine (41 mg, 0.402 mmol) in THF (2 mL) and DMF (2 mL), and the mixture was stirred at 0° C. for 1 h. After the reaction was completed as detected by TLC (DCM/MeOH=10/1), the reaction solution was directly purified by preparative chromatography to give L-II-27 (15 mg, yield 12%) as a white solid.

MS-ESI: m/z 926.3 [M+H]+.

1H NMR (400 MHz, DMSO-d6) δ 12.11 (s, 1H), 8.54-8.42 (m, 3H), 8.27-8.16 (m, 2H), 7.78 (d, J=11.0 Hz, 1H), 7.30 (s, 1H), 6.53 (s, 1H), 5.61-5.51 (m, 1H), 5.42 (s, 2H), 5.20-5.05 (m, 2H), 4.56-4.42 (m, 2H), 4.32-4.22 (m, 1H), 3.96-3.87 (m, 3H), 3.79 (d, J=5.6 Hz, 2H), 3.70 (d, J=5.9 Hz, 2H), 3.25-3.08 (m, 2H), 2.61-2.53 (m, 2H), 2.45-2.36 (m, 4H), 2.36-2.22 (m, 3H), 2.20-2.03 (m, 4H), 1.99-1.68 (m, 4H), 0.87 (t, J=7.3 Hz, 3H).

Preparation Example 1.33 (1R,3R)-3-(((S)-7-benzyl-16-bromo-3,6,9,12,15-pentaoxo-2,5,8,11,14-pentaazahexadecyl)oxy)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclobutane-1-carboxamide

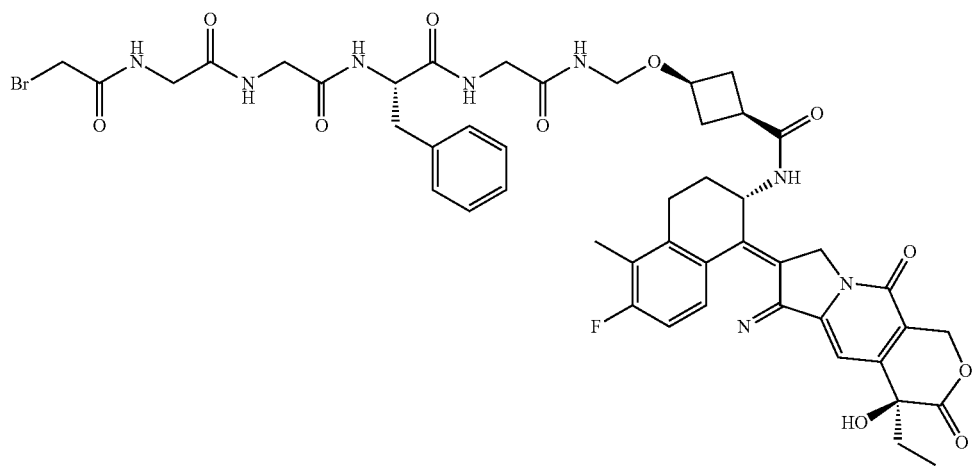

L-II-28

-continued
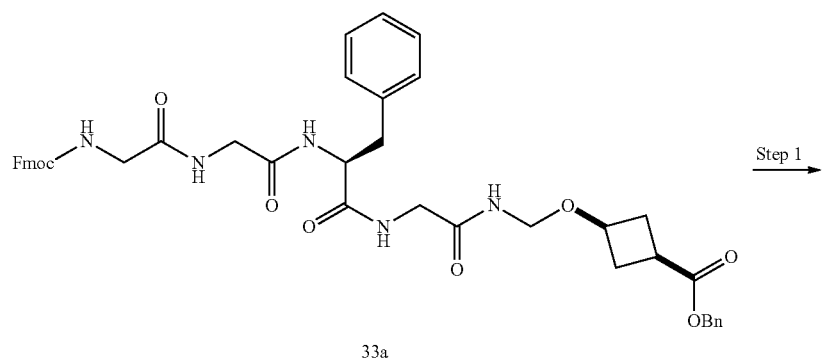
33a
Step 1 →
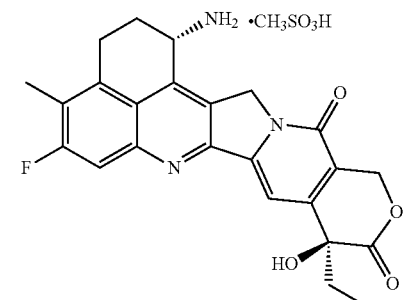
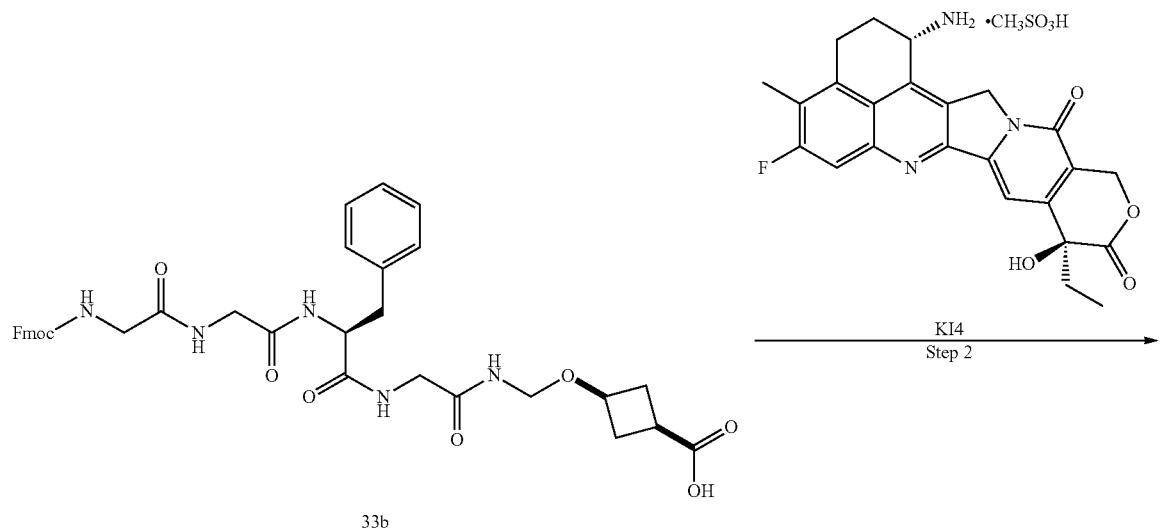
33b
KI4
Step 2 →
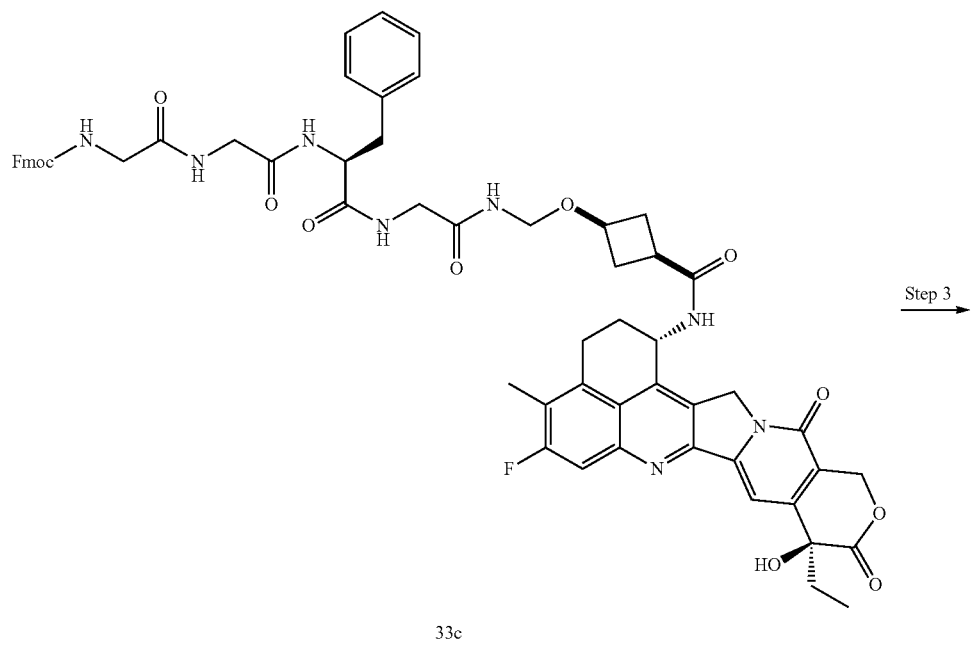
33c
Step 3 →

-continued

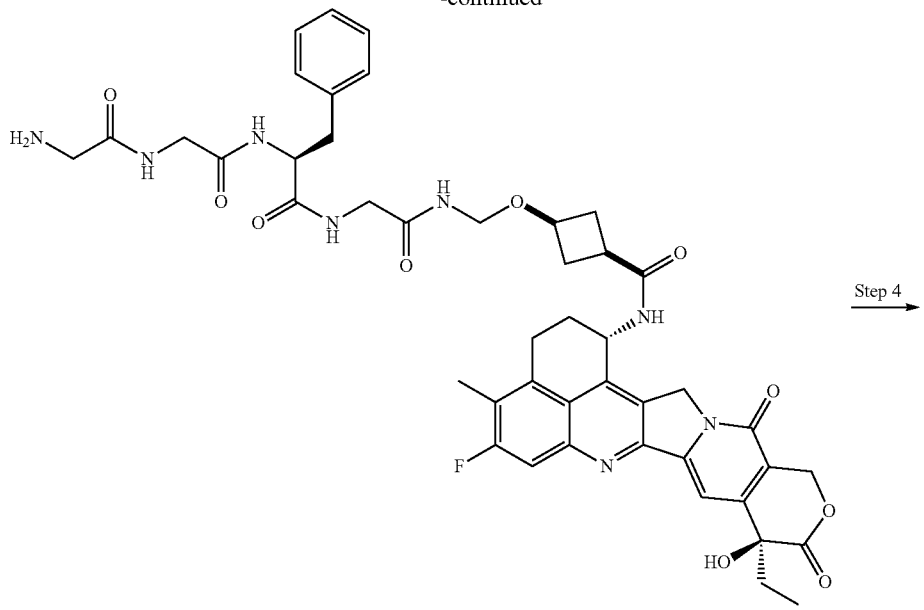

33d

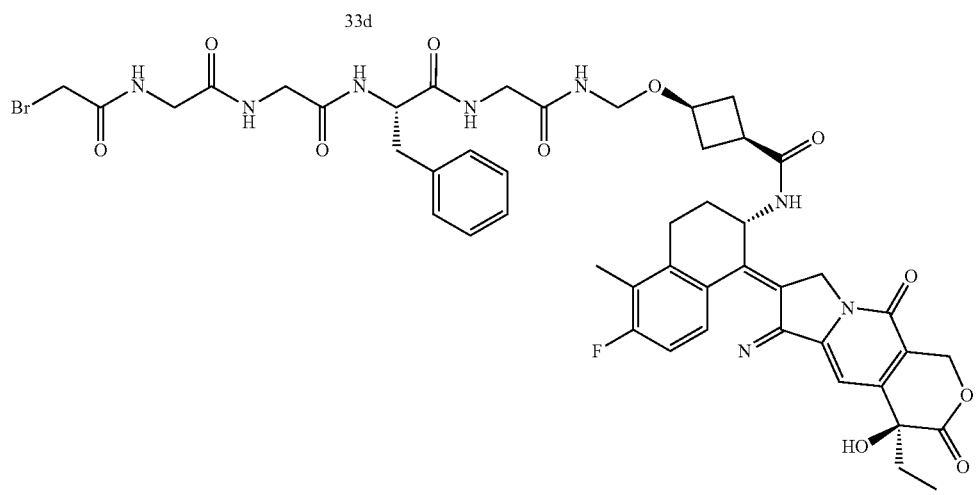

L-II-28

Step 1

Pd/C (400 mg, 10 wt. %) was added to a solution of 33a (2.00 g, 2.58 mmol) in MeOH (20 mL), and the mixture was stirred at 20° C. for 5 h. After the reaction was completed as detected by TLC (EA), the reaction solution was filtered and dried by rotary evaporation to give 33b (1.3 g, yield 74%) as a white solid.

Step 2

HATU (305 mg, 0.802 mmol) was added to a solution of 33b (0.55 g, 0.802 mmol), KI4 (427 mg, 0.802 mmol) and DIPEA (310 mg, 2.40 mmol) in DMF (5 mL), and the mixture was stirred at 0° C. for 2 h. After the reaction was completed as detected by TLC (DCM/MeOH=1/10), the reaction solution was poured into water (40 mL). The resulting mixture was filtered, and the filter cake was purified by column chromatography (DCM/MeOH=20/1) to give 33c (360 mg, yield 41%) as a yellow solid.

Step 3

Diethylamine (2 mL) was added to a solution of 33c (360 mg, 0.326 mmol) in DCM (10 mL), and the mixture was stirred at 25° C. for 17 h. After the reaction was completed as detected by TLC (DCM/MeOH=5/1), the reaction solution was poured into PE (100 mL), and the resulting mixture was filtered to give 33d (205 mg, yield 71%) as a white solid. MS-ESI: m/z 881.3 [M+H]+.

Step 4

A solution of bromoacetyl bromide (94 mg, 0.446 mmol) in THF (2 mL) was added to a solution of 33d (205 mg, 0.233 mmol) and triethylamine (118 mg, 1.17 mmol) in DMF (1 mL) and water (1 mL), and the mixture was stirred at 0° C. for 1 h. The reaction solution was purified by preparative chromatography to give L-II-28 (15 mg, yield 6%) as a white solid.

MS-ESI: m/z 1001.2 [M+H]+.

1H NMR (400 MHz, DMSO-d6) δ 8.57-8.50 (m, 1H), 8.50-8.43 (m, 2H), 8.35-8.29 (m, 1H), 8.19-8.12 (m, 2H), 7.80 (d, J=10.8 Hz, 1H), 7.27-7.14 (m, 7H), 6.53 (s, 1H), 5.59-5.51 (m, 1H), 5.44-5.39 (m, 2H), 5.20-5.07 (m, 2H), 4.56-4.44 (m, 3H), 3.92 (s, 3H), 3.80-3.68 (m, 5H), 3.41 (s, 1H), 3.21-3.12 (m, 2H), 2.83-2.74 (m, 1H), 2.58-2.55 (m, 3H), 2.39 (s, 4H), 2.18-2.03 (m, 4H), 1.93-1.78 (m, 2H), 0.87 (t, J=7.3 Hz, 3H).
Preparation Example 1.34. N-((7S,15S)-7-benzyl-17-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-15-methyl-2,5,8,11,17-pentaoxo-14-oxa-3,6,9,12-tetraazaheptadecyl)-6-(2,5-dioxo-2,5-dihydro-1H-pyrrol-1-yl)hexanamide
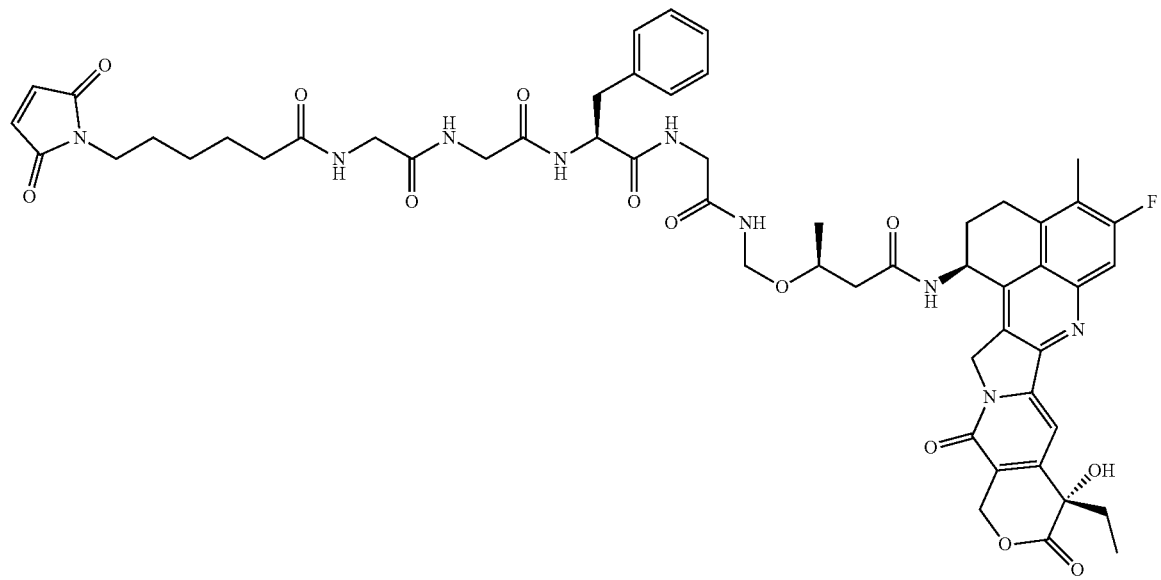
L-III-30
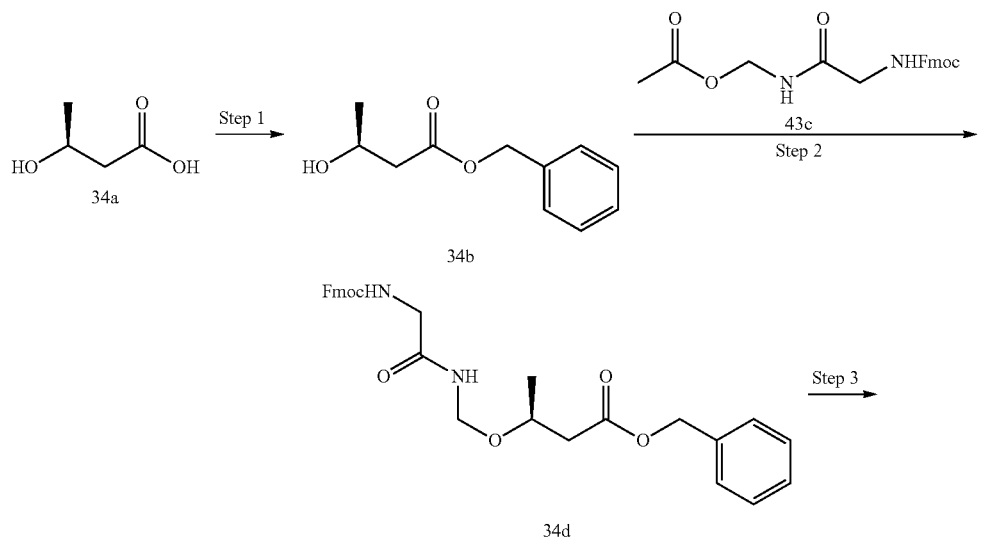

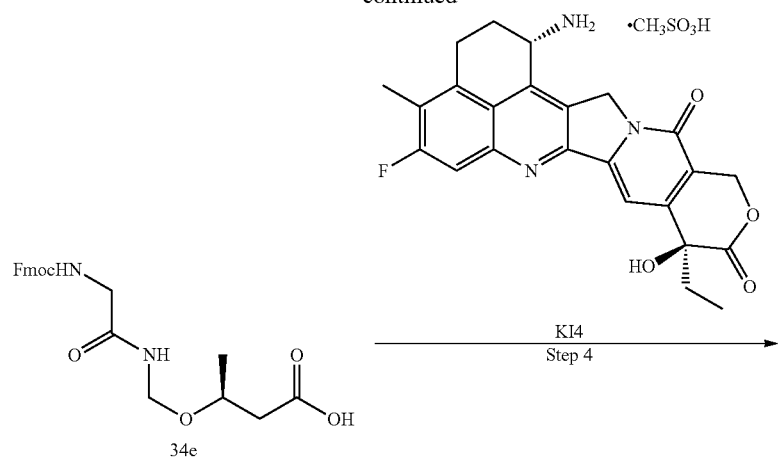
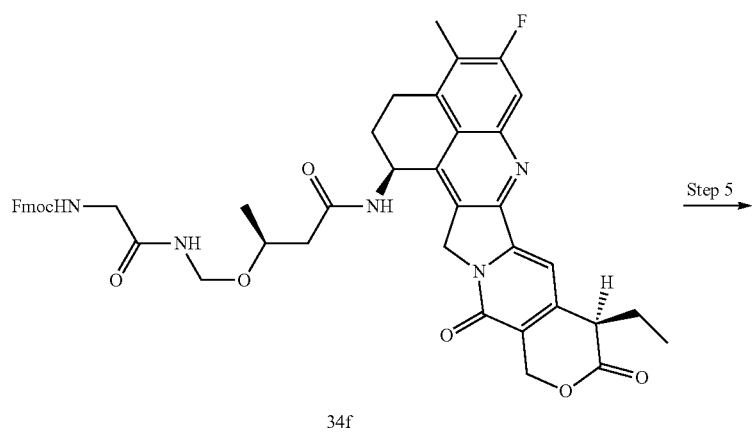
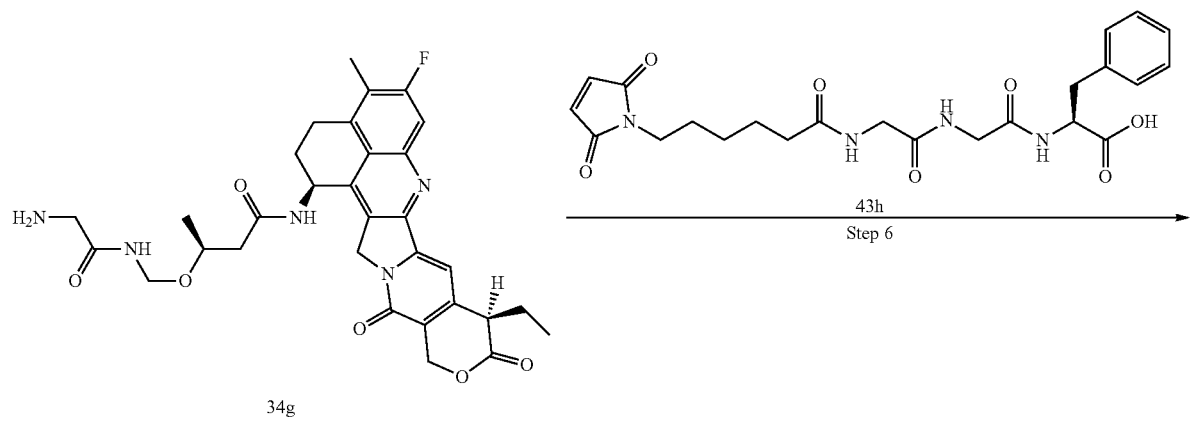

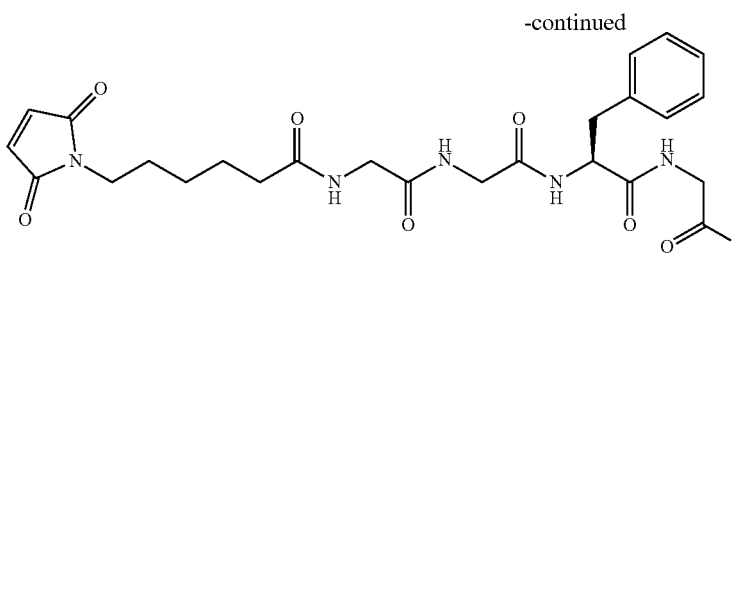

L-III-30

Step 1

34a (5 g, 48.0 mmol) and K$_2$CO$_3$ (19.9 g, 144.0 mmol) were dissolved in DMF (20 mL), followed by the dropwise addition of benzyl bromide (12.3 g, 72.0 mmol). The mixture was reacted at 25° C. for 17 h. After the starting material was consumed completely as detected by TLC (PE/EA=3/1), the reaction solution was added to water (200 mL), extracted with EA (250 mL), separated and washed with saturated NaCl. The organic phase was dried over anhydrous Na$_2$SO$_4$, concentrated and purified by column chromatography (PE:EA=2:1) to give 34b (8.7 g, yield 93%) as a colorless liquid. MS-ESI: m/z 195.1 [M+H]+.

Step 2

34c (7.3 g, 19.8 mmol) and TsOH (1.46 g, 8.5 mmol) were dissolved in THF (20 mL), and the mixture was cooled to 0° C. under nitrogen atmosphere, added dropwise with a solution of 43b (7.7 g, 39.6 mmol) in THF (10 mL) and reacted at 0° C. for 2 h after the addition was completed. After most of the starting material was consumed as detected by TLC (PE/EA=2/1), the reaction solution was poured into water (100 mL), extracted with DCM (100 mL), separated and washed with saturated NaCl. The organic phase was dried over anhydrous Na$_2$SO$_4$ and purified by column chromatography (PE/EA=1/1) to give 34d (3.9 g, yield 39%) as a colorless sticky substance. MS-ESI: m/z 503.3 [M+H]+.

Step 3

Pd/C (1 g, 10 wt. %) was added to a mixed solution of 34d (1.9 g, 3.78 mmol) in EtOH (100 mL) and EA (100 mL) at 0° C. under hydrogen atmosphere, and the mixture was reacted at 0° C. for 3 h. After the reaction was completed as detected by TLC (PE/EA=2/1), the reaction solution was filtered through celite, and the filter cake was washed with EA/EtOH (1:1, 100 mL×3). The filtrate was concentrated, and dissolved with THF (50 mL×3) and dried by rotary evaporation, which was repeated three times, to give 34e (1 g, yield 64%) as a gray solid. MS-ESI: m/z 435.2 [M+H]+.

Step 4

DIEA (303 mg, 2.35 mmol) was added dropwise to a solution of 34e (426 mg, 1.03 mmol), KI4 (500 mg, 0.94 mmol) and HATU (429 mg, 1.13 mmol) in DMF (20 mL) at 0° C. under nitrogen atmosphere, and the mixture was reacted at 0° C. for 2 h after the addition was completed. After the reaction was completed as detected by LCMS, the reaction solution was added dropwise to water (300 mL) and stirred. The resulting mixture was left to stand for 5 min and filtered, and the filter cake was dissolved with DCM/MeOH (10:1, 100 mL) solution, dried by rotary evaporation, mixed with silica gel and purified by column chromatography (EA:MeOH=30:1) to give 34f (600 mg, yield 77%) as a yellow solid. MS-ESI: m/z 830.3 [M+H]+.

Step 5

Diethylamine (5 mL) was added dropwise to a solution of 34f (150 mg, 0.18 mmol) in DCM (5 mL) at 0° C. under nitrogen atmosphere, and the mixture was reacted at 0° C. for 2 h. After the reaction was completed as detected by LCMS, a petroleum ether solution (100 mL×6) was added to the reaction solution, and a solid was precipitated. The resulting mixture was left to stand until the solid was adsorbed on the bottom of the flask, and the solution was poured out and dried with an oil pump to give 34g (120 mg, yield 76%) as a white powder, with the product content of 70% as detected by LCMS. MS-ESI: m/z 608.3 [M+H]+.

Step 6

A solution of HATU (45 mg, 0.118 mmol) in DMF (1 mL) was added to a solution of 34g (60 mg, 0.099 mmol), 43h (51 mg, 0.108 mmol) and DIEA (32 mg, 0.25 mmol) in DMF (1 mL) at 0° C. under nitrogen atmosphere, and the mixture was reacted at 0° C. for 2 h. After the starting material was consumed completely as detected by LCMS, the reaction solution was directly purified by reverse-phase column chromatography (eluent: (MeCN/MeOH=1/1):H$_2$O=60%: 40%) to give L-III-30 (14.8 mg, yield 14%) as a yellow solid.

MS-ESI: m/z 1062.4 [M+H]+.

1H NMR (400 MHz, Methanol-d4) δ 7.69-7.61 (m, 2H), 7.22-7.16 (m, 2H), 7.16-7.09 (m, 3H), 6.76 (s, 2H), 5.70-5.64 (m, 1H), 5.60 (d, J=16.4 Hz, 1H), 5.40-5.31 (m, 2H), 5.26 (d, J=19.0 Hz, 1H), 4.65-4.50 (m, 7H), 4.25-4.16 (m, 1H), 3.87 (d, J=16.7 Hz, 1H), 3.83-3.76 (m, 3H), 3.72 (d, J=17.0 Hz, 2H), 3.44 (t, J=7.1 Hz, 2H), 3.25-3.17 (m, 2H), 3.10-3.02 (m, 1H), 2.92-2.83 (m, 1H), 2.45-2.39 (m, 5H), 2.32-2.20 (m, 5H), 1.97-1.89 (m, 2H), 1.63-1.50 (m, 4H), 1.34-1.20 (m, 6H), 0.99 (t, J=7.3 Hz, 3H).

Preparation Example 1.35. N-((7S)-7-benzyl-17-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-15-methyl-2,5,8,11,17-pentaoxo-14-oxa-3,6,9,12-tetraazaheptadecyl)-6-(2,5-dioxo-2,5-dihydro-1H-pyrrol-1-yl)hexanamide

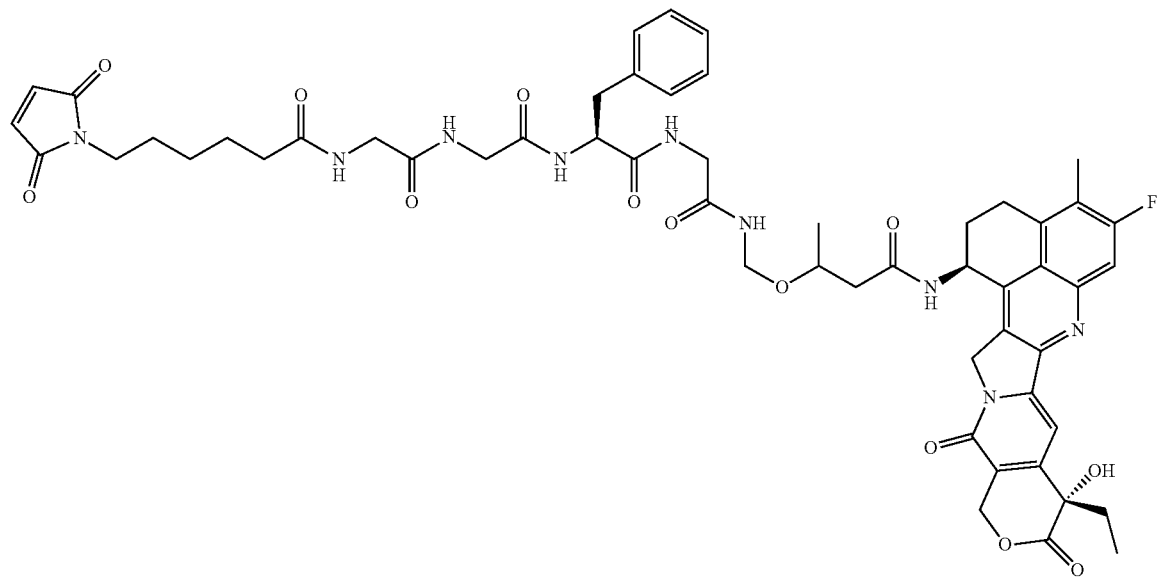

L-III-31

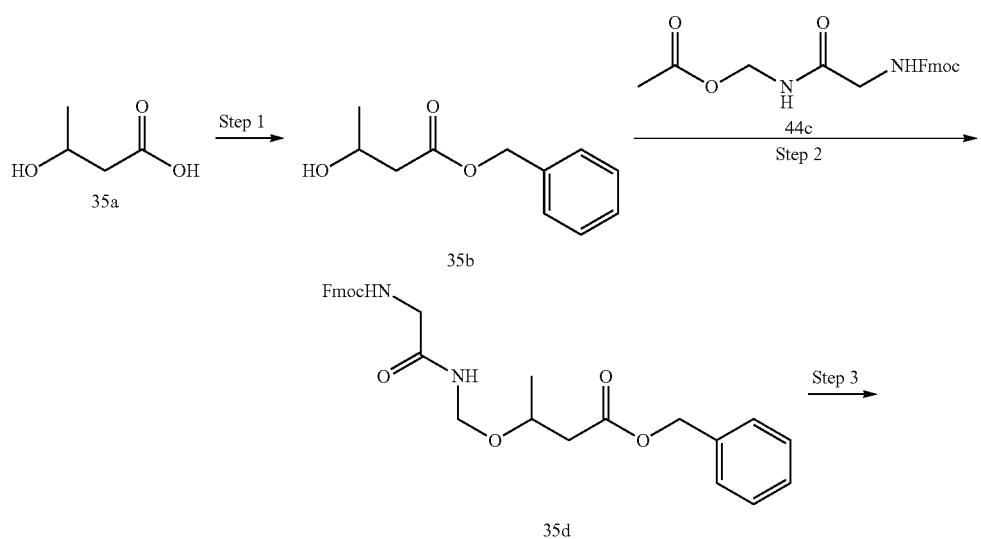

-continued
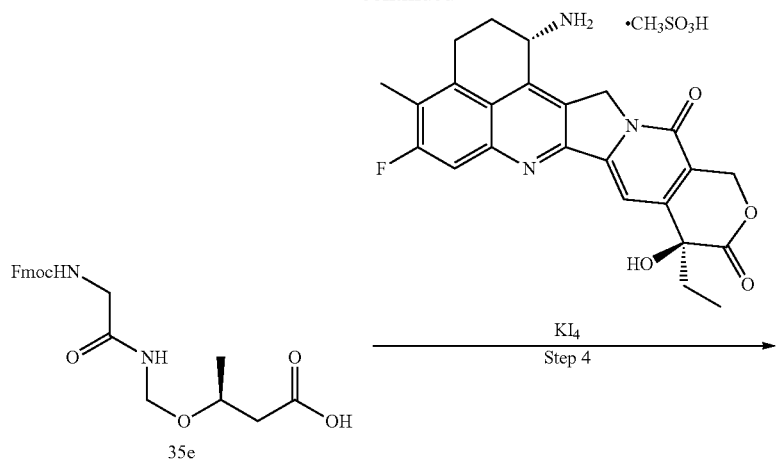
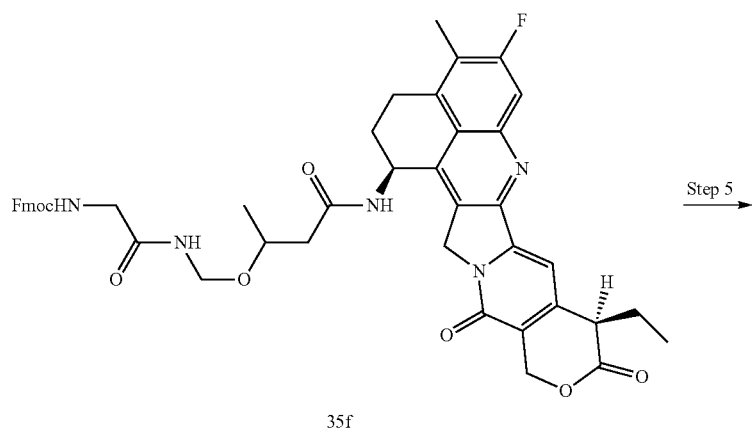
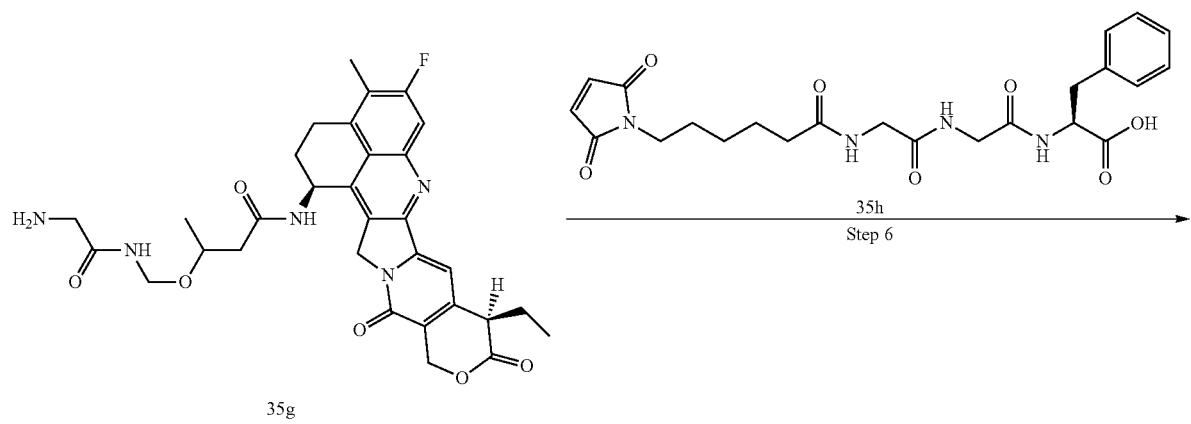

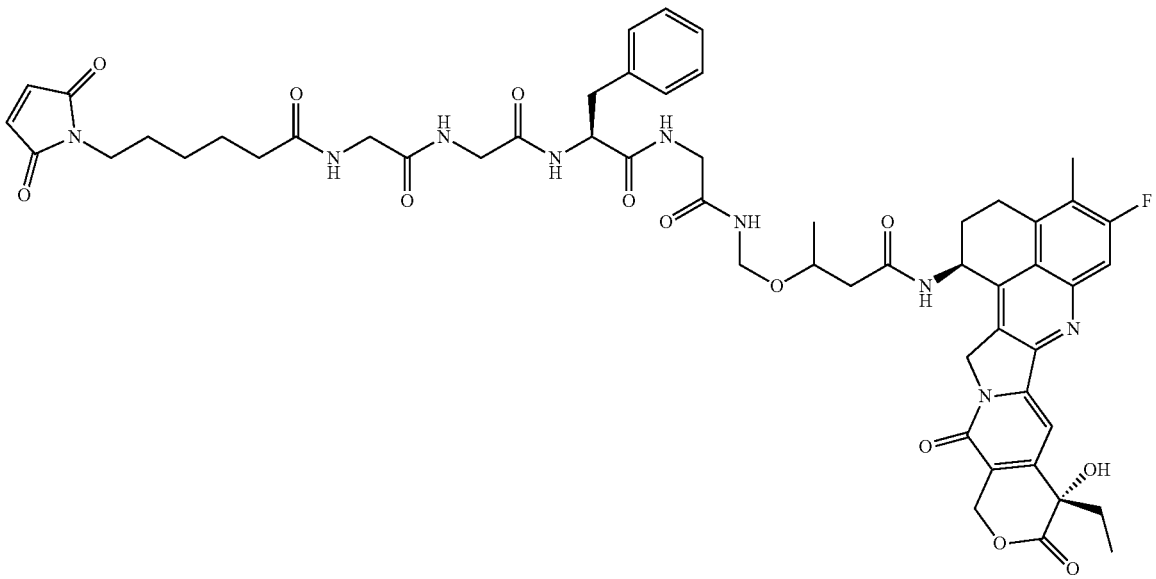

L-III-31

Step 1

35a (10.0 g, 96 mmol) and K₂CO₃ (39.8 g, 288 mmol) were dissolved in DMF (100 mL), followed by the dropwise addition of benzyl bromide (24.6 g, 144 mmol). The mixture was reacted at room temperature for 17 h. After the reaction was completed as detected by TLC (PE/EA=3/1), the reaction solution was added to water (200 mL), extracted with EA (250 mL), separated and washed with saturated NaCl. The organic phase was dried over anhydrous Na₂SO₄, concentrated and purified by column chromatography (PE:EA=4:1) to give 35b (15 g, yield 80%) as a colorless liquid. MS-ESI: m/z 195.1 [M+H]+.

Step 2

35c (6.6 g, 18 mmol) and 35b (7 g, 36 mmol) were dissolved in THF (50 mL), and the mixture was cooled to 0° C. under nitrogen atmosphere, added dropwise with a solution of TsOH (1.3 g, 7.5 mmol) in THF (10 mL) and reacted at 0° C. for 2 h after the addition was completed. After most of the starting material was consumed as detected by TLC (PE/EA=2/1), the reaction solution was poured into water (100 mL), extracted with DCM (100 mL), separated and washed with saturated NaCl. The organic phase was dried over anhydrous Na₂SO₄ and purified by column chromatography (PE/EA=1/1) to give 35d (4.9 g, yield 54%) as a pale yellow sticky substance. MS-ESI: m/z 503.2 [M+H]+.

Step 3

Pd/C (2 g, 10 wt. %) was added to a mixed solution of 35d (2.2 g, 4.4 mmol) in EtOH (20 mL) and EA (20 mL) at 0° C. under hydrogen atmosphere, and the mixture was reacted at 0° C. for 3 h. After the reaction was completed as detected by TLC (PE/EA=2/1), the reaction solution was filtered through celite, and the filter cake was washed with EA/EtOH (1:1, 100 mL×3). The filtrate was concentrated, and dissolved with THF (50 mL×3) and dried by rotary evaporation, which was repeated three times, to give 35e (1.5 g, yield 83%) as a white solid. MS-ESI: m/z 435.1 [M+H]+.

Step 4

DIEA (606 mg, 4.70 mmol) was added dropwise to a solution of 35e (852 mg, 2.07 mmol), KI4 (1 g, 1.88 mmol) and HATU (856 mg, 2.25 mmol) in DMF (50 mL) at 0° C. under nitrogen atmosphere, and the mixture was reacted at 0° C. for 2 h after the addition was completed. After the reaction was completed as detected by LCMS, the reaction solution was added dropwise to water (700 mL) and stirred. The resulting mixture was left to stand for 5 min and filtered, and the filter cake was dissolved with DCM/MeOH (10:1, 150 mL) solution, dried by rotary evaporation, mixed with silica gel and purified by column chromatography (EA:MeOH=30:1) to give 35f (900 mg, yield 79%) as a yellow solid. MS-ESI: m/z 830.3 [M+H]+.

Step 5

Diethylamine (1.5 mL) was added dropwise to a solution of 35f (800 mg, 0.96 mmol) in DCM (30 mL) at 0° C. under nitrogen atmosphere, and the mixture was reacted at RT for 17 h. After the reaction was completed as detected by LCMS, a petroleum ether solution (100 mL×6) was added to the reaction solution, and a solid was precipitated. The resulting mixture was left to stand until the solid was adsorbed on the bottom of the flask, and the solution was poured out and dried with an oil pump to give a white powder (640 mg). Then the solid was treated with TFA: MeOH (1:20) to give 35g (770 mg, yield 92%) as a yellow solid, with the content of 70% as detected by LCMS. MS-ESI: m/z 608.3 [M+H]+.

Step 6

A solution of HATU (487 mg, 1.28 mmol) in DMF (2 mL) was added to a solution of 35g (770 mg, 0.89 mmol), 43h (480 mg, 1.02 mmol) and DIEA (345 mg, 2.67 mmol) in DMF (8 mL) under nitrogen atmosphere, and the mixture was reacted at 0° C. for 2 h. After the starting material was consumed completely as detected by LCMS, the reaction solution was added to ice water (100 mL) and stirred, and a yellow solid was precipitated. The resulting mixture was left to stand until the solid was absorbed the bottom of the flask and to the solution, the solution was frozen to precipitate the product and filtered, and the solid was lyophilized, mixed with silica gel, and purified by column chromatography (EA/MeOH=20/1) to give 35 (568 mg, yield 42%) as a pale yellow solid.

MS-ESI: m/z 1062.8 [M+H]+.

1H NMR (400 MHz, DMSO-d6) δ 8.52-8.44 (m, 2H), 8.33-8.26 (m, 1H), 8.15-8.09 (m, 1H), 8.09-8.04 (m, 1H), 8.03-7.96 (m, 1H), 7.81 (d, J=10.9 Hz, 1H), 7.33 (s, 1H), 7.26-7.11 (m, 5H), 6.99 (s, 2H), 6.54 (s, 1H), 5.61-5.52 (m, 1H), 5.46-5.40 (m, 2H), 5.28 (d, J=19.1 Hz, 1H), 5.17 (d, J=18.9 Hz, 1H), 4.69-4.59 (m, 1H), 4.59-4.45 (m, 2H), 4.08-3.98 (m, 1H), 3.78-3.54 (m, 6H), 3.38-3.35 (m, 2H), 3.22-3.09 (m, 2H), 3.07-2.98 (m, 1H), 2.82-2.72 (m, 1H), 2.43-2.35 (m, 4H), 2.27-2.18 (m, 1H), 2.17-2.05 (m, 4H), 1.94-1.77 (m, 2H), 1.51-1.39 (m, 4H), 1.25-1.08 (m, 5H), 0.86 (t, J=7.3 Hz, 3H).

Preparation Example 1.36. (Dxd, Reference Example 5)

The reference compound (Dxd) was synthesized by referring to the method provided in Example 75 on page 183 of the specification of the patent "CN104755494A".

The reference compound (Deruxtecan) was synthesized by referring to the method provided in Example 58 on page 163 of the specification of the patent "CN104755494A". The reference ADC-1 (Trastuzumab-Deruxtecan) was synthesized by referring to the method provided in Example 58 on page 163 of the specification of the patent "CN104755494A" or by methods commonly used in the art as disclosed.

Preparation Example 1.37

The following ligands can be prepared according to the conventional methods for antibodies. For example, vectors can be constructed, transfected into eukaryotic cells such as HEK293 cells (Life Technologies, Cat No. 11625019), and purified for expression.

Preparation Example 1.37a. The Sequences of Trastuzumab are Shown as Follows

Light chain
(SEQ ID NO: 33)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Heavy chain
(SEQ ID NO: 37)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG

Preparation Example 1.37b. The Sequences of Pertuzumab Antibody are Shown as Follows Light chain
(SEQ ID NO: 34)
DIQMTQSPSSLSASVGDRVTITCKASQDVSIGVAWYQQKPGKAPKLLIYS

ASYRYTGVPSRFSGSGSGTDFTLTISSLQPEDFATYYCQQYYIYPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Heavy chain
(SEQ ID NO: 38)
EVQLVESGGGLVQPGGSLRLSCAASGFTFTDYTMDWVRQAPGKGLEWVAD

VNPNSGGSIYNQRFKGRFTLSVDRSKNTLYLQMNSLRAEDTAVYYCARNL

GPSFYFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPG

Preparation Example 1.37c. The Sequences of hRS7 Antibody (Sacituzumab) are Shown as Follows Light chain
(SEQ ID NO: 35)
DIQLTQSPSSLSASVGDRVSITCKASQDVSIAVAWYQQKPGKAPKLLIYS

ASYRYTGVPDRFSGSGSGTDFTLTISSLQPEDFAVYYCQQHYITPLTFGA

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Heavy chain
(SEQ ID NO: 39)
VQLQQSGSELKKPGASVKVSCKASGYTFTNYGMNWVKQAPGQGLKWMGWI

NTYTGEPTYTDDFKGRFAFSLDTSVSTAYLQISSLKADDTAVYFCARGGF

GSSYWYFDVWGQGSLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKSCDKTHTCPPCPAPELLGGPSVFLFPPKP

-continued
KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK

Preparation Example 1.37d. The Sequences of Zolbetuximab Antibody are Shown as Follows Light chain
(SEQ ID NO: 36)
DIVMTQSPSSLTVTAGEKVTMSCKSSQSLLNSGNQKNYLTWYQQKPGQPP

KLLIYWASTRESGVPDRFTGSGSGTDFTLTISSVQAEDLAVYYCQNDYSY

-continued
PFTFGSGTKLEIKRTVAAPSVFIFPPSDEQLKSGTASVVCLLNNFYPREA

KVQWKVDNALQSGNSQESVTEQDSKDSTYSLSSTLTLSKADYEKHKVYAC

EVTHQGLSSPVTKSFNRGEC

Heavy chain
(SEQ ID NO: 40)
QVQLQQPGAELVRPGASVKLSCKASGYTFTSYWINWVKQRPGQGLEWIGN

IYPSDSYTNYNQKFKDKATLTVDKSSSTAYMQLSSPTSEDSAVYYCTRSW

RGNSFDYWGQGTTLTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK

Preparation Example 1.38. ADC-II-1

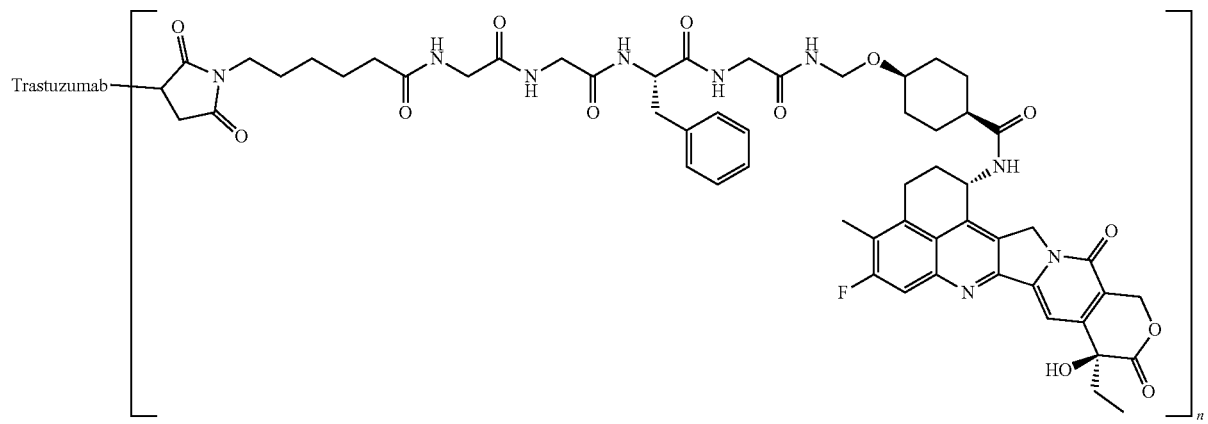

ADC-II-1

The prepared tris(2-carboxyethyl)phosphine (5 mM, 0.233 mL, 1.163 µmol) aqueous solution was added to the antibody Trastuzumab in aqueous PB buffer solution (0.04 M aqueous PB buffer solution at pH 7.0; 23 mg, 15 mg/mL, 0.155 µmol) at 37° C., and the mixture was placed in a water bath shaker and shaken at 37° C. for 3 h, and then the reaction was terminated;

L-II-1 (3.4 mg, 6.06 µmol) was dissolved in DMSO (0.10 mL), and the solution was added to the above solution (2.0 mL), placed in a water bath shaker and shaken at 25° C. for 3 h, and then the reaction was terminated. The reaction solution was desalted and purified on a Sephadex G25 gel column (eluent: 0.04 M aqueous PB buffer solution at pH 7.0, containing 0.002 M EDTA) to give a solution of the exemplary product ADC-II-1 in PB (3.08 mg/mL, 12 mg), which was stored at 4° C.

The mean n=7.42, as calculated by LC-MS.

Preparation Example 1.39. ADC-II-5

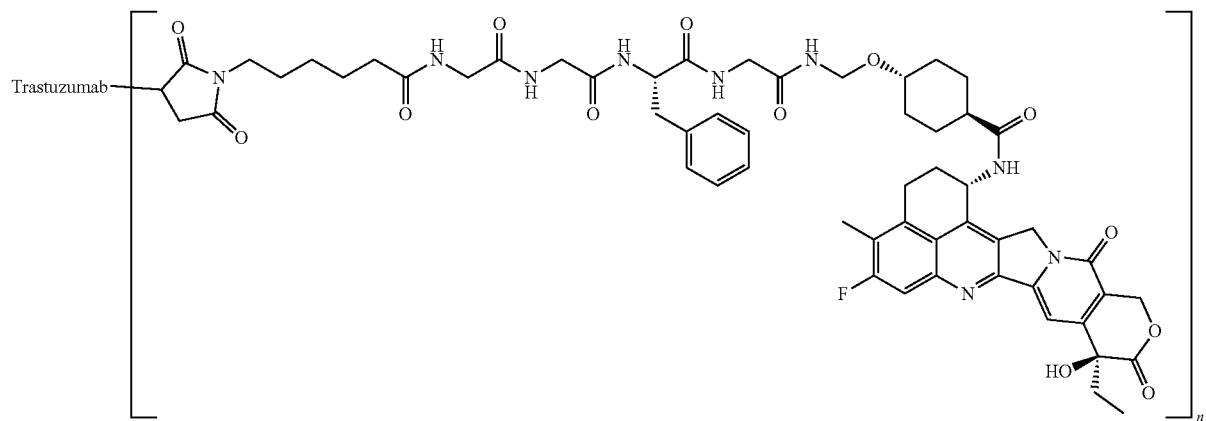

ADC-II-5

The prepared tris(2-carboxyethyl)phosphine (5 mM, 0.304 mL, 1.52 μmol) aqueous solution was added to the antibody Trastuzumab in aqueous PB buffer solution (0.04 M aqueous PB buffer solution at pH 7.0; 30 mg, 15 mg/mL, 0.203 μmol) at 37° C., and the mixture was placed in a water bath shaker and shaken at 37° C. for 3 h, and then the reaction was terminated; the reaction solution was cooled to 25° C. in a water bath and diluted to 5.0 mg/mL, and the diluted solution (2.0 mL) was taken for the next step.

L-II-2 (1.65 mg, 2.94 μmol) was dissolved in DMSO (0.10 mL), and the solution was added to the above solution (2.0 mL), placed in a water bath shaker and shaken at 25° C. for 3 h, and then the reaction was terminated. The reaction solution was desalted and purified on a Sephadex G25 gel column (eluent: 0.04 M aqueous PB buffer solution at pH 7.0, containing 0.002 M EDTA) to give a solution of the exemplary product ADC-II-5 in PB (6.37 mg/mL, 17 mg), which was frozen and stored at 4° C.

The mean n=7.58, as calculated by LC-MS.

Preparation Example 1.40. ADC-II-9

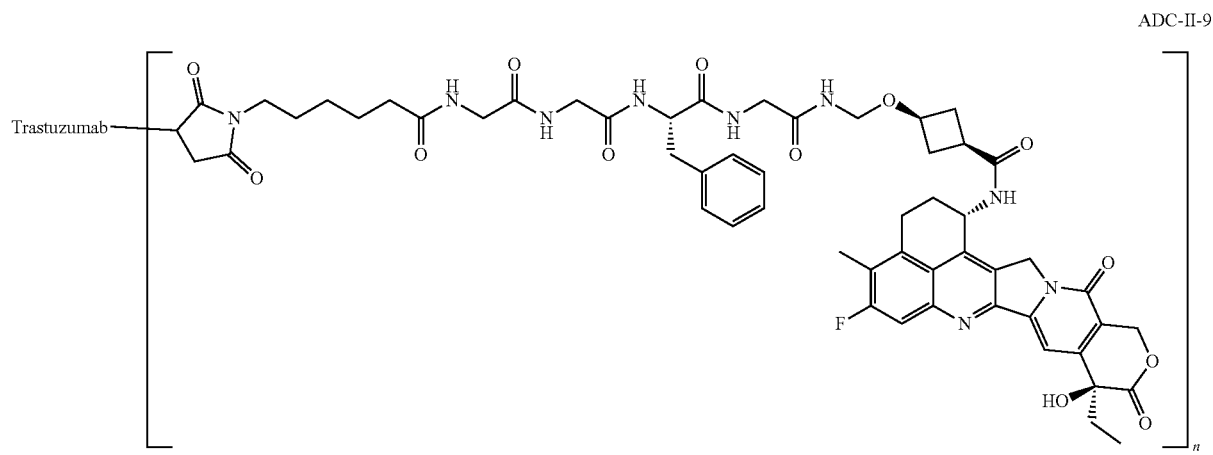

ADC-II-9

The prepared tris(2-carboxyethyl)phosphine (5 mM, 0.355 mL, 1.77 μmol) aqueous solution was added to the antibody trastuzumab in aqueous PB buffer solution (0.04 M aqueous PB buffer solution at pH 7.0; 35 mg, 15 mg/mL, 0.236 μmol) at 37° C., and the mixture was placed in a water bath shaker and shaken at 37° C. for 3 h, and then the reaction was terminated; the reaction solution was cooled to 25° C. in a water bath and diluted to 5.0 mg/mL, and the diluted solution (2.0 mL) was taken for the next step.

L-II-3 (4.51 mg, 2.84 μmol) was dissolved in DMSO (0.10 mL), and the solution was added to the above solution (2.0 mL), placed in a water bath shaker and shaken at 25° C. for 3 hours with shaking, and then the reaction was terminated. The reaction solution was desalted and purified on a Sephadex G25 gel column (eluent: 0.04 M aqueous PB buffer solution at pH 7.0, containing 0.002 M EDTA) to give a solution of the exemplary product ADC-II-9 in PB (7.00 mg/mL, 15 mg), which was frozen and stored at 4° C.

The mean n=8.05, as calculated by LC-MS.

Preparation Example 1.41. ADC-II-13

The prepared tris(2-carboxyethyl)phosphine (5 mM, 0.355 mL, 1.77 μmol) aqueous solution was added to the antibody Trastuzumab in aqueous PB buffer solution (0.04 M aqueous PB buffer solution at pH 7.0; 35 mg, 15 mg/mL, 0.236 μmol) at 37° C., and the mixture was placed in a water bath shaker and shaken at 37° C. for 3 h, and then the reaction was terminated; the reaction solution was cooled to 25° C. in a water bath and diluted to 5.0 mg/mL, and the diluted solution (2.0 mL) was taken for the next step.

L-II-4 (1.96 mg, 3.67 μmol) was dissolved in DMSO (0.10 mL), and the solution was added to the above solution (2.0 mL), placed in a water bath shaker and shaken at 25° C. for 3 h, and then the reaction was terminated. The reaction solution was desalted and purified on a Sephadex G25 gel column (eluent: 0.04 M aqueous PB buffer solution at pH 7.0, containing 0.002 M EDTA) to give a solution of the exemplary product ADC-III-13 in PB (6.94 mg/mL, 25 mg), which was frozen and stored at 4° C.

The mean n=7.89, as calculated by LC-MS.

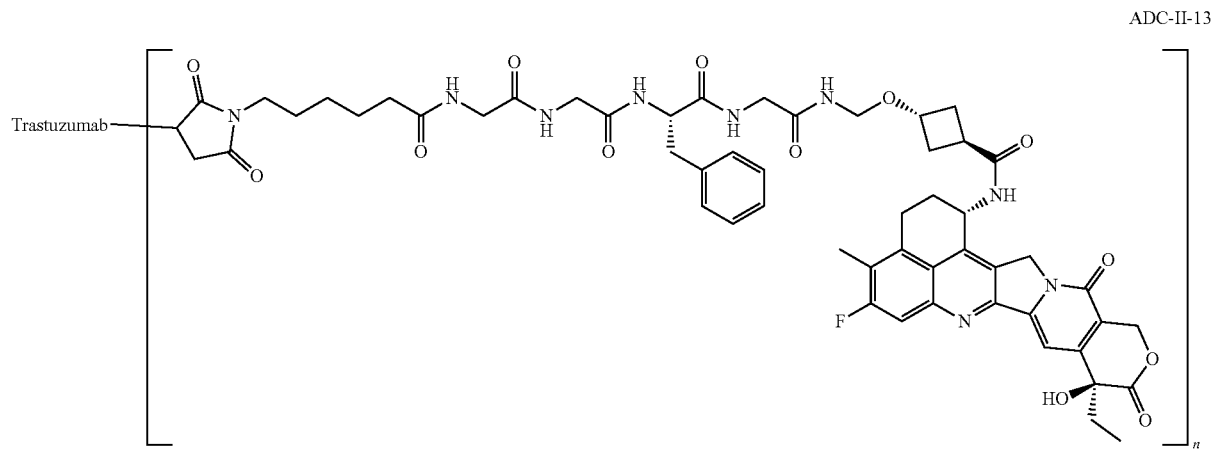

ADC-II-13

Preparation Example 1.42. ADC-I-1

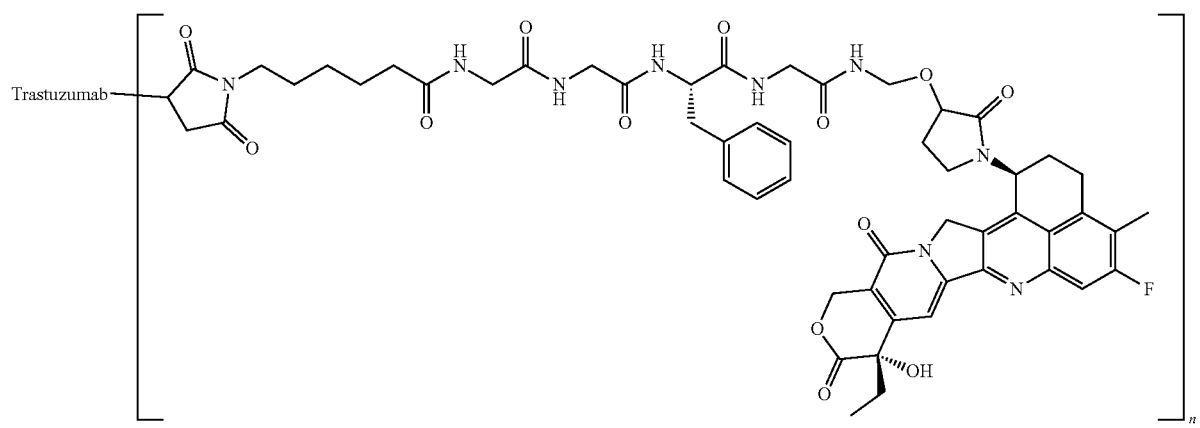

ADC-I-1

The prepared tris(2-carboxyethyl)phosphine (5 mM, 0.355 mL, 1.77 μmol) aqueous solution was added to the antibody Trastuzumab in aqueous PB buffer solution (0.04 M aqueous PB buffer solution at pH 7.0; 35 mg, 15 mg/mL, 0.236 μmol) at 37° C., and the mixture was placed in a water bath shaker and shaken at 37° C. for 3 h, and then the reaction was terminated; the reaction solution was cooled to 25° C. in a water bath and diluted to 5.0 mg/mL, and the diluted solution (2.0 mL) was taken for the next step.

L-I-1 (1.23 mg, 2.36 μmol) was dissolved in DMSO (0.10 mL), and the solution was added to the above solution (2.0 mL), placed in a water bath shaker and shaken at 25° C. for 3 h, and then the reaction was terminated. The reaction solution was desalted and purified on a Sephadex G25 gel column (eluent: 0.04 M aqueous PB buffer solution at pH 7.0, containing 0.002 M EDTA) to give a solution of the exemplary product ADC-I-1 in PB (9.33 mg/mL, 19 mg), which was frozen and stored at 4° C.

The mean n=7.98, as calculated by LC-MS.

Preparation Example 1.43. ADC-III-1

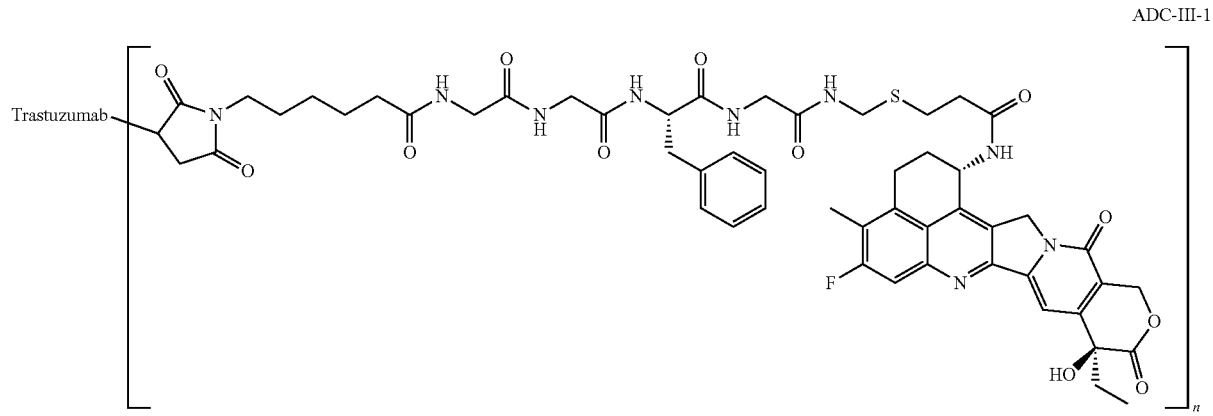

ADC-III-1

The prepared tris(2-carboxyethyl)phosphine (5 mM, 0.233 mL, 1.17 μmol) aqueous solution was added to the antibody Trastuzumab in PB buffer (0.04 M aqueous PB buffer solution at pH 7.0; 23 mg, 15 mg/mL, 0.155 μmol) at 37° C., and the mixture was placed in a water bath shaker and shaken at 37° C. for 3 h, and then the reaction was terminated; the reaction solution was cooled to 25° C. in a water bath and diluted to 5.0 mg/mL, and the diluted solution (2.0 mL) was taken for the next step.

L-III-2 (6.22 mg, 11.89 μmol) was dissolved in DMSO (0.10 mL), and the solution was added to the above solution (2.0 mL), placed in a water bath shaker and shaken at 25° C. for 3 h, and then the reaction was terminated. The reaction solution was desalted and purified on a Sephadex G25 gel column (eluent: 0.04 M aqueous PB buffer solution at pH 7.0, containing 0.002 M EDTA) to give a solution of the exemplary product ADC-III-1 in PB (1.25 mg/mL, 16 mg), which was frozen and stored at 4° C.

The mean n=8.34, as calculated by LC-MS.

Preparation Example 1.44. ADC-III-9

The prepared tris(2-carboxyethyl)phosphine (5 mM, 0.355 mL, 1.77 μmol) aqueous solution was added to the antibody Trastuzumab in aqueous PB buffer solution (0.04 M aqueous PB buffer solution at pH 7.0; 35 mg, 15 mg/mL, 0.236 μmol) at 37° C., and the mixture was placed in a water bath shaker and shaken at 37° C. for 3 h, and then the reaction was terminated; the reaction solution was cooled to 25° C. in a water bath and diluted to 5.0 mg/mL, and the diluted solution (2.0 mL) was taken for the next step.

L-III-20 (3.08 mg, 5.91 μmol) was dissolved in DMSO (0.10 mL), and the solution was added to the above solution (2.0 mL), placed in a water bath shaker and shaken at 25° C. for 3 h, and then the reaction was terminated. The reaction solution was desalted and purified on a Sephadex G25 gel column (eluent: 0.04 M aqueous PB buffer solution at pH 7.0, containing 0.002 M EDTA) to give a solution of the exemplary product ADC-III-9 in PB (6.61 mg/mL, 21 mg), which was frozen and stored at 4° C.

The mean n=8.05, as calculated by LC-MS.

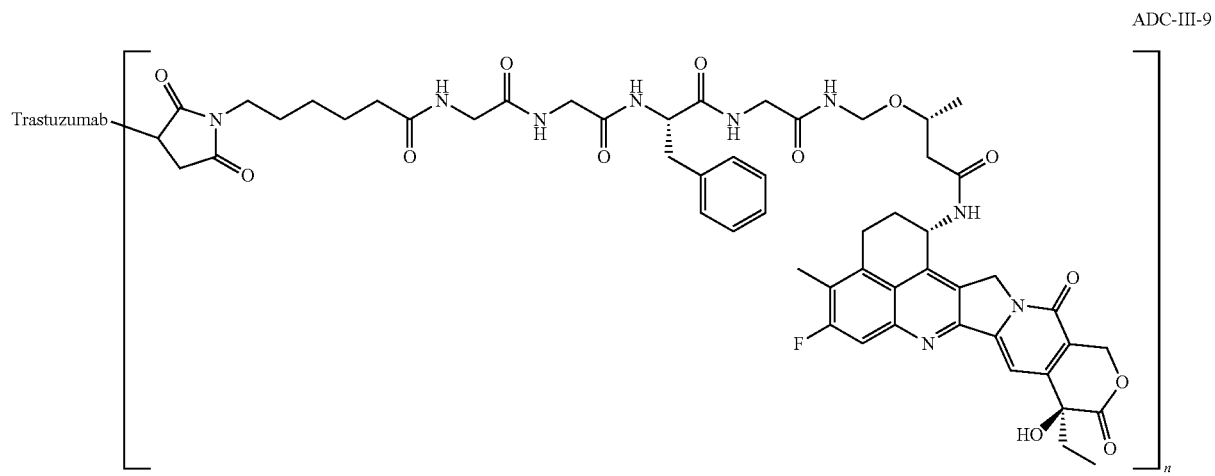

ADC-III-9

Preparation Example 1.45. ADC-II-3

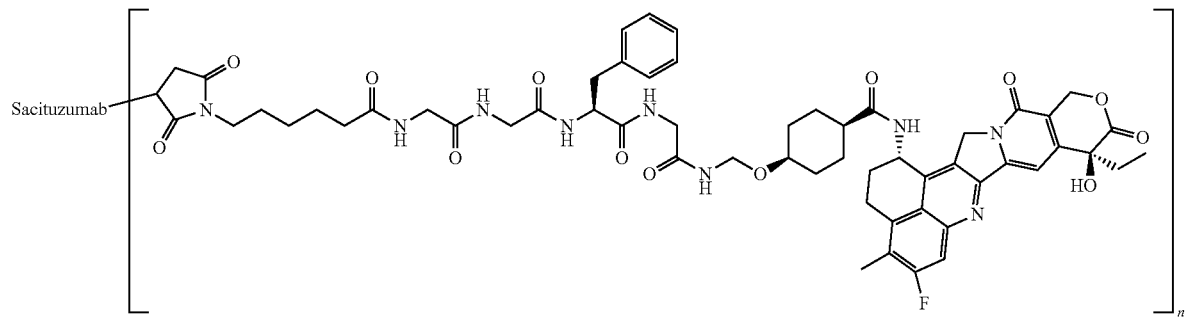

ADC-II-3

The prepared tris(2-carboxyethyl)phosphine (5 mM, 0.156 mL, 0.780 μmol) aqueous solution was added to the antibody Sacituzumab in aqueous PB buffer solution (0.04 M aqueous PB buffer solution at pH 7.0; 35 mg, 11 mg/mL, 0.236 μmol) at 25° C., and the mixture was placed in a water bath shaker and shaken at 25° C. for 3 h, and then the reaction was terminated; the reaction solution was diluted to 5.0 mg/mL.

L-II-1 (2.60 mg, 2.36 μmol) was dissolved in DMSO (0.10 mL), and the solution was added to the above solution, placed in a water bath shaker and shaken at 25° C. for 3 h, and then the reaction was terminated. The reaction solution was desalted and purified on a Sephadex G25 gel column (eluent: 0.02 M aqueous histidine buffer solution at pH 5.5) to give a solution of the exemplary product ADC-II-3 in histidine (4.1 mg/mL, 22 mg), which was refrigerated and stored at 4° C.

The mean n=3.89, as calculated by LC-MS.

Preparation Example 1.46. ADC-II-7

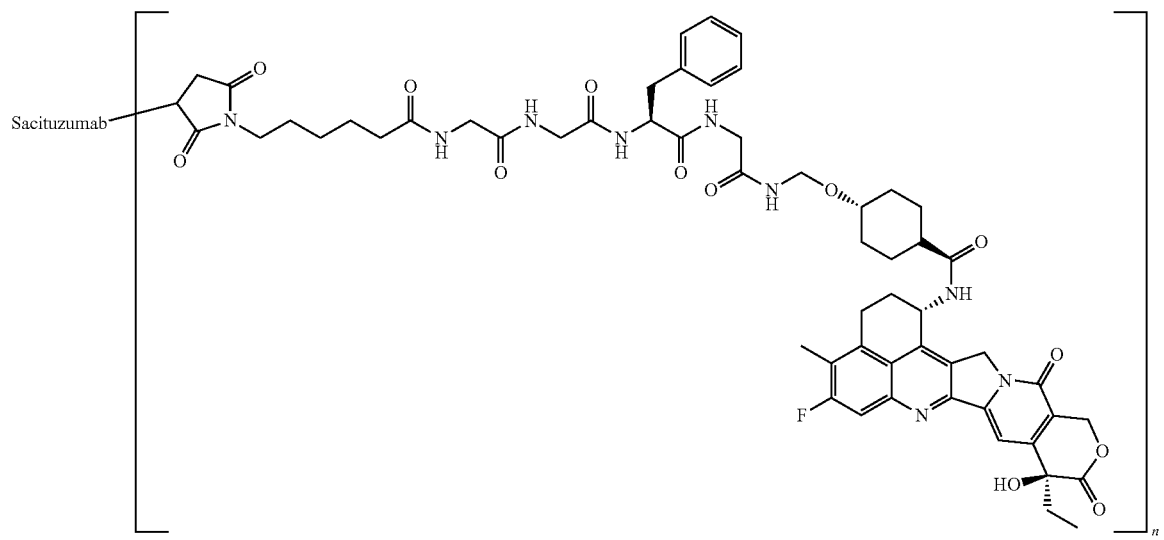

ADC-II-7

The prepared tris(2-carboxyethyl)phosphine (5 mM, 0.183 mL, 0.914 μmol) aqueous solution was added to the antibody Sacituzumab in PB buffer (0.04 M aqueous PB buffer solution at pH 7.0; 41 mg, 11 mg/mL, 0.277 μmol) at 25° C., and the mixture was placed in a water bath shaker and shaken at 25° C. for 3 h, and then the reaction was terminated; the reaction solution was diluted to 5.0 mg/mL.

L-II-2 (3.05 mg, 2.77 μmol) was dissolved in DMSO (0.10 mL), and the solution was added to the above solution, placed in a water bath shaker and shaken at 25° C. for 3 h, and then the reaction was terminated. The reaction solution was desalted and purified on a Sephadex G25 gel column (eluent: 0.02 M aqueous histidine buffer solution at pH 5.5) to give a solution of the exemplary product ADC-II-7 in histidine (3.7 mg/mL, 29.5 mg), which was refrigerated and stored at 4° C.

The mean n=4.12, as calculated by LC-MS.

Example 1.47. ADC-II-11-a

The prepared tris(2-carboxyethyl)phosphine (5 mM, 0.143 mL, 0.713 μmol) aqueous solution was added to the antibody Sacituzumab in PB buffer (0.04 M aqueous PB buffer solution at pH 7.0; 32 mg, 11 mg/mL, 0.216 μmol) at 25° C., and the mixture was placed in a water bath shaker and shaken at 25° C. for 3 h, and then the reaction was terminated; the reaction solution was diluted to 5.0 mg/mL.

L-II-3 (2.32 mg, 2.16 μmol) was dissolved in DMSO (0.10 mL), and the solution was added to the above solution, placed in a water bath shaker and shaken at 25° C. for 3 h, and then the reaction was terminated. The reaction solution was desalted and purified on a Sephadex G25 gel column (eluent: 0.02 M aqueous histidine buffer solution at pH 5.5) to give a solution of the exemplary product ADC-II-11-a in histidine (2.2 mg/mL, 15 mg), which was refrigerated and stored at 4° C.

The mean n=3.73, as calculated by LC-MS.

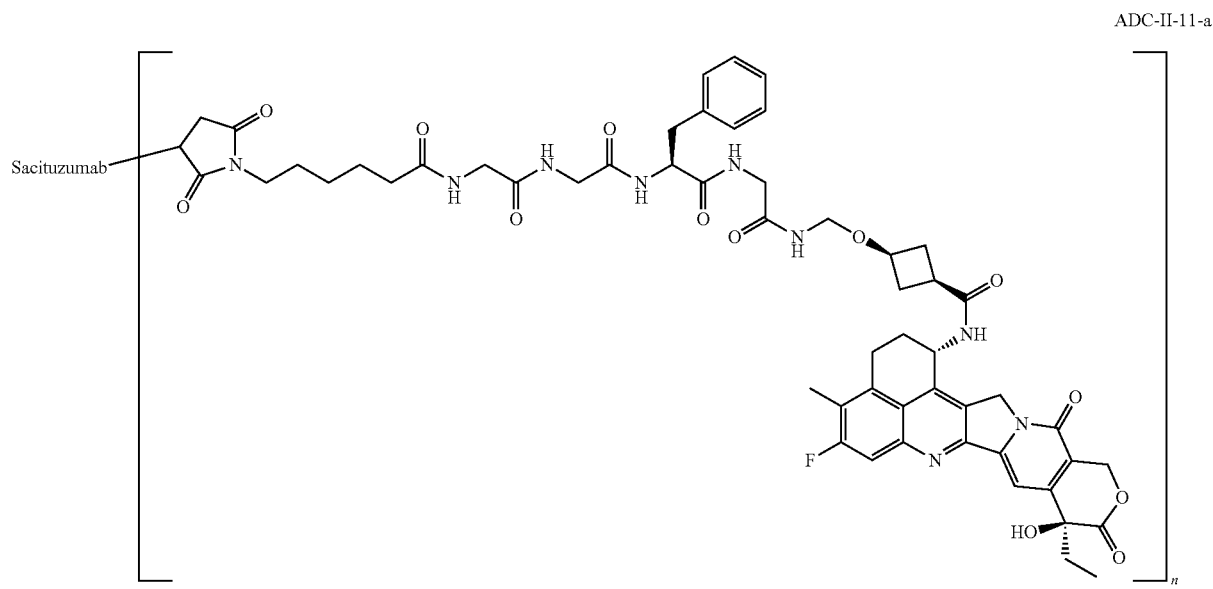

ADC-II-11-a

Example 1.48. ADC-II-15

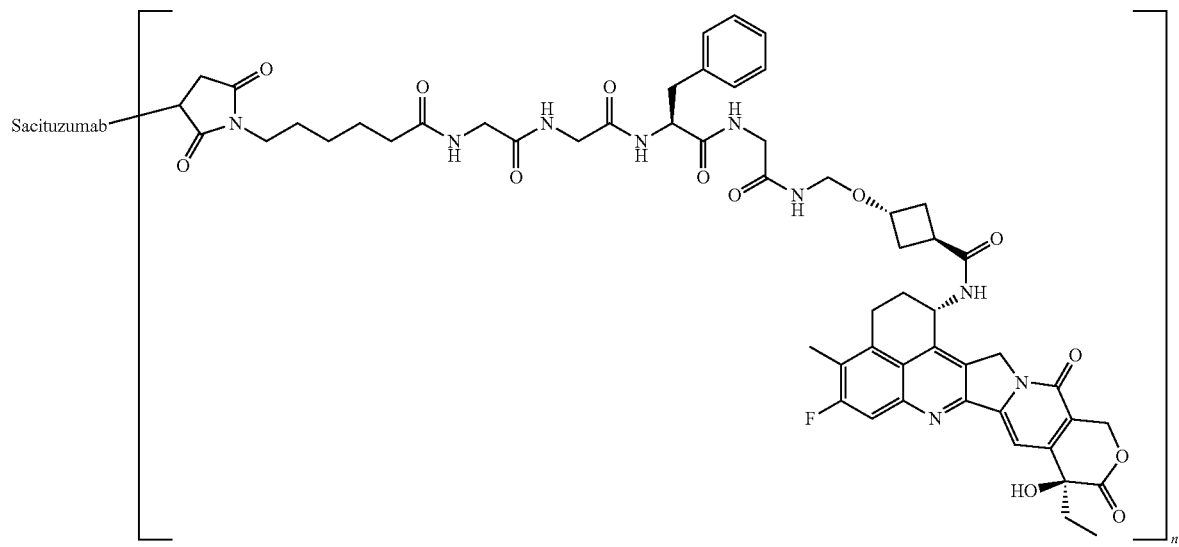

ADC-II-15

The prepared tris(2-carboxyethyl)phosphine (5 mM, 0.165 mL, 0.825 μmol) aqueous solution was added to the antibody Sacituzumab in aqueous PB buffer solution (0.04 M aqueous PB buffer solution at pH 7.0; 37 mg, 11 mg/mL, 0.250 μmol) at 25° C., and the mixture was placed in a water bath shaker and shaken at 25° C. for 3 h, and then the reaction was terminated; the reaction solution was diluted to 5.0 mg/mL.

L-II-4 (2.68 mg, 2.50 μmol) was dissolved in DMSO (0.10 mL), and the solution was added to the above solution, placed in a water bath shaker and shaken at 25° C. for 3 h, and then the reaction was terminated. The reaction solution was desalted and purified on a Sephadex G25 gel column (eluent: 0.02 M aqueous histidine buffer solution at pH 5.5) to give a solution of the exemplary product ADC-II-15 in histidine (4.0 mg/mL, 25 mg), which was refrigerated and stored at 4° C.

The mean n=4.03, as calculated by LC-MS.

Preparation Example 1.49. ADC-III-3

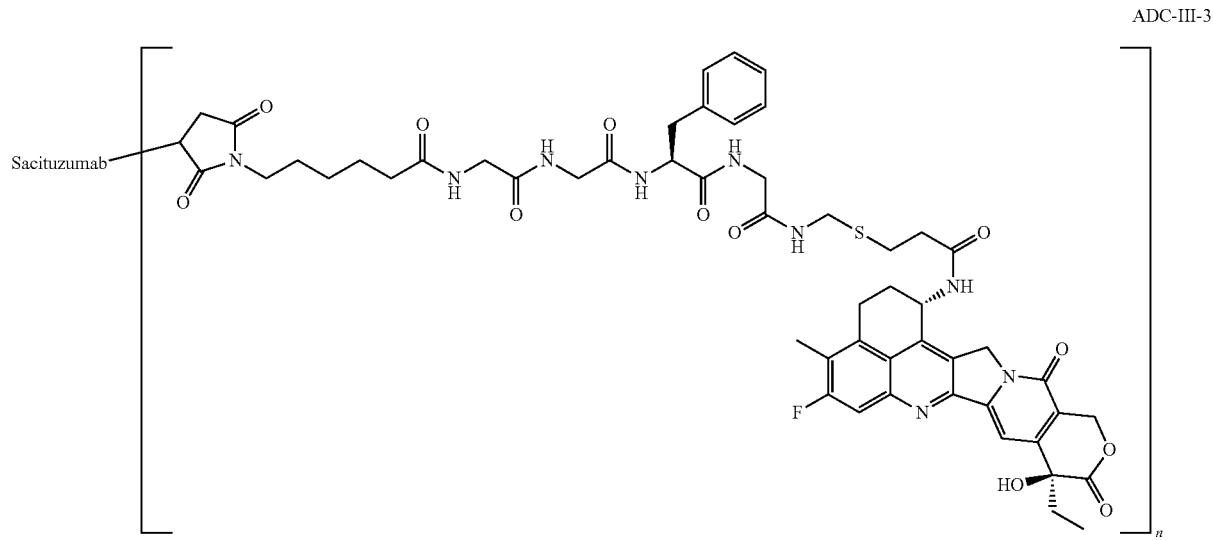

ADC-III-3

The prepared tris(2-carboxyethyl)phosphine (5 mM, 0.156 mL, 0.780 μmol) aqueous solution was added to the antibody Sacituzumab in aqueous PB buffer solution (0.04 M aqueous PB buffer solution at pH 7.0; 35 mg, 11 mg/mL, 0.236 μmol) at 25° C., and the mixture was placed in a water bath shaker and shaken at 25° C. for 3 h, and then the reaction was terminated; the reaction solution was diluted to 5.0 mg/mL.

L-III-2 (2.51 mg, 2.36 μmol) was dissolved in DMSO (0.10 mL), and the solution was added to the above solution, placed in a water bath shaker and shaken at 25° C. for 3 h, and then the reaction was terminated. The reaction solution was desalted and purified on a Sephadex G25 gel column (eluent: 0.02 M aqueous histidine buffer solution at pH 5.5) to give a solution of the exemplary product ADC-III-3 in histidine (2.7 mg/mL, 27 mg), which was refrigerated and stored at 4° C.

The mean n=4.45, as calculated by LC-MS.

Preparation Example 1.50. ADC-III-11

The prepared tris(2-carboxyethyl)phosphine (5 mM, 0.174 mL, 0.870 μmol) aqueous solution was added to the antibody Sacituzumab in aqueous PB buffer solution (0.04 M aqueous PB buffer solution at pH 7.0; 39 mg, 11 mg/mL, 0.264 μmol) at 25° C., and the mixture was placed in a water bath shaker and shaken at 25° C. for 3 h, and then the reaction was terminated;

L-III-20 (2.80 mg, 2.64 μmol) was dissolved in DMSO (0.10 mL), and the solution was added to the above solution, placed in a water bath shaker and shaken at 25° C. for 3 h, and then the reaction was terminated. The reaction solution was desalted and purified on a Sephadex G25 gel column (eluent: 0.02 M aqueous histidine buffer solution at pH 5.5) to give a solution of the exemplary product ADC-III-11 in histidine (7.89 mg/mL, 31 mg), which was refrigerated and stored at 4° C.

The mean n=4.37, as calculated by LC-MS.

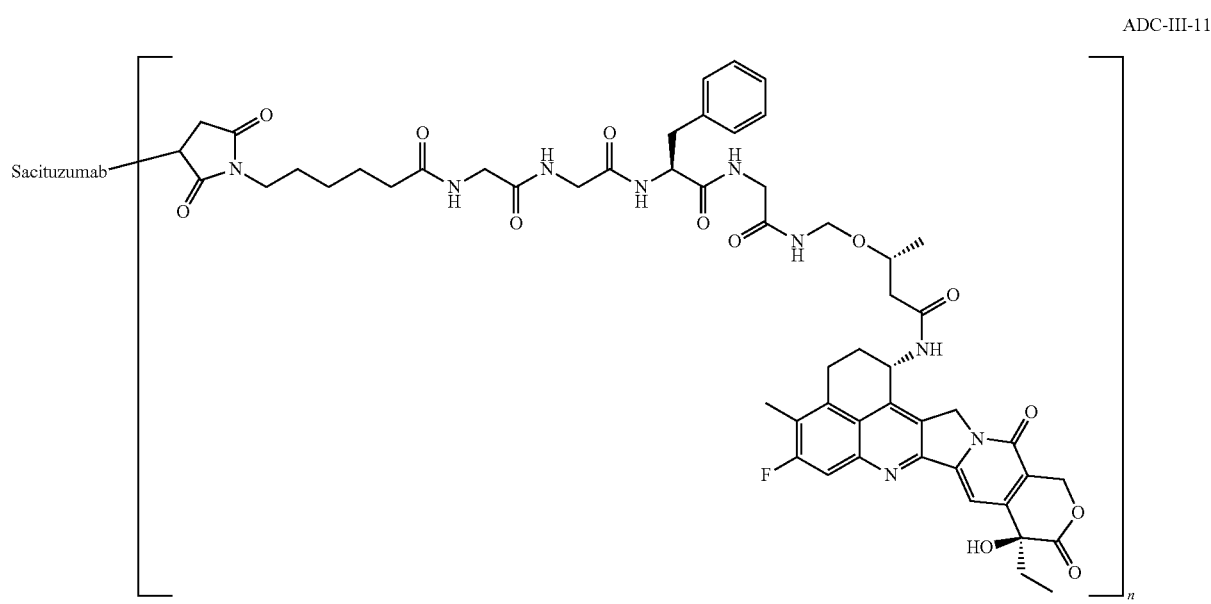

ADC-III-11

Example 1.50. ADC-II-11-b

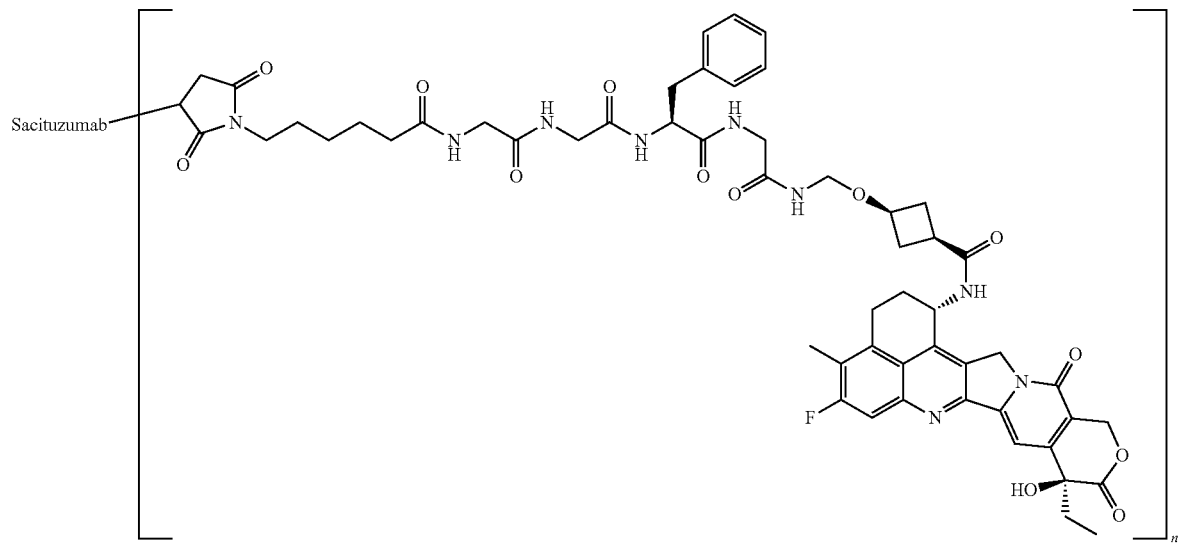

ADC-II-11-b

The prepared tris(2-carboxyethyl)phosphine (5 mM, 0.089 mL, 0.446 μmol) aqueous solution was added to the antibody Sacituzumab in aqueous PB buffer solution (0.04 M aqueous PB buffer solution at pH 7.0; 20 mg, 11 mg/mL, 0.135 μmol) at 25° C., and the mixture was placed in a water bath shaker and shaken at 25° C. for 3 h, and then the reaction was terminated; the reaction solution was diluted to 5.0 mg/mL.

L-II-3 (1.45 mg, 1.35 μmol) was dissolved in DMSO (0.10 mL), and the solution was added to the above solution, placed in a water bath shaker and shaken at 25° C. for 3 h, and then the reaction was terminated. The reaction solution was desalted and purified on a Sephadex G25 gel column (eluent: 0.02 M aqueous histidine buffer solution at pH 5.5) to give a solution of the exemplary product ADC-II-11-b in histidine (2.34 mg/mL, 9.5 mg), which was refrigerated and stored at 4° C.

The mean n=8.02, as calculated by LC-MS.

Preparation Example 1.52. ADC-II-53

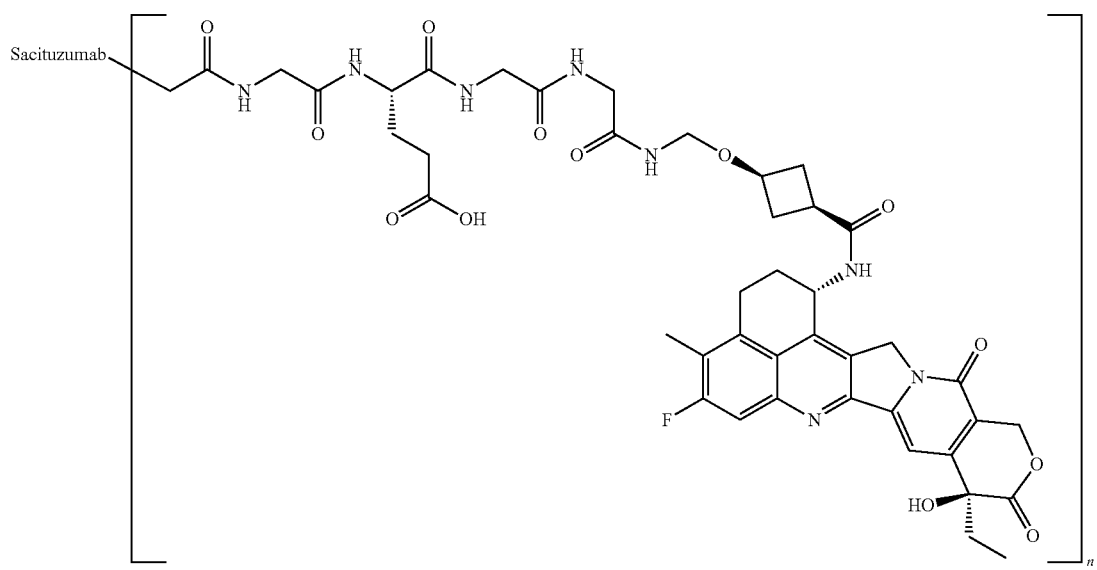

ADC-II-53

The prepared tris(2-carboxyethyl)phosphine (5 mM, 0.129 mL, 0.647 μmol) aqueous solution was added to the antibody Sacituzumab in aqueous PB buffer solution (0.04 M aqueous PB buffer solution at pH 7.0; 29 mg, 11 mg/mL, 0.196 μmol) at 25° C., and the mixture was placed in a water bath shaker and shaken at 25° C. for 3 h, and then the reaction was terminated; the reaction solution was diluted to 5.0 mg/mL.

L-II-27 (1.82 mg, 1.96 μmol) was dissolved in DMSO (0.10 mL), and the solution was added to the above solution, placed in a water bath shaker and shaken at 25° C. for 3 h, and then the reaction was terminated. The reaction solution was desalted and purified on a Sephadex G25 gel column (eluent: 0.02 M aqueous histidine buffer solution at pH 5.5) to give a solution of the exemplary product ADC-II-53 in histidine (4.4 mg/mL, 19.9 mg), which was refrigerated and stored at 4° C.

The mean n=4.46, as calculated by LC-MS.

Preparation Example 1.53. ADC-II-57

The prepared tris(2-carboxyethyl)phosphine (5 mM, 0.216 mL, 1.079 μmol) aqueous solution was added to the antibody Sacituzumab in aqueous PB buffer solution (0.04 M aqueous PB buffer solution at pH 7.0; 48.4 mg, 11 mg/mL, 0.327 μmol) at 25° C., and the mixture was placed in a water bath shaker and shaken at 25° C. for 3 h, and then the reaction was terminated; the reaction solution was diluted to 5.0 mg/mL.

L-II-28 (3.28 mg, 3.27 μmol) was dissolved in DMSO (0.10 mL), and the solution was added to the above solution, placed in a water bath shaker and shaken at 25° C. for 3 h, and then the reaction was terminated. The reaction solution was desalted and purified on a Sephadex G25 gel column (eluent: 0.02 M aqueous histidine buffer solution at pH 5.5) to give a solution of the exemplary product ADC-II-57 in histidine (4.15 mg/mL, 33.4 mg), which was refrigerated and stored at 4° C.

The mean n=3.78, as calculated by LC-MS.

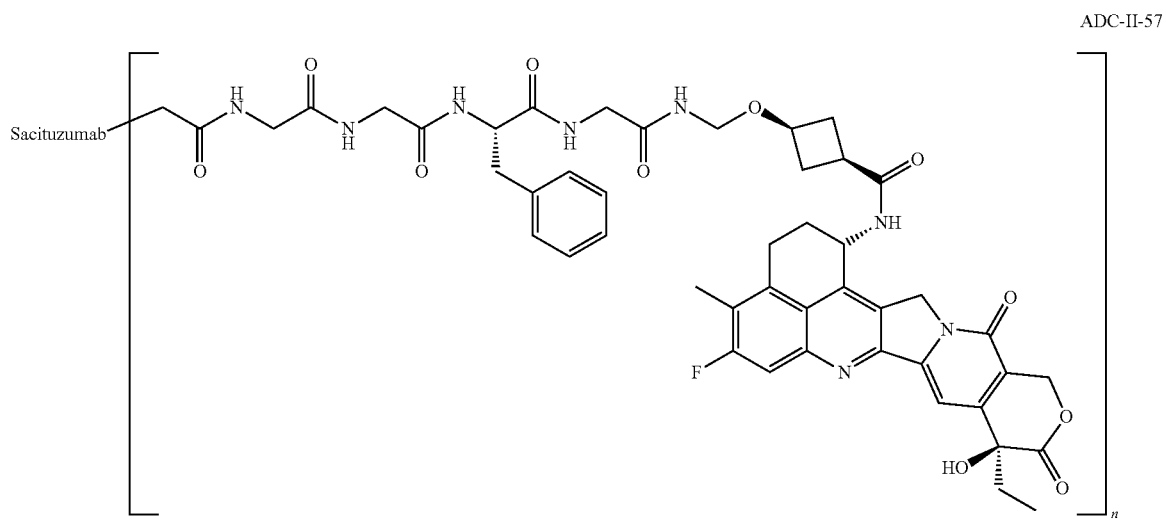

ADC-II-57

Preparation Example 1.54. ADC-III-28

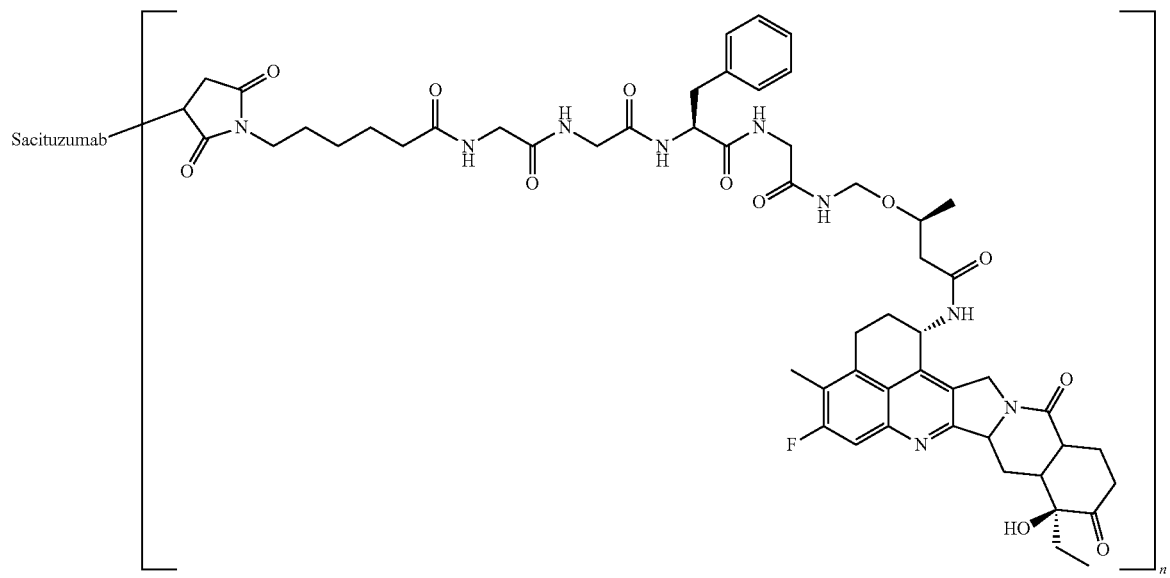

ADC-III-28

The prepared tris(2-carboxyethyl)phosphine (5 mM, 0.251 mL, 1.255 μmol) aqueous solution was added to the antibody Sacituzumab in aqueous PB buffer solution (0.04 M aqueous PB buffer solution at pH 7.0; 56.3 mg, 11 mg/mL, 0.381 μmol) at 25° C., and the mixture was placed in a water bath shaker and shaken at 25° C. for 3 h, and then the reaction was terminated.

L-III-30 (4.05 mg, 3.81 μmol) was dissolved in DMSO (0.10 mL), and the solution was added to the above solution, placed in a water bath shaker and shaken at 25° C. for 3 h, and then the reaction was terminated. The reaction solution was desalted and purified on a Sephadex G25 gel column (eluent: 0.02 M aqueous histidine buffer solution at pH 5.5) to give a solution of the exemplary product ADC-III-28 in histidine (4.83 mg/mL, 25.9 mg), which was refrigerated and stored at 4° C.

The mean n=3.67, as calculated by LC-MS.

Preparation Example 1.55. ADC-III-33

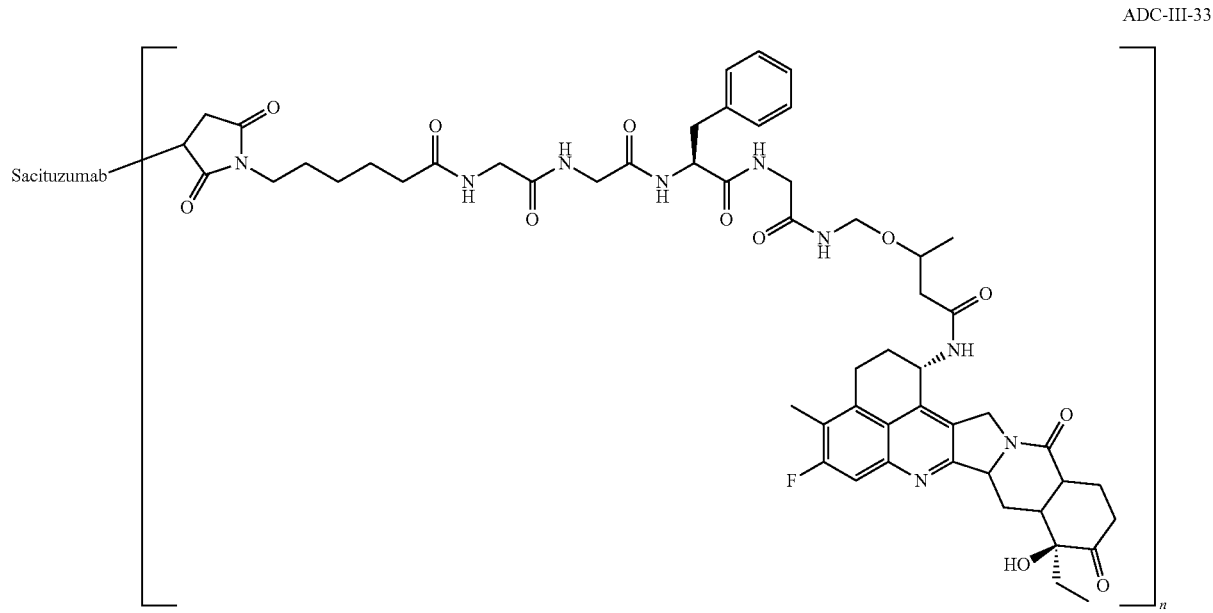

ADC-III-33

The prepared tris(2-carboxyethyl)phosphine (5 mM, 17.2 mL, 86.01 μmol) aqueous solution was added to the antibody Sacituzumab in aqueous PB buffer solution (0.04 M aqueous PB buffer solution at pH 7.0; 3857 mg, 11 mg/mL, 26.06 μmol) at 25° C., and the mixture was placed in a water bath shaker and shaken at 25° C. for 3 h, and then the reaction was terminated.

L-III-31 (4.05 mg, 3.81 μmol) was dissolved in DMSO (0.10 mL), and the solution was added to the above solution, placed in a water bath shaker and shaken at 25° C. for 3 h, and then the reaction was terminated. The reaction solution was desalted and purified on a Sephadex G25 gel column (eluent: 0.02 M aqueous histidine buffer solution at pH 5.5), and concentrated in an Amicon ultrafiltration tube to give a solution of the exemplary product ADC-III-33 in histidine (23.71 mg/mL, 3433 mg), which was refrigerated and stored at 4° C.

The mean n=4.05, as calculated by LC-MS.

Preparation Example 1.56. Reference ADC-2 (Sacituzumab-Deruxtecan)

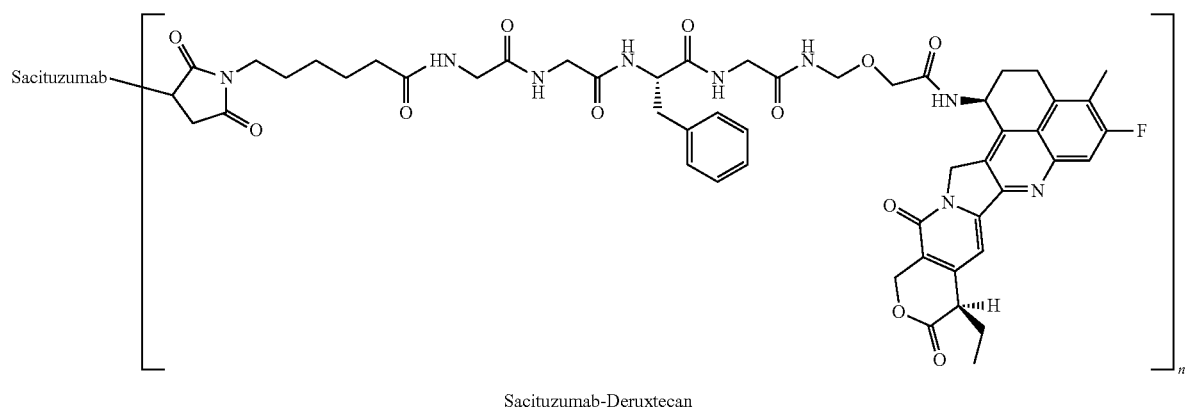

Sacituzumab-Deruxtecan

The prepared tris(2-carboxyethyl)phosphine (5 mM, 0.116 mL, 0.580 μmol) aqueous solution was added to the antibody Sacituzumab in aqueous PB buffer solution (0.04 M aqueous PB buffer solution at pH 7.0; 26 mg, 11 mg/mL, 0.176 μmol) at 25° C., and the mixture was placed in a water bath shaker and shaken at 25° C. for 3 h, and then the reaction was terminated.

Deruxtecan (1.82 mg, 1.76 μmol) was dissolved in DMSO (0.10 mL), and the solution was added to the above solution, placed in a water bath shaker and shaken at 25° C. for 3 h, and then the reaction was terminated. The reaction solution was desalted and purified on a Sephadex G25 gel column (eluent: 0.02 M aqueous histidine buffer solution at pH 5.5) to give a solution of the reference ADC-2 in histidine (7.46 mg/mL, 23.6 mg), which was refrigerated and stored at 4° C.

The mean n=4.18, as calculated by LC-MS.

Example 2

Test Example 2.1. Test for Inhibition of In Vitro Proliferation of Tumor Cells by Compounds Objective To test the inhibitory activity of the pharmaceutical compounds on the in vitro proliferation of NCI-N87, JIMT-1 and MBA-MB-231 tumor cells. The cells were treated with the compounds at different concentrations in vitro, and after 6 days of culture, the proliferation of cells was detected using the CTG (CellTiter-Glo® Luminescent Cell Viability Assay, Promega, Cat. No. G7558) reagent, and the in vitro activity of the compounds was evaluated according to the $IC_{50}$ value.

Procedures

In the following, the test for the inhibition of the in vitro proliferation of NCI-N87 cells was taken as an example to illustrate the method of the present application for testing the inhibitory activity of the compounds of the present application on the in vitro proliferation of tumor cells. The method was also applicable to, but not limited to, the test for the inhibitory activity on the in vitro proliferation of other tumor cells.

1. Culturing of cells: NCI-N87 cells were cultured in RPMI-1640 medium containing 10% FBS.
2. Preparation of cells: NCI-N87 cells in logarithmic phase were taken, washed with PBS once, and digested with 2-3 mL of trypsin for 2-3 min. After the cells were digested completely, 10-15 mL of cell culture was added to elute the digested cells. The eluate was centrifuged at 1000 rpm for 5 min, and the supernatant was discarded. The resulting cells were resuspended in 10-20 mL of cell culture to obtain a single cell suspension.
3. Cell plating: the NCI-N87 single cell suspension was mixed well and adjusted to a viable cell density of $6 \times 10^4$ cells/mL with cell culture. The cell suspension with the adjusted density was mixed well and added to a 96-well cell culture plate at 50 μL/well. The culture plate was incubated in an incubator for 18 h (37° C., 5% $CO_2$).
4. Preparation of compounds: the compounds were dissolved in DMSO to obtain stock solutions at an initial concentration of 10 mM.

There were 8 concentrations in total for the small molecule compounds: 300 nM, 100 nM, 30 nM, 10 nM, 3 nM, 1 nM, 0.3 nM, and 0.1 nM.

5. Sample adding: the prepared samples to be detected at different concentrations were added to the culture plate, and two duplicate wells were set for each sample. The culture plate was incubated in an incubator for 6 days (37° C., 5% $CO_2$).
6. Color developing: the 96-well cell culture plate was taken out, added with the CTG reagent at 50 μL/well, and incubated at room temperature for 10 min.

7. Plate reading: the 96-well cell culture plate was taken out, placed in a microplate reader, and measured for the chemiluminescence using the microplate reader.

Data Analysis

Data were processed and analyzed using Microsoft Excel and Graphpad Prism 5.

TABLE 1

$IC_{50}$ values for the inhibition of the in vitro proliferation of NCI-N87 and JIMT-1 cells by the small molecule fragments of the present application.

| Compound No. | NCI-N87 $IC_{50}$ (nM) | JIMT-1 $IC_{50}$ (nM) |
| --- | --- | --- |
| P-II-1 | 18.47 | 8.47 |
| P-II-2 | 22.1 | 17 |
| P-II-3 | 9.558 | 4.996 |
| P-II-4 | 8.032 | 6.637 |
| P-I-1 | 97.29 | 23.7 |
| P-I-1 | 61.56 | 21.81 |
| P-III-2 | 108.4 | 108.1 |
| P-III-20 | 5.888 | 4.351 |
| P-III-21 | 4.755 | 2.874 |

Conclusion: according to the results shown in Table 1, the small molecule fragments of the present application have significant inhibitory activity on the proliferation of NCI-N87 cells and JIMT-1 cells. The compounds of the present application all have similar inhibitory activity on tumor proliferation.

Test Example 2.2. Test for Inhibition of In Vitro Proliferation of Tumor Cells by Compounds Objective To test the inhibitory activity of the pharmaceutical compounds on the in vitro proliferation of NCI-N87, JIMT-1 and MBA-MB-231 tumor cells. The cells were treated with compounds at different concentrations in vitro, and after 6 days of culture, the proliferation of cells was detected using CTG (CellTiter-Glo® Luminescent Cell Viability Assay, Promega, Cat. No. G7558) reagents, and the in vitro activity of the compounds was evaluated according to the $IC_{50}$ value.

1. Culturing of cells: NCI-N87/JIMT-1/MBA-MB-231 cells were cultured in RPMI-1640 medium containing 10% FBS.
2. Preparation of cells: NCI-N87/JIMT-1/MBA-MB-231 cells in logarithmic phase were taken, washed with PBS once, and digested with 2-3 mL of trypsin for 2-3 min. After the cells were digested completely, 10-15 mL of cell culture was added to elute the digested cells. The eluate was centrifuged at 1000 rpm for 5 min, and the supernatant was discarded. The resulting cells were resuspended in 10-20 mL of cell culture to obtain a single cell suspension.
3. Cell plating: the NCI-N87/JIMT-1/MBA-MB-231 single cell suspension was mixed well and adjusted to a viable cell density of $6 \times 10^4$ cells/mL with cell culture. The cell suspension with the adjusted density was mixed well and added to a 96-well cell culture plate at 50 μL/well. The culture plate was incubated in an incubator for 18 h (37° C., 5% $CO_2$).
4. Preparation of compounds: the compounds were dissolved in DMSO to obtain stock solutions at an initial concentration of 10 mM.

There were 8 concentrations in total for the small molecule compounds: 300 nM, 100 nM, 30 nM, 10 nM, 3 nM, 1 nM, 0.3 nM, and 0.1 nM.

5. Sample adding: the prepared samples to be detected at different concentrations were added to the culture plate, and two duplicate wells were set for each sample. The culture plate was incubated in an incubator for 6 days (37° C., 5% $CO_2$).
6. Color developing: the 96-well cell culture plate was taken out, added with the CTG reagent at 50 μL/well, and incubated at room temperature for 10 min.
7. Plate reading: the 96-well cell culture plate was taken out, placed in a microplate reader, and measured for the chemiluminescence using the microplate reader.

Data analysis: data were processed and analyzed using Microsoft Excel and Graphpad Prism 5.

TABLE 2

$IC_{50}$ values for the inhibition of the in vitro proliferation of tumor cells by the small molecule fragments of the present application.

| Compound No. | NCI-N87 IC50 (nM) | JIMT-1 IC50 (nM) | MDA-MB-231 IC50 (nM) |
| --- | --- | --- | --- |
| Reference example 1 | — | 23.1 | — |
| P-II-1 | 18.47 | 8.5 | 12.9 |
| P-II-2 | 22.1 | 17.2 | 19.3 |
| P-II-3 | 9.558 | 5.0 | 9.4 |
| P-II-4 | 8.032 | 6.6 | 7.6 |
| P-II-22 | — | 3.2 | — |
| P-II-23 | — | — | 7.7 |
| P-II-24 | — | 20.8 | 8.5 |

"—": not detected

Conclusion: according to the results shown in Table 2, the small molecule fragments of the present application have significant inhibitory activity on the proliferation of NCI-N87, JIMT-1 and MDA-MB-231 cells. The compounds of the present application all have similar inhibitory activity on tumor proliferation.

Test Example 2.3. Test for Inhibition of In Vitro Proliferation of Tumor Cells by Compounds Objective To test the inhibitory activity of the pharmaceutical compounds on the in vitro proliferation of NCI-N87, JIMT-1 and MBA-MB-231 tumor cells. The cells were treated with compounds at different concentrations in vitro, and after 6 days of culture, the proliferation of cells was detected using CTG (CellTiter-Glo® Luminescent Cell Viability Assay, Promega, Cat. No. G7558) reagents, and the in vitro activity of the compounds was evaluated according to the $IC_{50}$ value.

1. Culturing of cells: NCI-N87/JIMT-1/MBA-MB-231 cells were cultured in RPMI-1640 medium containing 10% FBS.
2. Preparation of cells: NCI-N87/JIMT-1/MBA-MB-231 cells in logarithmic phase were taken, washed with PBS once, and digested with 2-3 mL of trypsin for 2-3 min. After the cells were digested completely, 10-15 mL of cell culture was added to elute the digested cells. The eluate was centrifuged at 1000 rpm for 5 min, and the supernatant was discarded. The resulting cells were resuspended in 10-20 mL of cell culture to obtain a single cell suspension.
3. Cell plating: the NCI-N87/JIMT-1/MBA-MB-231 single cell suspension was mixed well and adjusted to a viable cell density of 6×10⁴ cells/mL with cell culture. The cell suspension with the adjusted density was mixed well and added to a 96-well cell culture plate at 50 μL/well. The culture plate was incubated in an incubator for 18 h (37° C., 5% $CO_2$).

4. Preparation of compounds: the compounds were dissolved in DMSO to obtain stock solutions at an initial concentration of 10 mM.

There were 8 concentrations in total for the small molecule compounds: 300 nM, 100 nM, 30 nM, 10 nM, 3 nM, 1 nM, 0.3 nM, and 0.1 nM.

5. Sample adding: the prepared samples to be detected at different concentrations were added to the culture plate, and two duplicate wells were set for each sample. The culture plate was incubated in an incubator for 6 days (37° C., 5% $CO_2$).

6. Color developing: the 96-well cell culture plate was taken out, added with the CTG reagent at 50 μL/well, and incubated at room temperature for 10 min.

7. Plate reading: the 96-well cell culture plate was taken out, placed in a microplate reader, and measured for the chemiluminescence using the microplate reader.

Data analysis: data were processed and analyzed using Microsoft Excel and Graphpad Prism 5.

TABLE 3

$IC_{50}$ values for the inhibition of the in vitro proliferation of NCI-N87, JIMT-1 and MDA-MB-231 cells by the small molecule fragments of the present application.

| Compound No. | NCI-N87 IC50 (nM) | JIMT-1 IC50 (nM) | MDA-MB-231 IC50 (nM) |
|---|---|---|---|
| Reference example 2 | — | 36.2 | — |
| Reference example 3 | — | 81.2 | — |
| Reference example 4 | — | 32.3 | — |
| P-III-1 | — | — | 28.9 |
| P-III-2 | 108.4 | 108.1 | — |
| P-III-9 | — | — | 28.9 |
| P-III-20 | 5.888 | 4.351 | 6.65 |
| P-III-21 | 4.755 | 2.874 | 2.88 |
| P-III-22 | — | 12.5 | — |
| P-III-27 | 3.0 | — | — |
| P-III-28 | — | — | 1.2 |
| P-III-29 | — | 16.7 | 8.6 |
| P-III-30 | — | — | 28.5 |

"—": not detected

Conclusion: according to the results shown in Table 3, the small molecule fragments of the present application have significant inhibitory activity on the proliferation of NCI-N87, JIMT-1 and MDA-MB-231 cells. The compounds of the present application all have similar inhibitory activity on tumor proliferation.

Test Example 2.4. Test for Inhibition of In Vitro Proliferation of Tumor Cells by Compounds Objective To test the inhibitory activity of the pharmaceutical compounds on the in vitro proliferation of NCI-N87 and Colo205 tumor cells. The cells were treated with compounds at different concentrations in vitro, and after 6 days of culture, the proliferation of cells was detected using CTG (CellTiter-Glo® Luminescent Cell Viability Assay, Promega, Cat. No. G7558) reagents, and the in vitro activity of the compounds was evaluated according to the $IC_{50}$ value.

1. Culturing of cells: NCI-N87/Colo205 cells were cultured in RPMI-1640 medium containing 10% FBS.

2. Preparation of cells: NCI-N87/Colo205 cells in logarithmic phase were taken, washed with PBS once, and digested with 2-3 mL of trypsin for 2-3 min. After the cells were digested completely, 10-15 mL of cell culture was added to elute the digested cells. The eluate was centrifuged at 1000 rpm for 5 min, and the supernatant was discarded. The resulting cells were resuspended in 10-20 mL of cell culture to obtain a single cell suspension.

3. Cell plating: the NCI-N87/Colo205 single cell suspension was mixed well and adjusted to a viable cell density of 6×10⁴ cells/mL with cell culture. The cell suspension with the adjusted density was mixed well and added to a 96-well cell culture plate at 50 μL/well. The culture plate was incubated in an incubator for 18 h (37° C., 5% $CO_2$).

4. Preparation of compounds: the compounds were dissolved in DMSO to obtain stock solutions at an initial concentration of 10 mM.

There were 8 concentrations in total for the small molecule compounds: 300 nM, 100 nM, 30 nM, 10 nM, 3 nM, 1 nM, 0.3 nM, and 0.1 nM.

5. Sample adding: the prepared samples to be detected at different concentrations were added to the culture plate, and two duplicate wells were set for each sample. The culture plate was incubated in an incubator for 6 days (37° C., 5% $CO_2$).

6. Color developing: the 96-well cell culture plate was taken out, added with the CTG reagent at 50 μL/well, and incubated at room temperature for 10 min.

7. Plate reading: the 96-well cell culture plate was taken out, placed in a microplate reader, and measured for the chemiluminescence using the microplate reader.

Data analysis: data were processed and analyzed using Microsoft Excel and Graphpad Prism 5.

TABLE 4

$IC_{50}$ values for the inhibition of the in vitro proliferation of NCI-N87 and Colo205 cells by the small molecule fragments of the present application.

| Compound No. | NCI-N87 IC50 (nM) | Colo205 IC50 (nM) |
|---|---|---|
| P-III-20 | 5.9 | 20 |
| P-III-30 | 3 | 9 |

Conclusion: according to the results shown in Table 4, the small molecule fragments of the present application have significant inhibitory activity on the proliferation of NCI-N87 cells and Colo205 cells. The compounds of the present application all have similar inhibitory activity on tumor proliferation.

Test Example 2.5. Test for Inhibition of In Vitro Proliferation of Tumor Cells of HER2 Target by Antibody-Drug Conjugate Objective To test the inhibitory activity of the antibody drug conjugates against the HER2 target of the present application on the in vitro proliferation of NCI-N87, JIMT-1 and MBA-MB-231 tumor cells. The cells were treated with the ADCs at different concentrations in vitro, and after 6 days of culture, the proliferation of cells was detected using the CTG reagent, and the in vitro activity of the compounds was evaluated according to the $IC_{50}$ value.

Procedures

1. Culturing of cells: NCI-N87/JIMT-1 cells were cultured in RPMI-1640 medium containing 10% FBS.
2. Preparation of cells: NCI-N87/JIMT-1 cells in logarithmic phase were taken, washed with PBS once, and digested with 2-3 mL of trypsin for 2-3 min. After the cells were digested completely, 10-15 mL of cell culture was added to elute the digested cells. The eluate was centrifuged at 1000 rpm for 5 min, and the supernatant was discarded. The resulting cells were resuspended in 10-20 mL of cell culture to obtain a single cell suspension.
3. Cell plating: the NCI-N87/JIMT-1 single cell suspension was mixed well and adjusted to a viable cell density of $6\times10^4$ cells/mL with cell culture. The cell suspension with the adjusted density was mixed well and added to a 96-well cell culture plate at 50 µL/well. The culture plate was incubated in an incubator for 18 h (37° C., 5% $CO_2$).
4. ADC concentration: the ADCs were diluted in a 5-fold gradient starting from 150 nM to 0.000348 nM for a total of 9 concentrations.
5. Sample adding: the prepared samples to be detected at different concentrations were added to the culture plate, and two duplicate wells were set for each sample. The culture plate was incubated in an incubator for 6 days (37° C., 5% $CO_2$).
6. Color developing: the 96-well cell culture plate was taken out, added with the CTG reagent at 50 µL/well, and incubated at room temperature for 10 min.
7. Plate reading: the 96-well cell culture plate was taken out, placed in a microplate reader, and measured for the chemiluminescence using the microplate reader.

Data Analysis

Data were processed and analyzed using Microsoft Excel and Graphpad Prism 5.

TABLE 5

$IC_{50}$ values for the inhibition of the in vitro proliferation of NCI-N87 and JIMT-1 cells by the ADCs of the present application.

| ADC No. | NCI-N87 $IC_{50}$ (nM) | JIMT-1 $IC_{50}$ (nM) |
| --- | --- | --- |
| ADC-II-5 | 0.20 | — |
| ADC-II-9 | 0.08 | 39.91 |
| ADC-II-13 | 0.17 | 73.11 |
| Reference ADC-1 | 0.28 | 90.55 |

Conclusion: according to the results shown in Table 5, the antibody-drug conjugates against the HER2 target of the present application have significant inhibitory activity on the proliferation of HER2-positive high expression cells NCI-N87, meanwhile, they have weak inhibitory activity on the proliferation of HER2-low expressing cells JIMT-1, therefore, they have good selectivity. The other ADCs of the present application also have similar selective inhibitory activity.

Test Example 2.6. Test for Inhibition of In Vitro Proliferation of Tumor Cells of HER2 Target by Antibody-Drug Conjugate Objective To test the inhibitory activity of the antibody drug conjugates against the HER2 target of the present application on the in vitro proliferation of NCI-N87 and JIMT-1 tumor cells. The cells were treated with the ADCs at different concentrations in vitro, and after 6 days of culture, the proliferation of cells was detected using the CTG reagent, and the in vitro activity of the compounds was evaluated according to the $IC_{50}$ value.

Procedures

1. Culturing of cells: NCI-N87 or JIMT-1 cells were cultured in RPMI-1640 medium containing 10% FBS.
2. Preparation of cells: NCI-N87 or JIMT-1 cells in logarithmic phase were taken, washed with PBS once, and digested with 2-3 mL of trypsin for 2-3 min. After the cells were digested completely, 10-15 mL of cell culture was added to elute the digested cells. The eluate was centrifuged at 1000 rpm for 5 min, and the supernatant was discarded. The resulting cells were resuspended in 10-20 mL of cell culture to obtain a single cell suspension.
3. Cell plating: the NCI-N87 or JIMT-1 single cell suspension was mixed well and adjusted to a viable cell density of $6\times10^4$ cells/mL with cell culture. The cell suspension with the adjusted density was mixed well and added to a 96-well cell culture plate at 50 µL/well. The culture plate was incubated in an incubator for 18 h (37° C., 5% $CO_2$).
4. ADC concentration: The ADCs were diluted in a 5-fold gradient starting from 150 nM to 0.000348 nM for a total of 9 concentrations.
5. Sample adding: the prepared samples to be detected at different concentrations were added to the culture plate, and two duplicate wells were set for each sample. The culture plate was incubated in an incubator for 6 days (37° C., 5% $CO_2$).
6. Color developing: the 96-well cell culture plate was taken out, added with the CTG reagent at 50 µL/well, and incubated at room temperature for 10 min.
7. Plate reading: the 96-well cell culture plate was taken out, placed in a microplate reader, and measured for the chemiluminescence using the microplate reader.

Data Analysis

Data were processed and analyzed using Microsoft Excel and Graphpad Prism 5.

TABLE 6

$IC_{50}$ values for the inhibition of the in vitro proliferation of NCI-N87 and JIMT-1 cells by the ADCs of the present application.

| ADC No. | NCI-N87 IC50 (nM) | JIMT-1 IC50 (nM) |
| --- | --- | --- |
| Reference ADC-1 | 0.28 | 90.55 |
| ADC-II-1 | 0.14 | — |
| ADC-II-5 | 0.20 | — |
| ADC-II-9 | 0.095 | 28.1 |
| ADC-II-13 | 0.17 | 73.11 |
| ADC-III-1 | 0.16 | — |
| ADC-III-9 | 0.13 | 76.7 |

Conclusion: according to the results shown in Table 6, the antibody-drug conjugates against the HER2 target of the present application have significant inhibitory activity on the proliferation of HER2-positive high expression cells NCI-N87, and they also have good inhibitory activity on the proliferation of HER2-low expressing cells JIMT-1. The other ADCs of the present application also have similar inhibitory activity.

Test Example 2.7. Test for Inhibition of In Vitro Proliferation of Tumor Cells of Trop2 Target by Antibody-Drug Conjugate

Objective

To test the inhibitory activity of the antibody drug conjugates against the Trop2 target of the present application on the in vitro proliferation of Colo205 and SK-OV-3 tumor cells. The cells were treated with the ADCs at different concentrations in vitro, and after 6 days of culture, the proliferation of cells was detected using the CTG reagent, and the in vitro activity of the compounds was evaluated according to the $IC_{50}$ value.

Procedures

1. Culturing of cells: Colo205 or SK-OV-3 cells were cultured in RPMI-1640 medium containing 10% FBS.
2. Preparation of cells: Colo205 or SK-OV-3 cells in logarithmic phase were taken, washed with PBS once, and digested with 2-3 mL of trypsin for 2-3 min. After the cells were digested completely, 10-15 mL of cell culture was added to elute the digested cells. The eluate was centrifuged at 1000 rpm for 5 min, and the supernatant was discarded. The resulting cells were resuspended in 10-20 mL of cell culture to obtain a single cell suspension.
3. Cell plating: the Colo205 or SK-OV-3 single cell suspension was mixed well and adjusted to a viable cell density of $6 \times 10^4$ cells/mL with cell culture. The cell suspension with the adjusted density was mixed well and added to a 96-well cell culture plate at 50 μL/well. The culture plate was incubated in an incubator for 18 h (37° C., 5% $CO_2$).
4. ADC concentration: The ADCs were diluted in a 5-fold gradient starting from 150 nM to 0.000348 nM for a total of 9 concentrations.
5. Sample adding: the prepared samples to be detected at different concentrations were added to the culture plate, and two duplicate wells were set for each sample. The culture plate was incubated in an incubator for 6 days (37° C., 5% $CO_2$).
6. Color developing: the 96-well cell culture plate was taken out, added with the CTG reagent at 50 μL/well, and incubated at room temperature for 10 min.
7. Plate reading: the 96-well cell culture plate was taken out, placed in a microplate reader, and measured for the chemiluminescence using the microplate reader.

Data Analysis

Data were processed and analyzed using Microsoft Excel and Graphpad Prism 5.

TABLE 7

$IC_{50}$ values for the inhibition of the in vitro proliferation of Colo205 and SK-OV-3 cells by the ADCs of the present application.

| ADC No. | Colo205 IC50 (nM) | SK-OV-3 IC50 (nM) |
|---|---|---|
| Reference ADC-2 | 152.1 | 500.9 |
| ADC-II-11a | 120.8 | 447.5 |
| ADC-III-28 | 77.6 | 393.9 |

Conclusion: according to the results shown in Table 7, the antibody-drug conjugates against the Trop2 target of the present application have significant inhibitory activity on the proliferation of Trop2-positive high expression cells Colo205, meanwhile, they have weak inhibitory activity on the proliferation of HER2-low expressing cells JIMT-1, therefore, they have good selectivity. The other ADCs of the present application also have similar selective inhibitory activity.

Test Example 2.8. Her2-ADC Plasma Stability Experiment

ADC-II-5, ADC-II-9 and ADC-II-13 at a final concentration of 1500 nM were each added to sterile human plasma, and the resulting mixtures were each incubated in a cell incubator at 37° C., with the day of incubation recorded as day 0, and then detected for free toxins at days 1, 7 and 14. 50 μL of each of the mixtures was taken for RP-HPLC analysis.

The detection results for free toxins show that ADC-II-5, ADC-II-9 and ADC-II-13 are all quite stable in human plasma. The other ADCs of the present application also have similar stability.

Test Example 2.7. Her2-ADC Plasma Stability Experiment

Reference ADC-1, ADC-II-5, ADC-II-9 and ADC-II-13 at a final concentration of 1500 nM were each added to sterile human plasma, and the resulting mixtures were each incubated in a cell incubator at 37° C., with the day of incubation recorded as day 0, and then detected for n value at 0 h, 3 h, 27 h and 99 h. 50 μL of each of the mixtures was taken for LC-MS analysis.

TABLE 8

Test results of plasma stability for the exemplary ADCs in the present application

| | n | | | |
|---|---|---|---|---|
| ADC No. | T0 | 3 h | 27 h | 99 h |
| Reference ADC-1 | 7.56 | 6.47 | 5.63 | 3.55 |
| ADC-II-5 | 7.58 | 7.57 | 7.18 | 4.69 |
| ADC-II-9 | 8.05 | 7.89 | 7.48 | 6.40 |
| ADC-II-13 | 7.82 | 7.80 | 7.30 | 5.45 |

Conclusion: the results in Table 8 show that the conjugates formed by the small molecule linkers of the present invention have significantly less variation in n value in plasma than the reference ADC-1, showing superior plasma stability.

Test Example 2.9. Efficacy Evaluation of NCI-N87 Tumor-Bearing Mice

Objective

To evaluate the Her2-ADC antibodies of the present application using BALB/c nude mice as test animals;

to evaluate the efficacy of ADC-II-5 and reference ADC-1 on NCI-N87 xenograft tumor-bearing nude mice after the intraperitoneal injection.

Test Compounds and Materials

1. Test compounds
ADC-II-5: 0.5 mg/kg
ADC-II-5: 2 mg/kg
Reference ADC-1: 0.5 mg/kg
Reference ADC-1: 2 mg/kg
Blank control: PBS
2. Preparation method: all compounds were diluted with PBS.
3. Test animal
BALB/c Nude mice, purchased from Beijing Vital River.

Test Method

NCI-N87 cells were subcutaneously inoculated into the right flank of the mice, and after tumors were grown for 8 days, animals were randomly grouped, with 8 animals in each group for a total of 6 groups.

The compounds each were intraperitoneally injected once. The tumor volume and weight were measured twice a week, and the data were recorded.

Data were analyzed using Excel 2016 statistical software, wherein the mean value was calculated as avg; the SD value was calculated as STDEV; the SEM value was calculated as STDEV/SQRT; and the P-value of the difference between groups was calculated as TTEST.

The experimental results are shown, and it is observed from one intraperitoneal injection to the end of the experiment that the ADC molecules of the present application can significantly reduce the tumor volume, and have superior tumor inhibition effect to the reference ADC-1. The other ADCs of the present application also have similar tumor inhibition effect in vivo.

Test Example 2.10. Efficacy Evaluation of NCI-N87 Tumor-Bearing Mice

Objective

To evaluate the conjugates of the present application using BALB/c nude mice as test animals;
to evaluate the efficacy of ADC-II-9, ADC-II-13, ADC-III-9 and reference ADC-1 on NCI-N87 xenograft tumor-bearing nude mice after the intraperitoneal injection.

Test Compounds and Materials

1. Test compounds
ADC-II-9, ADC-II-13, ADC-III-9: 2 mg/kg
Reference ADC-1: 2 mg/kg
Blank control: PBS
2. Preparation method: all compounds were diluted with PBS.
3. Test animal
BALB/c Nude mice, purchased from Beijing Vital River.

Test Method

NCI-N87 cells were subcutaneously inoculated into the right flank of the mice, and after tumors were grown for 8 days, animals were randomly grouped, with 8 animals in each group for a total of 6 groups.

The compounds each were intraperitoneally injected once. The tumor volume and weight were measured twice a week, and the data were recorded.

Data were analyzed using Excel 2016 statistical software, wherein the mean value was calculated as avg; the SD value was calculated as STDEV; the SEM value was calculated as STDEV/SQRT; and the P-value of the difference between groups was calculated as TTEST.

TABLE 9

In vivo tumor inhibition effect of exemplary ADCs on the NCI-N87 xenograft tumor model

| ADC No. | Tumor growth inhibition % |
| --- | --- |
| Reference ADC-1 | 54.14 |
| ADC-II-9 | 134.29 |
| ADC-II-13 | 58.75 |
| ADC-III-9 | 93.79 |

The experimental results are shown in the table above and FIG. 1, and it is observed from one intraperitoneal injection to the end of the experiment that the ADC molecules of the present application can significantly reduce the tumor volume, and have superior tumor inhibition effect to the reference ADC-1. The other ADCs of the present application also have similar tumor inhibition effect in vivo.

Test Example 2.11. Efficacy Evaluation of NCI-N87 Tumor-Bearing Mice

Objective

To evaluate the conjugates of the present application using BALB/c nude mice as test animals;
to evaluate the efficacy of ADC-II-9, ADC-III-1, ADC-III-9 and reference ADC-1 on NCI-N87 xenograft tumor-bearing nude mice after the intraperitoneal injection.

Test Compounds and Materials

1. Test compounds
ADC-II-9, ADC-III-1, ADC-III-9: 2 mg/kg
Reference ADC-1: 2 mg/kg
Blank control: PBS
2. Preparation method: all compounds were diluted with PBS.
3. Test animal
BALB/c Nude mice, purchased from Beijing Vital River.

Test Method

NCI-N87 cells were subcutaneously inoculated into the right flank of the mice, and after tumors were grown for 8 days, animals were randomly grouped, with 8 animals in each group for a total of 6 groups.

The compounds each were intraperitoneally injected once. The tumor volume and weight were measured twice a week, and the data were recorded.

Data were analyzed using Excel 2016 statistical software, wherein the mean value was calculated as avg; the SD value was calculated as STDEV; the SEM value was calculated as STDEV/SQRT; and the P-value of the difference between groups was calculated as TTEST.

TABLE 10

In vivo tumor inhibition effect of exemplary ADCs on the NCI-N87 xenograft tumor model

| ADC No. | Tumor growth inhibition % |
|---|---|
| Reference ADC-1 | 54.14 |
| ADC-II-9 | 68.86 |
| ADC-III-1 | 80.39 |
| ADC-III-9 | 93.05 |

Figure 2:
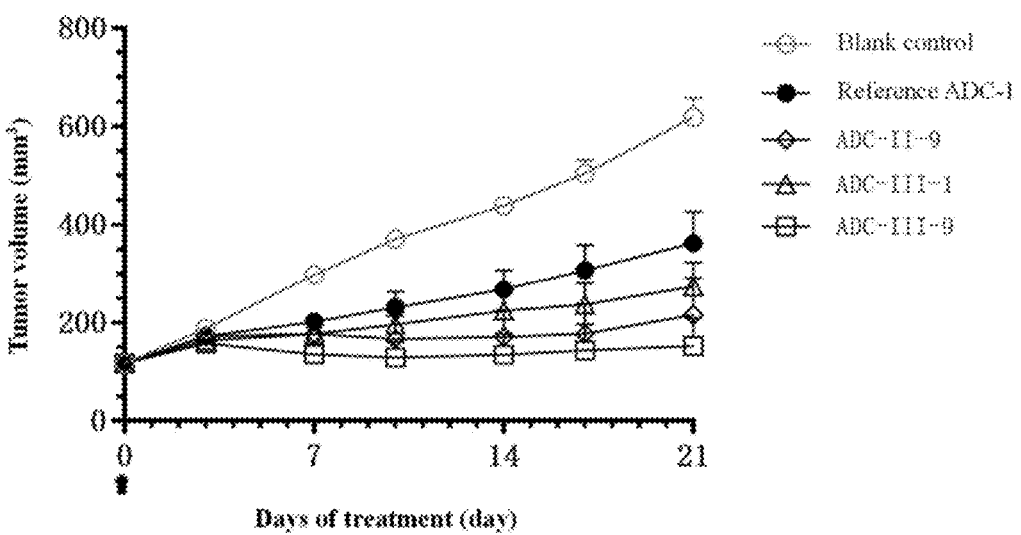

The experimental results are shown in the table above and FIG. 2, and it is observed from one intraperitoneal injection to the end of the experiment that the ADC molecules of the present application can significantly reduce the tumor volume, and have superior tumor inhibition effect to the reference ADC-1. The other ADCs of the present application also have similar tumor inhibition effect in vivo.

Test Example 2.12. Efficacy Evaluation of Colo205 Tumor-Bearing Mice

Objective

To evaluate the conjugates of the present application using BALB/c nude mice as test animals;

to evaluate the efficacy of ADC-III-28 and reference ADC-2 on Colo205 xenograft tumor-bearing nude mice after the intraperitoneal injection.

Test Compounds and Materials

1. Test compounds
ADC-III-28: 10 mg/kg
Reference ADC-2: 10 mg/kg
Blank control: PBS
2. Preparation method: all compounds were diluted with PBS.
3. Test animal
BALB/c Nude mice, purchased from Beijing Vital River.

Test Method

Colo205 cells were subcutaneously inoculated into the right flank of the mice, and after tumors were grown for 8 days, animals were randomly grouped, with 8 animals in each group for a total of 6 groups.

The compounds each were intraperitoneally injected once. The tumor volume and weight were measured twice a week, and the data were recorded.

Data were analyzed using Excel 2016 statistical software, wherein the mean value was calculated as avg; the SD value was calculated as STDEV; the SEM value was calculated as STDEV/SQRT; and the P-value of the difference between groups was calculated as TTEST.

TABLE 11

In vivo tumor inhibition effect of exemplary ADCs on the Colo205 xenograft tumor model

| ADC No. | Tumor growth inhibition % |
|---|---|
| Reference ADC-2 | 62.64 |
| ADC-III-28 | 96.84 |

Figure 3:
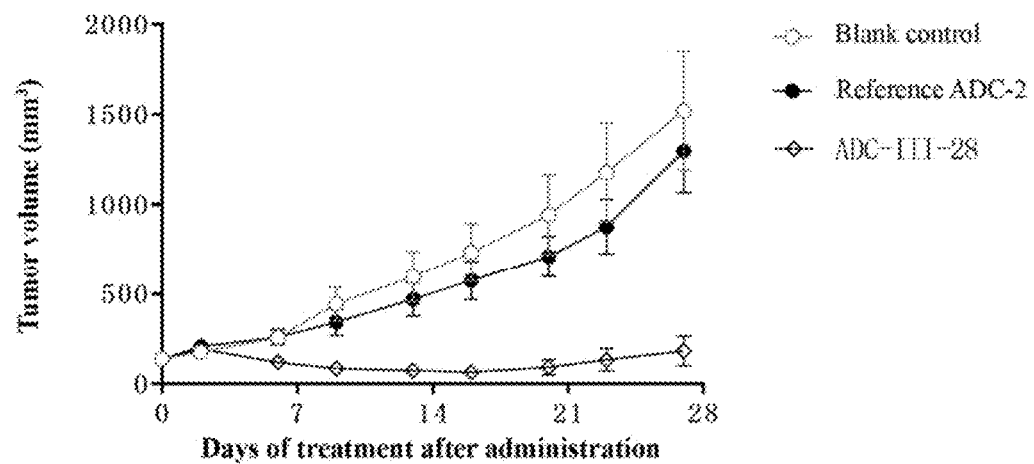

The experimental results are shown in the table above and FIG. 3, and it is observed from one intraperitoneal injection to the end of the experiment that the ADC molecules of the present application can significantly reduce the tumor volume, and have superior tumor inhibition effect to the reference ADC-2. The other ADCs of the present application also have similar tumor inhibition effect in vivo.

Test Example 2.13. Efficacy Evaluation of SK-OV-3 Tumor-Bearing Mice

Objective

To evaluate the conjugates of the present application using BALB/c nude mice as test animals;

to evaluate the efficacy of ADC-III-28 and reference ADC-2 on SK-OV-3 xenograft tumor-bearing nude mice after the intraperitoneal injection.

Test Compounds and Materials

1. Test compounds
ADC-111-28: 3 mg/kg, 10 mg/kg
Reference ADC-2: 3 mg/kg, 10 mg/kg
Blank control: PBS
2. Preparation method: all compounds were diluted with PBS.
3. Test animal
BALB/c Nude mice, purchased from Beijing Vital River.

Test Method

SK-OV-3 cells were subcutaneously inoculated into the right flank of the mice, and after tumors were grown for 8 days, animals were randomly grouped, with 8 animals in each group for a total of 6 groups.

The compounds each were intraperitoneally injected once. The tumor volume and weight were measured twice a week, and the data were recorded.

Data were analyzed using Excel 2016 statistical software, wherein the mean value was calculated as avg; the SD value was calculated as STDEV; the SEM value was calculated as STDEV/SQRT; and the P-value of the difference between groups was calculated as TTEST.

TABLE 12

In vivo tumor inhibition effect of exemplary ADCs on the SK-OV-3 xenograft tumor model

| ADC No. | Tumor growth inhibition % |
|---|---|
| Reference ADC-2 (3 mg/kg) | 33.73% |
| Reference ADC-2 (10 mg/kg) | 55.01% |
| ADC-III-28 (3 mg/kg) | 58.74% |
| ADC-III-28 (3 mg/kg) | 81.18% |

Figure 4:
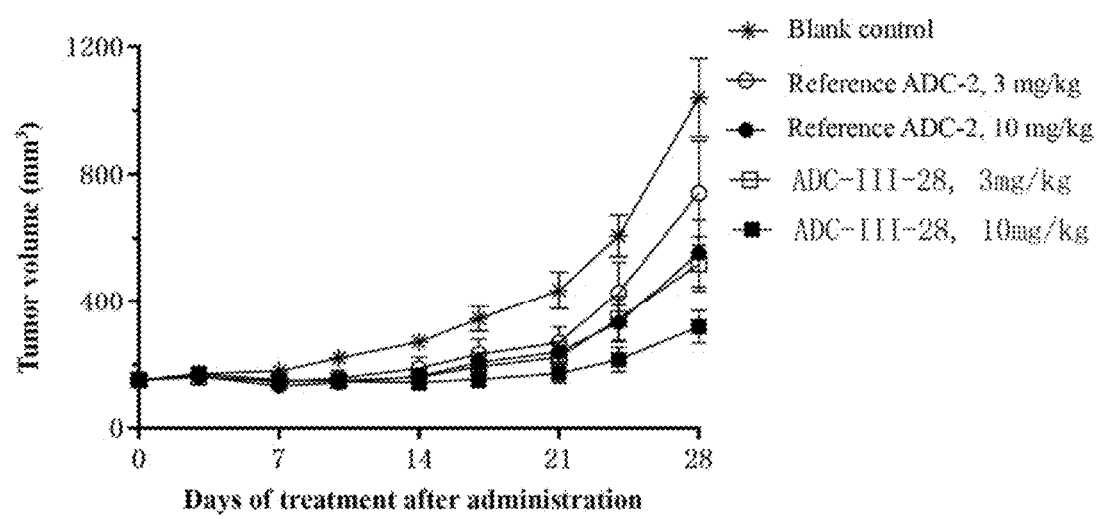
Figure 5:
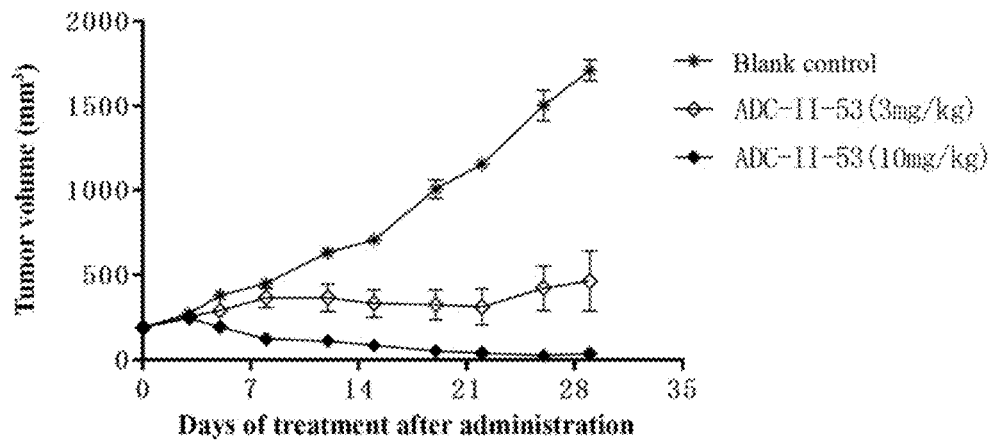
Figure 6:
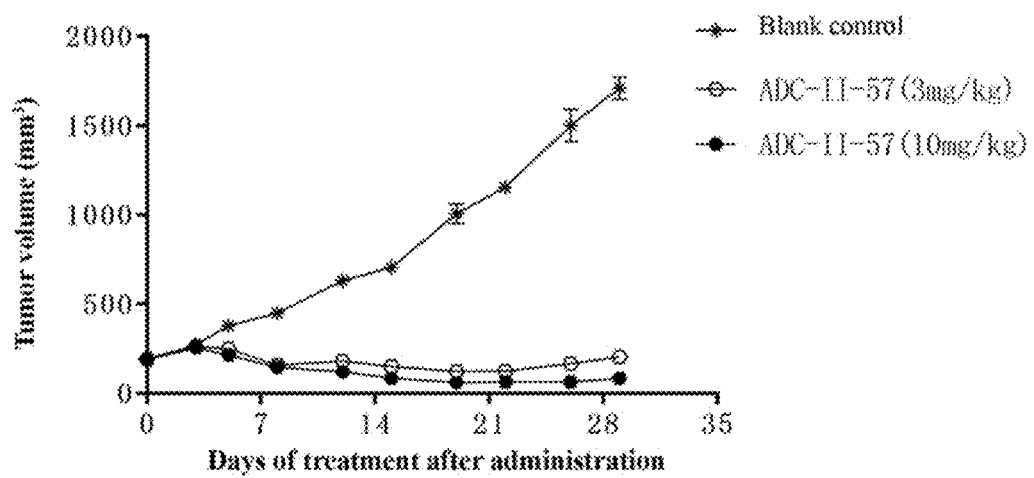
Figure 7:
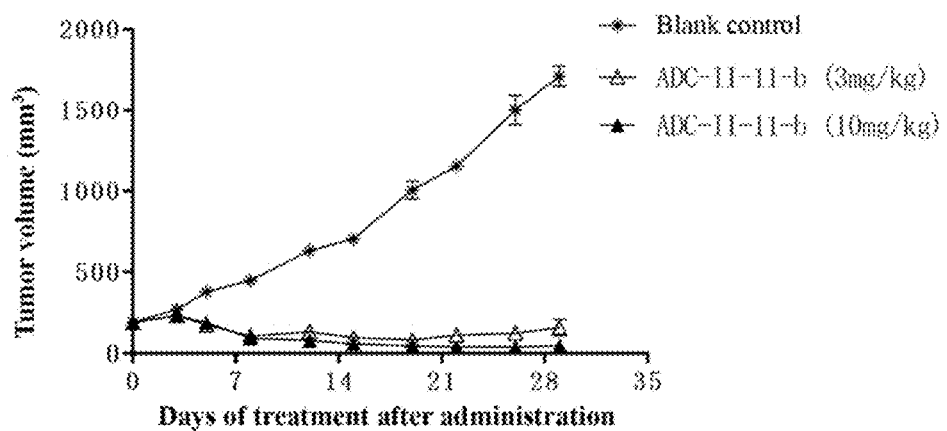
Figure 8:
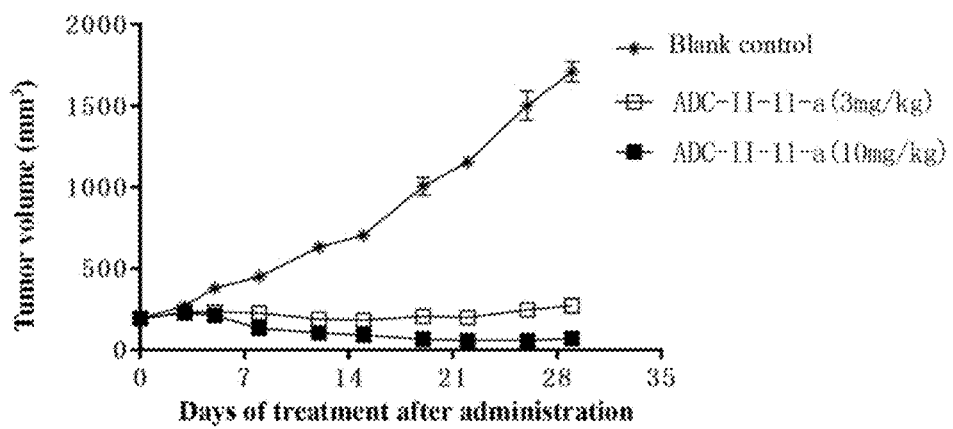
Figure 9:
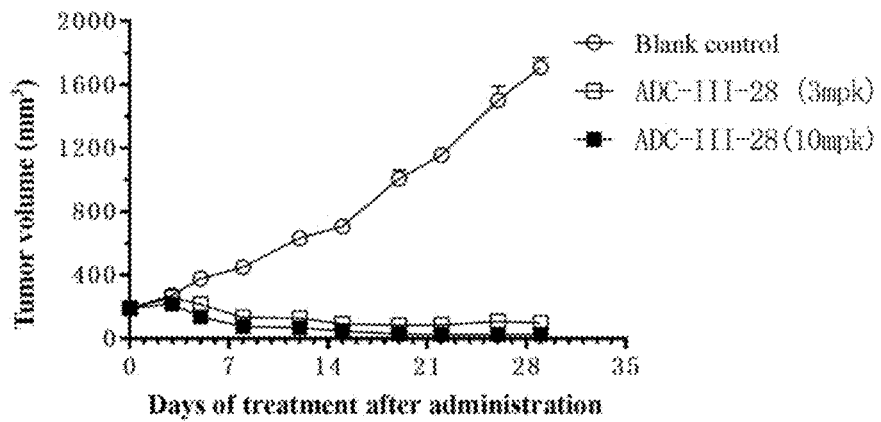

The experimental results are shown in the table above and FIG. 4, and it is observed from one intraperitoneal injection to the end of the experiment that the ADC molecules of the present application can significantly reduce the tumor volume, and have superior tumor inhibition effect to the reference ADC-2. The other ADCs of the present application also have similar tumor inhibition effect in vivo.

Test Example 2.14. Efficacy Evaluation of NCI-N87 Tumor-Bearing Mice

Objective

To evaluate the conjugates of the present application using BALB/c nude mice as test animals;
to evaluate the efficacy of ADC-II-11-a, ADC-II-11-b, ADC-II-53, ADC-II-57 and ADC-III-28 on NCI-N87 xenograft tumor-bearing nude mice after the intraperitoneal injection.

Test Compounds and Materials

1. Test compounds
ADC-II-11-a: 10 mg/kg
ADC-II-11-b: 10 mg/kg
ADC-II-53: 10 mg/kg
ADC-II-57: 10 mg/kg
ADC-III-28: 10 mg/kg
Blank control: PBS
2. Preparation method: all compounds were diluted with PBS.
3. Test animal
BALB/c Nude mice, purchased from Beijing Vital River.

Test Method

NCI-N87 cells were subcutaneously inoculated into the right flank of the mice, and after tumors were grown for 8 days, animals were randomly grouped, with 8 animals in each group for a total of 6 groups.

The compounds each were intraperitoneally injected once. The tumor volume and weight were measured twice a week, and the data were recorded.

Data were analyzed using Excel 2016 statistical software, wherein the mean value was calculated as avg; the SD value was calculated as STDEV; the SEM value was calculated as STDEV/SQRT; and the P-value of the difference between groups was calculated as TTEST.

The experimental results are shown in the table above and FIGS. 5, 6, 7, 8, 9 and 10, and it is observed from one intraperitoneal injection to the end of the experiment that the ADC molecules of the present application can significantly reduce the tumor volume. The other ADCs of the present application also have similar tumor inhibition effect in vivo.

Test Example 2.15. Efficacy Evaluation of Colo205 Tumor-Bearing Mice

Objective

To evaluate the conjugates of the present application using BALB/c nude mice as test animals;
to evaluate the efficacy of ADC-III-28 and reference ADC-2 on Colo205 xenograft tumor-bearing nude mice after the intraperitoneal injection.

Test Compounds and Materials

1. Test compounds
ADC-III-28: 10 mg/kg, one administration
Reference ADC-2: 10 mg/kg, two administrations
Blank control: PBS
2. Preparation method: all compounds were diluted with PBS.
3. Test animal
BALB/c Nude mice, purchased from Beijing Vital River.

Test Method

Colo205 cells were subcutaneously inoculated into the right flank of the mice, and after tumors were grown for 8 days, animals were randomly grouped, with 8 animals in each group for a total of 6 groups.

The compounds each were intraperitoneally injected once. The tumor volume and weight were measured twice a week, and the data were recorded.

Data were analyzed using Excel 2016 statistical software, wherein the mean value was calculated as avg; the SD value was calculated as STDEV; the SEM value was calculated as STDEV/SQRT; and the P-value of the difference between groups was calculated as TTEST.

Figure 10:
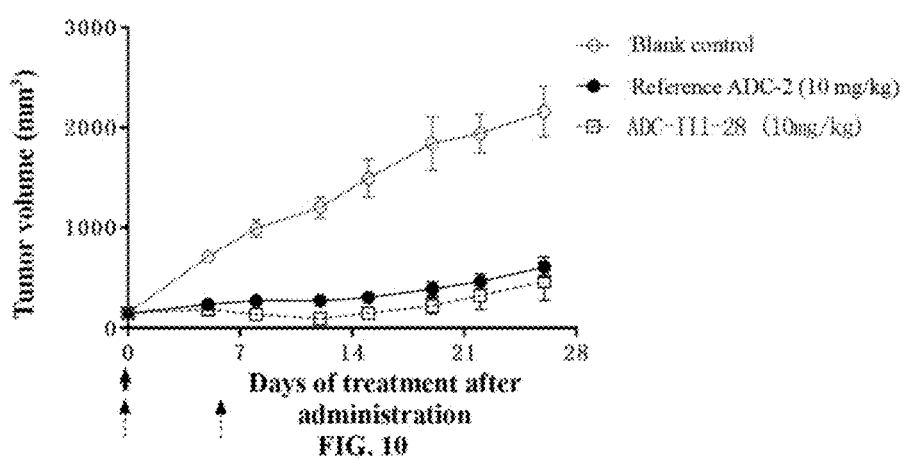

The experimental results are shown in FIG. 10, and it is observed from one intraperitoneal injection to the end of the experiment that ADC-III-28 can significantly reduce the tumor volume as compared to the reference ADC-2 (two intraperitoneal injections), and has superior tumor inhibition effect to the reference ADC-2. The other ADCs of the present application also have similar tumor inhibition effect in vivo.

Test Example 2.16. Efficacy Evaluation of JIMT-1 Tumor-Bearing Mice

Objective

To evaluate the conjugates of the present application using BALB/c nude mice as test animals;
to evaluate the efficacy of ADC-II-9 and reference ADC-1 on JIMT-1 xenograft tumor-bearing nude mice after the intraperitoneal injection.

Test Compounds and Materials

1. Test compounds
ADC-II-9: 3 mg/kg, 10 mg/kg, one administration
Reference ADC-1: 3 mg/kg, 10 mg/kg, one administration
Blank control: PBS
2. Preparation method: all compounds were diluted with PBS.
3. Test animal
BALB/c Nude mice, purchased from Beijing Vital River.

Test Method

JIMT-1 cells were subcutaneously inoculated into the right flank of the mice, and after tumors were grown for 8 days, animals were randomly grouped, with 8 animals in each group for a total of 6 groups.

The compounds each were intraperitoneally injected once. The tumor volume and weight were measured twice a week, and the data were recorded.

Data were analyzed using Excel 2016 statistical software, wherein the mean value was calculated as avg; the SD value was calculated as STDEV; the SEM value was calculated as STDEV/SQRT; and the P-value of the difference between groups was calculated as TTEST.

Figure 11:
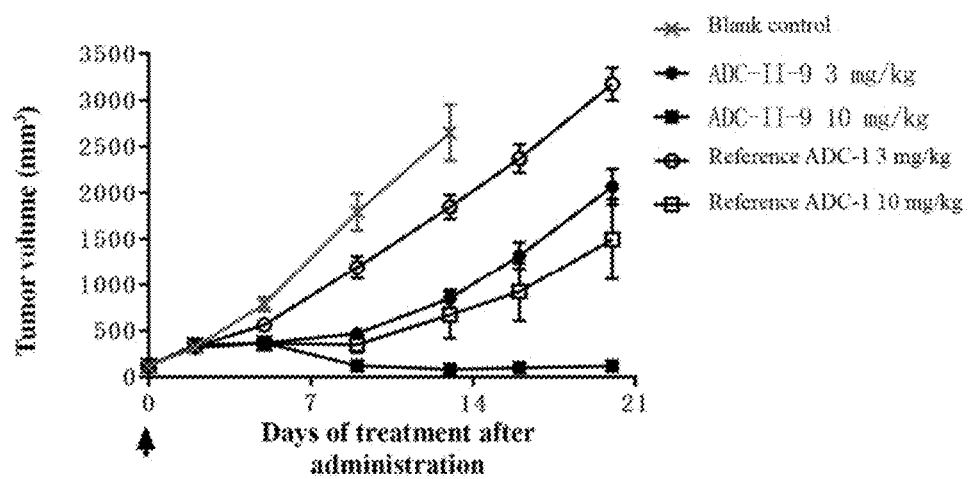
Figure 12:
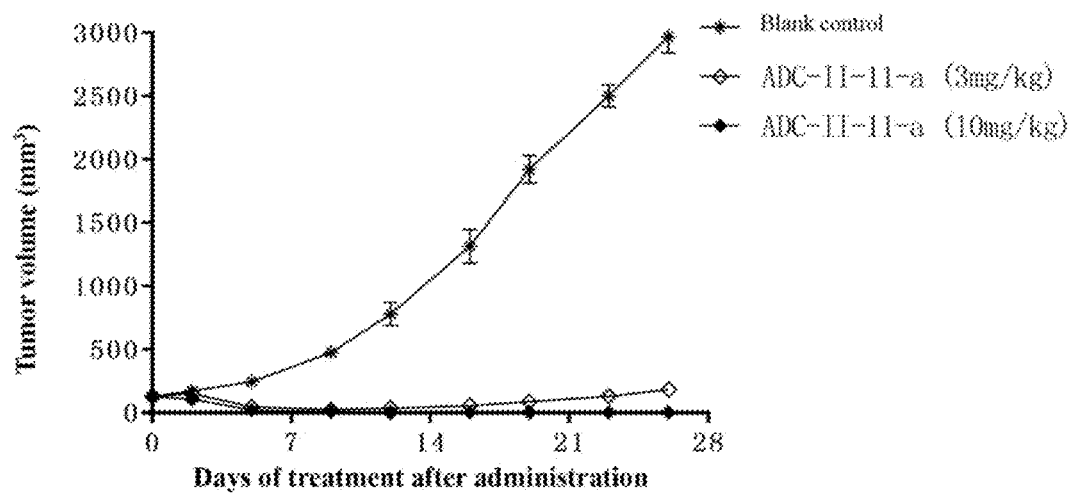
Figure 13:
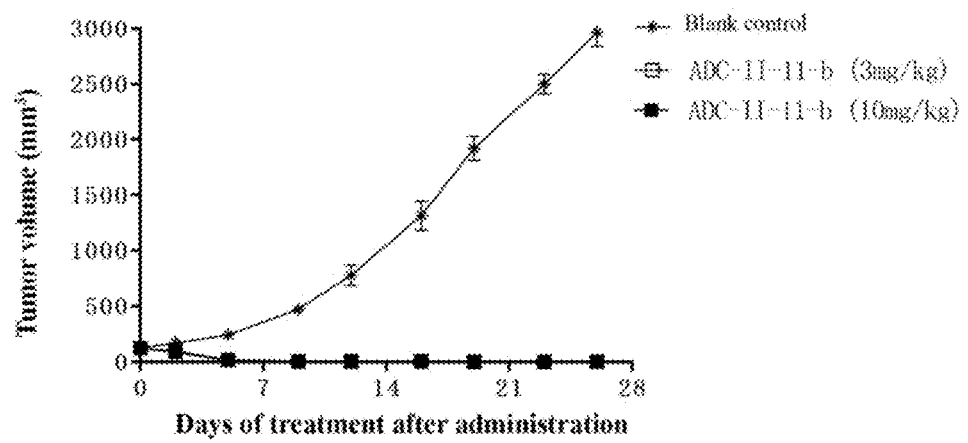
Figure 14:
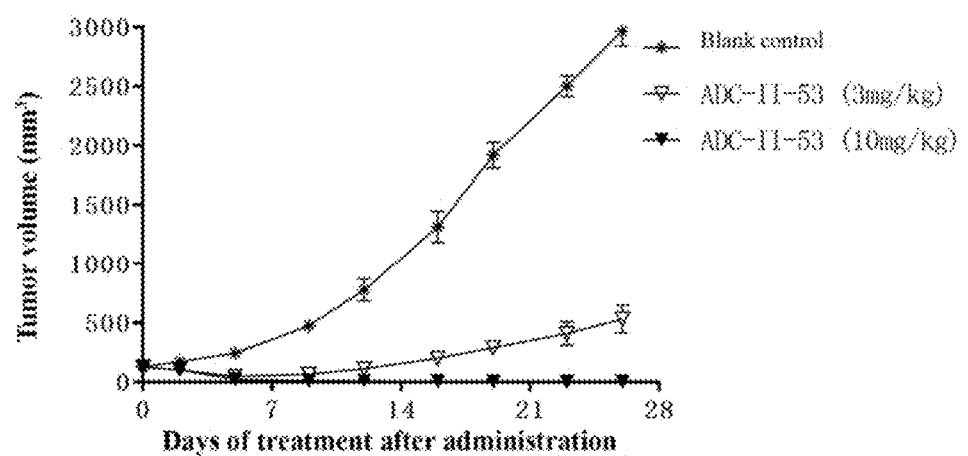
Figure 15:
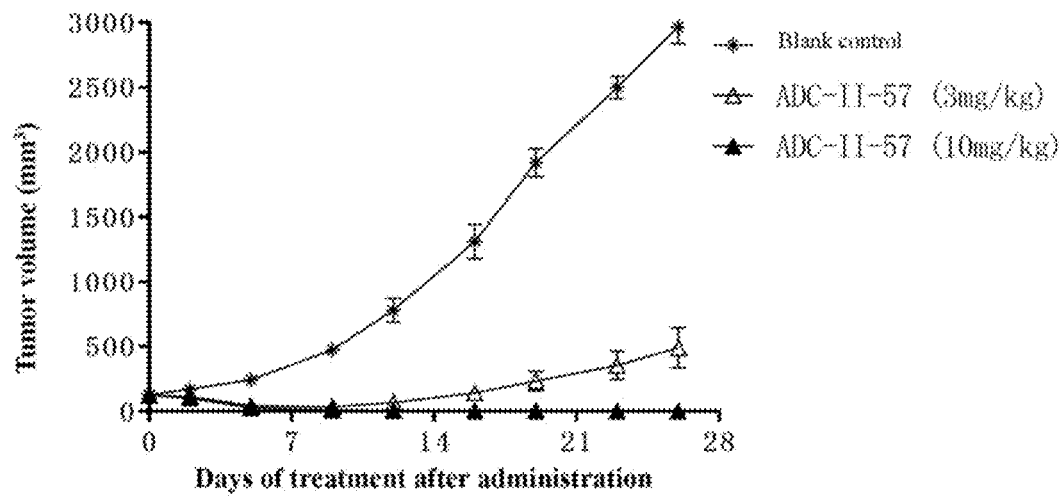
Figure 16:
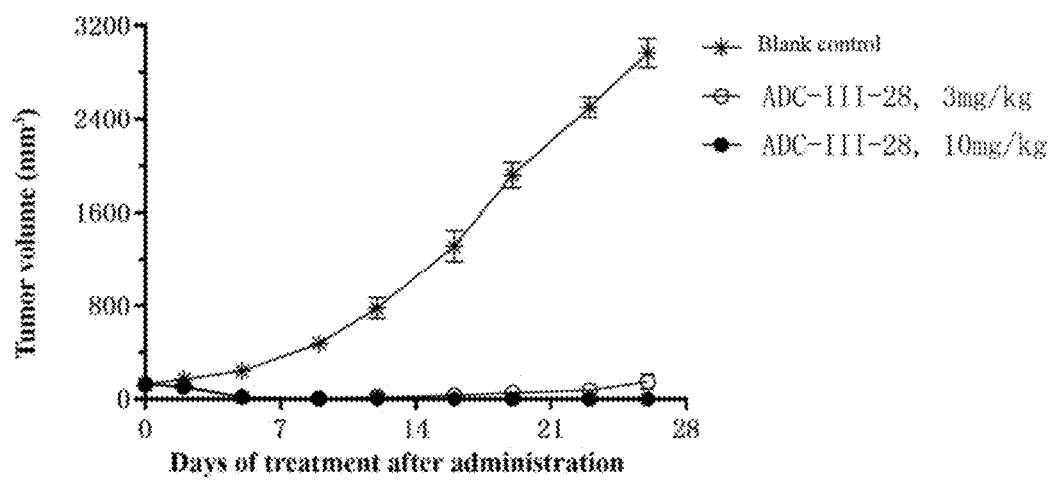

The experimental results are shown in FIG. 11, and it is observed from one intraperitoneal injection to the end of the experiment that ADC-II-9 can significantly reduce the tumor volume as compared to the reference ADC-1, and has superior tumor inhibition effect to the reference ADC-1. The other ADCs of the present application also have similar tumor inhibition effect in vivo.

Test Example 2.17. Efficacy Evaluation of Fadu Tumor-Bearing Mice

Objective

To evaluate the conjugates of the present application using BALB/c nude mice as test animals;

to evaluate the efficacy of ADC-II-11-a, ADC-II-11-b, ADC-II-53, ADC-II-57 and ADC-III-28 on Fadu xenograft tumor-bearing nude mice after the intraperitoneal injection.

Test Compounds and Materials

1. Test compounds
ADC-II-11-a: 10 mg/kg
ADC-II-11-b: 10 mg/kg
ADC-II-53: 10 mg/kg
ADC-II-57: 10 mg/kg
ADC-III-28: 10 mg/kg
Blank control: PBS
2. Preparation method: all compounds were diluted with PBS.
3. Test animal
BALB/c Nude mice, purchased from Beijing Vital River.

Test Method

Fadu cells were subcutaneously inoculated into the right flank of the mice, and after tumors were grown for 8 days, animals were randomly grouped, with 8 animals in each group for a total of 6 groups.

The compounds each were intraperitoneally injected once. The tumor volume and weight were measured twice a week, and the data were recorded.

Data were analyzed using Excel 2016 statistical software, wherein the mean value was calculated as avg; the SD value was calculated as STDEV; the SEM value was calculated as STDEV/SQRT; and the P-value of the difference between groups was calculated as TTEST.

The experimental results are shown in the table above and FIGS. 12, 13, 14, 15 and 16, and it is observed from one intraperitoneal injection to the end of the experiment that the ADCs of the present invention all can reduce the tumor volume. The other ADCs of the present application also have similar tumor inhibition effect in vivo.

Example 3

Test Example 3.1. Bystander Effect

Objective

To investigate the bystander effect of the ADCs under the condition of co-culture of HER2-positive tumor cells and HER2-negative tumor cells.

Test Method

Fluorescently Labeled Cells

Cells in the exponential phase were collected and viable cell were counted using a cell counter.

The cell suspension was adjusted to a certain cell density with the corresponding medium.

1 μL of each of Qtracker® components A and B was premixed in a 1.5 mL EP pipe to prepare the fluorescent labeling solutions. After incubation at room temperature for 5 min, step 4) was performed immediately.

0.2 mL of fresh complete medium was added to the EP tube and vortexed for 30 s.

$1 \times 10^6$ cells were added to the fluorescent labeling solution prepared above.

The mixture was incubated at 37° C. for 60 min.

The cell labeling was examined under a fluorescent microscope.

The complete medium was added for washing twice. The resulting cells were placed for later use.

Cell Inoculation

The 3 cell combinations as shown in Table 13 below were set up in a 96-well cell culture plate:

TABLE 13

| | Cell combinations (+ representing the presence of a cell in the cell combination) | | | |
|---|---|---|---|---|
| | N87 | | HCC1187 | |
| Cell number | labeled | Unlabeled | labeled | Unlabeled |
| Group 1 | + | + | — | — |
| Group 2 | — | + | + | — |
| Group 3 | — | — | + | + |

2) 90 μL of cell suspension was added to each well of a 96-well plate.

3) The 96-well plate was incubated in an incubator at 37° C. in 5% $CO_2$ overnight.

3. Compound adding

1) A 10× drug dilution was prepared.

2) The diluted candidate molecules and positive drugs was added to each well, and 3 duplicate wells were set for each compound.

3) The 96-well plate was incubated in an incubator at 37° C. in 5% $CO_2$ for 4 days.

4. Detection

1) Each set of images was observed and recorded under a fluorescence microscope.

2) A CTG solution which was pre-melted and equilibrated to room temperature was added to each well according to CTG operation instructions, and the solution was mixed well using a microplate shaker, left to stand at room temperature for a period of time, and measured for fluorescence signal values using a plate reader.

3) Cell viability was expressed as mean fluorescence signal (treatment group)/mean fluorescence signal (control group)×100%.

Under the experimental conditions, the ADC molecules of the present application have a significant killing effect on HER2-positive cells, but have no significant inhibition effect on HER2-negative cells. In cells co-cultured using HER2-positive cells and HER2-negative cells, the ADC molecules of the present application can significantly inhibit both HER2-positive cells and HER2-negative cells, and show significant bystander effects. The other ADCs of the present application also have similar bystander effects.

Test Example 3.2. Study on Transporter Substrates

Objective

To investigate whether the compounds of the present invention is a substrate for efflux transporters P-gp and BCRP in a Caco-2 cell model, thereby providing preclinical basis for analyzing the drug-drug interaction in pharmacokinetics.

Test Method

Preparation of Monolayer Cells

Cell culture medium was added to each well of the Transwell. The HTS Transwell plate was incubated under conditions of 37° C. and 5% $CO_2$ for 1 h prior to cell inoculation.

Caco-2 cells were diluted with culture medium and the cell suspension was dispensed into filter wells of the 96-well HTS Transwell plate. Cells were cultured under conditions of 37° C., 5% $CO_2$ and 95% relative humidity for more than ten days. The cell culture medium was changed periodically.

Monolayer cell resistance was measured using the Millicell Epithelial Volt-Ohm detection system. The resistance of each well was recorded. After all wells were measured, the Transwell plate was put back into the incubator.

TEER of each well was calculated according to the formula. The TEER value of each well should be greater than 230 ohm·cm².

Preparation for Transporter Test

The Caco-2 plate was taken out from the incubator. The monolayer cells were washed with pre-heated HBSS twice. The plate was then incubated at 37° C. for 30 min.

Stock solutions of the compounds were prepared in DMSO and diluted with HBSS to obtain working solutions. Digoxin was used as a reference substrate for P-gp and rosuvastatin was used as a reference substrate for BCRP. Propranolol was used as a high permeability marker.

The working solution (without inhibitor) was added to the Transwell insert (apical compartment) to determine the rate of drug transport in the apical to basolateral direction. The transfer buffer was added to the wells in the receiver plate (basolateral compartment). The working solution (without inhibitor) was added to the receiver plate wells (basolateral compartment) to determine the rate of drug transport in the basolateral to apical direction. The Transwell insert (apical compartment) was filled with the transport buffer. PSC833 was added to the apical and basolateral compartments to determine the rate of drug transport in the presence of P-gp inhibitors.

The sample was transferred from the working solution to the quenching solution, and a sample with a time of 0 was prepared. The Transwell plate was incubated under conditions of 37° C. and 5% $CO_2$ for 2 h.

At the end of the transport cycle, the samples were transferred from the apical and basolateral wells into a new 96-well plate. Cold acetonitrile or methanol containing the appropriate internal standard (IS) was added to each well of the plate. The plate was vortexed for 10 min. The samples were centrifuged. The supernatant of an aliquot was mixed with an appropriate amount of ultrapure water (depending on the LC-MS/MS signal response and peak shape) prior to the LC-MS/MS analysis.

The stock solution of lucifer yellow in DMSO was prepared and diluted with HBSS to determine the amount of lucifer yellow leakage after a 2-hour transport period. The lucifer yellow solution was added to the apical compartment. HBSS was added to the basolateral compartment. The plate was incubated at 37° C. for 30 min, and a certain amount of the solution was directly taken from the apical and basolateral wells and transferred to a new 96-well plate. The lucifer yellow fluorescence was measured in a fluorescence plate reader with 485 nm excitation and 530 nm emission (to monitor monolayer integrity).

Data Analysis

Data were calculated using Microsoft Excel. The percentage of the compound remaining at each time point was estimated by determining the peak area ratio from the extracted ion chromatogram.

For drug transport analysis in the Caco-2 cell model, the apparent permeability coefficient (Papp) can be calculated according to the following formula, in cm/s:

$$Papp = (C\text{receiving side} \times V\text{receiving side}) / (C\text{initiation} \times T\text{penetration time} \times S\text{membrane area})$$

wherein the concentration C is in nM, the volume V is in μL, the time T is in s, and the area S is in cm².

The recovery rate is calculated according to the following formula:

$$\text{Recovery rate} = \frac{C\text{receiving side} \times V\text{receiving side} + C\text{administrating side} \times V\text{administrating side} + C\text{cell lysis buffer} \times V\text{cell lysis buffer}}{C\text{initiation} \times V\text{administrating side}}$$

The efflux ratio (ER) is calculated according to the following formula:

$$\text{Efflux ratio } (ER) = \frac{PappB \to A}{PappA \to B}$$

The rate of change of the efflux ratio was calculated to evaluate whether a compound is a substrate form P-gp or BCRP.

Test Results

Dxd is a transporter BCRP substrate but not a transporter P-gp substrate under the test conditions as shown in Table 14. The test compounds P-II-1, P-II-2, P-II-3, P-II-4 and P-I-1 are neither transporter P-gp substrates nor transporter BCRP substrates.

The results show that the compounds of the present application have a lower risk of clinical drug-drug interactions than the reference drug Dxd. The compounds of the present application all have similar drug-drug interactions.

TABLE 14

Study on transporter substrates of the compounds of the present application

| Compound | KO143 | $P_{app\ (A-B)}$ ($10^{-6}$, cm/s) | $P_{app\ (B-A)}$ ($10^{-6}$, cm/s) | Efflux ratio | Recovery rate (%) AP-BL | Recovery rate (%) BL-AP | BCRP substrate |
|---|---|---|---|---|---|---|---|
| Propranolol | − | 17.30 | 18.92 | 1.09 | 62.16 | 82.36 | No |
| Rosuvastatin | − | 0.12 | 9.52 | 81.16 | 98.54 | 96.78 | Yes |
|  | + | 0.45 | 3.15 | 6.96 | 95.84 | 97.06 |  |
| Dxd | − | 0.07 | 4.82 | 74.03 | 57.76 | 56.20 | Yes |
|  | + | 0.21 | 4.42 | 21.23 | 76.51 | 74.87 |  |
| P-II-1 | − | 0.17 | 4.83 | 28.69 | 80.87 | 77.50 | No |
|  | + | 0.20 | 5.52 | 27.54 | 76.91 | 76.54 |  |
| P-II-3 | − | 0.17 | 4.83 | 28.69 | 80.87 | 77.50 | No |
|  | + | 0.20 | 5.52 | 27.54 | 76.91 | 76.54 |  |
| P-II-2 | − | 0.05 | 1.52 | 30.08 | 59.32 | 58.51 | No |
|  | + | 0.07 | 1.70 | 22.74 | 62.42 | 62.86 |  |
| P-II-4 | − | 0.05 | 1.72 | 36.09 | 63.84 | 63.97 | No |
|  | + | 0.06 | 1.65 | 25.47 | 65.05 | 63.02 |  |
| P-I-1 | − | 0.13 | 4.06 | 32.38 | 80.47 | 76.12 | No |
|  | + | 0.21 | 4.94 | 23.49 | 81.46 | 80.26 |  |

Test Example 3.3. Tissue Distribution Test in Tumor-Bearing Mice

Objective

After a single intravenous administration of $^{125}$I isotopically labeled ADC molecules of the present invention to mice bearing HER2-positive tumor cells, tissues/body fluids were collected at different time points for γ counting, and the tissue distribution profiles of the subjects were researched according to the exposure level of the drug in different tissues.

Test Method

The study on the tissue distribution of mice bearing HER2-positive tumor cells administered with the labeled subject $^{125}$I-ADC was performed by the $^{125}$I isotope labeling method. In the test, the subject was firstly labeled with [$^{125}$I] by an Iodogen method, the serum and tissue samples of the $^{125}$I-ADC were investigated by a TCA precipitation method, the [$^{125}$I]-labeled test sample was detected for biological activity, and an animal test was conducted after the quality control of 125I-ADC was passed.

Mice (females) bearing HER2-positive tumor cells were administered with $^{121}$I-ADC, and various body fluids and tissue samples were collected at different time points (6 animals at each time point) after the administration. The total radioactivity and the radioactivity precipitated after TCA precipitation were detected by a γ counter to obtain the radioactive substance concentration in each tissue/body fluid, and the exposure of each tissue was calculated.

Test Results

Labeling results: the quality control after labeling was passed, and RCP of different batches of labeled samples placed in a solvent for a certain period of time meets the test requirements at 2-8° C.; the biological activity after labeling meets the test requirements.

Results of tissue distribution test: the detection values of the total thyroid radioactivity content at different time points after the administration are all low, which does not affect the reliability of the tissue distribution test results.

After the administration to tumor-bearing mice, radioactivity is distributed primarily in serum, secondarily in tumors, and partially or sparingly in other tissues and organs. The ADCs of the present application all have similar tissue distribution profiles.

Test Example 3.4. Pharmacokinetic and Toxicity Studies of ADCs at a Single Administration

Objective

To investigate the pharmacokinetic properties of the drug in monkeys and observe the toxic manifestation of the animals after a single intravenous drip of ADC in monkeys.

Test Method

Pharmacokinetics: after the single intravenous drip of ADC drugs at difference doses in monkeys, blood samples were collected at a plurality of continuous time points, and the concentration of the drugs in the blood was detected by a proper specific detection method.

Toxicity study: after the single intravenous drip of ADC drugs at difference doses in monkeys, the tolerance of animals and drug-related toxicity toxic manifestation were investigated in multiple aspects such as clinical observation, body weight and food intake, hematology, blood biochemistry, urine and gross anatomy.

Test Results

After the single intravenous drip of ADCs in monkeys, the concentration of free toxins is very low, and the pharmacokinetic properties of the total antibody and ADCs are similar, suggesting that ADCs are slowly released in monkeys, have a stable conjugating mode, and can be used in a clinically planned administration frequency.

After the single intravenous drip of ADCs in monkeys, animals have good tolerance and do not show serious or intolerable drug-related toxicity, suggesting that ADCs have controllable safety, and can be further studied clinically. All ADCs of the present application have similar safety.

The foregoing detailed description is provided by way of illustration and example, and is not intended to limit the scope of the appended claims. Various modifications of the embodiments currently enumerated in the present application will be apparent to those of ordinary skill in the art and are intended to be within the scope of the appended claims and their equivalents.

What is claimed is:

1. An antibody-drug conjugate having the following structure:

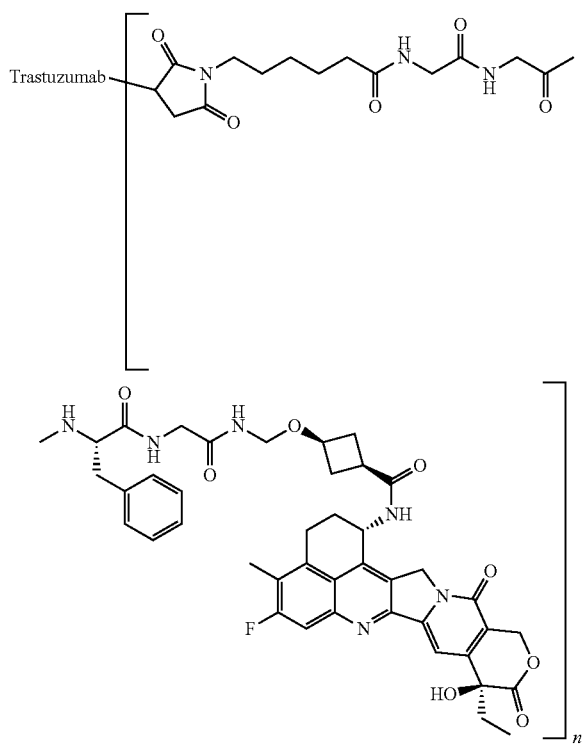

or a pharmaceutically acceptable salt thereof, wherein n is the connection number, and n is selected from the group consisting of 1 to 10.

2. The antibody-drug conjugate or pharmaceutically acceptable salt thereof according to claim 1, wherein n is 6 to 8.

3. The antibody-drug conjugate or pharmaceutically acceptable salt thereof according to claim 2, wherein n is 7.

4. The antibody-drug conjugate or pharmaceutically acceptable salt thereof according to claim 2, wherein n is 8.

5. The antibody-drug conjugate or pharmaceutically acceptable salt thereof according to claim 1, wherein trastuzumab comprises a light chain comprising an amino acid sequence set forth in SEQ ID NO: 33, and a heavy chain comprising an amino acid sequence set forth in SEQ ID NO: 37.

6. A pharmaceutical composition comprising an antibody-drug conjugate or pharmaceutically acceptable salt thereof of claim 1, or a mixture thereof, and a pharmaceutically acceptable carrier or diluent.

7. A method of treating cancer in a subject in need thereof, comprising administering to said subject the antibody-drug conjugate or pharmaceutically acceptable salt thereof of claim 1.

8. The method of claim 7, wherein the cancer is selected from the group consisting of lung cancer, kidney cancer, urinary tract carcinoma, colorectal cancer, prostatic cancer, glioblastoma multiforme, ovarian cancer, pancreatic cancer, breast cancer, melanoma, liver cancer, bladder cancer, stomach cancer and esophageal cancer.

9. The method of claim 8, wherein the cancer is selected from the group consisting of breast cancer and stomach cancer.

10. The antibody-drug conjugate or pharmaceutically acceptable salt thereof according to claim 2, wherein n is 6.

* * * * *